(12) United States Patent
Eden et al.

(10) Patent No.: US 9,709,565 B2
(45) Date of Patent: Jul. 18, 2017

(54) SIGNATURES AND DETERMINANTS FOR DISTINGUISHING BETWEEN A BACTERIAL AND VIRAL INFECTION AND METHODS OF USE THEREOF

(75) Inventors: Eran Eden, Haifa (IL); Kfir Oved, Hof HaCarmel (IL)

(73) Assignee: MeMed Diagnostics Ltd., Tirat HaCarmel (IL)

(*) Notice: Subject to any disclaimer, the term of this patent is extended or adjusted under 35 U.S.C. 154(b) by 119 days.

(21) Appl. No.: 13/090,893

(22) Filed: Apr. 20, 2011

(65) Prior Publication Data

US 2011/0275542 A1    Nov. 10, 2011

Related U.S. Application Data

(60) Provisional application No. 61/326,244, filed on Apr. 21, 2010.

(51) Int. Cl.
| C40B 40/10 | (2006.01) |
| G01N 33/569 | (2006.01) |
| A61K 45/06 | (2006.01) |
| C12Q 1/02 | (2006.01) |

(52) U.S. Cl.
CPC ....... *G01N 33/56983* (2013.01); *A61K 45/06* (2013.01); *G01N 33/569* (2013.01); *G01N 33/56911* (2013.01); *G01N 2333/4737* (2013.01); *G01N 2333/914* (2013.01)

(58) Field of Classification Search
CPC .................. G01N 33/5091; G01N 33/569
USPC .................................. 435/7.1, 7.24
See application file for complete search history.

(56) References Cited

U.S. PATENT DOCUMENTS

| 5,639,617 | A | 6/1997 | Bohuon |
| 5,910,421 | A | 6/1999 | Small, Jr. et al. |
| 6,077,665 | A | 6/2000 | Weirich et al. |
| 6,136,526 | A | 10/2000 | Venge |
| 6,210,661 | B1 | 4/2001 | Enssle et al. |
| 6,709,855 | B1 | 3/2004 | Stanton et al. |
| 6,756,483 | B1 | 6/2004 | Bergmann et al. |
| 7,132,246 | B2 | 11/2006 | Bergmann et al. |
| 7,153,662 | B2 | 12/2006 | Bergmann et al. |
| 7,157,081 | B2 | 1/2007 | Bergmann et al. |
| 7,598,031 | B2 | 10/2009 | Liew |
| 7,629,116 | B2 | 12/2009 | Ott |
| 2004/0038201 | A1 | 2/2004 | Nau et al. |
| 2004/0043379 | A1 | 3/2004 | Hashimoto et al. |
| 2004/0171013 | A1 | 9/2004 | Lilius et al. |
| 2005/0227223 | A1 | 10/2005 | Miyawaki |
| 2005/0233395 | A1 | 10/2005 | Weiser et al. |
| 2006/0099628 | A1 | 5/2006 | Ching et al. |
| 2007/0015172 | A1 | 1/2007 | Zhang et al. |
| 2007/0184460 | A1 | 8/2007 | Ching et al. |
| 2007/0231816 | A1 | 10/2007 | Chaussabel et al. |
| 2007/0281319 | A1 | 12/2007 | Kolopp-Sarda et al. |
| 2008/0020379 | A1 | 1/2008 | Agan et al. |
| 2008/0064113 | A1 | 3/2008 | Goix et al. |
| 2008/0171323 | A1 | 7/2008 | Banchereau et al. |
| 2009/0155180 | A1 | 6/2009 | Jump et al. |
| 2009/0203534 | A1 | 8/2009 | Hossain et al. |
| 2010/0028874 | A1 | 2/2010 | Ramachandran et al. |
| 2010/0068147 | A1 | 3/2010 | Hibberd et al. |
| 2010/0143372 | A1 | 6/2010 | Yao et al. |
| 2010/0297611 | A1 | 11/2010 | Sambursky et al. |
| 2011/0117563 | A1 | 5/2011 | Filipowicz et al. |
| 2015/0017630 | A1 | 1/2015 | Oved et al. |
| 2016/0153993 | A1 | 6/2016 | Eden et al. |
| 2017/0030909 | A1 | 2/2017 | Oved et al. |

FOREIGN PATENT DOCUMENTS

| CN | 1656378 | 8/2005 |
| CN | 101479389 | 7/2009 |
| CN | 101541976 | 9/2009 |
| CN | 101611314 | 12/2009 |
| CN | 101617056 | 12/2009 |
| EP | 1489416 | 12/2004 |
| WO | WO 2004/108899 | 12/2004 |
| WO | WO 2007/011412 | 1/2007 |
| WO | WO-2007088355 A2 | 8/2007 |
| WO | WO 2007/127801 | 11/2007 |
| WO | WO-2008024642 A2 | 2/2008 |
| WO | WO 2009/025743 | 2/2009 |
| WO | WO-2009015821 A1 | 2/2009 |
| WO | WO-2009025743 A2 | 2/2009 |
| WO | WO-2009130176 A1 | 10/2009 |
| WO | WO-2009158521 A2 | 12/2009 |
| WO | WO-2011008349 A2 | 1/2011 |
| WO | WO 2011/132086 | 10/2011 |
| WO | WO 2013/117746 | 8/2013 |
| WO | WO 2014/117873 | 8/2014 |
| WO | WO 2016/024278 | 2/2016 |
| WO | WO 2016/059636 | 4/2016 |
| WO | WO 2016/092554 | 6/2016 |

OTHER PUBLICATIONS

Crowe et al.; Quantitative Immunocytofluorographic Analysis of CD4 Surface Antigen Expression and HIV Infection of Human Peripheral Blood Monocyte/Macrophages; AIDS Research and Human Retroviruses; vol. 3, No. 2, 1987; pp. 135-145.*

Tworoger et al.; Collection, Processing, and Storage of Biological Samples in Epidemiologic Studies: Sex Hormones, Carotenoids, Inflammatory Markers, and Proteomics as Examples; Cancer Epidemiol Biomarkers Prev 2006;15(9); pp. 1578-1581.*

Aizik et al., "Effects of 30 min of aerobic exercise on gene expression in human neutrophils", J. Appl. Physiol., 104: 236-243 (2008).

(Continued)

*Primary Examiner* — Antonio Galisteo Gonzalez

(57) ABSTRACT

The present invention provides methods of detecting infection using biomarkers. The methods disclosed herein include measuring the expression level of one of more polypeptide determinant in which the alteration of the expression level indicates infection of the patient in a sample of the subject and determining a clinically significant alteration in the level of the one or more polypeptides in the sample, wherein the alteration indicates an infection in the subject. The methods provided herein are for distinguishing between bacterial infection, mixed infection and/or viral infection.

11 Claims, 87 Drawing Sheets

(56) References Cited

OTHER PUBLICATIONS

Boldrick et al., "Stereotyped and specific gene expression programs in human innate immune responses to bacteria", PNAS, 99(2):972-977 (2002).
Borjesson et al., "Insights into Pathogen Immune Evasion Mechanisms: *Anaplasma phagocytophilum* Fails to Induce an Apoptosis Differentiation Program in Human Neutrophils", J. Immunol., 174: 6364-6372 (2005).
Calvano et al., "A network-based analysis of systemic inflammation in humans", Nature, 437:1032-1037 (2005).
Carrol et al., "The Diagnostic and Prognostic Accuracy of Five Markers of Serious Bacterial Infection in Malawian Children with Signs of Severe Infection", PLoS ONE, www.plosone.org, Aug. 2009, vol. 4, Issue 8.
Chaussabel et al., "Gene-Expression Signatures in Patient Peripheral Blood Leukocytes", Ann. N.Y. Acad. Sci., 1062: 146-154 (2005).
Chieux et al., "MxA Protein in Capillary Blood of Children With Viral Infections", J. Med. Virol., 59:547-551 (1999).
Chieux et al., "The MxA protein levels in whole blood lysates of patients with various viral infections", J. Virol. Meth., 70:183-191 (1998).
Feezor et al., "Molecular Characterization of the Acute Inflammatory Response to Infections with Gram-Negative versus Gram-Positive Bacteria", Infect. Immun., 71(10):5803-5813 (2003).
Halminen et al., "Expression of MxA Protein in Blood Lymphocytes Discriminates between Viral and Bacterial Infections in Febrile Children", Pedi. Res., 41(5):647-650 (1997).
Holland et al., "*STAT3* Mutations in the Hyper-IgE Syndrome", N. Eng. J. Med., 357:1608-19 (2007).
Jenner et al., Insights Into Host Responses Against Pathogens From Transcritional Profiling, Nature Review, Microbiology, vol. 3, p. 281, Apr. 2005.
Kaizer et al., "Gene Expression in Peripheral Blood Mononuclear Cells from Children with Diabetes", J. Clin. Endocrinol. Metab., 92(9):3705-3711 (2007).
Kawada et al., "Analysis of gene-expression profiles by oligonucleotide microarray in children with influenza", J.Gen. Virol., 87:1677-1683 (2006).
Liu et al., "Early days: genomics and human responses to infection", Curr. Opin. Microbiol., 9:312-319 (2006).
Malcolm et al., "Microarray analysis of lipopolysaccharide-treated human neutrophils", Am. J. Physiol. Lung Cell Mol. Physiol., 284: L663-L670 (2003).
Nakabayashi et al., "MxA-Based Recognition of Viral Illness in Febrile Children by a Whole Blood Assay", Pedi. Res., 60(6):770-774 (2006).
Oda et al., "A comprehensive map of the toll-like receptor signaling network", Molecular Systems Biololgy, EMBO and Nature Publishing Group, Apr. 2006.
Ramilo et al., "Gene expression patterns in blood leukocytes discriminate patients with acute infections", Blood, 109:2066-2077 (2007).
Rosseau et al., "Comparative transcriptional profiling of the lung reveals shared and distinct features of *Streptococcus pneumoniae* and influenza A virus infection", Immunol., 120:380-391 (2006).
Smith et al., "Quantitative assessment of human whole blood RNA as a potential biomarker for infectious disease", Analyst, 132:1200-1209 (2007).
Tang et al., "Gene-expression profiling of Gram-positive and Gram-negative sepsis in critically ill patients", Crit. Care Med., 36(4):1125-1128(2008).
Tang et al., "The Use of Gene-Expression Profiling to Identify Candidate Genes in Human Sepsis", Am. J. Resp. Crit. Care Med., 176:676-684 (2007).
Wang et al., "Rotavirus Infection Alters Peripheral T-Cell Homeostasis in Children with Acute Diarrhea", J. Virol., 81(8):3904-3912 (2007).
Zaas et al., "Gene Expression Signatures Diagnosis Influenza and Other Symptomatic Respiratory Viral INfenctions in Humans", Cell Host & Microbe, 6:1-11 2009.
Zilliox et al., "Gene Expression Changes in Peripheral Blood Mononuclear Cells during Measles Virus Infection", Clin. Vac. Immun., 14(7):918-923 (2007).
Janols et al. "Lymphocyte and monocyte flow cytometry immunophenotyping as a diagnostic tool in uncharacteristic inflammatory disorders," *BMC Infectious Diseases*. 10.205(2010):1-9.
Le Roux. "Laboratory investigations in acute lower respiratory tract infections in children." *Archives de Pediatrie*. 5.Suppl. 1 (1998):28S-32S.
Shimetani et al. "Levels of three inflammation markers, C-reactive protein, serum amyloid A protein and procalcitonin, in the serum and cerebrospinal fluid of patients with meningitis." *Scandinavian Journal of Clinical and Laboratory Investigation*. 61.7(2001):567-574.
Thivierge et al. "Eukaryotic elongation factor 1A interacts with Turnip mosaic virus RNA-dependent RNA polymerase and VPg-Pro in virus-induced vesicles." *Virology*. 377.1(2008):216-255.
Yamaji et al. "Significance of eukaryotic translation elongation factor 1A in tobacco mosaic virus infection." *Archives of Virology*. 155.2(2010):263-268.
Niederman. "Biological Markers to Determine Eligibility in Trials for Community-Acquired Pneumonia: A Focus on Procalcitonin." *Clinical Infectious Diseases*. 47.Suppl.3(2008):S127-S132.
Zhu et al. "Use of differential display analysis to assess the effect of human cytomegalovirus infection on the accumulation of cellular RNAs: Induction of interferon-responsive RNAs." *Proceedings of the National Academy of Sciences of USA*, National Academy of Science, Washington, D.C. 94.25(1997):13985-13990.
International Search Report and the Written Opinion Dated Mar. 12, 2012 From the International Searching Authority Re. Application No. PCT/IB2011/001299.
Niederman "Biological Markers to Determine Eligibility in Trials for Community-Acquired Pneumonia: A Focus on Procalcitonin", Clinical Infectious Diseases, XP002670357, 47(Suppl.3): S127-S132, Dec. 2008. Abstract.
Notice on Office Action Dated May 6, 2014 From the State Intellectual Property Office of the People's Republic of China Re. Application No. 201180030792.1 and Its Translation Into English.
Search Report Dated May 6, 2014 From the State Intellectual Property Office of the People's Republic of China Re. Application No. 201180030792.1 and Its Translation Into English.
Notice on Office Action and the Search Report Dated Feb. 25, 2015 From The State Intellectual Property Office of the People's Republic of China Re. Application No. 201180030792.1 and Its Translation Into English.
International Search Report and the Written Opinion Dated Jan. 20, 2016 From the International Searching Authority Re. Application No. PCT/IL2015/051024.
International Search Report and the Written Opinion Dated Feb. 22, 2016 From the International Searching Authority Re. Application No. PCT/IL2015/051201.
International Search Report and the Written Opinion Dated Nov. 29, 2015 From the International Searching Authority Re. Application No. PCT/IL2015/050823.
International Search Report Dated Apr. 5, 2013 From the International Searching Authority Re. Application No. PCT/EP2013/052619.
Notification of Office Action and Search Report Dated Mar. 4, 2016 From the State Intellectual Property Office of the People's Republic of China Re. Application No. 201380019055.0.
Notification of Office Action Dated Jul. 3, 2015 From the State Intellectual Property Office of the People's Republic of China Re. Application No. 201380019055.0.
Office Action Dated Feb. 29, 2016 From the Israel Patent Office Re. Application No. 233998 and Its Translation Into English.
Official Action Dated Aug. 12, 2015 From the US Patent and Trademark Office Re. U.S. Appl. No. 14/377,887.
Restriction Official Action Dated May 15, 2015 From the US Patent and Trademark Office Re. U.S. Appl. No. 14/377,887.

(56) References Cited

OTHER PUBLICATIONS

Translation Dated Sep. 21, 2015 of Office Action Dated Jul. 3, 2015 From the State Intellectual Property Office of the People's Republic of China Re. Application No. 201380019055.0.
Cummins et al. "The TRAIL to Viral Pathogenesis: The Good, the Bad and the Ugly", Current Molecular Medicine, XP055056835, 9(4): 495-505, May 1, 2009.
Falsciflehner et al. "Following TRAIL's Path in the Immune System", Immunology, XP055056763, 127(2): 145-154, Jun. 1, 2009. Chapter 'TRAIL in Viral and Bacterial Infections'.
Hanley et al. "A Method of Comparing the Areas Under Receiver Operating Characteristics Curves Derived From the Same Cases", Radiology, 148(3): 839-843, Sep. 1983.
Kohavi et al. "Wrappers for Feature Subset Selection", Artifical Intelligence, 97: 273-324, 1997.
Kotelkin et al. "Respiratory Syncytial Virus Infections Sensitizes Cells to Apoptosis Mediated by Tumor Necrosis Factor-Related Apoptosis-Inducing Ligand", Journal of Virology, XP055056816, 77(17): 9156-9172, Aug. 12, 2003. Fig.5B.
Oved et al. "A Novel Host-Proteome Signature for Distinguishing Between Acute Bacterial and Viral Infections", PLOS ONE, 10(3): e0120012-1-e120012-18, Mar. 18, 2015.
Secchiero et al. "Potential Prognostic Significance of Decreased Serum Levels of TRAIL After Acute Myocardial Infarction", PLoS ONE, XP055056988, 4(2): e4442-1-e4442-6, Feb. 16, 2009. Fig. 1.
Torkkola "Feature Extraction by Non-Parametric Mutual Information Maximization", Journal of Machine Learning Research, 3: 1415-1438, Mar. 2003.
Whiteside et al. "Role of Human Natural Killer Cells in Health and Disease", Clinical and Diagnostic Laboratory Immunology, 1(2): 125-133, Mar. 31, 1994.
Xu et al. "Lipocalins as Biochemical Markers of Disease", Biochimica et Biophysica Acta, 1482(1): 298-307, Oct. 18, 2000.
Notification of Office Action Dated Jan. 21, 2016 From the State Intellectual Property Office of the People's Republic of China Re. Application No. 201180030792.1 and Its Translation Into English.
Notification of Office Action Dated Aug. 28, 2015 From The State Intellectual Property Office of the People's Republic of China Re. Application No. 201180030792.1 and Its Translation Into English.
Ramilo et al. "Gene Expression Patterns in Blood Leukocytes Discriminate Patients With Acute Infections", Blood, 109(5): 2066-2077, Published Online Nov. 14, 2006.
Zaas et al. "A Host-Based RT-PCR Gene Expression Signature to Identify Acute Respiratory Viral Infection", Science Translational Medicine, 5(203): 203ra126-1-203ra126-19, Sep. 18, 2013.
Zaas et al. "A Host-Based RT-PCR Gene Expression Signature to Identify Acute Respiratory Viral Infection", Supplementary Materials, Science Translational Medicine, 5(203): 203ra126-1-203ra126-21, Sep. 18, 2013.
Notification of Office Action Dated Aug. 4, 2016 From the State Intellectual Property Office of the People's Republic of China Re. Application No. 201380019055.0 and Its Translation Into English.
Communication Pursuant to Article 94(3) EPC Dated Jun. 17, 2016 From the European Patent Office Re. Application No. 11748712.4.
Applicant-Initiated Interview Summary Dated Jul. 6, 2016 From the US Patent and Trademark Office Re. U.S. Appl. No. 14/377,887.
Official Action Dated Apr. 13, 2016 From the US Patent and Trademark Office Re. U.S. Appl. No. 14/377,887.
Translation Dated Apr. 5, 2016 of Notification of Office Action Dated Mar. 4, 2016 From the State Intellectual Property Office of the People's Republic of China Re. Application No. 201380019055.0.
Official Action Dated Jan. 26, 2017 From the US Patent and Trademark Office Re. U.S. Appl. No. 15/015,309. (45 pages).
Communication Pursuant to Article 94(3) EPC Dated Dec. 9, 2016 From the European Patent Office Re. Application No. 13703112.6. (4 Pages).
Notice of Reasons for Rejection Dated Nov. 1, 2016 From the Japan Patent Office Re. Application No. 2014-556086 and Its Translation Into English. (12 Pages).
Official Action Dated Dec. 15, 2016 From the US Patent and Trademark Office Re. U.S. Appl. No. 14/377,887. (22 pages).
Official Action Dated Nov. 18, 2016 From the US Patent and Trademark Office Re. U.S. Appl. No. 15/237,728. (33 pages).
Leibovici et al. "The Benefit of Appropriate Empirical Antibiotic Treatment in Patients with Bloodstream Infection", Journal of Internal Medicine, 244(5): 379-386, Nov. 1, 1998.
Applicant-Initiated Interview Summary Dated Feb. 22, 2017 From the US Patent and Trademark Office Re. U.S. Appl. No. 14/377,887. (3 Pages).
Notification of Office Action and Search Report Dated Feb. 13, 2017 From the State Intellectual Property Office of the People's Republic of China Re. Application No. 201380019055.0 and Its Translation of Office Action Into English. (10 Pages).

* cited by examiner

FIG. 4A  Bacterial versus viral infected patients
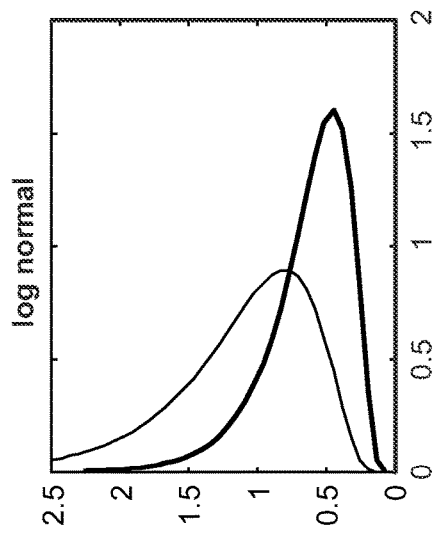
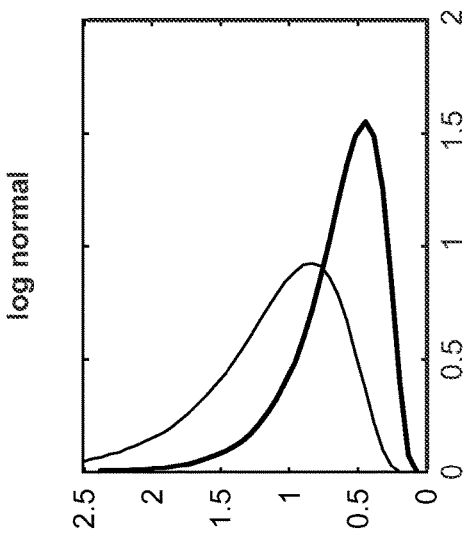
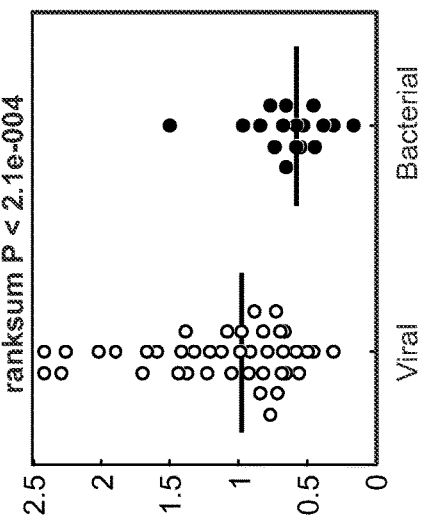
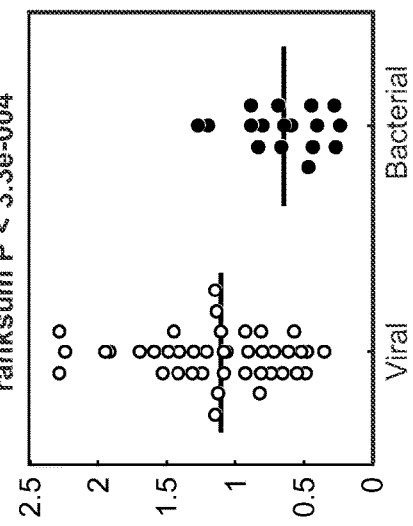

EIF4B_gran_intra.fig.

EIF4B_lymp_intra.fig.

EIF4B_mean_intra.fig.

HERC5_gran_intra.fig.

HERC5_mean_intra.fig.

IFI6_gran_intra.fig.

IFIT1_ gran_ intra.fig.

IFIT1_ mean_ intra.fig.

IFIT3_gran_intra.fig

IFIT3_lymp_intra.fig.

IFITM1_mono_membrane.fig.

IFITM3_gran_membrane.fig.

IFITM3_mean_membrane.fig.

IFITM3_mono_membrane.fig.

IL7R_total_membrane.fig.

KIAA0082_mean_intra.fig.

LOC26010_gran_intra.fig.

LOC26010_lymp_intra.fig.

MX1_gran_intra.fig.

MX1_lymp_intra.fig.

MX1_mean_intra.fig.

OAS2_gran_intra.fig.

OAS2_mean_intra.fig.

PARP12_gran_intra.fig.

PARP12_mean_intra.fig.

PARP9_lymp_intra.fig.

PTEN_gran_intra.fig.

RSAD2_gran_intra.fig.

RSAD2_lymp_intra.fig.

RSAD2_mean_intra.fig.

ANC.fig.

CRP.fig.

WBC.fig.

FIG. 4B  Mixed (bacterial and viral) versus viral infected patients
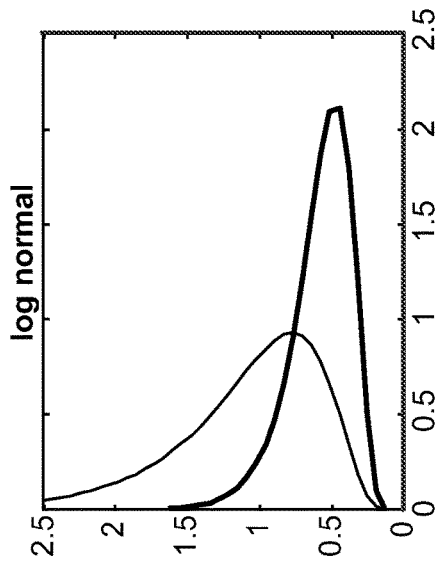
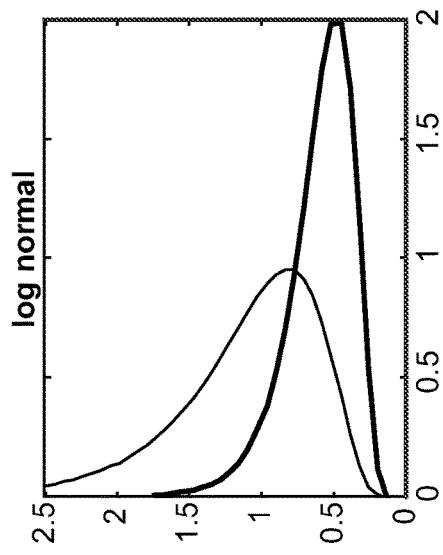
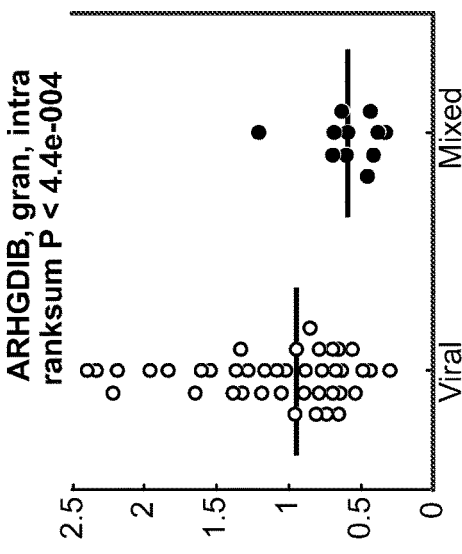
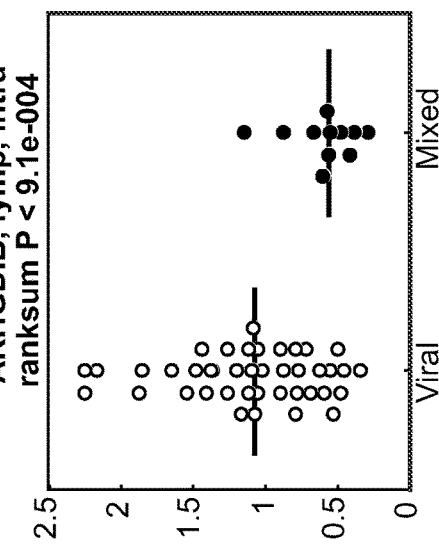

ARHGDIB_mean_intra.fig.

ARPC2_gran_intra.fig.

CES1_gran_intra.fig.

CES1_mean_intra.fig.

CORO1A_gran_intra.fig.

CORO1A_mean_intra.fig.

IFIT3_gran_intra.fig.

LIPT1_gran_intra.fig.

LOC26010_gran_intra.fig.

LOC26010_lymp_intra.fig.

LOC26010_mean_intra.fig.

Lym (%).fig.

MX1_gran_intra.fig.

MX1_lymp_intra.fig.

MX1_mean_intra.fig.

OAS2_gran_intra.fig.

PARP12_mean_intra.fig.

PARP9_lymp_intra.fig.

PTEN_gran_intra.fig.

PTEN_mean_intra.fig.

RSAD2_gran_intra.fig.

SOCS3_mean_intra.fig.

CRP.fig.

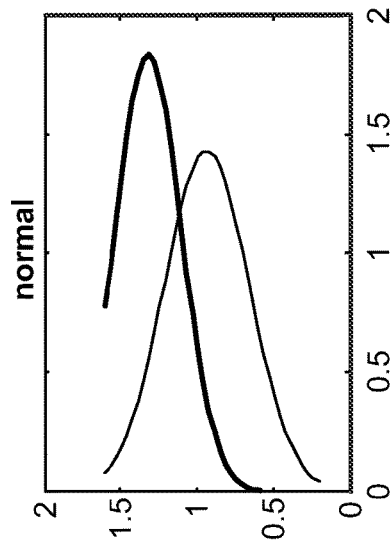
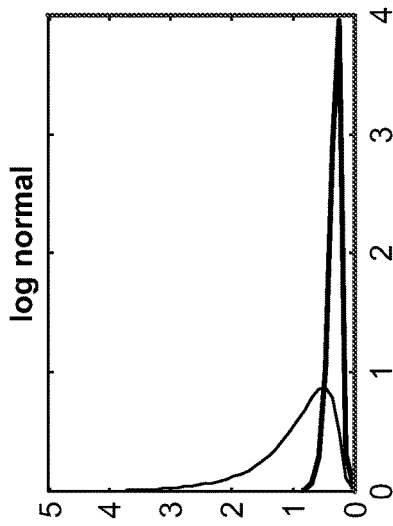
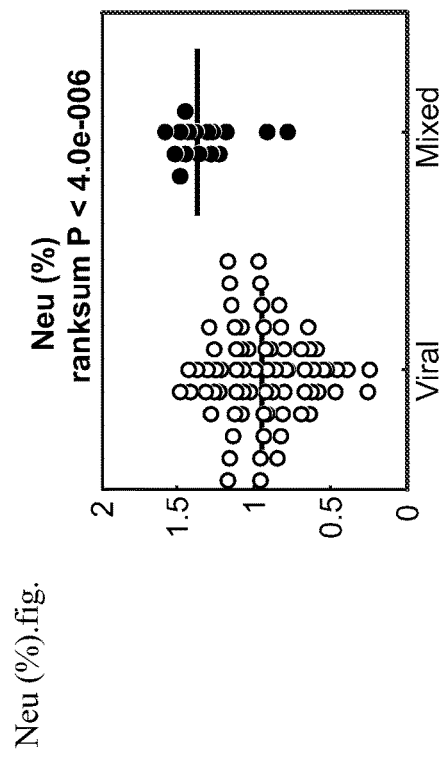
FIG. 4B Cont.
Neu (%).fig.
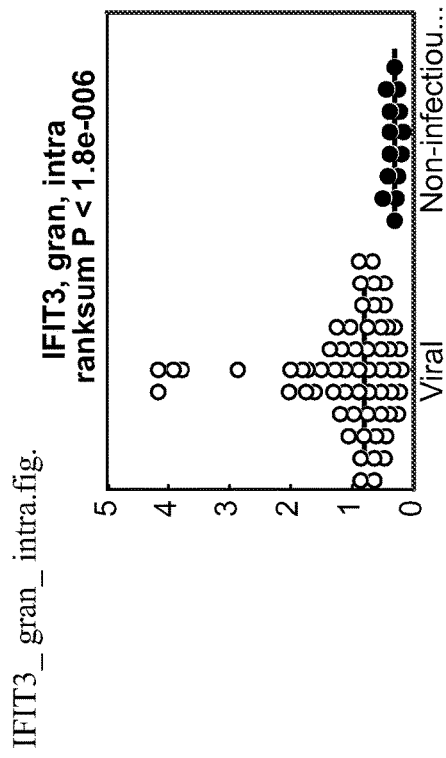
FIG. 4C Viral versus non-infectious and healthy patients
IFIT3_gran_intra.fig.

IFITM3_mono_membrane.fig.

IFIT3_total_intra.fig.

LOC26010_gran_intra.fig.

LOC26010_mean_intra.fig.

LOC26010_total_intra.fig.

MAN1C1_lymp_intra.fig.

MX1_gran_intra.fig.

MX1_lymp_intra.fig.

MX1_mean_intra.fig.

MX1_total_intra.fig.

Maximal temperature.fig.

OAS2_gran_intra.fig.

OAS2_mean_intra.fig.

OAS2_total_intra.fig.

RSAD2_gran_intra.fig.

RSAD2_mean_intra.fig.

RSAD2_total_intra.fig. RSAD2, total, intra ranksum P < 7.2e-006

SART3_gran_intra.fig. SART3, gran, intra ranksum P < 3.4e-005

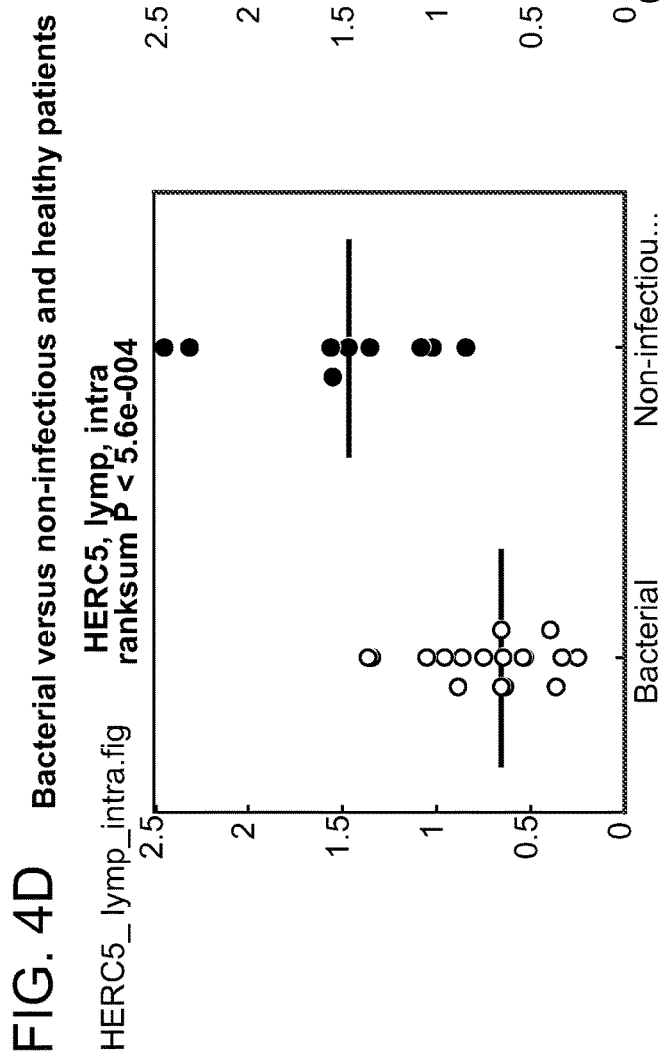
FIG. 4D  Bacterial versus non-infectious and healthy patients

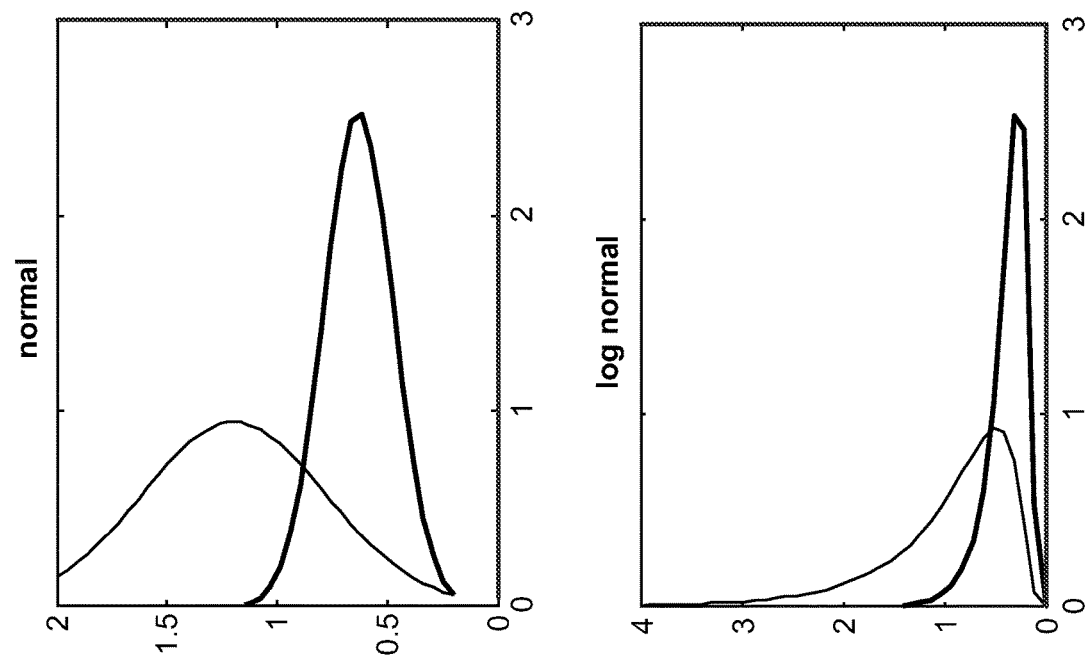
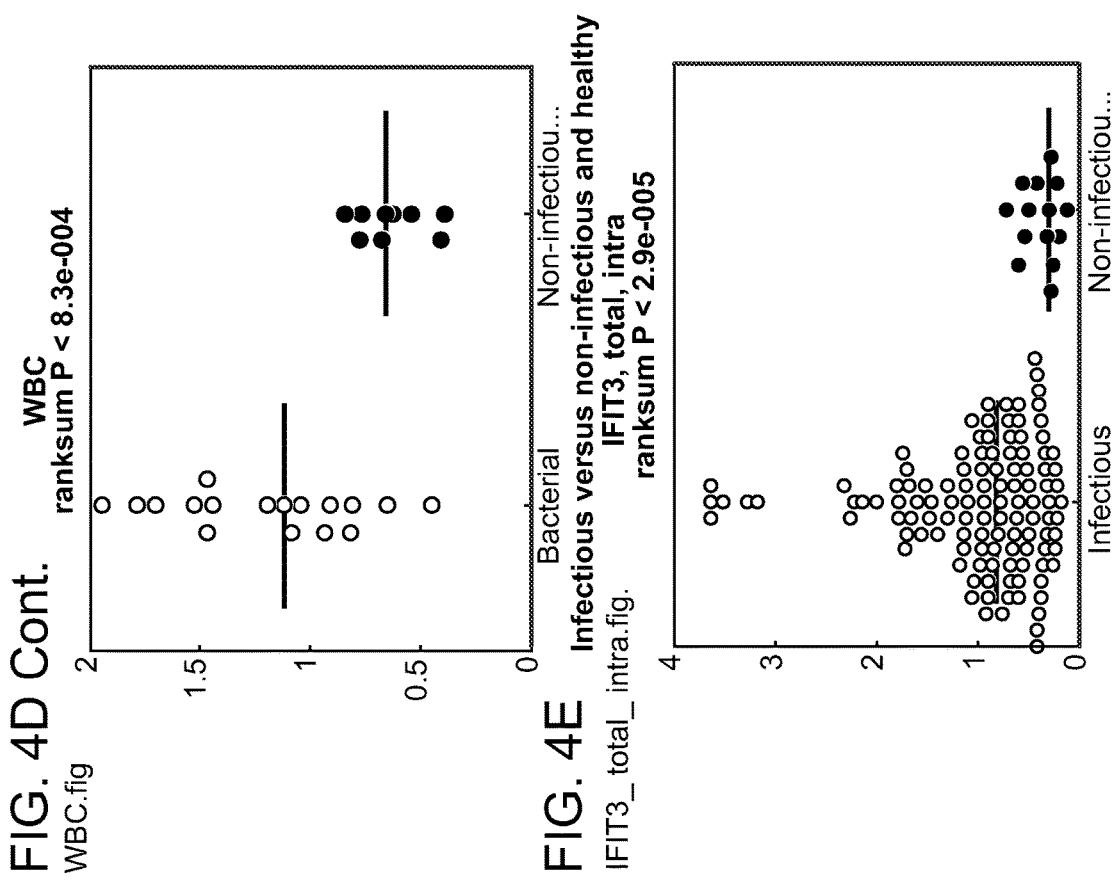
FIG. 4D Cont.
FIG. 4E

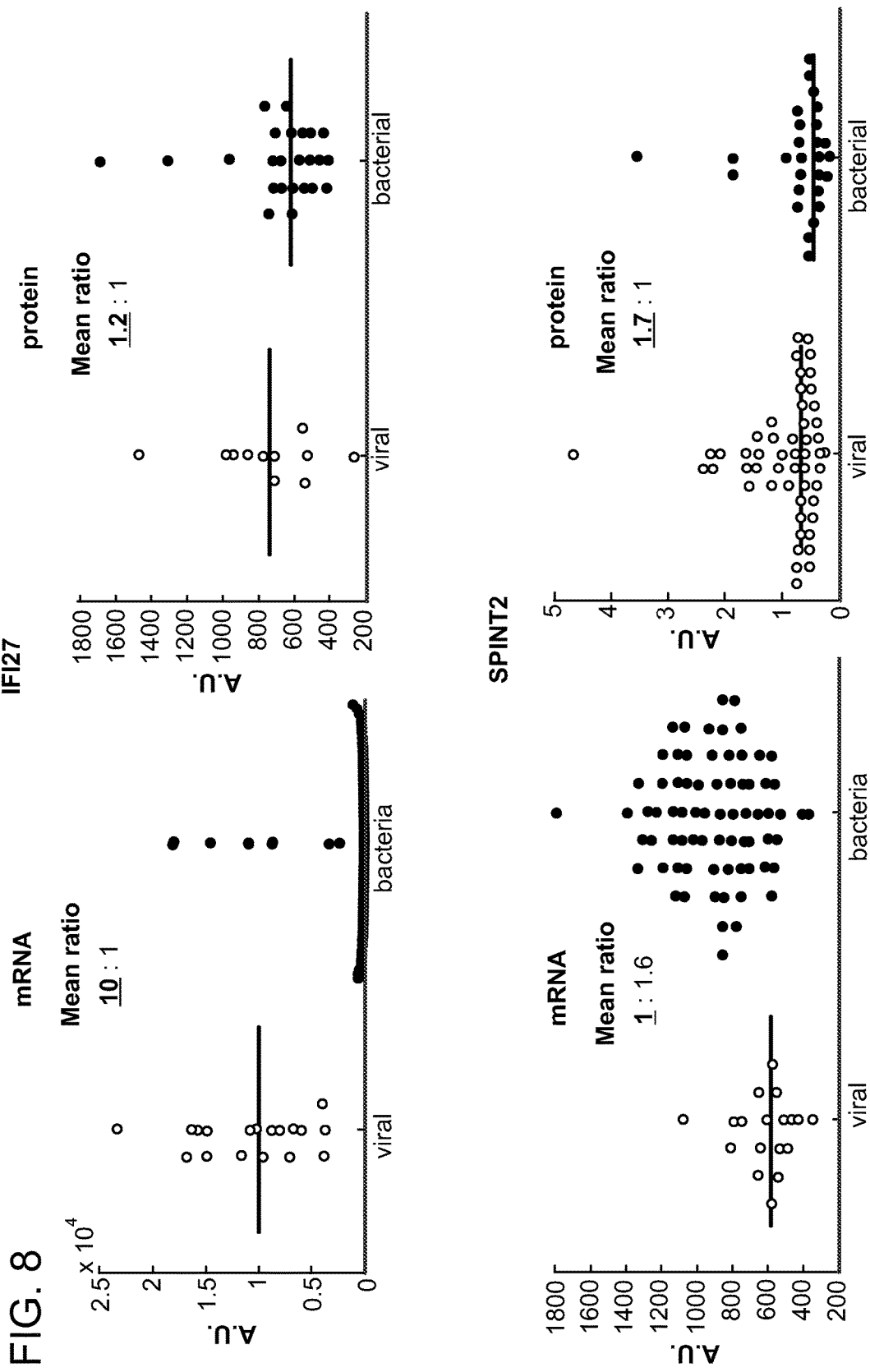

SIGNATURES AND DETERMINANTS FOR DISTINGUISHING BETWEEN A BACTERIAL AND VIRAL INFECTION AND METHODS OF USE THEREOF

RELATED APPLICATION

This application claims the benefit of U.S. Ser. No. 61/326,244, filed Apr. 21, 2010, the contents of which are incorporated herein by reference in its entirety.

FIELD OF THE INVENTION

The present invention relates generally to the identification of biological signatures and determinants associated with bacterial and viral infections and methods of using such biological signatures in the screening diagnosis, therapy, and monitoring of infection.

BACKGROUND OF THE INVENTION

Antibiotics (Abx) are the world's most prescribed class of drugs with a 25-30 billion $US global market. Numerous studies have shown that 40-70% of Abx are wrongly prescribed (Linder and Stafford 2001; Scott, Cohen et al. 2001; Davey, Brown et al. 2006; Cadieux, Tamblyn et al. 2007; Pulcini, Cua et al. 2007; 2011), making Abx the world's most misused drug (CDC 2011). Abx misuse can be classified into two types: (i) prescription to treat non-bacterial disease, such as a viral infection, for which Abx are ineffective and (ii) prescription in the case of a bacterial disease, but applying the wrong Abx spectrum. For example, according to the USA center for disease control and prevention over 60 Million wrong Abx prescriptions are given annually to treat flu in the US, for which they are ineffective and inappropriate. The major factors that limit the effectiveness of current diagnostic solutions for reducing erroneous prescription include: (i) time to diagnosis; (ii) inaccessible infection site; (iii) false positives due to non-pathogenic bacteria and (iv) the challenge of diagnosing mixed infection (i.e., bacterial and viral co-infection).

These factors are causing a diagnostic gap, which in turn often leads physicians to either over-prescribe Abx (the "Just-in-case-approach"), or under-prescribe Abx (the "Wait-and-see-approach") (Little and Williamson 1994; Little 2005; Spiro, Tay et al. 2006), both of which have far reaching health and financial consequences.

Ideally, a technological solution for assisting physicians in correctly prescribing Abx should enable diagnosis that: (i) accurately differentiates between a bacterial and viral infections; (ii) is rapid (within minutes); (iii) is able to differentiate between pathogenic and non-pathogenic bacteria that are part of the body's natural flora, (iv) can differentiate between mixed and pure viral infections and (v) is applicable in cases where the pathogen is inaccessible. Current solutions (such as culture, PCR and immunoassays) do not fulfill all these requirements: (i) most assays (with the exception of multiplex PCRs) are often constrained to a limited set of bacterial or viral strains; (ii) they usually require hours to days (e.g. culture and nucleic acid based assays); (iii) they often do not distinguish between pathogenic and non-pathogenic bacteria (Del March 1992); (iv) they are often incapable of distinguishing between a mixed and a pure viral infection and (v) they require direct sampling of the infection site in which traces of the disease causing agent are searched for. The latter prohibits diagnosis in cases where the pathogen resides in an inaccessible tissue, which is often the case.

Accordingly, a need exists for a method that accurately differentiates between bacterial viral and mixed infections.

SUMMARY OF THE INVENTION

The present invention is based on the identification of signatures and determinants associated with bacterial, viral and mixed (i.e., bacterial and viral co-infections) infections. The methods of the invention allow for the identification of type of infection a subject is suffering from, which in turn allows for the selection of an appropriate treatment regimen. Importantly, not only do the signatures and determinants of the present invention discriminate between viral and bacterial infections, the signatures and determinant also discriminate between mixed and viral infections. Thus, the methods of the invention allow for the selection of subjects whom antibiotic treatment is desired and prevent unnecessary antibiotic treatment of subject having only a viral infection or a non-infectious disease.

Accordingly, one aspect of the invention provides methods with a predetermined level of predictability for identifying an infection in a subject by measuring the expression level of one or more polypeptides selected from ABTB1, ADIPOR1, ARHGDIB, ARPC2, ATP6V0B, C1orf83, CD15, CES1, CORO1A, CSDA, EIF4B, EPSTI1, GAS7, HERC5, IFI6, KIAA0082, IFIT1, IFIT3, IFITM1, IFITM3, LIPT1, IL7R, ISG20, LOC26010, LY6E, LRDD, LTA4H, MAN1C1, MBOAT2, NPM1, OAS2, PARP12, PARP9, QARS, RAB13, RAB31, RAC2, RPL34, PDIA6, PTEN, RSAD2, SART3, SDCBP, SMAD9, SOCS3, TRIM 22, UBE2N, XAF1 and ZBP1 in a sample from the subject. A clinically significant alteration in the level of the one or more polypeptides in the sample indicates an infection in the subject. In some aspects the level of the one or more polypeptides is compared to a reference value, such as an index value.

In various aspects the method distinguishes a virally infected subject from either a subject with non-infectious disease or a healthy subject; a bacterially infected subject, from either a subject with non-infectious disease or a healthy subject; a subject with an infectious disease from either a subject with an non-infectious disease or a healthy subject; a bacterially infected subject from a virally infected subject or a mixed infected subject and a virally infected subject.

Optionally, the method further comprises measuring one or more non-protein features (i.e., non protein DETERMINANTS) such as white blood count, neutrophil %, Lymphocyte %, monocyte %, absolute lymphocyte count, absolute neutrophil count and maximimal temperature or measuring the expression level of CRP or MX1.

The sample is for example, whole blood or a fraction thereof. A blood fraction sample contains cells that include lymphocytes, monocytes and granulocytes. The expression level of the polypeptide is determined by electrophoretically, or immunochemically. The immunochemical detection is for example, by flow cytometry, radioimmunoassay, immunofluorescence assay or by an enzyme-linked immunosorbent assay.

In some aspects of the invention the DETERMINANTS are preferably selected such that their MCC is >=0.4.

In various aspects the method distinguishes a virally infected subject from either a subject with non-infectious disease or a healthy subject. In such methods, one or more polypeptides including IFIT3, IFITM3, LOC26010, MAN1C1, MX1, OAS2, RAB13, RSAD2, and SART3 are measured. In various embodiments, two or more DETERMINANTS are measured, for example:

a) C1orf83 is measured and a second DETERMINANT selected from IFIT3, IFITM3, LOC26010, LRDD, Maximaltemperature, MX1, OAS2, PTEN, RAB13, RPL34, RSAD2, and SART3 is measured.

b) IFIT3 is measured and a second DETERMINANT selected from of IFITM3, LOC26010, LRDD, Maximaltemperature, MX1, OAS2, PTEN, RAB13, RPL34, RSAD2, and SART3 is measured.

c) LOC26010 is measured and a second DETERMINANT selected from LRDD, Maximaltemperature, MX1, OAS2, PTEN, RAB13, RPL34, RSAD2, and SART3 is measured.

d) LRDD is measured and a second DETERMINANT selected from the group consisting of Maximaltemperature, MX1, OAS2, PTEN, RAB13, RPL34, RSAD2, and SART3.

e) Maximaltemperature is measured and a second DETERMINANT selected from the group consisting of OAS2, PTEN, RAB13, RPL34, RSAD2, and SART3 is measured.

f) MX1 is measured and a second DETERMINANT selected from the group consisting of Maximaltemperature, MX1, OAS2, PTEN, RAB13, RPL34, RSAD2, and SART3.

g) OAS2 is measured and a second DETERMINANT selected from the group consisting of PTEN, RAB13, RPL34, RSAD2, and SART3 is measured.

h) PTEN is measured and a second DETERMINANT selected from the group consisting of RAB13, RPL34, RSAD2, and SART3 is measured.

i) RAB13 is measured and a second DETERMINANT selected from the group consisting of RPL34, RSAD2, and SART3 is measured.

j) RPL34 is measured and RSAD2 or SART3 is measured.

In various other aspects the method distinguishes a bacterially infected subject, from either a subject with non-infectious disease or a healthy subject. In such methods, one or more polypeptides selected from HERC5, KIAA0082, LOC26010, MX1, OAS2, RAB13 and SMAD9 is measured. In various embodiments, two or more DETERMINANTS are measured, for example:

a) ANC is measured and a second DETERMINANT selected from C1orf83, CD15, CRP, IFIT3, ISG20, LOC26010, LRDD, LTA4H, Lym (%), Maximaltemperature, MX1, OAS2, PARP9, QARS, RAB13, RAB31, RAC2, RPL34, SART3, TRIM22, WBC, XAF1, or ZBP1 is measured.

b) C1orf83 is measured and a second DETERMINANT selected from CD15, CRP, IFIT3, ISG20, LOC26010, LRDD, LTA4H, Lym (%), Maximaltemperature, MX1, OAS2, PARP9, QARS, RAB13, RAB31, RAC2, RPL34, SART3, TRIM22, WBC, XAF1, and ZBP1 is measured.

c) CD15 is measured and a second DETERMINANT selected from CRP, IFIT3, ISG20, LOC26010, LRDD, LTA4H, Lym (%), Maximaltemperature, MX1, OAS2, PARP9, QARS, RAB13, RAB31, RAC2, RPL34, SART3, TRIM22, WBC, XAF1, and ZBP1 is measured.

d) CRP is measured and a second DETERMINANT selected from IFIT3, ISG20, LOC26010, LRDD, LTA4H, Lym (%), Maximaltemperature, MX1, OAS2, PARP9, QARS, RAB13, RAB31, RAC2, RPL34, SART3, TRIM22, WBC, XAF1, and ZBP1 is measured.

e) IFIT3 is measured and a second DETERMINANT selected from ISG20, LOC26010, LRDD, LTA4H, Lym (%), Maximaltemperature, MX1, OAS2, PARP9, QARS, RAB13, RAB31, RAC2, RPL34, SART3, TRIM22, WBC, XAF1, and ZBP1 is measured.

f) ISG20 is measured and a second DETERMINANT selected from LOC26010, LRDD, LTA4H, Lym (%), Maximaltemperature, MX1, OAS2, PARP9, QARS, RAB13, RAB31, RAC2, RPL34, SART3 is measured and a TRIM22, WBC, XAF1, and ZBP1 is measured.

g) LOC26010, second DETERMINANT selected from LRDD, LTA4H, Lym (%), Maximaltemperature, MX1, OAS2, PARP9, QARS, RAB13, RAB31, RAC2, RPL34, SART3, TRIM22, WBC, XAF1, and ZBP1 is measured.

h) LRDD is measured and a second DETERMINANT selected from LTA4H, Lym (%), Maximaltemperature, MX1, OAS2, PARP9, QARS, RAB13, RAB31, RAC2, RPL34, SART3, TRIM22, WBC, XAF1, and ZBP1 is measured.

i) LTA4H is measured and a second DETERMINANT selected from Lym (%), Maximaltemperature, MX1, OAS2, PARP9, QARS, RAB13, RAB31, RAC2, RPL34, SART3, TRIM22, WBC, XAF1, and ZBP1 is measured.

j) Lym (%) is measured and a second DETERMINANT selected from Maximaltemperature, MX1, OAS2, PARP9, QARS, RAB13, RAB31, RAC2, RPL34, SART3, TRIM22, WBC, XAF1, and ZBP1 is measured.

k) Maximaltemperature is measured and a second DETERMINANT selected from OAS2, PARP9, QARS, RAB13, RAB31, RAC2, RPL34, SART3, TRIM22, WBC, XAF1, and ZBP1 is measured.

l) MX1 is measured and a second DETERMINANT selected from Maximaltemperature, OAS2, PARP9, QARS, RAB13, RAB31, RAC2, RPL34, SART3, TRIM22, WBC, XAF1, and ZBP1 is measured.

m) OAS2 is measured and a second DETERMINANT selected from PARP9, QARS, RAB13, RAB31, RAC2, RPL34, SART3, TRIM22, WBC, XAF1, and ZBP1 is measured.

n) PARP9 is measured and a second DETERMINANT selected from QARS, RAB13, RAB31, RAC2, RPL34, SART3, TRIM22, WBC, XAF1, and ZBP1 is measured.

o) QARS is measured and a second DETERMINANT selected from RAB13, RAB31, RAC2, RPL34, SART3, TRIM22, WBC, XAF1, and ZBP1 is measured.

p) RAB13 is measured and a second DETERMINANT selected from RAB31, RAC2, RPL34, SART3, TRIM22, WBC, XAF1, and ZBP1 is measured.

q) RAB31 is measured and a second DETERMINANT selected from RAC2, RPL34, SART3, TRIM22, WBC, XAF1, and ZBP1 is measured.

r) RAC2 is measured and a second DETERMINANT selected from RPL34, SART3, TRIM22, WBC, XAF1, and ZBP1 is measured.

s) RPL34 is measured and a second DETERMINANT selected from SART3, TRIM22, WBC, XAF1, and ZBP1 is measured.

t) SART3 is measured and a second DETERMINANT selected from TRIM22, WBC, XAF1, and ZBP1 is measured.
u) TRIM22 is measured and a second DETERMINANT selected from WBC, XAF1, and ZBP1 is measured.
v) WBC is measured and XAF1 or ZBP1 is measured.
w) XAF1 and ZBP1 are measured.

In various other aspects the methods distinguish a subject with an infectious disease from either a subject with a non-infectious disease or a healthy subject. In such methods, one or polypeptides selected from IFIT3, LOC26010, MAN1C1, MX1, OAS2, RAB13, RSAD2, and SMAD9 is measured. In various embodiments, two or more DETERMINANTS are measured, for example:

a) C1orf83 is measured and a second DETERMINANT selected from CRP, IFIT3, LOC26010, LRDD, MX1, Maximaltemperature, OAS2, QARS, RAB13, RPL34, RSAD2, and SART3 is measured.
b) CRP is measured and a second DETERMINANT selected from IFIT3, LOC26010, LRDD, MX1, Maximaltemperature, OAS2, QARS, RAB13, RPL34, RSAD2, and SART3 is measured.
c) IFIT3 is measured and a second DETERMINANT selected from LOC26010, LRDD, MX1, Maximaltemperature, OAS2, QARS, RAB13, RPL34, RSAD2, and SART3 is measured.
d) LOC26010 is measured and a second DETERMINANT selected from LRDD, MX1, Maximaltemperature, OAS2, QARS, RAB13, RPL34, RSAD2, and SART3 is measured.
e) LRDD is measured and a second DETERMINANT selected from MX1, Maximaltemperature, OAS2, QARS, RAB13, RPL34, RSAD2, and SART3 is measured.
f) MX1 is measured and a second DETERMINANT selected from Maximaltemperature, OAS2, QARS, RAB13, RPL34, RSAD2, and SART3.
g) Maximaltemperature is measured and a second DETERMINANT selected from OAS2, QARS, RAB13, RPL34, RSAD2, and SART3 is measured.
h) OAS2 is measured and a second DETERMINANT selected from QARS, RAB13, RPL34, RSAD2, and SART3 is measured.
i) QARS is measured and a second DETERMINANT selected from RAB13, RPL34, RSAD2, and SART3 is measured.
j) RAB13 is measured and a second DETERMINANT selected from RPL34, RSAD2, and SART3 is measured.
k) RPL34 is measured and RSAD2 or SART3 is measured.
l) RSAD2 and SART3 are measured.

In various aspects the methods distinguish bacterially infected subject from a virally infected subject. In such methods one or more polypeptides selected from ABTB1, ADIPOR1, ARHGDIB, ARPC2, CD15, CORO1A, CSDA, EIF4B, EPSTI1, GAS7, HERC5, IFI6, IFIT1, IFIT3, IFITM1, IFITM3, IL7R, LOC26010, LY6E, MAN1C1, MBOAT2, MX1, NPM1, OAS2, PARP12, PARP9, PDIA6, PTEN, RSAD2, SDCBP, and TRIM 22 is measured. In various embodiments, two or more DETERMINANTS are measured, for example:

a) ANC is measured and a second DETERMINANT selected from CORO1A, CRP, EIF4B, IFIT3, IFITM1, IFITM3, LOC26010, Lym (%), MAN1C1, MX1, Neu (%), NPM1, OAS2, PARP12, PTEN, RSAD2, SDCBP and WBC is measured;
b) CORO1A is measured and a second DETERMINANT selected from CRP, EIF4B, IFIT3, IFITM1, IFITM3, LOC26010, Lym (%), MAN1C1, MX1, Neu (%), NPM1, OAS2, PARP12, PTEN, RSAD2, SDCBP, and WBC is measured;
c) CRP is measured and a second DETERMINANT selected from EIF4B, IFIT3, IFITM1, IFITM3, LOC26010, Lym (%), MAN1C1, MX1, Neu (%), NPM1, OAS2, PARP12, PTEN, RSAD2, SDCBP, and WBC is measured;
d) EIF4B is measured and a second DETERMINANT selected from IFIT3, IFITM1, LOC26010, Lym (%), MAN1C1, MX1, Neu (%), NPM1, OAS2, PARP12, PTEN, RSAD2, SDCBP, and WBC is measured;
e) IFIT3 is measured and a second DETERMINANT selected from IFITM1, IFITM3, LOC26010, Lym (%), MAN1C1, MX1, Neu (%), NPM1, OAS2, PARP12, PTEN, RSAD2, SDCBP, and WBC is measured;
f) IFITM1 is measured and a second DETERMINANT selected from IFITM3, LOC26010, Lym (%), MAN1C1, MX1, Neu (%), NPM1, OAS2, PARP12, PTEN, RSAD2, SDCBP, and WBC is measured;
g) IFITM3 is measured and a second DETERMINANT selected from LOC26010, Lym (%), MAN1C1, MX1, Neu (%), NPM1, OAS2, PARP12, PTEN, RSAD2, SDCBP, and WBC is measured;
h) LOC26010 is measured and a second DETERMINANT selected from Lym (%), MAN1C1, MX1, Neu (%), NPM1, OAS2, PARP12, PTEN, RSAD2, SDCBP, and WBC is measured,
i) Lym (%) is measured and a second DETERMINANT selected from MAN1C1, MX1, Neu (%), NPM1, OAS2, PARP12, PTEN, RSAD2, SDCBP, and WBC is measured;
j) MAN1C1 is measured and a second DETERMINANT selected from MX1, Neu (%), NPM1, OAS2, PARP12, PTEN, RSAD2, SDCBP, and WBC is measured,
k) MX1 is measured and a second DETERMINANT selected from Neu (%), NPM1, OAS2, PARP12, PTEN, RSAD2, SDCBP, and WBC is measured;
l) Neu (%) is measured and a second DETERMINANT selected from OAS2, PARP12, PTEN, RSAD2, SDCBP, and WBC is measured;
m) NPM1 is measured and a second DETERMINANT selected from Neu (%), OAS2, PARP12, PTEN, RSAD2, SDCBP, and WBC is measured;
n) OAS2 is measured and a second DETERMINANT selected from PARP12, PTEN, RSAD2, SDCBP, and WBC is measured;
o) PARP12 is measured and a second DETERMINANT selected from PTEN, RSAD2, SDCBP, and WBC is measured,
p) PTEN is measured and a second DETERMINANT selected from RSAD2, SDCBP, and WBC is measured,
q) RSAD2 is measured SDCBP or WBC is measured; or
r) SDCBP and WBC are measured.

Alternatively:
CRP and RSAD2 are measured;
CRP and PARP12 are measured;
CRP and MX1 are measured;
CRP and Lym (%) are measured;
CRP and IFIT3 are measured;
CRP and LOC26010 are measured;
CRP and PTEN are measured;
CRP and IFITM3 are measured;
Neu (%) and RSAD2 are measured;
OAS2 and RSAD2 are measured;

CRP and EIF4B are measured;
CRP and NPM1 are measured;
CRP and Neu (%) are measured;
CRP and OAS2 are measured;
CRP and SDCBP are measured;
CRP and IFIT1 are measured;
CRP and IFI6 are measured;
CRP and PDIA6 are measured; or
CRP and PARP9 are measured.

In another aspect for example, CRP and one or more DETERMINANTS selected from RSAD2, MX1, IFITM3, EIF4B, OAS2, IFITM1, IFIT3, PARP12, LOC26010, PTEN, CORO1A, MAN1C1, NPM1, SDCBP, IFIT1, IFI6, PDIA6, and PARP9 are measured.

In a further aspect CRP and one or more DETERMINANTS selected from RSAD2, IFITM3, EIF4B, MX1, OAS2, IFITM1, IFIT3, PARP12, LOC26010, PTEN, CORO1A, MAN1C1, NPM1, SDCBP, IFIT1, IFI6, PDIA6, PARP9, Neu (%), Lym (%), ANC, and WBC are measured In yet another aspect for example, one or more DETERMINANTS selected from Neu (%), Lym (%), ANC, WBC, and CRP is measured and one or more DETERMINANTS selected from RSAD2, IFITM3, EIF4B, OAS2, IFITM1, IFIT3, PARP12, LOC26010, PTEN, CORO1A, MAN1C1, NPM1, SDCBP, IFIT1, IFI6, PDIA6, and PARP9 is measured.

In a further aspect for example, two or more DETERMINANTS selected from RSAD2, CRP, MX1, IFITM3, EIF4B, OAS2, IFITM1, IFIT3, PARP12, LOC26010, PTEN, CORO1A, MAN1C1, NPM1, SDCBP, IFIT1, IFI6, PDIA6 and PARP9 are measured.

In yet a further aspect for example, two or more DETERMINANTS selected from RSAD2, CRP, Neu (%), Lym (%), MX1, ANC, IFITM3, EIF4B, OAS2, IFITM1, IFIT3, PARP12, WBC, LOC26010, PTEN, CORO1A, MAN1C1, NPM1, SDCBP, IFI6, PDIA6, and PARP9 are measured.

In another aspect for example, three or more DETERMINANTS selected from RSAD2, CRP, MX1, IFITM3, EIF4B, OAS2, IFITM1, IFIT3, PARP12, LOC26010, PTEN, CORO1A, MAN1C1, NPM1, SDCBP, IFI6, PDIA6, and PARP9 are measured.

In a further aspect for example three or more DETERMINANTS selected from RSAD2, CRP, Neu (%), Lym (%), MX1, ANC, IFITM3, EIF4B, OAS2, IFITM1, IFIT3, PARP12, WBC, LOC26010, PTEN, CORO1A, MAN1C1, NPM1, SDCBP, IFI6, PDIA6, and PARP9 are measured.

In another aspect for example, two or more DETERMINANTS selected from ABTB1, ANC, CORO1A, CRP, CSDA, EIF4B, EPSTI1, GAS7, IFI6, IFIT3, IFITM1, IFITM3, LOC26010, LY6E, Lym (%), MAN1C1, MX1, Neu (%), NPM1, OAS2, PARP12, PARP9, PDIA6, PTEN, RSAD2, SDCBP, and WBC are measured and where the DETERMINANTS are selected such that their p-value is less than $10^{-4}$.

In a further aspect for example, two or more DETERMINANTS selected from ABTB1, ANC, ARHGDIB, ARPC2, CD15, CORO1A, CRP, CSDA, EIF4B, EPSTI1, GAS7, HERC5, IFI6, IFIT1, IFIT3, IFITM1, IFITM3, IL7R, KIAA0082, LOC26010, Lym (%), MBOAT2, MX1, Neu (%), OAS2, PARP12, PARP9, PTEN, RSAD2, SDCBP, TRIM 22, WBC, ARHGDIB, ARPC2, HERC5, IFI6, IFIT3, MBOAT2, and TRIM 22 are measured and where the DETERMINANTS are selected such that the p-value is less than $10^{-3}$.

In yet a further aspect for example,
a) ABTB1 is measured and a second DETERMINANT selected from ANC, CORO1A, CRP, CSDA, EIF4B, EPSTI1, GAS7, IFI6, IFIT3, IFITM1, IFITM3, LOC26010, LY6E, Lym (%), MAN1C1, MX1, Neu (%), NPM1, OAS2, PARP12, PARP9, PDIA6, PTEN, RSAD2, SDCBP, and WBC is measured.
b) CSDA is measured and a second DETERMINANT selected from EIF4B, EPSTI1, GAS7, IFI6, IFIT3, IFITM1, IFITM3, LOC26010, LY6E, Lym (%), MAN1C1, MX1, Neu (%), NPM1, OAS2, PARP12, PARP9, PDIA6, PTEN, RSAD2, SDCBP, and WBC is measured.
c) EPSTI1 is measured and a second DETERMINANT selected from GAS7, IFI6, IFIT3, IFITM1, IFITM3, LOC26010, LY6E, Lym (%), MAN1C1, MX1, Neu (%), NPM1, OAS2, PARP12, PARP9, PDIA6, PTEN, RSAD2, SDCBP, and WBC is measured.
d) GAS7 is measured and a second DETERMINANT selected from IFI6, IFIT3, IFITM1, IFITM3, LOC26010, LY6E, Lym (%), MAN1C1, MX1, Neu (%), NPM1, OAS2, PARP12, PARP9, PDIA6, PTEN, RSAD2, SDCBP, and WBC is measured.
e) IFI6 is measured and a second DETERMINANT selected from IFIT3, IFITM1, IFITM3, LOC26010, LY6E, Lym (%), MAN1C1, MX1, Neu (%), NPM1, OAS2, PARP12, PARP9, PDIA6, PTEN, RSAD2, SDCBP, and WBC is measured.
f) LY6E is measured and a second DETERMINANT selected from Lym (%), MAN1C1, MX1, Neu (%), NPM1, OAS2, PARP12, PARP9, PDIA6, PTEN, RSAD2, SDCBP, and WBC is measured.
g) PARP9 is measured and a second DETERMINANT selected from PDIA6, PTEN, RSAD2, SDCBP, and WBC is measured.
h) PDIA6 is measured and a second DETERMINANT selected from PTEN, RSAD2, SDCBP, and WBC is measured.

In various aspects the methods distinguish between a mixed infected subject and a virally infected subject. In such methods, one or more polypeptides selected from ANC, ARHGDIB, ARPC2, ATP6V0B, CD15, CES1, CORO1A, HERC5, IFIT3, LIPT1, LOC26010, MX1, OAS2, PARP12, PARP9, PBS, PTEN, RSAD2, SART3, SOCS3, and UBE2N is measured.

For example:
a) ANC is measured and a second DETERMINANT selected from ARHGDIB, ARPC2, ATP6V0B, CES1, CORO1A, CRP, HERC5, IFIT3, LIPT1, LOC26010, Lym (%), MX1, Neu (%), OAS2, PARP12, PARP9, PTEN, RSAD2, SOCS3, or UBE2N is measured;
b) ARHGDIB is measured and a second DETERMINANT selected from ARPC2, ATP6V0B, CES1, CORO1A, CRP, HERC5, IFIT3, LIPT1, LOC26010, Lym (%), MX1, Neu (%), OAS2, PARP12, PARP9, PTEN, RSAD2, SOCS3, and UBE2N is measured;
c) ARPC2 is measured and a second DETERMINANT selected from ATP6V0B, CES1, CORO1A, CRP, HERC5, IFIT3, LIPT1, LOC26010, Lym (%), MX1, Neu (%), OAS2, PARP12, PARP9, PTEN, RSAD2, SOCS3, and UBE2N is measured;
d) ATP6V0B is measured and a second DETERMINANT selected from CES1, CORO1A, CRP, HERC5, IFIT3, LIPT1, LOC26010, Lym (%), MX1, Neu (%), OAS2, PARP12, PARP9, PTEN, RSAD2, SOCS3, and UBE2N is measured;
e) CES1 is measured and a second DETERMINANT selected from CORO1A, CRP, HERC5, IFIT3, LIPT1, LOC26010, Lym (%), MX1, Neu (%), OAS2, PARP12, PARP9, PTEN, RSAD2, SOCS3, and UBE2N is measured;
f) CORO1A is measured and a second DETERMINANT selected from CRP, HERC5, IFIT3, LIPT1, LOC26010, Lym (%), MX1, Neu (%), OAS2, PARP12, PARP9, PTEN, RSAD2, SOCS3, and UBE2N is measured;
g) CRP is measured and a second DETERMINANT selected from HERC5, IFIT3, LIPT1, LOC26010, Lym (%), MX1, Neu (%), OAS2, PARP12, PARP9, PTEN, RSAD2, SOCS3, and UBE2N is measured;
h) HERC5 is measured and a second DETERMINANT selected from IFIT3, LIPT1, LOC26010, Lym (%), MX1, Neu (%), OAS2, PARP12, PARP9, PTEN, RSAD2, SOCS3, and UBE2N is measured;
i) IFIT3 is measured and a second DETERMINANT selected from LIPT1, LOC26010, Lym (%), MX1, Neu (%), OAS2, PARP12, PARP9, PTEN, RSAD2, SOCS3, and UBE2N is measured;
j) LIPT1 is measured and a second DETERMINANT selected from LOC26010, Lym (%), MX1, Neu (%), OAS2, PARP12, PARP9, PTEN, RSAD2, SOCS3, and UBE2N is measured;
k) LOC26010 is measured and a second DETERMINANT selected from Lym (%), MX1, Neu (%), OAS2, PARP12, PARP9, PTEN, RSAD2, SOCS3, and UBE2N is measured;
l) Lym (%) is measured and a second DETERMINANT selected from MX1, Neu (%), OAS2, PARP12, PARP9, PTEN, RSAD2, SOCS3, and UBE2N is measured;
m) MX1 is measured and a second DETERMINANT selected from Neu (%), OAS2, PARP12, PARP9, PTEN, RSAD2, SOCS3, and UBE2N is measured;
n) Neu (%) is measured and a second DETERMINANT selected from OAS2, PARP12, PARP9, PTEN, RSAD2, SOCS3, and UBE2N is measured;
o) OAS2 is measured and a second DETERMINANT selected from PARP12, PARP9, PTEN, RSAD2, SOCS3, and UBE2N is measured;
p) PARP12 is measured and a second DETERMINANT selected from PARP9, PTEN, RSAD2, SOCS3, and UBE2N is measured;
q) PARP9 is measured and a second DETERMINANT selected from PTEN, RSAD2, SOCS3, and UBE2N is measured;
r) PTEN is measured and a second DETERMINANT selected from RSAD2, SOCS3, and UBE2N is measured;
s) RSAD2 is measured and SOCS3 or UBE2N is measured; or
t) SOCS3 and UBE2N are measured.

Any of the above described methods are useful in distinguishing between a bacterial or a mixed infected subject and a viral infection, a non-infectious disease or a healthy subject. Optionally, a treatment regimen for the subject is selected. For example, a subject identified as having a bacterial or a mixed infection is selected to receive an antibiotic treatment regimen whereas a subject identified as having a viral infection, a non-infectious disease or healthy is not selected to receive an antibiotic treatment regimen.

The invention also provides methods of selecting a treatment regimen for a subject by identifying an infection in accordance to any of the above described methods; and selecting a treatment regimen, thereby treating the subject suspected of having an infection.

The invention further provides methods with a predetermined level of predictability for monitoring the effectiveness of treatment for an infection by: detecting the level of one or more polypeptides selected from ABTB1, ADIPOR1, ARHGDIB, ARPC2, ATP6V0B, C1orf83, CD15, CES1, CORO1A, CRP, CSDA, EIF4B, EPSTI1, GAS7, HERC5, IFI6, KIAA0082, IFIT1, IFIT3, IFITM1, IFITM3, LIPT1, IL7R, ISG20, LOC26010, LY6E, LRDD, LTA4H, MAN1C1, MBOAT2, MX1, NPM1, OAS2, PARP12, PARP9, QARS, RAB13, RAB31, RAC2, RPL34, PDIA6, PTEN, RSAD2, SART3, SDCBP, SMAD9, SOCS3, TRIM 22, UBE2N, XAF1 and ZBP1 in a first sample from the subject at a first period of time; and detecting the level of one or more polypeptides selected from ABTB1, ADIPOR1, ARHGDIB, ARPC2, ATP6V0B, C1orf83, CD15, CES1, CORO1A, CRP, CSDA, EIF4B, EPSTI1, GAS7, HERC5, IFI6, KIAA0082, IFIT1, IFIT3, IFITM1, IFITM3, LIPT1, IL7R, ISG20, LOC26010, LY6E, LRDD, LTA4H, MAN1C1, MBOAT2, MX1, NPM1, OAS2, PARP12, PARP9, QARS, RAB13, RAB31, RAC2, RPL34, PDIA6, PTEN, RSAD2, SART3, SDCBP, SMAD9, SOCS3, TRIM 22, UBE2N, XAF1 and ZBP1 in a second sample from the subject at a second period of time. The level of the one or more polypeptides detected at the first period of time is compared to the level detected at the second period of time. Optionally, the level of the one or more polypeptides detected is compared to a reference value. The effectiveness of treatment is monitored by a change in the level of one or more polypeptides.

The subject has previously been treated for the infection. Alternatively the subject has not been previously treated for the infection. In some aspects the first sample is taken from the subject prior to being treated for the infection and the second sample is taken from the subject after being treated for the infection. In some aspects, the second sample is taken from the subject after recurrence of the infection or prior to recurrence of the infection.

The invention further comprises an infection reference expression profile, containing a pattern of polypeptide levels of two or more polypeptides selected from ABTB1, ADIPOR1, ARHGDIB, ARPC2, ATP6V0B, C1orf83, CD15, CES1, CORO1A, CRP, CSDA, EIF4B, EPSTI1, GAS7, HERC5, IFI6, KIAA0082, IFIT1, IFIT3, IFITM1, IFITM3, LIPT1, IL7R, ISG20, LOC26010, LY6E, LRDD, LTA4H, MAN1C1, MBOAT2, MX1NPM1, OAS2, PARP12, PARP9, QARS, RAB13, RAB31, RAC2, RPL34, PDIA6, PTEN, RSAD2, SART3, SMAD9, SDCBP, TRIM 22, SART3, SOCS3, UBE2N, XAF1 and ZBP1.

Also included in the invention is a kit containing a plurality of polypeptide detection reagents that detect the corresponding polypeptides selected from ABTB1, ADIPOR1, ARHGDIB, ARPC2, ATP6V0B, C1orf83, CD15, CES1, CORO1A, CRP, CSDA, EIF4B, EPSTI1, GAS7, HERC5, IFI6, KIAA0082, IFIT1, IFIT3, IFITM1, IFITM3, LIPT1, IL7R, ISG20, LOC26010, LY6E, LRDD, LTA4H, MAN1C1, MBOAT2, MX1, NPM1, OAS2, PARP12, PARP9, QARS, RAB13, RAB31, RAC2, RPL34, PDIA6, PTEN, RSAD2, SART3, SMAD9, SDCBP, TRIM 22, SART3, SOCS3, UBE2N, XAF1 and ZBP1. Preferably, the detection reagent comprises one or more antibodies or fragments thereof.

The invention further includes a machine readable media containing one or more infection reference expression profiles according to the invention, and optionally, additional test results and subject information.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

BRIEF DESCRIPTION OF THE DRAWINGS

FIG. 4 B Measurements of DETERMINANTS whose levels were differentially expressed in patients with mixed infections versus pure viral infections.

FIG. 4 C Measurements DETERMINANTS whose levels were differentially expressed in viral versus non-infectious disease and healthy patients.

FIG. 4 D Measurements DETERMINANTS whose levels were differentially expressed in bacterial versus non-infectious disease and healthy patients.

FIG. 4 E Measurements of DETERMINANTS whose levels were differentially expressed in infectious disease versus non-infectious disease and healthy patients FIG. 5 Proteins that have an established immunological role in the host response to an infection are not necessarily differentially expressed in viral versus bacterial infected patients. Each point represents a different patient whose protein levels were measured in lympocytes (blue and red are viral and bacterial infected patients respectively) and bars indicate group means.

DETAILED DESCRIPTION OF THE INVENTION

Figure 1:
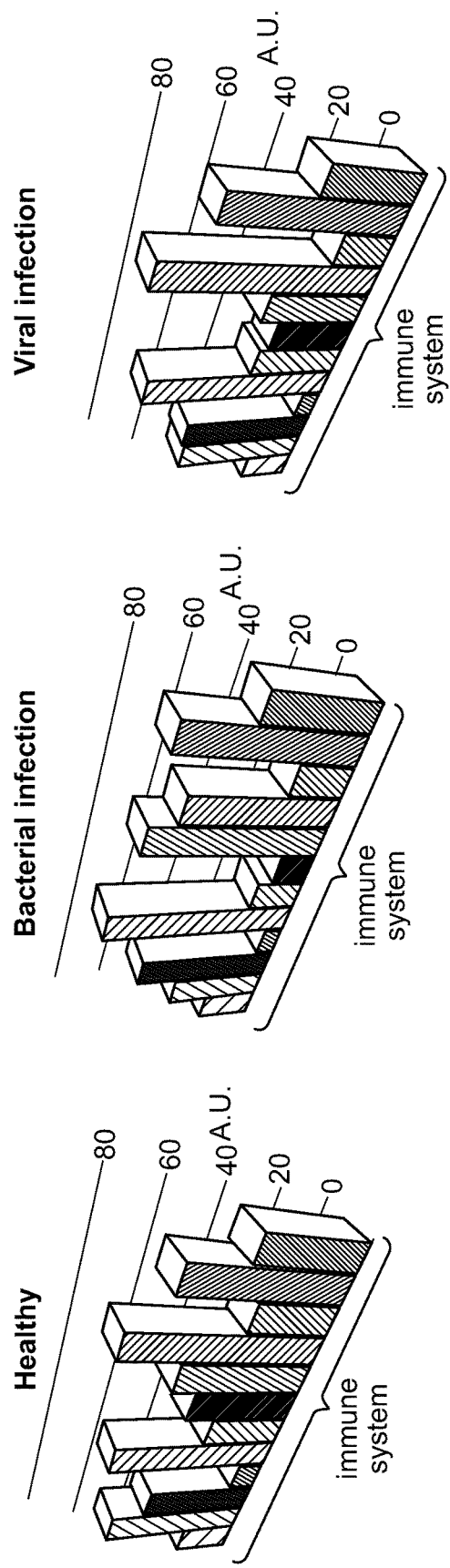
FIG. 1 is an illustration of the protein immuno-signature based diagnostics. The proteomic signatures of healthy, bacterial and viral infected individuals are illustrated with bars representing the norm levels of different proteins.

The present invention relates to the identification of signatures and determinants associated with bacterial, viral and mixed (i.e., bacterial and viral co-infections) infections. More specifically it was discovered that certain polypeptides are differentially expressed in a statistically significant manner in patients with bacteria, viral or mixed (i.e., bacterial and viral co-infections). These polypeptides include ABTB1, ADIPOR1, ARHGDIB, ARPC2, ATP6V0B, C1orf83, CD15, CES1, CORO1A, CSDA, EIF4B, EPSTI1, GAS7, HERC5, IFI6, KIAA0082, IFIT1, IFIT3, IFITM1, IFITM3, LIPT1, IL7R, ISG20, LOC26010, LY6E, LRDD, LTA4H, MAN1C1, MBOAT2, NPM1, OAS2, PARP12, PARP9, QARS, RAB13, RAB31, RAC2, RPL34, PDIA6, PTEN, RSAD2, SART3, SMAD9, SDCBP, SOCS3, TRIM 22, UBE2N, XAF1 and ZBP1.

Different infectious agents have unique molecular patterns that can be identified and targeted by the immune system. Pathogen-associated molecular patterns (PAMPs) are an example of such molecules that are associated with different groups of pathogens and may be recognized by cells of the innate immune system using Toll-like receptors (TLRs) and other pattern recognition receptors (e.g. NOD proteins) (Akira, Uematsu et al. 2006; Murphy, Travers et al. 2008). These patterns may vary considerably between different classes of pathogens and thus elicit different immune responses. For example, TLR-4 can recognize lipopolysaccharide, a constituent of gram negative bacteria, as well as lipoteichoic acids, constituent of gram positive bacteria, hence promoting an anti-microbial response of the immune system (Akira, Uematsu et al. 2006; Murphy, Travers et al. 2008). TLR-3 can recognize single stranded RNA (often indicative of a viral infection) and thus prompt the appropriate anti-viral response (Akira, Uematsu et al. 2006; Murphy, Travers et al. 2008). By distinguishing between different classes of pathogens (e.g bacterial versus viral) the immune system can mount the appropriate defense.

In the past few decades, several host markers have been identified that can be used for differential diagnosis of infection source in various indications. One example is Procalcitonin (PCT), a precursor of the hormone calcitonin produced by the C-cells of the thyroid gland. PCT levels in the blood stream of healthy individuals is hardly detectable (in the pg/ml range) but it might increase dramatically, as a result of a severe infection with levels rising up to 100 ng/ml. PCT is heavily used to diagnose patients with systemic infection, sepsis, with sensitivity of 76% and specificity of 70% (Jones, Fiechtl et al. 2007). However, studies that tested the diagnostic value of PCT in other non-systemic infection such as pneumonia or upper respiratory tract infections found it to be limited. (Brunkhorst, Al-Nawas et al. 2002).

Another widely used marker is the acute phase protein, C-reactive protein (CRP). CRP levels in the blood may rise in response to inflammation. However in some indications such as sepsis its specificity and sensitivity were found to be considerably lower than PCT (Hatherill, Tibby et al. 1999). Other proposed markers for detection of different sources of infection and sepsis include CD64 (Rudensky, Sirota et al. 2008), and HNL (Fjaertoft, Foucard et al. 2005). The reliability and accuracy of these markers for the purpose of diagnostics of viral versus bacterial infections in a broad setting is limited.

The present invention seeks to overcome the above mentioned diagnostic challenges by: (i) enabling accurate differentiation between a bacterial and a viral infection; (ii) enabling rapid diagnostics (within minutes); (iii) avoiding the "false positive" identification of non-pathogenic bacteria that are part of the body's natural flora, (iv) allowing accurate differentiation between mixed and pure viral infections and (v) allowing diagnosis in cases where the pathogen is inaccessible.

To this end the inventors sought to identify and test a novel set of biomarkers whose levels are differentially expressed in viral, bacterial and mixed infected patients, and to use the combined measurements of these biomarkers coupled with pattern recognition algorithms to accurately identify the source of infection with the aim of assisting physicians to accurately prescribe antibiotics.

To facilitate a solution that is generally applicable, the inventors recruited a heterogeneous cohort of patients (168 patients) comprising of different ages, ethnicities, pathogen types, clinical syndromes and time from appearance of symptoms (see FIG. 3), on which the solution was developed and tested.

To address the challenge of rapid diagnosis the invention focuses on biomarkers that can be rapidly measured, such as proteins, rather than biomarkers whose measurement may require hours to days, such as nucleic-acid based biomarkers. Note that high-throughput quantitative measurements of nucleic-acids for the purpose of biomarker discovery have become feasible in recent years using technologies such as microarrays and deep sequencing. However, performing such quantitative high-throughput measurements on the proteome level remains a challenge. The present invention focuses on the latter.

To address the clinical challenge of mixed infection diagnosis and treatment, the present invention includes a method for differentiating between mixed infections (which require Abx treatment despite the presence of a virus) and pure viral infections (which do not require Abx treatment).

The present invention also addresses the issue of "false-positive" diagnostics due to non-pathogenic strains of bacteria that are part of the body's natural flora. This is achieved by measuring biomarkers derived from the host rather than the pathogen.

Importantly, the current invention does not require direct access to the pathogen, because the immune system circulates in the entire body, thereby facilitating diagnosis in cases in which the pathogen is inaccessible.

Accordingly the invention provides methods for identifying subjects who have an infection by the detection of DETERMINANTS associated with an infection, including those subjects who are asymptomatic for the infection. These signatures and DETERMINANTS are also useful for monitoring subjects undergoing treatments and therapies for infection, and for selecting or modifying therapies and treatments that would be efficacious in subjects having an infection.

Exemplary Polypeptides Measured in the Present Invention

ABTB1: This gene encodes a protein with an ankyrin repeat region and two BTB/POZ domains, which are thought to be involved in protein-protein interactions. Expression of this gene is activated by the phosphatase and tensin homolog, a tumor suppressor. Alternate splicing results in three transcript variants. It may act as a mediator of the PTEN growth-suppressive signaling pathway. It may play a role in developmental processes.

ADIPOR1: ADIPOR1 is a receptor for globular and full-length adiponectin (APM1), an essential hormone secreted by adipocytes that acts as an antidiabetic. It is probably involved in metabolic pathways that regulate lipid metabolism such as fatty acid oxidation. It mediates increased AMPK, PPARA ligand activity, fatty acid oxidation and glucose uptake by adiponectin. ADIPOR1 has some high-affinity receptors for globular adiponectin and low-affinity receptors for full-length adiponectin.

ARHGDIB: Regulates the GDP/GTP exchange reaction of the Rho proteins by inhibiting the dissociation of GDP from them, and the subsequent binding of GTP to them.

ARPC2: Functions as actin-binding component of the Arp2/3 complex which is involved in regulation of actin polymerization and together with an activating nucleation-promoting factor (NPF) mediates the formation of branched actin networks. Seems to contact the mother actin filament.

ATP6V0B: $H^+$-ATPase (vacuolar ATPase, V-ATPase) is an enzyme transporter that functions to acidify intracellular compartments in eukaryotic cells. It is ubiquitously expressed and is present in endomembrane organelles such as vacuoles, lysosomes, endosomes, the Golgi apparatus, chromaffin granules and coated vesicles, as well as in the plasma membrane. $H^+$-ATPase is a multi-subunit complex composed of two domains. The V1 domain is responsible for ATP hydrolysis and the V0 domain is responsible for protein translocation. There are two main mechanisms of regulating $H^+$-ATPase activity; recycling of $H^+$-ATPase-containing vesicles to and from the plasma membrane and glucose-sensitive assembly/disassembly of the holo-enzyme complex. These transporters play an important role in processes such as receptor-mediated endocytosis, protein degradation and coupled transport. They have a function in bone reabsorption and mutations in the A3 gene cause recessive osteopetrosis. Furthermore, $H^+$-ATPases have been implicated in tumor metastasis and regulation of sperm motility and maturation.

C1orf83: Function not fully characterized.

CD15 (FUT4): The product of this gene transfers fucose to N-acetyllactosamine polysaccharides to generate fucosylated carbohydrate structures. It catalyzes the synthesis of the non-sialylated antigen, Lewis x (CD15).

CES1: Involved in the detoxification of xenobiotics and in the activation of ester and amide prodrugs. Hydrolyzes aromatic and aliphatic esters, but has no catalytic activity toward amides or a fatty acyl-CoA ester. Hydrolyzes the methyl ester group of cocaine to form benzoylecgonine. Catalyzes the transesterification of cocaine to form cocaethylene. Displays fatty acid ethyl ester synthase activity, catalyzing the ethyl esterification of oleic acid to ethyloleate.

CORO1A: May be a crucial component of the cytoskeleton of highly motile cells, functioning both in the invagination of large pieces of plasma membrane, as well as in forming protrusions of the plasma membrane involved in cell locomotion. In mycobacteria-infected cells, its retention on the phagosomal membrane prevents fusion between phagosomes and lysosomes.

CSDA: Binds to the GM-CSF promoter and seems to act as a repressor. Binds also to full length mRNA and to short RNA sequences containing the consensus site 5'-UCCAUCA-3'. May have a role in translation repression CRP: C-reactive protein. The protein encoded by this gene belongs to the pentaxin family. It is involved in several host defense related functions based on its ability to recognize foreign pathogens and damaged cells of the host and to initiate their elimination by interacting with humoral and cellular effector systems in the blood.

EIF4B: Required for the binding of mRNA to ribosomes. Functions in close association with EIF4-F and EIF4-A. It binds near the 5'-terminal cap of mRNA in the presence of EIF-4F and ATP. It promotes the ATPase activity and the ATP-dependent RNA unwinding activity of both EIF4-A and EIF4-F.

EPSTI1: Function was not fully characterized yet.

GAS7: Growth arrest-specific 7 is expressed primarily in terminally differentiated brain cells and predominantly in mature cerebellar Purkinje neurons. GAS7 plays a putative role in neuronal development. Several transcript variants encoding proteins which vary in the N-terminus have been described. It might play a role in promoting maturation and morphological differentiation of cerebellar neurons.

HERC5: Major E3 ligase for ISG15 conjugation. Acts as a positive regulator of innate antiviral response in cells induced by interferon. Makes part of the ISGylation machinery that recognizes target proteins in a broad and relatively non-specific manner. Catalyzes ISGylation of IRF3 which results in sustained activation. It attenuates IRF3-PIN1 interaction, which antagonizes IRF3 ubiquitination and degradation, and boosts the antiviral response. Catalyzes ISGylation of influenza A viral NS1 which attenuates virulence; ISGylated NS1 fails to form homodimers and thus to interact with its RNA targets. It catalyzes ISGylation of papillomavirus type 16 L1 protein which results in dominant-negative effect on virus infectivity. Physically associated with polyribosomes, broadly modifies newly synthesized proteins in a co-translational manner. In an interferon-stimulated cell, newly translated viral proteins are primary targets of ISG15.

IFI6: This gene was first identified as one of the many genes induced by interferon. The encoded protein may play a critical role in the regulation of apoptosis. A mini satellite that consists of 26 repeats of a 12 nucleotide repeating element resembling the mammalian splice donor consensus sequence begins near the end of the second exon. Alternatively spliced transcript variants that encode different isoforms by using the two downstream repeat units as splice donor sites have been described.

IFIT1: Interferon-induced protein with tetratricopeptide repeats.

IFIT3: Function was not fully characterized yet.

IFITM1: IFN-induced antiviral protein that mediate cellular innate immunity to at least three major human pathogens, namely influenza A H1N1 virus, West Nile virus, and dengue virus by inhibiting the early step(s) of replication. Plays a key role in the antiproliferative action of IFN-gamma either by inhibiting the ERK activation or by arresting cell growth in G1 phase in a p53-dependent manner. Implicated in the control of cell growth. Component of a multimeric complex involved in the transduction of antiproliferative and homotypic adhesion signals.

IFITM3/IFITM2: IFN-induced antiviral protein that mediates cellular innate immunity to at least three major human pathogens, namely influenza A H1N1 virus, West Nile virus (WNV), and dengue virus (WNV), by inhibiting the early step(s) of replication.

IL7R: The protein encoded by this gene is a receptor for interleukine 7 (IL7). The function of this receptor requires the interleukin 2 receptor, gamma chain (IL2RG), which is a common gamma chain shared by the receptors of various cytokines, including interleukin 2, 4, 7, 9, and 15. This protein has been shown to play a critical role in the V(D)J recombination during lymphocyte development. This protein is also found to control the accessibility of the TCR gamma locus by STAT5 and histone acetylation. Knockout studies in mice suggested that blocking apoptosis is an essential function of this protein during differentiation and activation of T lymphocytes. The functional defects in this protein may be associated with the pathogenesis of the severe combined immunodeficiency (SCID).

ISG20: Exonuclease with specificity for single-stranded RNA and, to a lesser extent for DNA. Degrades RNA at a rate that is approximately 35-fold higher than its rate for single-stranded DNA. Involved in the antiviral function of IFN against RNA viruses.

KIAA0082 (FTSJD2): S-adenosyl-L-methionine-dependent methyltransferase that mediates mRNA cap1 2'-O-ribose methylation to the 5'-cap structure of mRNAs. Methylates the ribose of the first nucleotide of a m(7)GpppG-capped mRNA to produce m(7)GpppNmp (cap1). Cap1 modification is linked to higher levels of translation. May be involved in the interferon response pathway.

LIPT1: The process of transferring lipoic acid to proteins is a two-step process. The first step is the activation of lipoic acid by lipoate-activating enzyme to form lipoyl-AMP. For the second step, the protein encoded by this gene transfers the lipoyl moiety to apoproteins. Alternative splicing in the 5' UTR of this gene results in five transcript variants that encode the same protein. (provided by RefSeq)

LOC26010(SPATS2): Function was not fully characterized yet.

LRDD: The protein encoded by this gene contains a leucine-rich repeat and a death domain. This protein has been shown to interact with other death domain proteins, such as Fas (TNFRSF6)-associated via death domain (FADD) and MAP-kinase activating death domain-containing protein (MADD), and thus may function as an adaptor protein in cell death-related signaling processes. The expression of the mouse counterpart of this gene has been found to be positively regulated by the tumor suppressor p53 and to induce cell apoptosis in response to DNA damage, which suggests a role for this gene as an effector of p53-dependent apoptosis. Alternative splicing results in multiple transcript variants.

LTA4H: Hydrolyzes an epoxide moiety of leukotriene A4 (LTA-4) to form leukotriene B4 (LTB-4). The enzyme also has some peptidase activity.

LY6E: Function was not fully characterized yet.

MAN1C1: Mannosidases are divided into two subtypes; I and II, (EC numbers 3.2.1.113 and 3.2.1.114 respectively) which display a wide expression pattern. Mannosidase I hydrolyzes (1,2)-linked alpha-D-mannose residues in the oligo-mannose oligosaccharide Man9(GlcNAc)2 and mannosidase II hydrolyzes (1,3)- and (1,6)-linked alpha-D- mannose residues in Man5(GlcNAc)3. Both subtypes require a divalent cation cofactor. Mutations in mannosidases can cause mannosidosis (mannosidase I deficiency).

MBOAT2: Acyltransferase which mediates the conversion of lysophosphatidyl-ethanolamine (1-acyl-sn-glycero-3-phosphoethanolamine or LPE) into phosphatidyl-ethanolamine (1,2-diacyl-sn-glycero-3-phosphoethanolamine or PE) (LPEAT activity). Catalyzes also the acylation of lysophosphatidic acid (LPA) into phosphatidic acid (PA) (LPAAT activity). Has also a very weak lysophosphatidylcholine acyltransferase (LPCAT activity). Prefers oleoyl-CoA as the acyl donor. Lysophospholipid acyltransferases (LPLATs) catalyze the reacylation step of the phospholipid remodeling pathway also known as the Lands cycle.

MX1/N1XA: In mouse, the interferon-inducible Mx protein is responsible for a specific antiviral state against influenza virus infection. The protein encoded by this gene is similar to the mouse protein as determined by its antigenic relatedness, induction conditions, physicochemical properties, and amino acid analysis. This cytoplasmic protein is a member of both the dynamin family and the family of large GTPases. Two transcript variants encoding the same protein have been found for this gene.

NPM1: It is involved in diverse cellular processes such as ribosome biogenesis, centrosome duplication, protein chaperoning, histone assembly, cell proliferation, and regulation of tumor suppressors TP53/p53 and ARF. It binds ribosome presumably to drive ribosome nuclear export. It is associated with nucleolar ribonucleoprotein structures and binds single stranded nucleic acids. Acts as a chaperonin for the core histones H3, H2B and H4.

OAS2: This gene encodes a member of the 2-5A synthetase family, essential proteins involved in the innate immune response to viral infection. The encoded protein is induced by interferons and uses adenosine triphosphate in 2'-specific nucleotidyl transfer reactions to synthesize 2',5'-oligoadenylates (2-5As). These molecules activate latent RNase L, which results in viral RNA degradation and the inhibition of viral replication. The three known members of this gene family are located in a cluster on chromosome 12. Alternatively spliced transcript variants encoding different isoforms have been described.

PARP9: Poly (ADP-ribose) polymerase (PARP) catalyzes the post-translational modification of proteins by the addition of multiple ADP-ribose moieties. PARP transfers ADP-ribose from nicotinamide dinucleotide (NAD) to glu/asp residues on the substrate protein, and also polymerizes ADP-ribose to form long/branched chain polymers. PARP inhibitors are being developed for use in a number of pathologies including cancer, diabetes, stroke and cardiovascular diseases.

PARP12: Poly (ADP-ribose) polymerase (PARP) catalyzes the post-translational modification of proteins by the addition of multiple ADP-ribose moieties. PARP transfers ADP-ribose from nicotinamide dinucleotide (NAD) to glu/asp residues on the substrate protein, and also polymerizes ADP-ribose to form long/branched chain polymers. PARP inhibitors are being developed for use in a number of pathologies including cancer, diabetes, stroke and cardiovascular diseases.

PDIA6: Protein disulfide isomerases (EC 5.3.4.1), such as PDIA6, are endoplasmic reticulum (ER) resident proteins that catalyze formation, reduction, and isomerization of disulfide bonds in proteins and are thought to play a role in folding of disulfide-bonded proteins. It might function as a chaperone that inhibits aggregation of mis-folded proteins. Plays a role in platelet aggregation and activation by agonists such as convulxin, collagen and thrombin.

PTEN: Tumor suppressor. Acts as a dual-specificity protein phosphatase, ephosphorylating tyrosine-, serine- and threonine-phosphorylated proteins. Also acts as a lipid phosphatase, removing the phosphate in the D3 position of the inositol ring from phosphatidylinositol (PI) 3,4,5-trisphosphate, PI 3,4-diphosphate, PI 3-phosphate and inositol 1,3, 4,5-tetrakisphosphate with order of substrate preference in vitro PtdIns(3,4,5)P3>PtdIns(3,4)P2>PtdIns3P>Ins(1,3,4,5) P4. The lipid phosphatase activity is critical for its tumor suppressor function. Antagonizes the PI3K-AKT/PKB signaling pathway by dephosphorylating phosphoinositides and thereby modulating cell cycle progression and cell survival. The un-phosphorylated form cooperates with AIP1 to suppress AKT1 activation. Dephosphorylates tyrosine-phosphorylated focal adhesion kinase and inhibits cell migration and integrin-mediated cell spreading and focal adhesion formation. Plays a role as a key modulator of the AKT-mTOR signaling pathway controlling the tempo of the process of newborn neurons integration during adult neurogenesis, including correct neuron positioning, dendritic development and synapse formation. May be a negative regulator of insulin signaling and glucose metabolism in adipose tissue. The nuclear monoubiquitinated form possesses greater apoptotic potential, whereas the cytoplasmic nonubiquitinated form induces less tumor suppressive ability.

RAB13: could participate in polarized transport, in the assembly and/or the activity of tight junctions.

QARS: Aminoacyl-tRNA synthetases catalyze the aminoacylation of tRNA by their cognate amino acid. Because of their central role in linking amino acids with nucleotide triplets contained in tRNAs, aminoacyl-tRNA synthetases are thought to be among the first proteins that appeared in evolution. In metazoans, 9 aminoacyl-tRNA synthetases specific for glutamine (gln), glutamic acid (glu), and 7 other amino acids are associated within a multienzyme complex. Although present in eukaryotes, glutaminyl-tRNA synthetase (QARS) is absent from many prokaryotes, mitochondria, and chloroplasts, in which Gln-tRNA(Gln) is formed by transamidation of the misacylated Glu-tRNA(Gln). Glutaminyl-tRNA synthetase belongs to the class-I aminoacyl-tRNA synthetase family.

RAB13: could participate in polarized transport, in the assembly and/or the activity of tight junctions RAB31: Small GTP-binding proteins of the RAB family, such as RAB31, play essential roles in vesicle and granule targeting.

RAC2: Small G proteins (small GTPases) are homologous to Galpha proteins and are often referred to as the Ras proto-oncogene superfamily. The Ras superfamily contains over 100 small GTPases grouped into eight families; Ras, Rho, Rab, Rap, Arf, Ran, Rheb and Rad. Small GTPases regulate a wide variety of processes in the cell, including growth, differentiation, movement and lipid vesicle transport. Like Galpha proteins, small GTPases alternate between an 'on' state (bound to GTP) and an 'off' state (bound to GDP). This cyclic process requires guanine nucleotide exchange factor (GEF) and GTPase-activating protein (GAP). Small GTPases are the downstream effectors of most receptor tyrosine kinases (RTKs) and are linked via two proteins, GRB2 and SOS. They are coupled to intracellular signaling cascades including the MAPK pathway, through interactions with Raf kinase. Normally, activation of small GTPases is induced by ligand binding to a RTK. In many transformed cells activating mutations of GTPases, often Ras, produce a cellular response in the absence of a ligand, thus promoting malignant progression.

RPL34: Ribosomes, the organelles that catalyze protein synthesis, consist of a small 40S subunit and a large 60S subunit. Together these subunits are composed of 4 RNA species and approximately 80 structurally distinct proteins. This gene encodes a ribosomal protein that is a component of the 60S subunit. The protein belongs to the L34E family of ribosomal proteins. It is located in the cytoplasm. This gene originally was thought to be located at 17q21, but it has been mapped to 4q. Transcript variants derived from alternative splicing, alternative transcription initiation sites, and/or alternative polyadenylation exist; these variants encode the same protein. As is typical for genes encoding ribosomal proteins, there are multiple processed pseudogenes of this gene dispersed through the genome.

RSAD2: Involved in antiviral defense. May impair virus budding by disrupting lipid rafts at the plasma membrane, a feature which is essential for the budding process of many viruses. Acts through binding with and inactivating FPPS, an enzyme involved in synthesis of cholesterol, farnesylated and geranylated proteins, ubiquinone dolichol and heme. Plays a role in the cell antiviral state induced by type I and type II interferon. Displays antiviral effect against HIV-1 virus, hepatitis C virus, human cytomegalovirus, and aphaviruses, but not vesiculovirus.

SART3: The protein encoded by this gene is an RNA-binding nuclear protein that is a tumor-rejection antigen. This antigen possesses tumor epitopes capable of inducing HLA-A24-restricted and tumor-specific cytotoxic T lymphocytes in cancer patients and may be useful for specific immunotherapy. This gene product is found to be an important cellular factor for HIV-1 gene expression and viral replication. It also associates transiently with U6 and U4/U6 snRNPs during the recycling phase of the spliceosome cycle. This encoded protein is thought to be involved in the regulation of mRNA splicing.

SDCBP: The protein encoded by this gene was initially identified as a molecule linking syndecan-mediated signaling to the cytoskeleton. The syntenin protein contains tandemly repeated PDZ domains that bind the cytoplasmic, C-terminal domains of a variety of transmembrane proteins. This protein may also affect cytoskeletal-membrane organization, cell adhesion, protein trafficking, and the activation of transcription factors. The protein is primarily localized to membrane-associated adherens junctions and focal adhesions but is also found at the endoplasmic reticulum and nucleus. Alternative splicing results in multiple transcript variants encoding different isoforms. It seems to couple transcription factor SOX4 to the IL-5 receptor (IL5RA). May play a role in vesicular trafficking and seems to be required for the targeting of TGFA to the cell surface in the early secretory pathway.

SMAD9: The protein encoded by this gene is a member of the SMAD family, which transduces signals from TGF-beta family members. The encoded protein is activated by bone morphogenetic proteins and interacts with SMAD4. Two transcript variants encoding different isoforms have been found for this gene. Transcriptional modulator activated by BMP (bone morphogenetic proteins) type 1 receptor kinase. SMAD9 is a receptor-regulated SMAD (R-SMAD).

SOCS3: SOCS family proteins form part of a classical negative feedback system that regulates cytokine signal transduction. SOCS3 is involved in negative regulation of cytokines that signal through the JAK/STAT pathway. Inhibits cytokine signal transduction by binding to tyrosine kinase receptors including gp130, LIF, erythropoietin, insulin, IL12, GCSF and leptin receptors. Binding to JAK2 inhibits its kinase activity. Suppresses fetal liver erythropoiesis. Regulates onset and maintenance of allergic responses mediated by T-helper type 2 cells. Regulates IL-6 signaling in vivo (By similarity). Probable substrate recognition component of a SCF-like ECS (Elongin BC-CUL2/5-SOCS-box protein) E3 ubiquitin-protein ligase complex which mediates the ubiquitination and subsequent proteasomal degradation of target proteins. Seems to recognize IL6ST (By similarity).

TRIM22: Interferon-induced antiviral protein involved in cell innate immunity. The antiviral activity could in part be mediated by TRIM22-dependent ubiquitination of viral proteins. Plays a role in restricting the replication of HIV-1, encephalomyocarditis virus (EMCV) and hepatitis B virus (HBV). Acts as a transcriptional repressor of HBV core promoter. May have E3 ubiquitin-protein ligase activity.

UBE2N: The UBE2V1-UBE2N and UBE2V2-UBE2N heterodimers catalyze the synthesis of non-canonical 'Lys-63'-linked polyubiquitin chains. This type of polyubiquitination does not lead to protein degradation by the proteasome. It mediates transcriptional activation of target genes. It plays a role in the control of progress through the cell cycle and differentiation. Plays a role in the error-free DNA repair pathway and contributes to the survival of cells after DNA damage. Acts together with the E3 ligases, HLTF and SHPRH, in the 'Lys-63'-linked poly ubiquitination of PCNA upon genotoxic stress, which is required for DNA repair. It appears to act together with E3 ligase RNF5 in the 'Lys-63'-linked polyubiquitination of JKAMP thereby regulating JKAMP function by decreasing its association with components of the proteasome and ERAD.

XAF1: Seems to function as a negative regulator of members of the IAP (inhibitor of apoptosis protein) family. Inhibits anti-caspase activity of BIRC4. Induces cleavage and inactivation of BIRC4 independent of caspase activation. Mediates TNF-alpha-induced apoptosis and is involved in apoptosis in trophoblast cells. May inhibit BIRC4 indirectly by activating the mitochondrial apoptosis pathway. After translocation to mitochondra, promotes translocation of BAX to mitochondria and cytochrome c release from mitochondria. Seems to promote the redistribution of BIRC4 from the cytoplasm to the nucleus, probably independent of BIRC4 inactivation which seems to occur in the cytoplasm. The BIRC4-XAF1 complex mediates down-regulation of BIRC5/survivin; the process requires the E3 ligase activity of BIRC4. Seems to be involved in cellular sensitivity to the proapoptotic actions of TRAIL. May be a tumor suppressor by mediating apoptosis resistance of cancer cells.

ZBP1: DLM1 encodes a Z-DNA binding protein. Z-DNA formation is a dynamic process, largely controlled by the amount of supercoiling. May play a role in host defense against tumors and pathogens. Binds Z-DNA (By similarity).

DEFINITIONS

"Accuracy" refers to the degree of conformity of a measured or calculated quantity (a test reported value) to its actual (or true) value. Clinical accuracy relates to the proportion of true outcomes (true positives (TP) or true negatives (TN) versus misclassified outcomes (false positives (FP) or false negatives (FN)), and may be stated as a sensitivity, specificity, positive predictive values (PPV) or negative predictive values (NPV), or as a likelihood, odds ratio, among other measures.

"DETERMINANTS" in the context of the present invention encompass, without limitation, polypeptides, peptide, proteins, protein isoforms (e.g. decoy receptor isoforms). DETERMINANTS can also include mutated proteins.

"DETERMINANT" OR "DETERMINANTS" encompass one or more of all polypeptides whose levels are changed in subjects who have an infection. Individual DETERMINANT include ABTB1, ADIPOR1, ARHGDIB, ARPC2, ATP6V0B, C1orf83, CD15, CES1, CORO1A, CRP, CSDA, EIF4B, EPSTI1, GAS7, HERC5, IFI6, KIAA0082, IFIT1, IFIT3, IFITM1, IFITM3, LIPT1, IL7R, ISG20, LOC26010, LY6E, LRDD, LTA4H, MAN1C1, MBOAT2, MX1, NPM1, OAS2, PARP12, PARP9, QARS, RAB13, RAB31, RAC2, RPL34, PDIA6, PTEN, RSAD2, SART3, SDCBP, TRIM 22, SMAD9, SOCS3, UBE2N, XAF1 and ZBP1 and are collectively referred to herein as, inter alia, "infection-associated proteins or infection-associated polypepetides", "DETERMINANT polypeptides", "polypeptide DETERMINANTS", "DETERMINANT proteins" or "protein DETERMINANTS". Unless indicated otherwise, "DETERMINANT", "infection-associated proteins" or "infection-associated polypepetide", is meant to refer to any of the proteins and polypeptides disclosed herein.

DETERMINANTS also encompass non-polypeptide factors, non-blood borne factors or non-analyte physiological markers of health status, such as "clinical parameters" defined herein, as well as "traditional laboratory risk factors", also defined herein.

For example, as used herein DETERMINANTS include non-polypeptide features (i.e. non-polypeptide DETERMINANTS) such as neutrophil % (abbreviated Neu (%)), lymphocyte % (abbreviated Lym (%)), monocyte % (abbreviated Mon (%)), absolute neutrophil count (abbreviated ANC) and absolute lymphocyte count (abbreviated ALC), white blood count (abbreviated WBC), age, gender, and maximal temperature (i.e. maximal core body temperature since initial appearance of symptoms).

DETERMINANTS also include any calculated indices created mathematically or combinations of any one or more of the foregoing measurements, including temporal trends and differences. Where available, and unless otherwise described herein, DETERMINANTS which are gene products are identified based on the official letter abbreviation or gene symbol assigned by the international Human Genome Organization Naming Committee (HGNC) and listed at the date of this filing at the US National Center for Biotechnology Information (NCBI) web site, also known as Entrez Gene.

In preferred embodiments, DETERMINANTS include protein and non-protein features.

"Clinical parameters" encompass all non-sample or non-analyte biomarkers of subject health status or other characteristics, such as, without limitation, age (Age), ethnicity (RACE), gender (Sex), core body temperature or family history (FamHX).

A "Infection Reference Expression Profile," is a set of values associated with two or more DETERMINANTS resulting from evaluation of a biological sample (or population or set of samples).

A "Subject with non-infectious disease" is one whose disease is not caused by an infectious disease agent (e.g. bacterial or virus). In the study presented herein this includes patients with acute myocardial infarction, physical injury, epileptic attack etc.

"FN" is false negative, means a result that appears negative but fails to reveal a situation. For example in the context of the present invention a FN, is for example but not limited to, falsly classifying a bacterial infection as a viral infection.

"FP" is false positive, means test result that is erroneously classified in a positive category. For example in the context of the present invention a FP, is for example but not limited to, falsly classifying a viral infection as a bacterial infection A "formula," "algorithm," or "model" is any mathematical equation, algorithmic, analytical or programmed process, or statistical technique that takes one or more continuous or categorical inputs (herein called "parameters") and calculates an output value, sometimes referred to as an "index" or "index value." Non-limiting examples of "formulas" include sums, ratios, and regression operators, such as coefficients or exponents, biomarker value transformations and normalizations (including, without limitation, those normalization schemes based on clinical parameters, such as gender, age, or ethnicity), rules and guidelines, statistical classification models, and neural networks trained on historical populations. Of particular use in combining DETERMINANTS are linear and non-linear equations and statistical classification analyses to determine the relationship between levels of DETERMINANTS detected in a subject sample and the subject's probability of having an infection or a certain type of infection. In panel and combination construction, of particular interest are structural and syntactic statistical classification algorithms, and methods of index construction, utilizing pattern recognition features, including established techniques such as cross-correlation, Principal Components Analysis (PCA), factor rotation, Logistic Regression (LogReg), Linear Discriminant Analysis (LDA), Eigengene Linear Discriminant Analysis (ELDA), Support Vector Machines (SVM), Random Forest (RF), Recursive Partitioning Tree (RPART), as well as other related decision tree classification techniques, Shrunken Centroids (SC), StepAIC, Kth-Nearest Neighbor, Boosting, Decision Trees, Neural Networks, Bayesian Networks, and Hidden Markov Models, among others. Other techniques may be used in survival and time to event hazard analysis, including Cox, Weibull, Kaplan-Meier and Greenwood models well known to those of skill in the art. Many of these techniques are useful either combined with a DETERMINANT selection technique, such as forward selection, backwards selection, or stepwise selection, complete enumeration of all potential panels of a given size, genetic algorithms, or they may themselves include biomarker selection methodologies in their own technique. These may be coupled with information criteria, such as Akaike's Information Criterion (AIC) or Bayes Information Criterion (BIC), in order to quantify the tradeoff between additional biomarkers and model improvement, and to aid in minimizing overfit. The resulting predictive models may be validated in other studies, or cross-validated in the study they were originally trained in, using such techniques as Bootstrap, Leave-One-Out (LOO) and 10-Fold cross-validation (10-Fold CV). At various steps, false discovery rates may be estimated by value permutation according to techniques known in the art. A "health economic utility function" is a formula that is derived from a combination of the expected probability of a range of clinical outcomes in an idealized applicable patient population, both before and after the introduction of a diagnostic or therapeutic intervention into the standard of care. It encompasses estimates of the accuracy, effectiveness and performance characteristics of such intervention, and a cost and/or value measurement (a utility) associated with each outcome, which may be derived from actual health system costs of care (services, supplies, devices and drugs, etc.) and/or as an estimated acceptable value per quality adjusted life year (QALY) resulting in each outcome. The sum, across all predicted outcomes, of the product of the predicted population size for an outcome multiplied by the respective outcome's expected utility is the total health economic utility of a given standard of care. The difference between (i) the total health economic utility calculated for the standard of care with the intervention versus (ii) the total health economic utility for the standard of care without the intervention results in an overall measure of the health economic cost or value of the intervention. This may itself be divided amongst the entire patient group being analyzed (or solely amongst the intervention group) to arrive at a cost per unit intervention, and to guide such decisions as market positioning, pricing, and assumptions of health system acceptance. Such health economic utility functions are commonly used to compare the cost-effectiveness of the intervention, but may also be transformed to estimate the acceptable value per QALY the health care system is willing to pay, or the acceptable cost-effective clinical performance characteristics required of a new intervention.

For diagnostic (or prognostic) interventions of the invention, as each outcome (which in a disease classifying diagnostic test may be a TP, FP, TN, or FN) bears a different cost, a health economic utility function may preferentially favor sensitivity over specificity, or PPV over NPV based on the clinical situation and individual outcome costs and value, and thus provides another measure of health economic performance and value which may be different from more direct clinical or analytical performance measures. These different measurements and relative trade-offs generally will converge only in the case of a perfect test, with zero error rate (a.k.a., zero predicted subject outcome misclassifications or FP and FN), which all performance measures will favor over imperfection, but to differing degrees.

"Measuring" or "measurement," or alternatively "detecting" or "detection," means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's non-analyte clinical parameters.

"Negative predictive value" or "NPV" is calculated by TN/(TN+FN) or the true negative fraction of all negative test results. It also is inherently impacted by the prevalence of the disease and pre-test probability of the population intended to be tested. See, e.g., O'Marcaigh A S, Jacobson R M, "Estimating The Predictive Value Of A Diagnostic Test, How To Prevent Misleading Or Confusing Results," Clin. Ped. 1993, 32(8): 485-491, which discusses specificity, sensitivity, and positive and negative predictive values of a test, e.g., a clinical diagnostic test. Often, for binary disease state classification approaches using a continuous diagnostic test measurement, the sensitivity and specificity is summarized by Receiver Operating Characteristics (ROC) curves according to Pepe et al, "Limitations of the Odds Ratio in Gauging the Performance of a Diagnostic, Prognostic, or Screening Marker," Am. J. Epidemiol 2004, 159 (9): 882-890, and summarized by the Area Under the Curve (AUC) or c-statistic, an indicator that allows representation of the sensitivity and specificity of a test, assay, or method over the entire range of test (or assay) cut points with just a single value. See also, e.g., Shultz, "Clinical Interpretation Of Laboratory Procedures," chapter 14 in Teitz, Fundamentals of Clinical Chemistry, Burtis and Ashwood (eds.), 4$^{th}$ edition 1996, W.B. Saunders Company, pages 192-199; and Zweig et al., "ROC Curve Analysis: An Example Showing The Relationships Among Serum Lipid And Apolipoprotein Concentrations In Identifying Subjects With Coronory Artery Disease," Clin. Chem., 1992, 38(8): 1425-1428. An alternative approach using likelihood functions, odds ratios, information theory, predictive values, calibration (including goodness-of-fit), and reclassification measurements is summarized according to Cook, "Use and Misuse of the Receiver Operating Characteristic Curve in Risk Prediction," Circulation 2007, 115: 928-935.

"Analytical accuracy" refers to the reproducibility and predictability of the measurement process itself, and may be summarized in such measurements as coefficients of variation, and tests of concordance and calibration of the same samples or controls with different times, users, equipment and/or reagents. These and other considerations in evaluating new biomarkers are also summarized in Vasan, 2006.

"Performance" is a term that relates to the overall usefulness and quality of a diagnostic or prognostic test, including, among others, clinical and analytical accuracy, other analytical and process characteristics, such as use characteristics (e.g., stability, ease of use), health economic value, and relative costs of components of the test. Any of these factors may be the source of superior performance and thus usefulness of the test, and may be measured by appropriate "performance metrics," such as AUC, MCC. time to result, shelf life, etc. as relevant.

"Positive predictive value" or "PPV" is calculated by TP/(TP+FP) or the true positive fraction of all positive test results. It is inherently impacted by the prevalence of the disease and pre-test probability of the population intended to be tested.

A "sample" in the context of the present invention is a biological sample isolated from a subject and can include, by way of example and not limitation, whole blood, serum, plasma, leukocytes or blood cells. Preferably, the sample is whole blood, serum or leukocytes.

"Sensitivity" is calculated by TP/(TP+FN) or the true positive fraction of disease subjects.

"Specificity" is calculated by TN/(TN+FP) or the true negative fraction of non-disease or normal subjects.

"MCC" (Mathwes Correlation coefficient) is calculated as follows:

$$MCC = (TP*TN - FP*FN)/\{(TP+FN)*(TP+FP)*(TN+FP)*(TN+FN)\}^{0.5}$$

where TP, FP, TN, FN are true-positives, false-positives, true-negatives, and false-negatives, respectively. Note that MCC values range between −1 to +1, indicating completely wrong and perfect classification, respectively. An MCC of 0 indicates random classification. MCC has been shown to be a useful for combining sensitivity and specificity into a single metric (Baldi, Brunak et al. 2000). It is also useful for measuring and optimizing classification accuracy in cases of unbalanced class sizes (Baldi, Brunak et al. 2000).

By "statistically significant", it is meant that the alteration is greater than what might be expected to happen by chance alone (which could be a "false positive"). Statistical significance can be determined by any method known in the art. Commonly used measures of significance include the p-value, which presents the probability of obtaining a result at least as extreme as a given data point, assuming the data point was the result of chance alone. A result is often considered highly significant at a p-value of 0.05 or less.

A "subject" in the context of the present invention is preferably a mammal. The mammal can be a human, non-human primate, mouse, rat, dog, cat, horse, or cow, but are not limited to these examples. A subject can be male or female. A subject can be one who has been previously diagnosed or identified as having an infection, and optionally has already undergone, or is undergoing, a therapeutic intervention for the infection. Alternatively, a subject can also be one who has not been previously diagnosed as having an infection. For example, a subject can be one who exhibits one or more risk factors for having an infection.

"TN" is true negative, means negative test result that accurately reflects the tested-for activity.

"TP" is true positive, means positive test result that accurately reflects the tested-for activity.

"Traditional laboratory risk factors" correspond to biomarkers isolated or derived from subject samples and which are currently evaluated in the clinical laboratory and used in traditional global risk assessment algorithms.

Methods and Uses of the Invention

The methods disclosed herein are used to identify subjects with an infection or a specific infection type. More specifically, the methods of the invention are used to distinguish subjects having a bacterial infection, a viral infection, a mixed infection (i.e., bacterial and viral co-infection), patients with a non-infectious disease and healthy individuals. The methods of the present invention can also be used to monitor or select a treatment regimen for a subject who has a an infection, and to screen subjects who have not been previously diagnosed as having an infection, such as subjects who exhibit risk factors developing an infection. The methods of the present invention are used to identify and/or diagnose subjects who are asymptomatic for an infection. "Asymptomatic" means not exhibiting the traditional signs and symptoms.

As used herein, infection is meant to include any infectious agent of viral or bacterial origin. The bacterial infection may be the result of gram-positive or gram-negative bacteria.

The term "Gram-positive bacteria" as used herein refers to bacteria characterized by having as part of their cell wall structure peptidoglycan as well as polysaccharides and/or teichoic acids and are characterized by their blue-violet color reaction in the Gram-staining procedure.

The term "Gram-negative bacteria" as used herein refer to bacteria characterized by the presence of a double membrane surrounding each bacterial cell.

A subject having an infection is identified by measuring the amounts (including the presence or absence) of an effective number (which can be one or more) of DETERMINANTS in a subject-derived sample. A clinically significant alteration in the level of the DETERMINANT is determined. Alternatively, the amounts are compared to a reference value. Alterations in the amounts and patterns of expression DETERMINANTS in the subject sample compared to the reference value are then identified.

In various embodiments, two, three, four, five, six, seven, eight, nine, ten or more DETERMINANTS are measured. For example the combination of DETERMINANTS are selected according to any of the models enumerated in Tables 1-8.

A reference value can be relative to a number or value derived from population studies, including without limitation, such subjects having the same infection, subject having the same or similar age range, subjects in the same or similar ethnic group, or relative to the starting sample of a subject undergoing treatment for a infection. Such reference values can be derived from statistical analyses and/or risk prediction data of populations obtained from mathematical algorithms and computed indices of infection. Reference DETERMINANT indices can also be constructed and used using algorithms and other methods of statistical and structural classification.

In one embodiment of the present invention, the reference value is the amount (i.e. level) of DETERMINANTS in a control sample derived from one or more subjects who do not have an infection (i.e., healthy, and or non infectious individuals). In a further embodiment, such subjects are monitored and/or periodically retested for a diagnostically relevant period of time ("longitudinal studies") following such test to verify continued absence of infection. Such period of time may be one day, two days, two to five days, five days, five to ten days, ten days, or ten or more days from the initial testing date for determination of the reference value. Furthermore, retrospective measurement of DETERMINANTS in properly banked historical subject samples may be used in establishing these reference values, thus shortening the study time required.

A reference value can also comprise the amounts of DETERMINANTS derived from subjects who show an improvement as a result of treatments and/or therapies for the infection. A reference value can also comprise the amounts of DETERMINANTS derived from subjects who have confirmed infection by known techniques.

In another embodiment, the reference value is an index value or a baseline value. An index value or baseline value is a composite sample of an effective amount of DETERMINANTS from one or more subjects who do not have an infection. A baseline value can also comprise the amounts of DETERMINANTS in a sample derived from a subject who has shown an improvement in treatments or therapies for the infection. In this embodiment, to make comparisons to the subject-derived sample, the amounts of DETERMINANTS are similarly calculated and compared to the index value. Optionally, subjects identified as having an infection, are chosen to receive a therapeutic regimen to slow the progression or eliminate the infection.

Additionally, the amount of the DETERMINANT can be measured in a test sample and compared to the "normal control level," utilizing techniques such as reference limits, discrimination limits, or risk defining thresholds to define cutoff points and abnormal values. The "normal control level" means the level of one or more DETERMINANTS or combined DETERMINANT indices typically found in a subject not suffering from an infection. Such normal control level and cutoff points may vary based on whether a DETERMINANT is used alone or in a formula combining with other DETERMINANTS into an index. Alternatively, the normal control level can be a database of DETERMINANT patterns from previously tested subjects.

The effectiveness of a treatment regimen can be monitored by detecting a DETERMINANT in an effective amount (which may be one or more) of samples obtained from a subject over time and comparing the amount of DETERMINANTS detected. For example, a first sample can be obtained prior to the subject receiving treatment and one or more subsequent samples are taken after or during treatment of the subject.

For example, the methods of the invention can be used to discriminate between bacterial, viral and mixed infections (i.e. bacterial and viral co-infections.) This will allow patients to be stratified and treated accordingly.

The present invention also comprises a kit with a detection reagent that binds to one or more DETERMINANT polypeptides. Also provided by the invention is an array of detection reagents, e.g., antibodies that can bind to one or more DETERMINANT polypeptides. In one embodiment, the DETERMINANTS are polypeptides and the array contains antibodies that bind one or more DETERMINANTS selected from ABTB1, ADIPOR1, ARHGDIB, ARPC2, ATP6V0B, C1orf83, CD15, CES1, CORO1A, CRP, CSDA, E1F4B, EPSTI1, GAS7, HERC5, IFI6, KIAA0082, IFIT1, IFIT3, IFITM1, IFITM3, LIPT1, IL7R, ISG20, LOC26010, LY6E, LRDD, LTA4H, MAN1C1, MBOAT2, MX1, NPM1, OAS2, PARP12, PARP9, QARS, RAB13, RAB31, RAC2, RPL34, PDIA6, PTEN, RSAD2, SART3, SDCBP, SMAD9, SOCS3, TRIM 22, UBE2N, XAF1 and ZBP1 sufficient to measure a statistically significant alteration in DETERMINANT expression.

The present invention can also be used to screen patient or subject populations in any number of settings. For example, a health maintenance organization, public health entity or school health program can screen a group of subjects to identify those requiring interventions, as described above, or for the collection of epidemiological data. Insurance companies (e.g., health, life or disability) may screen applicants in the process of determining coverage or pricing, or existing clients for possible intervention. Data collected in such population screens, particularly when tied to any clinical progression to conditions like infection, will be of value in the operations of, for example, health maintenance organizations, public health programs and insurance companies. Such data arrays or collections can be stored in machine-readable media and used in any number of health-related data management systems to provide improved healthcare services, cost effective healthcare, improved insurance operation, etc. See, for example, U.S. Patent Application No. 2002/0038227; U.S. Patent Application No. US 2004/0122296; U.S. Patent Application No. US 2004/0122297; and U.S. Pat. No. 5,018,067. Such systems can access the data directly from internal data storage or remotely from one or more data storage sites as further detailed herein.

A machine-readable storage medium can comprise a data storage material encoded with machine readable data or data arrays which, when using a machine programmed with instructions for using said data, is capable of use for a variety of purposes. Measurements of effective amounts of the biomarkers of the invention and/or the resulting evaluation of risk from those biomarkers can implemented in computer programs executing on programmable computers, comprising, inter alia, a processor, a data storage system (including volatile and non-volatile memory and/or storage elements), at least one input device, and at least one output device. Program code can be applied to input data to perform the functions described above and generate output information. The output information can be applied to one or more output devices, according to methods known in the art. The computer may be, for example, a personal computer, microcomputer, or workstation of conventional design.

Each program can be implemented in a high level procedural or object oriented programming language to communicate with a computer system. However, the programs can be implemented in assembly or machine language, if desired. The language can be a compiled or interpreted language. Each such computer program can be stored on a storage media or device (e.g., ROM or magnetic diskette or others as defined elsewhere in this disclosure) readable by a general or special purpose programmable computer, for configuring and operating the computer when the storage media or device is read by the computer to perform the procedures described herein. The health-related data management system of the invention may also be considered to be implemented as a computer-readable storage medium, configured with a computer program, where the storage medium so configured causes a computer to operate in a specific and predefined manner to perform various functions described herein.

The DETERMINANTS of the present invention can be used to generate a "reference DETERMINANT profile" of those subjects who do not have an infection. The DETERMINANTS disclosed herein can also be used to generate a "subject DETERMINANT profile" taken from subjects who have an infection. The subject DETERMINANT profiles can be compared to a reference DETERMINANT profile to diagnose or identify subjects with an infection. The reference and subject DETERMINANT profiles of the present invention can be contained in a machine-readable medium, such as but not limited to, analog tapes like those readable by a VCR, CD-ROM, DVD-ROM, USB flash media, among others. Such machine-readable media can also contain additional test results, such as, without limitation, measurements of clinical parameters and traditional laboratory risk factors. Alternatively or additionally, the machine-readable media can also comprise subject information such as medical history and any relevant family history. The machine-readable media can also contain information relating to other disease-risk algorithms and computed indices such as those described herein.

Performance and Accuracy Measures of the Invention

The performance and thus absolute and relative clinical usefulness of the invention may be assessed in multiple ways as noted above. Amongst the various assessments of performance, the invention is intended to provide accuracy in clinical diagnosis and prognosis. The accuracy of a diagnostic or prognostic test, assay, or method concerns the ability of the test, assay, or method to distinguish between subjects having an infection is based on whether the subjects have, a "significant alteration" (e.g., clinically significant "diagnostically significant) in the levels of a DETERMINANT. By "effective amount" it is meant that the measurement of an appropriate number of DETERMINANTS (which may be one or more) to produce a "significant alteration" (e.g. level of expression or activity of a DETERMINANT) that is different than the predetermined cut-off point (or threshold value) for that DETERMINANT(S) and therefore indicates that the subject has an infection for which the DETERMINANT(S) is a determinant. The difference in the level of DETERMINANT is preferably statistically significant. As noted below, and without any limitation of the invention, achieving statistical significance, and thus the preferred analytical, diagnostic, and clinical accuracy, generally but not always requires that combinations of several DETERMINANTS to be used together in panels and combined with mathematical algorithms in order to achieve a statistically significant DETERMINANT index.

In the categorical diagnosis of a disease state, changing the cut point or threshold value of a test (or assay) usually changes the sensitivity and specificity, but in a qualitatively inverse relationship. Therefore, in assessing the accuracy and usefulness of a proposed medical test, assay, or method for assessing a subject's condition, one should always take both sensitivity and specificity into account and be mindful of what the cut point is at which the sensitivity and specificity are being reported because sensitivity and specificity may vary significantly over the range of cut points. One way to achieve this is by using the MCC metric, which depends upon both sensitivity and specificity. Use of statistics such as AUC, encompassing all potential cut point values, is preferred for most categorical risk measures using the invention, while for continuous risk measures, statistics of goodness-of-fit and calibration to observed results or other gold standards, are preferred.

By predetermined level of predictability it is meant that the method provides an acceptable level of clinical or diagnostic specificity and sensitivity.

By predetermined level of predictability it is meant that the method provides an acceptable level of clinical or diagnostic accuracy. Using such statistics, an "acceptable degree of diagnostic accuracy", is herein defined as a test or assay (such as the test of the invention for determining the clinically significant presence of DETERMINANTS, which thereby indicates the presence a type of infection) in which the AUC (area under the ROC curve for the test or assay) is at least 0.60, desirably at least 0.65, more desirably at least 0.70, preferably at least 0.75, more preferably at least 0.80, and most preferably at least 0.85.

By a "very high degree of diagnostic accuracy", it is meant a test or assay in which the AUC (area under the ROC curve for the test or assay) is at least 0.75, 0.80, desirably at least 0.85, more desirably at least 0.875, preferably at least 0.90, more preferably at least 0.925, and most preferably at least 0.95.

Alternatively, the methods predict the presence or absence of an infection or response to therapy with at least 75% accuracy, more preferably 80%, 85%, 90%, 95%, 97%, 98%, 99% or greater accuracy.

The method predicts the presence or absence of an infection or response to therapy with an MCC>= to 0.4, 0.5, 0.6, 0.7. 0.8, 0.9 or 1.0.

The predictive value of any test depends on the sensitivity and specificity of the test, and on the prevalence of the condition in the population being tested. This notion, based on Bayes' theorem, provides that the greater the likelihood that the condition being screened for is present in an individual or in the population (pre-test probability), the greater the validity of a positive test and the greater the likelihood that the result is a true positive. Thus, the problem with using a test in any population where there is a low likelihood of the condition being present is that a positive result has limited value (i.e., more likely to be a false positive). Similarly, in populations at very high risk, a negative test result is more likely to be a false negative.

As a result, ROC and AUC can be misleading as to the clinical utility of a test in low disease prevalence tested populations (defined as those with less than 1% rate of occurrences (incidence) per annum, or less than 10% cumulative prevalence over a specified time horizon).

A health economic utility function is an yet another means of measuring the performance and clinical value of a given test, consisting of weighting the potential categorical test outcomes based on actual measures of clinical and economic value for each. Health economic performance is closely related to accuracy, as a health economic utility function specifically assigns an economic value for the benefits of correct classification and the costs of misclassification of tested subjects. As a performance measure, it is not unusual to require a test to achieve a level of performance which results in an increase in health economic value per test (prior to testing costs) in excess of the target price of the test.

In general, alternative methods of determining diagnostic accuracy are commonly used for continuous measures, when a disease category has not yet been clearly defined by the relevant medical societies and practice of medicine, where thresholds for therapeutic use are not yet established, or where there is no existing gold standard for diagnosis of the pre-disease. For continuous measures of risk, measures of diagnostic accuracy for a calculated index are typically based on curve fit and calibration between the predicted continuous value and the actual observed values (or a historical index calculated value) and utilize measures such as R squared, Hosmer-Lemeshow P-value statistics and confidence intervals. It is not unusual for predicted values using such algorithms to be reported including a confidence interval (usually 90% or 95% CI) based on a historical observed cohort's predictions, as in the test for risk of future breast cancer recurrence commercialized by Genomic Health, Inc. (Redwood City, Calif.).

In general, by defining the degree of diagnostic accuracy, i.e., cut points on a ROC curve, defining an acceptable AUC value, and determining the acceptable ranges in relative concentration of what constitutes an effective amount of the DETERMINANTS of the invention allows for one of skill in the art to use the DETERMINANTS to identify, diagnose, or prognose subjects with a pre-determined level of predictability and performance.

Furthermore, other unlisted biomarkers will be very highly correlated with the DETRMINANTS (for the purpose of this application, any two variables will be considered to be "very highly correlated" when they have a Coefficient of Determination ($R^2$) of 0.5 or greater). The present invention encompasses such functional and statistical equivalents to the aforementioned DETERMINANTS. Furthermore, the statistical utility of such additional DETERMINANTS is substantially dependent on the cross-correlation between multiple biomarkers and any new biomarkers will often be required to operate within a panel in order to elaborate the meaning of the underlying biology.

One or more, preferably two or more of the listed DETERMINANTS can be detected in the practice of the present invention. For example, two (2), three (3), four (4), five (5), ten (10), fifteen (15), twenty (20), forty (40), or more DETERMINANTS can be detected.

In some aspects, all DETERMINANTS listed herein can be detected. Preferred ranges from which the number of DETERMINANTS can be detected include ranges bounded by any minimum selected from between one and, particularly two, three, four, five, six, seven, eight, nine ten, twenty, or forty Particularly preferred ranges include two to five (2-5), two to ten (2-10), two to twenty (2-20), or two to forty (2-40).

Construction of DETERMINANT Panels

Groupings of DETERMINANTS can be included in "panels." A "panel" within the context of the present invention means a group of biomarkers (whether they are DETERMINANTS, clinical parameters, or traditional laboratory risk factors) that includes more than one DETERMINANT. A panel can also comprise additional biomarkers, e.g., clinical parameters, traditional laboratory risk factors, known to be present or associated with infection, in combination with a selected group of the DETERMINANTS listed herein.

As noted above, many of the individual DETERMINANTS, clinical parameters, and traditional laboratory risk factors listed, when used alone and not as a member of a multi-biomarker panel of DETERMINANTS, have little or no clinical use in reliably distinguishing individual normal subjects, subjects at risk for having an infection (e.g., bacterial, viral or co-infection), and thus cannot reliably be used alone in classifying any subject between those three states. Even where there are statistically significant differences in their mean measurements in each of these populations, as commonly occurs in studies which are sufficiently powered, such biomarkers may remain limited in their applicability to an individual subject, and contribute little to diagnostic or prognostic predictions for that subject. A common measure of statistical significance is the p-value, which indicates the probability that an observation has arisen by chance alone; preferably, such p-values are 0.05 or less, representing a 5% or less chance that the observation of interest arose by chance. Such p-values depend significantly on the power of the study performed.

Despite this individual DETERMINANT performance, and the general performance of formulas combining only the traditional clinical parameters and few traditional laboratory risk factors, the present inventors have noted that certain specific combinations of two or more DETERMINANTS can also be used as multi-biomarker panels comprising combinations of DETERMINANTS that are known to be involved in one or more physiological or biological pathways, and that such information can be combined and made clinically useful through the use of various formulae, including statistical classification algorithms and others, combining and in many cases extending the performance characteristics of the combination beyond that of the individual DETERMINANTS. These specific combinations show an acceptable level of diagnostic accuracy, and, when sufficient information from multiple DETERMINANTS is combined in a trained formula, often reliably achieve a high level of diagnostic accuracy transportable from one population to another.

The general concept of how two less specific or lower performing DETERMINANTS are combined into novel and more useful combinations for the intended indications, is a key aspect of the invention. Multiple biomarkers can often yield better performance than the individual components when proper mathematical and clinical algorithms are used; this is often evident in both sensitivity and specificity, and results in a greater AUC. Secondly, there is often novel unperceived information in the existing biomarkers, as such was necessary in order to achieve through the new formula an improved level of sensitivity or specificity. This hidden information may hold true even for biomarkers which are generally regarded to have suboptimal clinical performance on their own. In fact, the suboptimal performance in terms of high false positive rates on a single biomarker measured alone may very well be an indicator that some important additional information is contained within the biomarker results—information which would not be elucidated absent the combination with a second biomarker and a mathematical formula.

Several statistical and modeling algorithms known in the art can be used to both assist in DETERMINANT selection choices and optimize the algorithms combining these choices. Statistical tools such as factor and cross-biomarker correlation/covariance analyses allow more rationale approaches to panel construction. Mathematical clustering and classification tree showing the Euclidean standardized distance between the DETERMINANTS can be advantageously used. Pathway informed seeding of such statistical classification techniques also may be employed, as may rational approaches based on the selection of individual DETERMINANTS based on their participation across in particular pathways or physiological functions.

Ultimately, formula such as statistical classification algorithms can be directly used to both select DETERMINANTS and to generate and train the optimal formula necessary to combine the results from multiple DETERMINANTS into a single index. Often, techniques such as forward (from zero potential explanatory parameters) and backwards selection (from all available potential explanatory parameters) are used, and information criteria, such as AIC or BIC, are used to quantify the tradeoff between the performance and diagnostic accuracy of the panel and the number of DETERMINANTS used. The position of the individual DETERMINANT on a forward or backwards selected panel can be closely related to its provision of incremental information content for the algorithm, so the order of contribution is highly dependent on the other constituent DETERMINANTS in the panel.

Construction of Clinical Algorithms

Any formula may be used to combine DETERMINANT results into indices useful in the practice of the invention. As indicated above, and without limitation, such indices may indicate, among the various other indications, the probability, likelihood, absolute or relative risk, time to or rate of conversion from one to another disease states, or make predictions of future biomarker measurements of infection. This may be for a specific time period or horizon, or for remaining lifetime risk, or simply be provided as an index relative to another reference subject population.

Although various preferred formula are described here, several other model and formula types beyond those mentioned herein and in the definitions above are well known to one skilled in the art. The actual model type or formula used may itself be selected from the field of potential models based on the performance and diagnostic accuracy characteristics of its results in a training population. The specifics of the formula itself may commonly be derived from DETERMINANT results in the relevant training population. Amongst other uses, such formula may be intended to map the feature space derived from one or more DETERMINANT inputs to a set of subject classes (e.g. useful in predicting class membership of subjects as normal, having an infection), to derive an estimation of a probability function of risk using a Bayesian approach, or to estimate the class-conditional probabilities, then use Bayes' rule to produce the class probability function as in the previous case.

Preferred formulas include the broad class of statistical classification algorithms, and in particular the use of discriminant analysis. The goal of discriminant analysis is to predict class membership from a previously identified set of features. In the case of linear discriminant analysis (LDA), the linear combination of features is identified that maximizes the separation among groups by some criteria. Features can be identified for LDA using an eigengene based approach with different thresholds (ELDA) or a stepping algorithm based on a multivariate analysis of variance (MANOVA). Forward, backward, and stepwise algorithms can be performed that minimize the probability of no separation based on the Hotelling-Lawley statistic.

Eigengene-based Linear Discriminant Analysis (ELDA) is a feature selection technique developed by Shen et al. (2006). The formula selects features (e.g. biomarkers) in a multivariate framework using a modified eigen analysis to identify features associated with the most important eigenvectors. "Important" is defined as those eigenvectors that explain the most variance in the differences among samples that are trying to be classified relative to some threshold.

A support vector machine (SVM) is a classification formula that attempts to find a hyperplane that separates two classes. This hyperplane contains support vectors, data points that are exactly the margin distance away from the hyperplane. In the likely event that no separating hyperplane exists in the current dimensions of the data, the dimensionality is expanded greatly by projecting the data into larger dimensions by taking non-linear functions of the original variables (Venables and Ripley, 2002). Although not required, filtering of features for SVM often improves prediction. Features (e.g., biomarkers) can be identified for a support vector machine using a non-parametric Kruskal-Wallis (KW) test to select the best univariate features. A random forest (RF, Breiman, 2001) or recursive partitioning (RPART, Breiman et al., 1984) can also be used separately or in combination to identify biomarker combinations that are most important. Both KW and RF require that a number of features be selected from the total. RPART creates a single classification tree using a subset of available biomarkers.

Other formula may be used in order to pre-process the results of individual DETERMINANT measurement into more valuable forms of information, prior to their presentation to the predictive formula. Most notably, normalization of biomarker results, using either common mathematical transformations such as logarithmic or logistic functions, as normal or other distribution positions, in reference to a population's mean values, etc. are all well known to those skilled in the art. Of particular interest are a set of normalizations based on Clinical Parameters such as age, gender, race, or sex, where specific formula are used solely on subjects within a class or continuously combining a Clinical Parameter as an input. In other cases, analyte-based biomarkers can be combined into calculated variables which are subsequently presented to a formula.

In addition to the individual parameter values of one subject potentially being normalized, an overall predictive formula for all subjects, or any known class of subjects, may itself be recalibrated or otherwise adjusted based on adjustment for a population's expected prevalence and mean biomarker parameter values, according to the technique outlined in D'Agostino et al, (2001) JAMA 286:180-187, or other similar normalization and recalibration techniques. Such epidemiological adjustment statistics may be captured, confirmed, improved and updated continuously through a registry of past data presented to the model, which may be machine readable or otherwise, or occasionally through the retrospective query of stored samples or reference to historical studies of such parameters and statistics. Additional examples that may be the subject of formula recalibration or other adjustments include statistics used in studies by Pepe, M. S. et al, 2004 on the limitations of odds ratios; Cook, N. R., 2007 relating to ROC curves. Finally, the numeric result of a classifier formula itself may be transformed post-processing by its reference to an actual clinical population and study results and observed endpoints, in order to calibrate to absolute risk and provide confidence intervals for varying numeric results of the classifier or risk formula.

Measurement of DETERMINANTS

The actual measurement of levels or amounts of the DETERMINANTS can be determined at the protein level using any method known in the art. For example, by measuring the levels of peptides encoded by the gene products described herein, or subcellular localization or activities thereof. Such methods are well known in the art and include, e.g., immunoassays based on antibodies to proteins, aptamers or molecular imprints. Any biological material can be used for the detection/quantification of the protein or its activity. Alternatively, a suitable method can be selected to determine the activity of proteins encoded by the marker genes according to the activity of each protein analyzed.

The DETERMINANT proteins, polypeptides, mutations, and polymorphisms thereof can be detected in any suitable manner, but is typically detected by contacting a sample from the subject with an antibody which binds the DETERMINANT protein, polypeptide, mutation, polymorphism, or post translational modification additions (e.g. carbohydrates) and then detecting the presence or absence of a reaction product. The antibody may be monoclonal, polyclonal, chimeric, or a fragment of the foregoing, as discussed in detail above, and the step of detecting the reaction product may be carried out with any suitable immunoassay. The sample from the subject is typically a biological sample as described above, and may be the same sample of biological sample used to conduct the method described above.

Immunoassays carried out in accordance with the present invention may be homogeneous assays or heterogeneous assays. In a homogeneous assay the immunological reaction usually involves the specific antibody (e.g., anti-DETERMINANT protein antibody), a labeled analyte, and the sample of interest. The signal arising from the label is modified, directly or indirectly, upon the binding of the antibody to the labeled analyte. Both the immunological reaction and detection of the extent thereof can be carried out in a homogeneous solution. Immunochemical labels which may be employed include free radicals, radioisotopes, fluorescent dyes, enzymes, bacteriophages, or coenzymes.

In a heterogeneous assay approach, the reagents are usually the sample, the antibody, and means for producing a detectable signal. Samples as described above may be used. The antibody can be immobilized on a support, such as a bead (such as protein A and protein G agarose beads), plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the sample. Means for producing a detectable signal include the use of radioactive labels, fluorescent labels, or enzyme labels. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are oligonucleotides, immunoblotting, immunofluorescence methods, immunoprecipitation, chemiluminescence methods, electrochemiluminescence (ECL) or enzyme-linked immunoassays.

Those skilled in the art will be familiar with numerous specific immunoassay formats and variations thereof which may be useful for carrying out the method disclosed herein. See generally E. Maggio, Enzyme-Immunoassay, (1980) (CRC Press, Inc., Boca Raton, Fla.); see also U.S. Pat. No. 4,727,022 to Skold et al. titled "Methods for Modulating Ligand-Receptor Interactions and their Application," U.S. Pat. No. 4,659,678 to Forrest et al. titled "Immunoassay of Antigens," U.S. Pat. No. 4,376,110 to David et al., titled "Immunometric Assays Using Monoclonal Antibodies," U.S. Pat. No. 4,275,149 to Litman et al., titled "Macromolecular Environment Control in Specific Receptor Assays," U.S. Pat. No. 4,233,402 to Maggio et al., titled "Reagents and Method Employing Channeling," and U.S. Pat. No. 4,230,767 to Boguslaski et al., titled "Heterogenous Specific Binding Assay Employing a Coenzyme as Label." The DETERMINANT can also be detected with antibodies using flow cytometry. Those skilled in the art will be familiar with flow cytometric techniques which may be useful in carrying out the methods disclosed herein. (See, H. M. Shapiro, Practical Flow Cytometry, (2003))

Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies as described herein may likewise be conjugated to detectable labels or groups such as radiolabels (e.g., $^{35}$S, $^{125}$I, $^{131}$I), enzyme labels (e.g., horseradish peroxidase, alkaline phosphatase), and fluorescent labels (e.g., fluorescein, Alexa, green fluorescent protein, rhodamine) in accordance with known techniques.

Antibodies can also be useful for detecting post-translational modifications of DETERMINANT proteins, polypeptides, mutations, and polymorphisms, such as tyrosine phosphorylation, threonine phosphorylation, serine phosphorylation, glycosylation (e.g., O-GlcNAc). Such antibodies specifically detect the phosphorylated amino acids in a protein or proteins of interest, and can be used in immunoblotting, immunofluorescence, and ELISA assays described herein. These antibodies are well-known to those skilled in the art, and commercially available. Post-translational modifications can also be determined using metastable ions in reflector matrix-assisted laser desorption ionization-time of flight mass spectrometry (MALDI-TOF) (Wirth, U. et al. (2002) Proteomics 2(10): 1445-51).

For DETERMINANT proteins, polypeptides, mutations, and polymorphisms known to have enzymatic activity, the activities can be determined in vitro using enzyme assays known in the art. Such assays include, without limitation, kinase assays, phosphatase assays, reductase assays, among many others. Modulation of the kinetics of enzyme activities can be determined by measuring the rate constant $K_M$ using known algorithms, such as the Hill plot, Michaelis-Menten equation, linear regression plots such as Lineweaver-Burk analysis, and Scatchard plot.

Kits

The invention also includes a DETERMINANT-detection reagent, or antibodies packaged together in the form of a kit. The kit may contain in separate containers an antibody (either already bound to a solid matrix or packaged separately with reagents for binding them to the matrix), control formulations (positive and/or negative), and/or a detectable label such as fluorescein, green fluorescent protein, rhodamine, cyanine dyes, Alexa dyes, luciferase, radiolabels, among others. Instructions (e.g., written, tape, VCR, CD-ROM, etc.) for carrying out the assay may be included in the kit. The assay may for example be in the form of a sandwich ELISA as known in the art.

For example, DETERMINANT detection reagents can be immobilized on a solid matrix such as a porous strip to form at least one DETERMINANT detection site. The measurement or detection region of the porous strip may include a plurality of sites. A test strip may also contain sites for negative and/or positive controls. Alternatively, control sites can be located on a separate strip from the test strip. Optionally, the different detection sites may contain different amounts of immobilized detection reagents, e.g., a higher amount in the first detection site and lesser amounts in subsequent sites. Upon the addition of test sample, the number of sites displaying a detectable signal provides a quantitative indication of the amount of DETERMINANTS present in the sample. The detection sites may be configured in any suitably detectable shape and are typically in the shape of a bar or dot spanning the width of a test strip.

Suitable sources for antibodies for the detection of DETERMINANTS include commercially available sources such as, for example, Abazyme, Abnova, Affinity Biologicals, AntibodyShop, Aviva bioscience, Biogenesis, Biosense Laboratories, Calbiochem, Cell Sciences, Chemicon International, Chemokine, Clontech, Cytolab, DAKO, Diagnostic BioSystems, eBioscience, Endocrine Technologies, Enzo Biochem, Eurogentec, Fusion Antibodies, Genesis Biotech, GloboZymes, Haematologic Technologies, Immunodetect, Immunodiagnostik, Immunometrics, Immunostar, Immunovision, Biogenex, Invitrogen, Jackson ImmunoResearch Laboratory, KMI Diagnostics, Koma Biotech, LabFrontier Life Science Institute, Lee Laboratories, Lifescreen, Maine Biotechnology Services, Mediclone, MicroPharm Ltd., ModiQuest, Molecular Innovations, Molecular Probes, Neoclone, Neuromics, New England Biolabs, Novocastra, Novus Biologicals, Oncogene Research Products, Orbigen, Oxford Biotechnology, Panvera, PerkinElmer Life Sciences, Pharmingen, Phoenix Pharmaceuticals, Pierce Chemical Company, Polymun Scientific, Polysiences, Inc., Promega Corporation, Proteogenix, Protos Immunoresearch, QED Biosciences, Inc., R&D Systems, Repligen, Research Diagnostics, Roboscreen, Santa Cruz Biotechnology, Seikagaku America, Serological Corporation, Serotec, SigmaAldrich, StemCell Technologies, Synaptic Systems GmbH, Technopharm, Terra Nova Biotechnology, TiterMax, Trillium Diagnostics, Upstate Biotechnology, US Biological, Vector Laboratories, Wako Pure Chemical Industries, and Zeptometrix. However, the skilled artisan can routinely make antibodies, against any of the polypeptide DETERMINANTS described herein.

EXAMPLES

Example 1: General Methods

In-Vivo Clinical Study Protocol

Figure 2:
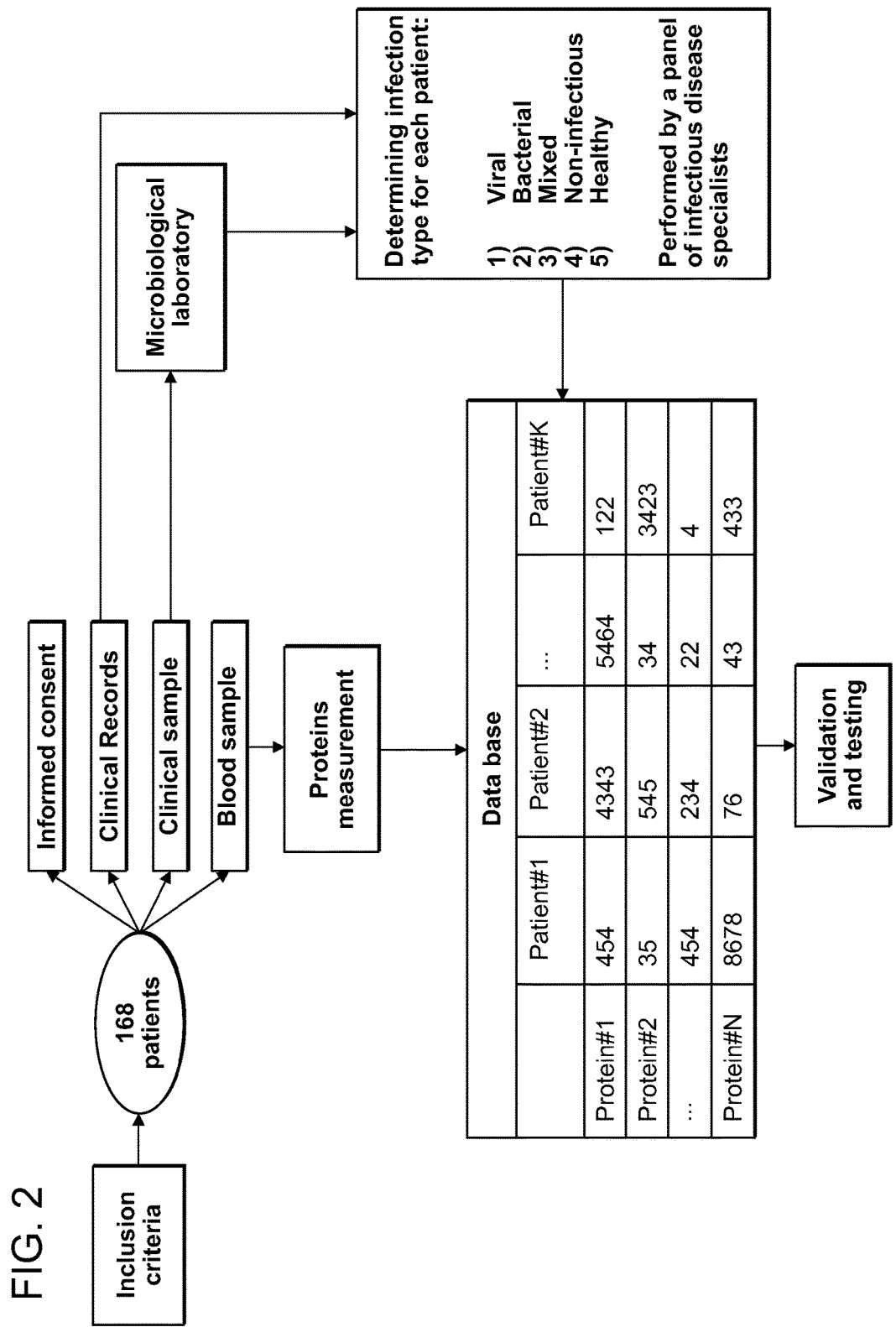
FIG. 2 is an illustration of the clinical study workflow.

To screen for potential DETERMINANTS that can separate between different sources of infection we performed a clinical study on 168 hospital patients. Study workflow is depicted in FIG. 2. Briefly, after signing an informed consent, 2-6 ml of peripheral venous blood was collected in EDTA containing CBC tubes. The blood was than stored in 4 degrees Celsius for 1-4 hours. Depending on the type of infection, patient specimens were also collected (e.g. nasal swab and urine) for microbiological analysis. The clinical history, the clinical lab results, the imaging data and the microbiological results are used to identify the source of infection by an infectious disease expert. DETERMINANT measurements and infection source related data were stored in a database that was used to screen and then test the differential accuracy of each individual DETERMINANT and the multi-DETERMINANT signature.

Patient Inclusion & Exclusion Criteria

Patient inclusion criteria were:
i) Acute infectious disease patients with a peak fever higher than 37.5° C. and 38.3° C. in adults and children respectively during the last 7 days, with symptoms that began no more than 8 days prior to inclusion date or,
ii) Healthy individuals or,
iii) Patients with a non-infectious disease Subject, or legal guardian, signed the informed consent was obtained in all cases.

Patient exclusion criteria were:
i. An acute infectious disease during the last four weeks,
ii. A Congenital Immune Deficiency,
iii. Patients under immunosuppressive regimen:
　Active chemotherapy
　Post-transplant drugs
　High dose steroids>80 mg prednisone per day or equivalent
　Active radiotherapy
　Cytotoxic drugs (anti-TNF drugs, Cyclosporine, Tacrolimus, Monoclonal Abs, Mycophenolate, MTX, Azathioprine, WIG)

iv. Patients under immune-simulative regimen:
   IL-2
   G-CSF/GM-CSF
   Interferons
v. Patients with an active hematological malignancy (e.g. CLL),
vi. Patients that had another infectious disease in the past 3 weeks,
vii. Patients with active malignancy of solid organ (e.g. NSCLC)
viii. Patients with myeloproliferative or myelodysplastic disorder. Patients who are HIV-1 or HCV carriers.

Determining Patient Source of Infection

The following criteria were used in order to determine whether a patient had a viral or bacterial infection:

Examples of Criteria for Bacterial Infections

1) Bacteremia: A positive blood culture/positive blood PCR.
2) Urinary tract infection: A positive urine culture ($>10^5$/ml for midstream, $>10^4$/ml for catheter collection, $>10^3$ for Supra pubic aspiration) of a pathogenic bacteria identified by culture accompanied by urinary complains or acute infection symptoms.
3) Pyelonephritis: UTI with cortical defects in technetium 99M-DMSA or abdominal US.
4) Lobar pneumonia: consolidation in a lobar territory diagnosed on a CXR by radiologist accompanied with clinical signs and symptoms of LRTI.
5) Bacterial meningitis: cerebrospinal fluid (CSF) pleocytosis of >10 cells/ul or positive culture or positive bacterial PCR.
6) Deep abscess: As assessed by CT scan or surgical exploration.
7) Septic arthritis: synovial fluid with >50,000 WBCs/ml and >80% neutrophils or a positive culture/PCR/Gram stain.
8) Atypical Pneumonia, a positive PCR for M. pneumonia (MP) accompanied with clinical signs and symptoms of LRTI.
9) Cellulites, Warmth skin, Erythema, edema, and tenderness of the affected area and a positive bacterial culture of a gram-positive cocci.

Examples of Criteria for Viral Infections:

1) Bronchiolitis, a positive RSV antigen/PCR with clinical findings of bronchiolitis (e.g. tachypnea, diffuse expiratory wheezing, intercostal retractions). Disease should resolve within five days without Abx.
2) Viral Pneumonia: clinical signs and symptoms of LRTI with a positive PCR for a respiratory virus (listed in 6.1) in the absence of radiological sign of consolidation and the presence of two or more of the following radiographic findings:
   a. Para-hilar/peri-bronchial infiltrates.
   b. Hyperinflation.
   c. Segmental/lobar atelectasis.
   d. Hilar adenopathy.
   e. Patchy diffuse consolidation
3) Croup or Laryngotracheobronchitis, a positive PCR for one of the following: Parainfluenza/Influenza A/RSV/Adenovirus in the presence of clinical features of croup (stridor, predominantly inspiratory, Normal voice or laryngitis, no drooling, nocturnal attack, self-limiting). Disease resolved within 5 days without Abx
4) Infectious mononucleosis, a positive PCR/IgM serology for Epstein-Ban virus (EBV) or Cytomegalovirus (CMV) accompanied by at least one of the following: lymphocytosis, more than 10% atypical lymphocytes on peripheral smear, positive blood PCR for EBV or CMV and Lymphadenopathy.
5) Viral Otitis Media, positive PCR of a respiratory virus isolated from middle ear aspirate in the absence of bacterial pathogens and clinical symptoms of acute Otitis Media. Disease resolved within 5 days without Abx.
6) Viral gastroenteritis—a positive PCR of Adenovirus/Rotavirus/Noroviruses or Rota antigen in the stool accompanied with clinical signs and symptoms of acute gastroenteritis (less than 1w) and negative stool culture for Salmonella, Shigella or Campylobacter. Disease resolve within 7 days without Abx
7) Aseptic meningitis, a positive PCR of CSF sample for one of the following: Enterovirus, HSV1/2, VZV, EBV or CMV accompanied with clinical signs and symptoms of meningitis/meningoenchephalitis (meningismus, with benign clinical course or resolution without Abx.
8) Roseola Infantum, positive HHV-6 PCR from the blood/positive HHV-6 serology in the presence of fever, Maculopapular/erythematous rash with/without Nagayama spots and diarrhea.
9) Erythema Infectiosum, positive human parvovirus B19 PCR or positive IgM test in the presence of clinics (slapped-cheek appearance, macular eruption on the extremities, polyarthropathy, self-limiting).
10) Hand-foot-and-mouth disease, a positive PCR for coxsackie virus or Enterovirus 71 or HSV in the presence of vesicular lesions on the mouth and exanthema on the hands and/or feet in association with fever.
11) Varicella—positive PCR for VZV or positive seroconversion in the presence of different stages of the vesicular rash.

Many of the infectious disease patients do not fall into the above mentioned criteria for viral and bacterial infections. In order to diagnose the source of infection in these patients their medical records were examined by an infectious disease (ID) specialist. Each patient was classified as having either a bacterial, viral, mixed or non-infectious disease. To assist ID specialists in accurate diagnosis the following pathogens were tested for:

1) Adenovirus A/B/C/D/E
2) Corona virus 229E
3) Corona virus NL63
4) Corona virus OC43
5) Parainfluenza virus 1
6) Parainfluenza virus 2
7) Parainfluenza virus 3
8) Parainfluenza virus 4
9) Rhinovirus A/B/C
10) Influenza A virus
11) Influenza B virus
12) Respiratory syncytial virus A
13) Respiratory syncytial virus B
14) Boca virus 1/2/3/4
15) Enterovirus
16) *Bordetella pertussis*
17) Mycoplasma Pneumoniae
18) Chlamydia Pneumoniae
19) Legionella Pneumonia
20) S. Pneumoniae (in adults only (i.e., above 18 years of age))
21) H. Influenza (in adults only (i.e., above 18 years of age))

Patients also underwent a CRP test, complete blood count and basic chemistry. Lastly, depending on the site of infection the following tests were also performed:

Urinary tract infections:
  Urine culture
  Urine test strip
Gastrointestinal infections:
  Stool culture for Salmonella, Shigella and Campylobacter
  In pediatrics patients only—Rota Ag in stool
In systemic infections:
  Blood culture
  Serology for EBV and CMV
In lower respiratory infections:
  CXR
  Saturation DETERMINANT Measurements & Normalization Whole blood was fractionated to cellular and serum fractions and subsequantially treated with red blood cell lysing buffer (BD Bioscience). White blood cells were subsequently washed three times with phosphate buffered saline pH 7.3. In order to measure the levels of membrane associated DETERMINANT polypeptides, the cells were incubated with primary antibodies for 40 minutes, washed twice and incubated with PE conjugated secondary antibody (Jackson Laboratories, emission 575 nm) for additional 20 minutes. In case of intracellular DETERMINANT polypeptides, cells were first fixed and permeabilized with fixation and permeabilization buffer kit (eBioscience). Following fixation and permeabilization cells were incubated with primary antibodies for 40 minutes, washed twice and incubated with PE conjugated secondary antibody for additional 20 minutes. IgG Isotype controls were used for each mode of staining as negative control background. Following the staining procedure, cells were analyzed by using an LSRII flow cytometer. Granulocytes, monocytes and lymphocytes were distinguished from each other by using an SSC/FSC dot plot. Background and specific staining were determined for lymphocytes, monocytes and granulocytes for each specific antigen. Total leukocytes mean levels was computed by summing the DETERMINANT polypeptides levels of all the cell types and dividing by the white blood count.

DETERMINANT levels were normalized to the population mean. To avoid numerical errors due to outlier measurements (>mean±3×std), these measurements were truncated and assigned the value mean±3×std.

DETERMINANT Diagnosis Statistical Analysis

Single DETERMINANT Statistical Significance

Classification accuracy was measured in terms of sensitivity, specificity, PPV, NPV and Mathews correlation coefficient (MCC) defined as follows:

Sensitivity=TP/(TP+FN),

Specificity=TN/(TN+FP),

PPV=TP(TP+FP),

NPV=TN/(TN+FN),

MCC=(TP*TN−FP*FN)/{(TP+FN)*(TP+FP)*(TN+FP)*(TN+FN)}^0.5, where TP, FP, TN, FN are true-positives, false-positives, true-negatives, and false-negatives, respectively. Note that MCC values range between −1 to +1, indicating completely wrong and perfect classification, respectively. An MCC of 0 indicates random classification. It has been shown that the MCC is especially useful for measuring and optimizing classification accuracy in cases of unbalanced class sizes (Baldi, Brunak et al. 2000). The differential diagnosis of DETERMINANTS was evaluated using a linear classification scheme, in which the cutoff that maximizes the MCC on the train set was computed and then used to classify the patients in the test set. To obtain the accuracy over the entire dataset we repeated this process using a leave-10%-cross validation scheme. The differential diagnosis of proteins was also evaluated using a Wilcoxon-Rank-Sum test.

Multi-DETERMINANT Signature Statistical Significance

The diagnostic accuracy of the multi-DETERMINANT signatures was determined using a leave-10%-out cross validation scheme for training and testing a support vector machine (SVM) with a linear kernel (CJC Burges, 1998). Classification accuracy was measured using the same criteria as in the single DETERMINANT. We also tested the classification accuracy using other multiparamteric models including: (i) an RBF kernel SVM, (ii) an artificial neural network (one hidden layer with three nodes, one output node and tansig transfer functions), (iii) a naïve bayes network and (iv) a k-nearest-neighbor classification algorithm. For most of the tested DETERMINANT combinations the linear SVM yielded either superior or equivalent MCC classification results compared the other models. We therefore report herein only the results of the linear SVM. To assess the improvement attained when combining multiple DETERMINANTS compared to single DETERMINANTS we used the dMCC criterion computed as follows: $MCC_{i,j}$−max ($MCC_i$, $MCC_j$), where $MCC_i$, $MCC_j$ and $MCC_{i,j}$ correspond to the MCC obtained for DETERMINANT i and j individually and for the pair.

Patient Cohort Characteristics

Figure 3A:
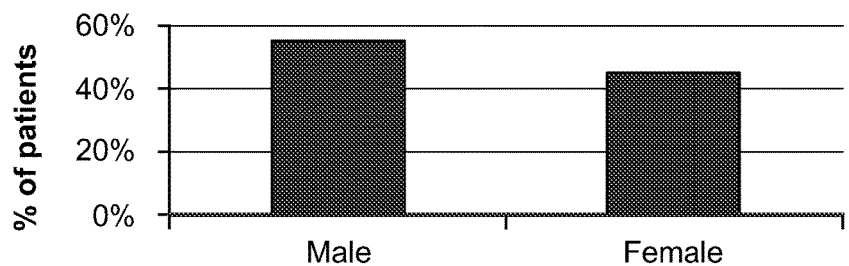
FIG. 3 is a series of bar charts showing patient and infection characteristics.
Figure 3B:
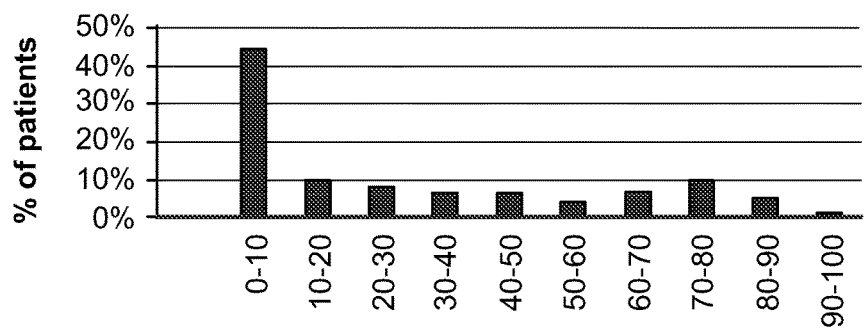
Figure 3C:
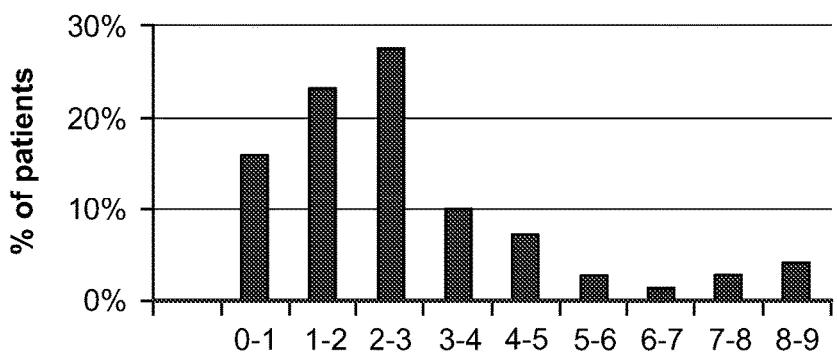
Figure 3D:
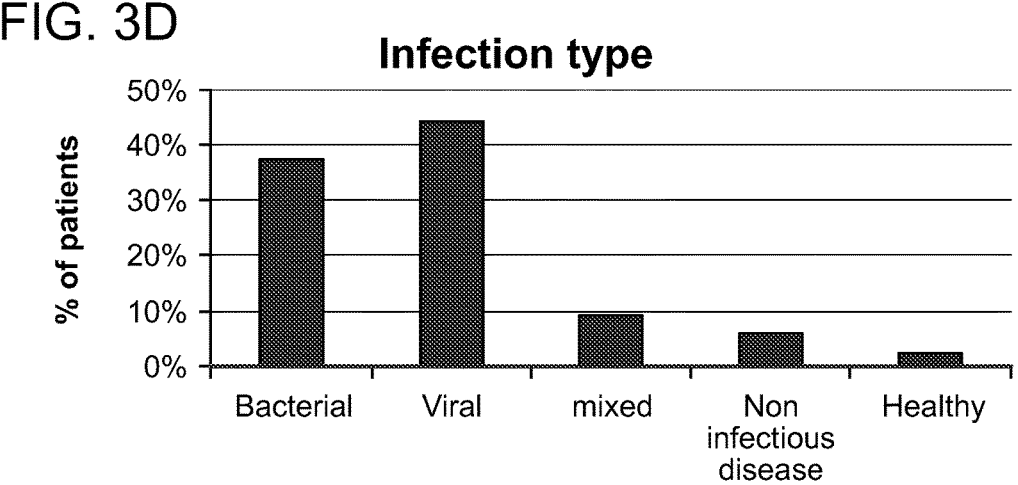
Figure 3E:
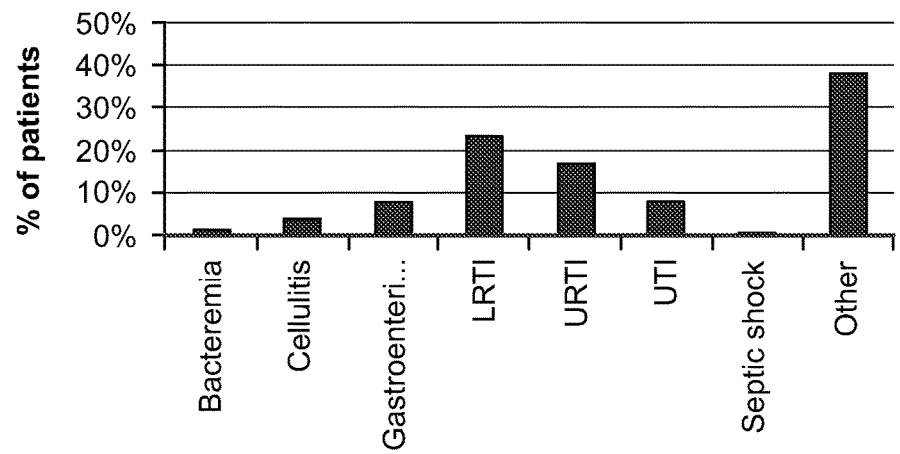
Figure 3F:
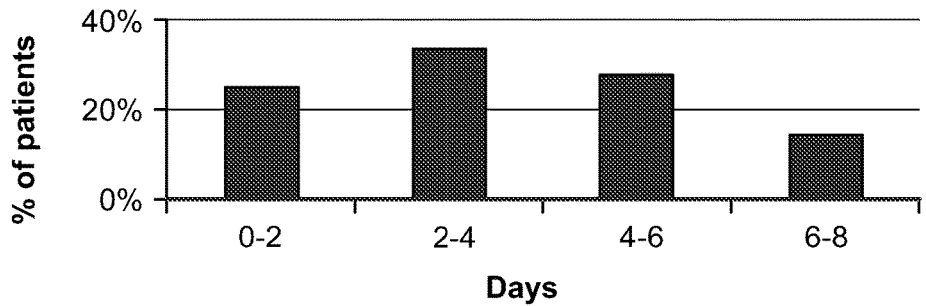
Figure 3G:
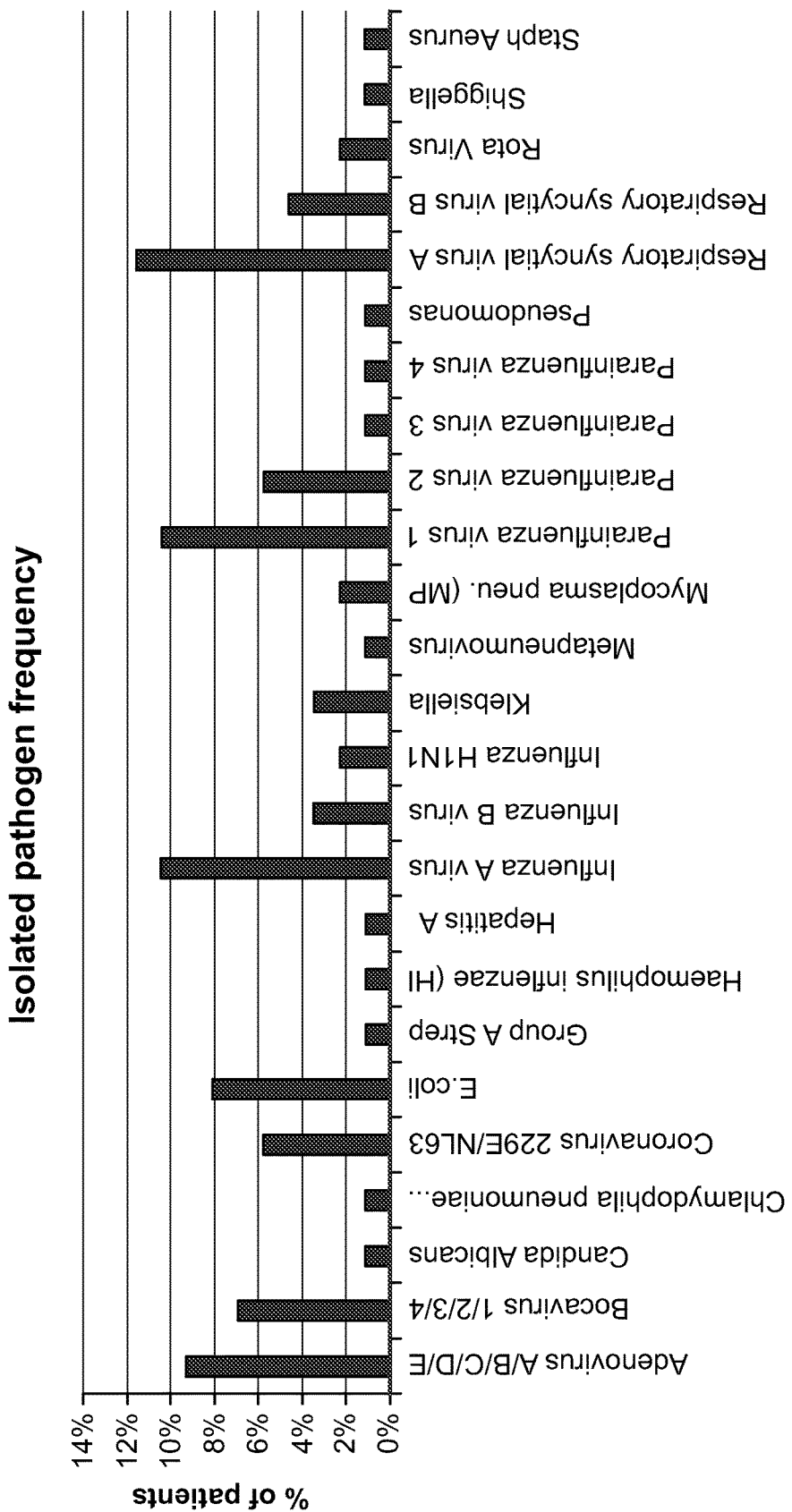

A cohort of 168 patients and healthy individuals were recruited at the Bnei-Zion hospital and the Hillel Yafe medical center in Israel. The number of male and female patients was roughly equal (FIG. 3A). Patient ages ranged between 1 month and 93 years with average 28.3+−28.4 and median 17 (for details see FIGS. 3B and 3C). Each patient was classified as viral, bacterial or mixed infections, and an additional cohort of non-infectious disease and healthy individuals were added as a control (FIG. 3D). Time from initial appearance of symptoms ranged between 0 to 8 days (FIG. 3E). Patients exhibited a wide range of clinical syndromes including bacteremia, cellulitis, lower respiratory tract infection (LRTI), upper respiratory tract infection (URTI), urinary tract infection (UTI) (FIG. 3F). In about 50% of the patients the pathogen was isolated exhibiting a wide distribution of over 26 disease causing agents (FIG. 3G).

Figure 5:
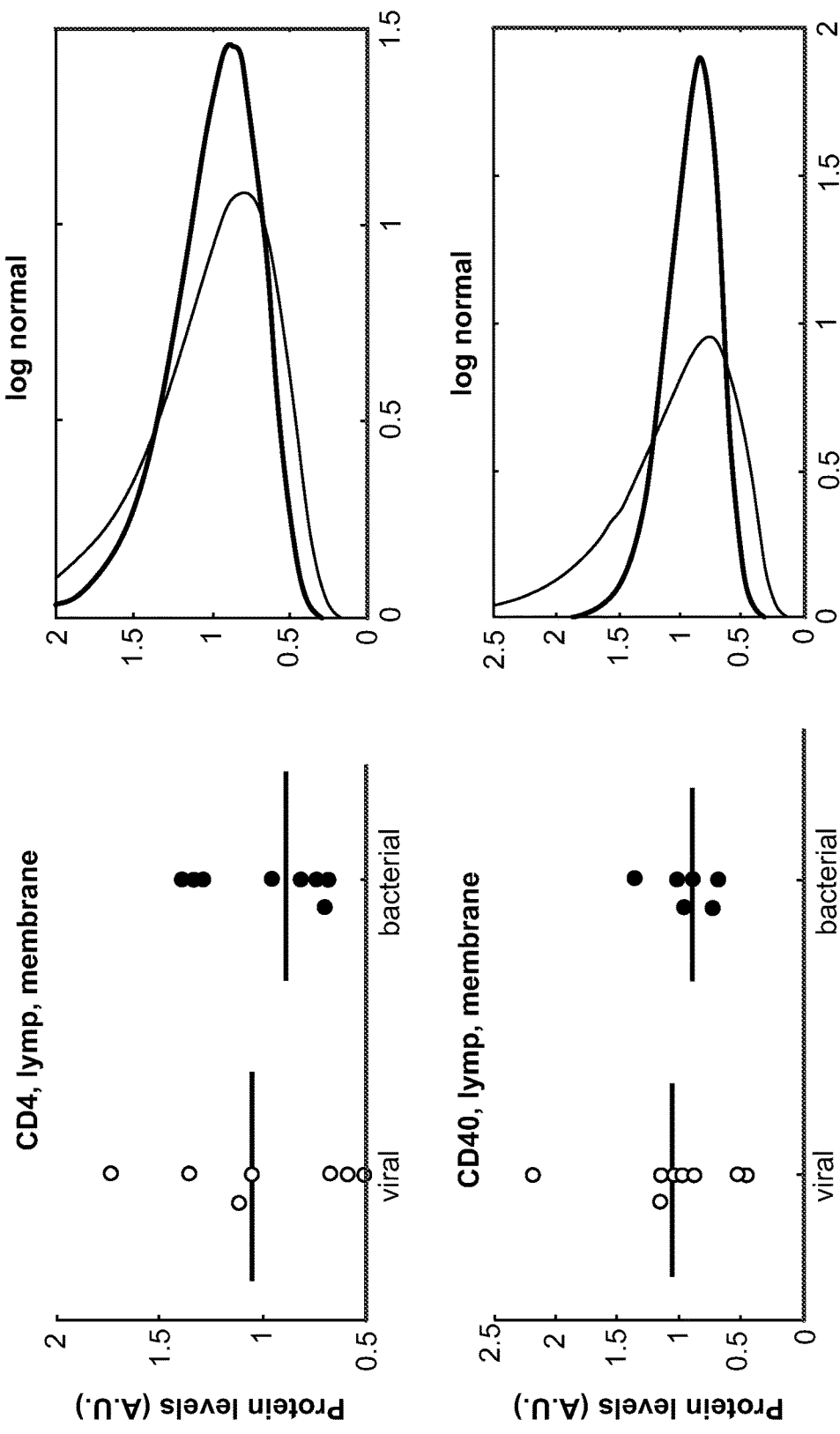
Figure 5:
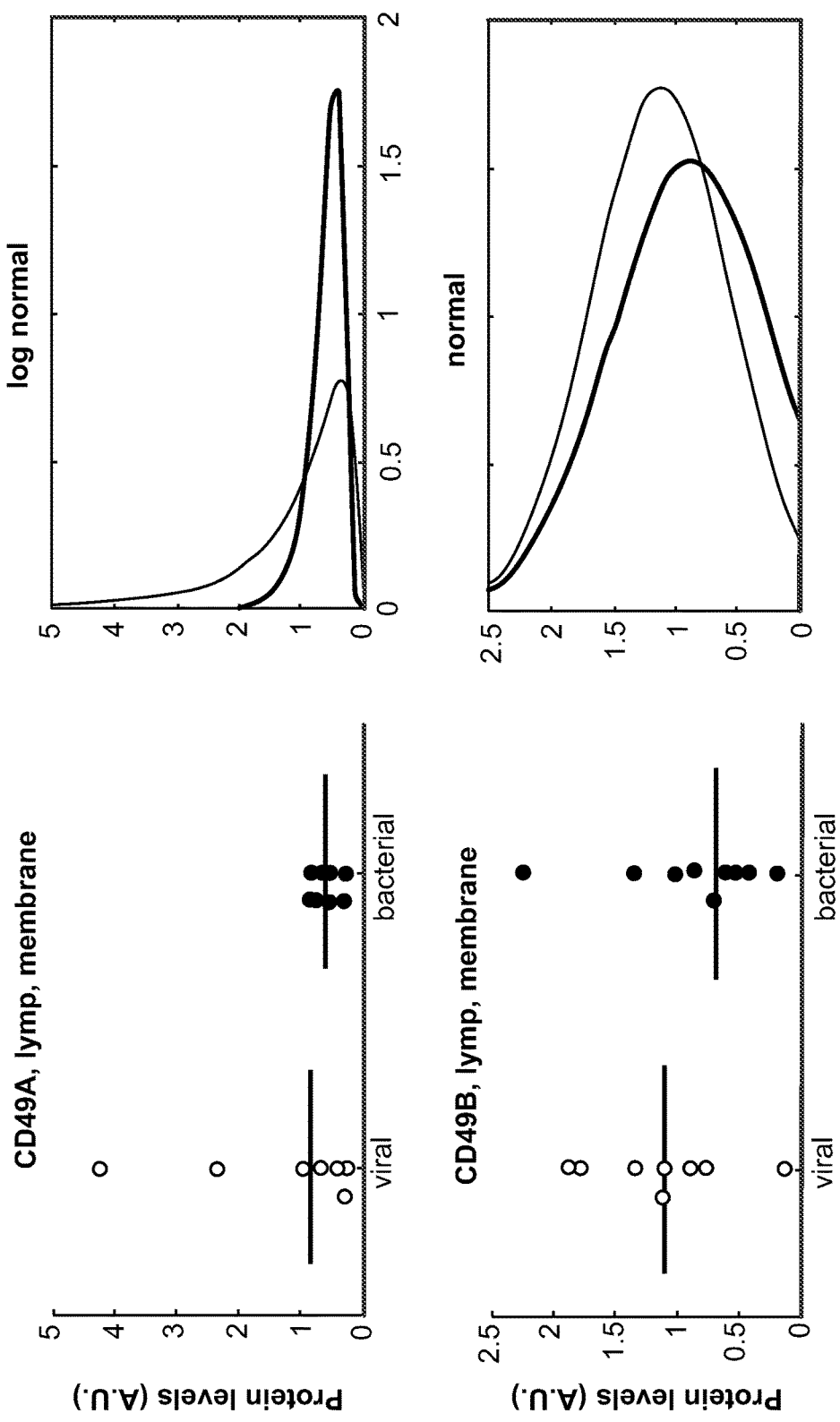
Figure 5:
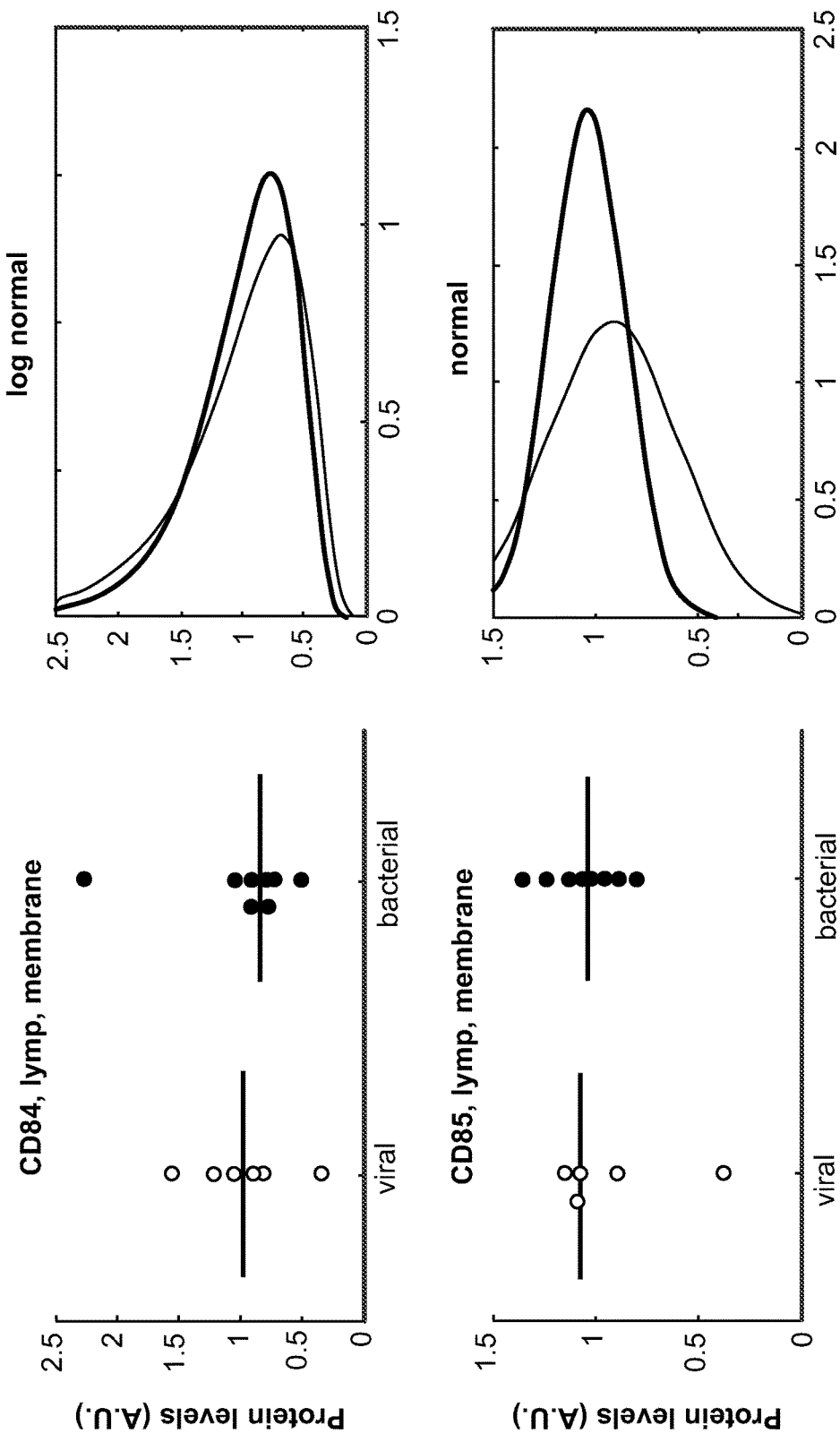
Figure 5:
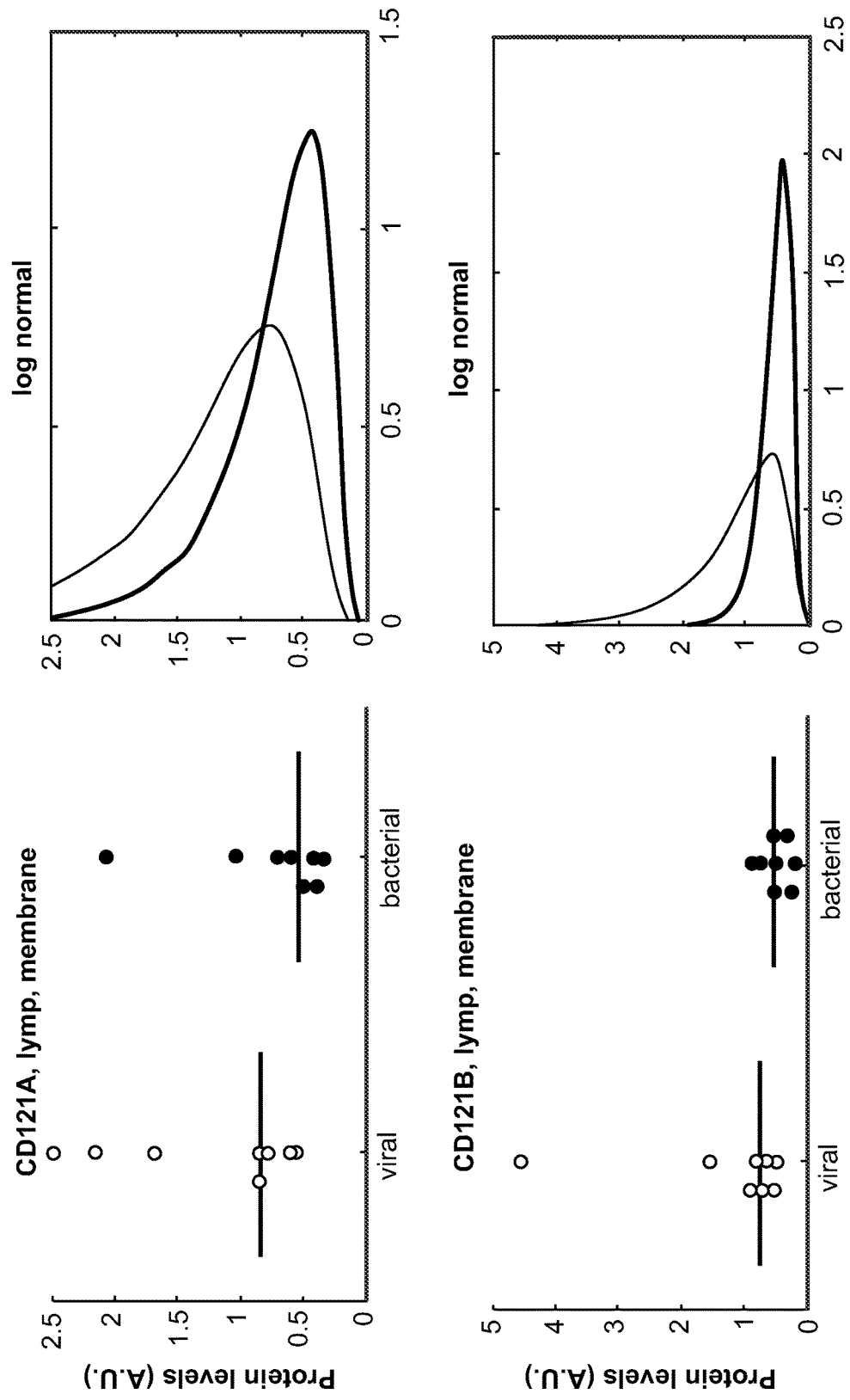
Figure 5:
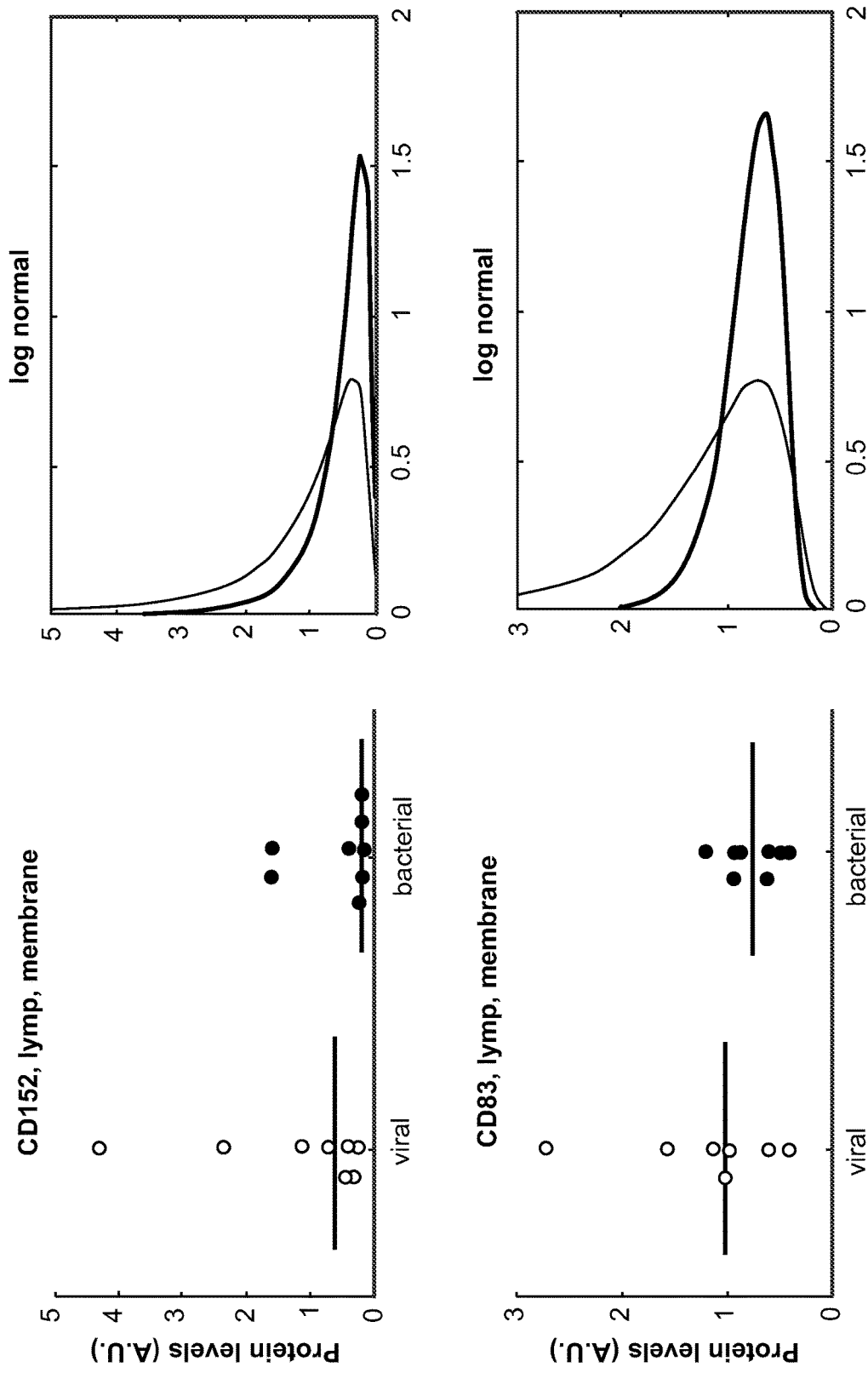
Figure 5:
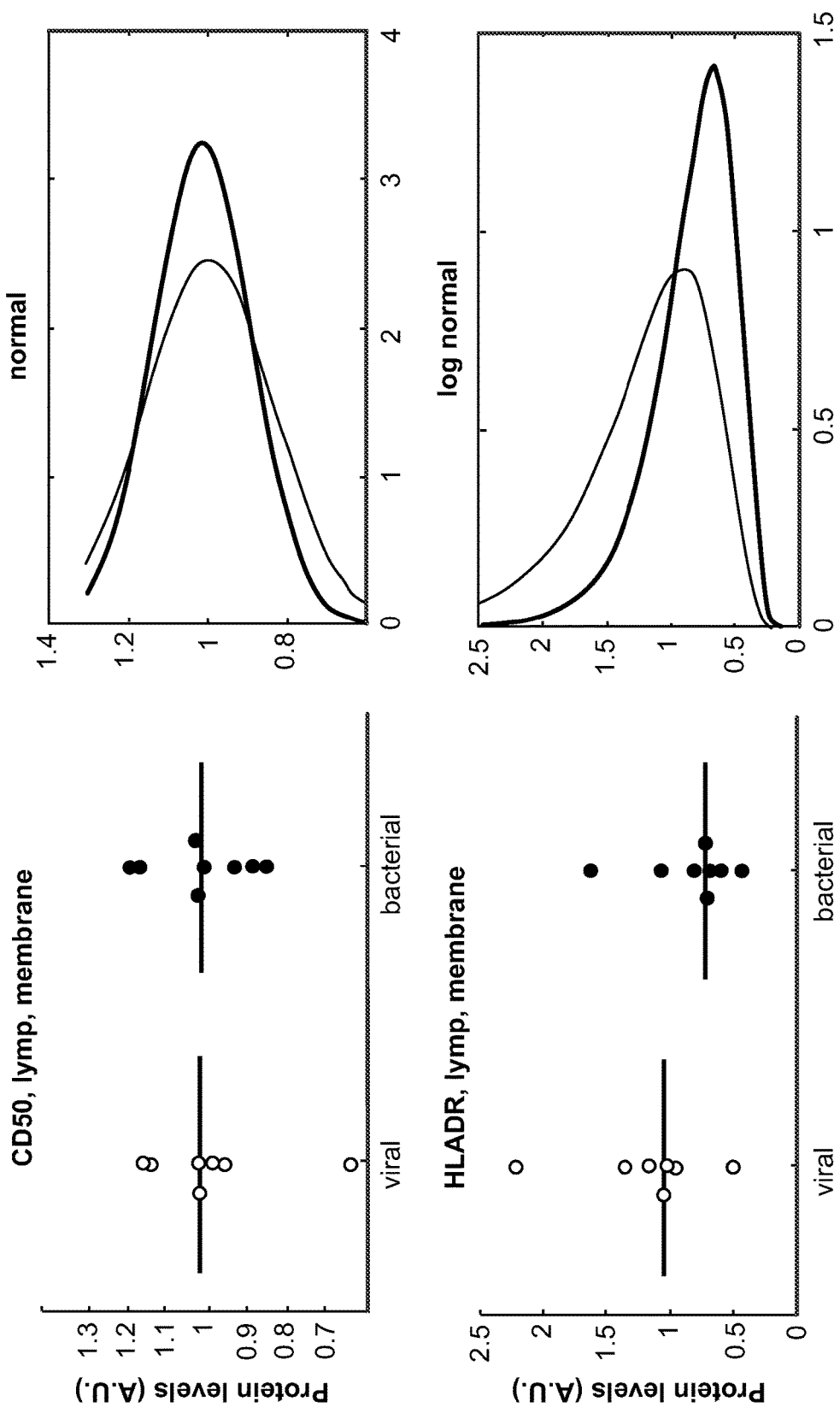
Figure 6:
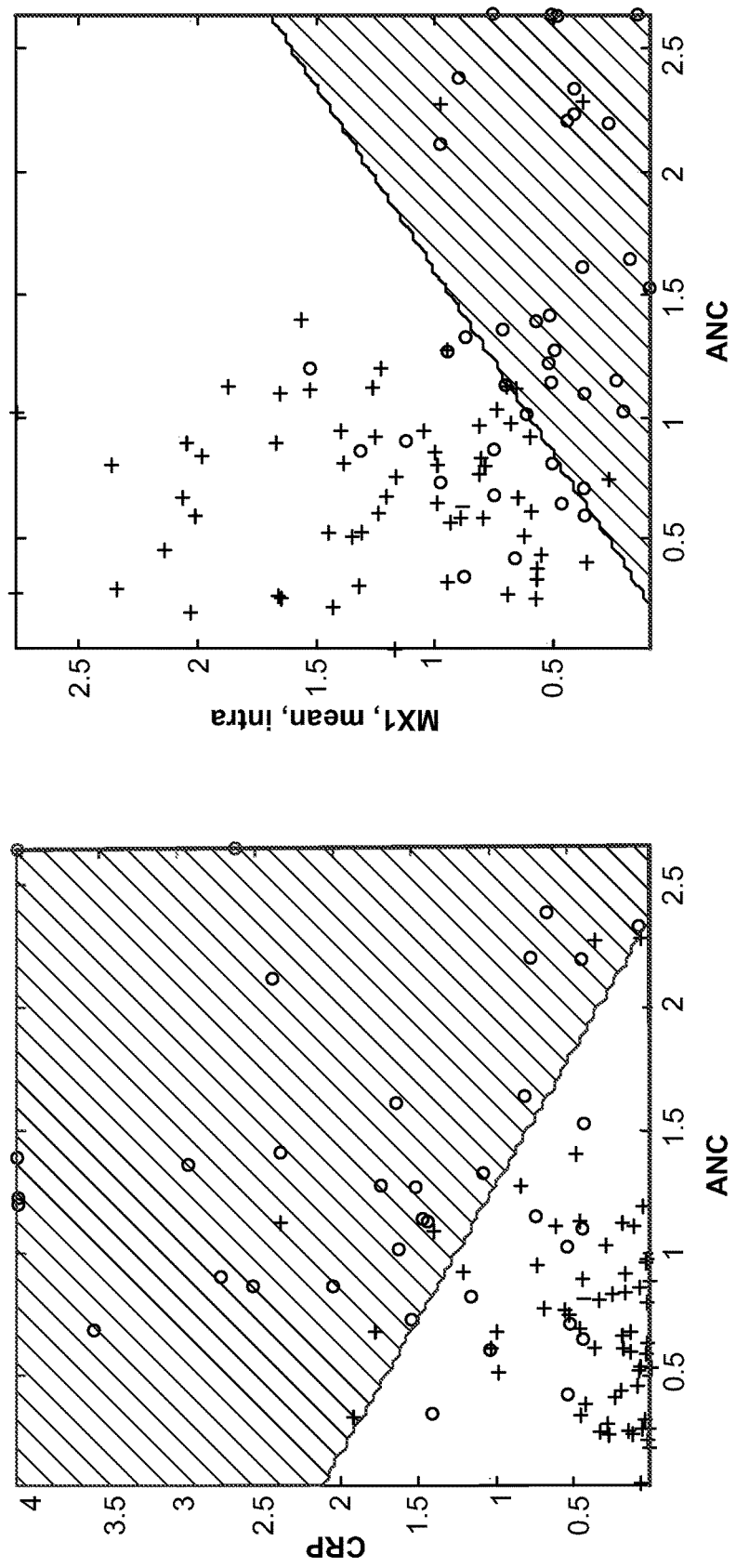
FIG. 6 is a scatter graph showing diagnosis of viral and bacterial infected patients using a combination of two DETERMINANTS. Viral and bacterial infected patients are indicated by red '+' and blue 'o' marks respectively. Patient classification was performed using a linear SVM trained on 90% of the data, where white and black regions indicate the space of DETERMINANT combinations that were classified as viral and bacterial respectively. Each plot corresponds to a different combination of two DETERMINANTS.
Figure 6:
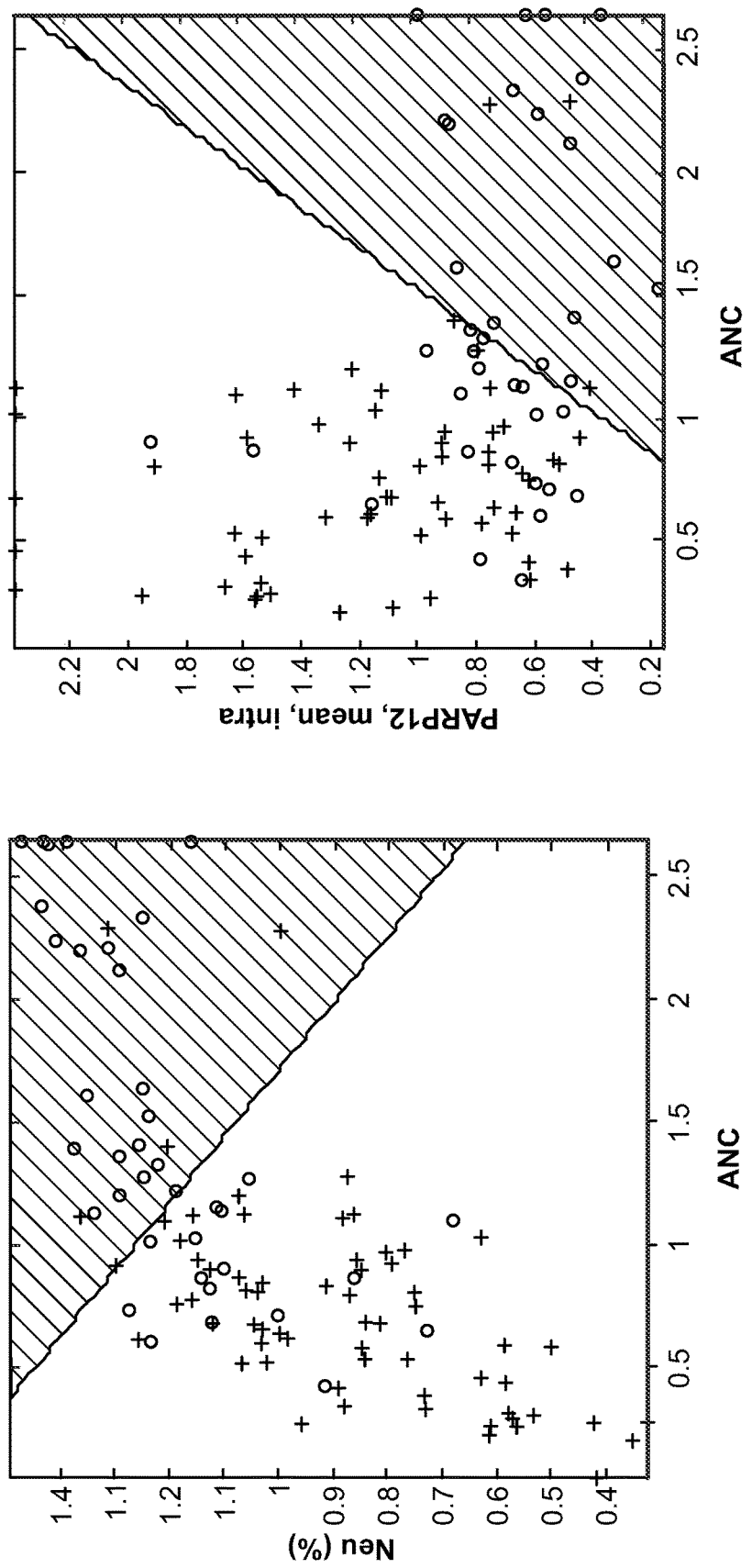
Figure 6:
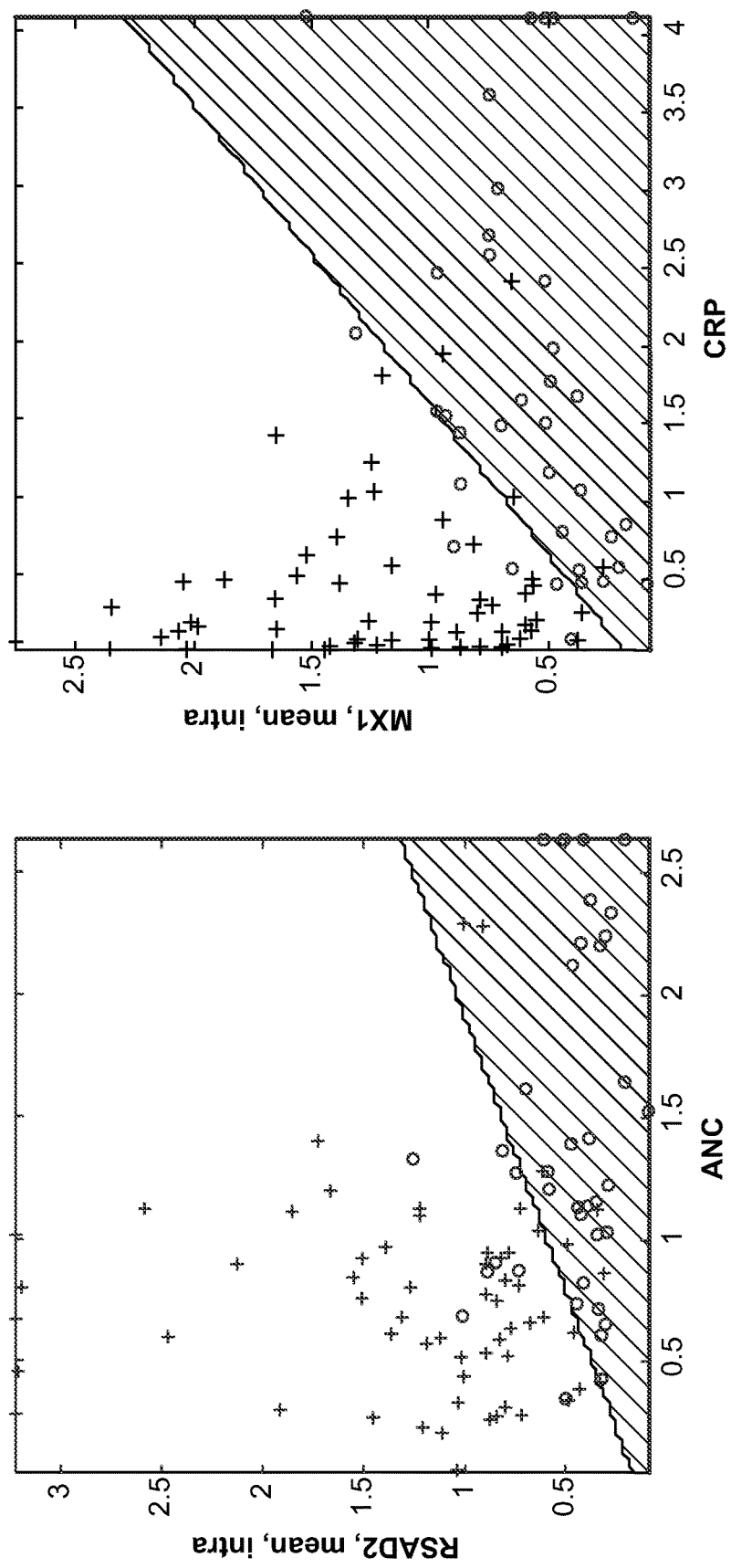
Figure 6:
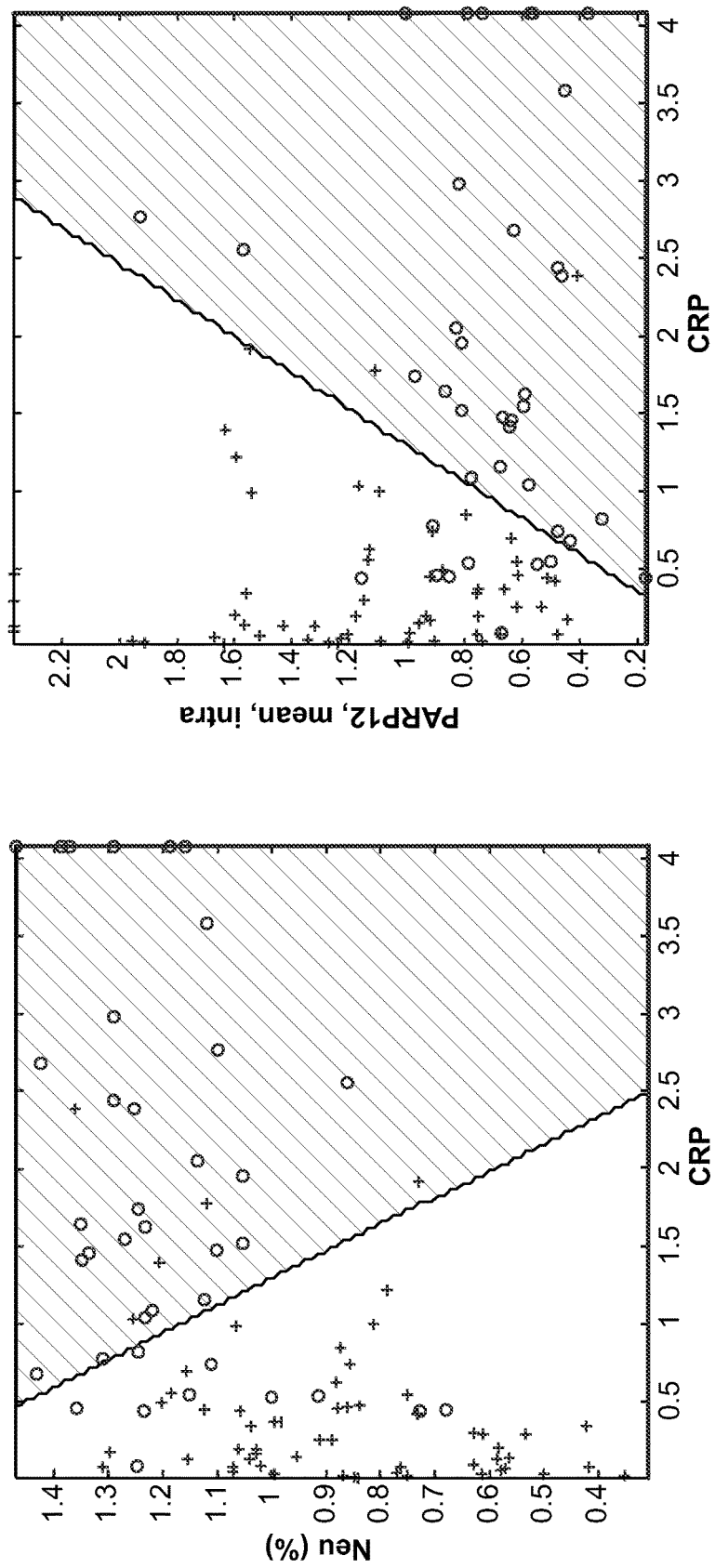
Figure 6:
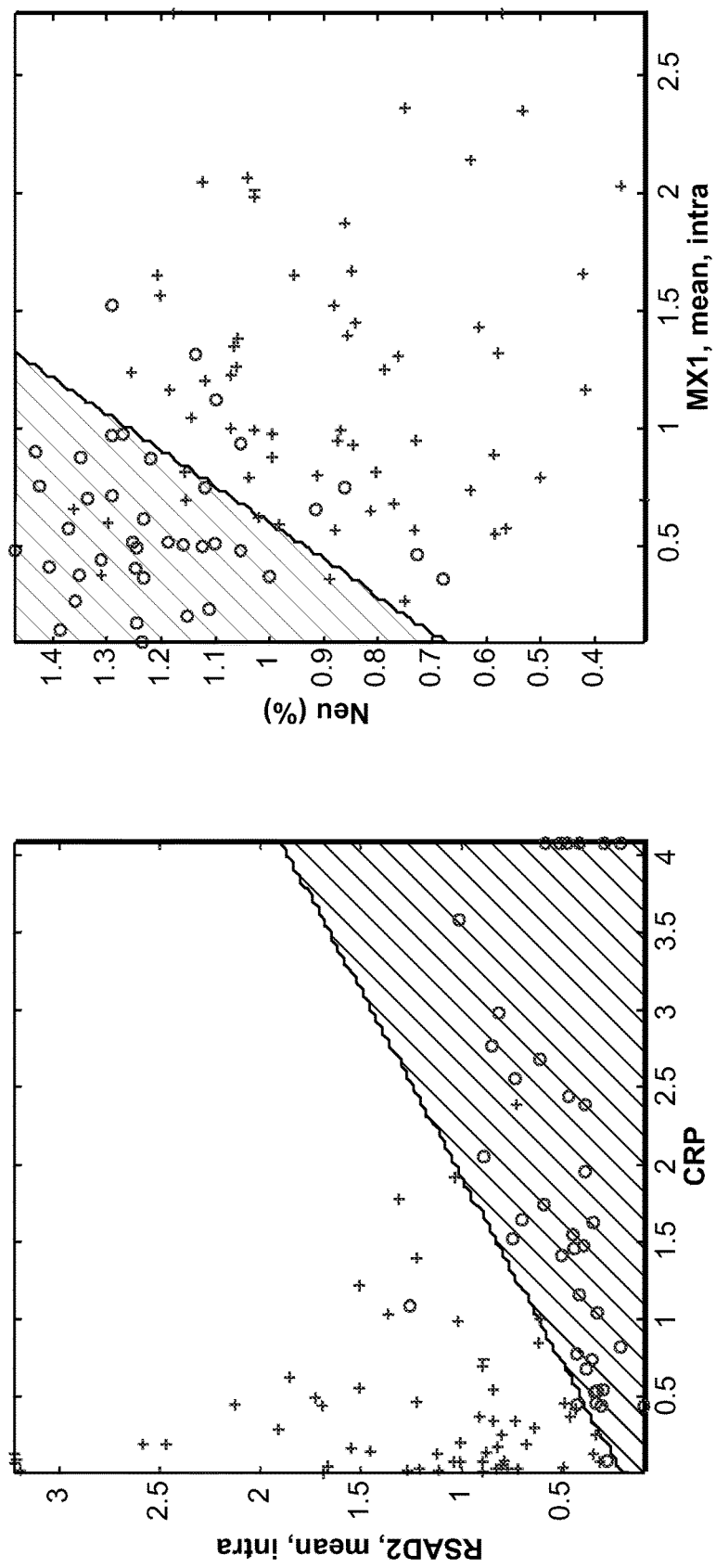
Figure 6:
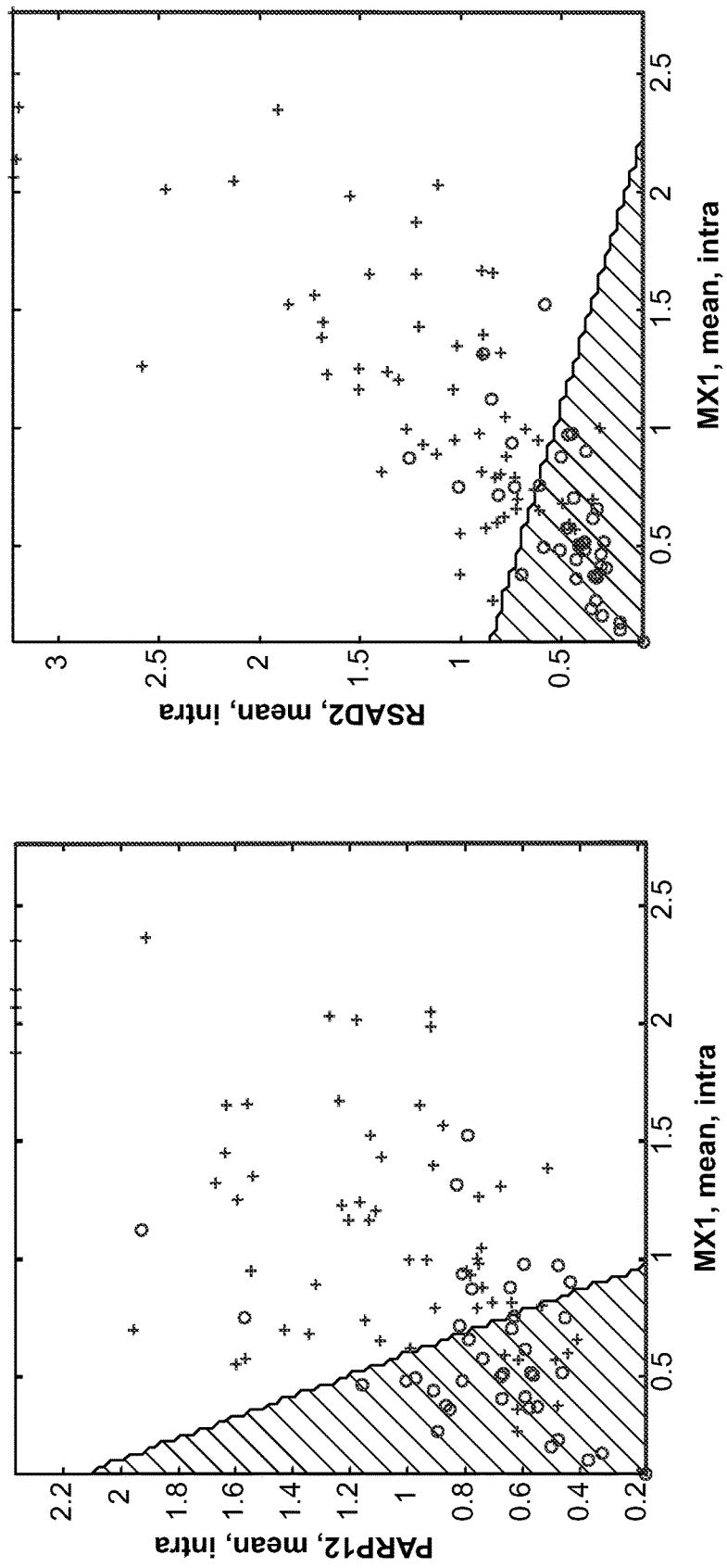
Figure 6:
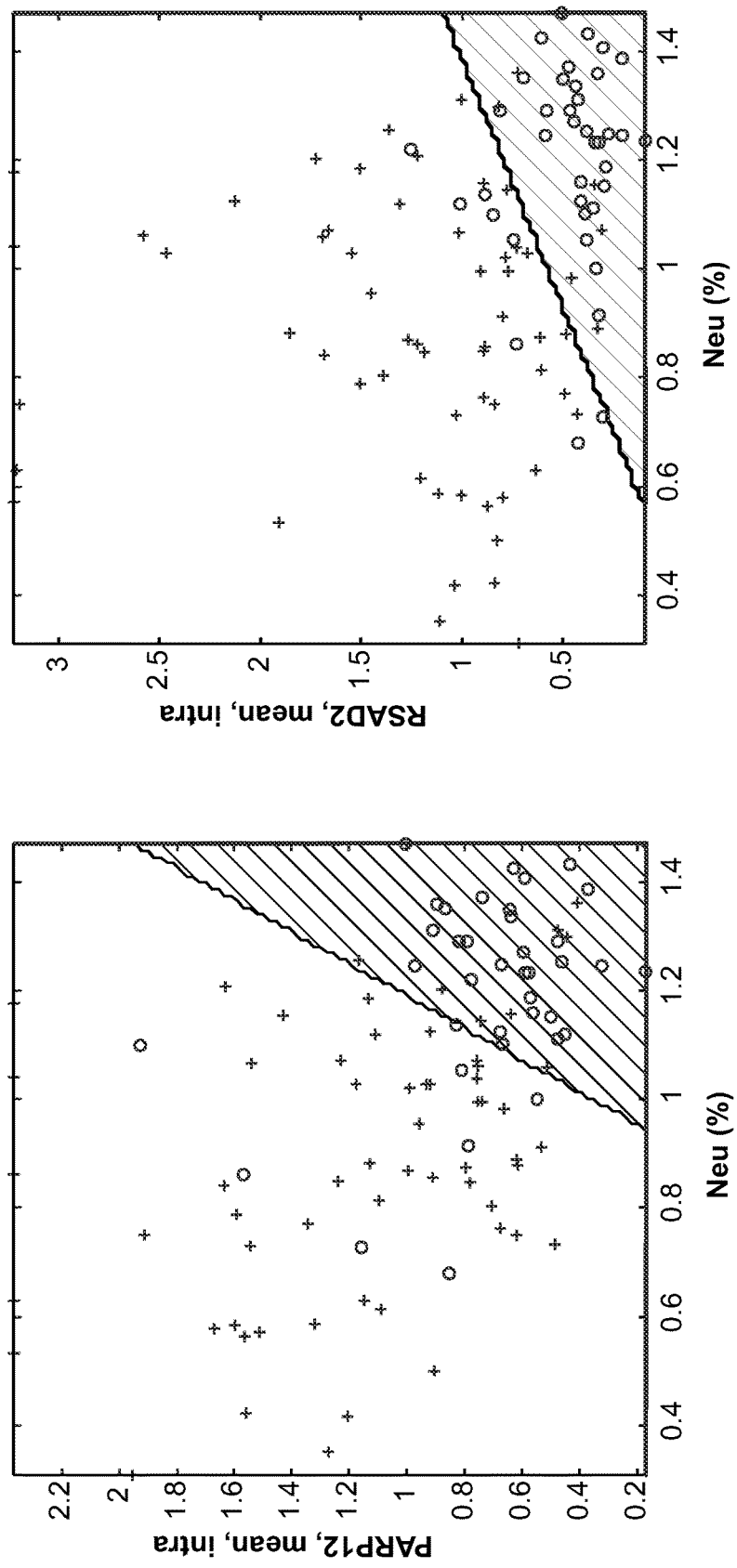
Figure 6:
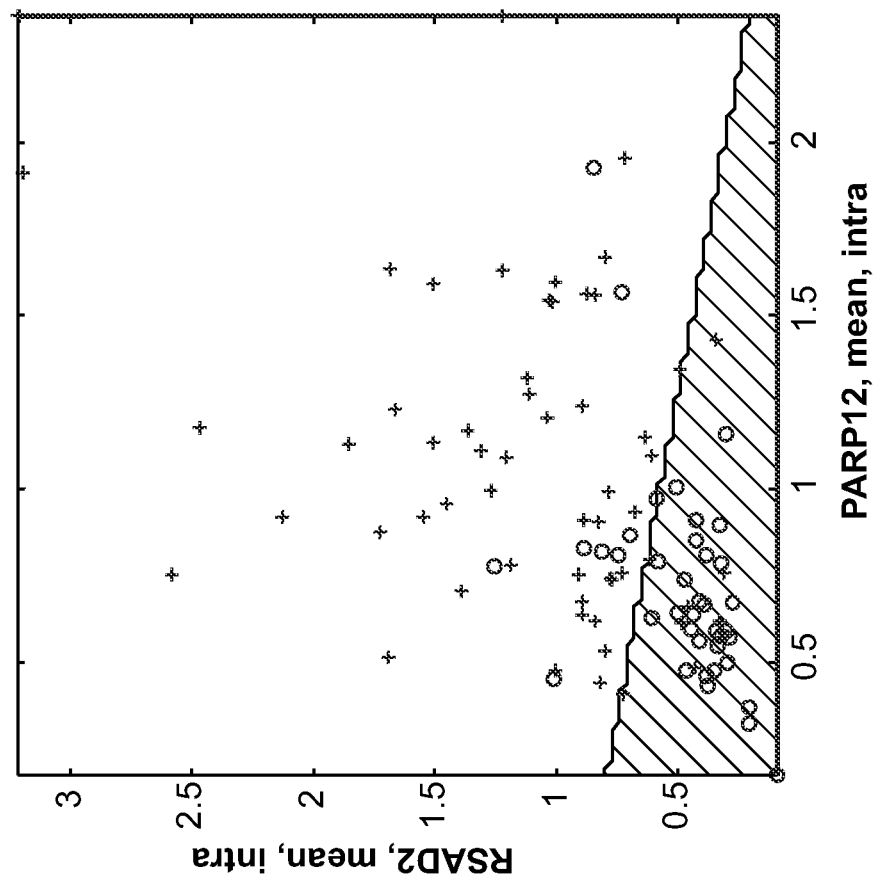

Example 2: Most Determinant Polypeptides are not Differentially Expressed in Different Types of Infections We have determined that most DETERMINANT polypeptides are not differentially expressed in patients with different types of infections. Moreover, DETERMINAT-polypeptides that have a well-established mechanistic role in the immune defense against infections are often not differentially expressed. Thus an immunological role of DETERMINAT-polypeptides does not necessarily imply diagnostic utility. This point is illustrated in FIG. 5, which shows examples of DETERMINANT polypeptides with an active immunological role in the host response to bacterial or viral infections. We find that the levels of these DETERMINANT polypeptides were not significantly differentially expressed in lymphocytes of patients with viral versus bacterial infections.

Figure 4A:
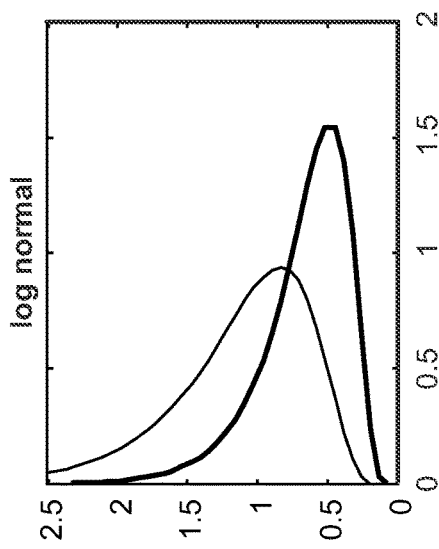
FIG. 4 A Measurements of DETERMINANTS whose levels were differentially expressed in patients with viral versus bacterial infections. Points correspond to patients and bars correspond to group means (left panel). DETERMINANT distributions were estimated using maximum likelihood (right panel). The abbreviations lym, gran, mono, mean and total are used to indicate whether a DETERMINANT polypeptide was differentially expressed in lymphocytes, granulocytes, monocytes, mean signal over all leukocytes or total signal of leukocytes respectively.
Figure 4A:
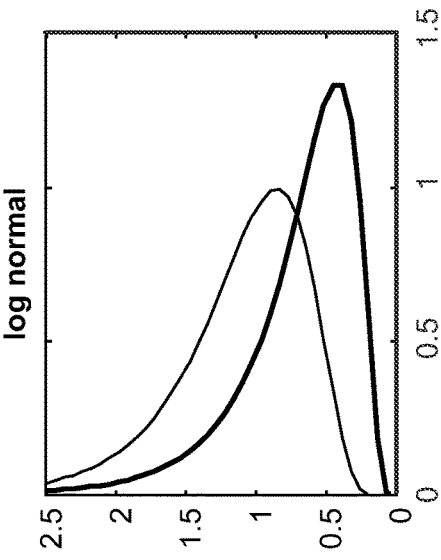
Figure 4A:
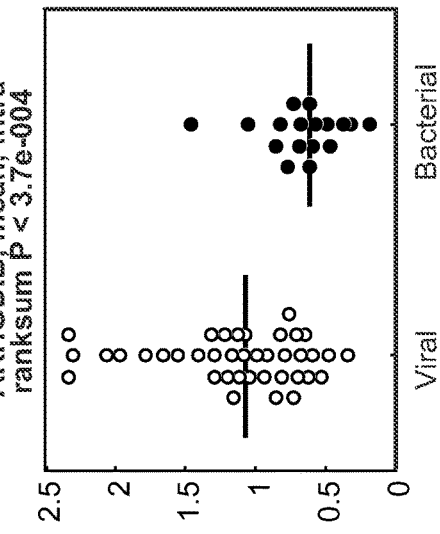
Figure 4A:
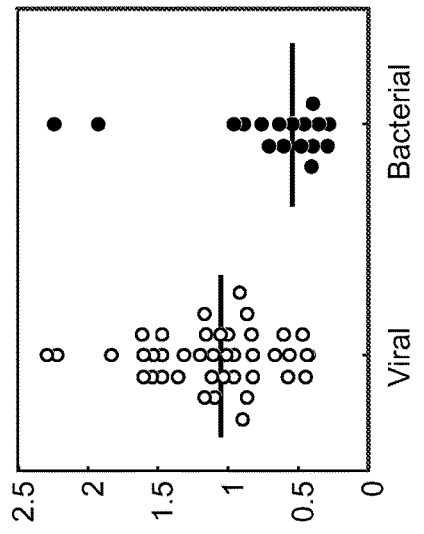
Figure 4A:
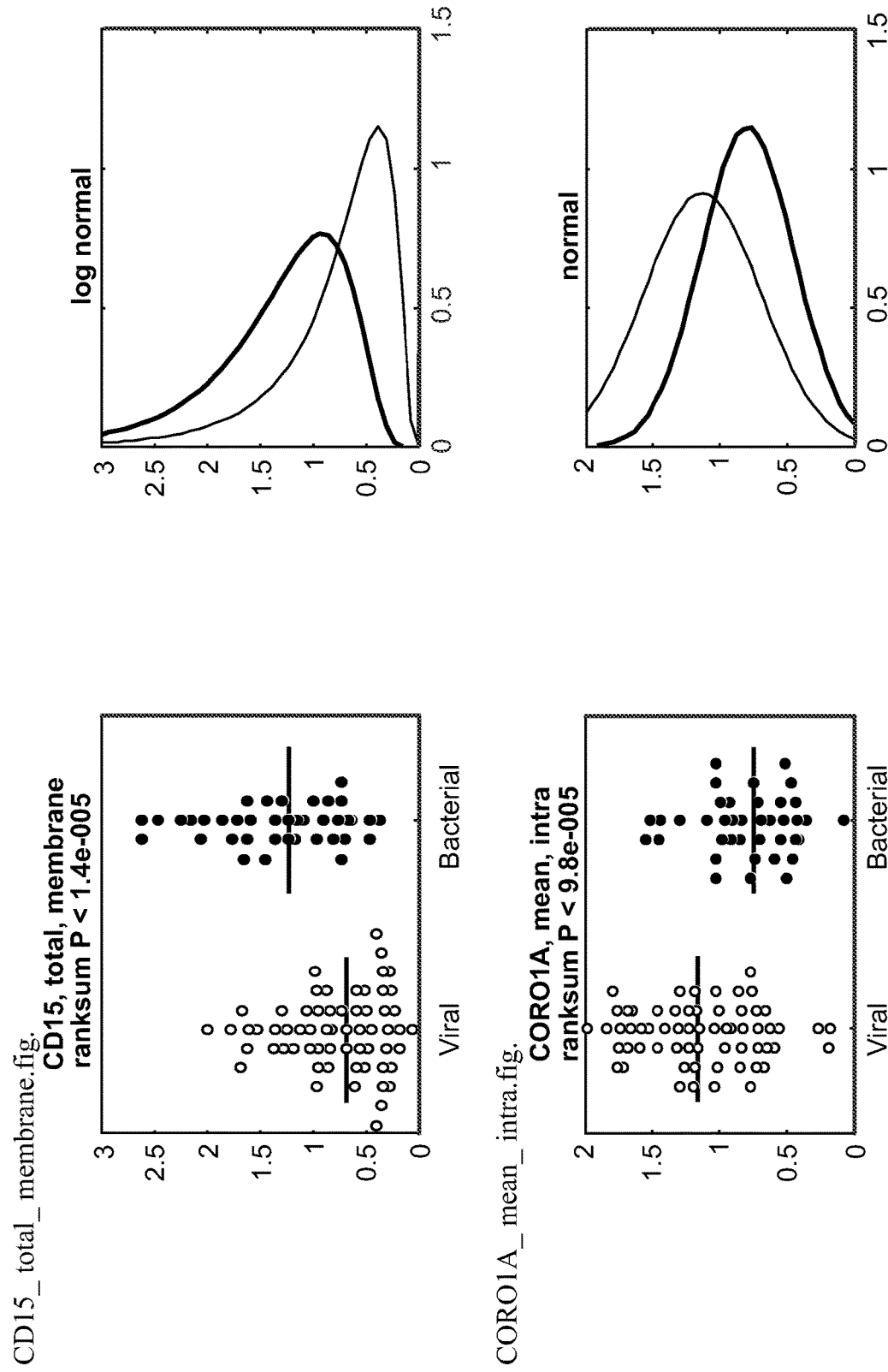
Figure 4A:
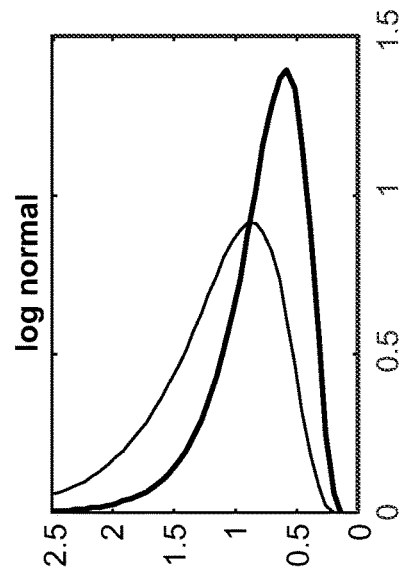
Figure 4A:
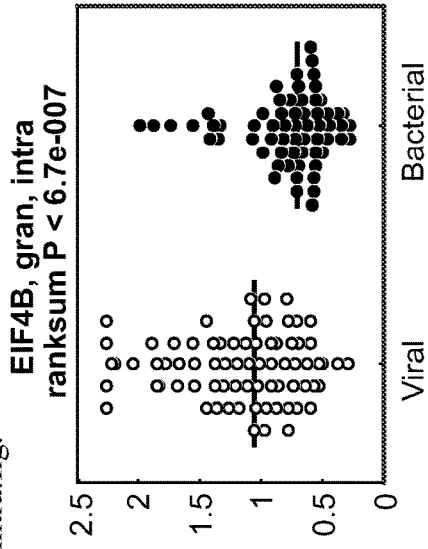
Figure 4A:
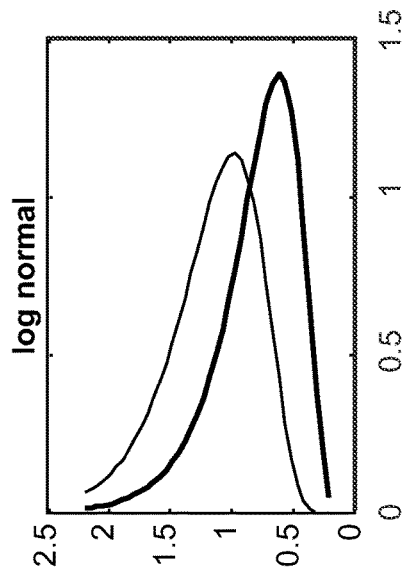
Figure 4A:
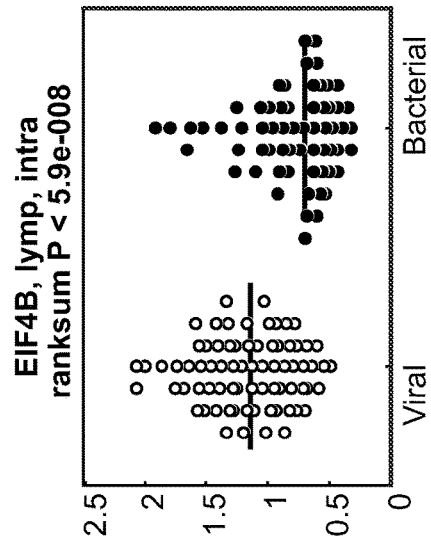
Figure 4A:
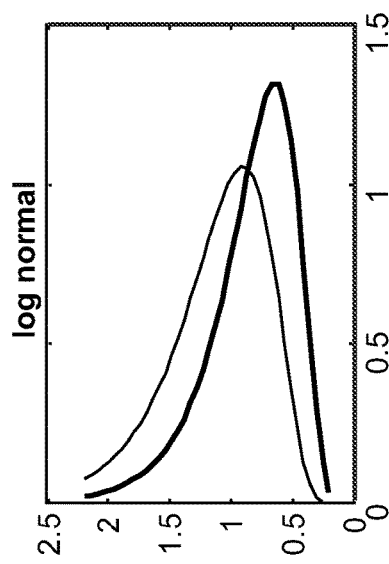
Figure 4A:
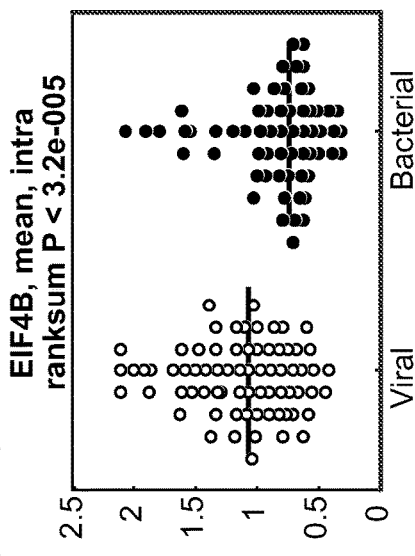
Figure 4A:
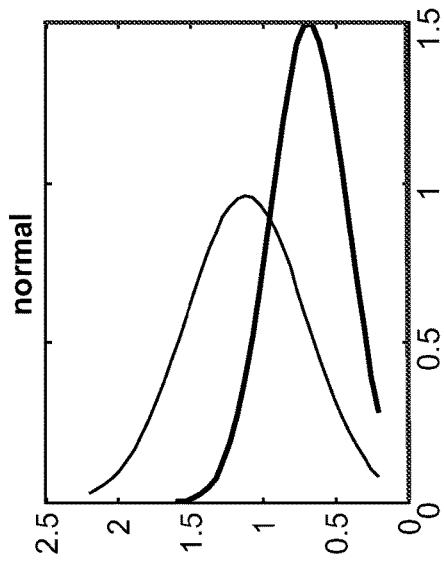
Figure 4A:
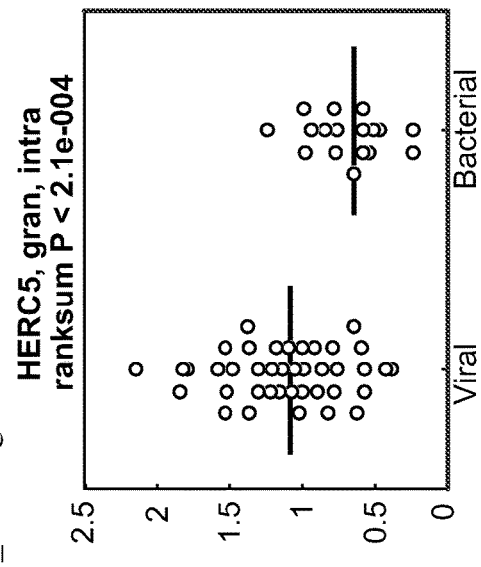
Figure 4A:
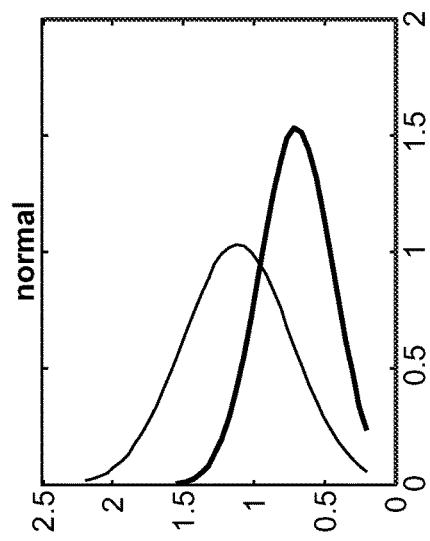
Figure 4A:
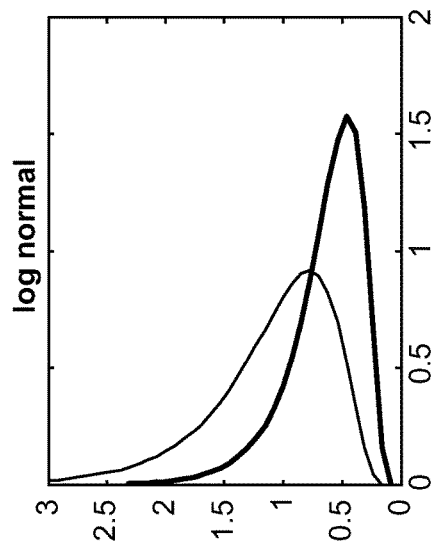
Figure 4A:
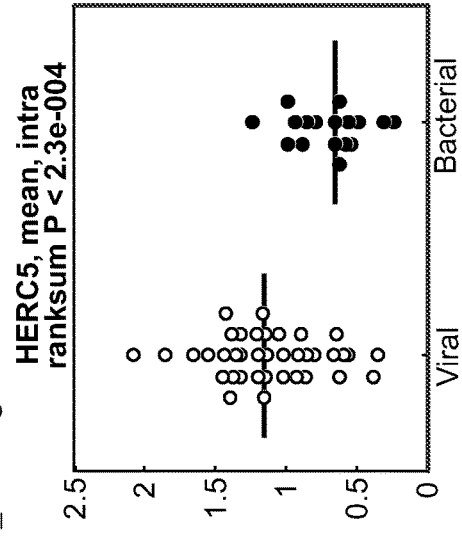
Figure 4A:
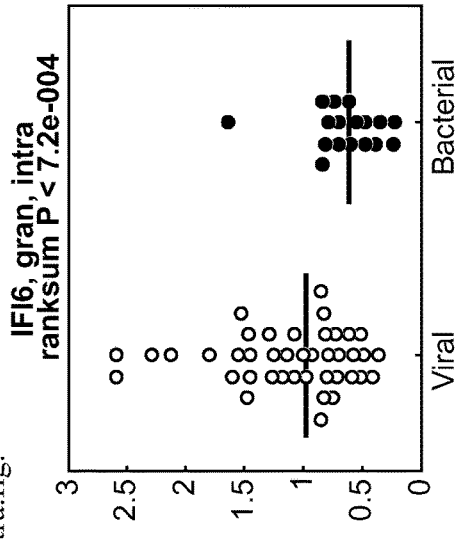
Figure 4A:
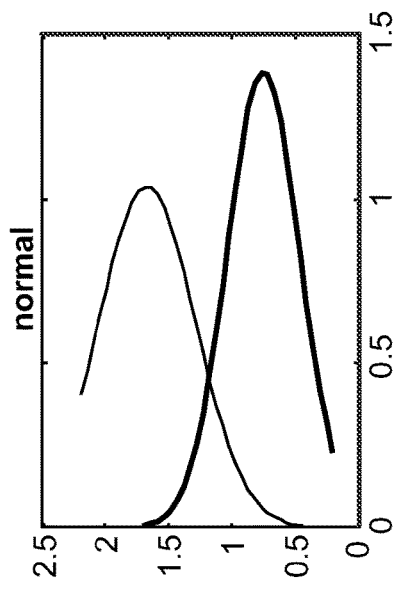
Figure 4A:
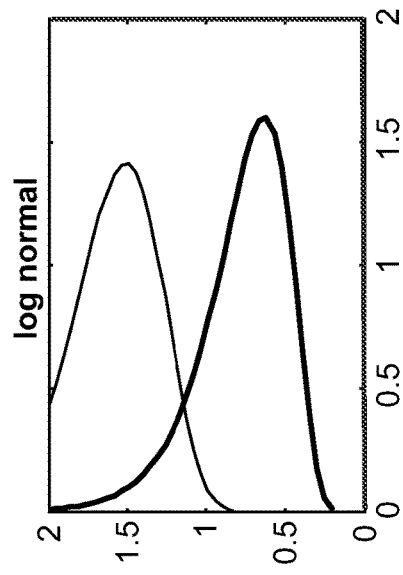
Figure 4A:
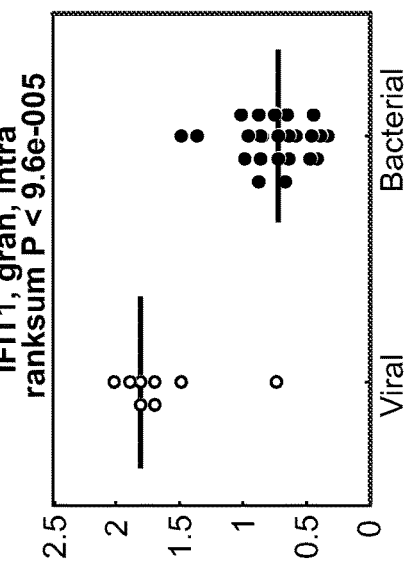
Figure 4A:
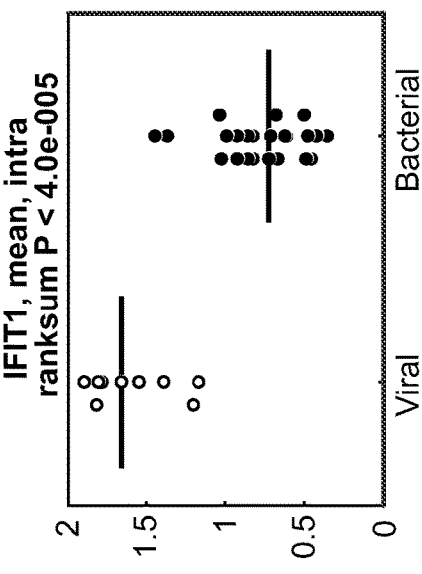
Figure 4A:
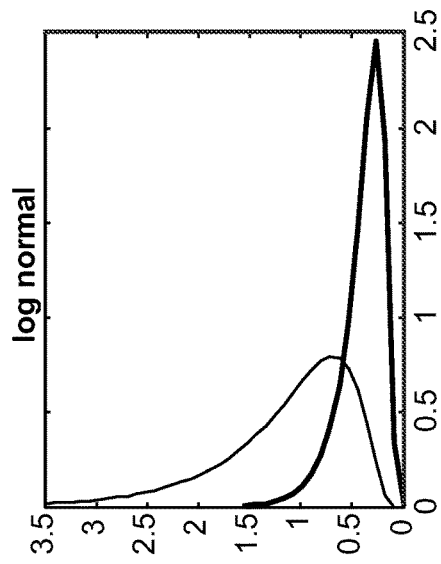
Figure 4A:
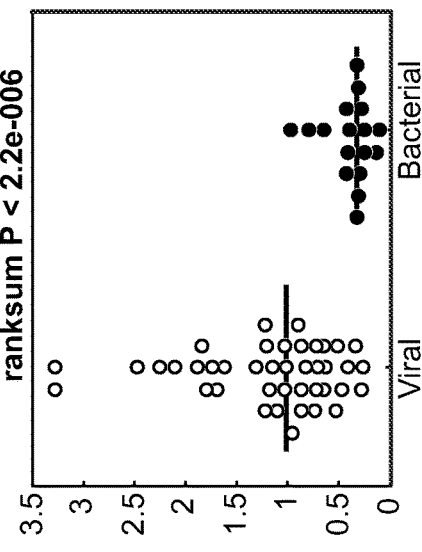
Figure 4A:
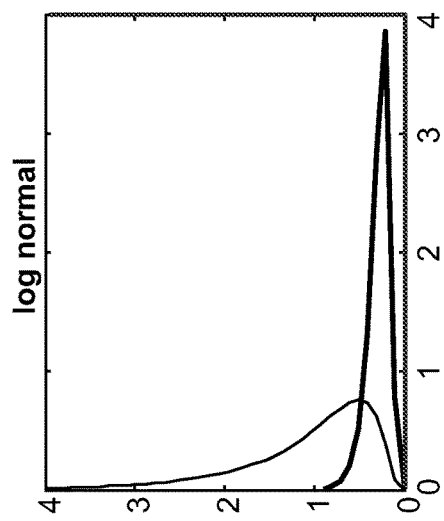
Figure 4A:
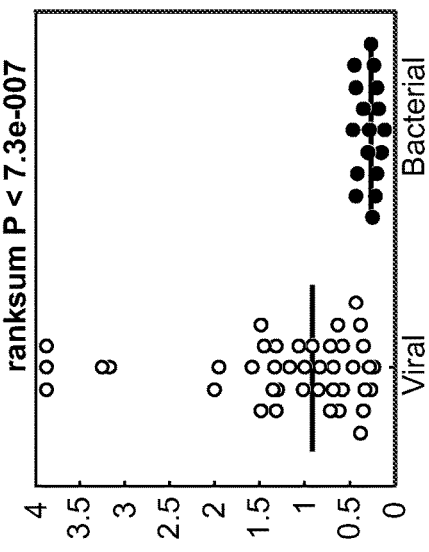
Figure 4A:
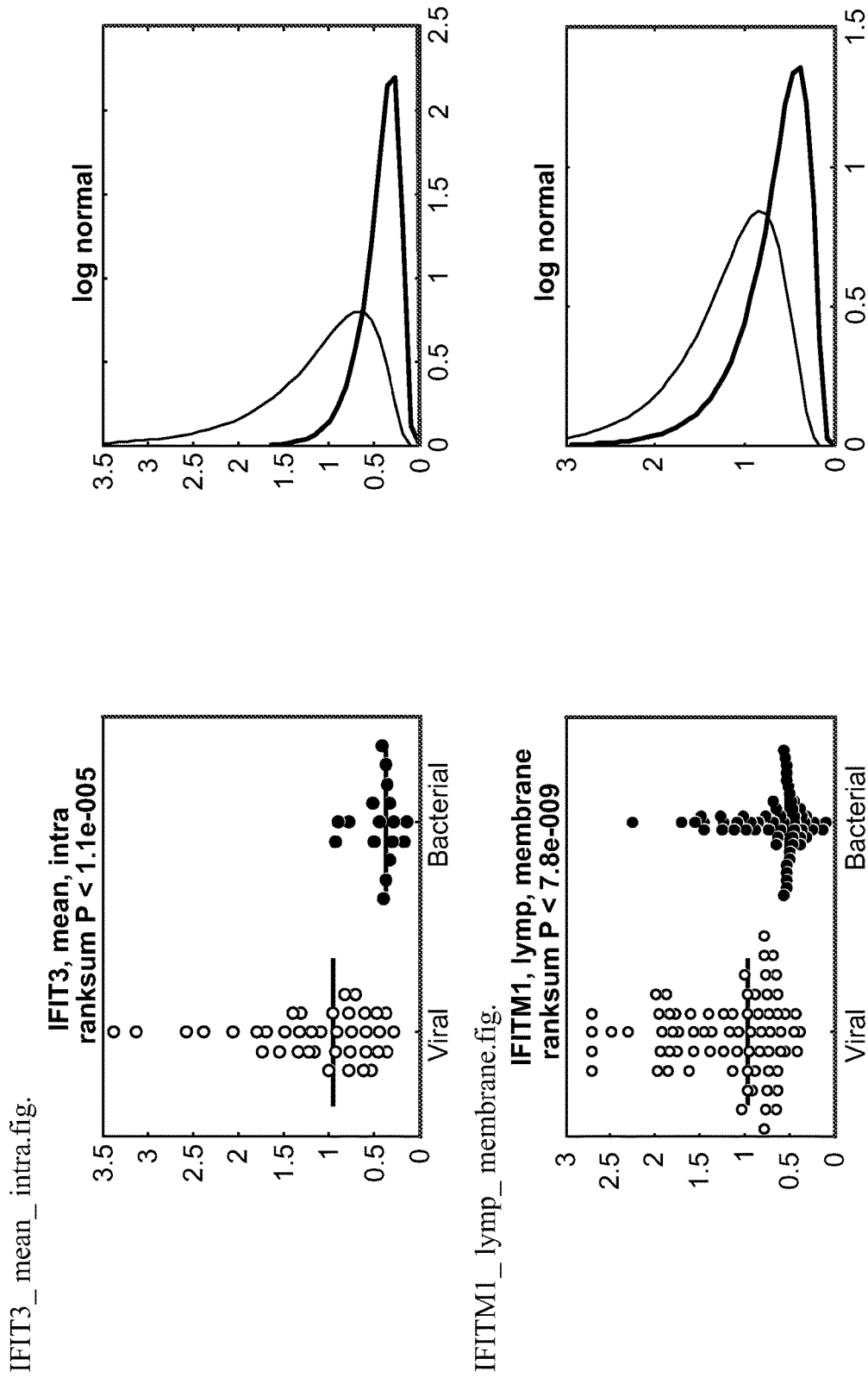
Figure 4A:
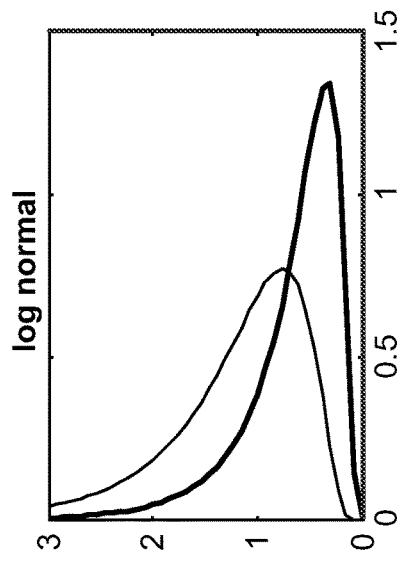
Figure 4A:
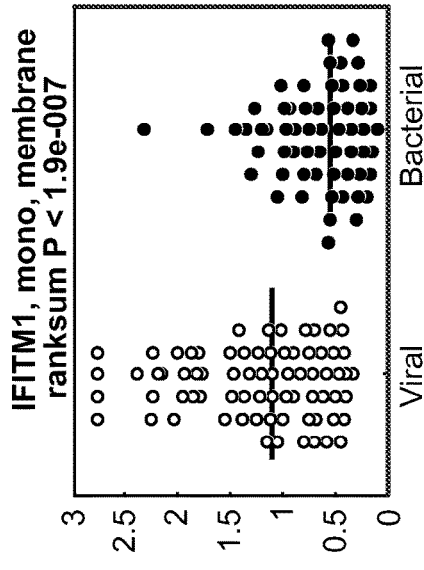
Figure 4A:
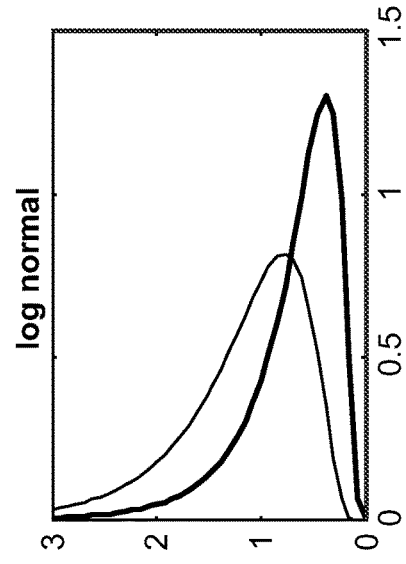
Figure 4A:
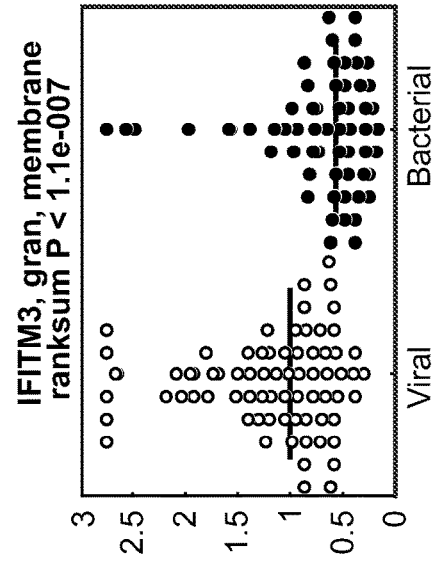
Figure 4A:
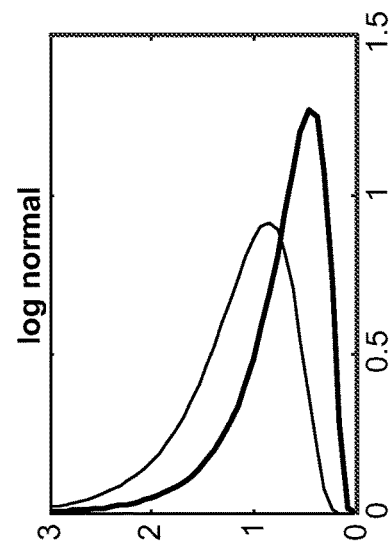
Figure 4A:
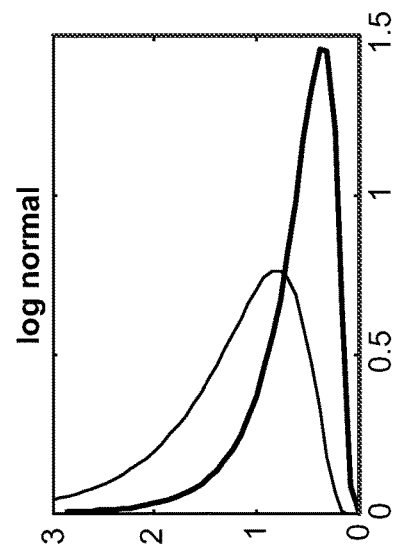
Figure 4A:
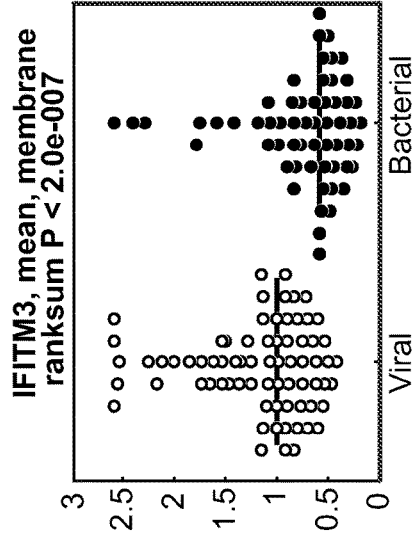
Figure 4A:
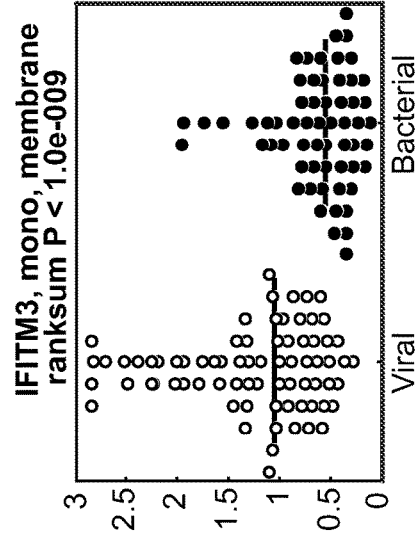
Figure 4A:
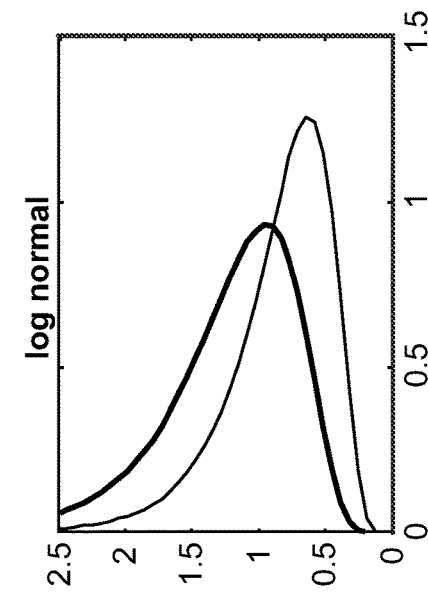
Figure 4A:
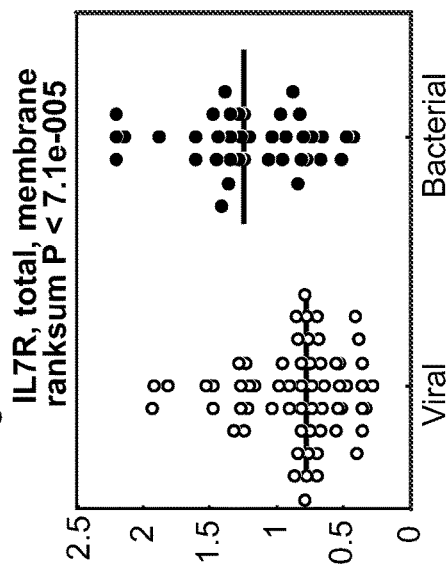
Figure 4A:
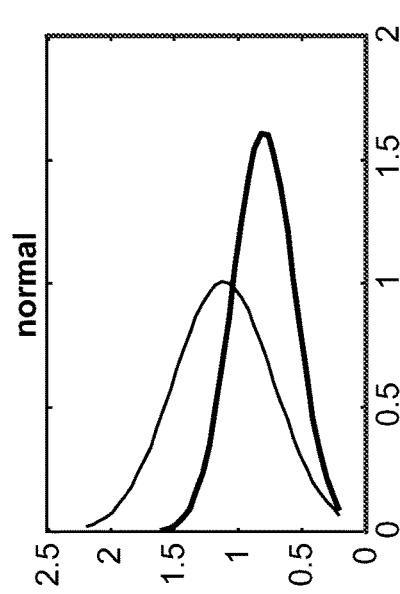
Figure 4A:
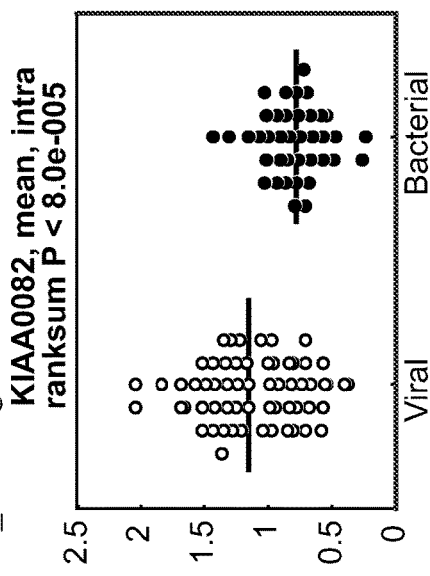
Figure 4A:
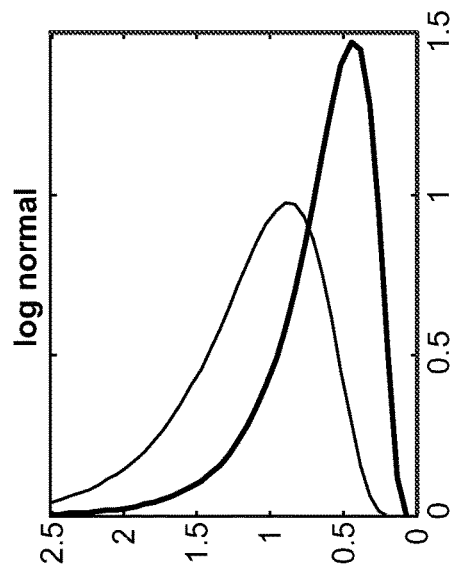
Figure 4A:
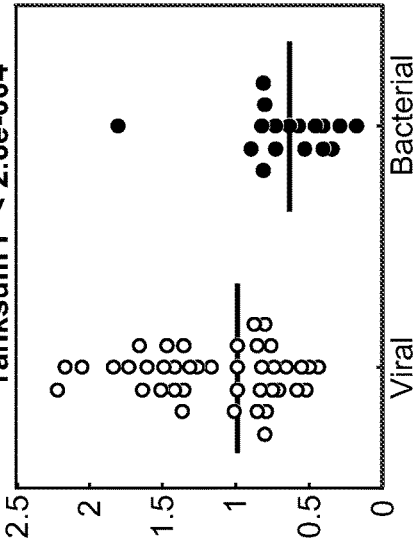
Figure 4A:
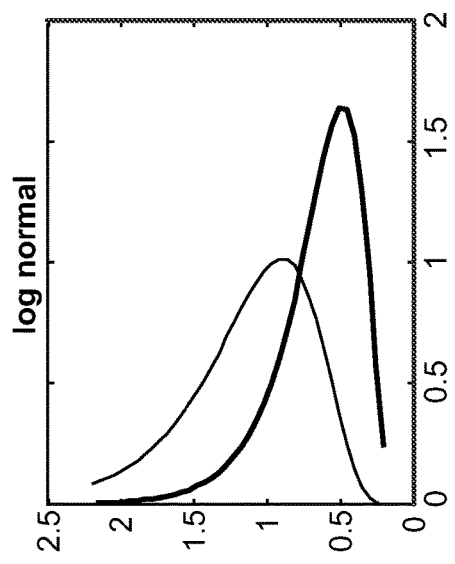
Figure 4A:
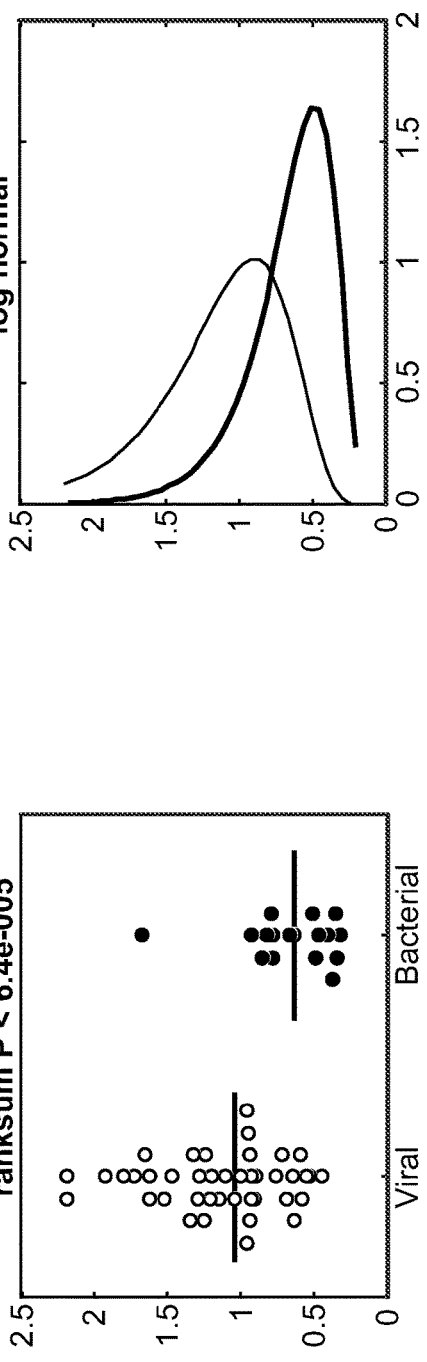
Figure 4A:
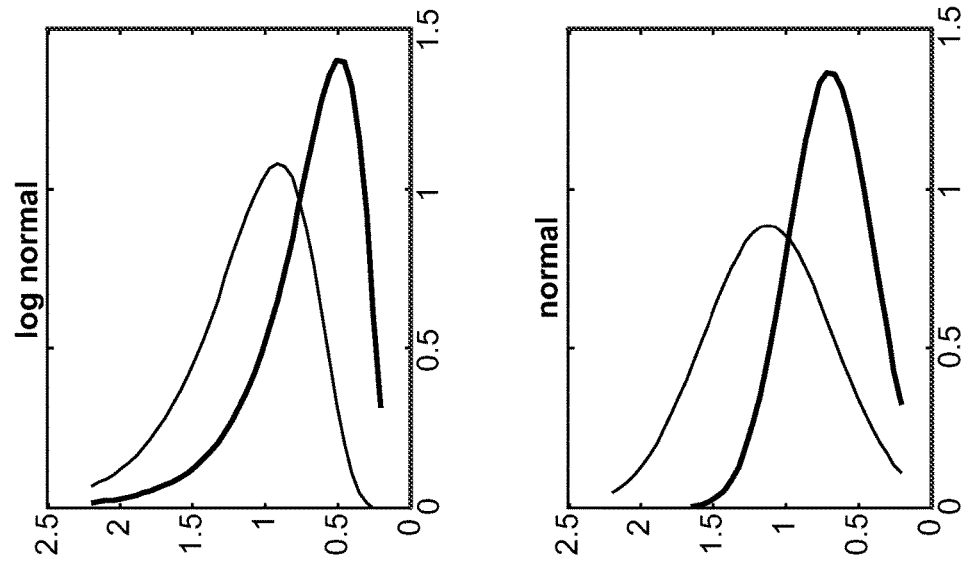
Figure 4A:
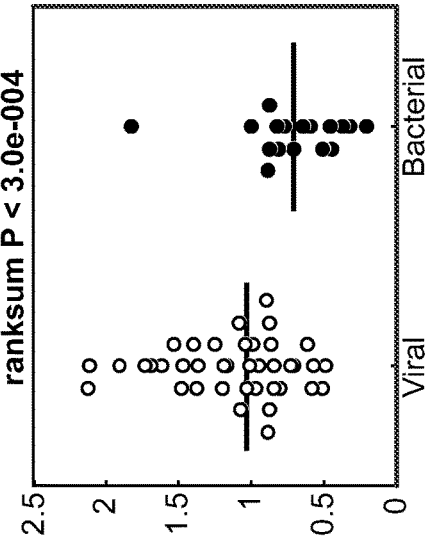
Figure 4A:
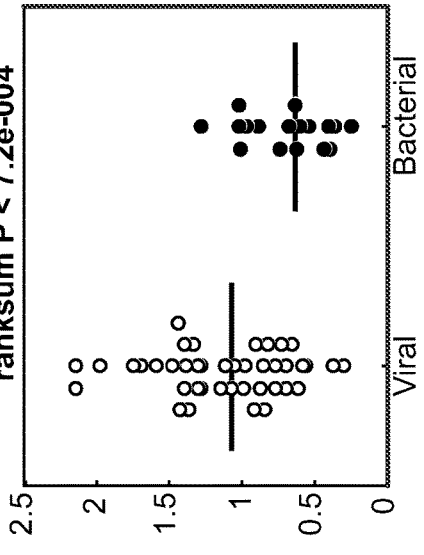
Figure 4A:
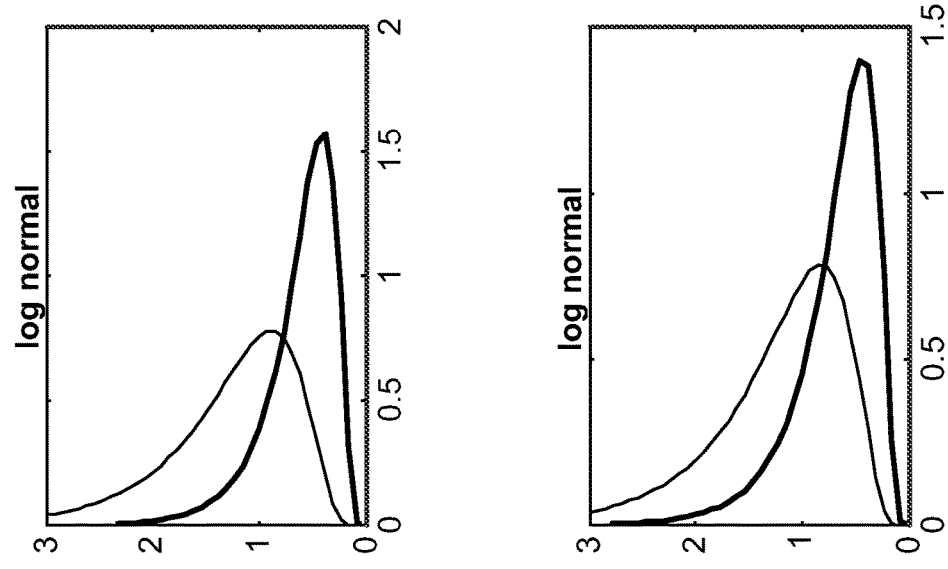
Figure 4A:
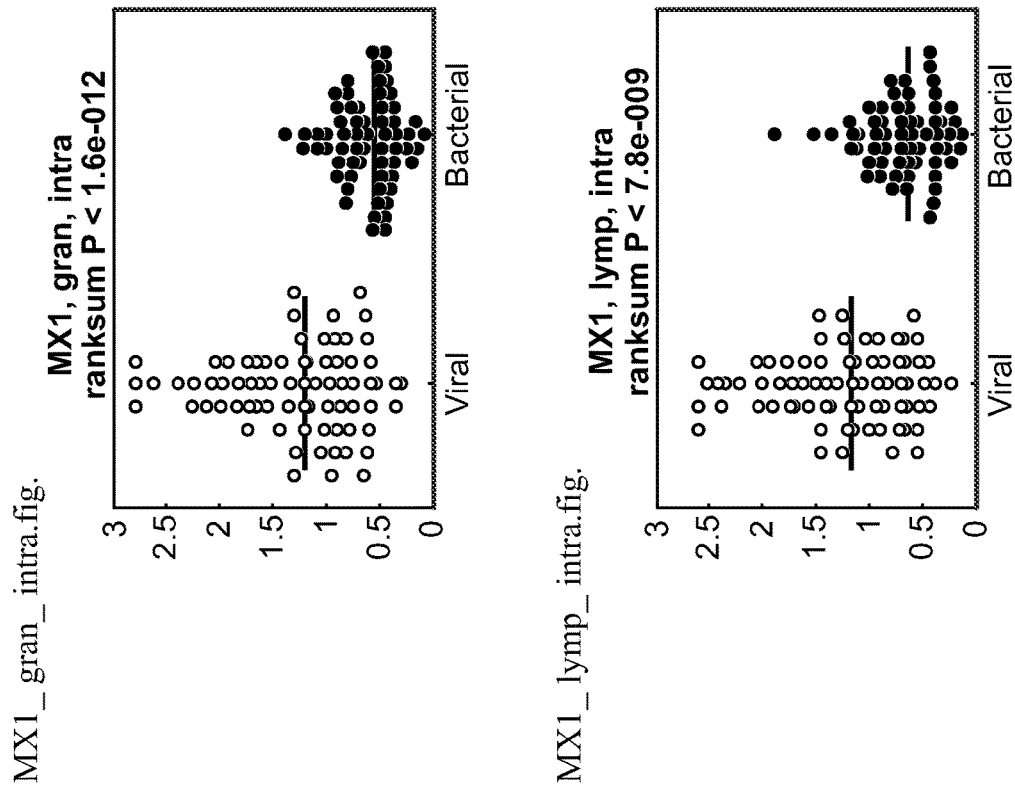
Figure 4A:
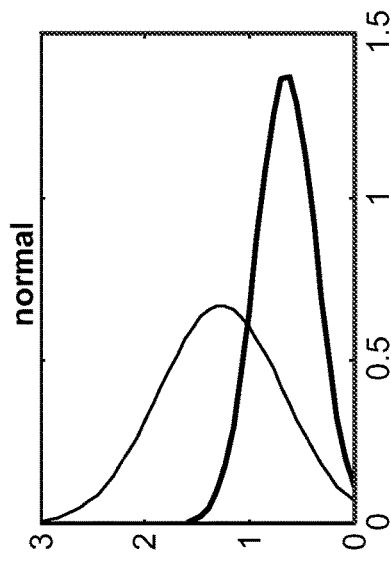
Figure 4A:
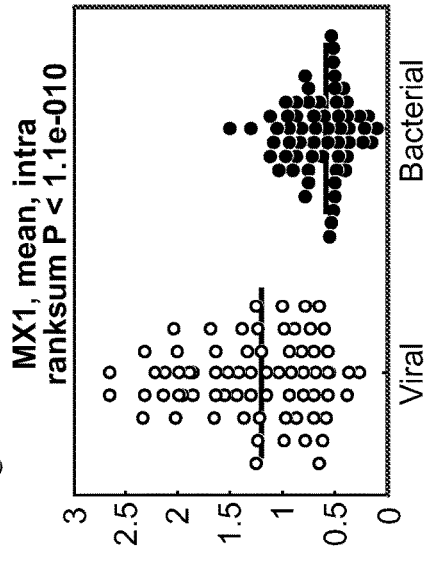
Figure 4A:
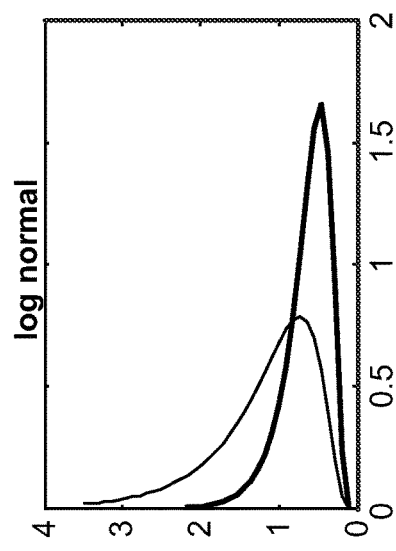
Figure 4A:
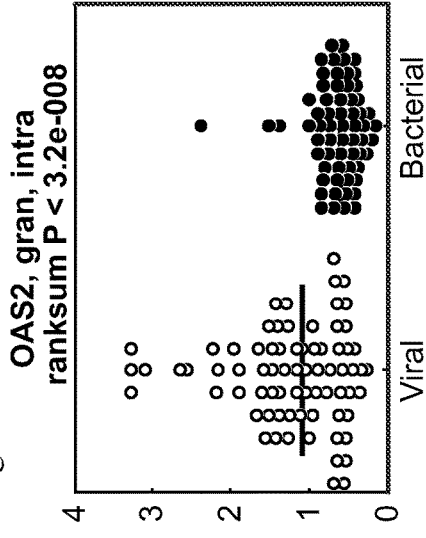
Figure 4A:
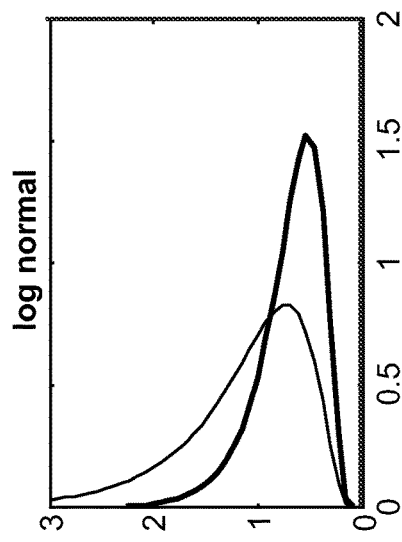
Figure 4A:
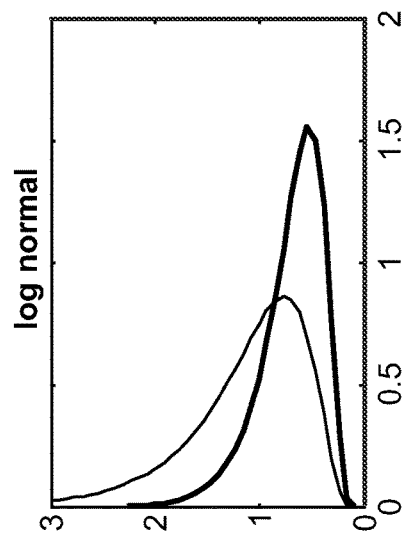
Figure 4A:
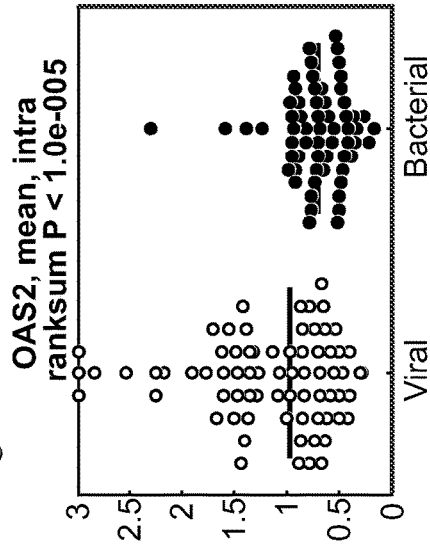
Figure 4A:
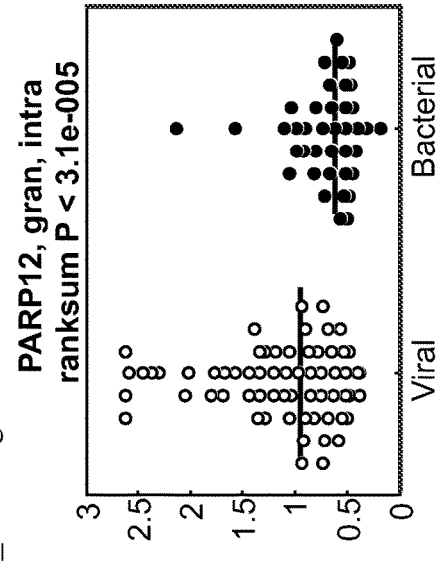
Figure 4A:
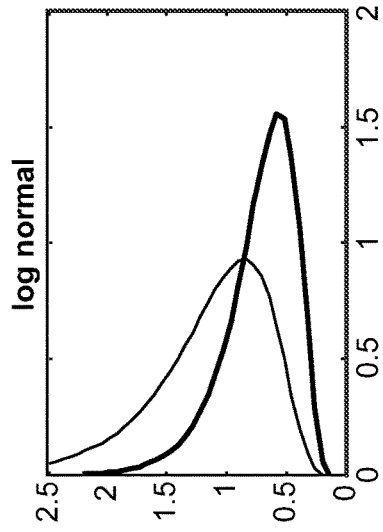
Figure 4A:
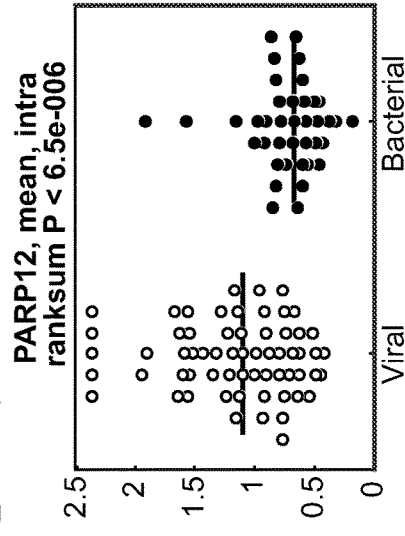
Figure 4A:
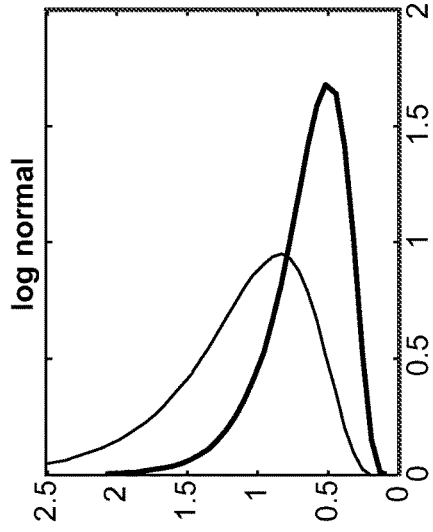
Figure 4A:
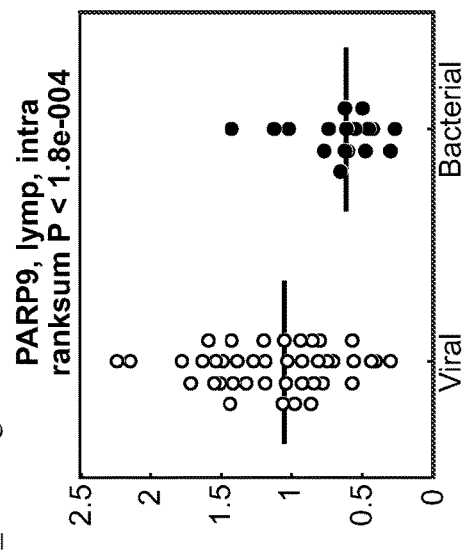
Figure 4A:
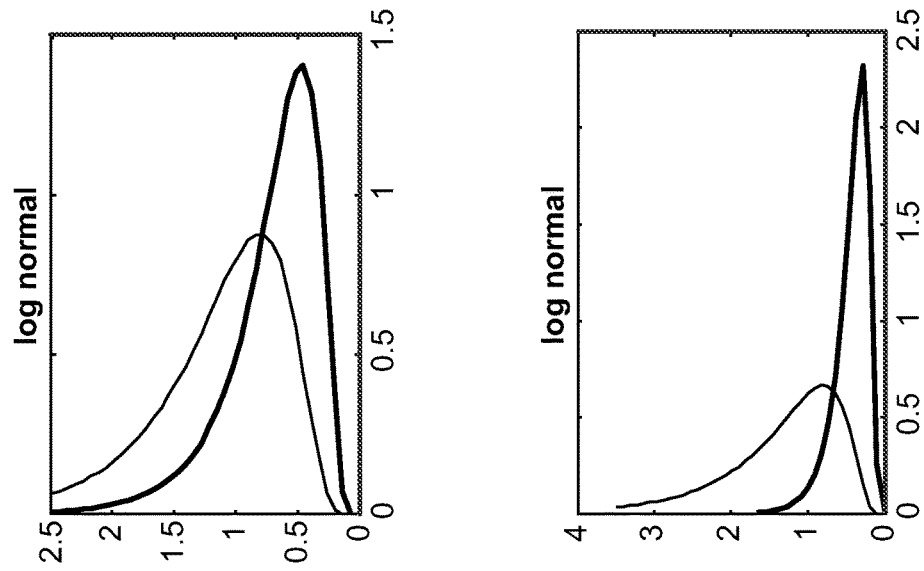
Figure 4A:
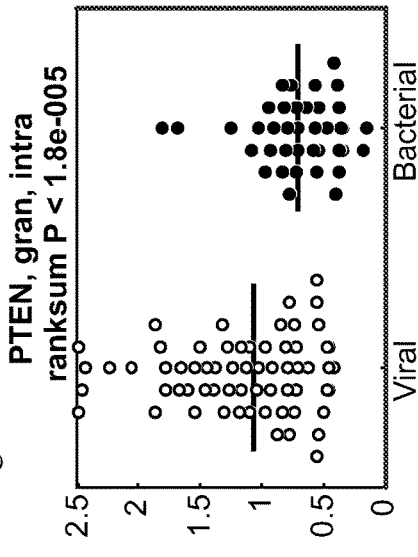
Figure 4A:
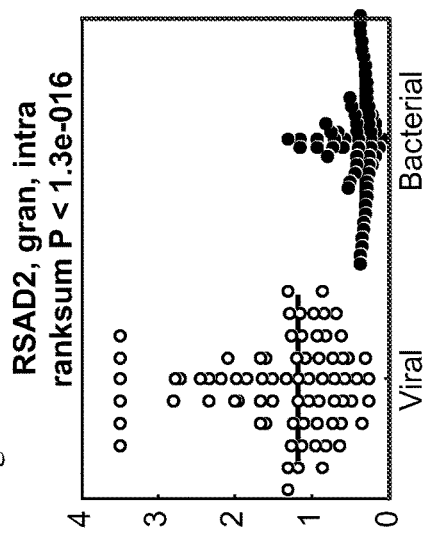
Figure 4A:
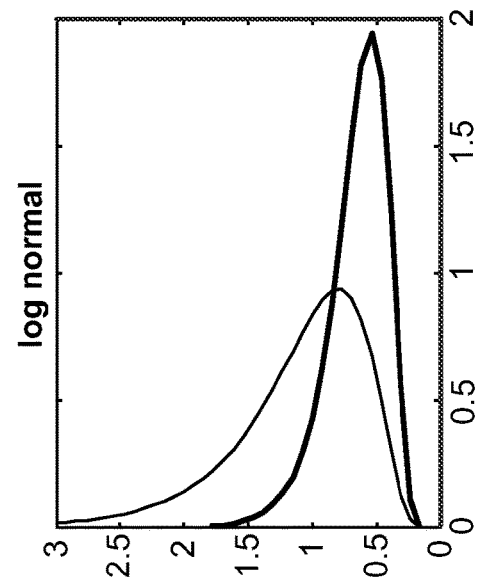
Figure 4A:
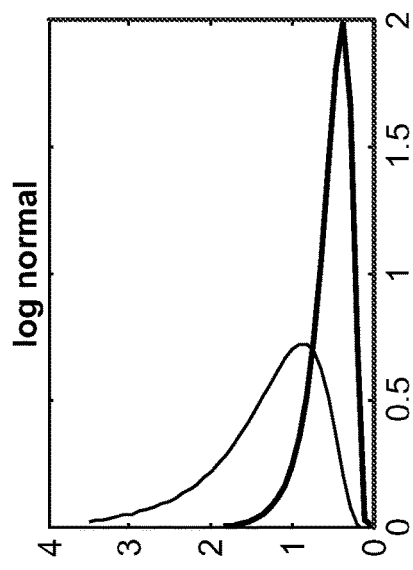
Figure 4A:
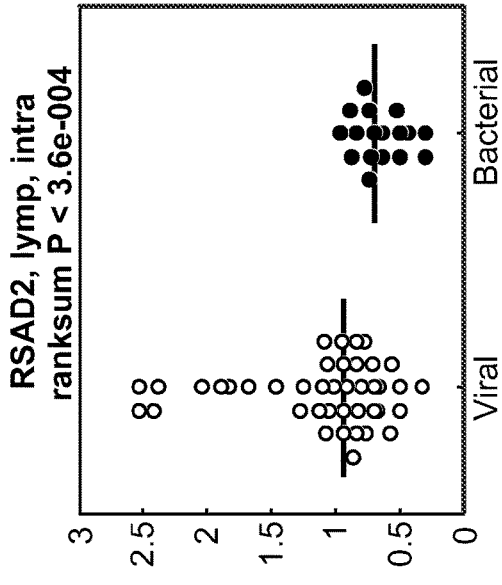
Figure 4A:
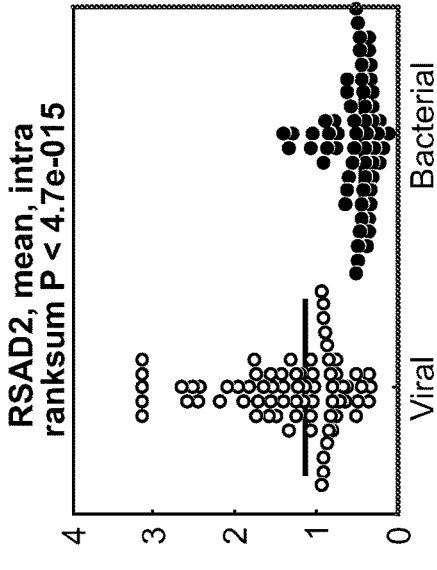
Figure 4A:
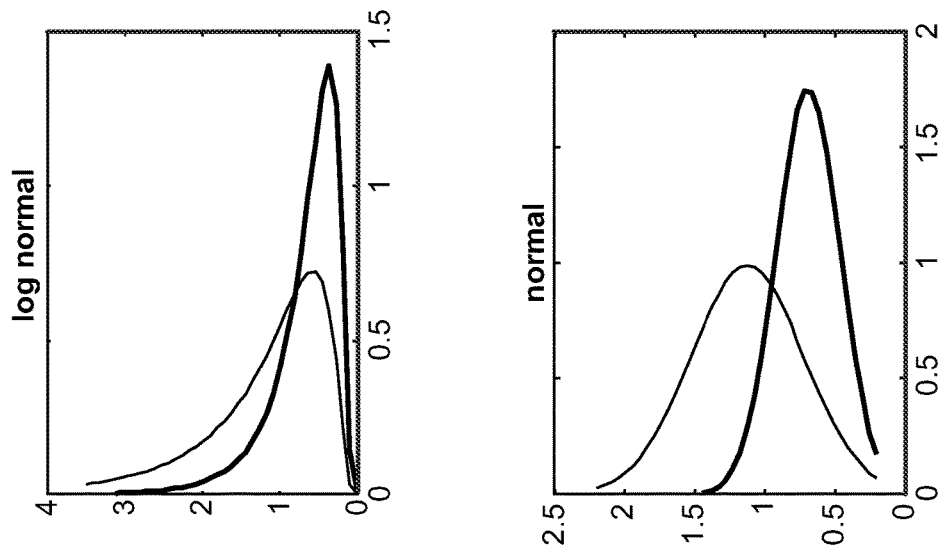
Figure 4A:
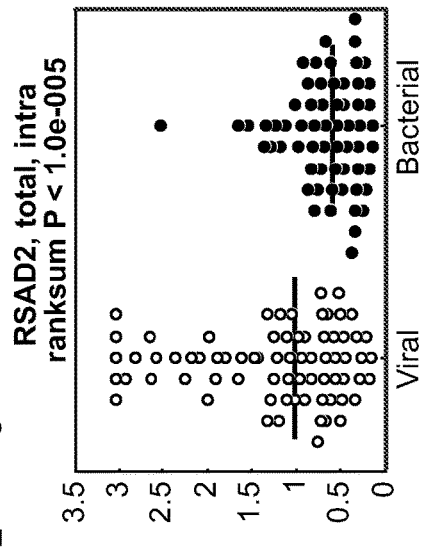
Figure 4A:
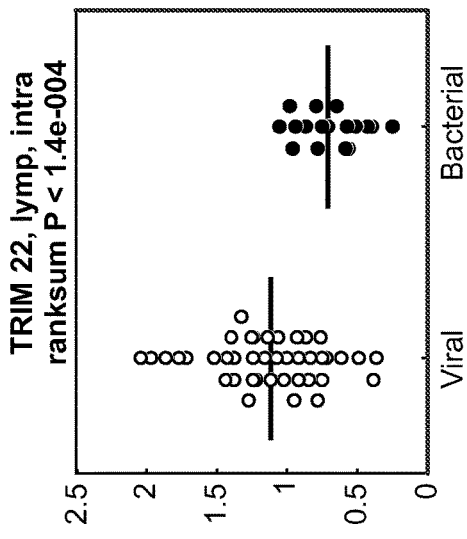
Figure 4A:
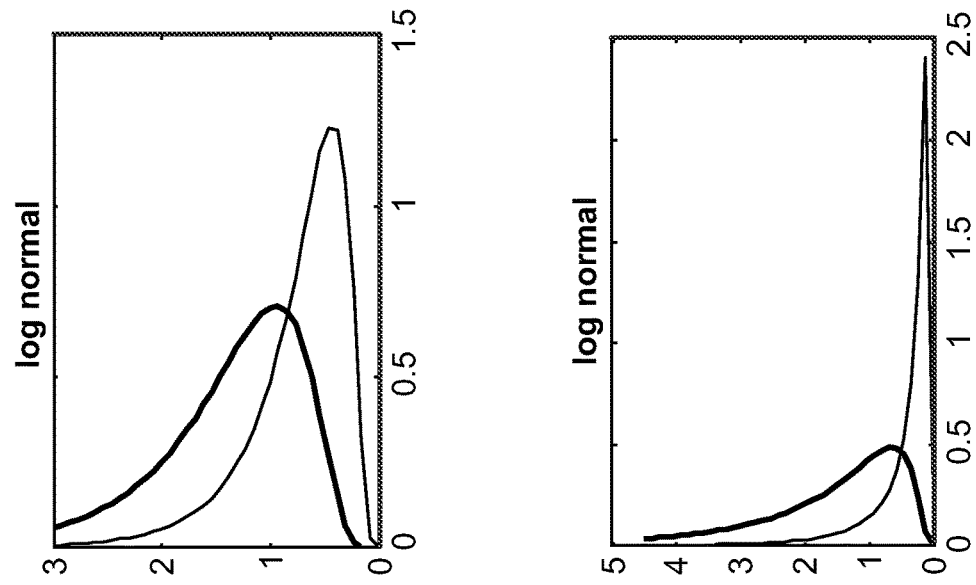
Figure 4A:
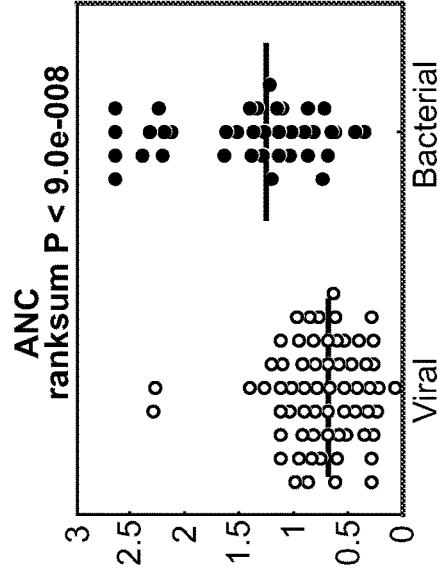
Figure 4A:
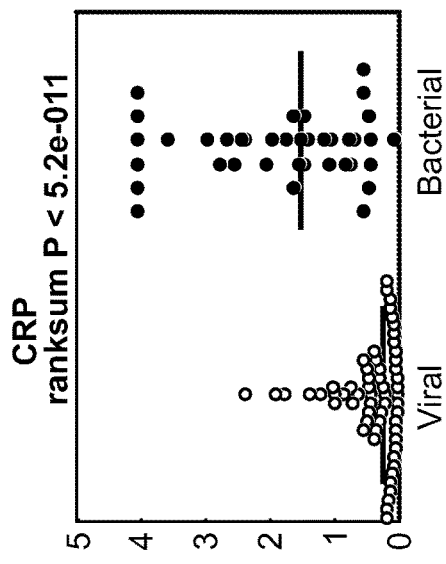
Figure 4A:
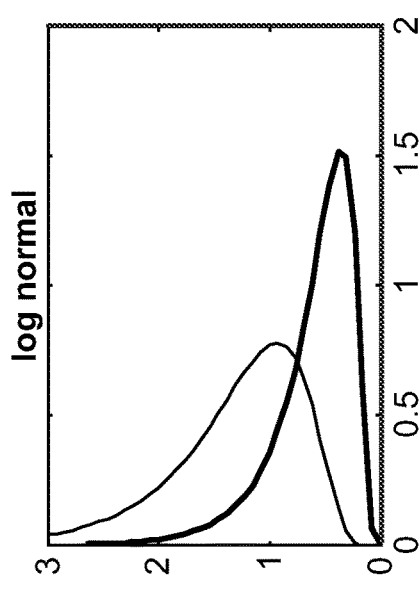
Figure 4A:
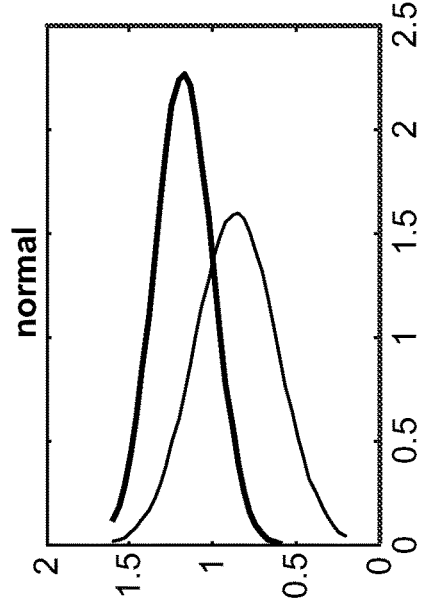
Figure 4A:
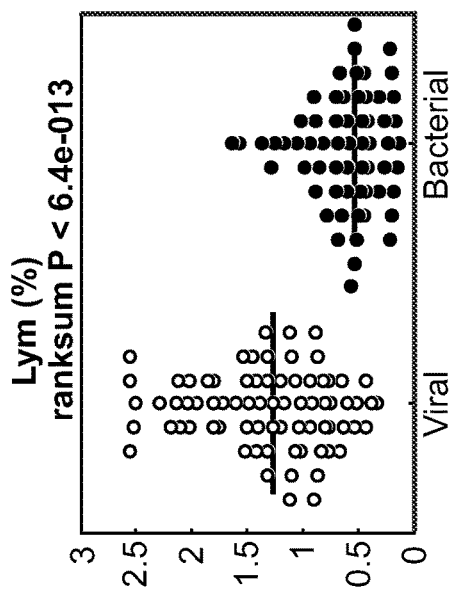
Figure 4A:
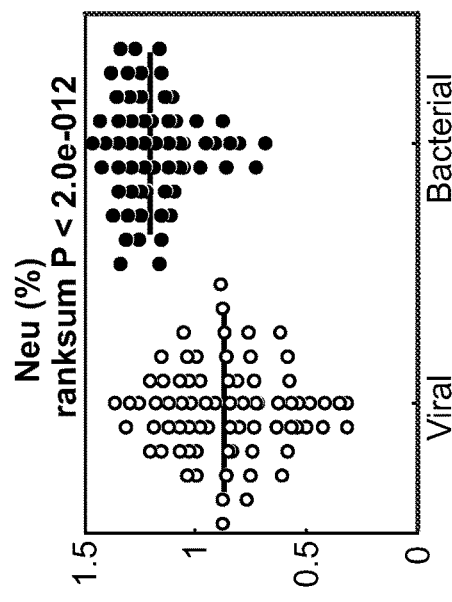
Figure 4A:
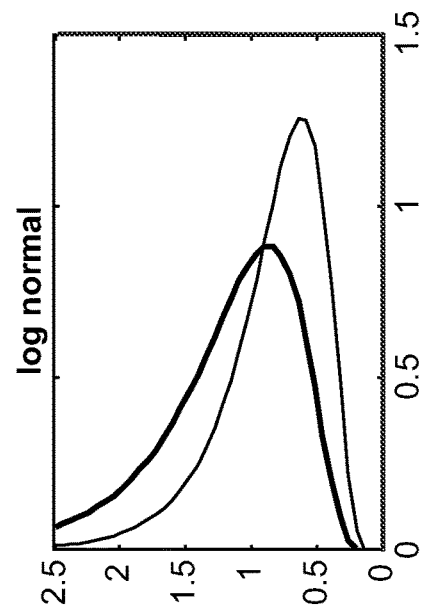
Figure 4A:
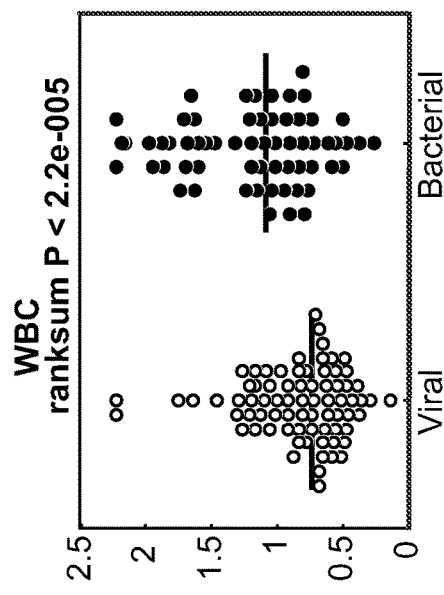

Example 3: Determinants that Differentiate Between Bacterial Versus Viral Infected Patients We identified a few DETERMINANTS that were differentially expressed in patients with bacterial versus viral infections in a statistically significant manner (Wilcoxon ranksum P<0.001). DETERMINANT names and classification accuracies are listed in Table 1A. The distributions and individual patient measurements for each of the DETERMINANTS are depicted in FIG. 4A (dots corresponds to DETERMINANTS measurement in individual patients and bars indicate group means). The abbreviations lym, gran, mono, mean and total are used to indicate whether a DETERMINANT polypeptide was differentially expressed in lymphocytes, granulocytes, monocytes, mean signal over all leukocytes or total signal of leukocytes respectively. The latter was measured in a constant volume of 1 ul of blood. Each subplot corresponds to a different DETERMINANT.

Figure 4B:
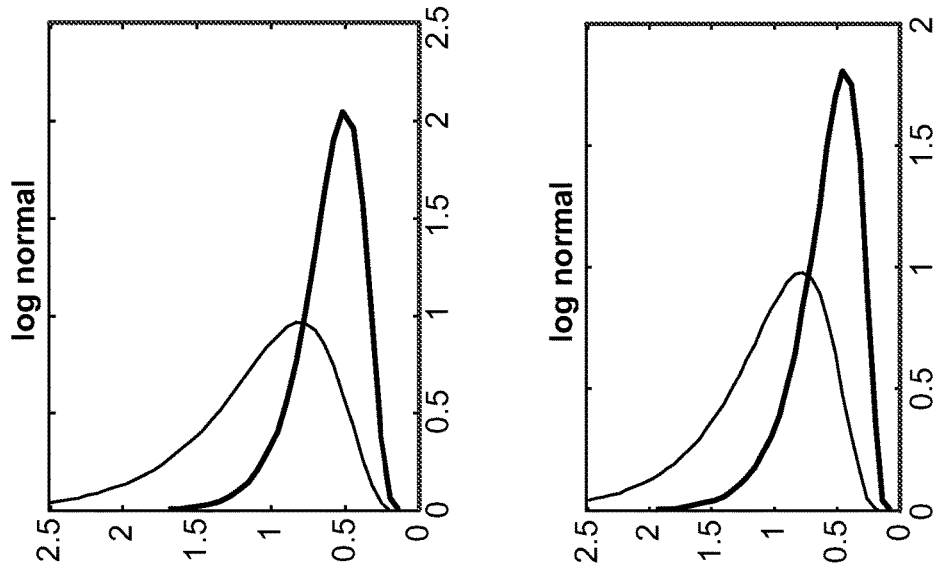
Figure 4B:
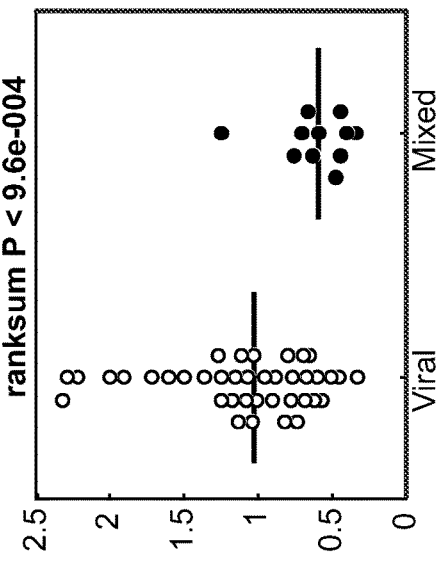
Figure 4B:
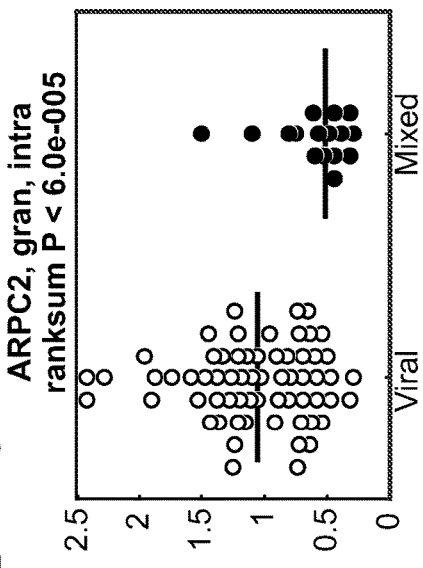
Figure 4B:
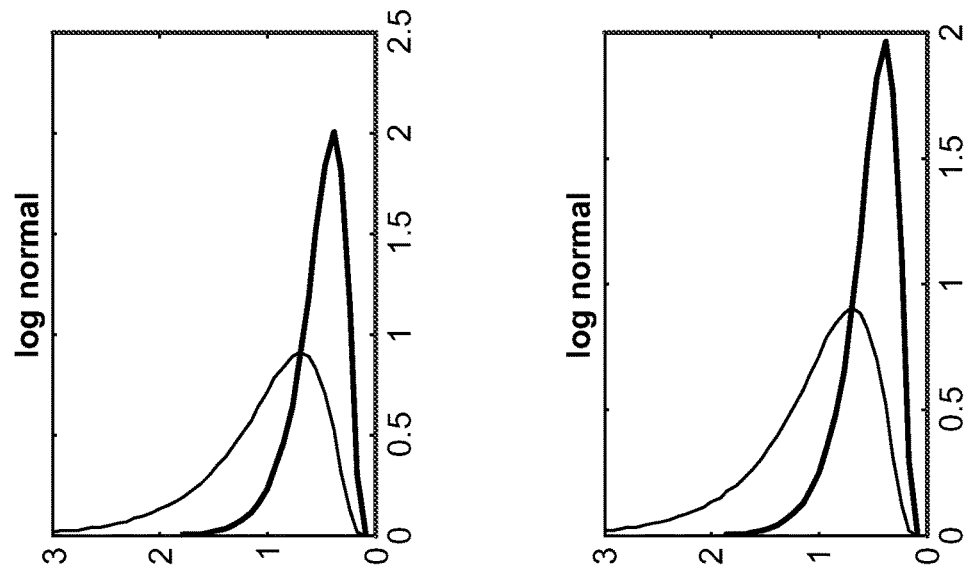
Figure 4B:
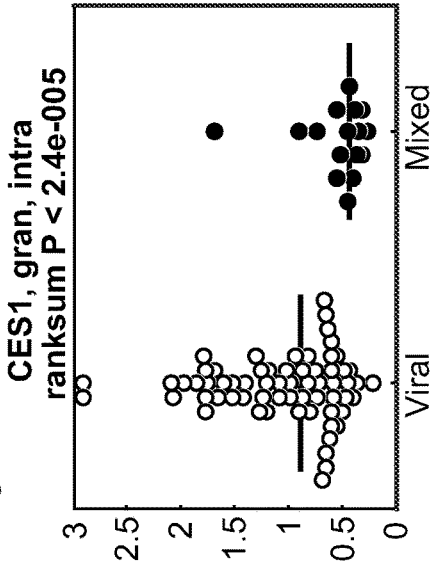
Figure 4B:
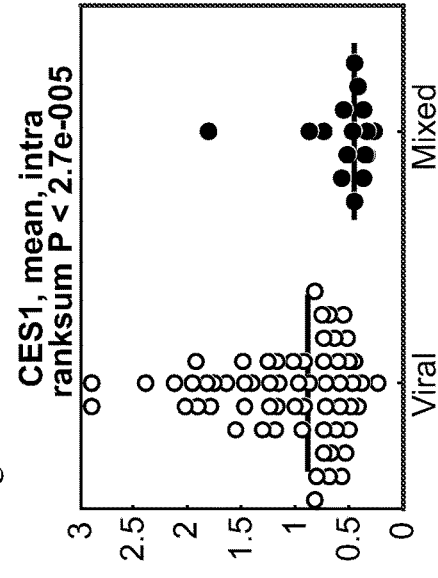
Figure 4B:
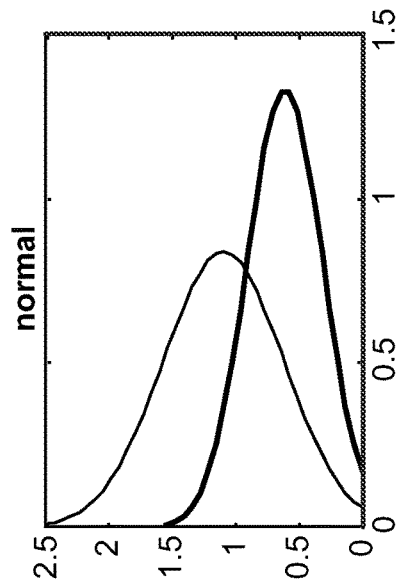
Figure 4B:
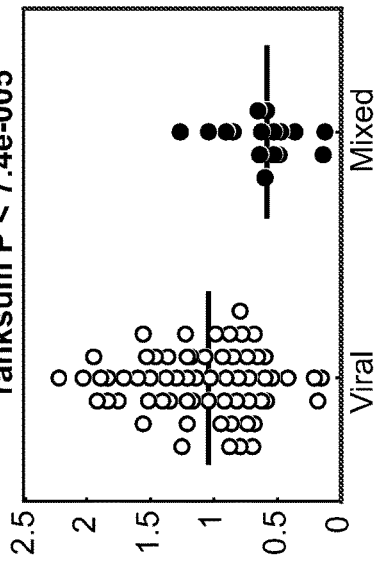
Figure 4B:
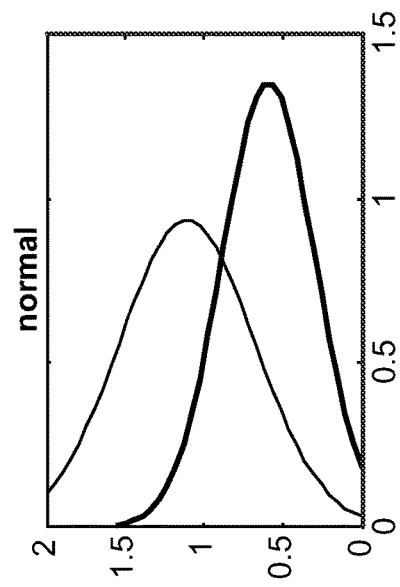
Figure 4B:
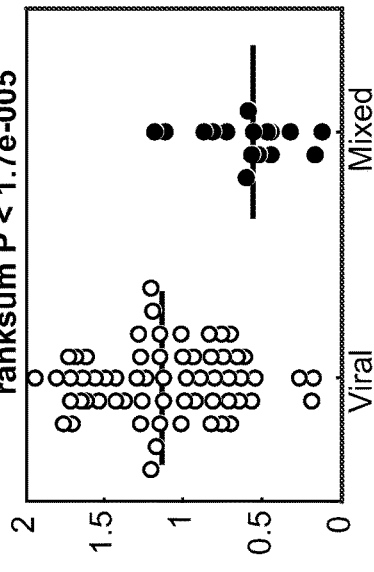
Figure 4B:
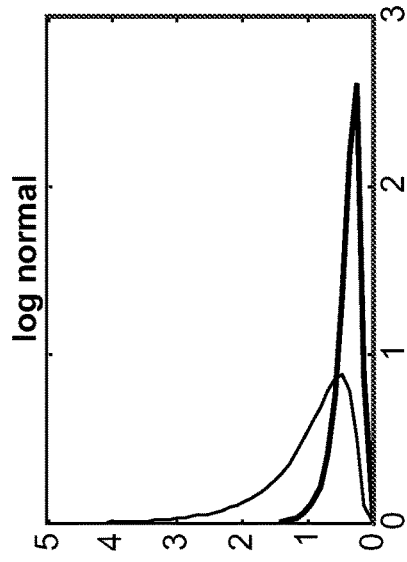
Figure 4B:
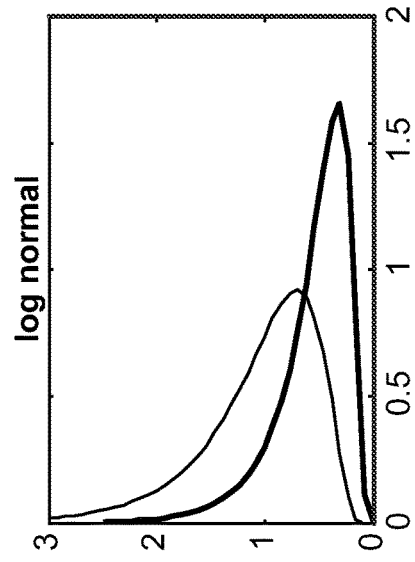
Figure 4B:
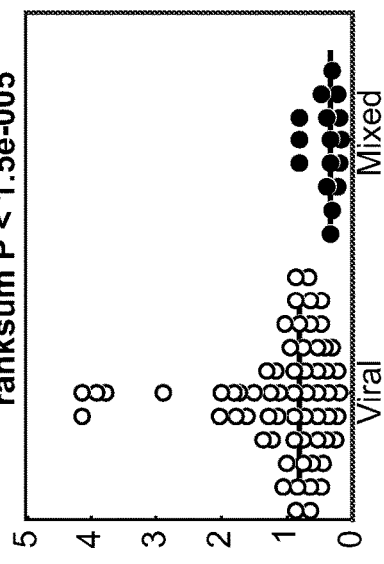
Figure 4B:
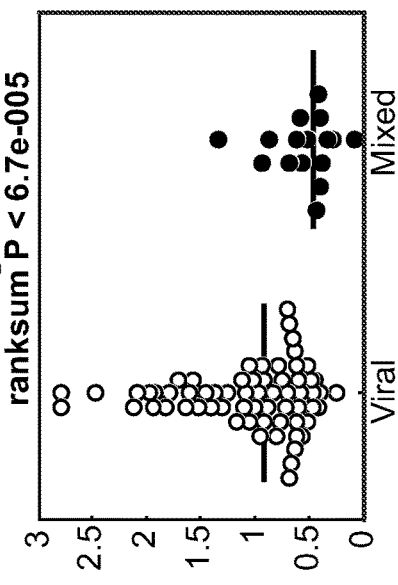
Figure 4B:
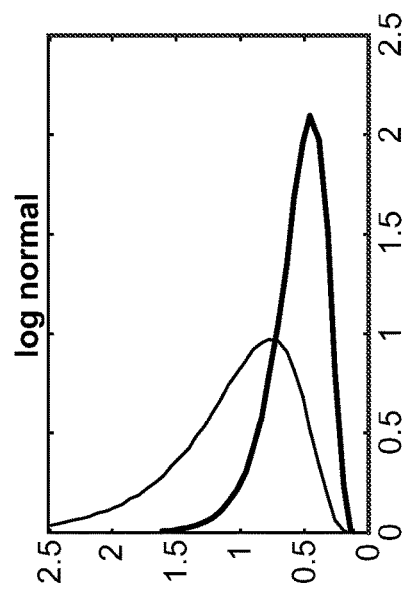
Figure 4B:
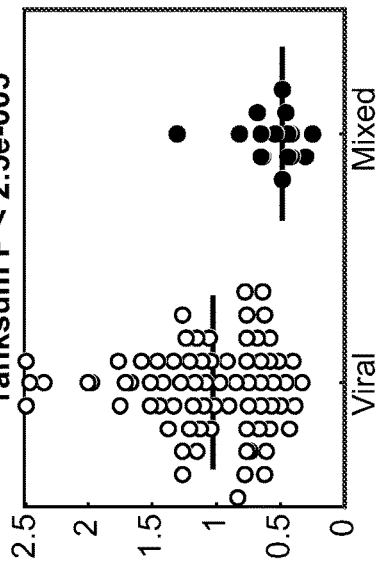
Figure 4B:
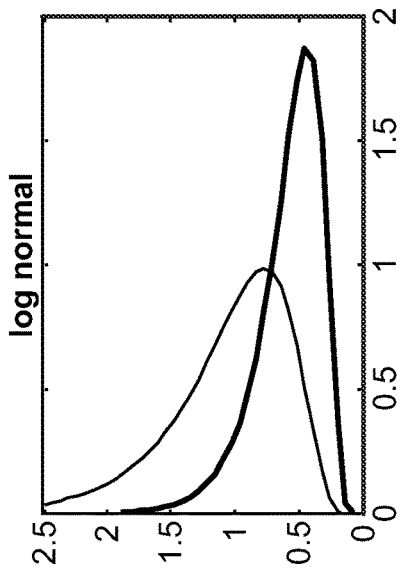
Figure 4B:
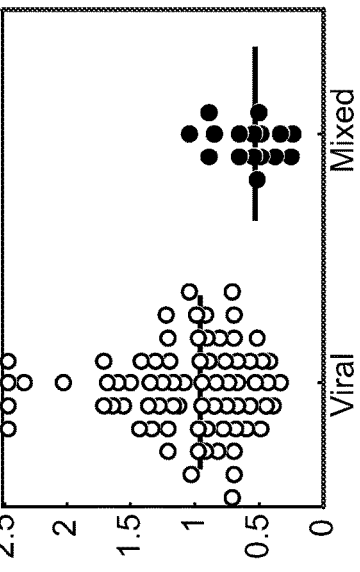
Figure 4B:
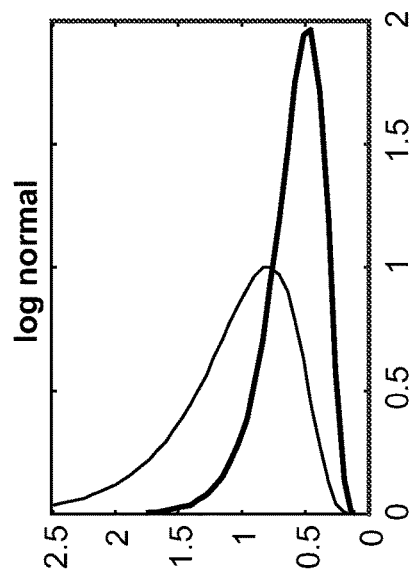
Figure 4B:
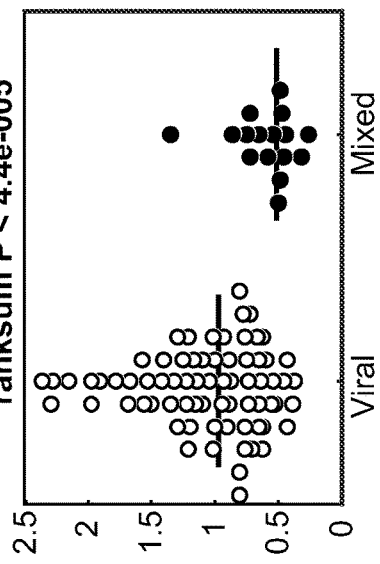
Figure 4B:
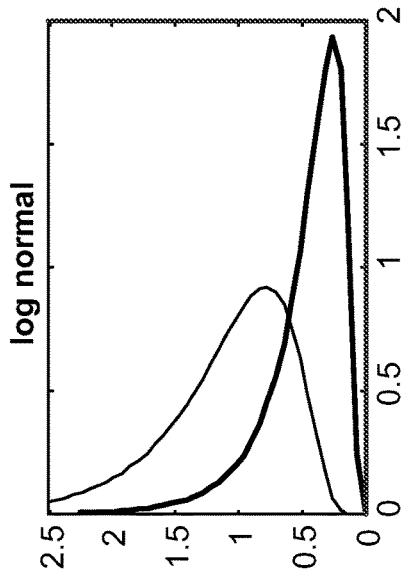
Figure 4B:
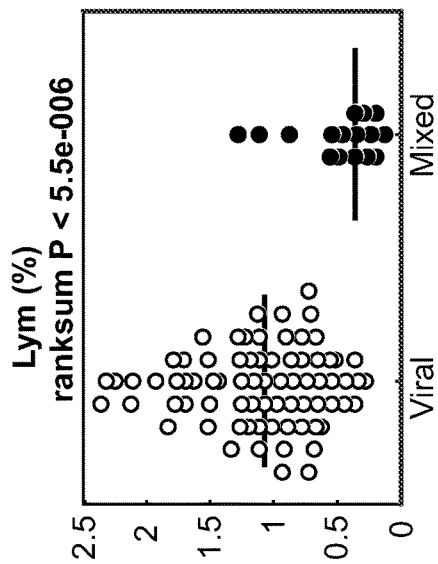
Figure 4B:
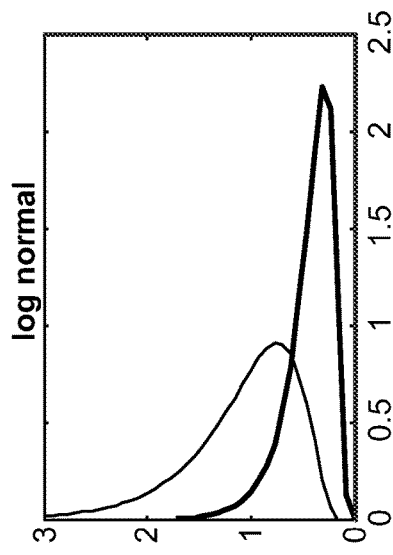
Figure 4B:
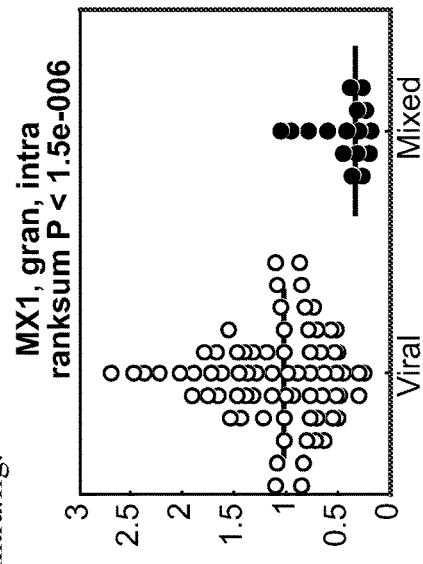
Figure 4B:
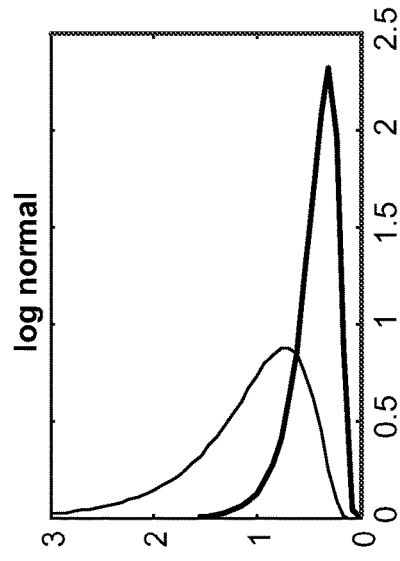
Figure 4B:
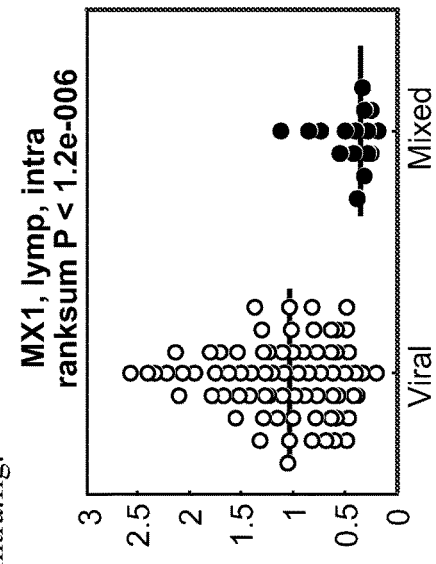
Figure 4B:
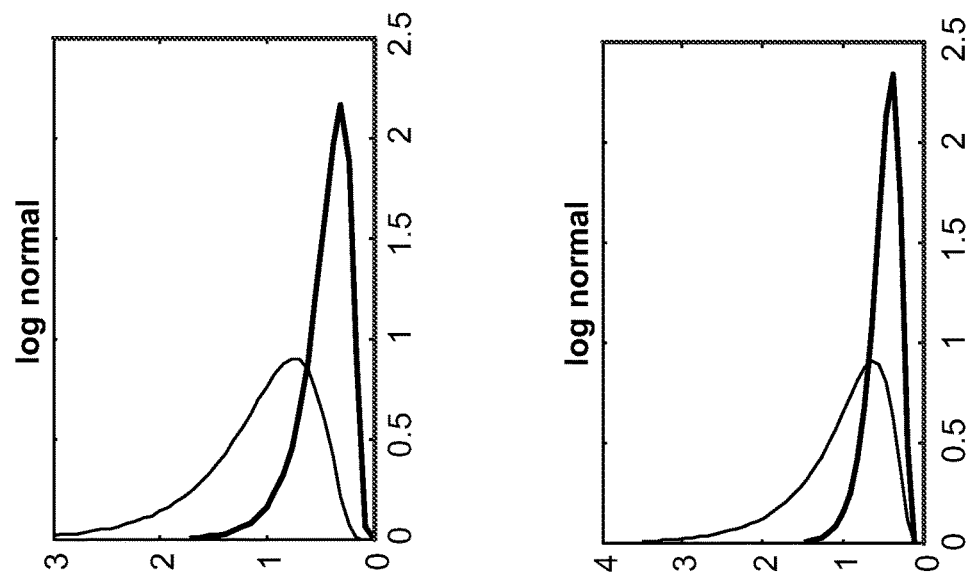
Figure 4B:
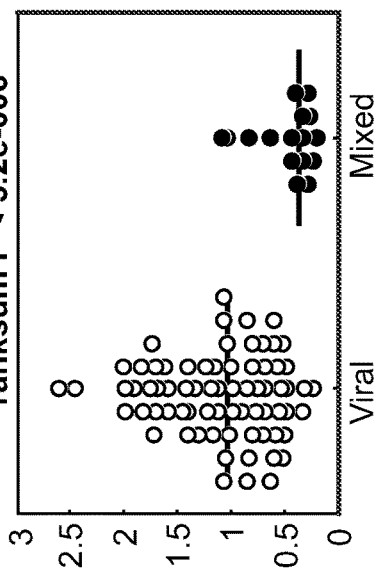
Figure 4B:
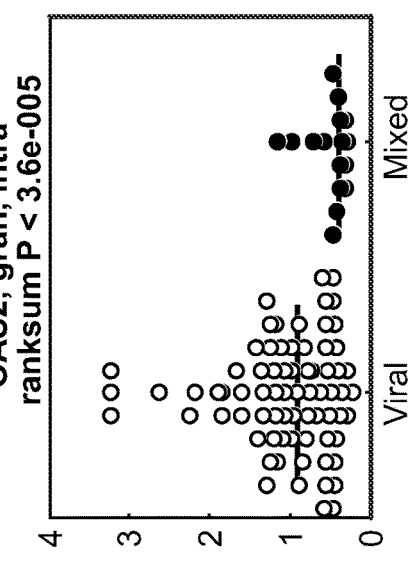
Figure 4B:
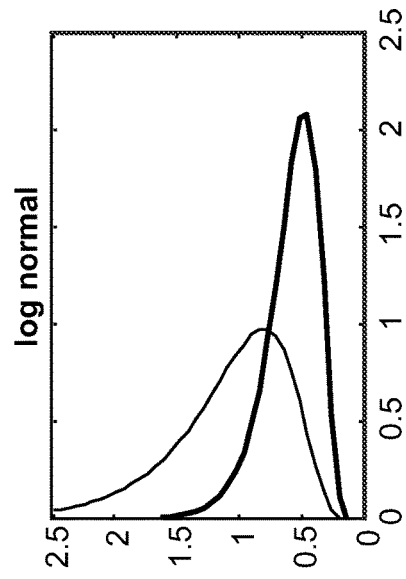
Figure 4B:
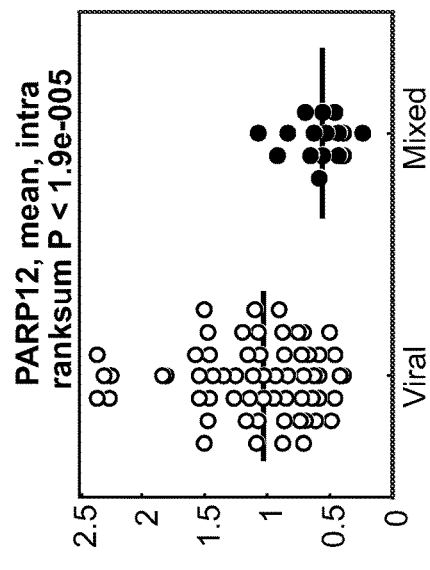
Figure 4B:
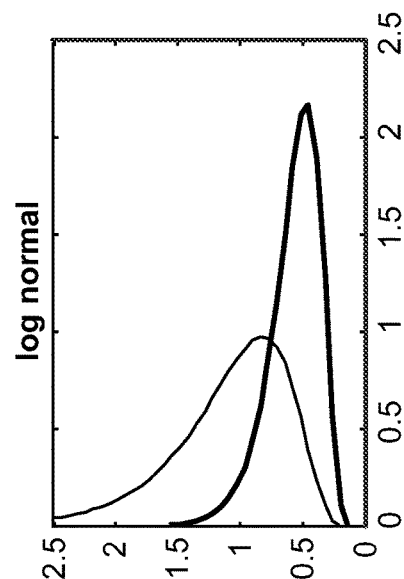
Figure 4B:
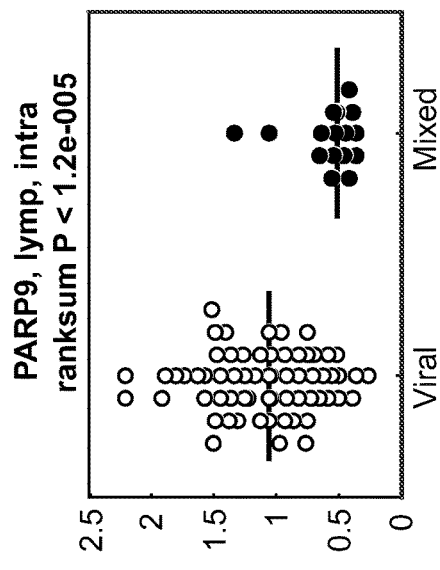
Figure 4B:
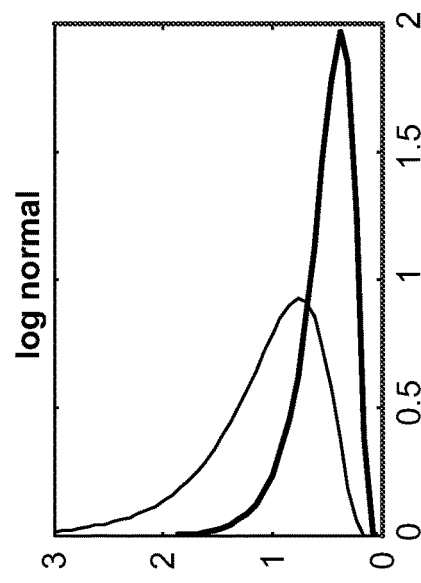
Figure 4B:
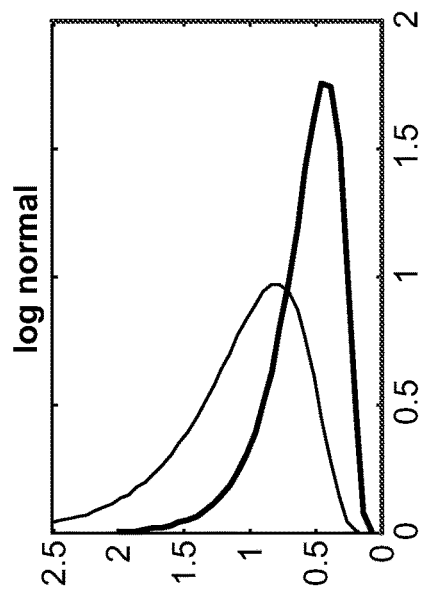
Figure 4B:
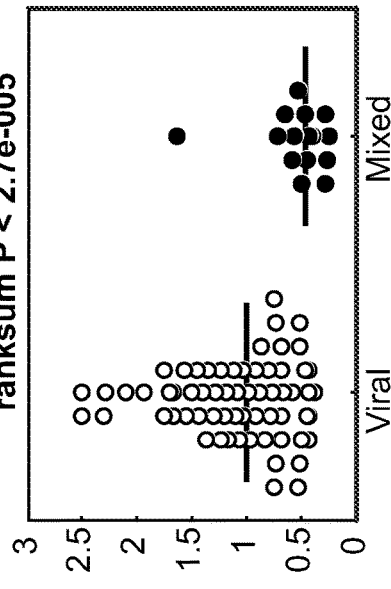
Figure 4B:
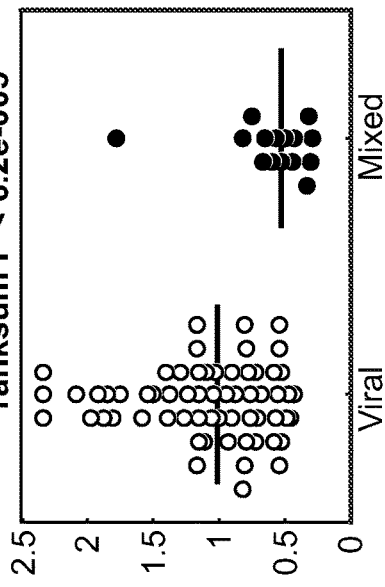
Figure 4B:
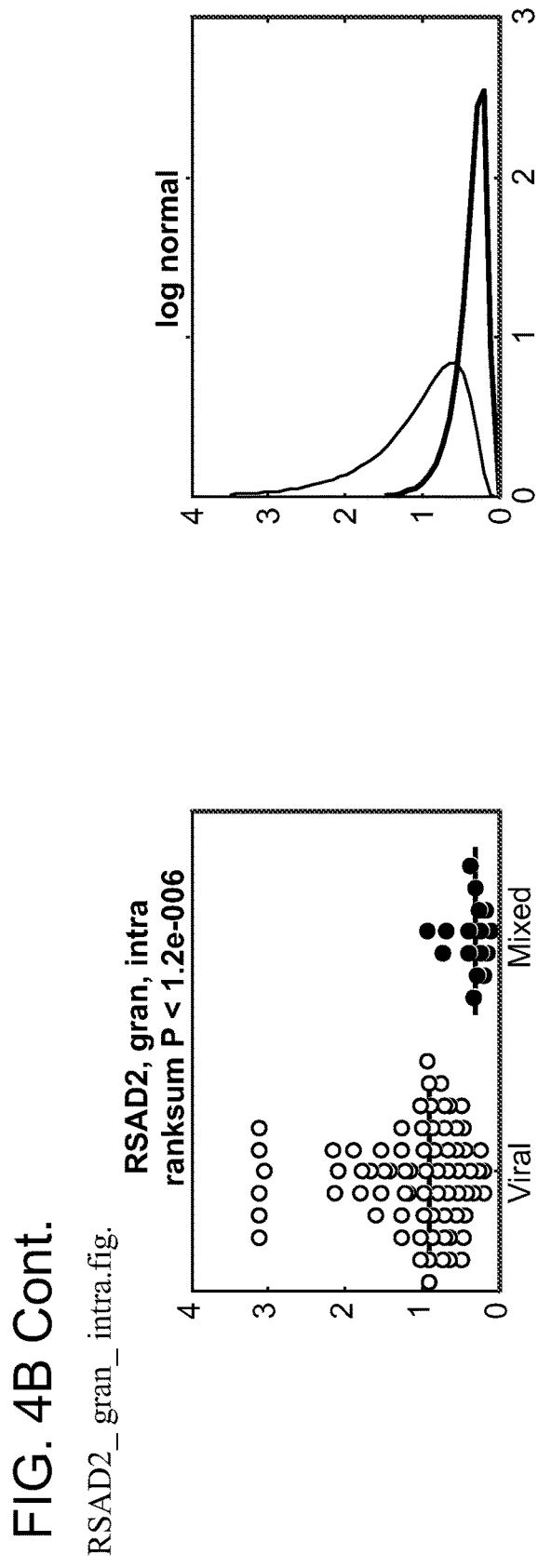
Figure 4B:
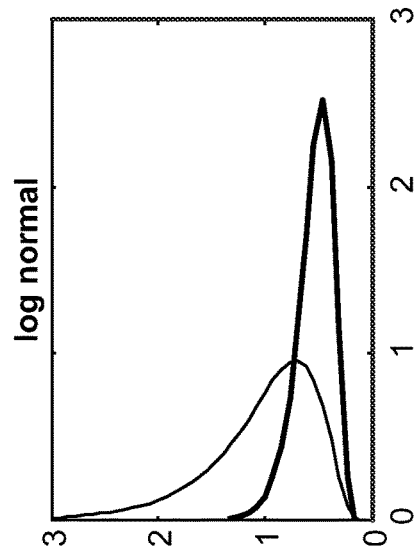
Figure 4B:
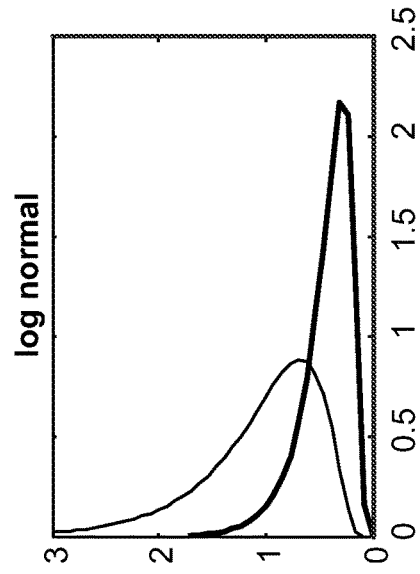
Figure 4B:
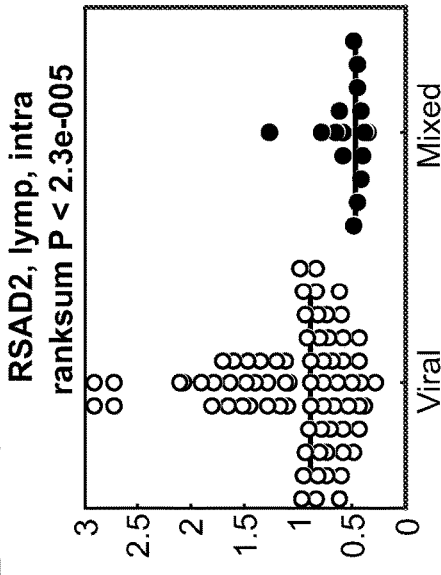
Figure 4B:
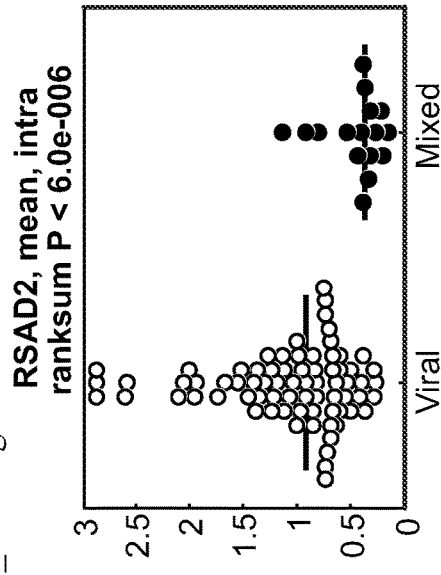
Figure 4B:
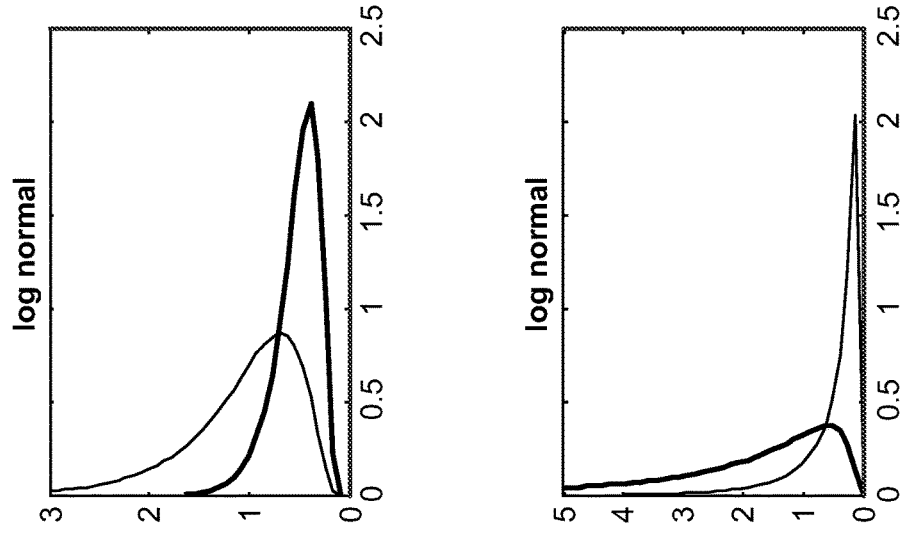
Figure 4B:
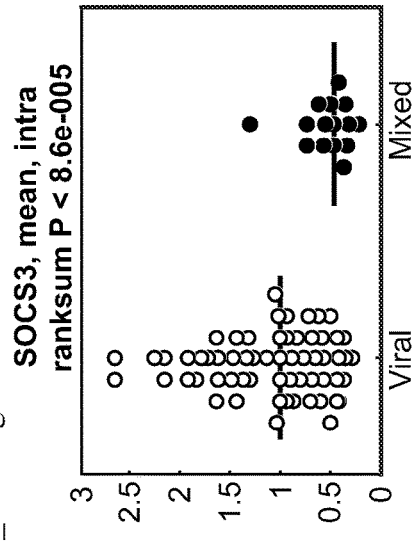
Figure 4B:
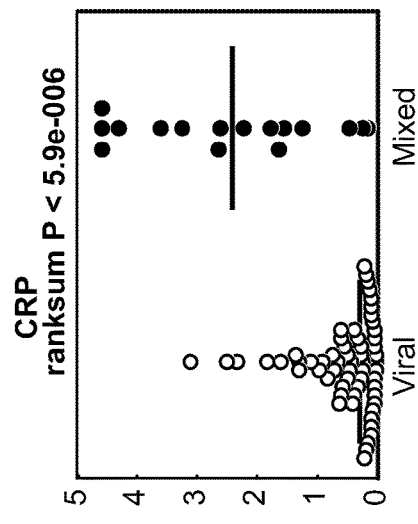

Example 4: Determinants that Differentiate Between Mixed Versus Viral Infected Patients Differentiating between a mixed infection (i.e. bacterial and viral co-infection) and a pure viral infection is important for deciding the appropriate treatment. To address this we identified a set of DETERMINANTS that were differentially expressed in patients with mixed infections versus viral infections in a statistically significant manner (Wilcoxon ranksum P<0.001). DETERMINANT names and classification accuracies are listed in Table 1B. The distributions and individual patient measurements for each of the DETERMINANTS are depicted in FIG. 4B.

Figure 4C:
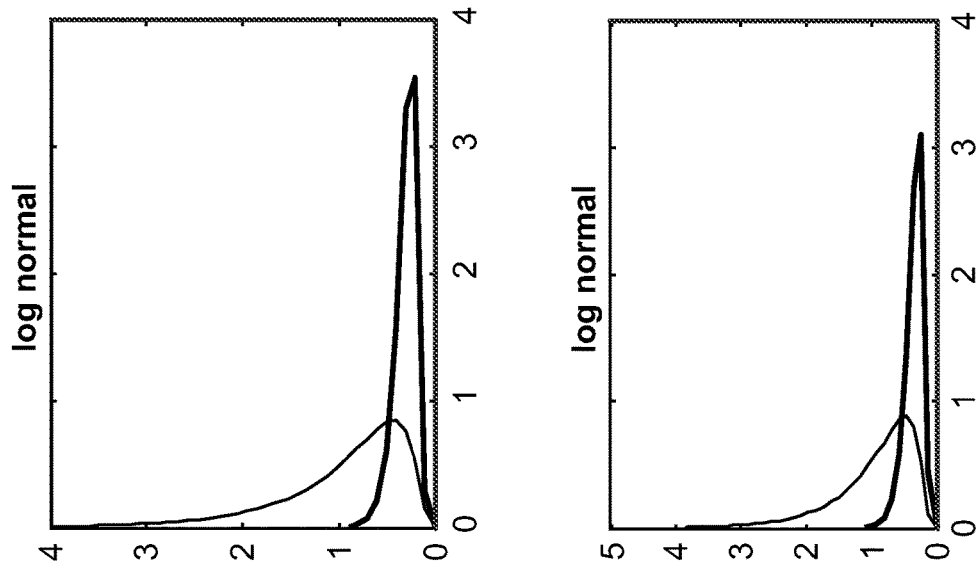
Figure 4C:
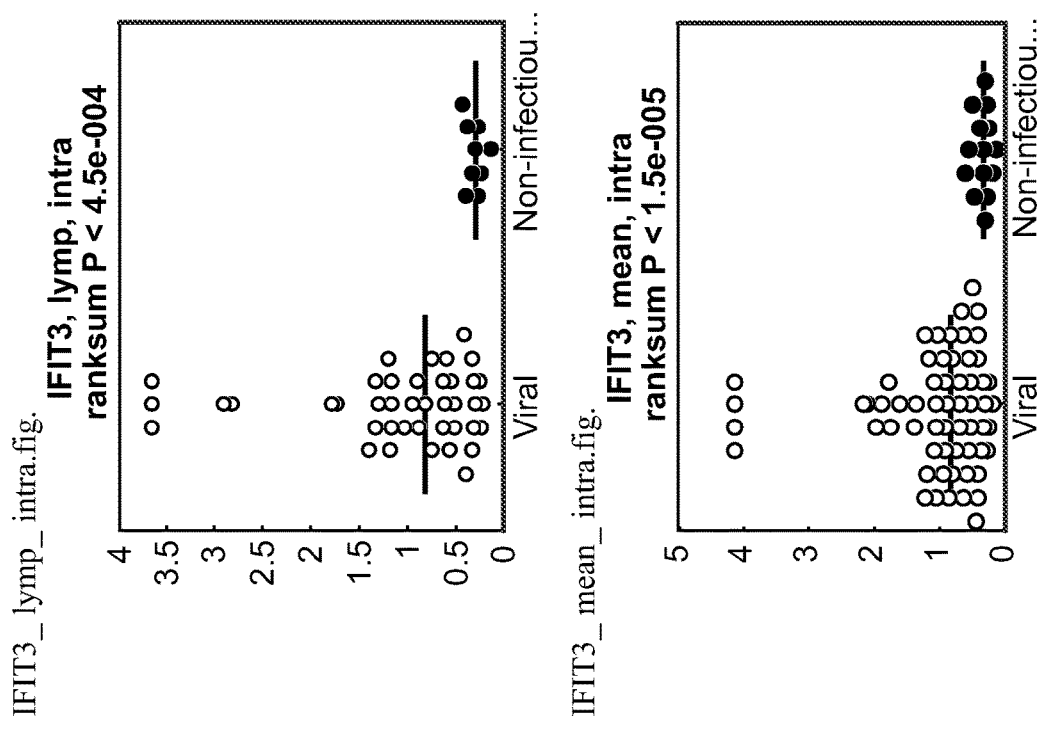
Figure 4C:
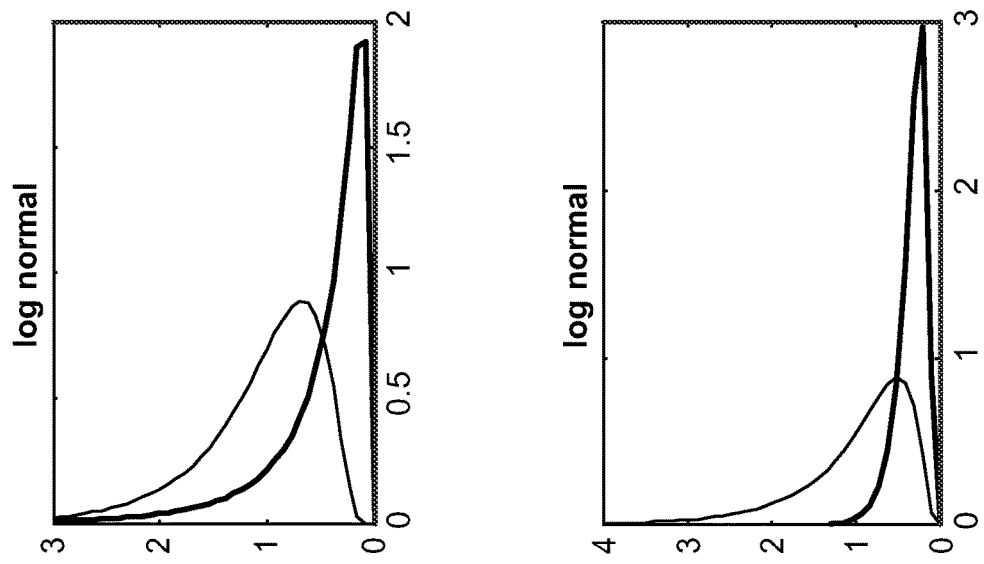
Figure 4C:
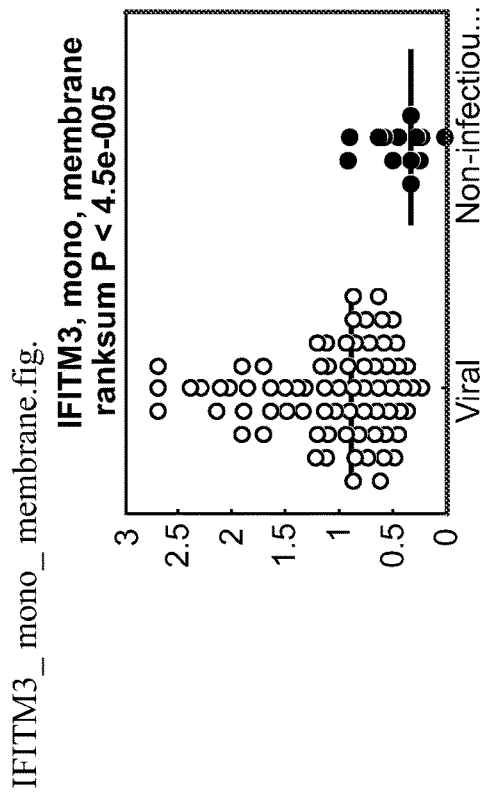
Figure 4C:
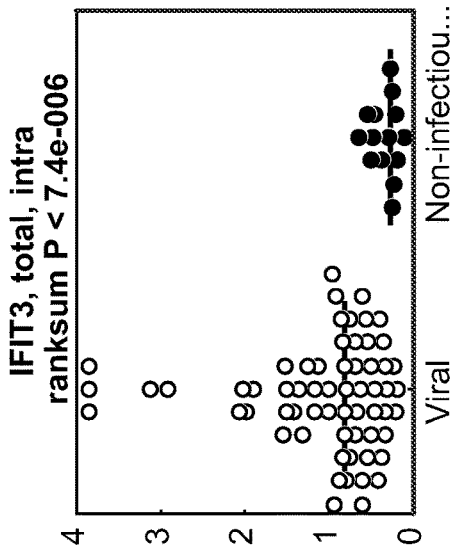
Figure 4C:
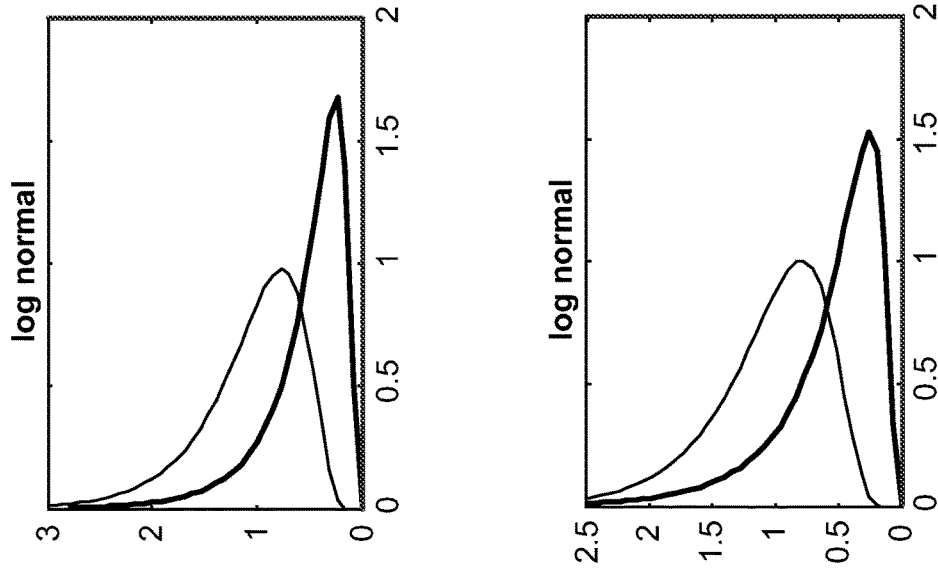
Figure 4C:
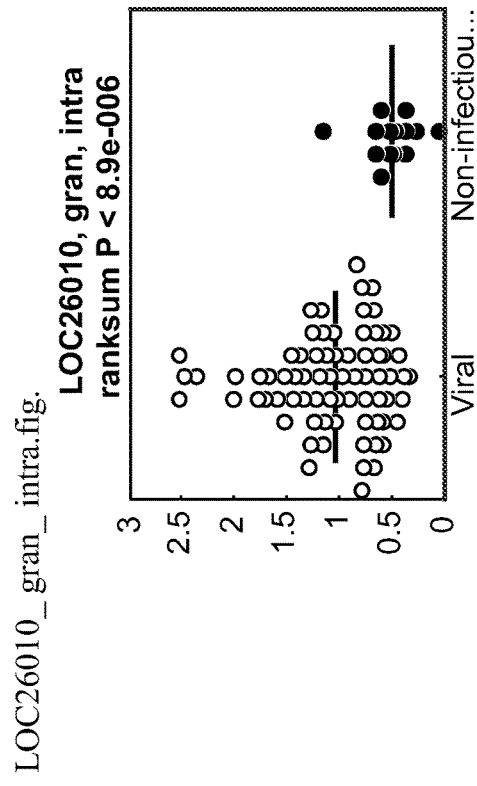
Figure 4C:
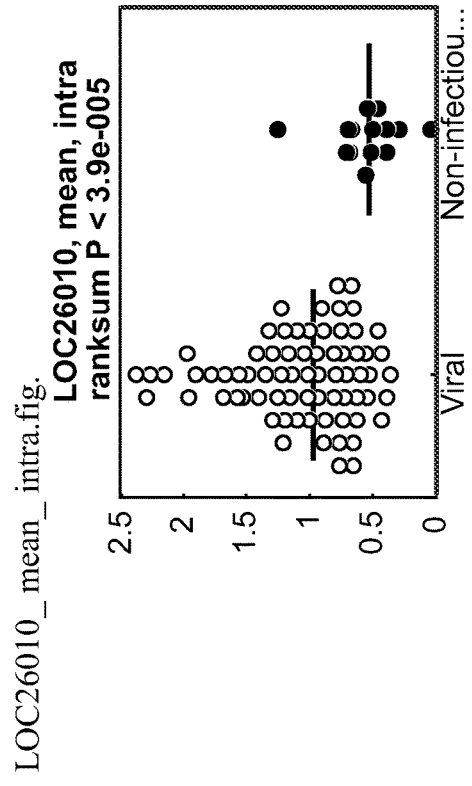
Figure 4C:
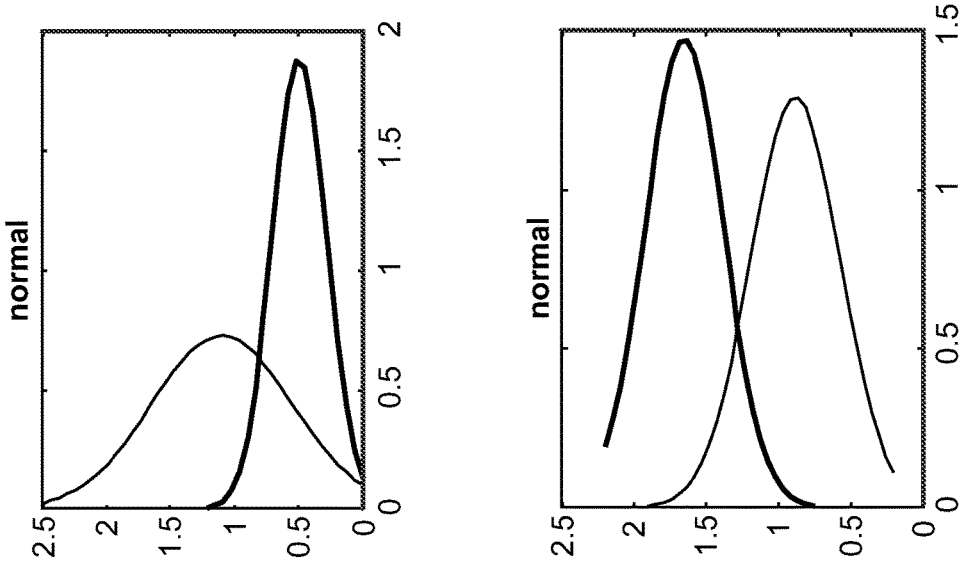
Figure 4C:
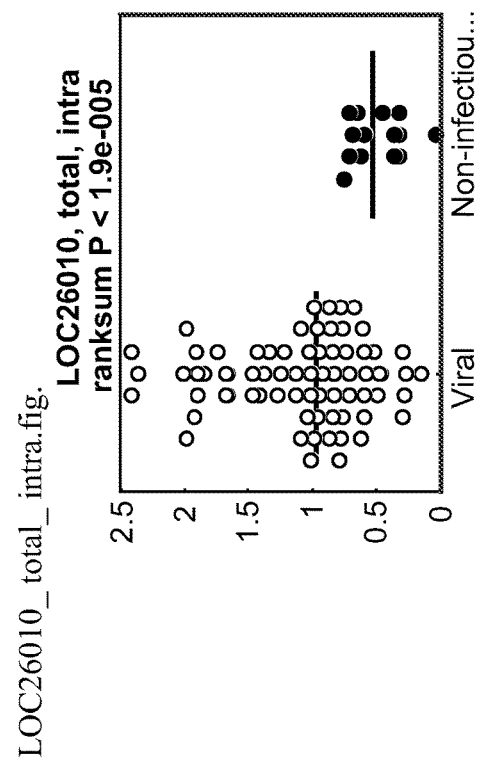
Figure 4C:
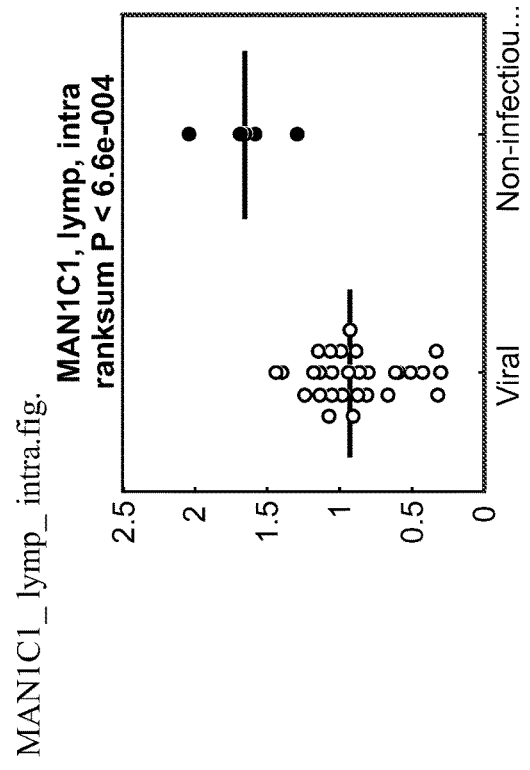
Figure 4C:
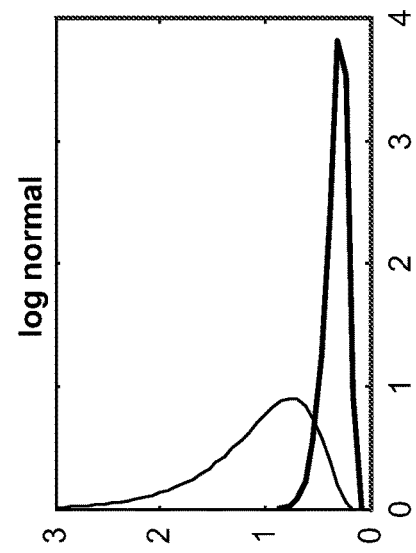
Figure 4C:
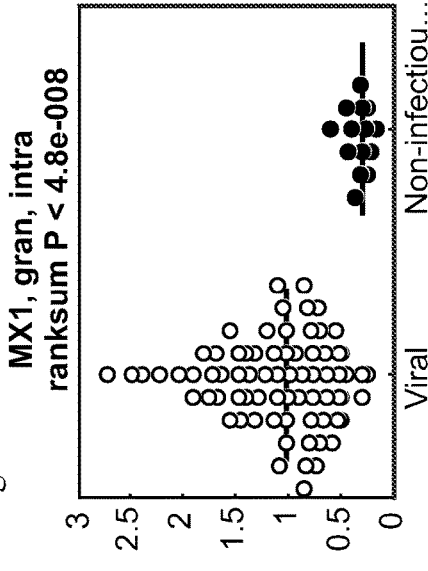
Figure 4C:
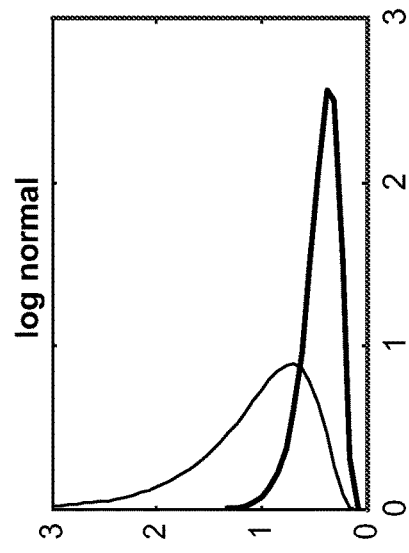
Figure 4C:
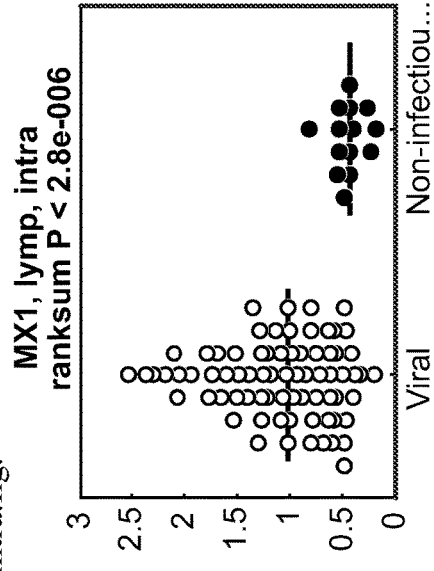
Figure 4C:
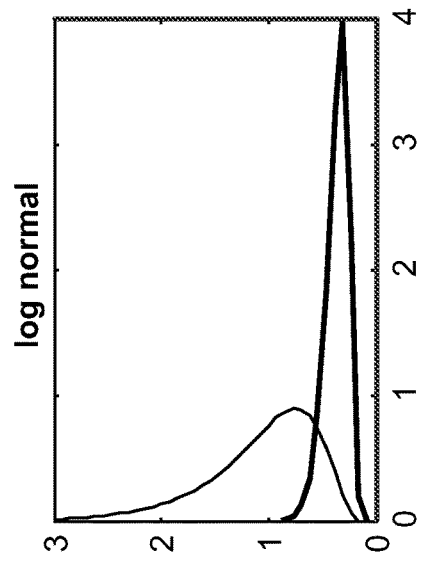
Figure 4C:
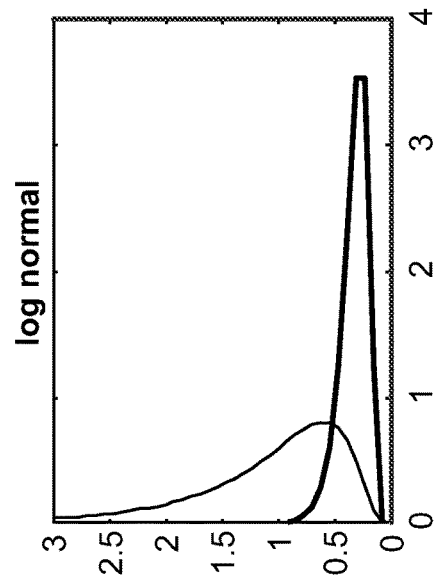
Figure 4C:
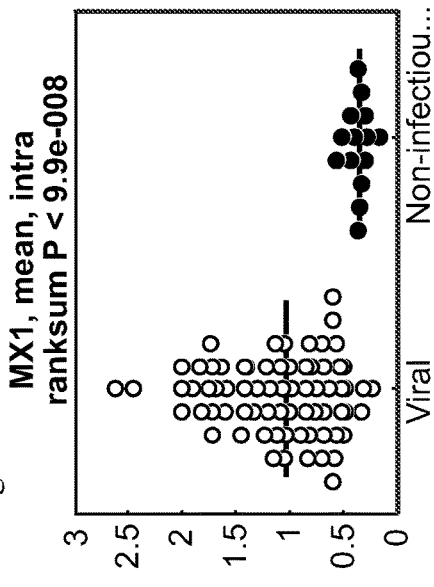
Figure 4C:
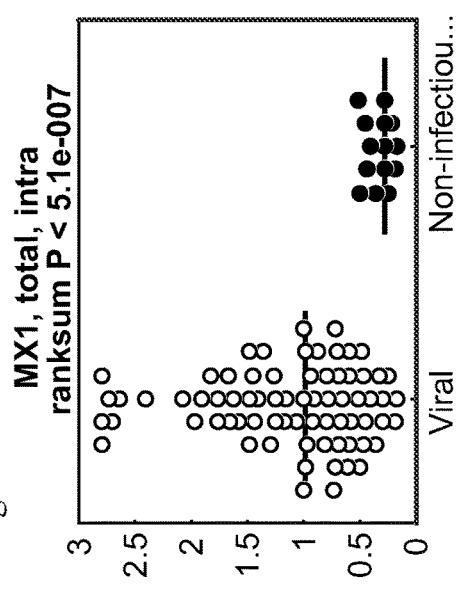
Figure 4C:
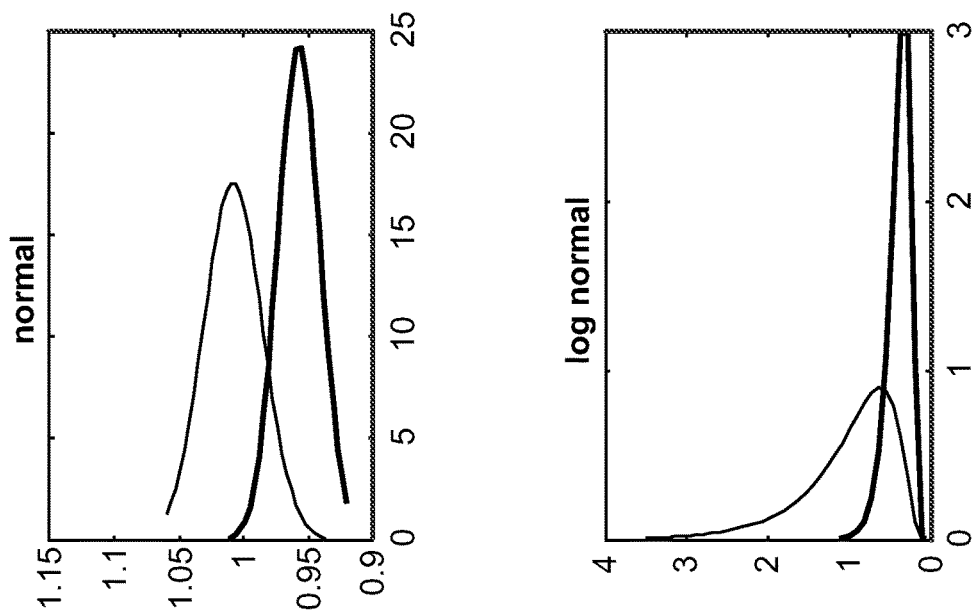
Figure 4C:
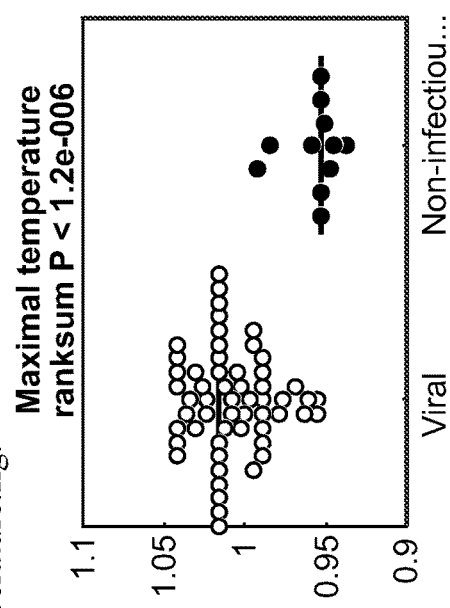
Figure 4C:
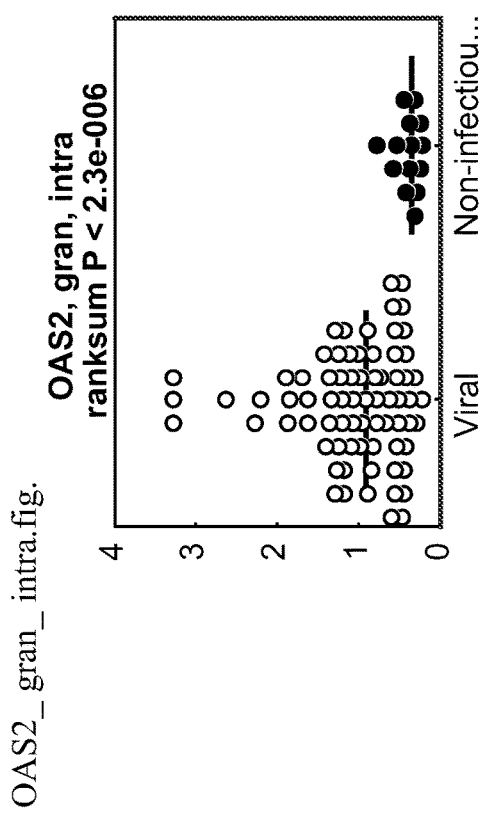
Figure 4C:
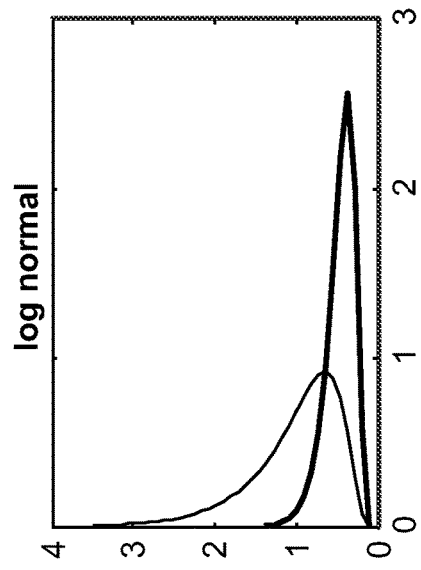
Figure 4C:
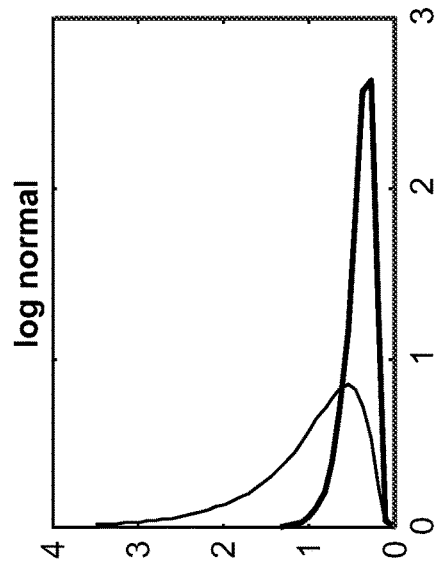
Figure 4C:
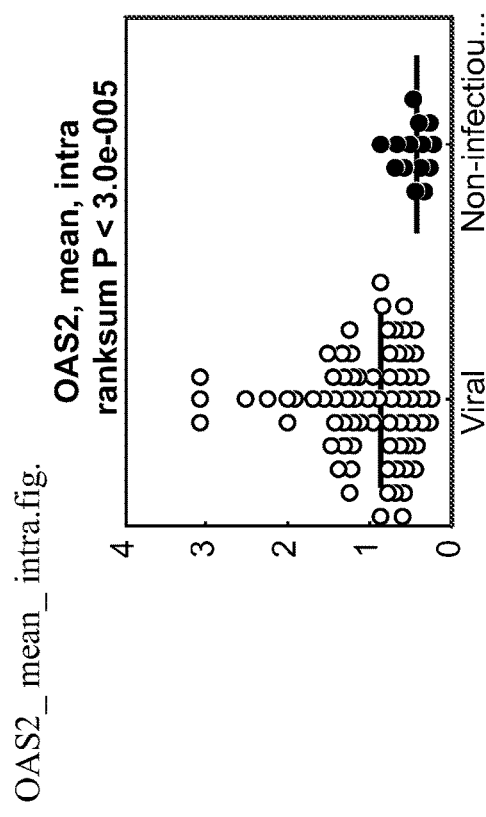
Figure 4C:
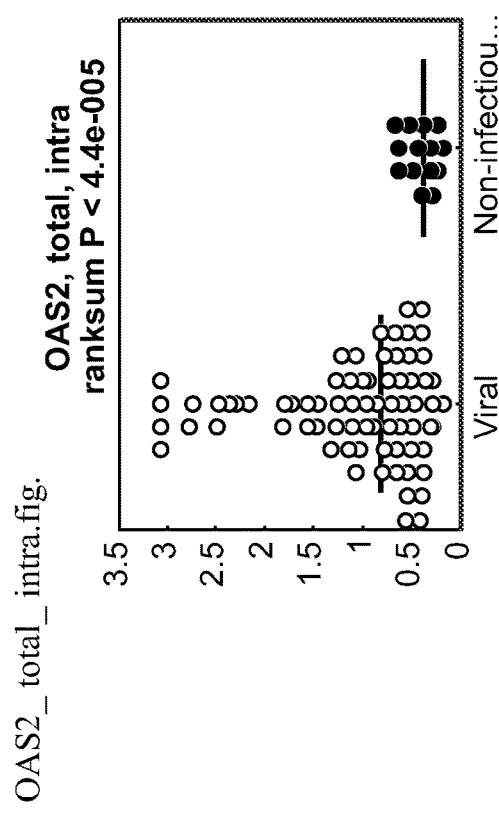
Figure 4C:
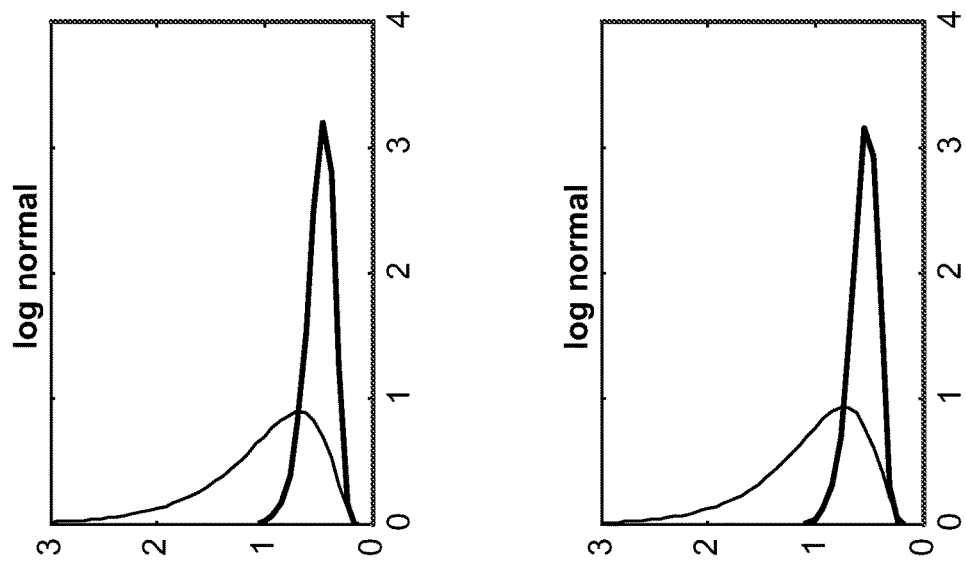
Figure 4C:
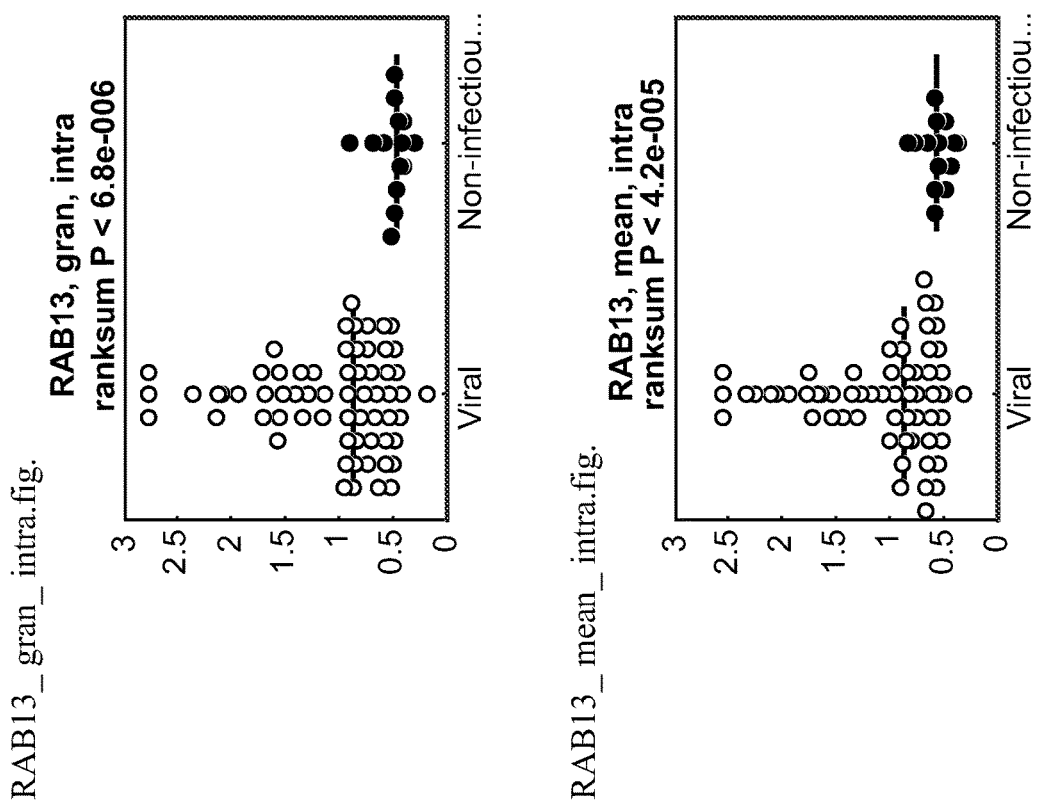
Figure 4C:
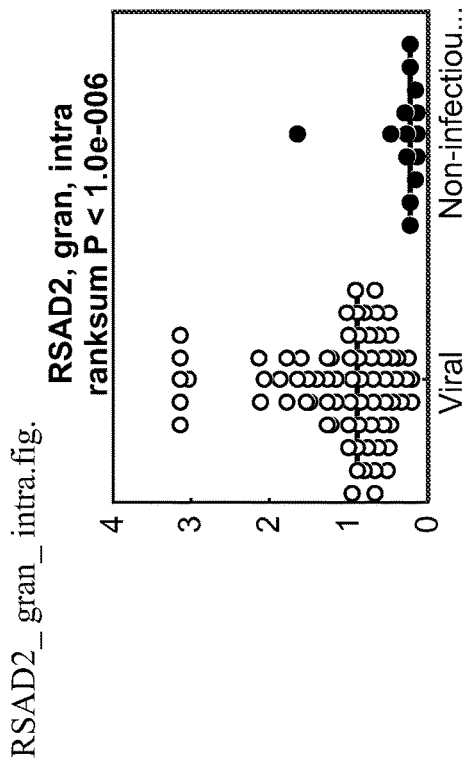
Figure 4C:
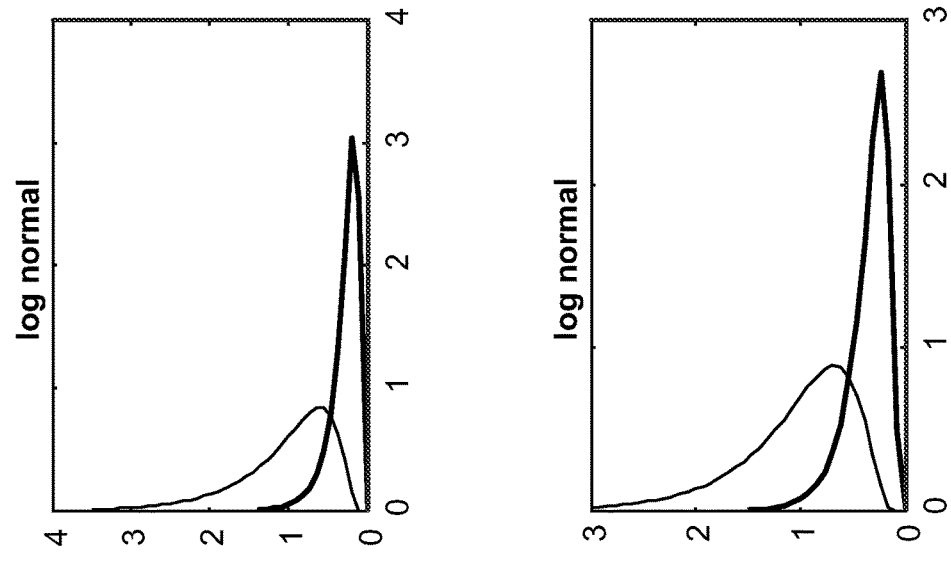
Figure 4C:
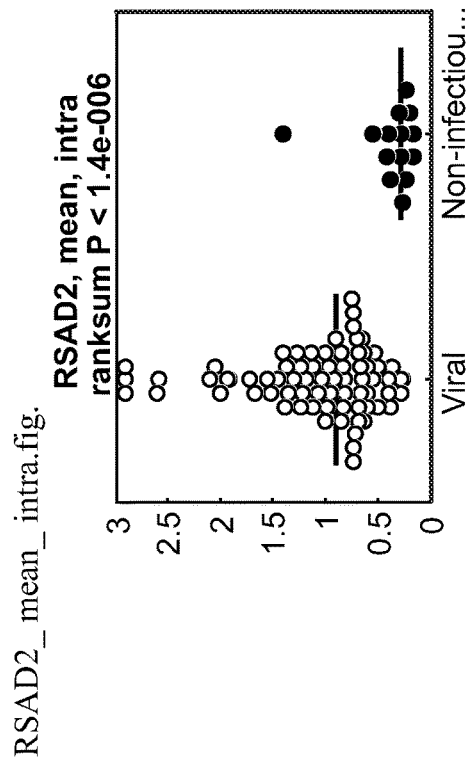
Figure 4C:
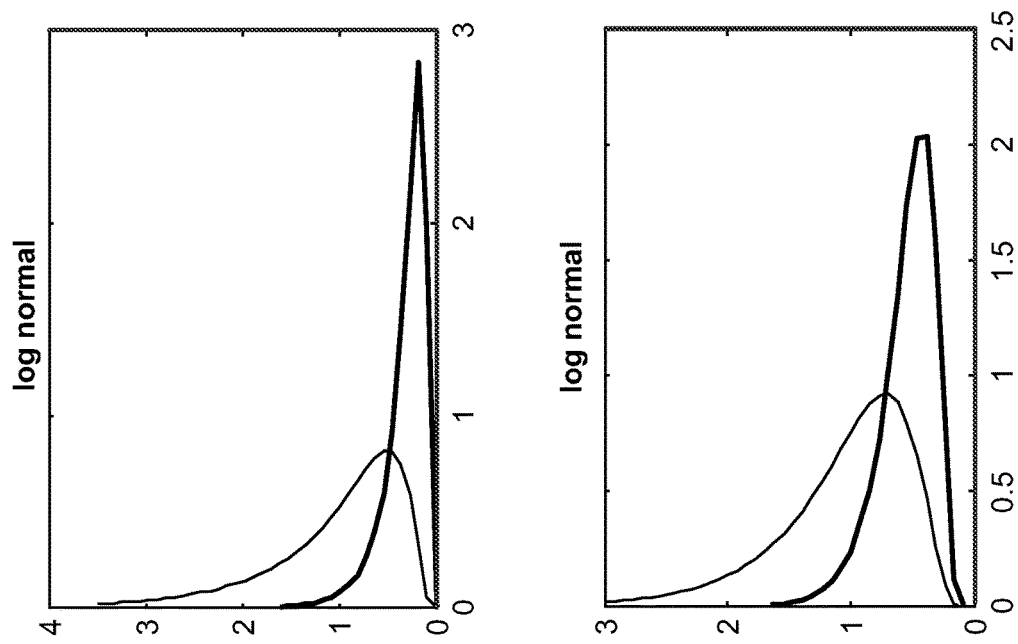
Figure 4C:
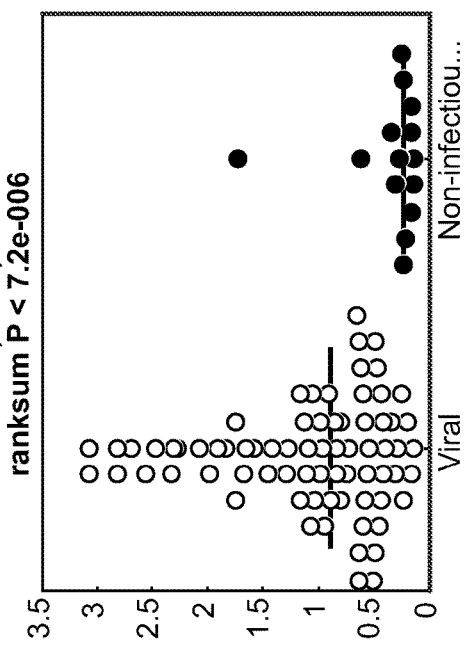
Figure 4C:
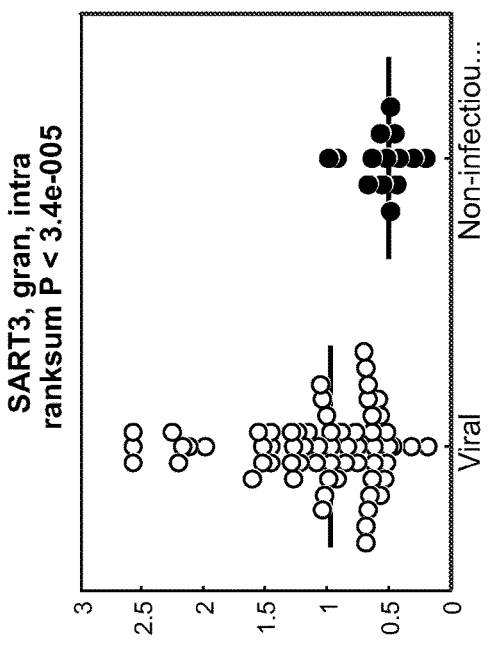

Example 5: Determinants that Differentiate Between Viral Versus Non-Infectious Disease or Healthy Subjects We identified a set of DETERMINANTS that were differentially expressed in patients with a viral infection versus patients with a non-infectious disease or healthy subjects in a statistically significant manner (Wilcoxon ranksum P<0.001). DETERMINANT names and classification accuracies are listed in Table 1C. The distributions and individual patient measurements for each of the DETERMINANTS are depicted in FIG. 4C.

Figure 4D:
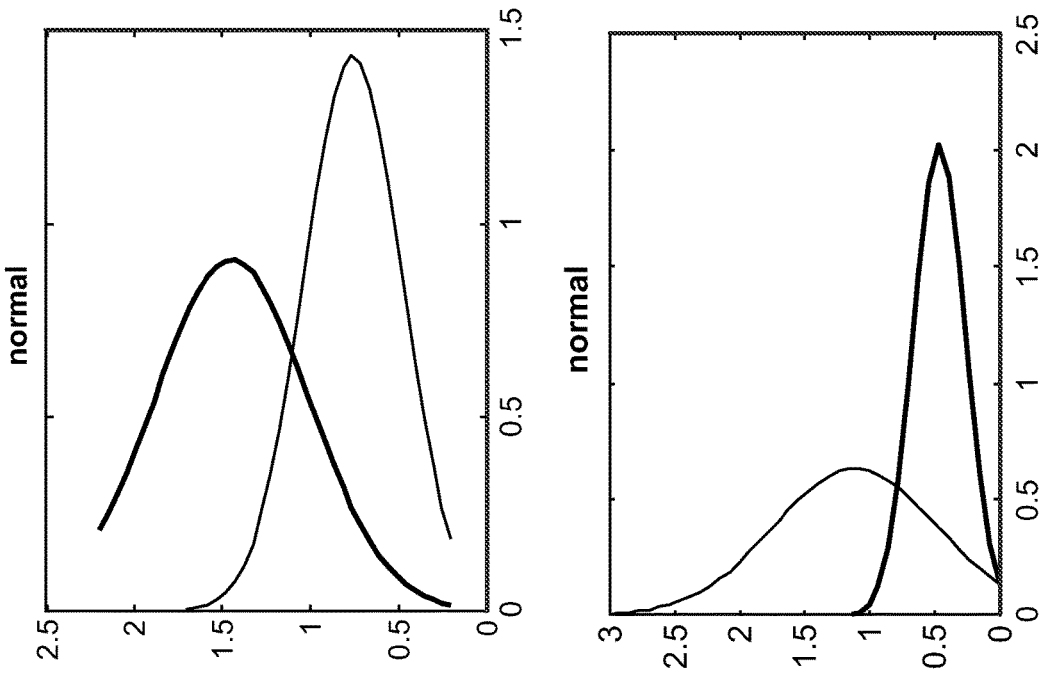
Figure 4D:
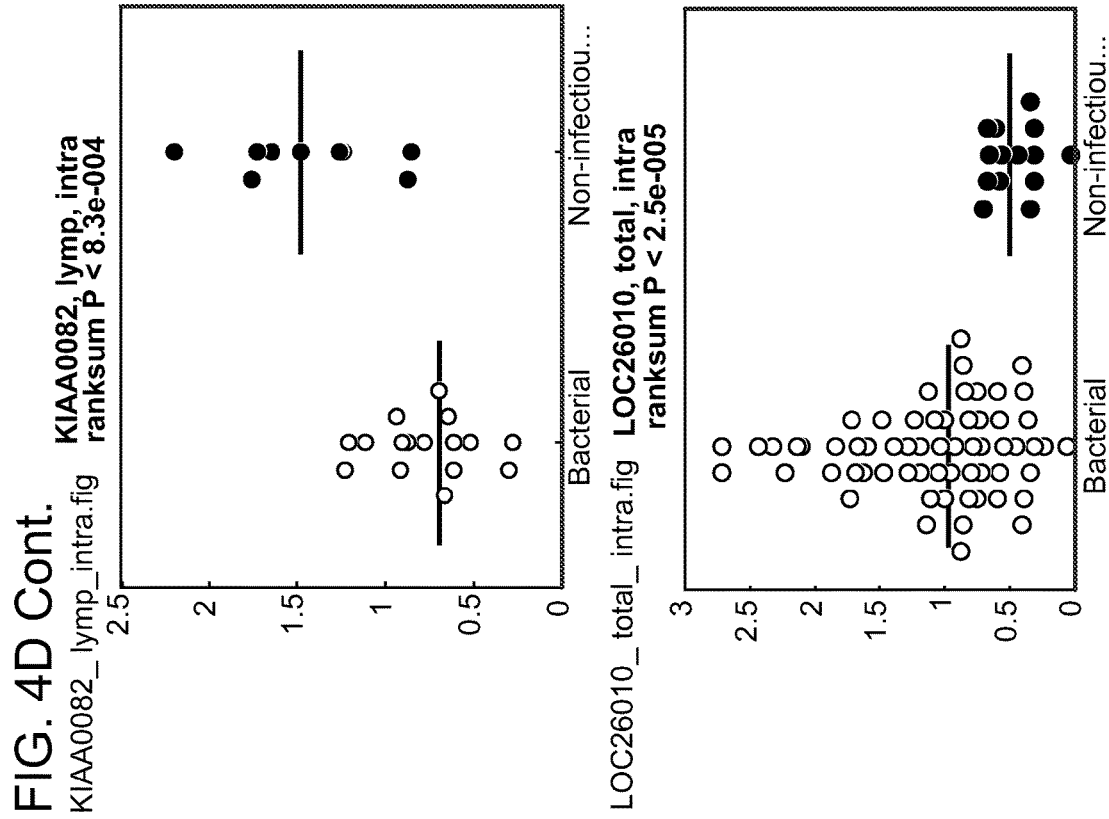
Figure 4D:
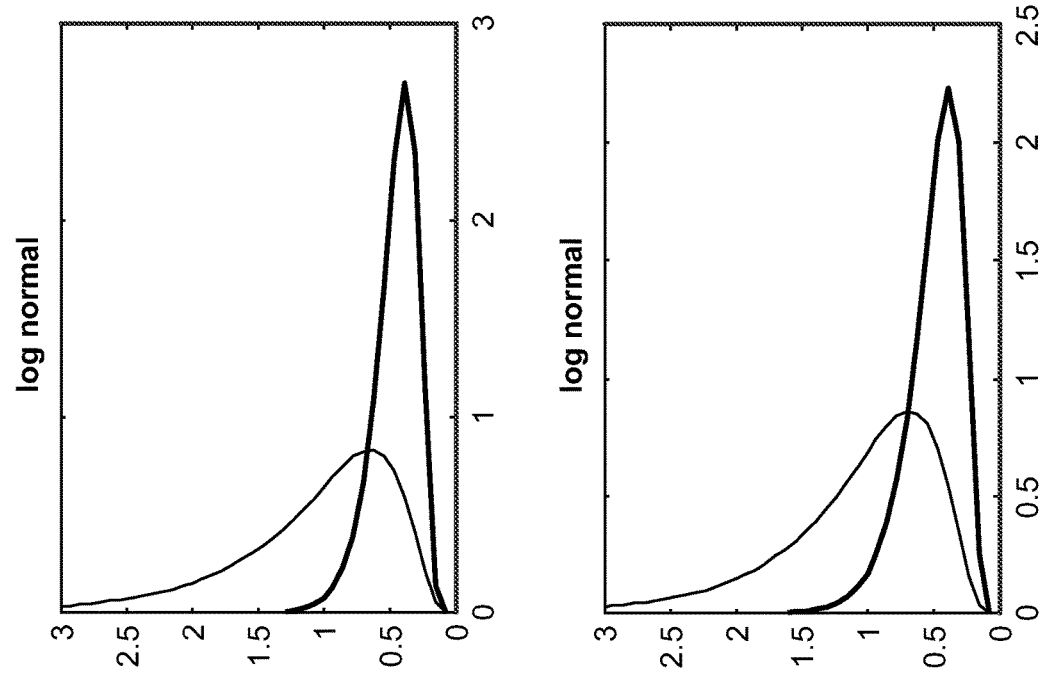
Figure 4D:
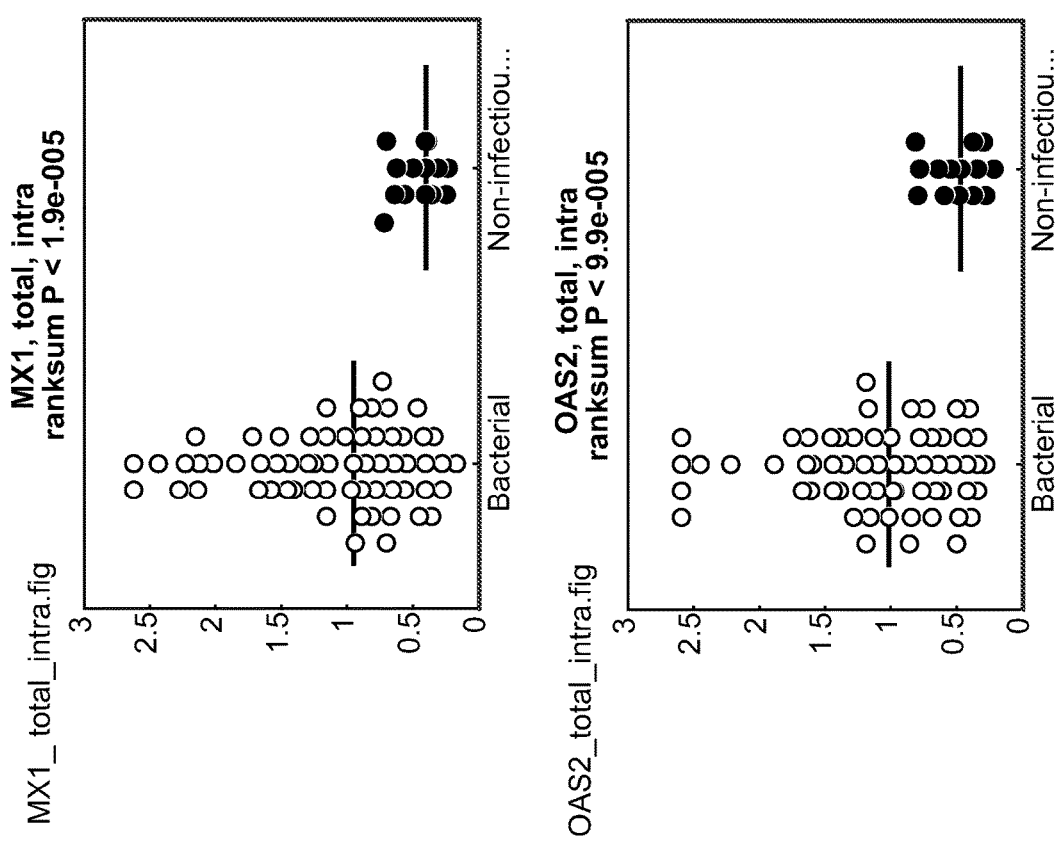
Figure 4D:
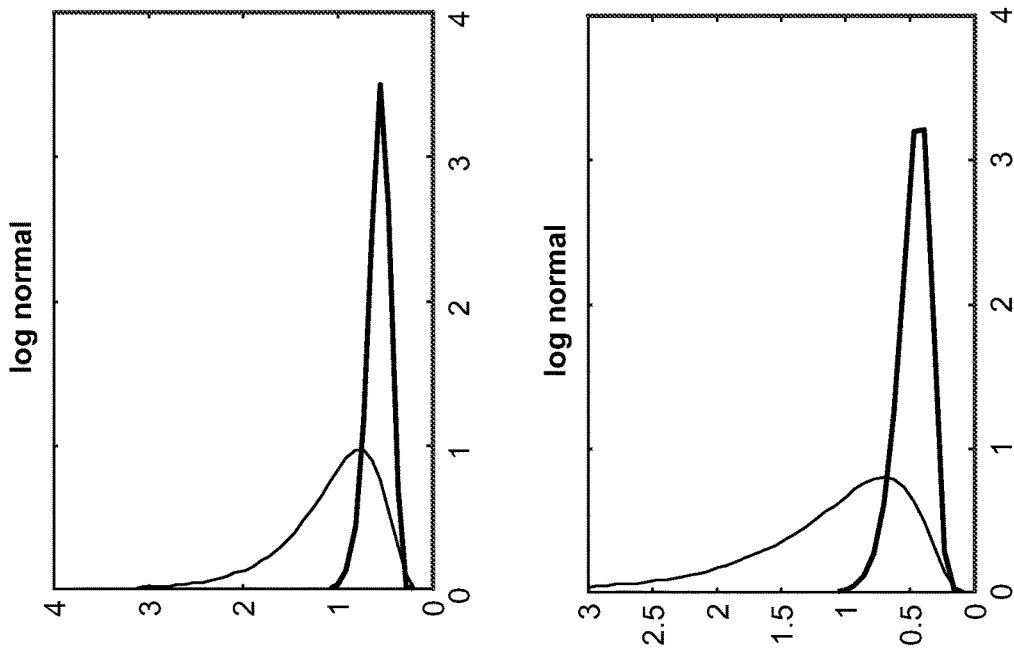
Figure 4D:
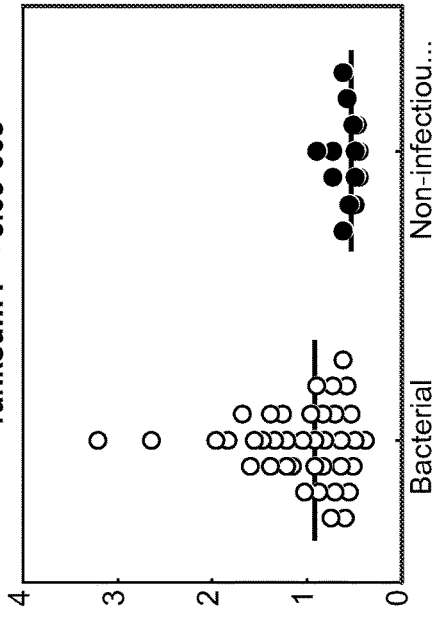
Figure 4D:
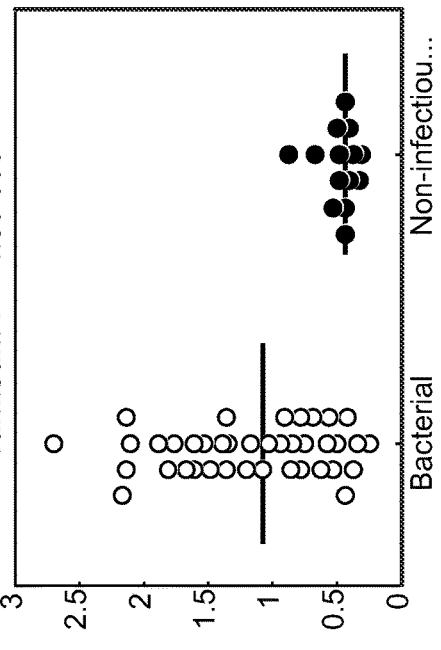
Figure 4D:
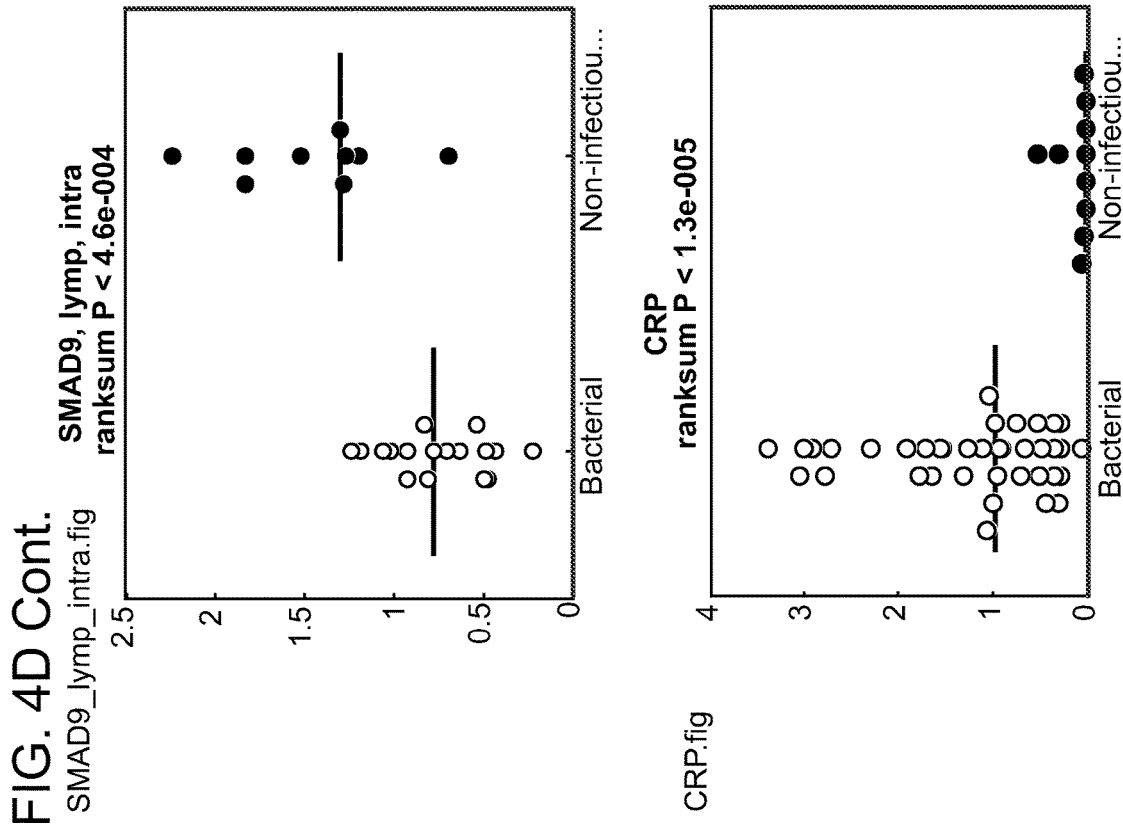

Example 6: Determinants that Differentiate Between Bacterial Versus Non-Infectious Disease or Healthy Patients We identified a set of DETERMINANTS that were differentially expressed in patients with a bacterial infection versus patients with a non-infections disease or healthy subjects in a statistically significant manner (Wilcoxon ranksum P<0.001). DETERMINANTS names and classification accuracies are listed in Table 1D. The distributions and individual patient measurements for each of the DETERMINANTS are depicted in FIG. 4D.

Figure 4E:
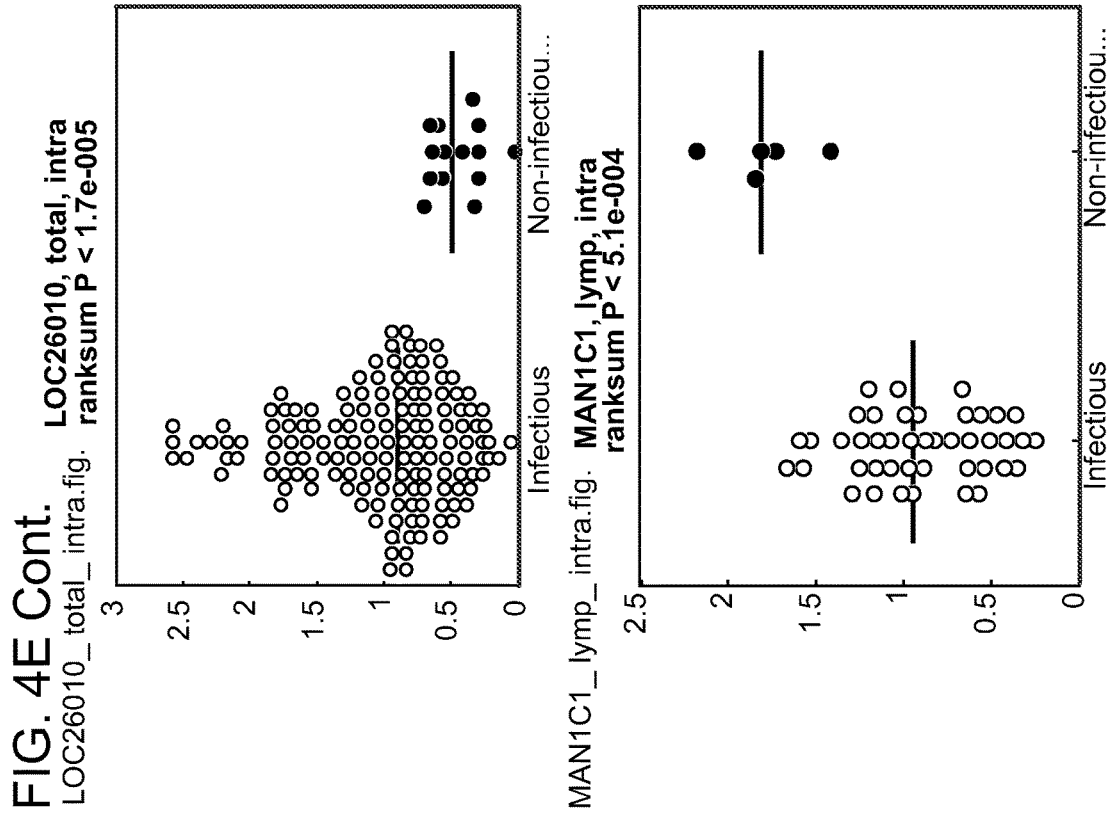
Figure 4E:
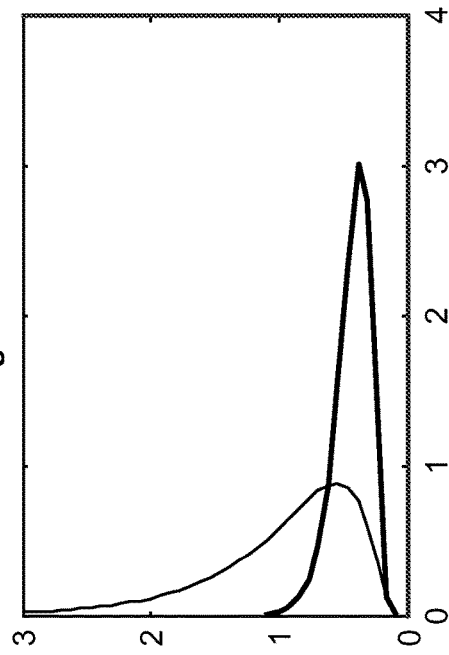
Figure 4E:
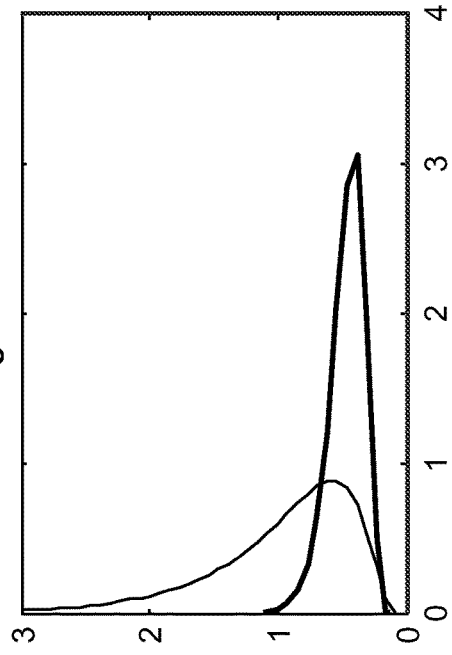
Figure 4E:
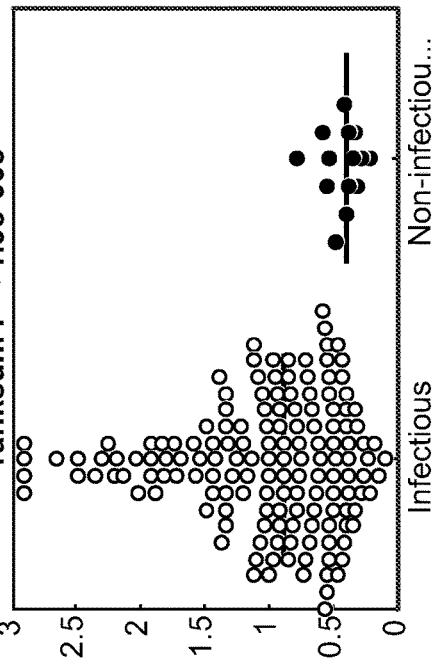
Figure 4E:
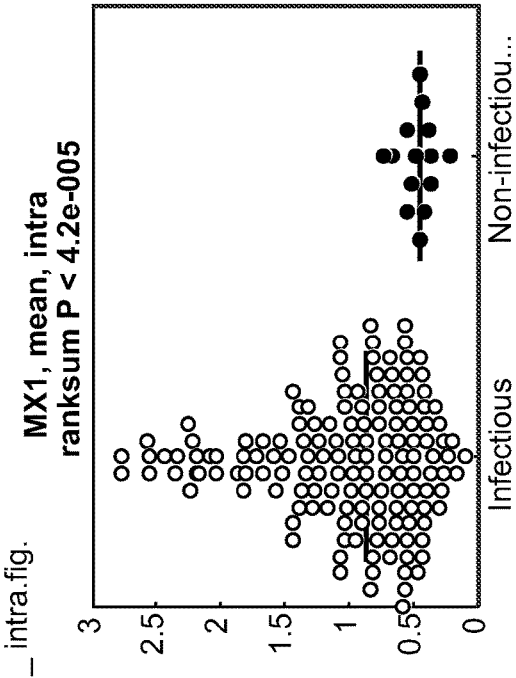
Figure 4E:
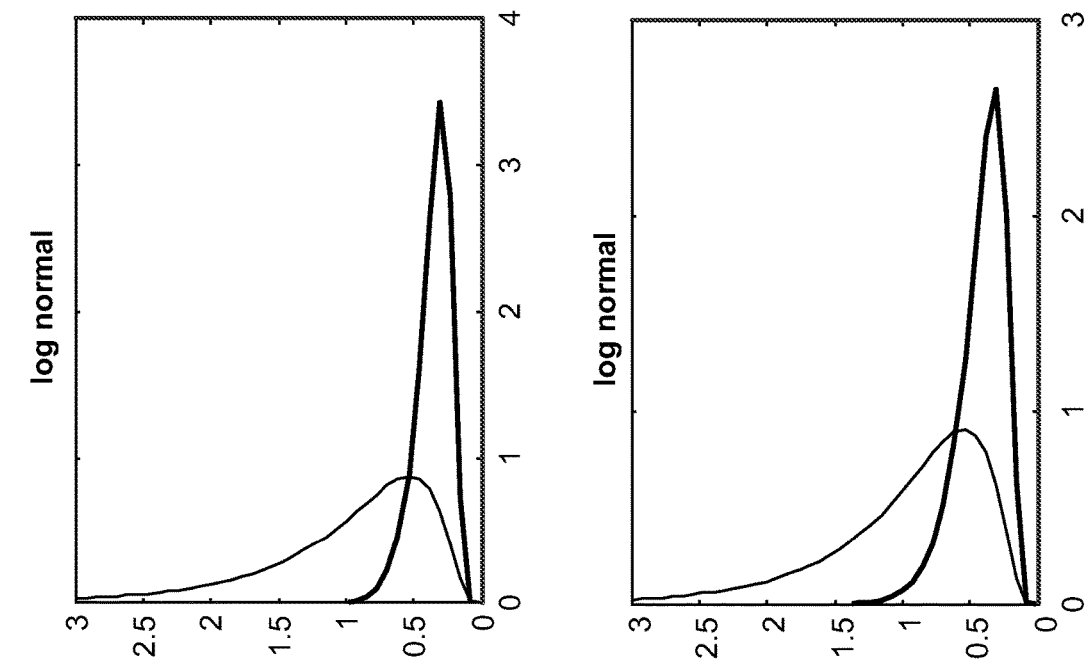
Figure 4E:
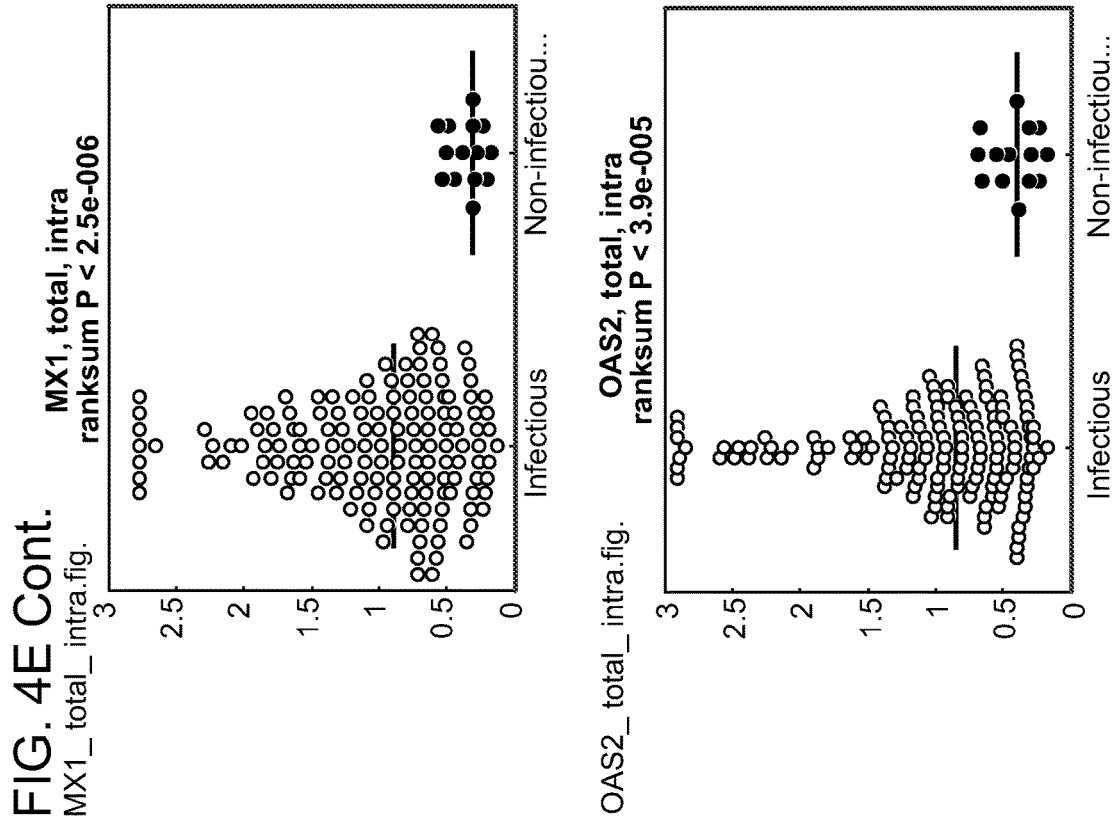
Figure 4E:
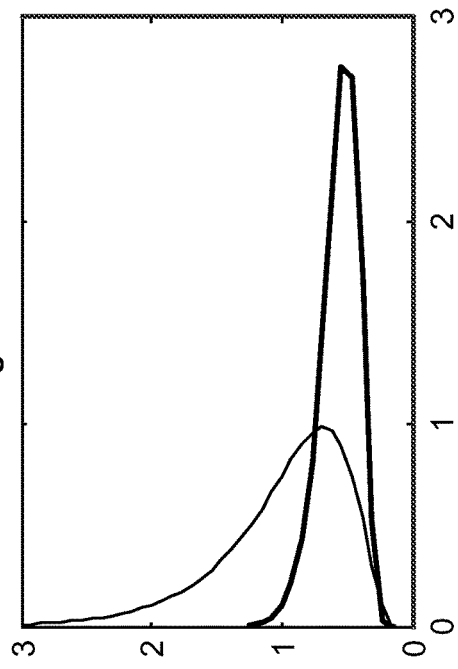
Figure 4E:
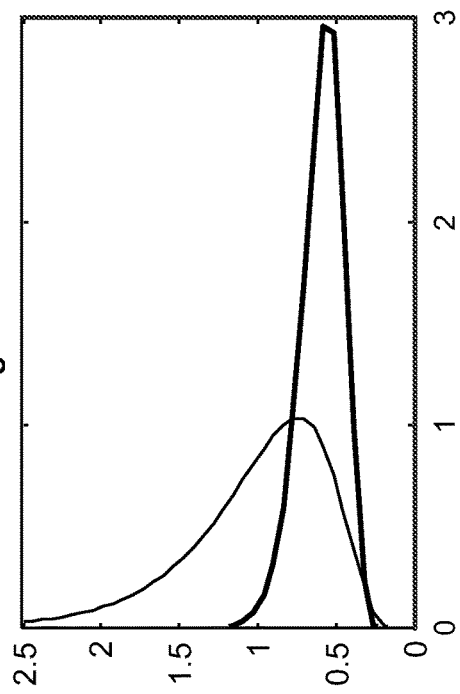
Figure 4E:
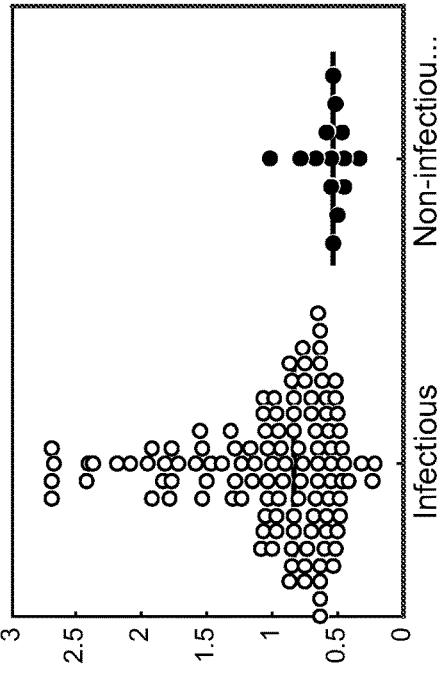
Figure 4E:
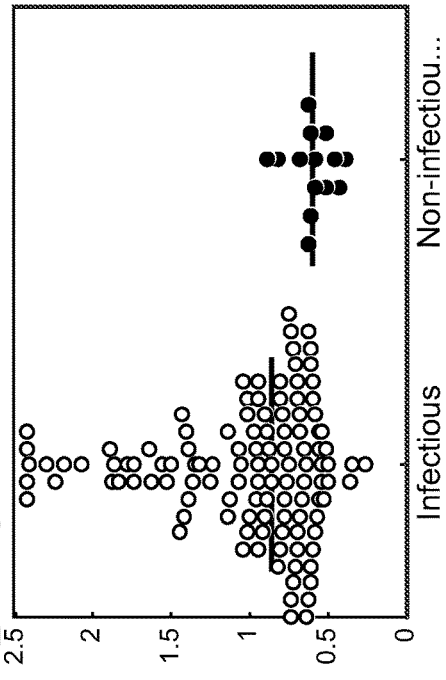
Figure 4E:
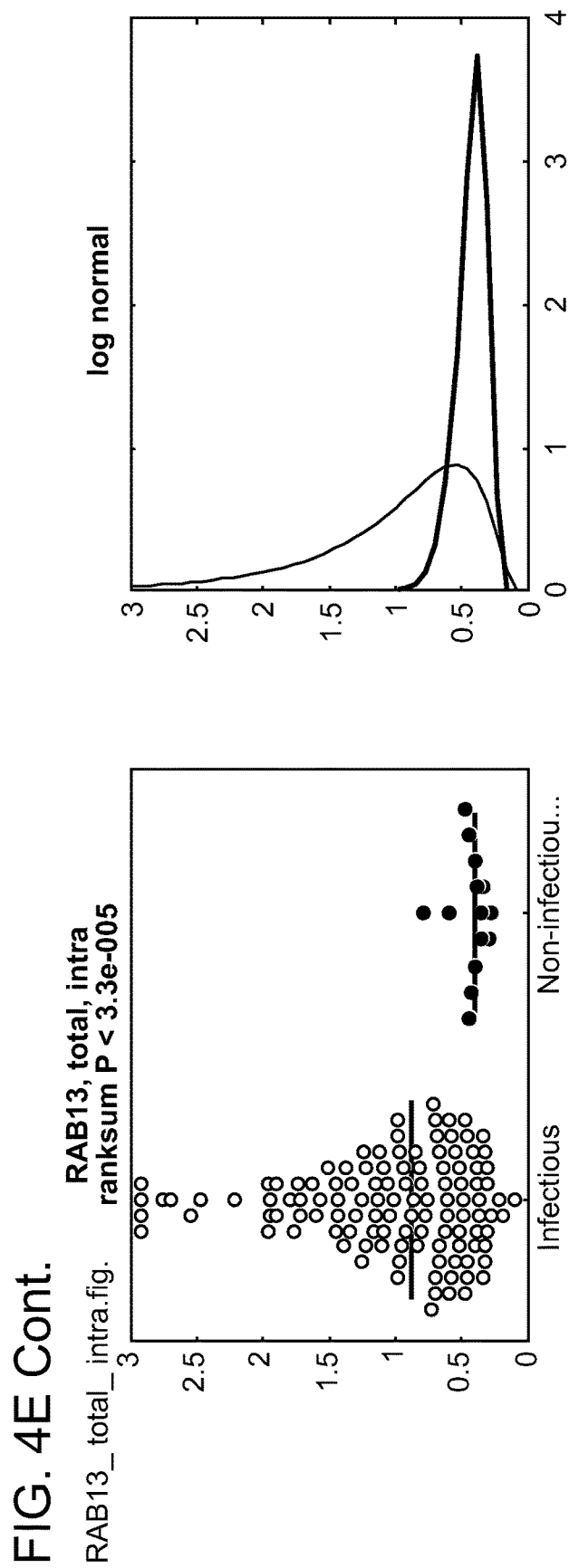
Figure 4E:
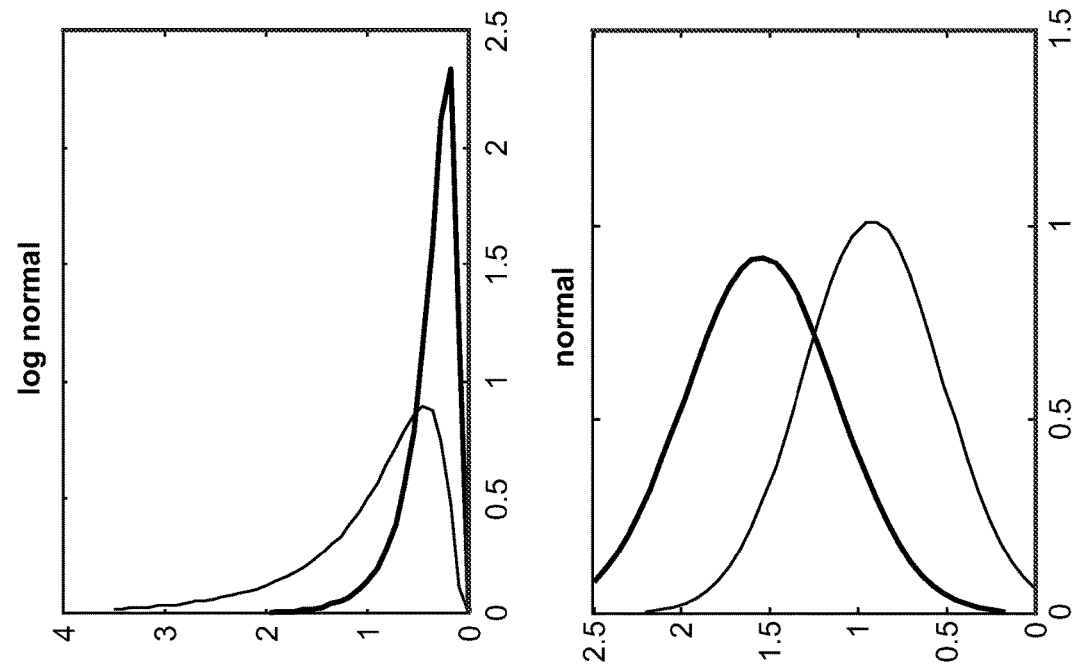
Figure 4E:
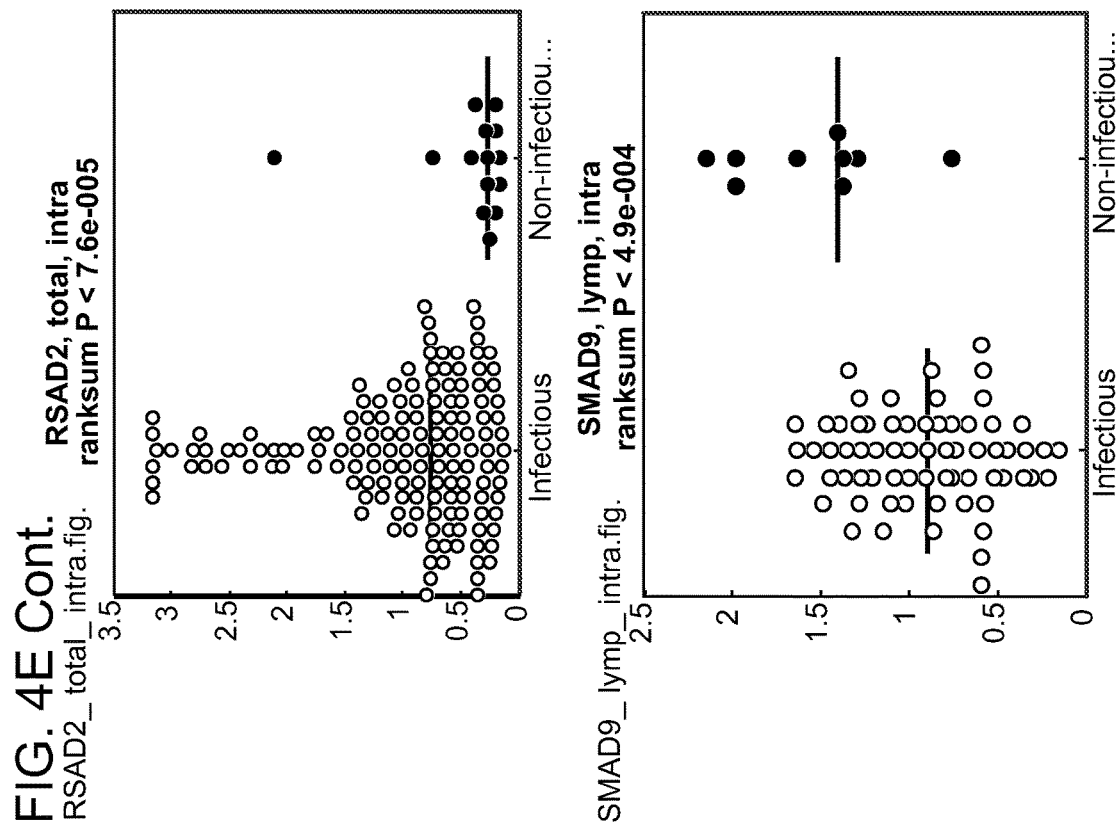

Example 7: Determinants that Differentiate Between Infectious Disease Versus Non-Infectious Disease or Healthy Patients We identified a set of DETERMINANTS that were differentially expressed in patients with an infectious disease versus patients with a non-infections disease or healthy subjects in a statistically significant manner (Wilcoxon ranksum P<0.001). DETERMINANT names and classification accuracy are listed in Table 1E. The distributions and individual patient measurements for each of the DETERMINANTS are depicted in FIG. 4E.

Figure 7:
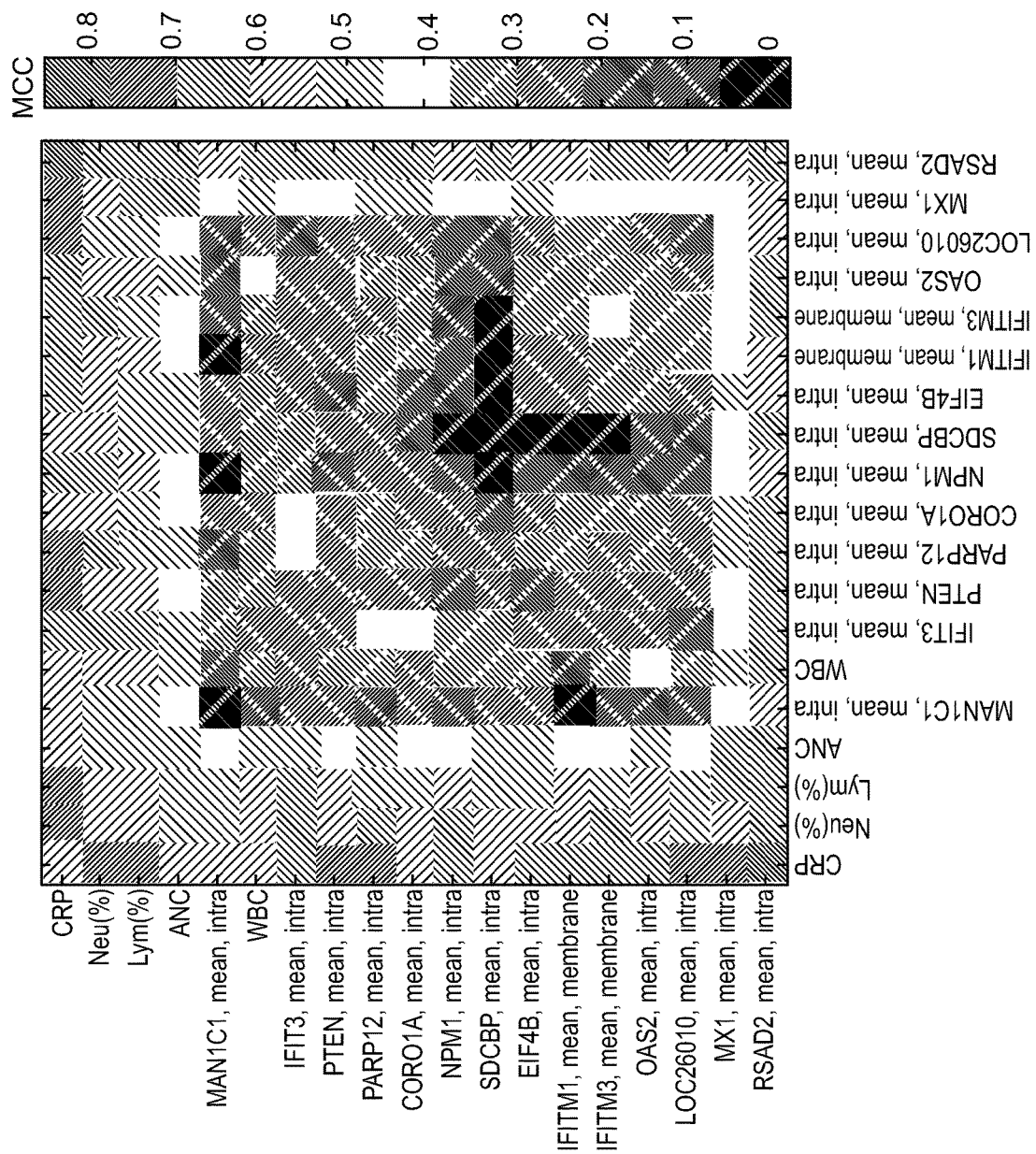
FIG. 7 Some DETERMINANT combinations exhibit an improved diagnostic accuracy compared to that of the corresponding individual DETERMINANT, whereas other combinations exhibit a reduced accuracy. (A) Classification accuracy in terms of MCC of viral versus bacterial infected patients attained for pairs of DETERMINANTS using a linear SVM model with a leave-10%-out cross-validation scheme. (B) The change in classification accuracy (dMCC) for pairs of DETERMINANTS compared to the accuracy obtained for the corresponding single DETERMINANT is computed as follows: MCCi,j−max(MCCi, MCCj), where MCCi and MCCj correspond to the MCC obtained for DETERMINANT i and j individually and MCCi,j is obtained for the pair. Hot and cold colors indicate pairs of DETERMINANTS whose combined classification accuracy compared to the individual DETERMINANT accuracy is higher and lower respectively.
Figure 7:
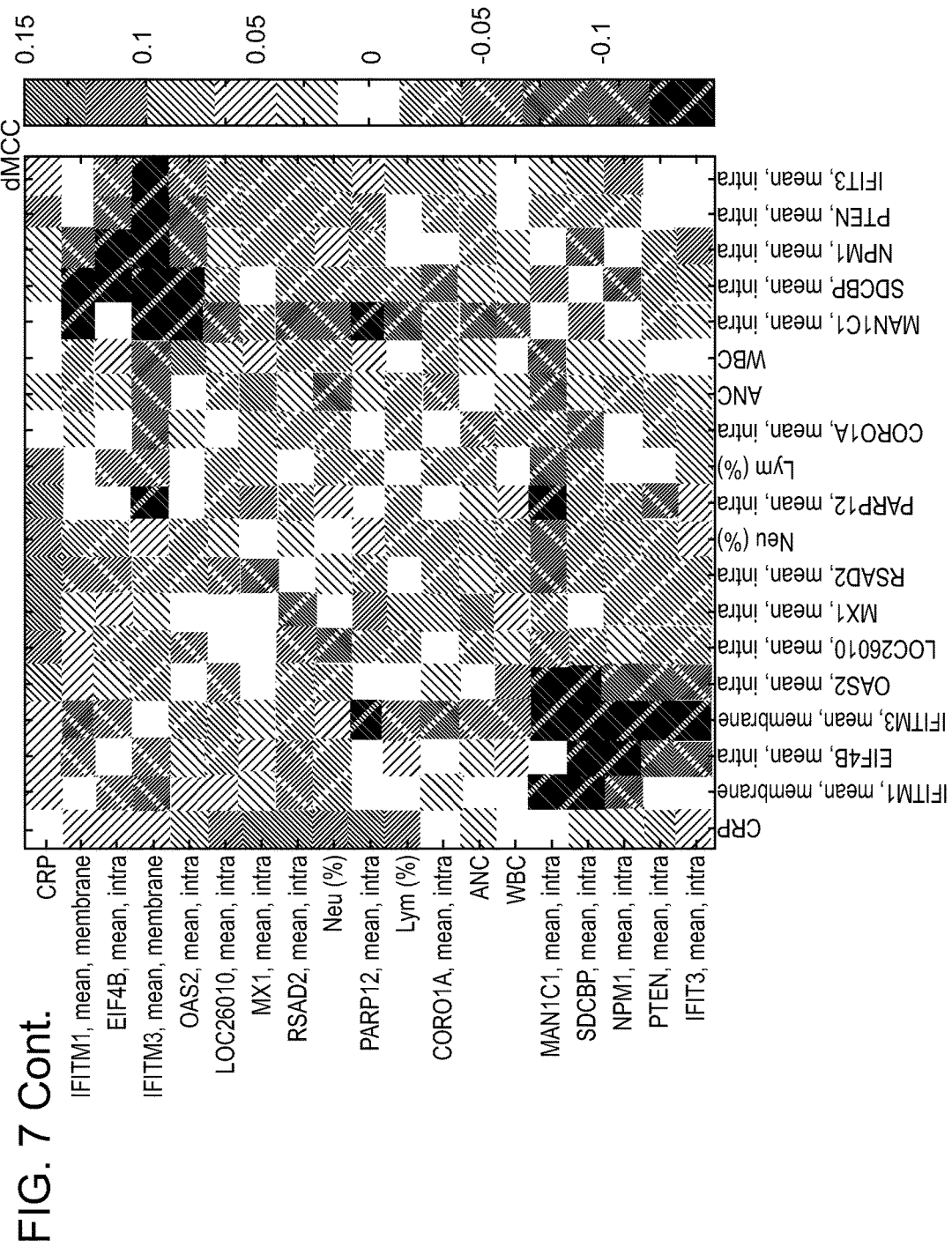

Example 8: Multi-Determinant Signatures May Improve the Accuracy of Differentiation Between Different Types of Infection Bacterial Versus Viral Infected Patients We scanned the space of DETERMINANT combinations and identified pairs and triplets of DETERMINANTS whose combined signature differentiated between patients with bacterial versus viral infections in a way that significantly improved over the classification accuracy of the corresponding individual DETERMINANTS (FIG. 7). The combined classification accuracies of pairs and triplets of total leukocytes mean level DETERMINANTS are depicted in Table 2 and 3 respectively. The combined classification accuracies of pairs of DETERMINATS measured in different cell types are depicted in Table 4.

Mixed Versus Viral Infected Patients

We identified pairs of DETERMINANTS whose combined signature differentiated between patients with mixed versus viral infections. The combined classification accuracies of DETERMINANT pairs are depicted in Table 5.

Infection Versus Non-Infectious and Healthy Patients

We identified pairs of DETERMINANTS whose combined signature differentiated between patients with an infectious disease versus patients with a non-infectious disease or healthy subjects. The combined classification accuracies of DETERMINANT pairs used to classify patients with a viral infection versus patients with a non-infectious disease or healthy subjects are depicted in Table 6; patients with a bacterial infection versus patients with a non-infectious disease or healthy subjects are depicted in Table 7; patients with an infectious disease versus patients with a non-infectious disease or healthy subjects are depicted in Table 8.

Figure 8:
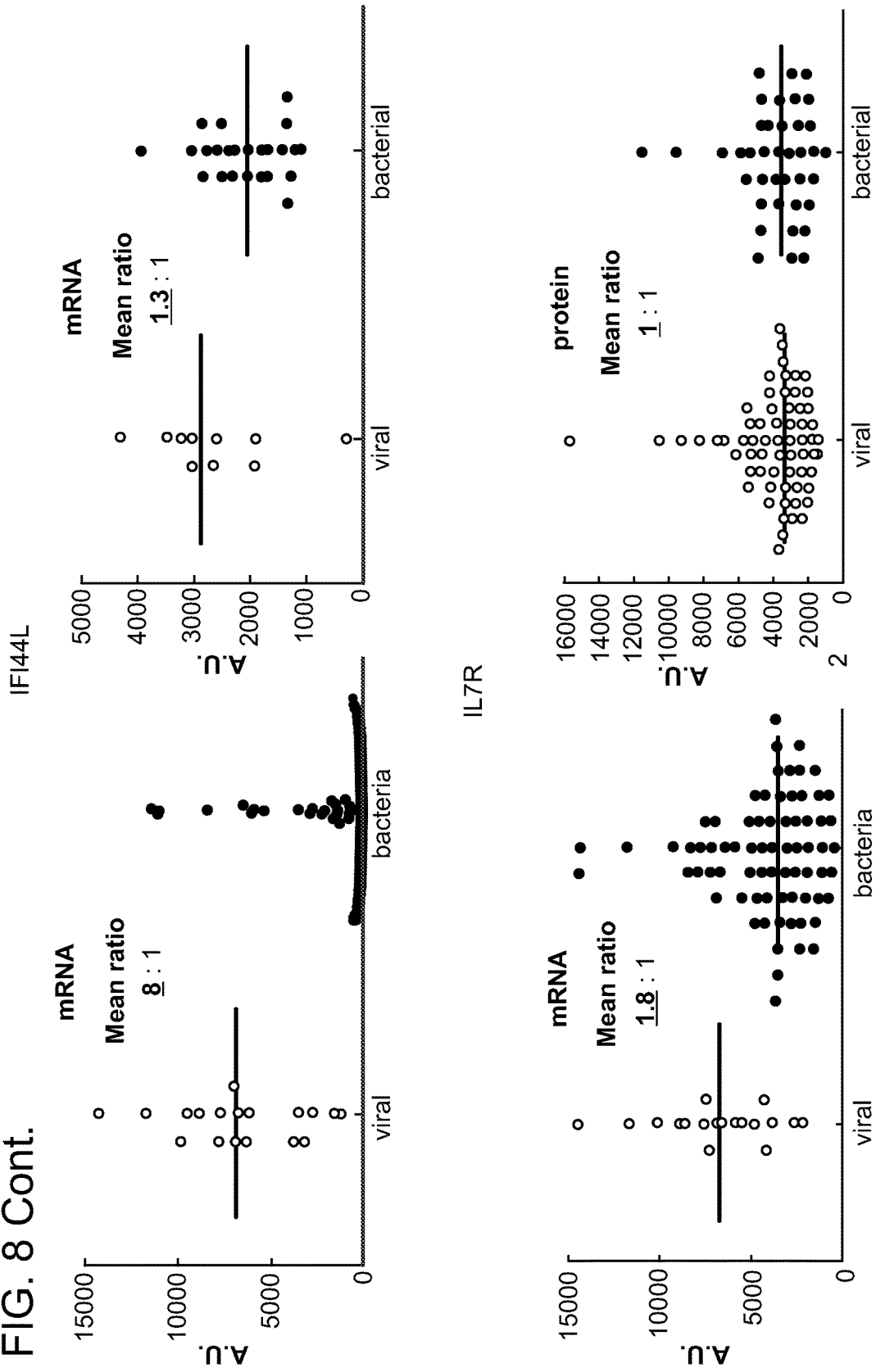
FIG. 8 Genes whose mRNA levels are differentially expressed in bacterial and viral infected patients often do not exhibit the same differential behavior in the corresponding proteins.
Figure 8:
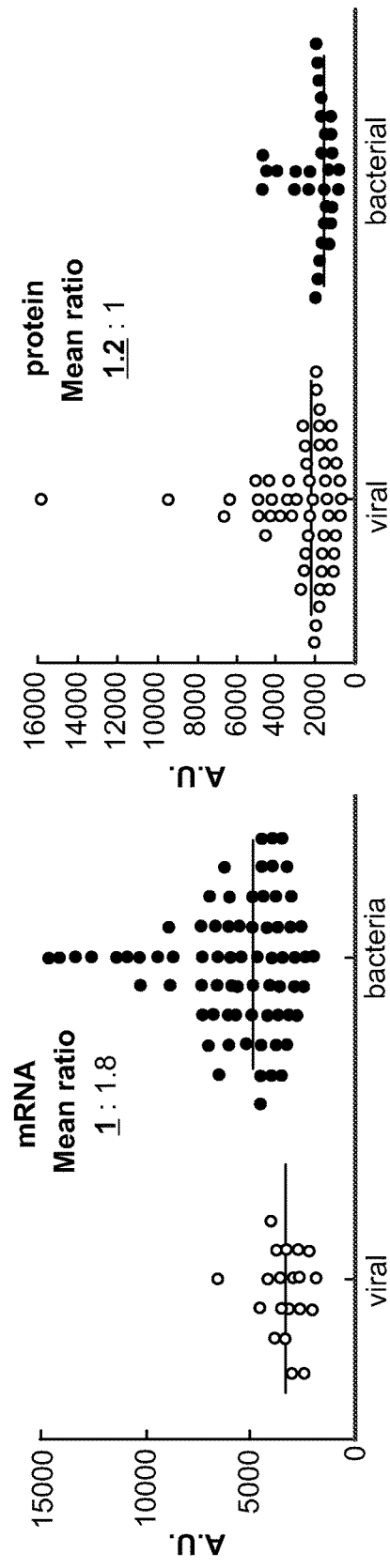
Figure 8:
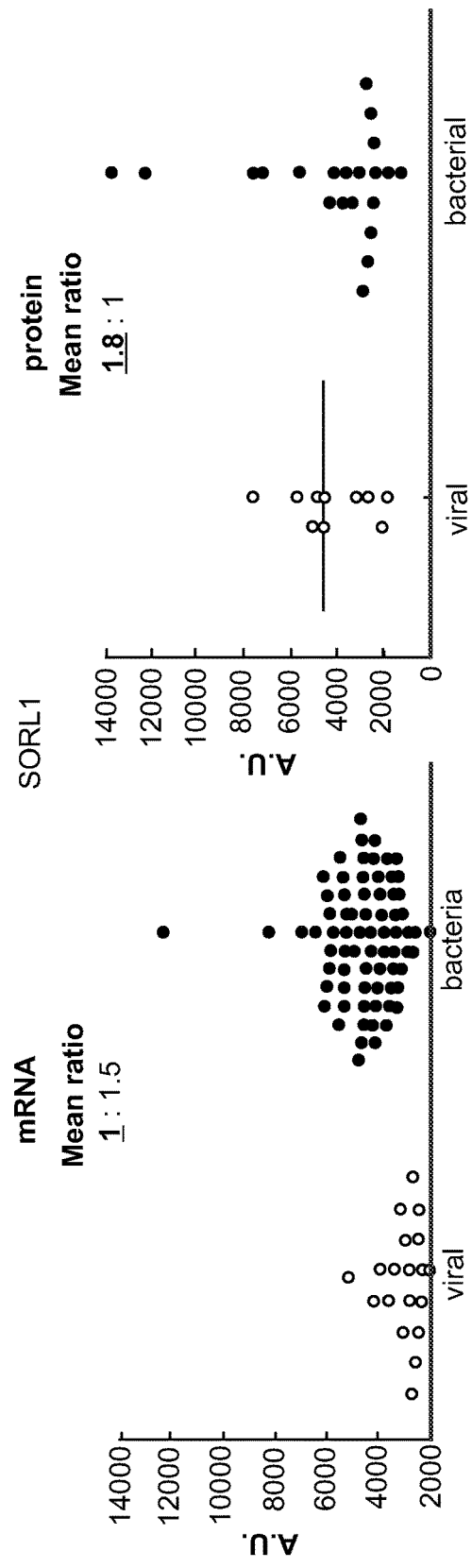

Example 9: Discorrelation Between Protein and mRNA Differential Behaviour in Bacterial Versus Viral Infections Genes whose mRNA levels are differentially expressed between bacterial and viral infections often do not exhibit the same differential behavior in the corresponding proteins. mRNAs whose levels were differentially expressed in PBMCs of patients with viral versus bacterial infections (t-test P-value<10−6) (analyzed data from Ramilo et al 2007) were compared to our protein measurements. Many genes that were differentially expressed on the mRNA level did not exhibit the same behavior on the protein level as shown in FIG. 8 (mRNA and the corresponding protein measurements are shown on the left and right panels respectively).

Each dot corresponds to a patient and the bars indicate viral and bacterial group means.

Example 10: Comparison of Protein Expression in Different Cell Types

Figure 9:
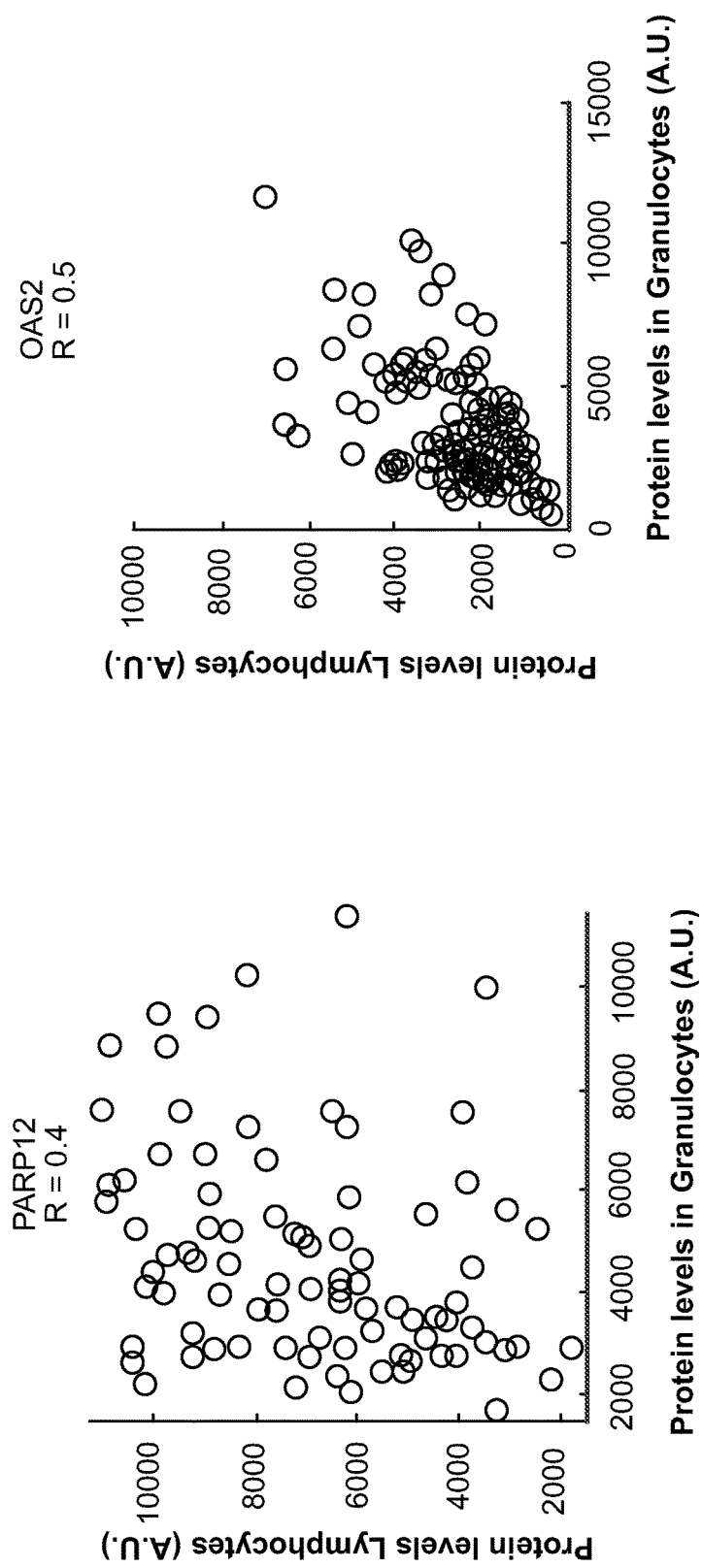
FIG. 9 The expression levels of some proteins are not well correlated across different cells types of the immune system. Two examples of proteins (PARP12 and OAS2) are shown whose expression levels on granulocytes and lymphocytes are poorly correlated.

The expression levels of some proteins are not well correlated across different cells types of the immune system. FIG. 9 depicts examples of two proteins (PARP12 and OAS2) whose levels on granulocytes and lymphocytes are poorly correlated. Each dot corresponds to patients whose protein levels were measured on granulocytes (x-axis) and lymphocytes (y-axis).

TABLE 1A

Bacterial versus viral infected patients

| DETERMINANT | Wilcoxon ranksum P-value | MCC | Total Accuracy | Sensitivity % | Specificity % | PPV % | NPV % | log2 (med1/med2) |
|---|---|---|---|---|---|---|---|---|
| ABTB1, gran, intra | 8.00E-04 | 0.14 | 55 | 66 | 49 | 43 | 71 | -0.4577 |
| Absolute neutrophil count (ANC) | 9.00E-08 | 0.593 | | 63 | 92 | 83 | 81 | 0.8719 |
| ABTB1, mono, intra | 8.00E-04 | 0.14 | 55 | 66 | 49 | 43 | 71 | -0.4577 |
| ADIPOR1, total, membrane | 4.00E-04 | 0.3 | 64 | 69 | 61 | 53 | 76 | 1.0834 |
| ARHGDIB, gran, intra | 2.00E-04 | 0.42 | 76 | 59 | 83 | 59 | 83 | -0.7392 |
| ARHGDIB, lymp, intra | 3.00E-04 | 0.12 | 62 | 41 | 71 | 37 | 74 | -0.7871 |
| ARHGDIB, mean, intra | 4.00E-04 | 0.16 | 61 | 53 | 64 | 39 | 76 | -0.8076 |
| ARPC2, lymp, intra | 6.00E-04 | 0.17 | 67 | 35 | 80 | 43 | 75 | -0.952 |
| CD15, total, membrane | 1.00E-05 | 0.31 | 62 | 79 | 52 | 51 | 80 | 0.8445 |
| CORO1A, gran, intra | 9.00E-04 | 0.02 | 53 | 41 | 61 | 39 | 63 | -0.5317 |
| CORO1A, mean, intra | 1.00E-04 | 0.11 | 56 | 51 | 60 | 44 | 66 | -0.6381 |
| CORO1A, mono, intra | 9.00E-04 | 0.02 | 53 | 41 | 61 | 39 | 63 | -0.5317 |
| CRP | 5.00E-11 | 0.51 | 76 | 79 | 73 | 65 | 85 | 2.7636 |
| CSDA, gran, intra | 8.00E-04 | 0.28 | 64 | 68 | 62 | 51 | 76 | -0.4731 |
| CSDA, mono, intra | 8.00E-04 | 0.28 | 64 | 68 | 62 | 51 | 76 | -0.4731 |
| EIF4B, gran, intra | 7.00E-07 | 0.38 | 69 | 73 | 65 | 64 | 74 | -0.597 |
| EIF4B, lymp, intra | 6.00E-08 | 0.29 | 65 | 49 | 78 | 66 | 64 | -0.7342 |
| EIF4B, mean, intra | 3.00E-05 | 0.24 | 62 | 63 | 61 | 58 | 66 | -0.5269 |
| EIF4B, mono, intra | 7.00E-07 | 0.38 | 69 | 73 | 65 | 64 | 74 | -0.597 |
| EPSTI1, lymp, membrane | 1.00E-04 | 0.23 | 56 | 81 | 42 | 45 | 79 | -0.3862 |
| GAS7, lymp, intra | 6.00E-04 | 0.16 | 52 | 77 | 38 | 42 | 74 | -0.6104 |
| HERC5, gran, intra | 2.00E-04 | 0.46 | 70 | 88 | 63 | 50 | 93 | -0.7506 |
| HERC5, mean, intra | 2.00E-04 | 0.55 | 75 | 94 | 66 | 55 | 96 | -0.818 |
| IFI6, gran, intra | 8.00E-04 | 0.31 | 63 | 77 | 55 | 51 | 80 | -0.5597 |
| IFI6, gran, intra | 7.00E-04 | 0.48 | 69 | 9459 | 59 | 4896 | 96 | -0.6788 |
| IFI6, mono, intra | 8.00E-04 | 0.31 | 63 | 77 | 55 | 51 | 80 | -0.5597 |
| IFIT1, gran, intra | 1.00E-04 | 0.77 | 91 | 96 | 78 | 92 | 88 | -1.3341 |
| IFIT1, lymp, intra | 4.00E-04 | 0.71 | 88 | 96 | 70 | 88 | 88 | -1.3187 |
| IFIT1, mean, intra | 4.00E-05 | 0.86 | 94 | 91 | 100 | 100 | 82 | -1.2072 |
| IFIT1, mono, intra | 1.00E-04 | 0.77 | 91 | 96 | 78 | 92 | 88 | -1.3341 |
| IFIT3, gran, intra | 2.00E-06 | 0.68 | 86 | 82 | 88 | 74 | 92 | -1.6387 |
| IFIT3, lymp, intra | 7.00E-07 | 0.64 | 81 | 94 | 76 | 62 | 97 | -1.8025 |
| IFIT3, mean, intra | 1.00E-05 | 0.49 | 79 | 65 | 85 | 65 | 85 | -1.3629 |
| IFITM1, gran, membrane | 2.00E-04 | 0.13 | 58 | 20 | 89 | 60 | 58 | -0.4164 |
| IFITM1, lymp, membrane | 8.00E-09 | 0.57 | 78 | 62 | 92 | 86 | 75 | -0.862 |
| IFITM1, mean, membrane | 2.00E-04 | 0.2 | 61 | 29 | 88 | 65 | 60 | -0.3102 |
| IFITM1, mono, membrane | 2.00E-07 | 0.23 | 63 | 45 | 77 | 61 | 63 | -1.013 |
| IFITM3, gran, membrane | 1.00E-07 | 0.3 | 66 | 50 | 78 | 65 | 66 | -0.8206 |
| IFITM3, mean, membrane | 2.00E-07 | 0.47 | 73 | 54 | 89 | 80 | 70 | -0.7955 |
| IFITM3, mono, membrane | 1.00E-09 | 0.32 | 66 | 63 | 69 | 62 | 70 | -0.9316 |
| IL7R, total, membrane | 7.00E-05 | 0.21 | 61 | 56 | 65 | 50 | 70 | 0.6816 |
| LOC26010, gran, intra | 2.00E-04 | 0.26 | 62 | 73 | 53 | 57 | 70 | -0.5838 |
| LOC26010, mean, intra | 8.00E-04 | 0.15 | 56 | 71 | 43 | 52 | 63 | -0.3595 |
| LOC26010, mono, intra | 2.00E-04 | 0.26 | 62 | 73 | 53 | 57 | 70 | -0.5838 |
| LY6E, lymp, membrane | 6.00E-04 | 0.08 | 54 | 58 | 51 | 49 | 59 | -0.4506 |
| Lym (%) | 6.00E-13 | 0.616 | 81 | 74 | 87 | 82 | 80 | -1.2551 |
| MAN1C1, gran, intra | 1.00E-03 | 0.2 | 55 | 77 | 42 | 44 | 76 | -0.4912 |
| MAN1C1, mean, intra | 7.00E-04 | 0.4 | 69 | 77 | 63 | 56 | 83 | -0.4595 |
| MAN1C1, mono, intra | 1.00E-03 | 0.2 | 55 | 77 | 42 | 44 | 76 | -0.4912 |
| MBOAT2, lymp, intra | 7.00E-04 | 0.06 | 53 | 53 | 54 | 32 | 73 | -0.7531 |
| MX1, gran, intra | 2.00E-12 | 0.45 | 72 | 83 | 62 | 65 | 81 | -1.1395 |
| MX1, lymp, intra | 8.00E-09 | 0.38 | 66 | 87 | 49 | 59 | 82 | -0.898 |
| MX1, mean, intra | 1.00E-10 | 0.56 | 75 | 97 | 56 | 65 | 95 | -1.0368 |
| MX1, mono, intra | 2.00E-12 | 0.45 | 72 | 83 | 62 | 65 | 81 | -1.1395 |
| Neu (%) | 2.00E-12 | 0.546 | 77 | 77 | 77 | 74 | 81 | 0.4759 |
| NPM1, gran, intra | 7.00E-04 | 0.29 | 59 | 85 | 43 | 48 | 82 | -0.4158 |
| NPM1, mean, intra | 6.00E-04 | 0.33 | 63 | 82 | 51 | 52 | 82 | -0.3911 |
| NPM1, mono, intra | 7.00E-04 | 0.29 | 59 | 85 | 43 | 48 | 82 | -0.4158 |
| OAS2, gran, intra | 3.00E-08 | 0.52 | 74 | 90 | 60 | 66 | 88 | -0.8708 |
| OAS2, mean, intra | 1.00E-05 | 0.43 | 68 | 90 | 49 | 60 | 86 | -0.4718 |
| OAS2, mono, intra | 3.00E-08 | 0.52 | 74 | 90 | 60 | 66 | 88 | -0.8708 |
| PARP12, gran, intra | 3.00E-05 | 0.19 | 58 | 67 | 53 | 46 | 72 | -0.6208 |
| PARP12, mean, intra | 6.00E-06 | 0.38 | 66 | 82 | 56 | 54 | 83 | -0.7165 |
| PARP12, mono, intra | 3.00E-05 | 0.19 | 58 | 67 | 53 | 46 | 72 | -0.6208 |
| PARP9, lymp, intra | 3.00E-04 | 0.4 | 67 | 85 | 56 | 54 | 86 | -0.5272 |
| PARP9, lymp, intra | 2.00E-04 | 0.46 | 76 | 78 | 71 | 86 | 57 | 0.7802 |
| PDIA6, gran, intra | 9.00E-04 | 0.4 | 67 | 84 | 57 | 53 | 86 | -0.7829 |
| PDIA6, lymp, intra | 5.00E-04 | 0.37 | 62 | 90 | 45 | 49 | 89 | -0.5593 |
| PDIA6, mono, intra | 9.00E-04 | 0.4 | 67 | 84 | 57 | 53 | 86 | -0.7829 |
| PTEN, gran, intra | 2.00E-05 | -0.05 | 50 | 36 | 59 | 35 | 60 | -0.5881 |
| PTEN, lymp, intra | 1.00E-04 | 0.08 | 57 | 41 | 67 | 43 | 65 | -0.5419 |
| PTEN, mean, intra | 2.00E-04 | -0.11 | 48 | 31 | 58 | 32 | 57 | -0.4633 |
| PTEN, mono, intra | 2.00E-05 | -0.05 | 50 | 36 | 59 | 35 | 60 | -0.5881 |
| RSAD2, gran, intra | 1.00E-16 | 0.63 | 82 | 78 | 85 | 82 | 82 | -1.7372 |
| RSAD2, lymp, intra | 2.00E-04 | 0.18 | 57 | 78 | 39 | 52 | 67 | -0.412 |

TABLE 1A-continued

Bacterial versus viral infected patients

| DETERMINANT | Wilcoxon ranksum P-value | MCC | Total Accuracy | Sensitivity % | Specificity % | PPV % | NPV % | log2 (med1/med2) |
|---|---|---|---|---|---|---|---|---|
| RSAD2, mean, intra | 5.00E−15 | 0.64 | 82 | 76 | 88 | 84 | 81 | −1.3804 |
| RSAD2, mono, intra | 1.00E−16 | 0.63 | 82 | 78 | 85 | 82 | 82 | −1.7372 |
| RSAD2, total, intra | 1.00E−05 | 0.32 | 64 | 81 | 51 | 58 | 76 | −0.7941 |
| SDCBP, mean, intra | 9.00E−04 | 0.16 | 54 | 74 | 41 | 45 | 71 | −0.424 |
| TRIM 22, lymp, intra | 1.00E−04 | 0.46 | 67 | 94 | 56 | 47 | 96 | −0.6477 |
| WBC | 2.00E−05 | 0.028 | 53 | 39 | 64 | 47 | 56 | 0.5448 |

*Positives and negatives correspond to Bacterial and Viral infected patients respectively

TABLE 1B

Mixed (bacterial and viral) versus viral infected patients

| DETERMINANT | Wilcoxon ranksum P-value | MCC | Total Accuracy | Sensitivity % | Specificity % | PPV % | NPV % | log2 (med1/med2) |
|---|---|---|---|---|---|---|---|---|
| ANC | 3.00E−04 | 0.62 | 89 | 97 | 56 | 90 | 82 | −1.2704 |
| ARHGDIB, gran, intra | 4.00E−04 | 0.4 | 83 | 92 | 44 | 87 | 58 | 1.1331 |
| ARHGDIB, lymp, intra | 4.00E−04 | 0.32 | 79 | 88 | 44 | 86 | 47 | 1.2267 |
| ARHGDIB, mean, intra | 9.00E−04 | 0.2 | 76 | 87 | 31 | 83 | 38 | 0.9582 |
| ARHGDIB, mono, intra | 4.00E−04 | 0.4 | 83 | 92 | 44 | 87 | 58 | 1.1331 |
| ARPC2, gran, intra | 6.00E−05 | 0.31 | 76 | 83 | 50 | 87 | 42 | 1.0578 |
| ARPC2, lymp, intra | 2.00E−04 | 0.22 | 75 | 84 | 38 | 84 | 38 | 0.8354 |
| ARPC2, mean, intra | 1.00E−04 | 0.23 | 73 | 81 | 44 | 85 | 37 | 0.9228 |
| ARPC2, mono, intra | 6.00E−05 | 0.31 | 76 | 83 | 50 | 87 | 42 | 1.0578 |
| ATP6V0B, mean, intra | 6.00E−04 | 0.36 | 73 | 74 | 69 | 90 | 41 | 0.7126 |
| CD15, gran, membrane | 8.00E−04 | 0.44 | 84 | 94 | 44 | 87 | 64 | 0.7065 |
| CES1, gran, intra | 2.00E−05 | 0.53 | 83 | 84 | 75 | 93 | 55 | 1.034 |
| CES1, lymp, intra | 5.00E−04 | 0.39 | 73 | 72 | 75 | 92 | 40 | 0.8815 |
| CES1, mean, intra | 3.00E−05 | 0.51 | 85 | 92 | 56 | 89 | 64 | 0.9951 |
| CES1, mono, intra | 2.00E−05 | 0.53 | 83 | 84 | 75 | 93 | 55 | 1.034 |
| CORO1A, gran, intra | 7.00E−05 | 0.43 | 80 | 84 | 63 | 90 | 50 | 0.8348 |
| CORO1A, lymp, intra | 3.00E−04 | 0.47 | 79 | 80 | 75 | 93 | 48 | 0.709 |
| CORO1A, mean, intra | 2.00E−05 | 0.58 | 86 | 90 | 69 | 92 | 65 | 1.031 |
| CORO1A, mono, intra | 7.00E−05 | 0.43 | 80 | 84 | 63 | 90 | 50 | 0.8348 |
| CRP | 6.00E−06 | 0.55 | 86 | 92 | 63 | 90 | 67 | −3.0326 |
| HERC5, gran, intra | 5.00E−04 | 0.5 | 83 | 87 | 67 | 92 | 56 | 0.7673 |
| HERC5, mean, intra | 5.00E−04 | 0.3 | 75 | 80 | 53 | 88 | 40 | 0.7926 |
| HERC5, mono, intra | 5.00E−04 | 0.5 | 83 | 87 | 67 | 92 | 56 | 0.7673 |
| IFIT3, gran, intra | 2.00E−05 | 0.41 | 79 | 83 | 63 | 90 | 48 | 1.3384 |
| IFIT3, lymp, intra | 7.00E−04 | 0.12 | 76 | 91 | 19 | 82 | 33 | 1.1029 |
| IFIT3, mean, intra | 1.00E−04 | 0.31 | 72 | 74 | 63 | 88 | 38 | 1.1795 |
| IFIT3, mono, intra | 2.00E−05 | 0.41 | 79 | 83 | 63 | 90 | 48 | 1.3384 |
| LIPT1, gran, intra | 7.00E−05 | 0.26 | 78 | 88 | 38 | 85 | 43 | 0.9803 |
| LIPT1, lymp, intra | 3.00E−04 | 0.38 | 83 | 94 | 38 | 86 | 60 | 1.0083 |
| LIPT1, mean, intra | 2.00E−04 | 0.3 | 76 | 82 | 50 | 86 | 42 | 0.7438 |
| LIPT1, mono, intra | 7.00E−05 | 0.26 | 78 | 88 | 38 | 85 | 43 | 0.9803 |
| LOC26010, gran, intra | 3.00E−05 | 0.47 | 84 | 91 | 56 | 91 | 56 | 1.092 |
| LOC26010, lymp, intra | 4.00E−05 | 0.41 | 80 | 84 | 63 | 91 | 45 | 0.8577 |
| LOC26010, mean, intra | 4.00E−05 | 0.35 | 80 | 86 | 50 | 89 | 44 | 0.9144 |
| LOC26010, mono, intra | 3.00E−05 | 0.47 | 84 | 91 | 56 | 91 | 56 | 1.092 |
| Lym (%) | 5.00E−06 | 0.35 | 80 | 87 | 50 | 89 | 44 | 1.5718 |
| MX1, gran, intra | 1.00E−06 | 0.65 | 90 | 95 | 69 | 93 | 73 | 1.6082 |
| MX1, lymp, intra | 1.00E−06 | 0.47 | 86 | 93 | 50 | 90 | 62 | 1.5425 |
| MX1, mean, intra | 3.00E−06 | 0.73 | 92 | 96 | 75 | 95 | 80 | 1.5264 |
| MX1, mono, intra | 1.00E−06 | 0.65 | 90 | 95 | 69 | 93 | 73 | 1.6082 |
| Neu (%) | 4.00E−06 | 0.46 | 81 | 84 | 69 | 93 | 48 | −0.5346 |
| OAS2, gran, intra | 4.00E−05 | 0.44 | 85 | 92 | 50 | 90 | 57 | 1.2302 |
| OAS2, lymp, intra | 8.00E−04 | 0.38 | 76 | 77 | 69 | 92 | 39 | 0.9389 |
| OAS2, mean, intra | 1.00E−04 | 0.49 | 81 | 82 | 75 | 94 | 48 | 0.9043 |
| OAS2, mono, intra | 4.00E−05 | 0.44 | 85 | 92 | 50 | 90 | 57 | 1.2302 |
| PARP12, gran, intra | 1.00E−04 | 0.33 | 68 | 66 | 75 | 91 | 35 | 0.7337 |
| PARP12, lymp, intra | 9.00E−04 | 0.22 | 79 | 92 | 25 | 83 | 44 | 0.8365 |
| PARP12, mean, intra | 2.00E−05 | 0.34 | 76 | 81 | 56 | 88 | 43 | 0.8935 |
| PARP12, mono, intra | 1.00E−04 | 0.33 | 68 | 66 | 75 | 91 | 35 | 0.7337 |
| PARP9, gran, intra | 3.00E−04 | 0.32 | 75 | 80 | 56 | 88 | 41 | 0.9399 |
| PARP9, lymp, intra | 1.00E−05 | 0.46 | 80 | 83 | 69 | 91 | 50 | 1.0354 |
| PARP9, mean, intra | 7.00E−04 | 0.38 | 78 | 84 | 56 | 88 | 47 | 0.7744 |
| PARP9, mono, intra | 3.00E−04 | 0.32 | 75 | 80 | 56 | 88 | 41 | 0.9399 |
| PTEN, gran, intra | 3.00E−05 | 0.38 | 76 | 78 | 67 | 91 | 42 | 1.0924 |
| PTEN, lymp, intra | 2.00E−04 | 0.37 | 84 | 95 | 33 | 86 | 63 | 0.7166 |
| PTEN, mean, intra | 6.00E−05 | 0.15 | 75 | 87 | 27 | 83 | 33 | 0.9682 |
| PTEN, mono, intra | 3.00E−05 | 0.38 | 76 | 78 | 67 | 91 | 42 | 1.0924 |

TABLE 1B-continued

Mixed (bacterial and viral) versus viral infected patients

| DETERMINANT | Wilcoxon ranksum P-value | MCC | Total Accuracy | Sensitivity % | Specificity % | PPV % | NPV % | log2 (med1/med2) |
|---|---|---|---|---|---|---|---|---|
| RSAD2, gran, intra | 1.00E−06 | 0.62 | 88 | 91 | 75 | 94 | 63 | 1.6165 |
| RSAD2, lymp, intra | 2.00E−05 | 0.3 | 75 | 79 | 56 | 89 | 36 | 0.933 |
| RSAD2, mean, intra | 6.00E−06 | 0.47 | 84 | 90 | 56 | 90 | 56 | 1.3028 |
| RSAD2, mono, intra | 1.00E−06 | 0.62 | 88 | 91 | 75 | 94 | 63 | 1.6165 |
| SART3, lymp, intra | 4.00E−04 | 0.35 | 79 | 86 | 50 | 87 | 47 | 0.8566 |
| SOCS3, gran, intra | 2.00E−04 | 0.1 | 65 | 71 | 40 | 83 | 25 | 1.0003 |
| SOCS3, lymp, intra | 1.00E−04 | 0.3 | 69 | 70 | 67 | 90 | 34 | 1.0643 |
| SOCS3, mean, intra | 9.00E−05 | 0.31 | 70 | 70 | 67 | 90 | 36 | 1.0804 |
| SOCS3, mono, intra | 2.00E−04 | 0.1 | 65 | 71 | 40 | 83 | 25 | 1.0003 |
| UBE2N, mean, intra | 1.00E−03 | 0.34 | 73 | 74 | 67 | 90 | 38 | 0.6314 |

*Positives and negatives correspond to Viral and Mixed infected patients respectively

TABLE 1C

Viral versus non-infectious and healthy patients

| DETERMINANT | Wilcoxon ranksum P-value | MCC | Total Accuracy | Sensitivity % | Specificity % | PPV % | NPV % | log2(med1/med2) |
|---|---|---|---|---|---|---|---|---|
| IFIT3, gran, intra | 2.00E−06 | 0.52 | 79 | 78 | 86 | 96 | 46 | 1.4768 |
| IFIT3, lymp, intra | 4.00E−04 | 0.516 | 78 | 76 | 89 | 97 | 44 | 1.4378 |
| IFIT3, mean, intra | 1.00E−05 | 0.478 | 83 | 87 | 64 | 92 | 53 | 1.3977 |
| IFIT3, total, intra | 7.00E−06 | 0.447 | 83 | 89 | 57 | 90 | 53 | 1.5834 |
| IFITM3, mono, membrane | 5.00E−05 | 0.599 | 91 | 97 | 54 | 92 | 78 | 1.409 |
| LOC26010, gran, intra | 9.00E−06 | 0.317 | 74 | 76 | 64 | 92 | 33 | 1.0447 |
| LOC26010, mean, intra | 4.00E−05 | 0.245 | 71 | 74 | 57 | 90 | 30 | 0.8998 |
| LOC26010, total, intra | 2.00E−05 | 0.508 | 77 | 74 | 93 | 98 | 41 | 0.8842 |
| MAN1C1, lymp, intra | 7.00E−04 | 0.679 | 91 | 93 | 80 | 96 | 67 | −0.8502 |
| MX1, gran, intra | 5.00E−08 | 0.762 | 93 | 95 | 86 | 97 | 75 | 1.7607 |
| MX1, lymp, intra | 3.00E−06 | 0.641 | 86 | 85 | 93 | 98 | 54 | 1.2356 |
| MX1, mean, intra | 1.00E−07 | 0.793 | 94 | 96 | 86 | 97 | 80 | 1.5771 |
| MX1, total, intra | 5.00E−07 | 0.533 | 81 | 81 | 86 | 97 | 46 | 1.7951 |
| OAS2, gran, intra | 2.00E−06 | 0.497 | 85 | 89 | 64 | 93 | 53 | 1.3996 |
| OAS2, mean, intra | 3.00E−05 | 0.179 | 76 | 84 | 36 | 87 | 29 | 1.0438 |
| OAS2, total, intra | 4.00E−05 | 0.171 | 60 | 59 | 64 | 90 | 23 | 1.0833 |
| RAB13, gran, intra | 7.00E−06 | 0.535 | 86 | 91 | 64 | 92 | 60 | 0.8966 |
| RAB13, mean, intra | 4.00E−05 | 0.465 | 80 | 82 | 71 | 93 | 48 | 0.6475 |
| RSAD2, gran, intra | 1.00E−06 | 0.732 | 92 | 93 | 86 | 97 | 71 | 2.0751 |
| RSAD2, mean, intra | 1.00E−06 | 0.471 | 84 | 88 | 64 | 93 | 50 | 1.6929 |
| RSAD2, total, intra | 7.00E−06 | 0.494 | 85 | 89 | 64 | 93 | 53 | 1.9603 |
| SART3, gran, intra | 3.00E−05 | 0.279 | 76 | 81 | 50 | 88 | 37 | 0.9517 |

*Positives and negatives correspond to viral versus healthy and non-infectious patients respectively

TABLE 1D

Bacterial versus non-infectious and healthy patients

| DETERMINANT | Wilcoxon ranksum P-value | MCC | Total Accuracy | Sensitivity % | Specificity % | PPV % | NPV % | log2(med1/med2) |
|---|---|---|---|---|---|---|---|---|
| CRP | 7.00E−04 | 0.795 | 91 | 94 | 86 | 94 | 86 | 5.9873 |
| HERC5, lymp, intra | 6.00E−04 | 0.32 | 69 | 76 | 56 | 76 | 56 | −1.1808 |
| KIAA0082, lymp, intra | 8.00E−04 | 0.652 | 85 | 94 | 67 | 84 | 86 | −1.088 |
| LOC26010, total, intra | 3.00E−05 | 0.535 | 78 | 74 | 93 | 98 | 45 | 0.9881 |
| MX1, total, intra | 2.00E−05 | 0.256 | 67 | 68 | 64 | 89 | 31 | 1.2637 |
| OAS2, total, intra | 1.00E−04 | 0.214 | 63 | 63 | 64 | 89 | 28 | 1.0966 |
| RAB13, total, intra | 5.00E−05 | 0.564 | 81 | 82 | 79 | 91 | 61 | 1.312 |
| SMAD9, lymp, intra | 5.00E−04 | 0.741 | 88 | 94 | 78 | 89 | 88 | −0.7465 |
| WBC | 8.00E−04 | 0.624 | 81 | 76 | 89 | 93 | 67 | 0.7744 |

*Positives and negatives correspond to Bacterial versus healthy and non-infectious patients respectively

TABLE 1E

Infectious versus non-infectious and healthy

| DETERMINANT | Wilcoxon ranksum P-value | MCC | Total Accuracy | Sensitivity % | Specificity % | PPV % | NPV % | log2(med1/med2) |
|---|---|---|---|---|---|---|---|---|
| CRP | 5.00E−04 | 0.75 | 96 | 98 | 71 | 97 | 83 | 5.2216 |
| IFIT3, total, intra | 7.00E−06 | 0.447 | 83 | 89 | 57 | 90 | 53 | 1.5834 |
| LOC26010, total, intra | 2.00E−05 | 0.508 | 77 | 74 | 93 | 98 | 41 | 0.8842 |
| MAN1C1, lymp, intra | 5.00E−04 | 0.637 | 94 | 98 | 60 | 95 | 75 | −0.9458 |
| MX1, gran, intra | 2.00E−05 | 0.16 | 69 | 70 | 57 | 95 | 15 | 1.1574 |
| MX1, mean, intra | 4.00E−05 | 0.289 | 75 | 75 | 71 | 97 | 21 | 0.9615 |
| MX1, total, intra | 5.00E−07 | 0.533 | 81 | 81 | 86 | 97 | 46 | 1.7951 |
| OAS2, total, intra | 4.00E−05 | 0.171 | 60 | 59 | 64 | 90 | 23 | 1.0833 |
| RAB13, gran, intra | 9.00E−05 | 0.332 | 80 | 82 | 64 | 95 | 29 | 0.6433 |
| RAB13, mean, intra | 8.00E−05 | 0.359 | 79 | 79 | 71 | 96 | 29 | 0.5312 |
| RSAD2, total, intra | 7.00E−06 | 0.494 | 85 | 89 | 64 | 93 | 53 | 1.9603 |
| SMAD9, lymp, intra | 5.00E−04 | 0.396 | 89 | 97 | 33 | 92 | 60 | −0.6464 |

*Positives and negatives correspond to Infectious versus healthy and non-infectious patients respectively

TABLE 2

The classification accuracy of bacterial vs. viral infected patients computed over pairs of features. DETERMINANT measurements were measured over population mean. (mean pairs)

| Feature #1 | Feature #2 | MCC | dMCC | Total accuracy % | Sen % | Spe % | PPV % | NPV % |
|---|---|---|---|---|---|---|---|---|
| ANC | CORO1A, mean, intra | 0.41 | −0.03 | 73 | 92 | 42 | 72 | 76 |
| ANC | CRP | 0.58 | 0.02 | 80 | 87 | 70 | 83 | 76 |
| ANC | EIF4B, mean, intra | 0.5 | 0.06 | 77 | 92 | 53 | 76 | 80 |
| ANC | IFIT3, mean, intra | 0.5 | 0.06 | 77 | 92 | 53 | 76 | 80 |
| ANC | IFITM1, mean, membrane | 0.43 | −0.01 | 74 | 94 | 42 | 73 | 80 |
| ANC | IFITM3, mean, membrane | 0.43 | −0.01 | 74 | 94 | 42 | 73 | 80 |
| ANC | LOC26010, mean, intra | 0.43 | −0.01 | 74 | 94 | 42 | 73 | 80 |
| ANC | Lym(%) | 0.5 | −0.02 | 77 | 88 | 61 | 79 | 74 |
| ANC | MAN1C1, mean, intra | 0.36 | −0.08 | 72 | 90 | 40 | 72 | 71 |
| ANC | MX1, mean, intra | 0.57 | 0.12 | 80 | 92 | 61 | 79 | 82 |
| ANC | Neu(%) | 0.53 | −0.03 | 78 | 91 | 58 | 78 | 79 |
| ANC | NPM1, mean, intra | 0.43 | −0.01 | 74 | 92 | 45 | 73 | 77 |
| ANC | OAS2, mean, intra | 0.4 | −0.04 | 73 | 90 | 45 | 73 | 74 |
| ANC | PARP12, mean, intra | 0.48 | 0.04 | 76 | 90 | 53 | 76 | 77 |
| ANC | PTEN, mean, intra | 0.43 | −0.01 | 74 | 92 | 45 | 73 | 77 |
| ANC | RSAD2, mean, intra | 0.64 | 0 | 83 | 85 | 79 | 87 | 77 |
| ANC | SDCBP, mean, intra | 0.45 | 0.01 | 75 | 90 | 50 | 74 | 76 |
| ANC | WBC | 0.53 | 0.09 | 78 | 95 | 50 | 76 | 86 |
| CORO1A, mean, intra | CRP | 0.56 | 0 | 79 | 91 | 61 | 78 | 82 |
| CORO1A, mean, intra | EIF4B, mean, intra | 0.31 | 0 | 68 | 81 | 49 | 71 | 61 |
| CORO1A, mean, intra | IFIT3, mean, intra | 0.39 | 0.14 | 71 | 79 | 59 | 75 | 64 |
| CORO1A, mean, intra | IFITM1, mean, membrane | 0.14 | −0.15 | 60 | 73 | 41 | 66 | 48 |
| CORO1A, mean, intra | IFITM3, mean, membrane | 0.16 | −0.19 | 61 | 74 | 41 | 67 | 50 |
| CORO1A, mean, intra | LOC26010, mean, intra | 0.16 | −0.05 | 61 | 74 | 41 | 67 | 50 |
| CORO1A, mean, intra | Lym(%) | 0.51 | −0.01 | 76 | 77 | 74 | 83 | 67 |
| CORO1A, mean, intra | MAN1C1, mean, intra | 0.25 | 0.1 | 66 | 79 | 45 | 71 | 56 |
| CORO1A, mean, intra | MX1, mean, intra | 0.48 | 0.03 | 75 | 81 | 67 | 79 | 68 |
| CORO1A, mean, intra | Neu(%) | 0.55 | −0.01 | 79 | 89 | 64 | 80 | 78 |
| CORO1A, mean, intra | NPM1, mean, intra | 0.2 | 0.05 | 63 | 75 | 44 | 68 | 53 |
| CORO1A, mean, intra | OAS2, mean, intra | 0.19 | −0.11 | 62 | 73 | 46 | 68 | 51 |
| CORO1A, mean, intra | PARP12, mean, intra | 0.28 | 0.03 | 66 | 76 | 51 | 71 | 57 |
| CORO1A, mean, intra | PTEN, mean, intra | 0.18 | −0.02 | 62 | 74 | 44 | 68 | 52 |
| CORO1A, mean, intra | RSAD2, mean, intra | 0.59 | −0.05 | 80 | 82 | 77 | 85 | 73 |
| CORO1A, mean, intra | SDCBP, mean, intra | 0.19 | 0.04 | 63 | 77 | 41 | 67 | 53 |
| CORO1A, mean, intra | WBC | 0.28 | 0.03 | 67 | 82 | 44 | 70 | 61 |
| CRP | EIF4B, mean, intra | 0.65 | 0.09 | 83 | 95 | 66 | 81 | 89 |
| CRP | IFIT3, mean, intra | 0.69 | 0.13 | 85 | 91 | 76 | 85 | 85 |
| CRP | IFITM1, mean, membrane | 0.58 | 0.02 | 80 | 91 | 63 | 79 | 83 |
| CRP | IFITM3, mean, membrane | 0.67 | 0.11 | 84 | 91 | 74 | 84 | 85 |
| CRP | LOC26010, mean, intra | 0.69 | 0.13 | 85 | 90 | 79 | 87 | 83 |
| CRP | Lym(%) | 0.7 | 0.14 | 86 | 92 | 76 | 86 | 85 |
| CRP | MAN1C1, mean, intra | 0.61 | 0.05 | 82 | 90 | 70 | 83 | 81 |
| CRP | MX1, mean, intra | 0.74 | 0.18 | 88 | 93 | 79 | 87 | 88 |
| CRP | Neu(%) | 0.65 | 0.09 | 84 | 92 | 71 | 83 | 84 |
| CRP | NPM1, mean, intra | 0.65 | 0.09 | 83 | 88 | 76 | 85 | 81 |
| CRP | OAS2, mean, intra | 0.65 | 0.09 | 83 | 91 | 71 | 83 | 84 |
| CRP | PARP12, mean, intra | 0.76 | 0.2 | 89 | 95 | 79 | 87 | 91 |
| CRP | PTEN, mean, intra | 0.69 | 0.13 | 85 | 93 | 74 | 84 | 88 |

TABLE 2-continued

The classification accuracy of bacterial vs. viral infected patients computed over pairs of
features. DETERMINANT measurements were measured over population mean. (mean pairs)

| Feature #1 | Feature #2 | MCC | dMCC | Total accuracy % | Sen % | Spe % | PPV % | NPV % |
|---|---|---|---|---|---|---|---|---|
| CRP | RSAD2, mean, intra | 0.85 | 0.21 | 93 | 93 | 92 | 95 | 90 |
| CRP | SDCBP, mean, intra | 0.65 | 0.09 | 83 | 89 | 74 | 84 | 82 |
| CRP | WBC | 0.54 | −0.02 | 79 | 88 | 63 | 79 | 77 |
| EIF4B, mean, intra | IFIT3, mean, intra | 0.23 | −0.08 | 64 | 76 | 46 | 69 | 55 |
| EIF4B, mean, intra | IFITM1, mean, membrane | 0.26 | −0.05 | 63 | 69 | 56 | 66 | 60 |
| EIF4B, mean, intra | IFITM3, mean, membrane | 0.32 | −0.03 | 66 | 68 | 64 | 70 | 62 |
| EIF4B, mean, intra | LOC26010, mean, intra | 0.3 | −0.01 | 65 | 63 | 68 | 69 | 61 |
| EIF4B, mean, intra | Lym(%) | 0.54 | 0.02 | 77 | 75 | 79 | 81 | 73 |
| EIF4B, mean, intra | MAN1C1, mean, intra | 0.25 | −0.06 | 66 | 79 | 45 | 71 | 56 |
| EIF4B, mean, intra | MX1, mean, intra | 0.46 | 0.01 | 72 | 67 | 79 | 79 | 67 |
| EIF4B, mean, intra | Neu(%) | 0.57 | 0.01 | 78 | 78 | 79 | 81 | 75 |
| EIF4B, mean, intra | NPM1, mean, intra | 0.08 | −0.23 | 58 | 72 | 36 | 64 | 45 |
| EIF4B, mean, intra | OAS2, mean, intra | 0.34 | 0.03 | 67 | 67 | 68 | 71 | 64 |
| EIF4B, mean, intra | PARP12, mean, intra | 0.26 | −0.05 | 65 | 74 | 51 | 71 | 56 |
| EIF4B, mean, intra | PTEN, mean, intra | 0.16 | −0.15 | 61 | 74 | 41 | 67 | 50 |
| EIF4B, mean, intra | RSAD2, mean, intra | 0.63 | −0.01 | 81 | 79 | 84 | 85 | 78 |
| EIF4B, mean, intra | SDCBP, mean, intra | 0.17 | −0.14 | 62 | 77 | 38 | 66 | 52 |
| EIF4B, mean, intra | WBC | 0.38 | 0.07 | 69 | 79 | 58 | 69 | 71 |
| IFIT3, mean, intra | IFITM1, mean, membrane | 0.25 | −0.04 | 65 | 76 | 49 | 70 | 56 |
| IFIT3, mean, intra | IFITM3, mean, membrane | 0.26 | −0.09 | 65 | 74 | 51 | 71 | 56 |
| IFIT3, mean, intra | LOC26010, mean, intra | 0.16 | −0.09 | 60 | 69 | 46 | 67 | 49 |
| IFIT3, mean, intra | Lym(%) | 0.56 | 0.04 | 79 | 85 | 69 | 82 | 75 |
| IFIT3, mean, intra | MAN1C1, mean, intra | 0.21 | −0.04 | 65 | 83 | 35 | 68 | 55 |
| IFIT3, mean, intra | MX1, mean, intra | 0.38 | −0.07 | 70 | 74 | 64 | 77 | 61 |
| IFIT3, mean, intra | Neu(%) | 0.62 | 0.06 | 82 | 89 | 72 | 83 | 80 |
| IFIT3, mean, intra | NPM1, mean, intra | 0.34 | 0.09 | 69 | 77 | 56 | 73 | 61 |
| IFIT3, mean, intra | OAS2, mean, intra | 0.21 | −0.09 | 63 | 74 | 46 | 69 | 53 |
| IFIT3, mean, intra | PARP12, mean, intra | 0.34 | 0.09 | 68 | 73 | 62 | 75 | 59 |
| IFIT3, mean, intra | PTEN, mean, intra | 0.16 | −0.09 | 60 | 69 | 46 | 67 | 49 |
| IFIT3, mean, intra | RSAD2, mean, intra | 0.59 | −0.05 | 80 | 81 | 79 | 86 | 72 |
| IFIT3, mean, intra | SDCBP, mean, intra | 0.23 | −0.02 | 63 | 69 | 54 | 70 | 53 |
| IFIT3, mean, intra | WBC | 0.3 | 0.05 | 67 | 77 | 51 | 72 | 59 |
| IFITM1, mean, membrane | IFITM3, mean, membrane | 0.33 | −0.02 | 66 | 64 | 69 | 72 | 61 |
| IFITM1, mean, membrane | LOC26010, mean, intra | 0.22 | −0.07 | 61 | 63 | 59 | 65 | 56 |
| IFITM1, mean, membrane | Lym(%) | 0.52 | 0 | 76 | 76 | 76 | 80 | 73 |
| IFITM1, mean, membrane | MAN1C1, mean, intra | 0.1 | −0.19 | 61 | 83 | 26 | 65 | 47 |
| IFITM1, mean, membrane | MX1, mean, intra | 0.48 | 0.03 | 74 | 72 | 76 | 79 | 69 |
| IFITM1, mean, membrane | Neu(%) | 0.53 | −0.03 | 76 | 75 | 78 | 81 | 72 |
| IFITM1, mean, membrane | NPM1, mean, intra | 0.08 | −0.21 | 58 | 72 | 36 | 64 | 45 |
| IFITM1, mean, membrane | OAS2, mean, intra | 0.31 | 0.01 | 66 | 65 | 66 | 70 | 61 |
| IFITM1, mean, membrane | PARP12, mean, intra | 0.23 | −0.06 | 64 | 74 | 49 | 70 | 54 |
| IFITM1, mean, membrane | PTEN, mean, intra | 0.2 | −0.09 | 63 | 77 | 41 | 68 | 53 |
| IFITM1, mean, membrane | RSAD2, mean, intra | 0.57 | −0.07 | 79 | 76 | 81 | 83 | 74 |
| IFITM1, mean, membrane | SDCBP, mean, intra | 0.04 | −0.25 | 57 | 75 | 28 | 62 | 42 |
| IFITM1, mean, membrane | WBC | 0.3 | 0.01 | 66 | 74 | 56 | 67 | 63 |
| IFITM3, mean, membrane | LOC26010, mean, intra | 0.34 | −0.01 | 66 | 63 | 71 | 73 | 61 |
| IFITM3, mean, membrane | Lym(%) | 0.48 | −0.04 | 74 | 76 | 71 | 76 | 71 |
| IFITM3, mean, membrane | MAN1C1, mean, intra | 0.08 | −0.27 | 60 | 81 | 26 | 65 | 44 |
| IFITM3, mean, membrane | MX1, mean, intra | 0.4 | −0.05 | 70 | 69 | 71 | 75 | 66 |
| IFITM3, mean, membrane | Neu(%) | 0.58 | 0.02 | 79 | 83 | 75 | 80 | 79 |
| IFITM3, mean, membrane | NPM1, mean, intra | 0.21 | −0.14 | 64 | 80 | 38 | 67 | 56 |
| IFITM3, mean, membrane | OAS2, mean, intra | 0.33 | −0.02 | 66 | 64 | 69 | 72 | 61 |
| IFITM3, mean, membrane | PARP12, mean, intra | 0.23 | −0.12 | 64 | 74 | 49 | 70 | 54 |
| IFITM3, mean, membrane | PTEN, mean, intra | 0.2 | −0.15 | 63 | 76 | 44 | 68 | 53 |
| IFITM3, mean, membrane | RSAD2, mean, intra | 0.63 | −0.01 | 82 | 81 | 83 | 85 | 78 |
| IFITM3, mean, membrane | SDCBP, mean, intra | 0.04 | −0.31 | 57 | 75 | 28 | 62 | 42 |
| IFITM3, mean, membrane | WBC | 0.37 | 0.02 | 69 | 74 | 63 | 71 | 66 |
| LOC26010, mean, intra | Lym(%) | 0.52 | 0 | 76 | 76 | 76 | 79 | 73 |
| LOC26010, mean, intra | MAN1C1, mean, intra | 0.18 | −0.03 | 64 | 81 | 35 | 68 | 52 |
| LOC26010, mean, intra | MX1, mean, intra | 0.44 | −0.01 | 72 | 68 | 76 | 77 | 67 |
| LOC26010, mean, intra | Neu(%) | 0.49 | −0.07 | 75 | 75 | 74 | 77 | 72 |
| LOC26010, mean, intra | NPM1, mean, intra | 0.14 | −0.07 | 61 | 77 | 36 | 65 | 50 |
| LOC26010, mean, intra | OAS2, mean, intra | 0.26 | −0.04 | 63 | 58 | 68 | 68 | 58 |
| LOC26010, mean, intra | PARP12, mean, intra | 0.26 | 0.01 | 65 | 74 | 51 | 71 | 56 |
| LOC26010, mean, intra | PTEN, mean, intra | 0.15 | −0.06 | 60 | 71 | 44 | 67 | 49 |
| LOC26010, mean, intra | RSAD2, mean, intra | 0.64 | 0 | 82 | 81 | 84 | 85 | 79 |
| LOC26010, mean, intra | SDCBP, mean, intra | 0.16 | −0.05 | 62 | 79 | 36 | 66 | 52 |
| LOC26010, mean, intra | WBC | 0.29 | 0.04 | 65 | 74 | 55 | 65 | 64 |
| Lym(%) | MAN1C1, mean, intra | 0.42 | −0.1 | 73 | 83 | 58 | 77 | 67 |
| Lym(%) | MX1, mean, intra | 0.62 | 0.1 | 81 | 83 | 79 | 82 | 80 |
| Lym(%) | Neu(%) | 0.53 | −0.03 | 77 | 75 | 79 | 81 | 72 |
| Lym(%) | NPM1, mean, intra | 0.54 | 0.02 | 78 | 82 | 72 | 82 | 72 |
| Lym(%) | OAS2, mean, intra | 0.55 | 0.03 | 78 | 78 | 77 | 80 | 75 |
| Lym(%) | PARP12, mean, intra | 0.56 | 0.04 | 79 | 82 | 74 | 84 | 73 |

TABLE 2-continued

The classification accuracy of bacterial vs. viral infected patients computed over pairs of features. DETERMINANT measurements were measured over population mean. (mean pairs)

| Feature #1 | Feature #2 | MCC | dMCC | Total accuracy % | Sen % | Spe % | PPV % | NPV % |
|---|---|---|---|---|---|---|---|---|
| Lym(%) | PTEN, mean, intra | 0.47 | −0.05 | 74 | 76 | 72 | 81 | 65 |
| Lym(%) | RSAD2, mean, intra | 0.61 | −0.03 | 81 | 81 | 81 | 83 | 78 |
| Lym(%) | SDCBP, mean, intra | 0.45 | −0.07 | 74 | 79 | 67 | 79 | 67 |
| Lym(%) | WBC | 0.58 | 0.06 | 79 | 79 | 79 | 82 | 75 |
| MAN1C1, mean, intra | MX1, mean, intra | 0.38 | −0.07 | 71 | 77 | 61 | 77 | 61 |
| MAN1C1, mean, intra | Neu(%) | 0.5 | −0.06 | 77 | 88 | 58 | 78 | 75 |
| MAN1C1, mean, intra | NPM1, mean, intra | 0.19 | 0.06 | 64 | 79 | 39 | 68 | 52 |
| MAN1C1, mean, intra | OAS2, mean, intra | 0.15 | −0.15 | 63 | 81 | 32 | 67 | 50 |
| MAN1C1, mean, intra | PARP12, mean, intra | 0.21 | −0.04 | 64 | 75 | 45 | 70 | 52 |
| MAN1C1, mean, intra | PTEN, mean, intra | 0.28 | 0.08 | 67 | 79 | 48 | 72 | 58 |
| MAN1C1, mean, intra | RSAD2, mean, intra | 0.58 | −0.06 | 81 | 87 | 71 | 83 | 76 |
| MAN1C1, mean, intra | SDCBP, mean, intra | 0.3 | 0.17 | 69 | 83 | 45 | 72 | 61 |
| MAN1C1, mean, intra | WBC | 0.22 | −0.03 | 66 | 88 | 29 | 68 | 60 |
| MX1, mean, intra | Neu(%) | 0.59 | 0.03 | 80 | 83 | 76 | 80 | 80 |
| MX1, mean, intra | NPM1, mean, intra | 0.36 | −0.09 | 69 | 72 | 64 | 76 | 60 |
| MX1, mean, intra | OAS2, mean, intra | 0.45 | 0 | 72 | 68 | 77 | 78 | 68 |
| MX1, mean, intra | PARP12, mean, intra | 0.53 | 0.08 | 77 | 79 | 74 | 83 | 69 |
| MX1, mean, intra | PTEN, mean, intra | 0.37 | −0.08 | 70 | 76 | 62 | 76 | 62 |
| MX1, mean, intra | RSAD2, mean, intra | 0.57 | −0.07 | 78 | 75 | 82 | 83 | 74 |
| MX1, mean, intra | SDCBP, mean, intra | 0.41 | −0.04 | 72 | 77 | 64 | 77 | 64 |
| MX1, mean, intra | WBC | 0.44 | −0.01 | 72 | 68 | 76 | 77 | 67 |
| Neu(%) | OAS2, mean, intra | 0.57 | 0.01 | 79 | 78 | 79 | 81 | 75 |
| Neu(%) | PARP12, mean, intra | 0.62 | 0.06 | 82 | 87 | 74 | 84 | 78 |
| Neu(%) | PTEN, mean, intra | 0.56 | 0 | 79 | 84 | 72 | 83 | 74 |
| Neu(%) | RSAD2, mean, intra | 0.66 | 0.02 | 83 | 84 | 82 | 85 | 81 |
| Neu(%) | SDCBP, mean, intra | 0.51 | −0.05 | 77 | 82 | 69 | 81 | 71 |
| Neu(%) | WBC | 0.54 | −0.02 | 77 | 80 | 74 | 79 | 75 |
| NPM1, mean, intra | Neu(%) | 0.6 | 0.04 | 81 | 87 | 72 | 83 | 78 |
| NPM1, mean, intra | OAS2, mean, intra | 0.04 | −0.26 | 56 | 70 | 33 | 62 | 42 |
| NPM1, mean, intra | PARP12, mean, intra | 0.22 | −0.03 | 63 | 70 | 51 | 69 | 53 |
| NPM1, mean, intra | PTEN, mean, intra | 0.14 | −0.06 | 60 | 72 | 41 | 66 | 48 |
| NPM1, mean, intra | RSAD2, mean, intra | 0.58 | −0.06 | 80 | 82 | 77 | 85 | 73 |
| NPM1, mean, intra | SDCBP, mean, intra | 0.07 | −0.06 | 58 | 75 | 31 | 63 | 44 |
| NPM1, mean, intra | WBC | 0.39 | 0.14 | 72 | 89 | 46 | 72 | 72 |
| OAS2, mean, intra | PARP12, mean, intra | 0.24 | −0.06 | 64 | 73 | 51 | 70 | 54 |
| OAS2, mean, intra | PTEN, mean, intra | 0.14 | −0.16 | 60 | 73 | 41 | 66 | 48 |
| OAS2, mean, intra | RSAD2, mean, intra | 0.66 | 0.02 | 83 | 82 | 84 | 86 | 80 |
| OAS2, mean, intra | SDCBP, mean, intra | 0.03 | −0.27 | 56 | 72 | 31 | 62 | 41 |
| OAS2, mean, intra | WBC | 0.34 | 0.04 | 67 | 75 | 58 | 68 | 67 |
| PARP12, mean, intra | PTEN, mean, intra | 0.25 | 0 | 65 | 76 | 49 | 70 | 56 |
| PARP12, mean, intra | RSAD2, mean, intra | 0.61 | −0.03 | 81 | 84 | 77 | 85 | 75 |
| PARP12, mean, intra | SDCBP, mean, intra | 0.21 | −0.04 | 63 | 72 | 49 | 69 | 53 |
| PARP12, mean, intra | WBC | 0.35 | 0.1 | 70 | 84 | 49 | 72 | 66 |
| PTEN, mean, intra | RSAD2, mean, intra | 0.61 | −0.03 | 81 | 82 | 79 | 86 | 74 |
| PTEN, mean, intra | SDCBP, mean, intra | 0.24 | 0.04 | 65 | 77 | 46 | 69 | 56 |
| PTEN, mean, intra | WBC | 0.3 | 0.05 | 68 | 85 | 41 | 70 | 64 |
| RSAD2, mean, intra | SDCBP, mean, intra | 0.61 | −0.03 | 81 | 82 | 79 | 86 | 74 |
| RSAD2, mean, intra | WBC | 0.63 | −0.01 | 81 | 78 | 85 | 86 | 77 |
| SDCBP, mean, intra | WBC | 0.27 | 0.02 | 67 | 84 | 41 | 69 | 62 |

* Positive and negative correspond to bacterial and viral infected patients respectively

TABLE 3

The classification accuracy of bacterial vs. viral infected patients computed over pairs of features. DETERMINANT measurements were measured over cell population mean. (mean triplets)

| Feature #1 | Feature #2 | Feature #3 | MCC | dMCC | Total accuracy % | Sen % | Spe % | PPV % | NPV % |
|---|---|---|---|---|---|---|---|---|---|
| ANC | CORO1A, mean, intra | CRP | 0.6 | 0.08 | 83 | 88 | 76 | 85 | 80 |
| ANC | CORO1A, mean, intra | EIF4B, mean, intra | 0.5 | 0.04 | 76 | 94 | 47 | 74 | 82 |
| ANC | CORO1A, mean, intra | IFIT3, mean, intra | 0.5 | 0.04 | 76 | 90 | 53 | 76 | 77 |
| ANC | CORO1A, mean, intra | IFITM1, mean, membrane | 0.4 | −0.01 | 74 | 92 | 45 | 73 | 77 |
| ANC | CORO1A, mean, intra | IFITM3, mean, membrane | 0.4 | −0.04 | 73 | 90 | 45 | 73 | 74 |
| ANC | CORO1A, mean, intra | LOC26010, mean, intra | 0.4 | −0.01 | 74 | 92 | 45 | 73 | 77 |
| ANC | CORO1A, mean, intra | Lym(%) | 0.5 | 0 | 78 | 89 | 61 | 79 | 77 |
| ANC | CORO1A, mean, intra | MAN1C1, mean, intra | 0.3 | −0.14 | 70 | 88 | 37 | 71 | 65 |
| ANC | CORO1A, mean, intra | MX1, mean, intra | 0.6 | 0.14 | 81 | 92 | 63 | 80 | 83 |
| ANC | CORO1A, mean, intra | Neu(%) | 0.5 | −0.06 | 77 | 90 | 55 | 77 | 78 |
| ANC | CORO1A, mean, intra | NPM1, mean, intra | 0.4 | −0.06 | 72 | 89 | 45 | 72 | 71 |
| ANC | CORO1A, mean, intra | OAS2, mean, intra | 0.4 | −0.03 | 73 | 92 | 42 | 72 | 76 |

TABLE 3-continued

The classification accuracy of bacterial vs. viral infected patients computed over pairs of features.
DETERMINANT measurements were measured over cell population mean. (mean triplets)

| Feature #1 | Feature #2 | Feature #3 | MCC | dMCC | Total accuracy % | Sen % | Spe % | PPV % | NPV % |
|---|---|---|---|---|---|---|---|---|---|
| ANC | CORO1A, mean, intra | PARP12, mean, intra | 0.5 | 0.04 | 76 | 90 | 53 | 76 | 77 |
| ANC | CORO1A, mean, intra | PTEN, mean, intra | 0.4 | −0.01 | 74 | 92 | 45 | 73 | 77 |
| ANC | CORO1A, mean, intra | RSAD2, mean, intra | 0.6 | 0 | 83 | 85 | 79 | 87 | 77 |
| ANC | CORO1A, mean, intra | SDCBP, mean, intra | 0.5 | 0.01 | 75 | 90 | 50 | 74 | 76 |
| ANC | CORO1A, mean, intra | WBC | 0.6 | 0.11 | 79 | 94 | 55 | 77 | 84 |
| ANC | CRP | EIF4B, mean, intra | 0.7 | 0.15 | 86 | 91 | 78 | 87 | 85 |
| ANC | CRP | IFIT3, mean, intra | 0.7 | 0.15 | 86 | 90 | 81 | 88 | 83 |
| ANC | CRP | IFITM1, mean, membrane | 0.7 | 0.13 | 85 | 90 | 78 | 87 | 83 |
| ANC | CRP | IFITM3, mean, membrane | 0.6 | 0.08 | 83 | 90 | 73 | 84 | 82 |
| ANC | CRP | LOC26010, mean, intra | 0.7 | 0.15 | 86 | 90 | 81 | 88 | 83 |
| ANC | CRP | Lym(%) | 0.7 | 0.11 | 85 | 90 | 76 | 86 | 82 |
| ANC | CRP | MAN1C1, mean, intra | 0.6 | 0.08 | 83 | 90 | 72 | 84 | 81 |
| ANC | CRP | MX1, mean, intra | 0.7 | 0.15 | 86 | 91 | 78 | 87 | 85 |
| ANC | CRP | Neu(%) | 0.7 | 0.11 | 85 | 92 | 73 | 85 | 84 |
| ANC | CRP | NPM1, mean, intra | 0.7 | 0.13 | 85 | 89 | 78 | 86 | 83 |
| ANC | CRP | OAS2, mean, intra | 0.7 | 0.11 | 84 | 88 | 78 | 86 | 81 |
| ANC | CRP | PARP12, mean, intra | 0.7 | 0.17 | 87 | 91 | 81 | 88 | 86 |
| ANC | CRP | PTEN, mean, intra | 0.7 | 0.17 | 87 | 91 | 81 | 88 | 86 |
| ANC | CRP | RSAD2, mean, intra | 0.8 | 0.2 | 93 | 97 | 86 | 92 | 94 |
| ANC | CRP | SDCBP, mean, intra | 0.8 | 0.19 | 88 | 91 | 84 | 90 | 86 |
| ANC | CRP | WBC | 0.6 | 0.06 | 82 | 90 | 70 | 83 | 81 |
| ANC | EIF4B, mean, intra | IFIT3, mean, intra | 0.5 | 0.1 | 79 | 92 | 58 | 78 | 81 |
| ANC | EIF4B, mean, intra | IFITM1, mean, membrane | 0.5 | 0.01 | 75 | 92 | 47 | 74 | 78 |
| ANC | EIF4B, mean, intra | IFITM3, mean, membrane | 0.5 | 0.04 | 76 | 92 | 50 | 75 | 79 |
| ANC | EIF4B, mean, intra | LOC26010, mean, intra | 0.5 | 0.04 | 76 | 92 | 50 | 75 | 79 |
| ANC | EIF4B, mean, intra | Lym(%) | 0.6 | 0.09 | 82 | 90 | 68 | 82 | 81 |
| ANC | EIF4B, mean, intra | MAN1C1, mean, intra | 0.4 | −0.08 | 72 | 90 | 40 | 72 | 71 |
| ANC | EIF4B, mean, intra | MX1, mean, intra | 0.6 | 0.18 | 83 | 92 | 68 | 83 | 84 |
| ANC | EIF4B, mean, intra | Neu(%) | 0.7 | 0.1 | 84 | 92 | 71 | 84 | 84 |
| ANC | EIF4B, mean, intra | NPM1, mean, intra | 0.5 | 0.06 | 77 | 93 | 50 | 75 | 83 |
| ANC | EIF4B, mean, intra | OAS2, mean, intra | 0.5 | 0.06 | 77 | 90 | 55 | 77 | 78 |
| ANC | EIF4B, mean, intra | PARP12, mean, intra | 0.6 | 0.13 | 80 | 92 | 61 | 79 | 82 |
| ANC | EIF4B, mean, intra | PTEN, mean, intra | 0.5 | 0.01 | 75 | 92 | 47 | 74 | 78 |
| ANC | EIF4B, mean, intra | RSAD2, mean, intra | 0.6 | 0 | 83 | 85 | 79 | 87 | 77 |
| ANC | EIF4B, mean, intra | SDCBP, mean, intra | 0.5 | 0.01 | 75 | 90 | 50 | 74 | 76 |
| ANC | EIF4B, mean, intra | WBC | 0.6 | 0.15 | 81 | 92 | 63 | 80 | 83 |
| ANC | IFIT3, mean, intra | IFITM1, mean, membrane | 0.4 | −0.04 | 73 | 89 | 47 | 73 | 72 |
| ANC | IFIT3, mean, intra | IFITM3, mean, membrane | 0.5 | 0.01 | 75 | 89 | 53 | 75 | 74 |
| ANC | IFIT3, mean, intra | LOC26010, mean, intra | 0.4 | −0.01 | 74 | 89 | 50 | 74 | 73 |
| ANC | IFIT3, mean, intra | Lym(%) | 0.6 | 0.07 | 81 | 89 | 68 | 82 | 79 |
| ANC | IFIT3, mean, intra | MAN1C1, mean, intra | 0.4 | −0.08 | 72 | 90 | 40 | 72 | 71 |
| ANC | IFIT3, mean, intra | MX1, mean, intra | 0.5 | 0.09 | 79 | 90 | 61 | 79 | 79 |
| ANC | IFIT3, mean, intra | Neu(%) | 0.6 | 0.01 | 80 | 89 | 66 | 81 | 78 |
| ANC | IFIT3, mean, intra | NPM1, mean, intra | 0.5 | 0.01 | 75 | 90 | 50 | 74 | 76 |
| ANC | IFIT3, mean, intra | OAS2, mean, intra | 0.5 | 0.04 | 76 | 92 | 50 | 75 | 79 |
| ANC | IFIT3, mean, intra | PARP12, mean, intra | 0.5 | 0.01 | 75 | 87 | 55 | 76 | 72 |
| ANC | IFIT3, mean, intra | PTEN, mean, intra | 0.5 | 0.01 | 75 | 92 | 47 | 74 | 78 |
| ANC | IFIT3, mean, intra | RSAD2, mean, intra | 0.7 | 0.04 | 85 | 87 | 82 | 89 | 79 |
| ANC | IFIT3, mean, intra | SDCBP, mean, intra | 0.5 | 0.03 | 76 | 90 | 53 | 75 | 77 |
| ANC | IFIT3, mean, intra | WBC | 0.5 | 0.1 | 79 | 89 | 63 | 80 | 77 |
| ANC | IFITM1, mean, membrane | IFITM3, mean, membrane | 0.5 | 0.02 | 75 | 94 | 45 | 73 | 81 |
| ANC | IFITM1, mean, membrane | LOC26010, mean, intra | 0.4 | −0.01 | 74 | 94 | 42 | 73 | 80 |
| ANC | IFITM1, mean, membrane | Lym(%) | 0.5 | −0.02 | 77 | 87 | 61 | 78 | 74 |
| ANC | IFITM1, mean, membrane | MAN1C1, mean, intra | 0.4 | −0.08 | 72 | 90 | 40 | 72 | 71 |
| ANC | IFITM1, mean, membrane | MX1, mean, intra | 0.6 | 0.14 | 81 | 92 | 63 | 80 | 83 |
| ANC | IFITM1, mean, membrane | Neu(%) | 0.5 | −0.06 | 77 | 89 | 58 | 77 | 76 |
| ANC | IFITM1, mean, membrane | NPM1, mean, intra | 0.4 | −0.06 | 72 | 89 | 45 | 72 | 71 |
| ANC | IFITM1, mean, membrane | OAS2, mean, intra | 0.5 | 0.01 | 75 | 90 | 50 | 75 | 76 |
| ANC | IFITM1, mean, membrane | PARP12, mean, intra | 0.5 | 0.04 | 76 | 90 | 53 | 76 | 77 |
| ANC | IFITM1, mean, membrane | PTEN, mean, intra | 0.5 | 0.01 | 75 | 92 | 47 | 74 | 78 |
| ANC | IFITM1, mean, membrane | RSAD2, mean, intra | 0.7 | 0.02 | 84 | 87 | 79 | 87 | 79 |
| ANC | IFITM1, mean, membrane | SDCBP, mean, intra | 0.5 | 0.01 | 75 | 90 | 50 | 74 | 76 |
| ANC | IFITM1, mean, membrane | WBC | 0.5 | 0.06 | 77 | 94 | 50 | 75 | 83 |
| ANC | IFITM3, mean, membrane | LOC26010, mean, intra | 0.4 | −0.03 | 73 | 94 | 39 | 72 | 79 |
| ANC | IFITM3, mean, membrane | Lym(%) | 0.5 | 0 | 78 | 89 | 61 | 79 | 77 |
| ANC | IFITM3, mean, membrane | MAN1C1, mean, intra | 0.4 | −0.08 | 72 | 92 | 37 | 72 | 73 |
| ANC | IFITM3, mean, membrane | MX1, mean, intra | 0.6 | 0.12 | 80 | 92 | 61 | 79 | 82 |
| ANC | IFITM3, mean, membrane | Neu(%) | 0.5 | −0.06 | 77 | 89 | 58 | 77 | 76 |
| ANC | IFITM3, mean, membrane | NPM1, mean, intra | 0.4 | −0.04 | 73 | 90 | 45 | 72 | 74 |
| ANC | IFITM3, mean, membrane | OAS2, mean, intra | 0.4 | −0.08 | 71 | 89 | 42 | 71 | 70 |
| ANC | IFITM3, mean, membrane | PARP12, mean, intra | 0.4 | −0.01 | 74 | 89 | 50 | 74 | 73 |
| ANC | IFITM3, mean, membrane | PTEN, mean, intra | 0.4 | −0.04 | 73 | 90 | 45 | 73 | 74 |
| ANC | IFITM3, mean, membrane | RSAD2, mean, intra | 0.6 | −0.09 | 79 | 84 | 71 | 83 | 73 |
| ANC | IFITM3, mean, membrane | SDCBP, mean, intra | 0.4 | −0.04 | 73 | 90 | 45 | 72 | 74 |

TABLE 3-continued

The classification accuracy of bacterial vs. viral infected patients computed over pairs of features.
DETERMINANT measurements were measured over cell population mean. (mean triplets)

| Feature #1 | Feature #2 | Feature #3 | MCC | dMCC | Total accuracy % | Sen % | Spe % | PPV % | NPV % |
|---|---|---|---|---|---|---|---|---|---|
| ANC | IFITM3, mean, membrane | WBC | 0.5 | 0.06 | 77 | 94 | 50 | 75 | 83 |
| ANC | LOC26010, mean, intra | Lym(%) | 0.6 | 0.03 | 79 | 87 | 66 | 81 | 76 |
| ANC | LOC26010, mean, intra | MAN1C1, mean, intra | 0.3 | −0.11 | 71 | 90 | 37 | 71 | 69 |
| ANC | LOC26010, mean, intra | MX1, mean, intra | 0.5 | 0.09 | 79 | 89 | 63 | 80 | 77 |
| ANC | LOC26010, mean, intra | Neu(%) | 0.6 | 0.03 | 81 | 92 | 63 | 80 | 83 |
| ANC | LOC26010, mean, intra | NPM1, mean, intra | 0.4 | −0.01 | 74 | 92 | 45 | 73 | 77 |
| ANC | LOC26010, mean, intra | OAS2, mean, intra | 0.4 | −0.04 | 73 | 90 | 45 | 73 | 74 |
| ANC | LOC26010, mean, intra | PARP12, mean, intra | 0.4 | −0.01 | 74 | 87 | 53 | 75 | 71 |
| ANC | LOC26010, mean, intra | PTEN, mean, intra | 0.4 | −0.04 | 73 | 90 | 45 | 73 | 74 |
| ANC | LOC26010, mean, intra | RSAD2, mean, intra | 0.6 | 0 | 83 | 85 | 79 | 87 | 77 |
| ANC | LOC26010, mean, intra | SDCBP, mean, intra | 0.4 | −0.01 | 74 | 90 | 47 | 73 | 75 |
| ANC | LOC26010, mean, intra | WBC | 0.5 | 0.08 | 78 | 92 | 55 | 77 | 81 |
| ANC | Lym(%) | MAN1C1, mean, intra | 0.4 | −0.09 | 74 | 87 | 53 | 76 | 70 |
| ANC | Lym(%) | MX1, mean, intra | 0.6 | 0.05 | 80 | 87 | 68 | 82 | 76 |
| ANC | Lym(%) | Neu(%) | 0.5 | −0.03 | 78 | 88 | 63 | 80 | 75 |
| ANC | Lym(%) | NPM1, mean, intra | 0.5 | 0.02 | 79 | 89 | 63 | 79 | 77 |
| ANC | Lym(%) | OAS2, mean, intra | 0.6 | 0.03 | 79 | 87 | 66 | 81 | 76 |
| ANC | Lym(%) | PARP12, mean, intra | 0.6 | 0.05 | 80 | 87 | 68 | 82 | 76 |
| ANC | Lym(%) | PTEN, mean, intra | 0.5 | −0.02 | 77 | 85 | 63 | 79 | 73 |
| ANC | Lym(%) | RSAD2, mean, intra | 0.7 | 0.02 | 84 | 89 | 76 | 86 | 81 |
| ANC | Lym(%) | SDCBP, mean, intra | 0.5 | 0 | 78 | 85 | 66 | 80 | 74 |
| ANC | Lym(%) | WBC | 0.5 | −0.04 | 76 | 86 | 61 | 79 | 72 |
| ANC | MAN1C1, mean, intra | MX1, mean, intra | 0.5 | 0.03 | 77 | 90 | 53 | 77 | 76 |
| ANC | MAN1C1, mean, intra | Neu(%) | 0.5 | −0.11 | 76 | 88 | 53 | 77 | 73 |
| ANC | MAN1C1, mean, intra | NPM1, mean, intra | 0.3 | −0.11 | 71 | 88 | 40 | 72 | 67 |
| ANC | MAN1C1, mean, intra | OAS2, mean, intra | 0.3 | −0.11 | 71 | 90 | 37 | 71 | 69 |
| ANC | MAN1C1, mean, intra | PARP12, mean, intra | 0.3 | −0.11 | 71 | 88 | 40 | 72 | 67 |
| ANC | MAN1C1, mean, intra | PTEN, mean, intra | 0.3 | −0.11 | 71 | 88 | 40 | 72 | 67 |
| ANC | MAN1C1, mean, intra | RSAD2, mean, intra | 0.6 | −0.06 | 80 | 85 | 73 | 85 | 73 |
| ANC | MAN1C1, mean, intra | SDCBP, mean, intra | 0.4 | −0.08 | 72 | 90 | 40 | 72 | 71 |
| ANC | MAN1C1, mean, intra | WBC | 0.4 | −0.05 | 73 | 90 | 43 | 73 | 72 |
| ANC | MX1, mean, intra | Neu(%) | 0.6 | 0.07 | 83 | 92 | 68 | 83 | 84 |
| ANC | MX1, mean, intra | NPM1, mean, intra | 0.6 | 0.12 | 80 | 92 | 61 | 79 | 82 |
| ANC | MX1, mean, intra | OAS2, mean, intra | 0.5 | 0.09 | 79 | 90 | 61 | 79 | 79 |
| ANC | MX1, mean, intra | PARP12, mean, intra | 0.6 | 0.18 | 83 | 92 | 68 | 83 | 84 |
| ANC | MX1, mean, intra | PTEN, mean, intra | 0.6 | 0.14 | 81 | 94 | 61 | 79 | 85 |
| ANC | MX1, mean, intra | RSAD2, mean, intra | 0.6 | −0.05 | 81 | 85 | 74 | 84 | 76 |
| ANC | MX1, mean, intra | SDCBP, mean, intra | 0.6 | 0.12 | 80 | 92 | 61 | 79 | 82 |
| ANC | MX1, mean, intra | WBC | 0.6 | 0.12 | 80 | 89 | 66 | 81 | 78 |
| ANC | Neu(%) | OAS2, mean, intra | 0.6 | 0.03 | 81 | 90 | 66 | 81 | 81 |
| ANC | Neu(%) | PARP12, mean, intra | 0.6 | 0.03 | 81 | 90 | 66 | 81 | 81 |
| ANC | Neu(%) | PTEN, mean, intra | 0.5 | −0.02 | 79 | 89 | 63 | 80 | 77 |
| ANC | Neu(%) | RSAD2, mean, intra | 0.6 | −0.03 | 82 | 87 | 74 | 84 | 78 |
| ANC | Neu(%) | SDCBP, mean, intra | 0.5 | −0.04 | 78 | 85 | 66 | 80 | 74 |
| ANC | Neu(%) | WBC | 0.5 | −0.03 | 78 | 91 | 58 | 78 | 79 |
| ANC | NPM1, mean, intra | Neu(%) | 0.5 | −0.02 | 79 | 89 | 63 | 79 | 77 |
| ANC | NPM1, mean, intra | OAS2, mean, intra | 0.4 | −0.04 | 73 | 90 | 45 | 72 | 74 |
| ANC | NPM1, mean, intra | PARP12, mean, intra | 0.4 | −0.01 | 74 | 89 | 50 | 74 | 73 |
| ANC | NPM1, mean, intra | PTEN, mean, intra | 0.4 | −0.06 | 72 | 89 | 45 | 72 | 71 |
| ANC | NPM1, mean, intra | RSAD2, mean, intra | 0.6 | 0 | 83 | 85 | 79 | 87 | 77 |
| ANC | NPM1, mean, intra | SDCBP, mean, intra | 0.5 | 0.01 | 75 | 90 | 50 | 74 | 76 |
| ANC | NPM1, mean, intra | WBC | 0.5 | 0.08 | 78 | 92 | 55 | 77 | 81 |
| ANC | OAS2, mean, intra | PARP12, mean, intra | 0.4 | −0.04 | 73 | 89 | 47 | 73 | 72 |
| ANC | OAS2, mean, intra | PTEN, mean, intra | 0.4 | −0.06 | 72 | 89 | 45 | 72 | 71 |
| ANC | OAS2, mean, intra | RSAD2, mean, intra | 0.6 | 0 | 83 | 85 | 79 | 87 | 77 |
| ANC | OAS2, mean, intra | SDCBP, mean, intra | 0.5 | 0.03 | 76 | 92 | 50 | 75 | 79 |
| ANC | OAS2, mean, intra | WBC | 0.5 | 0.04 | 76 | 90 | 53 | 76 | 77 |
| ANC | PARP12, mean, intra | PTEN, mean, intra | 0.5 | 0.04 | 76 | 90 | 53 | 76 | 77 |
| ANC | PARP12, mean, intra | RSAD2, mean, intra | 0.7 | 0.02 | 84 | 87 | 79 | 87 | 79 |
| ANC | PARP12, mean, intra | SDCBP, mean, intra | 0.5 | 0.01 | 75 | 90 | 50 | 74 | 76 |
| ANC | PARP12, mean, intra | WBC | 0.6 | 0.13 | 80 | 92 | 61 | 79 | 82 |
| ANC | PTEN, mean, intra | RSAD2, mean, intra | 0.6 | −0.02 | 82 | 85 | 76 | 85 | 76 |
| ANC | PTEN, mean, intra | SDCBP, mean, intra | 0.4 | −0.01 | 74 | 90 | 47 | 73 | 75 |
| ANC | PTEN, mean, intra | WBC | 0.5 | 0.08 | 78 | 90 | 58 | 78 | 79 |
| ANC | RSAD2, mean, intra | SDCBP, mean, intra | 0.6 | 0 | 83 | 85 | 79 | 87 | 77 |
| ANC | RSAD2, mean, intra | WBC | 0.6 | −0.03 | 82 | 87 | 74 | 84 | 78 |
| ANC | SDCBP, mean, intra | WBC | 0.5 | 0.03 | 76 | 90 | 53 | 75 | 77 |
| CORO1A, mean, intra | CRP | EIF4B, mean, intra | 0.6 | 0.02 | 80 | 90 | 66 | 80 | 81 |
| CORO1A, mean, intra | CRP | IFIT3, mean, intra | 0.7 | 0.13 | 85 | 91 | 76 | 85 | 85 |
| CORO1A, mean, intra | CRP | IFITM1, mean, membrane | 0.6 | 0.02 | 80 | 91 | 63 | 79 | 83 |
| CORO1A, mean, intra | CRP | IFITM3, mean, membrane | 0.7 | 0.13 | 85 | 91 | 76 | 85 | 85 |
| CORO1A, mean, intra | CRP | LOC26010, mean, intra | 0.7 | 0.13 | 85 | 90 | 79 | 87 | 83 |
| CORO1A, mean, intra | CRP | Lym(%) | 0.7 | 0.13 | 85 | 91 | 76 | 85 | 85 |
| CORO1A, mean, intra | CRP | MAN1C1, mean, intra | 0.6 | 0.05 | 82 | 90 | 70 | 83 | 81 |

TABLE 3-continued

The classification accuracy of bacterial vs. viral infected patients computed over pairs of features.
DETERMINANT measurements were measured over cell population mean. (mean triplets)

| Feature #1 | Feature #2 | Feature #3 | MCC | dMCC | Total accuracy % | Sen % | Spe % | PPV % | NPV % |
| --- | --- | --- | --- | --- | --- | --- | --- | --- | --- |
| CORO1A, mean, intra | CRP | MX1, mean, intra | 0.7 | 0.15 | 86 | 93 | 76 | 86 | 88 |
| CORO1A, mean, intra | CRP | Neu(%) | 0.7 | 0.15 | 86 | 93 | 76 | 86 | 88 |
| CORO1A, mean, intra | CRP | NPM1, mean, intra | 0.6 | 0.06 | 82 | 88 | 74 | 83 | 80 |
| CORO1A, mean, intra | CRP | OAS2, mean, intra | 0.7 | 0.13 | 85 | 91 | 76 | 85 | 85 |
| CORO1A, mean, intra | CRP | PARP12, mean, intra | 0.8 | 0.22 | 90 | 95 | 82 | 89 | 91 |
| CORO1A, mean, intra | CRP | PTEN, mean, intra | 0.7 | 0.13 | 85 | 93 | 74 | 84 | 88 |
| CORO1A, mean, intra | CRP | RSAD2, mean, intra | 0.8 | 0.17 | 91 | 88 | 95 | 96 | 84 |
| CORO1A, mean, intra | CRP | SDCBP, mean, intra | 0.6 | 0.06 | 82 | 89 | 71 | 82 | 82 |
| CORO1A, mean, intra | CRP | WBC | 0.7 | 0.09 | 83 | 88 | 76 | 85 | 81 |
| CORO1A, mean, intra | EIF4B, mean, intra | IFIT3, mean, intra | 0.3 | 0.02 | 68 | 76 | 56 | 73 | 59 |
| CORO1A, mean, intra | EIF4B, mean, intra | IFITM1, mean, membrane | 0.3 | −0.02 | 67 | 81 | 46 | 70 | 60 |
| CORO1A, mean, intra | EIF4B, mean, intra | IFITM3, mean, membrane | 0.3 | −0.06 | 67 | 81 | 46 | 70 | 60 |
| CORO1A, mean, intra | EIF4B, mean, intra | LOC26010, mean, intra | 0.2 | −0.09 | 64 | 77 | 44 | 69 | 55 |
| CORO1A, mean, intra | EIF4B, mean, intra | Lym(%) | 0.5 | −0.02 | 76 | 79 | 72 | 82 | 68 |
| CORO1A, mean, intra | EIF4B, mean, intra | MAN1C1, mean, intra | 0.4 | 0.08 | 72 | 85 | 52 | 75 | 67 |
| CORO1A, mean, intra | EIF4B, mean, intra | MX1, mean, intra | 0.5 | 0.04 | 76 | 82 | 67 | 80 | 70 |
| CORO1A, mean, intra | EIF4B, mean, intra | Neu(%) | 0.6 | 0.06 | 82 | 89 | 72 | 83 | 80 |
| CORO1A, mean, intra | EIF4B, mean, intra | NPM1, mean, intra | 0.2 | −0.1 | 64 | 79 | 41 | 68 | 55 |
| CORO1A, mean, intra | EIF4B, mean, intra | OAS2, mean, intra | 0.3 | −0.02 | 67 | 79 | 49 | 71 | 59 |
| CORO1A, mean, intra | EIF4B, mean, intra | PARP12, mean, intra | 0.2 | −0.08 | 64 | 74 | 49 | 70 | 54 |
| CORO1A, mean, intra | EIF4B, mean, intra | PTEN, mean, intra | 0.3 | −0.04 | 66 | 79 | 46 | 70 | 58 |
| CORO1A, mean, intra | EIF4B, mean, intra | RSAD2, mean, intra | 0.6 | −0.01 | 82 | 84 | 79 | 87 | 76 |
| CORO1A, mean, intra | EIF4B, mean, intra | SDCBP, mean, intra | 0.3 | −0.05 | 66 | 80 | 44 | 69 | 59 |
| CORO1A, mean, intra | EIF4B, mean, intra | WBC | 0.3 | −0.03 | 67 | 82 | 44 | 70 | 61 |
| CORO1A, mean, intra | IFIT3, mean, intra | IFITM1, mean, membrane | 0.3 | 0.02 | 68 | 79 | 51 | 72 | 61 |
| CORO1A, mean, intra | IFIT3, mean, intra | IFITM3, mean, membrane | 0.2 | −0.11 | 64 | 73 | 51 | 70 | 54 |
| CORO1A, mean, intra | IFIT3, mean, intra | LOC26010, mean, intra | 0.4 | 0.12 | 70 | 77 | 59 | 75 | 62 |
| CORO1A, mean, intra | IFIT3, mean, intra | Lym(%) | 0.6 | 0.04 | 79 | 85 | 69 | 82 | 75 |
| CORO1A, mean, intra | IFIT3, mean, intra | MAN1C1, mean, intra | 0.3 | 0.06 | 69 | 79 | 52 | 73 | 59 |
| CORO1A, mean, intra | IFIT3, mean, intra | MX1, mean, intra | 0.5 | 0.01 | 74 | 79 | 67 | 79 | 67 |
| CORO1A, mean, intra | IFIT3, mean, intra | Neu(%) | 0.6 | 0.04 | 81 | 87 | 72 | 83 | 78 |
| CORO1A, mean, intra | IFIT3, mean, intra | NPM1, mean, intra | 0.3 | 0.09 | 69 | 77 | 56 | 73 | 61 |
| CORO1A, mean, intra | IFIT3, mean, intra | OAS2, mean, intra | 0.3 | 0.03 | 68 | 76 | 56 | 73 | 59 |
| CORO1A, mean, intra | IFIT3, mean, intra | PARP12, mean, intra | 0.3 | 0.06 | 67 | 73 | 59 | 74 | 57 |
| CORO1A, mean, intra | IFIT3, mean, intra | PTEN, mean, intra | 0.3 | 0.08 | 68 | 74 | 59 | 74 | 59 |
| CORO1A, mean, intra | IFIT3, mean, intra | RSAD2, mean, intra | 0.6 | −0.07 | 79 | 81 | 77 | 85 | 71 |
| CORO1A, mean, intra | IFIT3, mean, intra | SDCBP, mean, intra | 0.4 | 0.11 | 70 | 79 | 56 | 74 | 63 |
| CORO1A, mean, intra | IFIT3, mean, intra | WBC | 0.2 | −0.02 | 64 | 76 | 46 | 69 | 55 |
| CORO1A, mean, intra | IFITM1, mean, membrane | IFITM3, mean, membrane | 0.2 | −0.19 | 61 | 74 | 41 | 67 | 50 |
| CORO1A, mean, intra | IFITM1, mean, membrane | LOC26010, mean, intra | 0.1 | −0.15 | 60 | 73 | 41 | 66 | 48 |
| CORO1A, mean, intra | IFITM1, mean, membrane | Lym(%) | 0.5 | −0.03 | 75 | 77 | 72 | 81 | 67 |
| CORO1A, mean, intra | IFITM1, mean, membrane | MAN1C1, mean, intra | 0.3 | −0.01 | 67 | 81 | 45 | 71 | 58 |
| CORO1A, mean, intra | IFITM1, mean, membrane | MX1, mean, intra | 0.5 | 0.02 | 75 | 82 | 64 | 78 | 69 |
| CORO1A, mean, intra | IFITM1, mean, membrane | Neu(%) | 0.5 | −0.05 | 77 | 84 | 67 | 80 | 72 |
| CORO1A, mean, intra | IFITM1, mean, membrane | NPM1, mean, intra | 0.2 | −0.12 | 62 | 75 | 41 | 67 | 52 |
| CORO1A, mean, intra | IFITM1, mean, membrane | OAS2, mean, intra | 0.2 | −0.13 | 61 | 71 | 46 | 68 | 50 |
| CORO1A, mean, intra | IFITM1, mean, membrane | PARP12, mean, intra | 0.3 | 0.01 | 67 | 76 | 54 | 72 | 58 |
| CORO1A, mean, intra | IFITM1, mean, membrane | PTEN, mean, intra | 0.2 | −0.06 | 64 | 76 | 46 | 69 | 55 |
| CORO1A, mean, intra | IFITM1, mean, membrane | RSAD2, mean, intra | 0.6 | −0.01 | 82 | 84 | 79 | 87 | 76 |
| CORO1A, mean, intra | IFITM1, mean, membrane | SDCBP, mean, intra | 0.2 | −0.14 | 61 | 75 | 38 | 66 | 50 |
| CORO1A, mean, intra | IFITM1, mean, membrane | WBC | 0.3 | −0.03 | 66 | 82 | 41 | 69 | 59 |
| CORO1A, mean, intra | IFITM3, mean, membrane | LOC26010, mean, intra | 0.2 | −0.19 | 61 | 74 | 41 | 67 | 50 |
| CORO1A, mean, intra | IFITM3, mean, membrane | Lym(%) | 0.4 | −0.09 | 73 | 79 | 64 | 78 | 66 |
| CORO1A, mean, intra | IFITM3, mean, membrane | MAN1C1, mean, intra | 0.2 | −0.12 | 65 | 77 | 45 | 70 | 54 |
| CORO1A, mean, intra | IFITM3, mean, membrane | MX1, mean, intra | 0.5 | 0.01 | 74 | 79 | 67 | 79 | 67 |
| CORO1A, mean, intra | IFITM3, mean, membrane | Neu(%) | 0.5 | −0.03 | 78 | 89 | 62 | 79 | 77 |
| CORO1A, mean, intra | IFITM3, mean, membrane | NPM1, mean, intra | 0.2 | −0.17 | 62 | 74 | 44 | 67 | 52 |
| CORO1A, mean, intra | IFITM3, mean, membrane | OAS2, mean, intra | 0.2 | −0.19 | 60 | 69 | 46 | 67 | 49 |
| CORO1A, mean, intra | IFITM3, mean, membrane | PARP12, mean, intra | 0.3 | −0.05 | 67 | 76 | 54 | 72 | 58 |
| CORO1A, mean, intra | IFITM3, mean, membrane | PTEN, mean, intra | 0.2 | −0.17 | 62 | 74 | 44 | 68 | 52 |
| CORO1A, mean, intra | IFITM3, mean, membrane | RSAD2, mean, intra | 0.7 | 0.01 | 83 | 84 | 82 | 88 | 76 |
| CORO1A, mean, intra | IFITM3, mean, membrane | SDCBP, mean, intra | 0.2 | −0.18 | 62 | 77 | 38 | 66 | 52 |
| CORO1A, mean, intra | IFITM3, mean, membrane | WBC | 0.2 | −0.11 | 65 | 81 | 41 | 68 | 57 |
| CORO1A, mean, intra | LOC26010, mean, intra | Lym(%) | 0.5 | −0.03 | 76 | 82 | 67 | 80 | 70 |
| CORO1A, mean, intra | LOC26010, mean, intra | MAN1C1, mean, intra | 0.3 | 0.07 | 67 | 81 | 45 | 71 | 58 |
| CORO1A, mean, intra | LOC26010, mean, intra | MX1, mean, intra | 0.5 | 0.05 | 76 | 81 | 69 | 81 | 69 |
| CORO1A, mean, intra | LOC26010, mean, intra | Neu(%) | 0.6 | 0.04 | 81 | 89 | 69 | 82 | 79 |
| CORO1A, mean, intra | LOC26010, mean, intra | NPM1, mean, intra | 0.2 | −0.01 | 63 | 75 | 44 | 68 | 53 |
| CORO1A, mean, intra | LOC26010, mean, intra | OAS2, mean, intra | 0.2 | −0.15 | 60 | 71 | 44 | 67 | 49 |
| CORO1A, mean, intra | LOC26010, mean, intra | PARP12, mean, intra | 0.3 | 0 | 65 | 76 | 49 | 70 | 56 |
| CORO1A, mean, intra | LOC26010, mean, intra | PTEN, mean, intra | 0.2 | −0.03 | 62 | 74 | 44 | 68 | 52 |
| CORO1A, mean, intra | LOC26010, mean, intra | RSAD2, mean, intra | 0.6 | −0.01 | 82 | 84 | 79 | 87 | 76 |
| CORO1A, mean, intra | LOC26010, mean, intra | SDCBP, mean, intra | 0.2 | −0.04 | 62 | 75 | 41 | 67 | 52 |
| CORO1A, mean, intra | LOC26010, mean, intra | WBC | 0.3 | 0 | 65 | 77 | 46 | 70 | 56 |

TABLE 3-continued

The classification accuracy of bacterial vs. viral infected patients computed over pairs of features.
DETERMINANT measurements were measured over cell population mean. (mean triplets)

| Feature #1 | Feature #2 | Feature #3 | MCC | dMCC | Total accuracy % | Sen % | Spe % | PPV % | NPV % |
|---|---|---|---|---|---|---|---|---|---|
| CORO1A, mean, intra | Lym(%) | MAN1C1, mean, intra | 0.5 | −0.05 | 76 | 85 | 61 | 79 | 70 |
| CORO1A, mean, intra | Lym(%) | MX1, mean, intra | 0.6 | 0.12 | 83 | 87 | 77 | 86 | 79 |
| CORO1A, mean, intra | Lym(%) | Neu(%) | 0.5 | −0.03 | 77 | 79 | 74 | 83 | 69 |
| CORO1A, mean, intra | Lym(%) | NPM1, mean, intra | 0.5 | −0.02 | 76 | 79 | 72 | 81 | 68 |
| CORO1A, mean, intra | Lym(%) | OAS2, mean, intra | 0.5 | 0.02 | 78 | 82 | 72 | 82 | 72 |
| CORO1A, mean, intra | Lym(%) | PARP12, mean, intra | 0.6 | 0.06 | 80 | 84 | 74 | 84 | 74 |
| CORO1A, mean, intra | Lym(%) | PTEN, mean, intra | 0.5 | −0.07 | 73 | 74 | 72 | 81 | 64 |
| CORO1A, mean, intra | Lym(%) | RSAD2, mean, intra | 0.7 | 0.01 | 83 | 85 | 79 | 87 | 78 |
| CORO1A, mean, intra | Lym(%) | SDCBP, mean, intra | 0.4 | −0.09 | 73 | 79 | 64 | 77 | 66 |
| CORO1A, mean, intra | Lym(%) | WBC | 0.5 | −0.05 | 75 | 84 | 62 | 78 | 71 |
| CORO1A, mean, intra | MAN1C1, mean, intra | MX1, mean, intra | 0.4 | −0.08 | 71 | 79 | 58 | 76 | 62 |
| CORO1A, mean, intra | MAN1C1, mean, intra | Neu(%) | 0.5 | −0.09 | 76 | 85 | 61 | 79 | 70 |
| CORO1A, mean, intra | MAN1C1, mean, intra | NPM1, mean, intra | 0.3 | 0.13 | 67 | 81 | 45 | 71 | 58 |
| CORO1A, mean, intra | MAN1C1, mean, intra | OAS2, mean, intra | 0.3 | −0.04 | 66 | 77 | 48 | 71 | 56 |
| CORO1A, mean, intra | MAN1C1, mean, intra | PARP12, mean, intra | 0.3 | 0.01 | 66 | 77 | 48 | 71 | 56 |
| CORO1A, mean, intra | MAN1C1, mean, intra | PTEN, mean, intra | 0.3 | 0.14 | 70 | 79 | 55 | 75 | 61 |
| CORO1A, mean, intra | MAN1C1, mean, intra | RSAD2, mean, intra | 0.6 | −0.05 | 81 | 85 | 74 | 85 | 74 |
| CORO1A, mean, intra | MAN1C1, mean, intra | SDCBP, mean, intra | 0.3 | 0.11 | 66 | 77 | 48 | 71 | 56 |
| CORO1A, mean, intra | MAN1C1, mean, intra | WBC | 0.2 | −0.04 | 65 | 81 | 39 | 69 | 55 |
| CORO1A, mean, intra | MX1, mean, intra | Neu(%) | 0.7 | 0.1 | 84 | 89 | 77 | 86 | 81 |
| CORO1A, mean, intra | MX1, mean, intra | NPM1, mean, intra | 0.4 | −0.02 | 73 | 79 | 64 | 77 | 66 |
| CORO1A, mean, intra | MX1, mean, intra | OAS2, mean, intra | 0.4 | −0.04 | 72 | 79 | 62 | 77 | 65 |
| CORO1A, mean, intra | MX1, mean, intra | PARP12, mean, intra | 0.5 | 0.05 | 76 | 81 | 69 | 81 | 69 |
| CORO1A, mean, intra | MX1, mean, intra | PTEN, mean, intra | 0.5 | 0.02 | 75 | 82 | 64 | 78 | 69 |
| CORO1A, mean, intra | MX1, mean, intra | RSAD2, mean, intra | 0.6 | −0.07 | 79 | 79 | 79 | 86 | 70 |
| CORO1A, mean, intra | MX1, mean, intra | SDCBP, mean, intra | 0.5 | 0 | 74 | 80 | 64 | 78 | 68 |
| CORO1A, mean, intra | MX1, mean, intra | WBC | 0.4 | −0.02 | 73 | 79 | 64 | 78 | 66 |
| CORO1A, mean, intra | Neu(%) | OAS2, mean, intra | 0.6 | 0.04 | 81 | 89 | 69 | 82 | 79 |
| CORO1A, mean, intra | Neu(%) | PARP12, mean, intra | 0.6 | 0.08 | 83 | 89 | 74 | 85 | 81 |
| CORO1A, mean, intra | Neu(%) | PTEN, mean, intra | 0.5 | −0.02 | 78 | 82 | 72 | 82 | 72 |
| CORO1A, mean, intra | Neu(%) | RSAD2, mean, intra | 0.7 | 0.02 | 84 | 89 | 77 | 86 | 81 |
| CORO1A, mean, intra | Neu(%) | SDCBP, mean, intra | 0.5 | −0.03 | 78 | 84 | 69 | 81 | 73 |
| CORO1A, mean, intra | Neu(%) | WBC | 0.5 | −0.05 | 77 | 89 | 59 | 77 | 77 |
| CORO1A, mean, intra | NPM1, mean, intra | Neu(%) | 0.6 | −0.01 | 79 | 85 | 69 | 81 | 75 |
| CORO1A, mean, intra | NPM1, mean, intra | OAS2, mean, intra | 0.2 | −0.12 | 62 | 74 | 44 | 67 | 52 |
| CORO1A, mean, intra | NPM1, mean, intra | PARP12, mean, intra | 0.3 | 0.01 | 65 | 72 | 54 | 71 | 55 |
| CORO1A, mean, intra | NPM1, mean, intra | PTEN, mean, intra | 0.2 | −0.03 | 62 | 75 | 41 | 67 | 52 |
| CORO1A, mean, intra | NPM1, mean, intra | RSAD2, mean, intra | 0.6 | −0.03 | 81 | 82 | 79 | 86 | 74 |
| CORO1A, mean, intra | NPM1, mean, intra | SDCBP, mean, intra | 0.2 | 0.02 | 62 | 75 | 41 | 67 | 52 |
| CORO1A, mean, intra | NPM1, mean, intra | WBC | 0.3 | 0.01 | 66 | 80 | 44 | 69 | 59 |
| CORO1A, mean, intra | OAS2, mean, intra | PARP12, mean, intra | 0.3 | −0.03 | 65 | 73 | 54 | 71 | 55 |
| CORO1A, mean, intra | OAS2, mean, intra | PTEN, mean, intra | 0.2 | −0.12 | 62 | 74 | 44 | 68 | 52 |
| CORO1A, mean, intra | OAS2, mean, intra | RSAD2, mean, intra | 0.6 | −0.01 | 82 | 84 | 79 | 87 | 76 |
| CORO1A, mean, intra | OAS2, mean, intra | SDCBP, mean, intra | 0.1 | −0.16 | 60 | 70 | 44 | 66 | 49 |
| CORO1A, mean, intra | OAS2, mean, intra | WBC | 0.3 | −0.04 | 66 | 81 | 44 | 69 | 59 |
| CORO1A, mean, intra | PARP12, mean, intra | PTEN, mean, intra | 0.3 | 0.01 | 65 | 74 | 51 | 71 | 56 |
| CORO1A, mean, intra | PARP12, mean, intra | RSAD2, mean, intra | 0.6 | −0.09 | 78 | 79 | 77 | 84 | 70 |
| CORO1A, mean, intra | PARP12, mean, intra | SDCBP, mean, intra | 0.3 | 0 | 65 | 74 | 51 | 70 | 56 |
| CORO1A, mean, intra | PARP12, mean, intra | WBC | 0.3 | 0.02 | 66 | 79 | 46 | 70 | 58 |
| CORO1A, mean, intra | PTEN, mean, intra | RSAD2, mean, intra | 0.6 | −0.05 | 80 | 81 | 79 | 86 | 72 |
| CORO1A, mean, intra | PTEN, mean, intra | SDCBP, mean, intra | 0.2 | −0.05 | 61 | 74 | 41 | 66 | 50 |
| CORO1A, mean, intra | PTEN, mean, intra | WBC | 0.2 | −0.01 | 65 | 79 | 44 | 69 | 57 |
| CORO1A, mean, intra | RSAD2, mean, intra | SDCBP, mean, intra | 0.6 | −0.05 | 80 | 80 | 79 | 86 | 72 |
| CORO1A, mean, intra | RSAD2, mean, intra | WBC | 0.6 | −0.05 | 80 | 82 | 77 | 85 | 73 |
| CORO1A, mean, intra | SDCBP, mean, intra | WBC | 0.3 | 0.03 | 67 | 80 | 46 | 70 | 60 |
| CRP | EIF4B, mean, intra | IFIT3, mean, intra | 0.7 | 0.11 | 84 | 91 | 74 | 84 | 85 |
| CRP | EIF4B, mean, intra | IFITM1, mean, membrane | 0.7 | 0.15 | 86 | 91 | 79 | 87 | 86 |
| CRP | EIF4B, mean, intra | IFITM3, mean, membrane | 0.7 | 0.13 | 85 | 91 | 76 | 85 | 85 |
| CRP | EIF4B, mean, intra | LOC26010, mean, intra | 0.7 | 0.13 | 85 | 90 | 79 | 87 | 83 |
| CRP | EIF4B, mean, intra | Lym(%) | 0.8 | 0.2 | 89 | 93 | 82 | 89 | 89 |
| CRP | EIF4B, mean, intra | MAN1C1, mean, intra | 0.6 | 0.05 | 82 | 90 | 70 | 83 | 81 |
| CRP | EIF4B, mean, intra | MX1, mean, intra | 0.7 | 0.18 | 88 | 93 | 79 | 87 | 88 |
| CRP | EIF4B, mean, intra | Neu(%) | 0.7 | 0.18 | 88 | 95 | 76 | 86 | 91 |
| CRP | EIF4B, mean, intra | NPM1, mean, intra | 0.7 | 0.09 | 83 | 88 | 76 | 85 | 81 |
| CRP | EIF4B, mean, intra | OAS2, mean, intra | 0.7 | 0.11 | 84 | 91 | 74 | 84 | 85 |
| CRP | EIF4B, mean, intra | PARP12, mean, intra | 0.8 | 0.22 | 90 | 95 | 82 | 89 | 91 |
| CRP | EIF4B, mean, intra | PTEN, mean, intra | 0.7 | 0.15 | 86 | 93 | 76 | 86 | 88 |
| CRP | EIF4B, mean, intra | RSAD2, mean, intra | 0.9 | 0.25 | 95 | 95 | 95 | 96 | 92 |
| CRP | EIF4B, mean, intra | SDCBP, mean, intra | 0.6 | 0.06 | 82 | 88 | 74 | 83 | 80 |
| CRP | EIF4B, mean, intra | WBC | 0.7 | 0.15 | 86 | 91 | 79 | 87 | 86 |
| CRP | IFIT3, mean, intra | IFITM1, mean, membrane | 0.7 | 0.15 | 86 | 93 | 76 | 86 | 88 |
| CRP | IFIT3, mean, intra | IFITM3, mean, membrane | 0.7 | 0.13 | 85 | 91 | 76 | 85 | 85 |
| CRP | IFIT3, mean, intra | LOC26010, mean, intra | 0.7 | 0.18 | 88 | 95 | 76 | 86 | 91 |
| CRP | IFIT3, mean, intra | Lym(%) | 0.7 | 0.18 | 88 | 91 | 82 | 88 | 86 |

TABLE 3-continued

The classification accuracy of bacterial vs. viral infected patients computed over pairs of features.
DETERMINANT measurements were measured over cell population mean. (mean triplets)

| Feature #1 | Feature #2 | Feature #3 | MCC | dMCC | Total accuracy % | Sen % | Spe % | PPV % | NPV % |
|---|---|---|---|---|---|---|---|---|---|
| CRP | IFIT3, mean, intra | MAN1C1, mean, intra | 0.6 | 0.03 | 81 | 88 | 70 | 82 | 78 |
| CRP | IFIT3, mean, intra | MX1, mean, intra | 0.8 | 0.2 | 89 | 93 | 82 | 89 | 89 |
| CRP | IFIT3, mean, intra | Neu(%) | 0.8 | 0.2 | 89 | 93 | 82 | 89 | 89 |
| CRP | IFIT3, mean, intra | NPM1, mean, intra | 0.8 | 0.2 | 88 | 93 | 82 | 88 | 89 |
| CRP | IFIT3, mean, intra | OAS2, mean, intra | 0.7 | 0.11 | 84 | 91 | 74 | 84 | 85 |
| CRP | IFIT3, mean, intra | PARP12, mean, intra | 0.7 | 0.11 | 84 | 91 | 74 | 84 | 85 |
| CRP | IFIT3, mean, intra | PTEN, mean, intra | 0.7 | 0.15 | 86 | 91 | 79 | 87 | 86 |
| CRP | IFIT3, mean, intra | RSAD2, mean, intra | 0.9 | 0.21 | 93 | 93 | 92 | 95 | 90 |
| CRP | IFIT3, mean, intra | SDCBP, mean, intra | 0.7 | 0.11 | 84 | 88 | 79 | 86 | 81 |
| CRP | IFIT3, mean, intra | WBC | 0.7 | 0.13 | 85 | 91 | 76 | 85 | 85 |
| CRP | IFITM1, mean, membrane | IFITM3, mean, membrane | 0.7 | 0.11 | 84 | 91 | 74 | 84 | 85 |
| CRP | IFITM1, mean, membrane | LOC26010, mean, intra | 0.7 | 0.13 | 85 | 90 | 79 | 87 | 83 |
| CRP | IFITM1, mean, membrane | Lym(%) | 0.8 | 0.26 | 92 | 95 | 87 | 92 | 92 |
| CRP | IFITM1, mean, membrane | MAN1C1, mean, intra | 0.6 | 0.05 | 82 | 90 | 70 | 83 | 81 |
| CRP | IFITM1, mean, membrane | MX1, mean, intra | 0.8 | 0.2 | 89 | 93 | 82 | 89 | 89 |
| CRP | IFITM1, mean, membrane | Neu(%) | 0.9 | 0.29 | 93 | 97 | 87 | 92 | 94 |
| CRP | IFITM1, mean, membrane | NPM1, mean, intra | 0.7 | 0.15 | 86 | 91 | 79 | 87 | 86 |
| CRP | IFITM1, mean, membrane | OAS2, mean, intra | 0.7 | 0.13 | 85 | 93 | 74 | 84 | 88 |
| CRP | IFITM1, mean, membrane | PARP12, mean, intra | 0.8 | 0.2 | 89 | 93 | 82 | 89 | 89 |
| CRP | IFITM1, mean, membrane | PTEN, mean, intra | 0.7 | 0.15 | 86 | 93 | 76 | 86 | 88 |
| CRP | IFITM1, mean, membrane | RSAD2, mean, intra | 0.8 | 0.19 | 92 | 93 | 89 | 93 | 89 |
| CRP | IFITM1, mean, membrane | SDCBP, mean, intra | 0.7 | 0.11 | 84 | 91 | 74 | 84 | 85 |
| CRP | IFITM1, mean, membrane | WBC | 0.7 | 0.09 | 83 | 90 | 74 | 84 | 82 |
| CRP | IFITM3, mean, membrane | LOC26010, mean, intra | 0.7 | 0.15 | 86 | 93 | 76 | 86 | 88 |
| CRP | IFITM3, mean, membrane | Lym(%) | 0.8 | 0.24 | 91 | 97 | 82 | 89 | 94 |
| CRP | IFITM3, mean, membrane | MAN1C1, mean, intra | 0.6 | 0.03 | 81 | 90 | 67 | 81 | 80 |
| CRP | IFITM3, mean, membrane | MX1, mean, intra | 0.7 | 0.18 | 88 | 93 | 79 | 87 | 88 |
| CRP | IFITM3, mean, membrane | Neu(%) | 0.8 | 0.22 | 90 | 95 | 82 | 89 | 91 |
| CRP | IFITM3, mean, membrane | NPM1, mean, intra | 0.7 | 0.11 | 84 | 89 | 76 | 85 | 83 |
| CRP | IFITM3, mean, membrane | OAS2, mean, intra | 0.7 | 0.11 | 84 | 91 | 74 | 84 | 85 |
| CRP | IFITM3, mean, membrane | PARP12, mean, intra | 0.7 | 0.18 | 88 | 95 | 76 | 86 | 91 |
| CRP | IFITM3, mean, membrane | PTEN, mean, intra | 0.7 | 0.18 | 88 | 95 | 76 | 86 | 91 |
| CRP | IFITM3, mean, membrane | RSAD2, mean, intra | 0.8 | 0.19 | 92 | 90 | 95 | 96 | 86 |
| CRP | IFITM3, mean, membrane | SDCBP, mean, intra | 0.7 | 0.11 | 84 | 89 | 76 | 85 | 83 |
| CRP | IFITM3, mean, membrane | WBC | 0.7 | 0.11 | 84 | 90 | 76 | 85 | 83 |
| CRP | LOC26010, mean, intra | Lym(%) | 0.8 | 0.24 | 91 | 95 | 84 | 90 | 91 |
| CRP | LOC26010, mean, intra | MAN1C1, mean, intra | 0.6 | 0.05 | 82 | 92 | 67 | 81 | 83 |
| CRP | LOC26010, mean, intra | MX1, mean, intra | 0.8 | 0.2 | 89 | 93 | 82 | 89 | 89 |
| CRP | LOC26010, mean, intra | Neu(%) | 0.8 | 0.27 | 92 | 97 | 84 | 90 | 94 |
| CRP | LOC26010, mean, intra | NPM1, mean, intra | 0.7 | 0.13 | 85 | 89 | 79 | 86 | 83 |
| CRP | LOC26010, mean, intra | OAS2, mean, intra | 0.7 | 0.13 | 85 | 91 | 76 | 85 | 85 |
| CRP | LOC26010, mean, intra | PARP12, mean, intra | 0.7 | 0.15 | 86 | 91 | 79 | 87 | 86 |
| CRP | LOC26010, mean, intra | PTEN, mean, intra | 0.7 | 0.18 | 88 | 93 | 79 | 87 | 88 |
| CRP | LOC26010, mean, intra | RSAD2, mean, intra | 0.8 | 0.17 | 91 | 90 | 92 | 95 | 85 |
| CRP | LOC26010, mean, intra | SDCBP, mean, intra | 0.7 | 0.11 | 84 | 91 | 74 | 84 | 85 |
| CRP | LOC26010, mean, intra | WBC | 0.7 | 0.11 | 84 | 88 | 79 | 86 | 81 |
| CRP | Lym(%) | MAN1C1, mean, intra | 0.7 | 0.14 | 86 | 92 | 77 | 86 | 85 |
| CRP | Lym(%) | MX1, mean, intra | 0.8 | 0.2 | 89 | 93 | 82 | 89 | 89 |
| CRP | Lym(%) | Neu(%) | 0.7 | 0.14 | 86 | 92 | 76 | 86 | 85 |
| CRP | Lym(%) | NPM1, mean, intra | 0.8 | 0.22 | 89 | 93 | 84 | 90 | 89 |
| CRP | Lym(%) | OAS2, mean, intra | 0.8 | 0.22 | 90 | 93 | 84 | 90 | 89 |
| CRP | Lym(%) | PARP12, mean, intra | 0.8 | 0.22 | 90 | 95 | 82 | 89 | 91 |
| CRP | Lym(%) | PTEN, mean, intra | 0.8 | 0.22 | 90 | 95 | 82 | 89 | 91 |
| CRP | Lym(%) | RSAD2, mean, intra | 0.9 | 0.21 | 93 | 95 | 89 | 93 | 92 |
| CRP | Lym(%) | SDCBP, mean, intra | 0.7 | 0.18 | 87 | 91 | 82 | 88 | 86 |
| CRP | Lym(%) | WBC | 0.7 | 0.11 | 85 | 90 | 76 | 86 | 83 |
| CRP | MAN1C1, mean, intra | MX1, mean, intra | 0.7 | 0.11 | 85 | 92 | 73 | 85 | 85 |
| CRP | MAN1C1, mean, intra | Neu(%) | 0.7 | 0.17 | 87 | 94 | 77 | 87 | 88 |
| CRP | MAN1C1, mean, intra | NPM1, mean, intra | 0.6 | 0.03 | 81 | 90 | 67 | 81 | 80 |
| CRP | MAN1C1, mean, intra | OAS2, mean, intra | 0.6 | 0.05 | 82 | 90 | 70 | 83 | 81 |
| CRP | MAN1C1, mean, intra | PARP12, mean, intra | 0.6 | 0.05 | 82 | 90 | 70 | 83 | 81 |
| CRP | MAN1C1, mean, intra | PTEN, mean, intra | 0.6 | 0.05 | 82 | 90 | 70 | 83 | 81 |
| CRP | MAN1C1, mean, intra | RSAD2, mean, intra | 0.9 | 0.22 | 94 | 96 | 90 | 94 | 93 |
| CRP | MAN1C1, mean, intra | SDCBP, mean, intra | 0.6 | 0.03 | 81 | 90 | 67 | 81 | 80 |
| CRP | MAN1C1, mean, intra | WBC | 0.6 | 0.08 | 83 | 90 | 73 | 84 | 81 |
| CRP | MX1, mean, intra | Neu(%) | 0.7 | 0.18 | 88 | 93 | 79 | 87 | 88 |
| CRP | MX1, mean, intra | NPM1, mean, intra | 0.7 | 0.15 | 86 | 91 | 79 | 87 | 86 |
| CRP | MX1, mean, intra | OAS2, mean, intra | 0.8 | 0.2 | 89 | 93 | 82 | 89 | 89 |
| CRP | MX1, mean, intra | PARP12, mean, intra | 0.8 | 0.24 | 91 | 95 | 84 | 90 | 91 |
| CRP | MX1, mean, intra | PTEN, mean, intra | 0.8 | 0.22 | 90 | 95 | 82 | 89 | 91 |
| CRP | MX1, mean, intra | RSAD2, mean, intra | 0.9 | 0.21 | 93 | 93 | 92 | 95 | 90 |
| CRP | MX1, mean, intra | SDCBP, mean, intra | 0.7 | 0.15 | 86 | 91 | 79 | 87 | 86 |
| CRP | MX1, mean, intra | WBC | 0.7 | 0.13 | 85 | 91 | 76 | 85 | 85 |
| CRP | Neu(%) | OAS2, mean, intra | 0.8 | 0.22 | 90 | 93 | 84 | 90 | 89 |

TABLE 3-continued

The classification accuracy of bacterial vs. viral infected patients computed over pairs of features.
DETERMINANT measurements were measured over cell population mean. (mean triplets)

| Feature #1 | Feature #2 | Feature #3 | MCC | dMCC | Total accuracy % | Sen % | Spe % | PPV % | NPV % |
|---|---|---|---|---|---|---|---|---|---|
| CRP | Neu(%) | PARP12, mean, intra | 0.8 | 0.24 | 91 | 97 | 82 | 89 | 94 |
| CRP | Neu(%) | PTEN, mean, intra | 0.8 | 0.22 | 90 | 95 | 82 | 89 | 91 |
| CRP | Neu(%) | RSAD2, mean, intra | 0.9 | 0.25 | 95 | 97 | 92 | 95 | 95 |
| CRP | Neu(%) | SDCBP, mean, intra | 0.7 | 0.18 | 87 | 91 | 82 | 88 | 86 |
| CRP | Neu(%) | WBC | 0.7 | 0.11 | 85 | 92 | 74 | 85 | 85 |
| CRP | NPM1, mean, intra | Neu(%) | 0.8 | 0.2 | 88 | 93 | 82 | 88 | 89 |
| CRP | NPM1, mean, intra | OAS2, mean, intra | 0.6 | 0.06 | 82 | 88 | 74 | 83 | 80 |
| CRP | NPM1, mean, intra | PARP12, mean, intra | 0.7 | 0.13 | 85 | 91 | 76 | 85 | 85 |
| CRP | NPM1, mean, intra | PTEN, mean, intra | 0.7 | 0.11 | 84 | 89 | 76 | 85 | 83 |
| CRP | NPM1, mean, intra | RSAD2, mean, intra | 0.8 | 0.17 | 91 | 88 | 95 | 96 | 84 |
| CRP | NPM1, mean, intra | SDCBP, mean, intra | 0.6 | 0.06 | 82 | 89 | 71 | 82 | 82 |
| CRP | NPM1, mean, intra | WBC | 0.7 | 0.09 | 83 | 88 | 76 | 85 | 81 |
| CRP | OAS2, mean, intra | PARP12, mean, intra | 0.7 | 0.18 | 88 | 93 | 79 | 87 | 88 |
| CRP | OAS2, mean, intra | PTEN, mean, intra | 0.7 | 0.15 | 86 | 93 | 76 | 86 | 88 |
| CRP | OAS2, mean, intra | RSAD2, mean, intra | 0.8 | 0.19 | 92 | 91 | 92 | 95 | 88 |
| CRP | OAS2, mean, intra | SDCBP, mean, intra | 0.7 | 0.09 | 83 | 88 | 76 | 85 | 81 |
| CRP | OAS2, mean, intra | WBC | 0.7 | 0.13 | 85 | 90 | 79 | 87 | 83 |
| CRP | PARP12, mean, intra | PTEN, mean, intra | 0.8 | 0.2 | 89 | 93 | 82 | 89 | 89 |
| CRP | PARP12, mean, intra | RSAD2, mean, intra | 0.8 | 0.19 | 92 | 93 | 89 | 93 | 89 |
| CRP | PARP12, mean, intra | SDCBP, mean, intra | 0.7 | 0.13 | 85 | 88 | 82 | 88 | 82 |
| CRP | PARP12, mean, intra | WBC | 0.7 | 0.15 | 86 | 91 | 79 | 87 | 86 |
| CRP | PTEN, mean, intra | RSAD2, mean, intra | 0.8 | 0.19 | 92 | 91 | 92 | 95 | 88 |
| CRP | PTEN, mean, intra | SDCBP, mean, intra | 0.7 | 0.11 | 84 | 88 | 79 | 86 | 81 |
| CRP | PTEN, mean, intra | WBC | 0.8 | 0.2 | 89 | 93 | 82 | 89 | 89 |
| CRP | RSAD2, mean, intra | SDCBP, mean, intra | 0.8 | 0.19 | 92 | 89 | 95 | 96 | 86 |
| CRP | RSAD2, mean, intra | WBC | 0.9 | 0.25 | 95 | 97 | 92 | 95 | 95 |
| CRP | SDCBP, mean, intra | WBC | 0.7 | 0.11 | 84 | 88 | 79 | 86 | 81 |
| EIF4B, mean, intra | IFIT3, mean, intra | IFITM1, mean, membrane | 0.2 | −0.1 | 63 | 74 | 46 | 69 | 53 |
| EIF4B, mean, intra | IFIT3, mean, intra | IFITM3, mean, membrane | 0.2 | −0.12 | 64 | 76 | 46 | 69 | 55 |
| EIF4B, mean, intra | IFIT3, mean, intra | LOC26010, mean, intra | 0.2 | −0.09 | 63 | 73 | 49 | 69 | 53 |
| EIF4B, mean, intra | IFIT3, mean, intra | Lym(%) | 0.6 | 0.08 | 81 | 89 | 69 | 82 | 79 |
| EIF4B, mean, intra | IFIT3, mean, intra | MAN1C1, mean, intra | 0.3 | 0 | 69 | 81 | 48 | 72 | 60 |
| EIF4B, mean, intra | IFIT3, mean, intra | MX1, mean, intra | 0.4 | −0.07 | 70 | 74 | 64 | 77 | 61 |
| EIF4B, mean, intra | IFIT3, mean, intra | Neu(%) | 0.6 | −0.02 | 80 | 85 | 72 | 83 | 76 |
| EIF4B, mean, intra | IFIT3, mean, intra | NPM1, mean, intra | 0.3 | 0.02 | 69 | 79 | 54 | 73 | 62 |
| EIF4B, mean, intra | IFIT3, mean, intra | OAS2, mean, intra | 0.2 | −0.08 | 64 | 76 | 46 | 69 | 55 |
| EIF4B, mean, intra | IFIT3, mean, intra | PARP12, mean, intra | 0.3 | 0.03 | 68 | 73 | 62 | 75 | 59 |
| EIF4B, mean, intra | IFIT3, mean, intra | PTEN, mean, intra | 0.2 | −0.14 | 61 | 71 | 46 | 68 | 50 |
| EIF4B, mean, intra | IFIT3, mean, intra | RSAD2, mean, intra | 0.6 | −0.01 | 82 | 84 | 79 | 87 | 76 |
| EIF4B, mean, intra | IFIT3, mean, intra | SDCBP, mean, intra | 0.2 | −0.07 | 64 | 72 | 51 | 70 | 54 |
| EIF4B, mean, intra | IFIT3, mean, intra | WBC | 0.3 | −0.03 | 66 | 76 | 51 | 71 | 57 |
| EIF4B, mean, intra | IFITM1, mean, membrane | IFITM3, mean, membrane | 0.3 | −0.04 | 66 | 67 | 64 | 70 | 61 |
| EIF4B, mean, intra | IFITM1, mean, membrane | LOC26010, mean, intra | 0.2 | −0.07 | 62 | 61 | 63 | 67 | 57 |
| EIF4B, mean, intra | IFITM1, mean, membrane | Lym(%) | 0.6 | 0.05 | 79 | 76 | 81 | 83 | 74 |
| EIF4B, mean, intra | IFITM1, mean, membrane | MAN1C1, mean, intra | 0.3 | −0.03 | 67 | 81 | 45 | 71 | 58 |
| EIF4B, mean, intra | IFITM1, mean, membrane | MX1, mean, intra | 0.4 | −0.05 | 69 | 65 | 75 | 76 | 64 |
| EIF4B, mean, intra | IFITM1, mean, membrane | Neu(%) | 0.6 | 0.06 | 81 | 82 | 80 | 83 | 78 |
| EIF4B, mean, intra | IFITM1, mean, membrane | NPM1, mean, intra | 0.1 | −0.24 | 57 | 70 | 36 | 63 | 44 |
| EIF4B, mean, intra | IFITM1, mean, membrane | OAS2, mean, intra | 0.3 | −0.03 | 64 | 63 | 66 | 69 | 59 |
| EIF4B, mean, intra | IFITM1, mean, membrane | PARP12, mean, intra | 0.2 | −0.09 | 63 | 73 | 49 | 69 | 53 |
| EIF4B, mean, intra | IFITM1, mean, membrane | PTEN, mean, intra | 0.1 | −0.17 | 60 | 73 | 41 | 66 | 48 |
| EIF4B, mean, intra | IFITM1, mean, membrane | RSAD2, mean, intra | 0.6 | −0.08 | 78 | 76 | 80 | 82 | 73 |
| EIF4B, mean, intra | IFITM1, mean, membrane | SDCBP, mean, intra | 0.1 | −0.19 | 60 | 75 | 36 | 65 | 48 |
| EIF4B, mean, intra | IFITM1, mean, membrane | WBC | 0.3 | 0.01 | 66 | 75 | 56 | 68 | 65 |
| EIF4B, mean, intra | IFITM3, mean, membrane | LOC26010, mean, intra | 0.3 | −0.02 | 66 | 65 | 68 | 71 | 62 |
| EIF4B, mean, intra | IFITM3, mean, membrane | Lym(%) | 0.6 | 0.06 | 79 | 81 | 78 | 82 | 77 |
| EIF4B, mean, intra | IFITM3, mean, membrane | MAN1C1, mean, intra | 0.3 | −0.1 | 66 | 79 | 45 | 71 | 56 |
| EIF4B, mean, intra | IFITM3, mean, membrane | MX1, mean, intra | 0.5 | 0 | 72 | 67 | 78 | 79 | 66 |
| EIF4B, mean, intra | IFITM3, mean, membrane | Neu(%) | 0.6 | 0.05 | 81 | 85 | 76 | 81 | 80 |
| EIF4B, mean, intra | IFITM3, mean, membrane | NPM1, mean, intra | 0.1 | −0.21 | 60 | 72 | 41 | 66 | 48 |
| EIF4B, mean, intra | IFITM3, mean, membrane | OAS2, mean, intra | 0.4 | 0.05 | 70 | 72 | 68 | 73 | 67 |
| EIF4B, mean, intra | IFITM3, mean, membrane | PARP12, mean, intra | 0.2 | −0.12 | 64 | 74 | 49 | 70 | 54 |
| EIF4B, mean, intra | IFITM3, mean, membrane | PTEN, mean, intra | 0.2 | −0.15 | 63 | 76 | 44 | 68 | 53 |
| EIF4B, mean, intra | IFITM3, mean, membrane | RSAD2, mean, intra | 0.6 | −0.01 | 82 | 81 | 83 | 85 | 78 |
| EIF4B, mean, intra | IFITM3, mean, membrane | SDCBP, mean, intra | 0.2 | −0.18 | 62 | 77 | 38 | 66 | 52 |
| EIF4B, mean, intra | IFITM3, mean, membrane | WBC | 0.4 | 0.01 | 69 | 75 | 61 | 70 | 67 |
| EIF4B, mean, intra | LOC26010, mean, intra | Lym(%) | 0.5 | 0.02 | 77 | 78 | 76 | 79 | 75 |
| EIF4B, mean, intra | LOC26010, mean, intra | MAN1C1, mean, intra | 0.3 | −0.03 | 67 | 79 | 48 | 72 | 58 |
| EIF4B, mean, intra | LOC26010, mean, intra | MX1, mean, intra | 0.5 | 0.06 | 75 | 67 | 84 | 83 | 68 |
| EIF4B, mean, intra | LOC26010, mean, intra | Neu(%) | 0.5 | −0.04 | 76 | 79 | 73 | 77 | 75 |
| EIF4B, mean, intra | LOC26010, mean, intra | NPM1, mean, intra | 0.2 | −0.12 | 63 | 79 | 38 | 67 | 54 |
| EIF4B, mean, intra | LOC26010, mean, intra | OAS2, mean, intra | 0.3 | −0.02 | 64 | 61 | 68 | 69 | 60 |
| EIF4B, mean, intra | LOC26010, mean, intra | PARP12, mean, intra | 0.3 | −0.03 | 66 | 74 | 54 | 72 | 57 |
| EIF4B, mean, intra | LOC26010, mean, intra | PTEN, mean, intra | 0.2 | −0.13 | 62 | 74 | 44 | 68 | 52 |

TABLE 3-continued

The classification accuracy of bacterial vs. viral infected patients computed over pairs of features.
DETERMINANT measurements were measured over cell population mean. (mean triplets)

| Feature #1 | Feature #2 | Feature #3 | MCC | dMCC | Total accuracy % | Sen % | Spe % | PPV % | NPV % |
|---|---|---|---|---|---|---|---|---|---|
| EIF4B, mean, intra | LOC26010, mean, intra | RSAD2, mean, intra | 0.6 | −0.01 | 81 | 79 | 84 | 85 | 78 |
| EIF4B, mean, intra | LOC26010, mean, intra | SDCBP, mean, intra | 0.2 | −0.14 | 62 | 77 | 38 | 66 | 52 |
| EIF4B, mean, intra | LOC26010, mean, intra | WBC | 0.3 | 0 | 66 | 74 | 56 | 66 | 65 |
| EIF4B, mean, intra | Lym(%) | MAN1C1, mean, intra | 0.6 | 0.03 | 80 | 88 | 65 | 81 | 77 |
| EIF4B, mean, intra | Lym(%) | MX1, mean, intra | 0.6 | 0.09 | 81 | 81 | 81 | 83 | 78 |
| EIF4B, mean, intra | Lym(%) | Neu(%) | 0.5 | −0.02 | 77 | 75 | 79 | 81 | 73 |
| EIF4B, mean, intra | Lym(%) | NPM1, mean, intra | 0.5 | 0 | 77 | 79 | 74 | 83 | 69 |
| EIF4B, mean, intra | Lym(%) | OAS2, mean, intra | 0.6 | 0.05 | 78 | 78 | 79 | 81 | 75 |
| EIF4B, mean, intra | Lym(%) | PARP12, mean, intra | 0.5 | 0.01 | 77 | 79 | 74 | 83 | 69 |
| EIF4B, mean, intra | Lym(%) | PTEN, mean, intra | 0.5 | −0.03 | 75 | 77 | 72 | 81 | 67 |
| EIF4B, mean, intra | Lym(%) | RSAD2, mean, intra | 0.6 | 0 | 82 | 82 | 82 | 84 | 80 |
| EIF4B, mean, intra | Lym(%) | SDCBP, mean, intra | 0.5 | −0.06 | 74 | 77 | 69 | 80 | 66 |
| EIF4B, mean, intra | Lym(%) | WBC | 0.6 | 0.03 | 78 | 76 | 79 | 81 | 74 |
| EIF4B, mean, intra | MAN1C1, mean, intra | MX1, mean, intra | 0.4 | −0.05 | 72 | 81 | 58 | 76 | 64 |
| EIF4B, mean, intra | MAN1C1, mean, intra | Neu(%) | 0.5 | −0.04 | 78 | 90 | 58 | 78 | 78 |
| EIF4B, mean, intra | MAN1C1, mean, intra | NPM1, mean, intra | 0.3 | 0 | 69 | 79 | 52 | 73 | 59 |
| EIF4B, mean, intra | MAN1C1, mean, intra | OAS2, mean, intra | 0.3 | −0.03 | 67 | 81 | 45 | 71 | 58 |
| EIF4B, mean, intra | MAN1C1, mean, intra | PARP12, mean, intra | 0.2 | −0.09 | 64 | 73 | 48 | 70 | 52 |
| EIF4B, mean, intra | MAN1C1, mean, intra | PTEN, mean, intra | 0.3 | 0.02 | 70 | 83 | 48 | 73 | 63 |
| EIF4B, mean, intra | MAN1C1, mean, intra | RSAD2, mean, intra | 0.6 | −0.08 | 80 | 85 | 71 | 83 | 73 |
| EIF4B, mean, intra | MAN1C1, mean, intra | SDCBP, mean, intra | 0.3 | −0.05 | 66 | 77 | 48 | 71 | 56 |
| EIF4B, mean, intra | MAN1C1, mean, intra | WBC | 0.3 | −0.04 | 67 | 83 | 42 | 70 | 59 |
| EIF4B, mean, intra | MX1, mean, intra | Neu(%) | 0.6 | 0.03 | 80 | 82 | 77 | 81 | 79 |
| EIF4B, mean, intra | MX1, mean, intra | NPM1, mean, intra | 0.4 | −0.09 | 69 | 72 | 64 | 76 | 60 |
| EIF4B, mean, intra | MX1, mean, intra | OAS2, mean, intra | 0.5 | 0 | 72 | 64 | 81 | 79 | 66 |
| EIF4B, mean, intra | MX1, mean, intra | PARP12, mean, intra | 0.5 | 0.07 | 77 | 81 | 72 | 82 | 70 |
| EIF4B, mean, intra | MX1, mean, intra | PTEN, mean, intra | 0.4 | −0.08 | 70 | 76 | 62 | 76 | 62 |
| EIF4B, mean, intra | MX1, mean, intra | RSAD2, mean, intra | 0.6 | −0.07 | 78 | 75 | 82 | 83 | 74 |
| EIF4B, mean, intra | MX1, mean, intra | SDCBP, mean, intra | 0.4 | −0.07 | 70 | 74 | 64 | 76 | 61 |
| EIF4B, mean, intra | MX1, mean, intra | WBC | 0.5 | 0.04 | 75 | 74 | 76 | 78 | 71 |
| EIF4B, mean, intra | Neu(%) | OAS2, mean, intra | 0.6 | 0.02 | 79 | 79 | 79 | 81 | 77 |
| EIF4B, mean, intra | Neu(%) | PARP12, mean, intra | 0.7 | 0.1 | 84 | 89 | 77 | 86 | 81 |
| EIF4B, mean, intra | Neu(%) | PTEN, mean, intra | 0.5 | −0.02 | 78 | 84 | 69 | 81 | 73 |
| EIF4B, mean, intra | Neu(%) | RSAD2, mean, intra | 0.7 | 0.05 | 84 | 85 | 84 | 86 | 83 |
| EIF4B, mean, intra | Neu(%) | SDCBP, mean, intra | 0.5 | −0.05 | 77 | 82 | 69 | 81 | 71 |
| EIF4B, mean, intra | Neu(%) | WBC | 0.6 | 0.06 | 81 | 85 | 77 | 81 | 81 |
| EIF4B, mean, intra | NPM1, mean, intra | Neu(%) | 0.6 | 0.03 | 81 | 89 | 69 | 82 | 79 |
| EIF4B, mean, intra | NPM1, mean, intra | OAS2, mean, intra | 0.1 | −0.2 | 59 | 72 | 38 | 65 | 47 |
| EIF4B, mean, intra | NPM1, mean, intra | PARP12, mean, intra | 0.3 | −0.04 | 65 | 70 | 56 | 72 | 55 |
| EIF4B, mean, intra | NPM1, mean, intra | PTEN, mean, intra | 0.2 | −0.16 | 61 | 74 | 41 | 66 | 50 |
| EIF4B, mean, intra | NPM1, mean, intra | RSAD2, mean, intra | 0.6 | −0.06 | 80 | 82 | 77 | 85 | 73 |
| EIF4B, mean, intra | NPM1, mean, intra | SDCBP, mean, intra | 0.2 | −0.13 | 62 | 74 | 44 | 67 | 52 |
| EIF4B, mean, intra | NPM1, mean, intra | WBC | 0.3 | −0.01 | 68 | 85 | 41 | 69 | 64 |
| EIF4B, mean, intra | OAS2, mean, intra | PARP12, mean, intra | 0.3 | −0.02 | 66 | 73 | 56 | 73 | 56 |
| EIF4B, mean, intra | OAS2, mean, intra | PTEN, mean, intra | 0.1 | −0.21 | 58 | 71 | 38 | 65 | 45 |
| EIF4B, mean, intra | OAS2, mean, intra | RSAD2, mean, intra | 0.6 | −0.01 | 81 | 79 | 84 | 85 | 78 |
| EIF4B, mean, intra | OAS2, mean, intra | SDCBP, mean, intra | 0.2 | −0.16 | 61 | 75 | 38 | 66 | 50 |
| EIF4B, mean, intra | OAS2, mean, intra | WBC | 0.4 | 0.04 | 68 | 75 | 60 | 68 | 67 |
| EIF4B, mean, intra | PARP12, mean, intra | PTEN, mean, intra | 0.3 | −0.03 | 66 | 74 | 54 | 72 | 57 |
| EIF4B, mean, intra | PARP12, mean, intra | RSAD2, mean, intra | 0.7 | 0.03 | 84 | 85 | 82 | 88 | 78 |
| EIF4B, mean, intra | PARP12, mean, intra | SDCBP, mean, intra | 0.2 | −0.07 | 64 | 72 | 51 | 70 | 54 |
| EIF4B, mean, intra | PARP12, mean, intra | WBC | 0.3 | 0.02 | 69 | 84 | 46 | 71 | 64 |
| EIF4B, mean, intra | PTEN, mean, intra | RSAD2, mean, intra | 0.6 | −0.02 | 81 | 81 | 82 | 88 | 73 |
| EIF4B, mean, intra | PTEN, mean, intra | SDCBP, mean, intra | 0.2 | −0.07 | 65 | 77 | 46 | 69 | 56 |
| EIF4B, mean, intra | PTEN, mean, intra | WBC | 0.3 | 0.01 | 69 | 87 | 41 | 70 | 67 |
| EIF4B, mean, intra | RSAD2, mean, intra | SDCBP, mean, intra | 0.6 | −0.07 | 79 | 80 | 77 | 84 | 71 |
| EIF4B, mean, intra | RSAD2, mean, intra | WBC | 0.6 | 0 | 82 | 79 | 85 | 86 | 78 |
| EIF4B, mean, intra | SDCBP, mean, intra | WBC | 0.2 | −0.1 | 64 | 80 | 38 | 67 | 56 |
| IFIT3, mean, intra | IFITM1, mean, membrane | IFITM3, mean, membrane | 0.2 | −0.12 | 64 | 74 | 49 | 70 | 54 |
| IFIT3, mean, intra | IFITM1, mean, membrane | LOC26010, mean, intra | 0.1 | −0.15 | 59 | 68 | 46 | 67 | 47 |
| IFIT3, mean, intra | IFITM1, mean, membrane | Lym(%) | 0.5 | 0.02 | 78 | 82 | 72 | 82 | 72 |
| IFIT3, mean, intra | IFITM1, mean, membrane | MAN1C1, mean, intra | 0.2 | −0.06 | 66 | 85 | 35 | 69 | 58 |
| IFIT3, mean, intra | IFITM1, mean, membrane | MX1, mean, intra | 0.4 | −0.05 | 71 | 76 | 64 | 77 | 63 |
| IFIT3, mean, intra | IFITM1, mean, membrane | Neu(%) | 0.6 | 0.04 | 81 | 89 | 69 | 82 | 79 |
| IFIT3, mean, intra | IFITM1, mean, membrane | NPM1, mean, intra | 0.3 | 0.01 | 67 | 75 | 54 | 72 | 58 |
| IFIT3, mean, intra | IFITM1, mean, membrane | OAS2, mean, intra | 0.2 | −0.1 | 62 | 71 | 49 | 69 | 51 |
| IFIT3, mean, intra | IFITM1, mean, membrane | PARP12, mean, intra | 0.4 | 0.13 | 72 | 76 | 67 | 78 | 63 |
| IFIT3, mean, intra | IFITM1, mean, membrane | PTEN, mean, intra | 0.2 | −0.08 | 62 | 69 | 51 | 69 | 51 |
| IFIT3, mean, intra | IFITM1, mean, membrane | RSAD2, mean, intra | 0.6 | −0.05 | 80 | 81 | 79 | 86 | 72 |
| IFIT3, mean, intra | IFITM1, mean, membrane | SDCBP, mean, intra | 0.2 | −0.12 | 61 | 70 | 46 | 67 | 50 |
| IFIT3, mean, intra | IFITM1, mean, membrane | WBC | 0.2 | −0.09 | 63 | 76 | 44 | 68 | 53 |
| IFIT3, mean, intra | IFITM3, mean, membrane | LOC26010, mean, intra | 0.2 | −0.17 | 61 | 69 | 49 | 68 | 50 |
| IFIT3, mean, intra | IFITM3, mean, membrane | Lym(%) | 0.6 | 0.04 | 79 | 84 | 72 | 83 | 74 |
| IFIT3, mean, intra | IFITM3, mean, membrane | MAN1C1, mean, intra | 0.3 | −0.09 | 67 | 85 | 39 | 70 | 60 |

TABLE 3-continued

The classification accuracy of bacterial vs. viral infected patients computed over pairs of features.
DETERMINANT measurements were measured over cell population mean. (mean triplets)

| Feature #1 | Feature #2 | Feature #3 | MCC | dMCC | Total accuracy % | Sen % | Spe % | PPV % | NPV % |
|---|---|---|---|---|---|---|---|---|---|
| IFIT3, mean, intra | IFITM3, mean, membrane | MX1, mean, intra | 0.4 | −0.06 | 70 | 73 | 67 | 78 | 60 |
| IFIT3, mean, intra | IFITM3, mean, membrane | Neu(%) | 0.6 | 0.02 | 80 | 85 | 72 | 83 | 76 |
| IFIT3, mean, intra | IFITM3, mean, membrane | NPM1, mean, intra | 0.3 | −0.05 | 67 | 75 | 54 | 72 | 58 |
| IFIT3, mean, intra | IFITM3, mean, membrane | OAS2, mean, intra | 0.2 | −0.12 | 64 | 74 | 49 | 70 | 54 |
| IFIT3, mean, intra | IFITM3, mean, membrane | PARP12, mean, intra | 0.4 | 0.09 | 73 | 76 | 69 | 80 | 64 |
| IFIT3, mean, intra | IFITM3, mean, membrane | PTEN, mean, intra | 0.2 | −0.14 | 62 | 69 | 51 | 69 | 51 |
| IFIT3, mean, intra | IFITM3, mean, membrane | RSAD2, mean, intra | 0.6 | −0.03 | 81 | 82 | 79 | 86 | 74 |
| IFIT3, mean, intra | IFITM3, mean, membrane | SDCBP, mean, intra | 0.2 | −0.14 | 63 | 72 | 49 | 69 | 53 |
| IFIT3, mean, intra | IFITM3, mean, membrane | WBC | 0.3 | −0.07 | 66 | 76 | 51 | 71 | 57 |
| IFIT3, mean, intra | LOC26010, mean, intra | Lym(%) | 0.6 | 0.04 | 79 | 85 | 69 | 82 | 75 |
| IFIT3, mean, intra | LOC26010, mean, intra | MAN1C1, mean, intra | 0.2 | −0.04 | 65 | 83 | 35 | 68 | 55 |
| IFIT3, mean, intra | LOC26010, mean, intra | MX1, mean, intra | 0.4 | −0.04 | 71 | 73 | 69 | 79 | 61 |
| IFIT3, mean, intra | LOC26010, mean, intra | Neu(%) | 0.6 | 0.06 | 82 | 89 | 72 | 83 | 80 |
| IFIT3, mean, intra | LOC26010, mean, intra | NPM1, mean, intra | 0.4 | 0.1 | 69 | 75 | 59 | 74 | 61 |
| IFIT3, mean, intra | LOC26010, mean, intra | OAS2, mean, intra | 0.2 | −0.14 | 60 | 69 | 46 | 67 | 49 |
| IFIT3, mean, intra | LOC26010, mean, intra | PARP12, mean, intra | 0.3 | 0.09 | 68 | 73 | 62 | 75 | 59 |
| IFIT3, mean, intra | LOC26010, mean, intra | PTEN, mean, intra | 0.2 | −0.09 | 60 | 69 | 46 | 67 | 49 |
| IFIT3, mean, intra | LOC26010, mean, intra | RSAD2, mean, intra | 0.6 | −0.05 | 80 | 81 | 79 | 86 | 72 |
| IFIT3, mean, intra | LOC26010, mean, intra | SDCBP, mean, intra | 0.2 | −0.07 | 61 | 69 | 49 | 68 | 50 |
| IFIT3, mean, intra | LOC26010, mean, intra | WBC | 0.3 | 0.03 | 66 | 76 | 51 | 71 | 57 |
| IFIT3, mean, intra | Lym(%) | MAN1C1, mean, intra | 0.5 | −0.02 | 77 | 88 | 58 | 78 | 75 |
| IFIT3, mean, intra | Lym(%) | MX1, mean, intra | 0.6 | 0.1 | 82 | 87 | 74 | 84 | 78 |
| IFIT3, mean, intra | Lym(%) | Neu(%) | 0.6 | 0 | 79 | 85 | 69 | 82 | 75 |
| IFIT3, mean, intra | Lym(%) | NPM1, mean, intra | 0.6 | 0.05 | 80 | 87 | 69 | 82 | 77 |
| IFIT3, mean, intra | Lym(%) | OAS2, mean, intra | 0.5 | 0.02 | 78 | 84 | 69 | 81 | 73 |
| IFIT3, mean, intra | Lym(%) | PARP12, mean, intra | 0.6 | 0.06 | 80 | 85 | 72 | 83 | 76 |
| IFIT3, mean, intra | Lym(%) | PTEN, mean, intra | 0.5 | 0.02 | 78 | 84 | 69 | 81 | 73 |
| IFIT3, mean, intra | Lym(%) | RSAD2, mean, intra | 0.7 | 0.01 | 83 | 85 | 79 | 87 | 78 |
| IFIT3, mean, intra | Lym(%) | SDCBP, mean, intra | 0.6 | 0.03 | 79 | 85 | 69 | 81 | 75 |
| IFIT3, mean, intra | Lym(%) | WBC | 0.6 | 0.05 | 80 | 89 | 67 | 81 | 79 |
| IFIT3, mean, intra | MAN1C1, mean, intra | MX1, mean, intra | 0.4 | −0.02 | 73 | 79 | 65 | 79 | 65 |
| IFIT3, mean, intra | MAN1C1, mean, intra | Neu(%) | 0.5 | −0.06 | 77 | 88 | 58 | 78 | 75 |
| IFIT3, mean, intra | MAN1C1, mean, intra | NPM1, mean, intra | 0.3 | 0.03 | 67 | 79 | 48 | 72 | 58 |
| IFIT3, mean, intra | MAN1C1, mean, intra | OAS2, mean, intra | 0.1 | −0.17 | 61 | 77 | 35 | 67 | 48 |
| IFIT3, mean, intra | MAN1C1, mean, intra | PARP12, mean, intra | 0.2 | −0.04 | 64 | 75 | 45 | 70 | 52 |
| IFIT3, mean, intra | MAN1C1, mean, intra | PTEN, mean, intra | 0.3 | 0.06 | 69 | 81 | 48 | 72 | 60 |
| IFIT3, mean, intra | MAN1C1, mean, intra | RSAD2, mean, intra | 0.5 | −0.11 | 78 | 85 | 68 | 81 | 72 |
| IFIT3, mean, intra | MAN1C1, mean, intra | SDCBP, mean, intra | 0.4 | 0.11 | 71 | 85 | 48 | 73 | 65 |
| IFIT3, mean, intra | MAN1C1, mean, intra | WBC | 0.3 | 0.01 | 67 | 87 | 35 | 69 | 61 |
| IFIT3, mean, intra | MX1, mean, intra | Neu(%) | 0.6 | 0.04 | 81 | 85 | 74 | 84 | 76 |
| IFIT3, mean, intra | MX1, mean, intra | NPM1, mean, intra | 0.4 | −0.09 | 69 | 72 | 64 | 76 | 60 |
| IFIT3, mean, intra | MX1, mean, intra | OAS2, mean, intra | 0.4 | −0.05 | 71 | 76 | 64 | 77 | 63 |
| IFIT3, mean, intra | MX1, mean, intra | PARP12, mean, intra | 0.5 | 0.08 | 77 | 79 | 74 | 83 | 69 |
| IFIT3, mean, intra | MX1, mean, intra | PTEN, mean, intra | 0.4 | −0.09 | 69 | 74 | 62 | 75 | 60 |
| IFIT3, mean, intra | MX1, mean, intra | RSAD2, mean, intra | 0.6 | −0.01 | 82 | 84 | 79 | 87 | 76 |
| IFIT3, mean, intra | MX1, mean, intra | SDCBP, mean, intra | 0.4 | −0.07 | 70 | 74 | 64 | 76 | 61 |
| IFIT3, mean, intra | MX1, mean, intra | WBC | 0.5 | 0.02 | 75 | 82 | 64 | 78 | 69 |
| IFIT3, mean, intra | Neu(%) | OAS2, mean, intra | 0.6 | 0.04 | 81 | 87 | 72 | 83 | 78 |
| IFIT3, mean, intra | Neu(%) | PARP12, mean, intra | 0.6 | 0.02 | 80 | 85 | 72 | 83 | 76 |
| IFIT3, mean, intra | Neu(%) | PTEN, mean, intra | 0.6 | 0.06 | 82 | 89 | 72 | 83 | 80 |
| IFIT3, mean, intra | Neu(%) | RSAD2, mean, intra | 0.6 | 0 | 83 | 87 | 77 | 86 | 79 |
| IFIT3, mean, intra | Neu(%) | SDCBP, mean, intra | 0.5 | −0.03 | 78 | 84 | 69 | 81 | 73 |
| IFIT3, mean, intra | Neu(%) | WBC | 0.6 | 0.01 | 80 | 89 | 67 | 81 | 79 |
| IFIT3, mean, intra | NPM1, mean, intra | Neu(%) | 0.6 | 0.06 | 82 | 89 | 72 | 83 | 80 |
| IFIT3, mean, intra | NPM1, mean, intra | OAS2, mean, intra | 0.2 | −0.07 | 64 | 74 | 49 | 69 | 54 |
| IFIT3, mean, intra | NPM1, mean, intra | PARP12, mean, intra | 0.4 | 0.13 | 70 | 74 | 64 | 76 | 61 |
| IFIT3, mean, intra | NPM1, mean, intra | PTEN, mean, intra | 0.3 | 0 | 65 | 74 | 51 | 70 | 56 |
| IFIT3, mean, intra | NPM1, mean, intra | RSAD2, mean, intra | 0.6 | −0.05 | 80 | 80 | 79 | 86 | 72 |
| IFIT3, mean, intra | NPM1, mean, intra | SDCBP, mean, intra | 0.3 | 0.09 | 69 | 77 | 56 | 73 | 61 |
| IFIT3, mean, intra | NPM1, mean, intra | WBC | 0.4 | 0.14 | 72 | 85 | 51 | 73 | 69 |
| IFIT3, mean, intra | OAS2, mean, intra | PARP12, mean, intra | 0.4 | 0.06 | 69 | 74 | 62 | 75 | 60 |
| IFIT3, mean, intra | OAS2, mean, intra | PTEN, mean, intra | 0.2 | −0.08 | 63 | 71 | 51 | 70 | 53 |
| IFIT3, mean, intra | OAS2, mean, intra | RSAD2, mean, intra | 0.6 | −0.03 | 81 | 82 | 79 | 86 | 74 |
| IFIT3, mean, intra | OAS2, mean, intra | SDCBP, mean, intra | 0.2 | −0.14 | 61 | 72 | 44 | 67 | 50 |
| IFIT3, mean, intra | OAS2, mean, intra | WBC | 0.3 | 0 | 67 | 77 | 51 | 72 | 59 |
| IFIT3, mean, intra | PARP12, mean, intra | PTEN, mean, intra | 0.3 | 0.01 | 64 | 69 | 56 | 72 | 54 |
| IFIT3, mean, intra | PARP12, mean, intra | RSAD2, mean, intra | 0.6 | −0.02 | 82 | 85 | 77 | 85 | 77 |
| IFIT3, mean, intra | PARP12, mean, intra | SDCBP, mean, intra | 0.3 | 0.05 | 67 | 74 | 56 | 73 | 58 |
| IFIT3, mean, intra | PARP12, mean, intra | WBC | 0.4 | 0.11 | 70 | 79 | 56 | 74 | 63 |
| IFIT3, mean, intra | PTEN, mean, intra | RSAD2, mean, intra | 0.6 | −0.05 | 80 | 81 | 79 | 86 | 72 |
| IFIT3, mean, intra | PTEN, mean, intra | SDCBP, mean, intra | 0.3 | 0.02 | 66 | 75 | 51 | 71 | 57 |
| IFIT3, mean, intra | PTEN, mean, intra | WBC | 0.3 | 0.04 | 67 | 79 | 49 | 71 | 59 |
| IFIT3, mean, intra | RSAD2, mean, intra | SDCBP, mean, intra | 0.6 | −0.05 | 80 | 80 | 79 | 86 | 72 |
| IFIT3, mean, intra | RSAD2, mean, intra | WBC | 0.6 | −0.03 | 81 | 82 | 79 | 86 | 74 |

TABLE 3-continued

The classification accuracy of bacterial vs. viral infected patients computed over pairs of features.
DETERMINANT measurements were measured over cell population mean. (mean triplets)

| Feature #1 | Feature #2 | Feature #3 | MCC | dMCC | Total accuracy % | Sen % | Spe % | PPV % | NPV % |
|---|---|---|---|---|---|---|---|---|---|
| IFIT3, mean, intra | SDCBP, mean, intra | WBC | 0.3 | 0.01 | 66 | 79 | 46 | 70 | 58 |
| IFITM1, mean, membrane | IFITM3, mean, membrane | LOC26010, mean, intra | 0.3 | −0.06 | 64 | 60 | 69 | 70 | 59 |
| IFITM1, mean, membrane | IFITM3, mean, membrane | Lym(%) | 0.5 | −0.06 | 73 | 75 | 71 | 76 | 70 |
| IFITM1, mean, membrane | IFITM3, mean, membrane | MAN1C1, mean, intra | 0.1 | −0.25 | 61 | 83 | 26 | 65 | 47 |
| IFITM1, mean, membrane | IFITM3, mean, membrane | MX1, mean, intra | 0.4 | −0.03 | 71 | 69 | 73 | 76 | 66 |
| IFITM1, mean, membrane | IFITM3, mean, membrane | Neu(%) | 0.6 | 0.01 | 79 | 81 | 76 | 81 | 76 |
| IFITM1, mean, membrane | IFITM3, mean, membrane | NPM1, mean, intra | 0.1 | −0.22 | 60 | 74 | 38 | 65 | 48 |
| IFITM1, mean, membrane | IFITM3, mean, membrane | OAS2, mean, intra | 0.4 | 0 | 67 | 65 | 69 | 72 | 62 |
| IFITM1, mean, membrane | IFITM3, mean, membrane | PARP12, mean, intra | 0.2 | −0.14 | 63 | 74 | 46 | 69 | 53 |
| IFITM1, mean, membrane | IFITM3, mean, membrane | PTEN, mean, intra | 0.2 | −0.19 | 61 | 74 | 41 | 67 | 50 |
| IFITM1, mean, membrane | IFITM3, mean, membrane | RSAD2, mean, intra | 0.5 | −0.11 | 76 | 75 | 78 | 81 | 72 |
| IFITM1, mean, membrane | IFITM3, mean, membrane | SDCBP, mean, intra | 0 | −0.31 | 57 | 75 | 28 | 62 | 42 |
| IFITM1, mean, membrane | IFITM3, mean, membrane | WBC | 0.4 | 0.04 | 70 | 78 | 61 | 71 | 69 |
| IFITM1, mean, membrane | LOC26010, mean, intra | Lym(%) | 0.6 | 0.05 | 79 | 81 | 76 | 81 | 76 |
| IFITM1, mean, membrane | LOC26010, mean, intra | MAN1C1, mean, intra | 0.2 | −0.11 | 64 | 81 | 35 | 68 | 52 |
| IFITM1, mean, membrane | LOC26010, mean, intra | MX1, mean, intra | 0.5 | 0.04 | 74 | 71 | 78 | 80 | 69 |
| IFITM1, mean, membrane | LOC26010, mean, intra | Neu(%) | 0.5 | −0.02 | 77 | 78 | 76 | 80 | 74 |
| IFITM1, mean, membrane | LOC26010, mean, intra | NPM1, mean, intra | 0.1 | −0.19 | 59 | 74 | 36 | 64 | 47 |
| IFITM1, mean, membrane | LOC26010, mean, intra | OAS2, mean, intra | 0.3 | 0 | 65 | 64 | 66 | 70 | 60 |
| IFITM1, mean, membrane | LOC26010, mean, intra | PARP12, mean, intra | 0.2 | −0.09 | 63 | 76 | 44 | 68 | 53 |
| IFITM1, mean, membrane | LOC26010, mean, intra | PTEN, mean, intra | 0.1 | −0.17 | 59 | 73 | 38 | 65 | 47 |
| IFITM1, mean, membrane | LOC26010, mean, intra | RSAD2, mean, intra | 0.6 | −0.07 | 79 | 78 | 80 | 82 | 75 |
| IFITM1, mean, membrane | LOC26010, mean, intra | SDCBP, mean, intra | 0.2 | −0.1 | 63 | 79 | 38 | 67 | 54 |
| IFITM1, mean, membrane | LOC26010, mean, intra | WBC | 0.3 | −0.03 | 63 | 69 | 56 | 66 | 60 |
| IFITM1, mean, membrane | Lym(%) | MAN1C1, mean, intra | 0.4 | −0.1 | 73 | 83 | 58 | 77 | 67 |
| IFITM1, mean, membrane | Lym(%) | MX1, mean, intra | 0.7 | 0.17 | 85 | 88 | 81 | 85 | 84 |
| IFITM1, mean, membrane | Lym(%) | Neu(%) | 0.5 | −0.02 | 77 | 78 | 76 | 80 | 74 |
| IFITM1, mean, membrane | Lym(%) | NPM1, mean, intra | 0.5 | −0.02 | 76 | 79 | 72 | 81 | 68 |
| IFITM1, mean, membrane | Lym(%) | OAS2, mean, intra | 0.6 | 0.05 | 79 | 79 | 78 | 81 | 75 |
| IFITM1, mean, membrane | Lym(%) | PARP12, mean, intra | 0.6 | 0.04 | 79 | 82 | 74 | 84 | 73 |
| IFITM1, mean, membrane | Lym(%) | PTEN, mean, intra | 0.5 | −0.05 | 74 | 76 | 72 | 81 | 65 |
| IFITM1, mean, membrane | Lym(%) | RSAD2, mean, intra | 0.6 | −0.02 | 81 | 82 | 80 | 83 | 78 |
| IFITM1, mean, membrane | Lym(%) | SDCBP, mean, intra | 0.4 | −0.08 | 73 | 77 | 67 | 78 | 65 |
| IFITM1, mean, membrane | Lym(%) | WBC | 0.6 | 0.05 | 79 | 82 | 75 | 80 | 77 |
| IFITM1, mean, membrane | MAN1C1, mean, intra | MX1, mean, intra | 0.3 | −0.13 | 69 | 77 | 55 | 74 | 59 |
| IFITM1, mean, membrane | MAN1C1, mean, intra | Neu(%) | 0.5 | −0.11 | 75 | 85 | 58 | 77 | 69 |
| IFITM1, mean, membrane | MAN1C1, mean, intra | NPM1, mean, intra | 0.2 | −0.12 | 63 | 77 | 39 | 68 | 50 |
| IFITM1, mean, membrane | MAN1C1, mean, intra | OAS2, mean, intra | 0.1 | −0.18 | 61 | 79 | 32 | 66 | 48 |
| IFITM1, mean, membrane | MAN1C1, mean, intra | PARP12, mean, intra | 0.2 | −0.12 | 63 | 77 | 39 | 68 | 50 |
| IFITM1, mean, membrane | MAN1C1, mean, intra | PTEN, mean, intra | 0.3 | 0.02 | 69 | 81 | 48 | 72 | 60 |
| IFITM1, mean, membrane | MAN1C1, mean, intra | RSAD2, mean, intra | 0.6 | 0 | 83 | 87 | 77 | 87 | 77 |
| IFITM1, mean, membrane | MAN1C1, mean, intra | SDCBP, mean, intra | 0.3 | 0.01 | 69 | 83 | 45 | 72 | 61 |
| IFITM1, mean, membrane | MAN1C1, mean, intra | WBC | 0.2 | −0.1 | 65 | 87 | 29 | 67 | 56 |
| IFITM1, mean, membrane | MX1, mean, intra | Neu(%) | 0.6 | 0.07 | 82 | 85 | 78 | 82 | 81 |
| IFITM1, mean, membrane | MX1, mean, intra | NPM1, mean, intra | 0.3 | −0.12 | 68 | 72 | 62 | 75 | 59 |
| IFITM1, mean, membrane | MX1, mean, intra | OAS2, mean, intra | 0.4 | −0.02 | 71 | 67 | 76 | 77 | 65 |
| IFITM1, mean, membrane | MX1, mean, intra | PARP12, mean, intra | 0.5 | 0.03 | 75 | 81 | 67 | 79 | 68 |
| IFITM1, mean, membrane | MX1, mean, intra | PTEN, mean, intra | 0.4 | −0.04 | 72 | 81 | 59 | 76 | 66 |
| IFITM1, mean, membrane | MX1, mean, intra | RSAD2, mean, intra | 0.5 | −0.11 | 76 | 74 | 80 | 82 | 71 |
| IFITM1, mean, membrane | MX1, mean, intra | SDCBP, mean, intra | 0.4 | −0.08 | 70 | 75 | 62 | 75 | 62 |
| IFITM1, mean, membrane | MX1, mean, intra | WBC | 0.5 | 0.01 | 73 | 69 | 76 | 78 | 67 |
| IFITM1, mean, membrane | Neu(%) | OAS2, mean, intra | 0.5 | −0.04 | 76 | 78 | 75 | 79 | 73 |
| IFITM1, mean, membrane | Neu(%) | PARP12, mean, intra | 0.6 | 0.02 | 80 | 85 | 72 | 83 | 76 |
| IFITM1, mean, membrane | Neu(%) | PTEN, mean, intra | 0.5 | −0.02 | 78 | 82 | 72 | 82 | 72 |
| IFITM1, mean, membrane | Neu(%) | RSAD2, mean, intra | 0.7 | 0.01 | 82 | 83 | 81 | 85 | 80 |
| IFITM1, mean, membrane | Neu(%) | SDCBP, mean, intra | 0.5 | −0.09 | 75 | 80 | 67 | 79 | 68 |
| IFITM1, mean, membrane | Neu(%) | WBC | 0.6 | 0.01 | 79 | 81 | 76 | 81 | 76 |
| IFITM1, mean, membrane | NPM1, mean, intra | Neu(%) | 0.6 | −0.01 | 79 | 85 | 69 | 81 | 75 |
| IFITM1, mean, membrane | NPM1, mean, intra | OAS2, mean, intra | 0 | −0.28 | 55 | 69 | 33 | 62 | 41 |
| IFITM1, mean, membrane | NPM1, mean, intra | PARP12, mean, intra | 0.2 | −0.07 | 63 | 70 | 51 | 69 | 53 |
| IFITM1, mean, membrane | NPM1, mean, intra | PTEN, mean, intra | 0.2 | −0.14 | 61 | 74 | 41 | 66 | 50 |
| IFITM1, mean, membrane | NPM1, mean, intra | RSAD2, mean, intra | 0.6 | −0.01 | 82 | 82 | 82 | 88 | 74 |
| IFITM1, mean, membrane | NPM1, mean, intra | SDCBP, mean, intra | 0.1 | −0.2 | 59 | 75 | 33 | 64 | 46 |
| IFITM1, mean, membrane | NPM1, mean, intra | WBC | 0.3 | 0.03 | 69 | 85 | 44 | 70 | 65 |
| IFITM1, mean, membrane | OAS2, mean, intra | PARP12, mean, intra | 0.2 | −0.08 | 63 | 73 | 49 | 69 | 53 |
| IFITM1, mean, membrane | OAS2, mean, intra | PTEN, mean, intra | 0.1 | −0.16 | 60 | 73 | 41 | 66 | 48 |
| IFITM1, mean, membrane | OAS2, mean, intra | RSAD2, mean, intra | 0.6 | −0.02 | 81 | 81 | 81 | 84 | 77 |
| IFITM1, mean, membrane | OAS2, mean, intra | SDCBP, mean, intra | 0.1 | −0.25 | 57 | 74 | 31 | 63 | 43 |
| IFITM1, mean, membrane | OAS2, mean, intra | WBC | 0.3 | −0.01 | 65 | 72 | 56 | 67 | 62 |
| IFITM1, mean, membrane | PARP12, mean, intra | PTEN, mean, intra | 0.2 | −0.09 | 62 | 71 | 49 | 69 | 51 |
| IFITM1, mean, membrane | PARP12, mean, intra | RSAD2, mean, intra | 0.7 | 0.03 | 84 | 87 | 79 | 87 | 79 |
| IFITM1, mean, membrane | PARP12, mean, intra | SDCBP, mean, intra | 0.1 | −0.15 | 60 | 70 | 44 | 66 | 49 |
| IFITM1, mean, membrane | PARP12, mean, intra | WBC | 0.3 | 0.02 | 68 | 82 | 46 | 71 | 62 |
| IFITM1, mean, membrane | PTEN, mean, intra | RSAD2, mean, intra | 0.6 | −0.03 | 81 | 82 | 79 | 86 | 74 |

TABLE 3-continued

The classification accuracy of bacterial vs. viral infected patients computed over pairs of features.
DETERMINANT measurements were measured over cell population mean. (mean triplets)

| Feature #1 | Feature #2 | Feature #3 | MCC | dMCC | Total accuracy % | Sen % | Spe % | PPV % | NPV % |
|---|---|---|---|---|---|---|---|---|---|
| IFITM1, mean, membrane | PTEN, mean, intra | SDCBP, mean, intra | 0.3 | −0.04 | 65 | 75 | 49 | 70 | 56 |
| IFITM1, mean, membrane | PTEN, mean, intra | WBC | 0.3 | 0.03 | 69 | 87 | 41 | 70 | 67 |
| IFITM1, mean, membrane | RSAD2, mean, intra | SDCBP, mean, intra | 0.6 | −0.03 | 81 | 82 | 79 | 86 | 74 |
| IFITM1, mean, membrane | RSAD2, mean, intra | WBC | 0.6 | −0.05 | 79 | 76 | 83 | 85 | 74 |
| IFITM1, mean, membrane | SDCBP, mean, intra | WBC | 0.3 | −0.02 | 67 | 84 | 41 | 69 | 62 |
| IFITM3, mean, membrane | LOC26010, mean, intra | Lym(%) | 0.5 | −0.05 | 74 | 78 | 69 | 76 | 72 |
| IFITM3, mean, membrane | LOC26010, mean, intra | MAN1C1, mean, intra | 0.2 | −0.14 | 65 | 83 | 35 | 68 | 55 |
| IFITM3, mean, membrane | LOC26010, mean, intra | MX1, mean, intra | 0.5 | 0.01 | 73 | 69 | 76 | 78 | 67 |
| IFITM3, mean, membrane | LOC26010, mean, intra | Neu(%) | 0.6 | −0.01 | 78 | 82 | 73 | 79 | 77 |
| IFITM3, mean, membrane | LOC26010, mean, intra | NPM1, mean, intra | 0.1 | −0.23 | 60 | 75 | 36 | 65 | 48 |
| IFITM3, mean, membrane | LOC26010, mean, intra | OAS2, mean, intra | 0.4 | 0.01 | 68 | 65 | 71 | 73 | 63 |
| IFITM3, mean, membrane | LOC26010, mean, intra | PARP12, mean, intra | 0.2 | −0.14 | 63 | 74 | 46 | 69 | 53 |
| IFITM3, mean, membrane | LOC26010, mean, intra | PTEN, mean, intra | 0.1 | −0.23 | 59 | 71 | 41 | 66 | 47 |
| IFITM3, mean, membrane | LOC26010, mean, intra | RSAD2, mean, intra | 0.6 | −0.02 | 81 | 79 | 83 | 85 | 77 |
| IFITM3, mean, membrane | LOC26010, mean, intra | SDCBP, mean, intra | 0.2 | −0.17 | 63 | 80 | 36 | 66 | 54 |
| IFITM3, mean, membrane | LOC26010, mean, intra | WBC | 0.3 | −0.06 | 65 | 69 | 59 | 68 | 61 |
| IFITM3, mean, membrane | Lym(%) | MAN1C1, mean, intra | 0.4 | −0.1 | 73 | 83 | 58 | 77 | 67 |
| IFITM3, mean, membrane | Lym(%) | MX1, mean, intra | 0.6 | 0.11 | 82 | 83 | 80 | 83 | 80 |
| IFITM3, mean, membrane | Lym(%) | Neu(%) | 0.5 | −0.08 | 74 | 76 | 71 | 76 | 71 |
| IFITM3, mean, membrane | Lym(%) | NPM1, mean, intra | 0.5 | −0.05 | 75 | 80 | 67 | 79 | 68 |
| IFITM3, mean, membrane | Lym(%) | OAS2, mean, intra | 0.6 | 0.05 | 79 | 79 | 78 | 81 | 75 |
| IFITM3, mean, membrane | Lym(%) | PARP12, mean, intra | 0.5 | 0 | 77 | 82 | 69 | 81 | 71 |
| IFITM3, mean, membrane | Lym(%) | PTEN, mean, intra | 0.4 | −0.12 | 71 | 74 | 67 | 78 | 62 |
| IFITM3, mean, membrane | Lym(%) | RSAD2, mean, intra | 0.6 | −0.02 | 81 | 81 | 81 | 84 | 77 |
| IFITM3, mean, membrane | Lym(%) | SDCBP, mean, intra | 0.5 | −0.04 | 75 | 79 | 69 | 80 | 68 |
| IFITM3, mean, membrane | Lym(%) | WBC | 0.5 | −0.03 | 75 | 78 | 71 | 77 | 72 |
| IFITM3, mean, membrane | MAN1C1, mean, intra | MX1, mean, intra | 0.4 | −0.09 | 70 | 75 | 61 | 76 | 59 |
| IFITM3, mean, membrane | MAN1C1, mean, intra | Neu(%) | 0.5 | −0.06 | 77 | 88 | 58 | 78 | 75 |
| IFITM3, mean, membrane | MAN1C1, mean, intra | NPM1, mean, intra | 0.1 | −0.21 | 61 | 75 | 39 | 67 | 48 |
| IFITM3, mean, membrane | MAN1C1, mean, intra | OAS2, mean, intra | 0.2 | −0.19 | 63 | 79 | 35 | 67 | 50 |
| IFITM3, mean, membrane | MAN1C1, mean, intra | PARP12, mean, intra | 0.1 | −0.24 | 59 | 69 | 42 | 67 | 45 |
| IFITM3, mean, membrane | MAN1C1, mean, intra | PTEN, mean, intra | 0.3 | −0.07 | 67 | 79 | 48 | 72 | 58 |
| IFITM3, mean, membrane | MAN1C1, mean, intra | RSAD2, mean, intra | 0.6 | −0.05 | 81 | 85 | 74 | 85 | 74 |
| IFITM3, mean, membrane | MAN1C1, mean, intra | SDCBP, mean, intra | 0.3 | −0.1 | 66 | 81 | 42 | 70 | 57 |
| IFITM3, mean, membrane | MAN1C1, mean, intra | WBC | 0.2 | −0.13 | 66 | 88 | 29 | 68 | 60 |
| IFITM3, mean, membrane | MX1, mean, intra | Neu(%) | 0.6 | 0.02 | 79 | 83 | 75 | 80 | 79 |
| IFITM3, mean, membrane | MX1, mean, intra | NPM1, mean, intra | 0.4 | −0.03 | 72 | 74 | 69 | 79 | 63 |
| IFITM3, mean, membrane | MX1, mean, intra | OAS2, mean, intra | 0.4 | −0.06 | 69 | 67 | 73 | 75 | 64 |
| IFITM3, mean, membrane | MX1, mean, intra | PARP12, mean, intra | 0.5 | 0.01 | 74 | 77 | 69 | 80 | 66 |
| IFITM3, mean, membrane | MX1, mean, intra | PTEN, mean, intra | 0.4 | −0.07 | 70 | 74 | 64 | 77 | 61 |
| IFITM3, mean, membrane | MX1, mean, intra | RSAD2, mean, intra | 0.6 | −0.05 | 79 | 78 | 81 | 84 | 75 |
| IFITM3, mean, membrane | MX1, mean, intra | SDCBP, mean, intra | 0.5 | 0.02 | 74 | 75 | 72 | 81 | 65 |
| IFITM3, mean, membrane | MX1, mean, intra | WBC | 0.4 | −0.05 | 70 | 69 | 71 | 75 | 66 |
| IFITM3, mean, membrane | Neu(%) | OAS2, mean, intra | 0.5 | −0.02 | 77 | 79 | 75 | 79 | 75 |
| IFITM3, mean, membrane | Neu(%) | PARP12, mean, intra | 0.6 | 0.04 | 81 | 87 | 72 | 83 | 78 |
| IFITM3, mean, membrane | Neu(%) | PTEN, mean, intra | 0.5 | −0.03 | 78 | 85 | 67 | 80 | 74 |
| IFITM3, mean, membrane | Neu(%) | RSAD2, mean, intra | 0.6 | 0 | 82 | 85 | 80 | 84 | 81 |
| IFITM3, mean, membrane | Neu(%) | SDCBP, mean, intra | 0.5 | −0.05 | 77 | 82 | 69 | 81 | 71 |
| IFITM3, mean, membrane | Neu(%) | WBC | 0.6 | 0.01 | 79 | 83 | 73 | 79 | 78 |
| IFITM3, mean, membrane | NPM1, mean, intra | Neu(%) | 0.6 | 0.01 | 80 | 89 | 67 | 81 | 79 |
| IFITM3, mean, membrane | NPM1, mean, intra | OAS2, mean, intra | 0.1 | −0.29 | 57 | 72 | 33 | 63 | 43 |
| IFITM3, mean, membrane | NPM1, mean, intra | PARP12, mean, intra | 0.2 | −0.17 | 61 | 67 | 51 | 68 | 50 |
| IFITM3, mean, membrane | NPM1, mean, intra | PTEN, mean, intra | 0.1 | −0.23 | 59 | 70 | 41 | 65 | 47 |
| IFITM3, mean, membrane | NPM1, mean, intra | RSAD2, mean, intra | 0.6 | −0.01 | 82 | 84 | 79 | 86 | 76 |
| IFITM3, mean, membrane | NPM1, mean, intra | SDCBP, mean, intra | 0.1 | −0.23 | 60 | 75 | 36 | 65 | 48 |
| IFITM3, mean, membrane | NPM1, mean, intra | WBC | 0.3 | −0.03 | 69 | 84 | 46 | 71 | 64 |
| IFITM3, mean, membrane | OAS2, mean, intra | PARP12, mean, intra | 0.2 | −0.15 | 62 | 71 | 49 | 69 | 51 |
| IFITM3, mean, membrane | OAS2, mean, intra | PTEN, mean, intra | 0.1 | −0.21 | 60 | 73 | 41 | 66 | 48 |
| IFITM3, mean, membrane | OAS2, mean, intra | RSAD2, mean, intra | 0.6 | −0.02 | 81 | 79 | 83 | 85 | 77 |
| IFITM3, mean, membrane | OAS2, mean, intra | SDCBP, mean, intra | 0 | −0.34 | 55 | 70 | 31 | 61 | 40 |
| IFITM3, mean, membrane | OAS2, mean, intra | WBC | 0.3 | −0.02 | 67 | 74 | 59 | 69 | 65 |
| IFITM3, mean, membrane | PARP12, mean, intra | PTEN, mean, intra | 0.2 | −0.14 | 63 | 74 | 46 | 69 | 53 |
| IFITM3, mean, membrane | PARP12, mean, intra | RSAD2, mean, intra | 0.7 | 0.01 | 83 | 85 | 79 | 87 | 78 |
| IFITM3, mean, membrane | PARP12, mean, intra | SDCBP, mean, intra | 0.1 | −0.22 | 59 | 67 | 46 | 66 | 47 |
| IFITM3, mean, membrane | PARP12, mean, intra | WBC | 0.3 | −0.04 | 68 | 81 | 49 | 71 | 61 |
| IFITM3, mean, membrane | PTEN, mean, intra | RSAD2, mean, intra | 0.7 | 0.01 | 83 | 85 | 79 | 87 | 78 |
| IFITM3, mean, membrane | PTEN, mean, intra | SDCBP, mean, intra | 0.2 | −0.14 | 63 | 74 | 46 | 68 | 53 |
| IFITM3, mean, membrane | PTEN, mean, intra | WBC | 0.3 | −0.07 | 67 | 82 | 44 | 70 | 61 |
| IFITM3, mean, membrane | RSAD2, mean, intra | SDCBP, mean, intra | 0.6 | −0.01 | 82 | 84 | 79 | 86 | 76 |
| IFITM3, mean, membrane | RSAD2, mean, intra | WBC | 0.6 | 0 | 82 | 79 | 85 | 86 | 77 |
| IFITM3, mean, membrane | SDCBP, mean, intra | WBC | 0.2 | −0.12 | 65 | 80 | 41 | 68 | 57 |
| LOC26010, mean, intra | Lym(%) | MAN1C1, mean, intra | 0.4 | −0.1 | 73 | 83 | 58 | 77 | 67 |
| LOC26010, mean, intra | Lym(%) | MX1, mean, intra | 0.6 | 0.11 | 81 | 82 | 81 | 83 | 79 |
| LOC26010, mean, intra | Lym(%) | Neu(%) | 0.5 | −0.05 | 75 | 74 | 77 | 79 | 72 |

TABLE 3-continued

The classification accuracy of bacterial vs. viral infected patients computed over pairs of features.
DETERMINANT measurements were measured over cell population mean. (mean triplets)

| Feature #1 | Feature #2 | Feature #3 | MCC | dMCC | Total accuracy % | Sen % | Spe % | PPV % | NPV % |
|---|---|---|---|---|---|---|---|---|---|
| LOC26010, mean, intra | Lym(%) | NPM1, mean, intra | 0.5 | 0.01 | 78 | 84 | 69 | 81 | 73 |
| LOC26010, mean, intra | Lym(%) | OAS2, mean, intra | 0.6 | 0.03 | 78 | 76 | 79 | 81 | 74 |
| LOC26010, mean, intra | Lym(%) | PARP12, mean, intra | 0.6 | 0.06 | 80 | 85 | 72 | 83 | 76 |
| LOC26010, mean, intra | Lym(%) | PTEN, mean, intra | 0.5 | −0.03 | 75 | 77 | 72 | 81 | 67 |
| LOC26010, mean, intra | Lym(%) | RSAD2, mean, intra | 0.6 | 0 | 82 | 83 | 81 | 83 | 81 |
| LOC26010, mean, intra | Lym(%) | SDCBP, mean, intra | 0.5 | −0.07 | 74 | 79 | 67 | 79 | 67 |
| LOC26010, mean, intra | Lym(%) | WBC | 0.5 | 0 | 76 | 78 | 74 | 78 | 74 |
| LOC26010, mean, intra | MAN1C1, mean, intra | MX1, mean, intra | 0.4 | −0.1 | 70 | 77 | 58 | 75 | 60 |
| LOC26010, mean, intra | MAN1C1, mean, intra | Neu(%) | 0.5 | −0.06 | 77 | 87 | 61 | 79 | 73 |
| LOC26010, mean, intra | MAN1C1, mean, intra | NPM1, mean, intra | 0.2 | −0.04 | 63 | 77 | 39 | 68 | 50 |
| LOC26010, mean, intra | MAN1C1, mean, intra | OAS2, mean, intra | 0.2 | −0.12 | 64 | 81 | 35 | 68 | 52 |
| LOC26010, mean, intra | MAN1C1, mean, intra | PARP12, mean, intra | 0.2 | −0.09 | 61 | 73 | 42 | 68 | 48 |
| LOC26010, mean, intra | MAN1C1, mean, intra | PTEN, mean, intra | 0.2 | 0.02 | 65 | 77 | 45 | 70 | 54 |
| LOC26010, mean, intra | MAN1C1, mean, intra | RSAD2, mean, intra | 0.6 | −0.06 | 81 | 87 | 71 | 83 | 76 |
| LOC26010, mean, intra | MAN1C1, mean, intra | SDCBP, mean, intra | 0.2 | 0 | 65 | 81 | 39 | 69 | 55 |
| LOC26010, mean, intra | MAN1C1, mean, intra | WBC | 0.3 | 0.04 | 69 | 87 | 39 | 70 | 63 |
| LOC26010, mean, intra | MX1, mean, intra | Neu(%) | 0.6 | 0.02 | 79 | 81 | 77 | 81 | 77 |
| LOC26010, mean, intra | MX1, mean, intra | NPM1, mean, intra | 0.4 | −0.08 | 69 | 70 | 67 | 77 | 59 |
| LOC26010, mean, intra | MX1, mean, intra | OAS2, mean, intra | 0.5 | 0 | 72 | 68 | 77 | 78 | 68 |
| LOC26010, mean, intra | MX1, mean, intra | PARP12, mean, intra | 0.5 | 0.08 | 77 | 79 | 74 | 83 | 69 |
| LOC26010, mean, intra | MX1, mean, intra | PTEN, mean, intra | 0.4 | −0.03 | 72 | 76 | 67 | 78 | 63 |
| LOC26010, mean, intra | MX1, mean, intra | RSAD2, mean, intra | 0.6 | −0.04 | 80 | 76 | 84 | 85 | 75 |
| LOC26010, mean, intra | MX1, mean, intra | SDCBP, mean, intra | 0.4 | −0.05 | 71 | 74 | 67 | 78 | 62 |
| LOC26010, mean, intra | MX1, mean, intra | WBC | 0.4 | −0.04 | 70 | 68 | 73 | 74 | 66 |
| LOC26010, mean, intra | Neu(%) | OAS2, mean, intra | 0.6 | 0.01 | 78 | 78 | 79 | 81 | 75 |
| LOC26010, mean, intra | Neu(%) | PARP12, mean, intra | 0.6 | 0.06 | 82 | 87 | 74 | 84 | 78 |
| LOC26010, mean, intra | Neu(%) | PTEN, mean, intra | 0.6 | 0.02 | 80 | 87 | 69 | 82 | 77 |
| LOC26010, mean, intra | Neu(%) | RSAD2, mean, intra | 0.7 | 0.03 | 84 | 85 | 82 | 85 | 82 |
| LOC26010, mean, intra | Neu(%) | SDCBP, mean, intra | 0.5 | −0.05 | 77 | 82 | 69 | 81 | 71 |
| LOC26010, mean, intra | Neu(%) | WBC | 0.6 | −0.01 | 78 | 82 | 73 | 78 | 78 |
| LOC26010, mean, intra | NPM1, mean, intra | Neu(%) | 0.6 | −0.01 | 79 | 85 | 69 | 81 | 75 |
| LOC26010, mean, intra | NPM1, mean, intra | OAS2, mean, intra | 0.1 | −0.2 | 59 | 74 | 36 | 64 | 47 |
| LOC26010, mean, intra | NPM1, mean, intra | PARP12, mean, intra | 0.2 | −0.07 | 61 | 67 | 51 | 68 | 50 |
| LOC26010, mean, intra | NPM1, mean, intra | PTEN, mean, intra | 0.1 | −0.07 | 60 | 72 | 41 | 66 | 48 |
| LOC26010, mean, intra | NPM1, mean, intra | RSAD2, mean, intra | 0.6 | −0.06 | 80 | 82 | 77 | 85 | 73 |
| LOC26010, mean, intra | NPM1, mean, intra | SDCBP, mean, intra | 0.1 | −0.1 | 60 | 77 | 33 | 64 | 48 |
| LOC26010, mean, intra | NPM1, mean, intra | WBC | 0.4 | 0.12 | 71 | 85 | 49 | 72 | 68 |
| LOC26010, mean, intra | OAS2, mean, intra | PARP12, mean, intra | 0.2 | −0.1 | 62 | 71 | 49 | 69 | 51 |
| LOC26010, mean, intra | OAS2, mean, intra | PTEN, mean, intra | 0.1 | −0.17 | 59 | 69 | 44 | 66 | 47 |
| LOC26010, mean, intra | OAS2, mean, intra | RSAD2, mean, intra | 0.6 | 0 | 82 | 81 | 84 | 85 | 79 |
| LOC26010, mean, intra | OAS2, mean, intra | SDCBP, mean, intra | 0.1 | −0.21 | 59 | 75 | 33 | 64 | 46 |
| LOC26010, mean, intra | OAS2, mean, intra | WBC | 0.3 | 0.02 | 66 | 75 | 56 | 67 | 66 |
| LOC26010, mean, intra | PARP12, mean, intra | PTEN, mean, intra | 0.2 | −0.02 | 64 | 76 | 46 | 69 | 55 |
| LOC26010, mean, intra | PARP12, mean, intra | RSAD2, mean, intra | 0.6 | −0.02 | 82 | 85 | 77 | 85 | 77 |
| LOC26010, mean, intra | PARP12, mean, intra | SDCBP, mean, intra | 0.2 | −0.08 | 61 | 70 | 46 | 67 | 50 |
| LOC26010, mean, intra | PARP12, mean, intra | WBC | 0.3 | 0.08 | 69 | 82 | 49 | 72 | 63 |
| LOC26010, mean, intra | PTEN, mean, intra | RSAD2, mean, intra | 0.6 | −0.05 | 80 | 82 | 77 | 85 | 73 |
| LOC26010, mean, intra | PTEN, mean, intra | SDCBP, mean, intra | 0.3 | 0.08 | 67 | 79 | 49 | 71 | 59 |
| LOC26010, mean, intra | PTEN, mean, intra | WBC | 0.3 | 0.08 | 69 | 84 | 46 | 71 | 64 |
| LOC26010, mean, intra | RSAD2, mean, intra | SDCBP, mean, intra | 0.6 | −0.03 | 81 | 82 | 79 | 86 | 74 |
| LOC26010, mean, intra | RSAD2, mean, intra | WBC | 0.7 | 0.02 | 83 | 82 | 84 | 86 | 80 |
| LOC26010, mean, intra | SDCBP, mean, intra | WBC | 0.3 | 0 | 66 | 82 | 41 | 68 | 59 |
| Lym(%) | MAN1C1, mean, intra | MX1, mean, intra | 0.7 | 0.14 | 84 | 90 | 74 | 85 | 82 |
| Lym(%) | MAN1C1, mean, intra | Neu(%) | 0.4 | −0.14 | 73 | 83 | 58 | 77 | 67 |
| Lym(%) | MAN1C1, mean, intra | NPM1, mean, intra | 0.5 | −0.07 | 75 | 83 | 61 | 78 | 68 |
| Lym(%) | MAN1C1, mean, intra | OAS2, mean, intra | 0.4 | −0.09 | 73 | 81 | 61 | 78 | 66 |
| Lym(%) | MAN1C1, mean, intra | PARP12, mean, intra | 0.4 | −0.1 | 73 | 83 | 58 | 77 | 67 |
| Lym(%) | MAN1C1, mean, intra | PTEN, mean, intra | 0.5 | −0.07 | 75 | 85 | 58 | 77 | 69 |
| Lym(%) | MAN1C1, mean, intra | RSAD2, mean, intra | 0.6 | −0.02 | 82 | 85 | 77 | 86 | 75 |
| Lym(%) | MAN1C1, mean, intra | SDCBP, mean, intra | 0.5 | 0.01 | 78 | 87 | 65 | 80 | 74 |
| Lym(%) | MAN1C1, mean, intra | WBC | 0.4 | −0.11 | 73 | 87 | 52 | 75 | 70 |
| Lym(%) | MX1, mean, intra | Neu(%) | 0.6 | 0.06 | 81 | 85 | 77 | 81 | 81 |
| Lym(%) | MX1, mean, intra | NPM1, mean, intra | 0.6 | 0.06 | 80 | 84 | 74 | 84 | 74 |
| Lym(%) | MX1, mean, intra | OAS2, mean, intra | 0.6 | 0.1 | 81 | 83 | 79 | 82 | 80 |
| Lym(%) | MX1, mean, intra | PARP12, mean, intra | 0.6 | 0.1 | 82 | 87 | 74 | 84 | 78 |
| Lym(%) | MX1, mean, intra | PTEN, mean, intra | 0.6 | 0.06 | 80 | 85 | 72 | 83 | 76 |
| Lym(%) | MX1, mean, intra | RSAD2, mean, intra | 0.6 | 0 | 82 | 82 | 82 | 84 | 80 |
| Lym(%) | MX1, mean, intra | SDCBP, mean, intra | 0.6 | 0.12 | 83 | 87 | 77 | 85 | 79 |
| Lym(%) | MX1, mean, intra | WBC | 0.7 | 0.15 | 84 | 86 | 81 | 84 | 83 |
| Lym(%) | Neu(%) | OAS2, mean, intra | 0.6 | −0.01 | 78 | 78 | 77 | 80 | 75 |
| Lym(%) | Neu(%) | PARP12, mean, intra | 0.6 | −0.01 | 78 | 81 | 74 | 83 | 71 |
| Lym(%) | Neu(%) | PTEN, mean, intra | 0.5 | −0.11 | 73 | 74 | 72 | 81 | 64 |
| Lym(%) | Neu(%) | RSAD2, mean, intra | 0.6 | −0.03 | 81 | 81 | 81 | 83 | 78 |
| Lym(%) | Neu(%) | SDCBP, mean, intra | 0.5 | −0.08 | 75 | 79 | 69 | 80 | 68 |

TABLE 3-continued

The classification accuracy of bacterial vs. viral infected patients computed over pairs of features.
DETERMINANT measurements were measured over cell population mean. (mean triplets)

| Feature #1 | Feature #2 | Feature #3 | MCC | dMCC | Total accuracy % | Sen % | Spe % | PPV % | NPV % |
|---|---|---|---|---|---|---|---|---|---|
| Lym(%) | Neu(%) | WBC | 0.6 | 0 | 78 | 77 | 79 | 82 | 74 |
| Lym(%) | NPM1, mean, intra | Neu(%) | 0.6 | 0 | 79 | 84 | 72 | 82 | 74 |
| Lym(%) | NPM1, mean, intra | OAS2, mean, intra | 0.5 | 0.02 | 78 | 80 | 74 | 83 | 71 |
| Lym(%) | NPM1, mean, intra | PARP12, mean, intra | 0.6 | 0.04 | 79 | 82 | 74 | 83 | 73 |
| Lym(%) | NPM1, mean, intra | PTEN, mean, intra | 0.5 | 0.02 | 78 | 82 | 72 | 82 | 72 |
| Lym(%) | NPM1, mean, intra | RSAD2, mean, intra | 0.7 | 0.02 | 84 | 87 | 79 | 87 | 79 |
| Lym(%) | NPM1, mean, intra | SDCBP, mean, intra | 0.5 | −0.06 | 74 | 77 | 69 | 80 | 66 |
| Lym(%) | NPM1, mean, intra | WBC | 0.5 | 0.01 | 78 | 87 | 64 | 79 | 76 |
| Lym(%) | OAS2, mean, intra | PARP12, mean, intra | 0.5 | 0 | 77 | 81 | 72 | 82 | 70 |
| Lym(%) | OAS2, mean, intra | PTEN, mean, intra | 0.6 | 0.03 | 78 | 81 | 74 | 83 | 71 |
| Lym(%) | OAS2, mean, intra | RSAD2, mean, intra | 0.6 | −0.01 | 81 | 81 | 82 | 84 | 78 |
| Lym(%) | OAS2, mean, intra | SDCBP, mean, intra | 0.4 | −0.08 | 73 | 75 | 69 | 79 | 64 |
| Lym(%) | OAS2, mean, intra | WBC | 0.6 | 0.06 | 79 | 81 | 77 | 81 | 77 |
| Lym(%) | PARP12, mean, intra | PTEN, mean, intra | 0.6 | 0.03 | 78 | 81 | 74 | 83 | 71 |
| Lym(%) | PARP12, mean, intra | RSAD2, mean, intra | 0.7 | 0.03 | 84 | 87 | 79 | 87 | 79 |
| Lym(%) | PARP12, mean, intra | SDCBP, mean, intra | 0.5 | −0.06 | 74 | 77 | 69 | 80 | 66 |
| Lym(%) | PARP12, mean, intra | WBC | 0.6 | 0.08 | 81 | 89 | 69 | 82 | 79 |
| Lym(%) | PTEN, mean, intra | RSAD2, mean, intra | 0.7 | 0.05 | 85 | 89 | 79 | 87 | 82 |
| Lym(%) | PTEN, mean, intra | SDCBP, mean, intra | 0.5 | −0.06 | 74 | 77 | 69 | 80 | 66 |
| Lym(%) | PTEN, mean, intra | WBC | 0.5 | −0.01 | 77 | 85 | 64 | 79 | 74 |
| Lym(%) | RSAD2, mean, intra | SDCBP, mean, intra | 0.6 | −0.01 | 82 | 84 | 79 | 86 | 76 |
| Lym(%) | RSAD2, mean, intra | WBC | 0.6 | −0.03 | 81 | 84 | 77 | 81 | 80 |
| Lym(%) | SDCBP, mean, intra | WBC | 0.5 | −0.03 | 76 | 84 | 64 | 78 | 71 |
| MAN1C1, mean, intra | MX1, mean, intra | Neu(%) | 0.7 | 0.1 | 84 | 90 | 74 | 85 | 82 |
| MAN1C1, mean, intra | MX1, mean, intra | NPM1, mean, intra | 0.3 | −0.12 | 69 | 75 | 58 | 75 | 58 |
| MAN1C1, mean, intra | MX1, mean, intra | OAS2, mean, intra | 0.3 | −0.12 | 69 | 75 | 58 | 75 | 58 |
| MAN1C1, mean, intra | MX1, mean, intra | PARP12, mean, intra | 0.5 | 0.03 | 76 | 83 | 65 | 80 | 69 |
| MAN1C1, mean, intra | MX1, mean, intra | PTEN, mean, intra | 0.4 | −0.08 | 71 | 81 | 55 | 75 | 63 |
| MAN1C1, mean, intra | MX1, mean, intra | RSAD2, mean, intra | 0.6 | −0.05 | 81 | 85 | 74 | 85 | 74 |
| MAN1C1, mean, intra | MX1, mean, intra | SDCBP, mean, intra | 0.3 | −0.14 | 67 | 73 | 58 | 75 | 56 |
| MAN1C1, mean, intra | MX1, mean, intra | WBC | 0.3 | −0.11 | 70 | 79 | 55 | 75 | 61 |
| MAN1C1, mean, intra | Neu(%) | OAS2, mean, intra | 0.5 | −0.09 | 76 | 85 | 61 | 79 | 70 |
| MAN1C1, mean, intra | Neu(%) | PARP12, mean, intra | 0.5 | −0.09 | 76 | 85 | 61 | 79 | 70 |
| MAN1C1, mean, intra | Neu(%) | PTEN, mean, intra | 0.5 | −0.09 | 76 | 85 | 61 | 79 | 70 |
| MAN1C1, mean, intra | Neu(%) | RSAD2, mean, intra | 0.6 | −0.05 | 81 | 85 | 74 | 85 | 74 |
| MAN1C1, mean, intra | Neu(%) | SDCBP, mean, intra | 0.6 | −0.01 | 80 | 88 | 65 | 81 | 77 |
| MAN1C1, mean, intra | Neu(%) | WBC | 0.4 | −0.15 | 73 | 87 | 52 | 75 | 70 |
| MAN1C1, mean, intra | NPM1, mean, intra | Neu(%) | 0.5 | −0.09 | 76 | 85 | 61 | 79 | 70 |
| MAN1C1, mean, intra | NPM1, mean, intra | OAS2, mean, intra | 0.2 | −0.1 | 64 | 77 | 42 | 69 | 52 |
| MAN1C1, mean, intra | NPM1, mean, intra | PARP12, mean, intra | 0.3 | 0.03 | 66 | 73 | 55 | 73 | 55 |
| MAN1C1, mean, intra | NPM1, mean, intra | PTEN, mean, intra | 0.3 | 0.09 | 67 | 77 | 52 | 73 | 57 |
| MAN1C1, mean, intra | NPM1, mean, intra | RSAD2, mean, intra | 0.6 | −0.05 | 81 | 85 | 74 | 85 | 74 |
| MAN1C1, mean, intra | NPM1, mean, intra | SDCBP, mean, intra | 0.4 | 0.24 | 71 | 81 | 55 | 75 | 63 |
| MAN1C1, mean, intra | NPM1, mean, intra | WBC | 0.3 | 0.01 | 67 | 85 | 39 | 70 | 60 |
| MAN1C1, mean, intra | OAS2, mean, intra | PARP12, mean, intra | 0.2 | −0.11 | 63 | 73 | 45 | 69 | 50 |
| MAN1C1, mean, intra | OAS2, mean, intra | PTEN, mean, intra | 0.3 | −0.04 | 66 | 77 | 48 | 71 | 56 |
| MAN1C1, mean, intra | OAS2, mean, intra | RSAD2, mean, intra | 0.6 | −0.08 | 80 | 85 | 71 | 83 | 73 |
| MAN1C1, mean, intra | OAS2, mean, intra | SDCBP, mean, intra | 0.3 | −0.02 | 67 | 81 | 45 | 71 | 58 |
| MAN1C1, mean, intra | OAS2, mean, intra | WBC | 0.2 | −0.13 | 64 | 83 | 32 | 67 | 53 |
| MAN1C1, mean, intra | PARP12, mean, intra | PTEN, mean, intra | 0.2 | −0.07 | 63 | 75 | 42 | 68 | 50 |
| MAN1C1, mean, intra | PARP12, mean, intra | RSAD2, mean, intra | 0.6 | −0.07 | 80 | 81 | 77 | 86 | 71 |
| MAN1C1, mean, intra | PARP12, mean, intra | SDCBP, mean, intra | 0.3 | 0.02 | 66 | 75 | 52 | 72 | 55 |
| MAN1C1, mean, intra | PARP12, mean, intra | WBC | 0.2 | −0.09 | 63 | 79 | 35 | 67 | 50 |
| MAN1C1, mean, intra | PTEN, mean, intra | RSAD2, mean, intra | 0.6 | −0.05 | 81 | 85 | 74 | 85 | 74 |
| MAN1C1, mean, intra | PTEN, mean, intra | SDCBP, mean, intra | 0.2 | 0.03 | 65 | 77 | 45 | 70 | 54 |
| MAN1C1, mean, intra | PTEN, mean, intra | WBC | 0.3 | 0.04 | 69 | 87 | 39 | 70 | 63 |
| MAN1C1, mean, intra | RSAD2, mean, intra | SDCBP, mean, intra | 0.6 | −0.03 | 82 | 87 | 74 | 85 | 77 |
| MAN1C1, mean, intra | RSAD2, mean, intra | WBC | 0.6 | −0.08 | 80 | 85 | 71 | 83 | 73 |
| MAN1C1, mean, intra | SDCBP, mean, intra | WBC | 0.2 | −0.08 | 64 | 83 | 32 | 67 | 53 |
| MX1, mean, intra | Neu(%) | OAS2, mean, intra | 0.6 | 0.03 | 80 | 83 | 76 | 80 | 80 |
| MX1, mean, intra | Neu(%) | PARP12, mean, intra | 0.6 | 0.04 | 81 | 85 | 74 | 84 | 76 |
| MX1, mean, intra | Neu(%) | PTEN, mean, intra | 0.6 | 0.06 | 82 | 87 | 74 | 84 | 78 |
| MX1, mean, intra | Neu(%) | RSAD2, mean, intra | 0.6 | −0.03 | 81 | 81 | 81 | 83 | 78 |
| MX1, mean, intra | Neu(%) | SDCBP, mean, intra | 0.7 | 0.1 | 84 | 87 | 79 | 87 | 79 |
| MX1, mean, intra | Neu(%) | WBC | 0.6 | 0.08 | 82 | 85 | 79 | 82 | 82 |
| MX1, mean, intra | NPM1, mean, intra | Neu(%) | 0.6 | 0.06 | 82 | 85 | 77 | 85 | 77 |
| MX1, mean, intra | NPM1, mean, intra | OAS2, mean, intra | 0.3 | −0.11 | 68 | 70 | 64 | 75 | 58 |
| MX1, mean, intra | NPM1, mean, intra | PARP12, mean, intra | 0.5 | 0.03 | 75 | 77 | 72 | 81 | 67 |
| MX1, mean, intra | NPM1, mean, intra | PTEN, mean, intra | 0.3 | −0.13 | 67 | 70 | 62 | 74 | 57 |
| MX1, mean, intra | NPM1, mean, intra | RSAD2, mean, intra | 0.6 | −0.01 | 82 | 84 | 79 | 86 | 76 |
| MX1, mean, intra | NPM1, mean, intra | SDCBP, mean, intra | 0.4 | −0.09 | 69 | 72 | 64 | 76 | 60 |
| MX1, mean, intra | NPM1, mean, intra | WBC | 0.5 | 0.02 | 75 | 82 | 64 | 78 | 69 |
| MX1, mean, intra | OAS2, mean, intra | PARP12, mean, intra | 0.5 | 0.02 | 74 | 76 | 72 | 81 | 65 |
| MX1, mean, intra | OAS2, mean, intra | PTEN, mean, intra | 0.4 | −0.02 | 73 | 81 | 62 | 77 | 67 |

TABLE 3-continued

The classification accuracy of bacterial vs. viral infected patients computed over pairs of features.
DETERMINANT measurements were measured over cell population mean. (mean triplets)

| Feature #1 | Feature #2 | Feature #3 | MCC | dMCC | Total accuracy % | Sen % | Spe % | PPV % | NPV % |
|---|---|---|---|---|---|---|---|---|---|
| MX1, mean, intra | OAS2, mean, intra | RSAD2, mean, intra | 0.6 | −0.06 | 79 | 76 | 82 | 83 | 75 |
| MX1, mean, intra | OAS2, mean, intra | SDCBP, mean, intra | 0.4 | −0.04 | 72 | 77 | 64 | 77 | 64 |
| MX1, mean, intra | OAS2, mean, intra | WBC | 0.4 | −0.01 | 72 | 68 | 76 | 77 | 67 |
| MX1, mean, intra | PARP12, mean, intra | PTEN, mean, intra | 0.5 | 0.03 | 75 | 79 | 69 | 80 | 68 |
| MX1, mean, intra | PARP12, mean, intra | RSAD2, mean, intra | 0.6 | −0.03 | 81 | 82 | 79 | 86 | 74 |
| MX1, mean, intra | PARP12, mean, intra | SDCBP, mean, intra | 0.5 | 0.07 | 77 | 79 | 74 | 83 | 69 |
| MX1, mean, intra | PARP12, mean, intra | WBC | 0.4 | −0.02 | 73 | 79 | 64 | 78 | 66 |
| MX1, mean, intra | PTEN, mean, intra | RSAD2, mean, intra | 0.6 | −0.03 | 81 | 82 | 79 | 86 | 74 |
| MX1, mean, intra | PTEN, mean, intra | SDCBP, mean, intra | 0.4 | −0.06 | 71 | 77 | 62 | 76 | 63 |
| MX1, mean, intra | PTEN, mean, intra | WBC | 0.4 | −0.02 | 73 | 79 | 64 | 78 | 66 |
| MX1, mean, intra | RSAD2, mean, intra | SDCBP, mean, intra | 0.6 | −0.01 | 82 | 84 | 79 | 86 | 76 |
| MX1, mean, intra | RSAD2, mean, intra | WBC | 0.6 | −0.06 | 79 | 78 | 81 | 82 | 76 |
| MX1, mean, intra | SDCBP, mean, intra | WBC | 0.5 | 0.02 | 75 | 82 | 64 | 78 | 69 |
| Neu(%) | OAS2, mean, intra | PARP12, mean, intra | 0.6 | 0.08 | 83 | 87 | 77 | 86 | 79 |
| Neu(%) | OAS2, mean, intra | PTEN, mean, intra | 0.6 | 0.08 | 83 | 89 | 74 | 85 | 81 |
| Neu(%) | OAS2, mean, intra | RSAD2, mean, intra | 0.7 | 0.05 | 84 | 85 | 84 | 86 | 83 |
| Neu(%) | OAS2, mean, intra | SDCBP, mean, intra | 0.5 | −0.08 | 75 | 79 | 69 | 80 | 68 |
| Neu(%) | OAS2, mean, intra | WBC | 0.5 | −0.04 | 76 | 78 | 74 | 78 | 74 |
| Neu(%) | PARP12, mean, intra | PTEN, mean, intra | 0.6 | 0.06 | 82 | 89 | 72 | 83 | 80 |
| Neu(%) | PARP12, mean, intra | RSAD2, mean, intra | 0.6 | 0 | 83 | 87 | 77 | 86 | 79 |
| Neu(%) | PARP12, mean, intra | SDCBP, mean, intra | 0.5 | −0.04 | 77 | 80 | 72 | 82 | 70 |
| Neu(%) | PARP12, mean, intra | WBC | 0.6 | 0.01 | 80 | 89 | 67 | 81 | 79 |
| Neu(%) | PTEN, mean, intra | RSAD2, mean, intra | 0.7 | 0.02 | 84 | 89 | 77 | 86 | 81 |
| Neu(%) | PTEN, mean, intra | SDCBP, mean, intra | 0.5 | −0.03 | 78 | 84 | 69 | 81 | 73 |
| Neu(%) | PTEN, mean, intra | WBC | 0.5 | −0.03 | 78 | 87 | 64 | 79 | 76 |
| Neu(%) | RSAD2, mean, intra | SDCBP, mean, intra | 0.6 | 0 | 83 | 87 | 77 | 85 | 79 |
| Neu(%) | RSAD2, mean, intra | WBC | 0.7 | 0.02 | 83 | 82 | 84 | 86 | 80 |
| Neu(%) | SDCBP, mean, intra | WBC | 0.5 | −0.07 | 76 | 84 | 64 | 78 | 71 |
| NPM1, mean, intra | Neu(%) | OAS2, mean, intra | 0.6 | −0.01 | 79 | 85 | 69 | 81 | 75 |
| NPM1, mean, intra | Neu(%) | PARP12, mean, intra | 0.6 | 0 | 79 | 84 | 72 | 82 | 74 |
| NPM1, mean, intra | Neu(%) | PTEN, mean, intra | 0.6 | −0.01 | 79 | 85 | 69 | 81 | 75 |
| NPM1, mean, intra | Neu(%) | RSAD2, mean, intra | 0.6 | 0 | 83 | 87 | 77 | 85 | 79 |
| NPM1, mean, intra | Neu(%) | SDCBP, mean, intra | 0.5 | −0.05 | 77 | 82 | 69 | 81 | 71 |
| NPM1, mean, intra | Neu(%) | WBC | 0.5 | −0.03 | 78 | 89 | 62 | 78 | 77 |
| NPM1, mean, intra | OAS2, mean, intra | PARP12, mean, intra | 0.2 | −0.08 | 63 | 70 | 51 | 69 | 53 |
| NPM1, mean, intra | OAS2, mean, intra | PTEN, mean, intra | 0.1 | −0.2 | 58 | 69 | 41 | 65 | 46 |
| NPM1, mean, intra | OAS2, mean, intra | RSAD2, mean, intra | 0.6 | −0.01 | 82 | 84 | 79 | 86 | 76 |
| NPM1, mean, intra | OAS2, mean, intra | SDCBP, mean, intra | 0.1 | −0.23 | 58 | 75 | 31 | 63 | 44 |
| NPM1, mean, intra | OAS2, mean, intra | WBC | 0.3 | 0 | 68 | 82 | 46 | 70 | 62 |
| NPM1, mean, intra | PARP12, mean, intra | PTEN, mean, intra | 0.2 | −0.04 | 63 | 72 | 49 | 69 | 53 |
| NPM1, mean, intra | PARP12, mean, intra | RSAD2, mean, intra | 0.6 | −0.07 | 79 | 80 | 77 | 84 | 71 |
| NPM1, mean, intra | PARP12, mean, intra | SDCBP, mean, intra | 0.2 | −0.05 | 62 | 69 | 51 | 69 | 51 |
| NPM1, mean, intra | PARP12, mean, intra | WBC | 0.3 | 0.06 | 68 | 80 | 49 | 71 | 61 |
| NPM1, mean, intra | PTEN, mean, intra | RSAD2, mean, intra | 0.6 | −0.06 | 80 | 82 | 77 | 85 | 73 |
| NPM1, mean, intra | PTEN, mean, intra | SDCBP, mean, intra | 0.2 | −0.05 | 61 | 74 | 41 | 66 | 50 |
| NPM1, mean, intra | PTEN, mean, intra | WBC | 0.3 | 0.05 | 68 | 84 | 44 | 70 | 63 |
| NPM1, mean, intra | RSAD2, mean, intra | SDCBP, mean, intra | 0.6 | −0.06 | 80 | 82 | 77 | 85 | 73 |
| NPM1, mean, intra | RSAD2, mean, intra | WBC | 0.6 | −0.04 | 81 | 84 | 77 | 85 | 75 |
| NPM1, mean, intra | SDCBP, mean, intra | WBC | 0.3 | 0.07 | 69 | 84 | 46 | 71 | 64 |
| OAS2, mean, intra | PARP12, mean, intra | PTEN, mean, intra | 0.2 | −0.11 | 62 | 73 | 46 | 68 | 51 |
| OAS2, mean, intra | PARP12, mean, intra | RSAD2, mean, intra | 0.7 | 0.03 | 84 | 87 | 79 | 87 | 79 |
| OAS2, mean, intra | PARP12, mean, intra | SDCBP, mean, intra | 0.2 | −0.11 | 62 | 70 | 49 | 68 | 51 |
| OAS2, mean, intra | PARP12, mean, intra | WBC | 0.3 | 0.01 | 68 | 82 | 46 | 71 | 62 |
| OAS2, mean, intra | PTEN, mean, intra | RSAD2, mean, intra | 0.6 | −0.01 | 82 | 84 | 79 | 87 | 76 |
| OAS2, mean, intra | PTEN, mean, intra | SDCBP, mean, intra | 0.2 | −0.09 | 63 | 74 | 46 | 68 | 53 |
| OAS2, mean, intra | PTEN, mean, intra | WBC | 0.3 | 0 | 68 | 85 | 41 | 70 | 64 |
| OAS2, mean, intra | RSAD2, mean, intra | SDCBP, mean, intra | 0.6 | −0.04 | 81 | 84 | 77 | 85 | 75 |
| OAS2, mean, intra | RSAD2, mean, intra | WBC | 0.6 | −0.01 | 81 | 79 | 84 | 85 | 78 |
| OAS2, mean, intra | SDCBP, mean, intra | WBC | 0.2 | −0.07 | 65 | 80 | 41 | 68 | 57 |
| PARP12, mean, intra | PTEN, mean, intra | RSAD2, mean, intra | 0.6 | −0.01 | 82 | 84 | 79 | 87 | 76 |
| PARP12, mean, intra | PTEN, mean, intra | SDCBP, mean, intra | 0.2 | −0.04 | 63 | 74 | 46 | 68 | 53 |
| PARP12, mean, intra | PTEN, mean, intra | WBC | 0.3 | 0.04 | 67 | 81 | 46 | 70 | 60 |
| PARP12, mean, intra | RSAD2, mean, intra | SDCBP, mean, intra | 0.6 | −0.07 | 79 | 80 | 77 | 84 | 71 |
| PARP12, mean, intra | RSAD2, mean, intra | WBC | 0.6 | −0.05 | 80 | 82 | 77 | 85 | 73 |
| PARP12, mean, intra | SDCBP, mean, intra | WBC | 0.3 | 0.05 | 68 | 84 | 44 | 70 | 63 |
| PTEN, mean, intra | RSAD2, mean, intra | SDCBP, mean, intra | 0.6 | −0.03 | 81 | 82 | 79 | 86 | 74 |
| PTEN, mean, intra | RSAD2, mean, intra | WBC | 0.6 | −0.07 | 79 | 79 | 79 | 86 | 70 |
| PTEN, mean, intra | SDCBP, mean, intra | WBC | 0.3 | 0.03 | 67 | 82 | 44 | 69 | 61 |
| RSAD2, mean, intra | SDCBP, mean, intra | WBC | 0.6 | −0.05 | 80 | 80 | 79 | 86 | 72 |

* Positive and negative correspond to bacterial and viral infected patients respectively
*dMCC is the improvement of the MCC of a triplet over the maximal MCC attained in any of the corresponding individual features.

TABLE 4

The classification accuracy of bacterial vs. viral infected patients computed over pairs of features. DETERMINANT measurements were measured over different cell types.

| Feature #1 | Feature #2 | MCC | dMCC | Total accuracy % | Sen % | Spe % | PPV % | NPV % |
|---|---|---|---|---|---|---|---|---|
| ABTB1, gran, intra | ABTB1, mono, intra | 0.12 | 0 | 63 | 87 | 22 | 66 | 50 |
| ABTB1, gran, intra | ANC | 0.42 | −0.02 | 74 | 95 | 39 | 73 | 80 |
| ABTB1, gran, intra | CORO1A, gran, intra | 0.25 | 0.09 | 67 | 80 | 44 | 71 | 56 |
| ABTB1, gran, intra | CORO1A, mean, intra | 0.29 | 0.14 | 68 | 78 | 50 | 73 | 57 |
| ABTB1, gran, intra | CORO1A, mono, intra | 0.25 | 0.09 | 67 | 80 | 44 | 71 | 56 |
| ABTB1, gran, intra | CRP | 0.74 | 0.18 | 88 | 96 | 74 | 86 | 92 |
| ABTB1, gran, intra | CSDA, gran, intra | 0.34 | 0.22 | 70 | 79 | 55 | 75 | 61 |
| ABTB1, gran, intra | CSDA, mono, intra | 0.34 | 0.22 | 70 | 79 | 55 | 75 | 61 |
| ABTB1, gran, intra | EIF4B, gran, intra | 0.26 | −0.12 | 67 | 78 | 47 | 72 | 56 |
| ABTB1, gran, intra | EIF4B, lymp, intra | 0.36 | −0.04 | 71 | 82 | 53 | 75 | 63 |
| ABTB1, gran, intra | EIF4B, mean, intra | 0.25 | −0.06 | 67 | 82 | 41 | 70 | 57 |
| ABTB1, gran, intra | EIF4B, mono, intra | 0.26 | −0.12 | 67 | 78 | 47 | 72 | 56 |
| ABTB1, gran, intra | EPSTI1, lymp, membrane | 0.32 | 0.13 | 69 | 79 | 52 | 74 | 59 |
| ABTB1, gran, intra | GAS7, lymp, intra | 0.27 | 0.15 | 67 | 77 | 48 | 72 | 56 |
| ABTB1, gran, intra | IFI6, gran, intra | 0.07 | −0.05 | 61 | 84 | 22 | 65 | 44 |
| ABTB1, gran, intra | IFI6, mono, intra | 0.07 | −0.05 | 61 | 84 | 22 | 65 | 44 |
| ABTB1, gran, intra | IFIT3, gran, intra | 0.28 | −0.11 | 68 | 82 | 44 | 71 | 58 |
| ABTB1, gran, intra | IFIT3, lymp, intra | 0.25 | −0.18 | 66 | 75 | 50 | 72 | 53 |
| ABTB1, gran, intra | IFIT3, mean, intra | 0.13 | −0.12 | 61 | 75 | 38 | 67 | 46 |
| ABTB1, gran, intra | IFIT3, mono, intra | 0.28 | −0.11 | 68 | 82 | 44 | 71 | 58 |
| ABTB1, gran, intra | IFITM1, gran, membrane | 0.04 | −0.22 | 61 | 87 | 16 | 64 | 42 |
| ABTB1, gran, intra | IFITM1, lymp, membrane | 0.31 | −0.07 | 69 | 82 | 47 | 73 | 60 |
| ABTB1, gran, intra | IFITM1, mean, membrane | 0.04 | −0.25 | 61 | 87 | 16 | 64 | 42 |
| ABTB1, gran, intra | IFITM1, mono, membrane | 0.02 | −0.29 | 57 | 76 | 25 | 64 | 38 |
| ABTB1, gran, intra | IFITM3, gran, membrane | 0.06 | −0.29 | 61 | 85 | 19 | 64 | 43 |
| ABTB1, gran, intra | IFITM3, mean, membrane | 0.06 | −0.29 | 61 | 85 | 19 | 64 | 43 |
| ABTB1, gran, intra | IFITM3, mono, membrane | 0.23 | −0.18 | 66 | 78 | 44 | 70 | 54 |
| ABTB1, gran, intra | LOC26010, gran, intra | 0.11 | −0.12 | 62 | 84 | 25 | 66 | 47 |
| ABTB1, gran, intra | LOC26010, mean, intra | 0.07 | −0.14 | 61 | 84 | 22 | 65 | 44 |
| ABTB1, gran, intra | LOC26010, mono, intra | 0.11 | −0.12 | 62 | 84 | 25 | 66 | 47 |
| ABTB1, gran, intra | LY6E, lymp, membrane | 0.3 | 0.07 | 69 | 85 | 42 | 71 | 62 |
| ABTB1, gran, intra | Lym(%) | 0.55 | 0.03 | 79 | 85 | 69 | 82 | 73 |
| ABTB1, gran, intra | MAN1C1, gran, intra | 0.27 | 0.15 | 67 | 83 | 42 | 70 | 59 |
| ABTB1, gran, intra | MAN1C1, mean, intra | 0.24 | 0.11 | 66 | 83 | 39 | 69 | 57 |
| ABTB1, gran, intra | MAN1C1, mono, intra | 0.27 | 0.15 | 67 | 83 | 42 | 70 | 59 |
| ABTB1, gran, intra | MX1, gran, intra | 0.42 | −0.12 | 74 | 82 | 59 | 78 | 66 |
| ABTB1, gran, intra | MX1, lymp, intra | 0.29 | −0.06 | 68 | 78 | 50 | 73 | 57 |
| ABTB1, gran, intra | MX1, mean, intra | 0.4 | −0.05 | 72 | 80 | 59 | 77 | 63 |
| ABTB1, gran, intra | MX1, mono, intra | 0.42 | −0.12 | 74 | 82 | 59 | 78 | 66 |
| ABTB1, gran, intra | Neu(%) | 0.58 | 0.02 | 80 | 85 | 72 | 84 | 74 |
| ABTB1, gran, intra | NPM1, gran, intra | 0.12 | 0 | 62 | 80 | 31 | 66 | 48 |
| ABTB1, gran, intra | NPM1, mean, intra | 0.18 | 0.05 | 64 | 81 | 34 | 68 | 52 |
| ABTB1, gran, intra | NPM1, mono, intra | 0.12 | 0 | 62 | 80 | 31 | 66 | 48 |
| ABTB1, gran, intra | OAS2, gran, intra | 0.1 | −0.26 | 61 | 78 | 31 | 66 | 45 |
| ABTB1, gran, intra | OAS2, mean, intra | 0.06 | −0.24 | 61 | 85 | 19 | 64 | 43 |
| ABTB1, gran, intra | OAS2, mono, intra | 0.1 | −0.26 | 61 | 78 | 31 | 66 | 45 |
| ABTB1, gran, intra | PARP12, gran, intra | 0.08 | −0.11 | 60 | 76 | 31 | 66 | 43 |
| ABTB1, gran, intra | PARP12, mean, intra | 0.21 | −0.04 | 64 | 76 | 44 | 70 | 52 |
| ABTB1, gran, intra | PARP12, mono, intra | 0.08 | −0.11 | 60 | 76 | 31 | 66 | 43 |
| ABTB1, gran, intra | PARP9, lymp, intra | 0.12 | −0.02 | 63 | 87 | 22 | 66 | 50 |
| ABTB1, gran, intra | PDIA6, gran, intra | 0.23 | 0.1 | 65 | 79 | 42 | 70 | 54 |
| ABTB1, gran, intra | PDIA6, lymp, intra | 0.27 | 0.15 | 67 | 77 | 48 | 72 | 56 |
| ABTB1, gran, intra | PDIA6, mono, intra | 0.23 | 0.1 | 65 | 79 | 42 | 70 | 54 |
| ABTB1, gran, intra | PTEN, gran, intra | 0.18 | −0.04 | 63 | 76 | 41 | 69 | 50 |
| ABTB1, gran, intra | PTEN, lymp, intra | 0.19 | 0.07 | 64 | 80 | 38 | 69 | 52 |
| ABTB1, gran, intra | PTEN, mean, intra | 0.16 | −0.04 | 63 | 80 | 34 | 68 | 50 |
| ABTB1, gran, intra | PTEN, mono, intra | 0.18 | −0.04 | 63 | 76 | 41 | 69 | 50 |
| ABTB1, gran, intra | RSAD2, gran, intra | 0.68 | 0.05 | 85 | 89 | 78 | 88 | 81 |
| ABTB1, gran, intra | RSAD2, lymp, intra | 0.23 | 0 | 66 | 78 | 44 | 70 | 54 |
| ABTB1, gran, intra | RSAD2, mean, intra | 0.63 | −0.01 | 83 | 87 | 75 | 86 | 77 |
| ABTB1, gran, intra | RSAD2, mono, intra | 0.68 | 0.05 | 85 | 89 | 78 | 88 | 81 |
| ABTB1, gran, intra | SDCBP, mean, intra | 0.18 | 0.06 | 64 | 81 | 34 | 68 | 52 |
| ABTB1, gran, intra | WBC | 0.32 | 0.07 | 70 | 89 | 38 | 71 | 67 |
| ABTB1, mono, intra | ANC | 0.42 | −0.02 | 74 | 95 | 39 | 73 | 80 |
| ABTB1, mono, intra | CORO1A, gran, intra | 0.25 | 0.09 | 67 | 80 | 44 | 71 | 56 |
| ABTB1, mono, intra | CORO1A, mean, intra | 0.29 | 0.14 | 68 | 78 | 50 | 73 | 57 |
| ABTB1, mono, intra | CORO1A, mono, intra | 0.25 | 0.09 | 67 | 80 | 44 | 71 | 56 |
| ABTB1, mono, intra | CRP | 0.74 | 0.18 | 88 | 96 | 74 | 86 | 92 |
| ABTB1, mono, intra | CSDA, gran, intra | 0.34 | 0.22 | 70 | 79 | 55 | 75 | 61 |
| ABTB1, mono, intra | CSDA, mono, intra | 0.34 | 0.22 | 70 | 79 | 55 | 75 | 61 |
| ABTB1, mono, intra | EIF4B, gran, intra | 0.26 | −0.12 | 67 | 78 | 47 | 72 | 56 |
| ABTB1, mono, intra | EIF4B, lymp, intra | 0.36 | −0.04 | 71 | 82 | 53 | 75 | 63 |
| ABTB1, mono, intra | EIF4B, mean, intra | 0.25 | −0.06 | 67 | 82 | 41 | 70 | 57 |
| ABTB1, mono, intra | EIF4B, mono, intra | 0.26 | −0.12 | 67 | 78 | 47 | 72 | 56 |

TABLE 4-continued

The classification accuracy of bacterial vs. viral infected patients computed over pairs of features. DETERMINANT measurements were measured over different cell types.

| Feature #1 | Feature #2 | MCC | dMCC | Total accuracy % | Sen % | Spe % | PPV % | NPV % |
|---|---|---|---|---|---|---|---|---|
| ABTB1, mono, intra | EPSTI1, lymp, membrane | 0.32 | 0.13 | 69 | 79 | 52 | 74 | 59 |
| ABTB1, mono, intra | GAS7, lymp, intra | 0.27 | 0.15 | 67 | 77 | 48 | 72 | 56 |
| ABTB1, mono, intra | IFI6, gran, intra | 0.07 | −0.05 | 61 | 84 | 22 | 65 | 44 |
| ABTB1, mono, intra | IFI6, mono, intra | 0.07 | −0.05 | 61 | 84 | 22 | 65 | 44 |
| ABTB1, mono, intra | IFIT3, gran, intra | 0.28 | −0.11 | 68 | 82 | 44 | 71 | 58 |
| ABTB1, mono, intra | IFIT3, lymp, intra | 0.25 | −0.18 | 66 | 75 | 50 | 72 | 53 |
| ABTB1, mono, intra | IFIT3, mean, intra | 0.13 | −0.12 | 61 | 75 | 38 | 67 | 46 |
| ABTB1, mono, intra | IFIT3, mono, intra | 0.28 | −0.11 | 68 | 82 | 44 | 71 | 58 |
| ABTB1, mono, intra | IFITM1, gran, membrane | 0.04 | −0.22 | 61 | 87 | 16 | 64 | 42 |
| ABTB1, mono, intra | IFITM1, lymp, membrane | 0.31 | −0.07 | 69 | 82 | 47 | 73 | 60 |
| ABTB1, mono, intra | IFITM1, mean, membrane | 0.04 | −0.25 | 61 | 87 | 16 | 64 | 42 |
| ABTB1, mono, intra | IFITM1, mono, membrane | 0.02 | −0.29 | 57 | 76 | 25 | 64 | 38 |
| ABTB1, mono, intra | IFITM3, gran, membrane | 0.06 | −0.29 | 61 | 85 | 19 | 64 | 43 |
| ABTB1, mono, intra | IFITM3, mean, membrane | 0.06 | −0.29 | 61 | 85 | 19 | 64 | 43 |
| ABTB1, mono, intra | IFITM3, mono, membrane | 0.23 | −0.18 | 66 | 78 | 44 | 70 | 54 |
| ABTB1, mono, intra | LOC26010, gran, intra | 0.11 | −0.12 | 62 | 84 | 25 | 66 | 47 |
| ABTB1, mono, intra | LOC26010, mean, intra | 0.07 | −0.14 | 61 | 84 | 22 | 65 | 44 |
| ABTB1, mono, intra | LOC26010, mono, intra | 0.11 | −0.12 | 62 | 84 | 25 | 66 | 47 |
| ABTB1, mono, intra | LY6E, lymp, membrane | 0.3 | 0.07 | 69 | 85 | 42 | 71 | 62 |
| ABTB1, mono, intra | Lym(%) | 0.55 | 0.03 | 79 | 85 | 69 | 82 | 73 |
| ABTB1, mono, intra | MAN1C1, gran, intra | 0.27 | 0.15 | 67 | 83 | 42 | 70 | 59 |
| ABTB1, mono, intra | MAN1C1, mean, intra | 0.24 | 0.11 | 66 | 83 | 39 | 69 | 57 |
| ABTB1, mono, intra | MAN1C1, mono, intra | 0.27 | 0.15 | 67 | 83 | 42 | 70 | 59 |
| ABTB1, mono, intra | MX1, gran, intra | 0.42 | −0.12 | 74 | 82 | 59 | 78 | 66 |
| ABTB1, mono, intra | MX1, lymp, intra | 0.29 | −0.06 | 68 | 78 | 50 | 73 | 57 |
| ABTB1, mono, intra | MX1, mean, intra | 0.4 | −0.05 | 72 | 80 | 59 | 77 | 63 |
| ABTB1, mono, intra | MX1, mono, intra | 0.42 | −0.12 | 74 | 82 | 59 | 78 | 66 |
| ABTB1, mono, intra | Neu(%) | 0.58 | 0.02 | 80 | 85 | 72 | 84 | 74 |
| ABTB1, mono, intra | NPM1, gran, intra | 0.12 | 0 | 62 | 80 | 31 | 66 | 48 |
| ABTB1, mono, intra | NPM1, mean, intra | 0.18 | 0.05 | 64 | 81 | 34 | 68 | 52 |
| ABTB1, mono, intra | NPM1, mono, intra | 0.12 | 0 | 62 | 80 | 31 | 66 | 48 |
| ABTB1, mono, intra | OAS2, gran, intra | 0.1 | −0.26 | 61 | 78 | 31 | 66 | 45 |
| ABTB1, mono, intra | OAS2, mean, intra | 0.06 | −0.24 | 61 | 85 | 19 | 64 | 43 |
| ABTB1, mono, intra | OAS2, mono, intra | 0.1 | −0.26 | 61 | 78 | 31 | 66 | 45 |
| ABTB1, mono, intra | PARP12, gran, intra | 0.08 | −0.11 | 60 | 76 | 31 | 66 | 43 |
| ABTB1, mono, intra | PARP12, mean, intra | 0.21 | −0.04 | 64 | 76 | 44 | 70 | 52 |
| ABTB1, mono, intra | PARP12, mono, intra | 0.08 | −0.11 | 60 | 76 | 31 | 66 | 43 |
| ABTB1, mono, intra | PARP9, lymp, intra | 0.12 | −0.02 | 63 | 87 | 22 | 66 | 50 |
| ABTB1, mono, intra | PDIA6, gran, intra | 0.23 | 0.1 | 65 | 79 | 42 | 70 | 54 |
| ABTB1, mono, intra | PDIA6, lymp, intra | 0.27 | 0.15 | 67 | 77 | 48 | 72 | 56 |
| ABTB1, mono, intra | PDIA6, mono, intra | 0.23 | 0.1 | 65 | 79 | 42 | 70 | 54 |
| ABTB1, mono, intra | PTEN, gran, intra | 0.18 | −0.04 | 63 | 76 | 41 | 69 | 50 |
| ABTB1, mono, intra | PTEN, lymp, intra | 0.19 | 0.07 | 64 | 80 | 38 | 69 | 52 |
| ABTB1, mono, intra | PTEN, mean, intra | 0.16 | −0.04 | 63 | 80 | 34 | 68 | 50 |
| ABTB1, mono, intra | PTEN, mono, intra | 0.18 | −0.04 | 63 | 76 | 41 | 69 | 50 |
| ABTB1, mono, intra | RSAD2, gran, intra | 0.68 | 0.05 | 85 | 89 | 78 | 88 | 81 |
| ABTB1, mono, intra | RSAD2, lymp, intra | 0.23 | 0 | 66 | 78 | 44 | 70 | 54 |
| ABTB1, mono, intra | RSAD2, mean, intra | 0.63 | −0.01 | 83 | 87 | 75 | 86 | 77 |
| ABTB1, mono, intra | RSAD2, mono, intra | 0.68 | 0.05 | 85 | 89 | 78 | 88 | 81 |
| ABTB1, mono, intra | SDCBP, mean, intra | 0.18 | 0.06 | 64 | 81 | 34 | 68 | 52 |
| ABTB1, mono, intra | WBC | 0.32 | 0.07 | 70 | 89 | 38 | 71 | 67 |
| ANC | CORO1A, gran, intra | 0.41 | −0.03 | 74 | 92 | 42 | 73 | 76 |
| ANC | CORO1A, mean, intra | 0.41 | −0.03 | 73 | 92 | 42 | 72 | 76 |
| ANC | CORO1A, mono, intra | 0.41 | −0.03 | 74 | 92 | 42 | 73 | 76 |
| ANC | CRP | 0.58 | 0.02 | 80 | 87 | 70 | 83 | 76 |
| ANC | CSDA, gran, intra | 0.39 | −0.05 | 73 | 90 | 43 | 73 | 72 |
| ANC | CSDA, mono, intra | 0.39 | −0.05 | 73 | 90 | 43 | 73 | 72 |
| ANC | EIF4B, gran, intra | 0.53 | 0.09 | 78 | 91 | 58 | 78 | 79 |
| ANC | EIF4B, lymp, intra | 0.5 | 0.06 | 77 | 92 | 53 | 77 | 80 |
| ANC | EIF4B, mean, intra | 0.5 | 0.06 | 77 | 92 | 53 | 76 | 80 |
| ANC | EIF4B, mono, intra | 0.53 | 0.09 | 78 | 91 | 58 | 78 | 79 |
| ANC | EPSTI1, lymp, membrane | 0.37 | −0.07 | 72 | 87 | 47 | 74 | 67 |
| ANC | GAS7, lymp, intra | 0.4 | −0.04 | 73 | 91 | 43 | 74 | 72 |
| ANC | IFI6, gran, intra | 0.38 | −0.06 | 73 | 91 | 42 | 73 | 73 |
| ANC | IFI6, mono, intra | 0.38 | −0.06 | 73 | 91 | 42 | 73 | 73 |
| ANC | IFIT3, gran, intra | 0.48 | 0.04 | 76 | 91 | 53 | 76 | 77 |
| ANC | IFIT3, lymp, intra | 0.46 | 0.02 | 75 | 86 | 58 | 77 | 71 |
| ANC | IFIT3, mean, intra | 0.5 | 0.06 | 77 | 92 | 53 | 76 | 80 |
| ANC | IFIT3, mono, intra | 0.48 | 0.04 | 76 | 91 | 53 | 76 | 77 |
| ANC | IFITM1, gran, membrane | 0.41 | −0.03 | 74 | 94 | 39 | 72 | 79 |
| ANC | IFITM1, lymp, membrane | 0.46 | 0.02 | 75 | 91 | 50 | 75 | 76 |
| ANC | IFITM1, mean, membrane | 0.43 | −0.01 | 74 | 94 | 42 | 73 | 80 |
| ANC | IFITM1, mono, membrane | 0.48 | 0.04 | 76 | 89 | 55 | 77 | 75 |
| ANC | IFITM3, gran, membrane | 0.44 | 0 | 75 | 94 | 42 | 73 | 80 |

TABLE 4-continued

The classification accuracy of bacterial vs. viral infected patients computed over pairs of features. DETERMINANT measurements were measured over different cell types.

| Feature #1 | Feature #2 | MCC | dMCC | Total accuracy % | Sen % | Spe % | PPV % | NPV % |
|---|---|---|---|---|---|---|---|---|
| ANC | IFITM3, mean, membrane | 0.43 | −0.01 | 74 | 94 | 42 | 73 | 80 |
| ANC | IFITM3, mono, membrane | 0.48 | 0.04 | 76 | 91 | 53 | 76 | 77 |
| ANC | LOC26010, gran, intra | 0.46 | 0.02 | 75 | 94 | 45 | 74 | 81 |
| ANC | LOC26010, mean, intra | 0.43 | −0.01 | 74 | 94 | 42 | 73 | 80 |
| ANC | LOC26010, mono, intra | 0.46 | 0.02 | 75 | 94 | 45 | 74 | 81 |
| ANC | LY6E, lymp, membrane | 0.36 | −0.08 | 72 | 92 | 37 | 72 | 73 |
| ANC | Lym(%) | 0.5 | −0.02 | 77 | 88 | 61 | 79 | 74 |
| ANC | MAN1C1, gran, intra | 0.39 | −0.05 | 73 | 92 | 40 | 73 | 75 |
| ANC | MAN1C1, mean, intra | 0.36 | −0.08 | 72 | 90 | 40 | 72 | 71 |
| ANC | MAN1C1, mono, intra | 0.39 | −0.05 | 73 | 92 | 40 | 73 | 75 |
| ANC | MX1, gran, intra | 0.62 | 0.08 | 82 | 89 | 71 | 84 | 79 |
| ANC | MX1, lymp, intra | 0.53 | 0.09 | 78 | 94 | 53 | 77 | 83 |
| ANC | MX1, mean, intra | 0.57 | 0.12 | 80 | 92 | 61 | 79 | 82 |
| ANC | MX1, mono, intra | 0.62 | 0.08 | 82 | 89 | 71 | 84 | 79 |
| ANC | Neu(%) | 0.53 | −0.03 | 78 | 91 | 58 | 78 | 79 |
| ANC | NPM1, gran, intra | 0.48 | 0.04 | 76 | 94 | 47 | 75 | 82 |
| ANC | NPM1, mean, intra | 0.43 | −0.01 | 74 | 92 | 45 | 73 | 77 |
| ANC | NPM1, mono, intra | 0.48 | 0.04 | 76 | 94 | 47 | 75 | 82 |
| ANC | OAS2, gran, intra | 0.43 | −0.01 | 75 | 89 | 50 | 75 | 73 |
| ANC | OAS2, mean, intra | 0.4 | −0.04 | 73 | 90 | 45 | 73 | 74 |
| ANC | OAS2, mono, intra | 0.43 | −0.01 | 75 | 89 | 50 | 75 | 73 |
| ANC | PARP12, gran, intra | 0.5 | 0.06 | 77 | 91 | 55 | 77 | 78 |
| ANC | PARP12, mean, intra | 0.48 | 0.04 | 76 | 90 | 53 | 76 | 77 |
| ANC | PARP12, mono, intra | 0.5 | 0.06 | 77 | 91 | 55 | 77 | 78 |
| ANC | PARP9, lymp, intra | 0.46 | 0.02 | 75 | 91 | 50 | 75 | 76 |
| ANC | PDIA6, gran, intra | 0.34 | −0.1 | 71 | 87 | 43 | 73 | 65 |
| ANC | PDIA6, lymp, intra | 0.43 | −0.01 | 75 | 94 | 40 | 74 | 80 |
| ANC | PDIA6, mono, intra | 0.34 | −0.1 | 71 | 87 | 43 | 73 | 65 |
| ANC | PTEN, gran, intra | 0.41 | −0.03 | 74 | 89 | 47 | 74 | 72 |
| ANC | PTEN, lymp, intra | 0.46 | 0.02 | 75 | 91 | 50 | 75 | 76 |
| ANC | PTEN, mean, intra | 0.43 | −0.01 | 74 | 92 | 45 | 73 | 77 |
| ANC | PTEN, mono, intra | 0.41 | −0.03 | 74 | 89 | 47 | 74 | 72 |
| ANC | RSAD2, gran, intra | 0.66 | 0.03 | 84 | 88 | 79 | 88 | 79 |
| ANC | RSAD2, lymp, intra | 0.41 | −0.03 | 74 | 88 | 50 | 75 | 70 |
| ANC | RSAD2, mean, intra | 0.64 | 0 | 83 | 85 | 79 | 87 | 77 |
| ANC | RSAD2, mono, intra | 0.66 | 0.03 | 84 | 88 | 79 | 88 | 79 |
| ANC | SDCBP, mean, intra | 0.45 | 0.01 | 75 | 90 | 50 | 74 | 76 |
| ANC | WBC | 0.53 | 0.09 | 78 | 95 | 50 | 76 | 86 |
| CORO1A, gran, intra | CORO1A, mean, intra | 0.13 | −0.03 | 60 | 74 | 38 | 66 | 48 |
| CORO1A, gran, intra | CORO1A, mono, intra | 0.16 | 0 | 63 | 81 | 33 | 67 | 52 |
| CORO1A, gran, intra | CRP | 0.54 | −0.02 | 79 | 90 | 61 | 78 | 79 |
| CORO1A, gran, intra | CSDA, gran, intra | 0.17 | 0.01 | 63 | 77 | 39 | 68 | 50 |
| CORO1A, gran, intra | CSDA, mono, intra | 0.17 | 0.01 | 63 | 77 | 39 | 68 | 50 |
| CORO1A, gran, intra | EIF4B, gran, intra | 0.27 | −0.11 | 67 | 81 | 44 | 70 | 59 |
| CORO1A, gran, intra | EIF4B, lymp, intra | 0.16 | −0.24 | 63 | 81 | 33 | 67 | 52 |
| CORO1A, gran, intra | EIF4B, mean, intra | 0.23 | −0.08 | 65 | 82 | 38 | 68 | 58 |
| CORO1A, gran, intra | EIF4B, mono, intra | 0.27 | −0.11 | 67 | 81 | 44 | 70 | 59 |
| CORO1A, gran, intra | EPSTI1, lymp, membrane | 0.13 | −0.06 | 62 | 79 | 32 | 67 | 48 |
| CORO1A, gran, intra | GAS7, lymp, intra | 0.18 | 0.02 | 63 | 75 | 42 | 69 | 50 |
| CORO1A, gran, intra | IFI6, gran, intra | 0.17 | 0.01 | 62 | 75 | 41 | 68 | 50 |
| CORO1A, gran, intra | IFI6, mono, intra | 0.17 | 0.01 | 62 | 75 | 41 | 68 | 50 |
| CORO1A, gran, intra | IFIT3, gran, intra | 0.35 | −0.04 | 69 | 72 | 64 | 77 | 58 |
| CORO1A, gran, intra | IFIT3, lymp, intra | 0.35 | −0.08 | 69 | 73 | 62 | 76 | 59 |
| CORO1A, gran, intra | IFIT3, mean, intra | 0.27 | 0.02 | 65 | 73 | 54 | 71 | 55 |
| CORO1A, gran, intra | IFIT3, mono, intra | 0.35 | −0.04 | 69 | 72 | 64 | 77 | 58 |
| CORO1A, gran, intra | IFITM1, gran, membrane | 0.14 | −0.12 | 62 | 81 | 31 | 66 | 50 |
| CORO1A, gran, intra | IFITM1, lymp, membrane | 0.3 | −0.08 | 67 | 73 | 56 | 73 | 56 |
| CORO1A, gran, intra | IFITM1, mean, membrane | 0.1 | −0.19 | 59 | 76 | 33 | 64 | 46 |
| CORO1A, gran, intra | IFITM1, mono, membrane | 0.27 | −0.04 | 67 | 80 | 46 | 71 | 58 |
| CORO1A, gran, intra | IFITM3, gran, membrane | 0.12 | −0.23 | 61 | 80 | 31 | 65 | 48 |
| CORO1A, gran, intra | IFITM3, mean, membrane | 0.21 | −0.14 | 64 | 81 | 38 | 68 | 56 |
| CORO1A, gran, intra | IFITM3, mono, membrane | 0.32 | −0.09 | 68 | 75 | 56 | 74 | 58 |
| CORO1A, gran, intra | LOC26010, gran, intra | 0.17 | −0.06 | 62 | 75 | 41 | 68 | 50 |
| CORO1A, gran, intra | LOC26010, mean, intra | 0.2 | −0.01 | 63 | 76 | 44 | 68 | 53 |
| CORO1A, gran, intra | LOC26010, mono, intra | 0.17 | −0.06 | 62 | 75 | 41 | 68 | 50 |
| CORO1A, gran, intra | LY6E, lymp, membrane | 0.11 | −0.12 | 61 | 77 | 32 | 66 | 45 |
| CORO1A, gran, intra | Lym(%) | 0.49 | −0.03 | 76 | 78 | 72 | 82 | 67 |
| CORO1A, gran, intra | MAN1C1, gran, intra | 0.25 | 0.09 | 66 | 79 | 45 | 71 | 56 |
| CORO1A, gran, intra | MAN1C1, mean, intra | 0.28 | 0.12 | 67 | 81 | 45 | 71 | 58 |
| CORO1A, gran, intra | MAN1C1, mono, intra | 0.25 | 0.09 | 66 | 79 | 45 | 71 | 56 |
| CORO1A, gran, intra | MX1, gran, intra | 0.49 | −0.05 | 76 | 80 | 69 | 81 | 68 |
| CORO1A, gran, intra | MX1, lymp, intra | 0.37 | 0.02 | 71 | 80 | 56 | 75 | 63 |
| CORO1A, gran, intra | MX1, mean, intra | 0.38 | −0.07 | 70 | 74 | 64 | 77 | 61 |
| CORO1A, gran, intra | MX1, mono, intra | 0.49 | −0.05 | 76 | 80 | 69 | 81 | 68 |

TABLE 4-continued

The classification accuracy of bacterial vs. viral infected patients computed over pairs of features. DETERMINANT measurements were measured over different cell types.

| Feature #1 | Feature #2 | MCC | dMCC | Total accuracy % | Sen % | Spe % | PPV % | NPV % |
|---|---|---|---|---|---|---|---|---|
| CORO1A, gran, intra | Neu(%) | 0.58 | 0.02 | 81 | 89 | 67 | 81 | 79 |
| CORO1A, gran, intra | NPM1, gran, intra | 0.17 | 0.01 | 63 | 78 | 38 | 67 | 52 |
| CORO1A, gran, intra | NPM1, mean, intra | 0.15 | −0.01 | 61 | 75 | 38 | 66 | 50 |
| CORO1A, gran, intra | NPM1, mono, intra | 0.17 | 0.01 | 63 | 78 | 38 | 67 | 52 |
| CORO1A, gran, intra | OAS2, gran, intra | 0.18 | −0.18 | 62 | 72 | 46 | 69 | 50 |
| CORO1A, gran, intra | OAS2, mean, intra | 0.12 | −0.18 | 59 | 71 | 41 | 66 | 47 |
| CORO1A, gran, intra | OAS2, mono, intra | 0.18 | −0.18 | 62 | 72 | 46 | 69 | 50 |
| CORO1A, gran, intra | PARP12, gran, intra | 0.21 | 0.02 | 64 | 77 | 44 | 69 | 53 |
| CORO1A, gran, intra | PARP12, mean, intra | 0.26 | 0.01 | 65 | 74 | 51 | 71 | 56 |
| CORO1A, gran, intra | PARP12, mono, intra | 0.21 | 0.02 | 64 | 77 | 44 | 69 | 53 |
| CORO1A, gran, intra | PARP9, lymp, intra | 0.15 | −0.01 | 62 | 80 | 33 | 66 | 50 |
| CORO1A, gran, intra | PDIA6, gran, intra | 0.32 | 0.16 | 69 | 79 | 52 | 74 | 59 |
| CORO1A, gran, intra | PDIA6, lymp, intra | 0.24 | 0.08 | 65 | 75 | 48 | 71 | 54 |
| CORO1A, gran, intra | PDIA6, mono, intra | 0.32 | 0.16 | 69 | 79 | 52 | 74 | 59 |
| CORO1A, gran, intra | PTEN, gran, intra | 0.15 | −0.07 | 61 | 73 | 41 | 67 | 48 |
| CORO1A, gran, intra | PTEN, lymp, intra | 0.08 | −0.08 | 58 | 72 | 36 | 65 | 44 |
| CORO1A, gran, intra | PTEN, mean, intra | 0.14 | −0.06 | 60 | 73 | 41 | 66 | 48 |
| CORO1A, gran, intra | PTEN, mono, intra | 0.15 | −0.07 | 61 | 73 | 41 | 67 | 48 |
| CORO1A, gran, intra | RSAD2, gran, intra | 0.66 | 0.03 | 83 | 84 | 82 | 89 | 76 |
| CORO1A, gran, intra | RSAD2, lymp, intra | 0.14 | −0.09 | 62 | 81 | 31 | 66 | 50 |
| CORO1A, gran, intra | RSAD2, mean, intra | 0.57 | −0.07 | 79 | 81 | 77 | 85 | 71 |
| CORO1A, gran, intra | RSAD2, mono, intra | 0.66 | 0.03 | 83 | 84 | 82 | 89 | 76 |
| CORO1A, gran, intra | SDCBP, mean, intra | 0.14 | −0.02 | 61 | 77 | 36 | 65 | 50 |
| CORO1A, gran, intra | WBC | 0.35 | 0.1 | 71 | 89 | 41 | 71 | 70 |
| CORO1A, mean, intra | CORO1A, mono, intra | 0.13 | −0.03 | 60 | 74 | 38 | 66 | 48 |
| CORO1A, mean, intra | CRP | 0.56 | 0 | 79 | 91 | 61 | 78 | 82 |
| CORO1A, mean, intra | CSDA, gran, intra | 0.31 | 0.16 | 69 | 79 | 52 | 73 | 59 |
| CORO1A, mean, intra | CSDA, mono, intra | 0.31 | 0.16 | 69 | 79 | 52 | 73 | 59 |
| CORO1A, mean, intra | EIF4B, gran, intra | 0.31 | −0.07 | 68 | 81 | 49 | 71 | 61 |
| CORO1A, mean, intra | EIF4B, lymp, intra | 0.22 | −0.18 | 64 | 77 | 44 | 69 | 55 |
| CORO1A, mean, intra | EIF4B, mean, intra | 0.31 | 0 | 68 | 81 | 49 | 71 | 61 |
| CORO1A, mean, intra | EIF4B, mono, intra | 0.31 | −0.07 | 68 | 81 | 49 | 71 | 61 |
| CORO1A, mean, intra | EPSTI1, lymp, membrane | 0.38 | 0.19 | 71 | 79 | 58 | 76 | 62 |
| CORO1A, mean, intra | GAS7, lymp, intra | 0.2 | 0.05 | 64 | 77 | 42 | 69 | 52 |
| CORO1A, mean, intra | IFI6, gran, intra | 0.18 | 0.03 | 62 | 74 | 44 | 68 | 52 |
| CORO1A, mean, intra | IFI6, mono, intra | 0.18 | 0.03 | 62 | 74 | 44 | 68 | 52 |
| CORO1A, mean, intra | IFIT3, gran, intra | 0.38 | −0.01 | 70 | 74 | 64 | 77 | 61 |
| CORO1A, mean, intra | IFIT3, lymp, intra | 0.4 | −0.03 | 71 | 76 | 64 | 77 | 63 |
| CORO1A, mean, intra | IFIT3, mean, intra | 0.39 | 0.14 | 71 | 79 | 59 | 75 | 64 |
| CORO1A, mean, intra | IFIT3, mono, intra | 0.38 | −0.01 | 70 | 74 | 64 | 77 | 61 |
| CORO1A, mean, intra | IFITM1, gran, membrane | 0.12 | −0.14 | 59 | 73 | 38 | 65 | 47 |
| CORO1A, mean, intra | IFITM1, lymp, membrane | 0.37 | −0.01 | 70 | 77 | 59 | 75 | 62 |
| CORO1A, mean, intra | IFITM1, mean, membrane | 0.14 | −0.15 | 60 | 73 | 41 | 66 | 48 |
| CORO1A, mean, intra | IFITM1, mono, membrane | 0.29 | −0.02 | 67 | 79 | 49 | 71 | 59 |
| CORO1A, mean, intra | IFITM3, gran, membrane | 0.18 | −0.17 | 62 | 76 | 41 | 67 | 52 |
| CORO1A, mean, intra | IFITM3, mean, membrane | 0.16 | −0.19 | 61 | 74 | 41 | 67 | 50 |
| CORO1A, mean, intra | IFITM3, mono, membrane | 0.37 | −0.04 | 70 | 77 | 59 | 75 | 62 |
| CORO1A, mean, intra | LOC26010, gran, intra | 0.18 | −0.05 | 62 | 74 | 44 | 68 | 52 |
| CORO1A, mean, intra | LOC26010, mean, intra | 0.16 | −0.05 | 61 | 74 | 41 | 67 | 50 |
| CORO1A, mean, intra | LOC26010, mono, intra | 0.18 | −0.05 | 62 | 74 | 44 | 68 | 52 |
| CORO1A, mean, intra | LY6E, lymp, membrane | 0.18 | −0.05 | 63 | 75 | 42 | 69 | 50 |
| CORO1A, mean, intra | Lym(%) | 0.51 | −0.01 | 76 | 77 | 74 | 83 | 67 |
| CORO1A, mean, intra | MAN1C1, gran, intra | 0.26 | 0.11 | 66 | 77 | 48 | 71 | 56 |
| CORO1A, mean, intra | MAN1C1, mean, intra | 0.25 | 0.1 | 66 | 79 | 45 | 71 | 56 |
| CORO1A, mean, intra | MAN1C1, mono, intra | 0.26 | 0.11 | 66 | 77 | 48 | 71 | 56 |
| CORO1A, mean, intra | MX1, gran, intra | 0.5 | −0.04 | 76 | 81 | 69 | 81 | 69 |
| CORO1A, mean, intra | MX1, lymp, intra | 0.41 | 0.06 | 72 | 81 | 59 | 76 | 66 |
| CORO1A, mean, intra | MX1, mean, intra | 0.48 | 0.03 | 75 | 81 | 67 | 79 | 68 |
| CORO1A, mean, intra | MX1, mono, intra | 0.5 | −0.04 | 76 | 81 | 69 | 81 | 69 |
| CORO1A, mean, intra | Neu(%) | 0.55 | −0.01 | 79 | 89 | 64 | 80 | 78 |
| CORO1A, mean, intra | NPM1, gran, intra | 0.24 | 0.09 | 65 | 79 | 44 | 69 | 57 |
| CORO1A, mean, intra | NPM1, mean, intra | 0.2 | 0.05 | 63 | 75 | 44 | 68 | 53 |
| CORO1A, mean, intra | NPM1, mono, intra | 0.24 | 0.09 | 65 | 79 | 44 | 69 | 57 |
| CORO1A, mean, intra | OAS2, gran, intra | 0.2 | −0.16 | 62 | 71 | 49 | 69 | 51 |
| CORO1A, mean, intra | OAS2, mean, intra | 0.19 | −0.11 | 62 | 73 | 46 | 68 | 51 |
| CORO1A, mean, intra | OAS2, mono, intra | 0.2 | −0.16 | 62 | 71 | 49 | 69 | 51 |
| CORO1A, mean, intra | PARP12, gran, intra | 0.25 | 0.06 | 65 | 77 | 46 | 70 | 56 |
| CORO1A, mean, intra | PARP12, mean, intra | 0.28 | 0.03 | 66 | 76 | 51 | 71 | 57 |
| CORO1A, mean, intra | PARP12, mono, intra | 0.25 | 0.06 | 65 | 77 | 46 | 70 | 56 |
| CORO1A, mean, intra | PARP9, lymp, intra | 0.14 | −0.01 | 61 | 77 | 36 | 66 | 50 |
| CORO1A, mean, intra | PDIA6, gran, intra | 0.31 | 0.16 | 69 | 81 | 48 | 73 | 60 |
| CORO1A, mean, intra | PDIA6, lymp, intra | 0.21 | 0.06 | 64 | 75 | 45 | 70 | 52 |
| CORO1A, mean, intra | PDIA6, mono, intra | 0.31 | 0.16 | 69 | 81 | 48 | 73 | 60 |
| CORO1A, mean, intra | PTEN, gran, intra | 0.21 | −0.01 | 63 | 74 | 46 | 69 | 53 |

TABLE 4-continued

The classification accuracy of bacterial vs. viral infected patients computed over pairs of features. DETERMINANT measurements were measured over different cell types.

| Feature #1 | Feature #2 | MCC | dMCC | Total accuracy % | Sen % | Spe % | PPV % | NPV % |
|---|---|---|---|---|---|---|---|---|
| CORO1A, mean, intra | PTEN, lymp, intra | 0.07 | −0.08 | 57 | 71 | 36 | 64 | 44 |
| CORO1A, mean, intra | PTEN, mean, intra | 0.18 | −0.02 | 62 | 74 | 44 | 68 | 52 |
| CORO1A, mean, intra | PTEN, mono, intra | 0.21 | −0.01 | 63 | 74 | 46 | 69 | 53 |
| CORO1A, mean, intra | RSAD2, gran, intra | 0.62 | −0.01 | 81 | 81 | 82 | 88 | 73 |
| CORO1A, mean, intra | RSAD2, lymp, intra | 0.16 | −0.07 | 62 | 79 | 36 | 66 | 52 |
| CORO1A, mean, intra | RSAD2, mean, intra | 0.59 | −0.05 | 80 | 82 | 77 | 85 | 73 |
| CORO1A, mean, intra | RSAD2, mono, intra | 0.62 | −0.01 | 81 | 81 | 82 | 88 | 73 |
| CORO1A, mean, intra | SDCBP, mean, intra | 0.19 | 0.04 | 63 | 77 | 41 | 67 | 53 |
| CORO1A, mean, intra | WBC | 0.28 | 0.03 | 67 | 82 | 44 | 70 | 61 |
| CORO1A, mono, intra | CRP | 0.54 | −0.02 | 79 | 90 | 61 | 78 | 79 |
| CORO1A, mono, intra | CSDA, gran, intra | 0.17 | 0.01 | 63 | 77 | 39 | 68 | 50 |
| CORO1A, mono, intra | CSDA, mono, intra | 0.17 | 0.01 | 63 | 77 | 39 | 68 | 50 |
| CORO1A, mono, intra | EIF4B, gran, intra | 0.27 | −0.11 | 67 | 81 | 44 | 70 | 59 |
| CORO1A, mono, intra | EIF4B, lymp, intra | 0.16 | −0.24 | 63 | 81 | 33 | 67 | 52 |
| CORO1A, mono, intra | EIF4B, mean, intra | 0.23 | −0.08 | 65 | 82 | 38 | 68 | 58 |
| CORO1A, mono, intra | EIF4B, mono, intra | 0.27 | −0.11 | 67 | 81 | 44 | 70 | 59 |
| CORO1A, mono, intra | EPSTI1, lymp, membrane | 0.13 | −0.06 | 62 | 79 | 32 | 67 | 48 |
| CORO1A, mono, intra | GAS7, lymp, intra | 0.18 | 0.02 | 63 | 75 | 42 | 69 | 50 |
| CORO1A, mono, intra | IFI6, gran, intra | 0.17 | 0.01 | 62 | 75 | 41 | 68 | 50 |
| CORO1A, mono, intra | IFI6, mono, intra | 0.17 | 0.01 | 62 | 75 | 41 | 68 | 50 |
| CORO1A, mono, intra | IFIT3, gran, intra | 0.35 | −0.04 | 69 | 72 | 64 | 77 | 58 |
| CORO1A, mono, intra | IFIT3, lymp, intra | 0.35 | −0.08 | 69 | 73 | 62 | 76 | 59 |
| CORO1A, mono, intra | IFIT3, mean, intra | 0.27 | 0.02 | 65 | 73 | 54 | 71 | 55 |
| CORO1A, mono, intra | IFIT3, mono, intra | 0.35 | −0.04 | 69 | 72 | 64 | 77 | 58 |
| CORO1A, mono, intra | IFITM1, gran, membrane | 0.14 | −0.12 | 62 | 81 | 31 | 66 | 50 |
| CORO1A, mono, intra | IFITM1, lymp, membrane | 0.3 | −0.08 | 67 | 73 | 56 | 73 | 56 |
| CORO1A, mono, intra | IFITM1, mean, membrane | 0.1 | −0.19 | 59 | 76 | 33 | 64 | 46 |
| CORO1A, mono, intra | IFITM1, mono, membrane | 0.27 | −0.04 | 67 | 80 | 46 | 71 | 58 |
| CORO1A, mono, intra | IFITM3, gran, membrane | 0.12 | −0.23 | 61 | 80 | 31 | 65 | 48 |
| CORO1A, mono, intra | IFITM3, mean, membrane | 0.21 | −0.14 | 64 | 81 | 38 | 68 | 56 |
| CORO1A, mono, intra | IFITM3, mono, membrane | 0.32 | −0.09 | 68 | 75 | 56 | 74 | 58 |
| CORO1A, mono, intra | LOC26010, gran, intra | 0.17 | −0.06 | 62 | 75 | 41 | 68 | 50 |
| CORO1A, mono, intra | LOC26010, mean, intra | 0.2 | −0.01 | 63 | 76 | 44 | 68 | 53 |
| CORO1A, mono, intra | LOC26010, mono, intra | 0.17 | −0.06 | 62 | 75 | 41 | 68 | 50 |
| CORO1A, mono, intra | LY6E, lymp, membrane | 0.11 | −0.12 | 61 | 77 | 32 | 66 | 45 |
| CORO1A, mono, intra | Lym(%) | 0.49 | −0.03 | 76 | 78 | 72 | 82 | 67 |
| CORO1A, mono, intra | MAN1C1, gran, intra | 0.25 | 0.09 | 66 | 79 | 45 | 71 | 56 |
| CORO1A, mono, intra | MAN1C1, mean, intra | 0.28 | 0.12 | 67 | 81 | 45 | 71 | 58 |
| CORO1A, mono, intra | MAN1C1, mono, intra | 0.25 | 0.09 | 66 | 79 | 45 | 71 | 56 |
| CORO1A, mono, intra | MX1, gran, intra | 0.49 | −0.05 | 76 | 80 | 69 | 81 | 68 |
| CORO1A, mono, intra | MX1, lymp, intra | 0.37 | 0.02 | 71 | 80 | 56 | 75 | 63 |
| CORO1A, mono, intra | MX1, mean, intra | 0.38 | −0.07 | 70 | 74 | 64 | 77 | 61 |
| CORO1A, mono, intra | MX1, mono, intra | 0.49 | −0.05 | 76 | 80 | 69 | 81 | 68 |
| CORO1A, mono, intra | Neu(%) | 0.58 | 0.02 | 81 | 89 | 67 | 81 | 79 |
| CORO1A, mono, intra | NPM1, gran, intra | 0.17 | 0.01 | 63 | 78 | 38 | 67 | 52 |
| CORO1A, mono, intra | NPM1, mean, intra | 0.15 | −0.01 | 61 | 75 | 38 | 66 | 50 |
| CORO1A, mono, intra | NPM1, mono, intra | 0.17 | 0.01 | 63 | 78 | 38 | 67 | 52 |
| CORO1A, mono, intra | OAS2, gran, intra | 0.18 | −0.18 | 62 | 72 | 46 | 69 | 50 |
| CORO1A, mono, intra | OAS2, mean, intra | 0.12 | −0.18 | 59 | 71 | 41 | 66 | 47 |
| CORO1A, mono, intra | OAS2, mono, intra | 0.18 | −0.18 | 62 | 72 | 46 | 69 | 50 |
| CORO1A, mono, intra | PARP12, gran, intra | 0.21 | 0.02 | 64 | 77 | 44 | 69 | 53 |
| CORO1A, mono, intra | PARP12, mean, intra | 0.26 | 0.01 | 65 | 74 | 51 | 71 | 56 |
| CORO1A, mono, intra | PARP12, mono, intra | 0.21 | 0.02 | 64 | 77 | 44 | 69 | 53 |
| CORO1A, mono, intra | PARP9, lymp, intra | 0.15 | −0.01 | 62 | 80 | 33 | 66 | 50 |
| CORO1A, mono, intra | PDIA6, gran, intra | 0.32 | 0.16 | 69 | 79 | 52 | 74 | 59 |
| CORO1A, mono, intra | PDIA6, lymp, intra | 0.24 | 0.08 | 65 | 75 | 48 | 71 | 54 |
| CORO1A, mono, intra | PDIA6, mono, intra | 0.32 | 0.16 | 69 | 79 | 52 | 74 | 59 |
| CORO1A, mono, intra | PTEN, gran, intra | 0.15 | −0.07 | 61 | 73 | 41 | 67 | 48 |
| CORO1A, mono, intra | PTEN, lymp, intra | 0.08 | −0.08 | 58 | 72 | 36 | 65 | 44 |
| CORO1A, mono, intra | PTEN, mean, intra | 0.14 | −0.06 | 60 | 73 | 41 | 66 | 48 |
| CORO1A, mono, intra | PTEN, mono, intra | 0.15 | −0.07 | 61 | 73 | 41 | 67 | 48 |
| CORO1A, mono, intra | RSAD2, gran, intra | 0.66 | 0.03 | 83 | 84 | 82 | 89 | 76 |
| CORO1A, mono, intra | RSAD2, lymp, intra | 0.14 | −0.09 | 62 | 81 | 31 | 66 | 50 |
| CORO1A, mono, intra | RSAD2, mean, intra | 0.57 | −0.07 | 79 | 81 | 77 | 85 | 71 |
| CORO1A, mono, intra | RSAD2, mono, intra | 0.66 | 0.03 | 83 | 84 | 82 | 89 | 76 |
| CORO1A, mono, intra | SDCBP, mean, intra | 0.14 | −0.02 | 61 | 77 | 36 | 65 | 50 |
| CORO1A, mono, intra | WBC | 0.35 | 0.1 | 71 | 89 | 41 | 71 | 70 |
| CRP | CSDA, gran, intra | 0.59 | 0.03 | 81 | 90 | 67 | 81 | 80 |
| CRP | CSDA, mono, intra | 0.59 | 0.03 | 81 | 90 | 67 | 81 | 80 |
| CRP | EIF4B, gran, intra | 0.65 | 0.09 | 84 | 93 | 68 | 82 | 87 |
| CRP | EIF4B, lymp, intra | 0.61 | 0.05 | 82 | 93 | 63 | 80 | 86 |
| CRP | EIF4B, mean, intra | 0.65 | 0.09 | 83 | 95 | 66 | 81 | 89 |
| CRP | EIF4B, mono, intra | 0.65 | 0.09 | 84 | 93 | 68 | 82 | 87 |
| CRP | EPSTI1, lymp, membrane | 0.59 | 0.03 | 81 | 90 | 67 | 81 | 80 |

TABLE 4-continued

The classification accuracy of bacterial vs. viral infected patients computed over pairs of features. DETERMINANT measurements were measured over different cell types.

| Feature #1 | Feature #2 | MCC | dMCC | Total accuracy % | Sen % | Spe % | PPV % | NPV % |
|---|---|---|---|---|---|---|---|---|
| CRP | GAS7, lymp, intra | 0.59 | 0.03 | 81 | 90 | 67 | 81 | 80 |
| CRP | IFI6, gran, intra | 0.74 | 0.18 | 88 | 93 | 79 | 88 | 88 |
| CRP | IFI6, mono, intra | 0.74 | 0.18 | 88 | 93 | 79 | 88 | 88 |
| CRP | IFIT3, gran, intra | 0.7 | 0.14 | 86 | 92 | 76 | 86 | 85 |
| CRP | IFIT3, lymp, intra | 0.61 | 0.05 | 82 | 88 | 71 | 83 | 79 |
| CRP | IFIT3, mean, intra | 0.69 | 0.13 | 85 | 91 | 76 | 85 | 85 |
| CRP | IFIT3, mono, intra | 0.7 | 0.14 | 86 | 92 | 76 | 86 | 85 |
| CRP | IFITM1, gran, membrane | 0.63 | 0.07 | 83 | 95 | 63 | 80 | 89 |
| CRP | IFITM1, lymp, membrane | 0.63 | 0.07 | 83 | 92 | 68 | 82 | 84 |
| CRP | IFITM1, mean, membrane | 0.58 | 0.02 | 80 | 91 | 63 | 79 | 83 |
| CRP | IFITM1, mono, membrane | 0.7 | 0.14 | 86 | 92 | 76 | 86 | 85 |
| CRP | IFITM3, gran, membrane | 0.63 | 0.07 | 83 | 92 | 68 | 82 | 84 |
| CRP | IFITM3, mean, membrane | 0.67 | 0.11 | 84 | 91 | 74 | 84 | 85 |
| CRP | IFITM3, mono, membrane | 0.81 | 0.25 | 91 | 95 | 84 | 90 | 91 |
| CRP | LOC26010, gran, intra | 0.72 | 0.16 | 87 | 92 | 79 | 87 | 86 |
| CRP | LOC26010, mean, intra | 0.69 | 0.13 | 85 | 90 | 79 | 87 | 83 |
| CRP | LOC26010, mono, intra | 0.72 | 0.16 | 87 | 92 | 79 | 87 | 86 |
| CRP | LY6E, lymp, membrane | 0.59 | 0.03 | 81 | 92 | 63 | 80 | 83 |
| CRP | Lym(%) | 0.7 | 0.14 | 86 | 92 | 76 | 86 | 85 |
| CRP | MAN1C1, gran, intra | 0.61 | 0.05 | 82 | 90 | 70 | 83 | 81 |
| CRP | MAN1C1, mean, intra | 0.61 | 0.05 | 82 | 90 | 70 | 83 | 81 |
| CRP | MAN1C1, mono, intra | 0.61 | 0.05 | 82 | 90 | 70 | 83 | 81 |
| CRP | MX1, gran, intra | 0.78 | 0.22 | 90 | 93 | 84 | 90 | 89 |
| CRP | MX1, lymp, intra | 0.72 | 0.16 | 87 | 93 | 76 | 86 | 88 |
| CRP | MX1, mean, intra | 0.74 | 0.18 | 88 | 93 | 79 | 87 | 88 |
| CRP | MX1, mono, intra | 0.78 | 0.22 | 90 | 93 | 84 | 90 | 89 |
| CRP | Neu(%) | 0.65 | 0.09 | 84 | 92 | 71 | 83 | 84 |
| CRP | NPM1, gran, intra | 0.67 | 0.11 | 85 | 90 | 76 | 85 | 83 |
| CRP | NPM1, mean, intra | 0.65 | 0.09 | 83 | 88 | 76 | 85 | 81 |
| CRP | NPM1, mono, intra | 0.67 | 0.11 | 85 | 90 | 76 | 85 | 83 |
| CRP | OAS2, gran, intra | 0.65 | 0.09 | 84 | 92 | 71 | 83 | 84 |
| CRP | OAS2, mean, intra | 0.65 | 0.09 | 83 | 91 | 71 | 83 | 84 |
| CRP | OAS2, mono, intra | 0.65 | 0.09 | 84 | 92 | 71 | 83 | 84 |
| CRP | PARP12, gran, intra | 0.79 | 0.23 | 90 | 97 | 79 | 88 | 94 |
| CRP | PARP12, mean, intra | 0.76 | 0.2 | 89 | 95 | 79 | 87 | 91 |
| CRP | PARP12, mono, intra | 0.79 | 0.23 | 90 | 97 | 79 | 88 | 94 |
| CRP | PARP9, lymp, intra | 0.7 | 0.14 | 86 | 93 | 74 | 85 | 88 |
| CRP | PDIA6, gran, intra | 0.73 | 0.17 | 87 | 96 | 73 | 85 | 92 |
| CRP | PDIA6, lymp, intra | 0.62 | 0.06 | 82 | 92 | 67 | 82 | 83 |
| CRP | PDIA6, mono, intra | 0.73 | 0.17 | 87 | 96 | 73 | 85 | 92 |
| CRP | PTEN, gran, intra | 0.78 | 0.22 | 90 | 95 | 82 | 89 | 91 |
| CRP | PTEN, lymp, intra | 0.65 | 0.09 | 84 | 92 | 71 | 83 | 84 |
| CRP | PTEN, mean, intra | 0.69 | 0.13 | 85 | 93 | 74 | 84 | 88 |
| CRP | PTEN, mono, intra | 0.78 | 0.22 | 90 | 95 | 82 | 89 | 91 |
| CRP | RSAD2, gran, intra | 0.89 | 0.26 | 95 | 95 | 95 | 97 | 92 |
| CRP | RSAD2, lymp, intra | 0.61 | 0.05 | 82 | 90 | 68 | 82 | 81 |
| CRP | RSAD2, mean, intra | 0.85 | 0.21 | 93 | 93 | 92 | 95 | 90 |
| CRP | RSAD2, mono, intra | 0.89 | 0.26 | 95 | 95 | 95 | 97 | 92 |
| CRP | SDCBP, mean, intra | 0.65 | 0.09 | 83 | 89 | 74 | 84 | 82 |
| CRP | WBC | 0.54 | −0.02 | 79 | 88 | 63 | 79 | 77 |
| CSDA, gran, intra | CSDA, mono, intra | 0.08 | −0.01 | 60 | 81 | 26 | 65 | 44 |
| CSDA, gran, intra | EIF4B, gran, intra | 0.34 | −0.04 | 70 | 79 | 55 | 75 | 61 |
| CSDA, gran, intra | EIF4B, lymp, intra | 0.2 | −0.2 | 64 | 77 | 42 | 69 | 52 |
| CSDA, gran, intra | EIF4B, mean, intra | 0.36 | 0.05 | 71 | 85 | 48 | 73 | 65 |
| CSDA, gran, intra | EIF4B, mono, intra | 0.34 | −0.04 | 70 | 79 | 55 | 75 | 61 |
| CSDA, gran, intra | EPSTI1, lymp, membrane | 0.28 | 0.09 | 67 | 81 | 45 | 71 | 58 |
| CSDA, gran, intra | GAS7, lymp, intra | 0.14 | 0.04 | 61 | 75 | 39 | 67 | 48 |
| CSDA, gran, intra | IFI6, gran, intra | 0.09 | 0 | 60 | 79 | 29 | 65 | 45 |
| CSDA, gran, intra | IFI6, mono, intra | 0.09 | 0 | 60 | 79 | 29 | 65 | 45 |
| CSDA, gran, intra | IFIT3, gran, intra | 0.33 | −0.06 | 70 | 83 | 48 | 73 | 63 |
| CSDA, gran, intra | IFIT3, lymp, intra | 0.26 | −0.17 | 66 | 77 | 48 | 71 | 56 |
| CSDA, gran, intra | IFIT3, mean, intra | 0.23 | −0.02 | 65 | 77 | 45 | 70 | 54 |
| CSDA, gran, intra | IFIT3, mono, intra | 0.33 | −0.06 | 70 | 83 | 48 | 73 | 63 |
| CSDA, gran, intra | IFITM1, gran, membrane | 0.07 | −0.19 | 59 | 77 | 29 | 65 | 43 |
| CSDA, gran, intra | IFITM1, lymp, membrane | 0.28 | −0.1 | 67 | 79 | 48 | 72 | 58 |
| CSDA, gran, intra | IFITM1, mean, membrane | 0.1 | −0.19 | 60 | 77 | 32 | 66 | 45 |
| CSDA, gran, intra | IFITM1, mono, membrane | 0.39 | 0.08 | 72 | 83 | 55 | 75 | 65 |
| CSDA, gran, intra | IFITM3, gran, membrane | 0.1 | −0.25 | 61 | 83 | 26 | 65 | 47 |
| CSDA, gran, intra | IFITM3, mean, membrane | 0.09 | −0.26 | 60 | 79 | 29 | 65 | 45 |
| CSDA, gran, intra | IFITM3, mono, membrane | 0.43 | 0.02 | 73 | 81 | 61 | 78 | 66 |
| CSDA, gran, intra | LOC26010, gran, intra | 0.22 | −0.01 | 65 | 79 | 42 | 69 | 54 |
| CSDA, gran, intra | LOC26010, mean, intra | 0.22 | 0.01 | 65 | 79 | 42 | 69 | 54 |
| CSDA, gran, intra | LOC26010, mono, intra | 0.22 | −0.01 | 65 | 79 | 42 | 69 | 54 |
| CSDA, gran, intra | LY6E, lymp, membrane | −0.06 | −0.29 | 55 | 79 | 16 | 61 | 31 |

TABLE 4-continued

The classification accuracy of bacterial vs. viral infected patients computed over pairs of features. DETERMINANT measurements were measured over different cell types.

| Feature #1 | Feature #2 | MCC | dMCC | Total accuracy % | Sen % | Spe % | PPV % | NPV % |
|---|---|---|---|---|---|---|---|---|
| CSDA, gran, intra | Lym(%) | 0.52 | 0 | 77 | 79 | 74 | 84 | 68 |
| CSDA, gran, intra | MAN1C1, gran, intra | 0.34 | 0.23 | 70 | 79 | 55 | 75 | 61 |
| CSDA, gran, intra | MAN1C1, mean, intra | 0.31 | 0.18 | 69 | 81 | 48 | 72 | 60 |
| CSDA, gran, intra | MAN1C1, mono, intra | 0.34 | 0.23 | 70 | 79 | 55 | 75 | 61 |
| CSDA, gran, intra | MX1, gran, intra | 0.46 | −0.08 | 75 | 79 | 68 | 80 | 66 |
| CSDA, gran, intra | MX1, lymp, intra | 0.21 | −0.14 | 64 | 75 | 45 | 70 | 52 |
| CSDA, gran, intra | MX1, mean, intra | 0.42 | −0.03 | 71 | 69 | 74 | 82 | 59 |
| CSDA, gran, intra | MX1, mono, intra | 0.46 | −0.08 | 75 | 79 | 68 | 80 | 66 |
| CSDA, gran, intra | Neu(%) | 0.59 | 0.03 | 81 | 85 | 74 | 85 | 74 |
| CSDA, gran, intra | NPM1, gran, intra | 0.13 | 0.03 | 61 | 77 | 35 | 67 | 48 |
| CSDA, gran, intra | NPM1, mean, intra | 0.13 | 0 | 61 | 77 | 35 | 67 | 48 |
| CSDA, gran, intra | NPM1, mono, intra | 0.13 | 0.03 | 61 | 77 | 35 | 67 | 48 |
| CSDA, gran, intra | OAS2, gran, intra | 0.22 | −0.14 | 65 | 79 | 42 | 69 | 54 |
| CSDA, gran, intra | OAS2, mean, intra | 0.09 | −0.21 | 60 | 79 | 29 | 65 | 45 |
| CSDA, gran, intra | OAS2, mono, intra | 0.22 | −0.14 | 65 | 79 | 42 | 69 | 54 |
| CSDA, gran, intra | PARP12, gran, intra | 0.18 | −0.01 | 63 | 75 | 42 | 68 | 50 |
| CSDA, gran, intra | PARP12, mean, intra | 0.3 | 0.05 | 67 | 75 | 55 | 74 | 57 |
| CSDA, gran, intra | PARP12, mono, intra | 0.18 | −0.01 | 63 | 75 | 42 | 68 | 50 |
| CSDA, gran, intra | PARP9, lymp, intra | 0.13 | −0.01 | 61 | 77 | 35 | 67 | 48 |
| CSDA, gran, intra | PDIA6, gran, intra | 0.18 | 0.05 | 63 | 75 | 42 | 68 | 50 |
| CSDA, gran, intra | PDIA6, lymp, intra | 0.06 | −0.03 | 58 | 73 | 32 | 64 | 42 |
| CSDA, gran, intra | PDIA6, mono, intra | 0.18 | 0.05 | 63 | 75 | 42 | 68 | 50 |
| CSDA, gran, intra | PTEN, gran, intra | 0.21 | −0.01 | 64 | 75 | 45 | 70 | 52 |
| CSDA, gran, intra | PTEN, lymp, intra | 0.18 | 0.09 | 63 | 75 | 42 | 68 | 50 |
| CSDA, gran, intra | PTEN, mean, intra | 0.18 | −0.02 | 63 | 75 | 42 | 68 | 50 |
| CSDA, gran, intra | PTEN, mono, intra | 0.21 | −0.01 | 64 | 75 | 45 | 70 | 52 |
| CSDA, gran, intra | RSAD2, gran, intra | 0.62 | −0.01 | 82 | 85 | 77 | 86 | 75 |
| CSDA, gran, intra | RSAD2, lymp, intra | 0.11 | −0.12 | 61 | 81 | 29 | 66 | 47 |
| CSDA, gran, intra | RSAD2, mean, intra | 0.64 | 0 | 83 | 87 | 77 | 87 | 77 |
| CSDA, gran, intra | RSAD2, mono, intra | 0.62 | −0.01 | 82 | 85 | 77 | 86 | 75 |
| CSDA, gran, intra | SDCBP, mean, intra | 0.34 | 0.25 | 70 | 79 | 55 | 75 | 61 |
| CSDA, gran, intra | WBC | 0.25 | 0 | 67 | 88 | 32 | 69 | 63 |
| CSDA, mono, intra | EIF4B, gran, intra | 0.34 | −0.04 | 70 | 79 | 55 | 75 | 61 |
| CSDA, mono, intra | EIF4B, lymp, intra | 0.2 | −0.2 | 64 | 77 | 42 | 69 | 52 |
| CSDA, mono, intra | EIF4B, mean, intra | 0.36 | 0.05 | 71 | 85 | 48 | 73 | 65 |
| CSDA, mono, intra | EIF4B, mono, intra | 0.34 | −0.04 | 70 | 79 | 55 | 75 | 61 |
| CSDA, mono, intra | EPSTI1, lymp, membrane | 0.28 | 0.09 | 67 | 81 | 45 | 71 | 58 |
| CSDA, mono, intra | GAS7, lymp, intra | 0.14 | 0.04 | 61 | 75 | 39 | 67 | 48 |
| CSDA, mono, intra | IFI6, gran, intra | 0.09 | 0 | 60 | 79 | 29 | 65 | 45 |
| CSDA, mono, intra | IFI6, mono, intra | 0.09 | 0 | 60 | 79 | 29 | 65 | 45 |
| CSDA, mono, intra | IFIT3, gran, intra | 0.33 | −0.06 | 70 | 83 | 48 | 73 | 63 |
| CSDA, mono, intra | IFIT3, lymp, intra | 0.26 | −0.17 | 66 | 77 | 48 | 71 | 56 |
| CSDA, mono, intra | IFIT3, mean, intra | 0.23 | −0.02 | 65 | 77 | 45 | 70 | 54 |
| CSDA, mono, intra | IFIT3, mono, intra | 0.33 | −0.06 | 70 | 83 | 48 | 73 | 63 |
| CSDA, mono, intra | IFITM1, gran, membrane | 0.07 | −0.19 | 59 | 77 | 29 | 65 | 43 |
| CSDA, mono, intra | IFITM1, lymp, membrane | 0.28 | −0.1 | 67 | 79 | 48 | 72 | 58 |
| CSDA, mono, intra | IFITM1, mean, membrane | 0.1 | −0.19 | 60 | 77 | 32 | 66 | 45 |
| CSDA, mono, intra | IFITM1, mono, membrane | 0.39 | 0.08 | 72 | 83 | 55 | 75 | 65 |
| CSDA, mono, intra | IFITM3, gran, membrane | 0.1 | −0.25 | 61 | 83 | 26 | 65 | 47 |
| CSDA, mono, intra | IFITM3, mean, membrane | 0.09 | −0.26 | 60 | 79 | 29 | 65 | 45 |
| CSDA, mono, intra | IFITM3, mono, membrane | 0.43 | 0.02 | 73 | 81 | 61 | 78 | 66 |
| CSDA, mono, intra | LOC26010, gran, intra | 0.22 | −0.01 | 65 | 79 | 42 | 69 | 54 |
| CSDA, mono, intra | LOC26010, mean, intra | 0.22 | 0.01 | 65 | 79 | 42 | 69 | 54 |
| CSDA, mono, intra | LOC26010, mono, intra | 0.22 | −0.01 | 65 | 79 | 42 | 69 | 54 |
| CSDA, mono, intra | LY6E, lymp, membrane | −0.06 | −0.29 | 55 | 79 | 16 | 61 | 31 |
| CSDA, mono, intra | Lym(%) | 0.52 | 0 | 77 | 79 | 74 | 84 | 68 |
| CSDA, mono, intra | MAN1C1, gran, intra | 0.34 | 0.23 | 70 | 79 | 55 | 75 | 61 |
| CSDA, mono, intra | MAN1C1, mean, intra | 0.31 | 0.18 | 69 | 81 | 48 | 72 | 60 |
| CSDA, mono, intra | MAN1C1, mono, intra | 0.34 | 0.23 | 70 | 79 | 55 | 75 | 61 |
| CSDA, mono, intra | MX1, gran, intra | 0.46 | −0.08 | 75 | 79 | 68 | 80 | 66 |
| CSDA, mono, intra | MX1, lymp, intra | 0.21 | −0.14 | 64 | 75 | 45 | 70 | 52 |
| CSDA, mono, intra | MX1, mean, intra | 0.42 | −0.03 | 71 | 69 | 74 | 82 | 59 |
| CSDA, mono, intra | MX1, mono, intra | 0.46 | −0.08 | 75 | 79 | 68 | 80 | 66 |
| CSDA, mono, intra | Neu(%) | 0.59 | 0.03 | 81 | 85 | 74 | 85 | 74 |
| CSDA, mono, intra | NPM1, gran, intra | 0.13 | 0.03 | 61 | 77 | 35 | 67 | 48 |
| CSDA, mono, intra | NPM1, mean, intra | 0.13 | 0 | 61 | 77 | 35 | 67 | 48 |
| CSDA, mono, intra | NPM1, mono, intra | 0.13 | 0.03 | 61 | 77 | 35 | 67 | 48 |
| CSDA, mono, intra | OAS2, gran, intra | 0.22 | −0.14 | 65 | 79 | 42 | 69 | 54 |
| CSDA, mono, intra | OAS2, mean, intra | 0.09 | −0.21 | 60 | 79 | 29 | 65 | 45 |
| CSDA, mono, intra | OAS2, mono, intra | 0.22 | −0.14 | 65 | 79 | 42 | 69 | 54 |
| CSDA, mono, intra | PARP12, gran, intra | 0.18 | −0.01 | 63 | 75 | 42 | 68 | 50 |
| CSDA, mono, intra | PARP12, mean, intra | 0.3 | 0.05 | 67 | 75 | 55 | 74 | 57 |
| CSDA, mono, intra | PARP12, mono, intra | 0.18 | −0.01 | 63 | 75 | 42 | 68 | 50 |
| CSDA, mono, intra | PARP9, lymp, intra | 0.13 | −0.01 | 61 | 77 | 35 | 67 | 48 |

TABLE 4-continued

The classification accuracy of bacterial vs. viral infected patients computed over pairs of features. DETERMINANT measurements were measured over different cell types.

| Feature #1 | Feature #2 | MCC | dMCC | Total accuracy % | Sen % | Spe % | PPV % | NPV % |
|---|---|---|---|---|---|---|---|---|
| CSDA, mono, intra | PDIA6, gran, intra | 0.18 | 0.05 | 63 | 75 | 42 | 68 | 50 |
| CSDA, mono, intra | PDIA6, lymp, intra | 0.06 | −0.03 | 58 | 73 | 32 | 64 | 42 |
| CSDA, mono, intra | PDIA6, mono, intra | 0.18 | 0.05 | 63 | 75 | 42 | 68 | 50 |
| CSDA, mono, intra | PTEN, gran, intra | 0.21 | −0.01 | 64 | 75 | 45 | 70 | 52 |
| CSDA, mono, intra | PTEN, lymp, intra | 0.18 | 0.09 | 63 | 75 | 42 | 68 | 50 |
| CSDA, mono, intra | PTEN, mean, intra | 0.18 | −0.02 | 63 | 75 | 42 | 68 | 50 |
| CSDA, mono, intra | PTEN, mono, intra | 0.21 | −0.01 | 64 | 75 | 45 | 70 | 52 |
| CSDA, mono, intra | RSAD2, gran, intra | 0.62 | −0.01 | 82 | 85 | 77 | 86 | 75 |
| CSDA, mono, intra | RSAD2, lymp, intra | 0.11 | −0.12 | 61 | 81 | 29 | 66 | 47 |
| CSDA, mono, intra | RSAD2, mean, intra | 0.64 | 0 | 83 | 87 | 77 | 87 | 77 |
| CSDA, mono, intra | RSAD2, mono, intra | 0.62 | −0.01 | 82 | 85 | 77 | 86 | 75 |
| CSDA, mono, intra | SDCBP, mean, intra | 0.34 | 0.25 | 70 | 79 | 55 | 75 | 61 |
| CSDA, mono, intra | WBC | 0.25 | 0 | 67 | 88 | 32 | 69 | 63 |
| EIF4B, gran, intra | EIF4B, lymp, intra | 0.43 | 0.03 | 72 | 69 | 75 | 76 | 67 |
| EIF4B, gran, intra | EIF4B, mean, intra | 0.38 | 0 | 69 | 63 | 76 | 75 | 64 |
| EIF4B, gran, intra | EIF4B, mono, intra | 0.38 | 0 | 69 | 62 | 76 | 75 | 63 |
| EIF4B, gran, intra | EPSTI1, lymp, membrane | 0.37 | −0.01 | 70 | 74 | 65 | 78 | 59 |
| EIF4B, gran, intra | GAS7, lymp, intra | 0.34 | −0.04 | 69 | 74 | 61 | 76 | 58 |
| EIF4B, gran, intra | IFI6, gran, intra | 0.19 | −0.19 | 63 | 77 | 41 | 68 | 52 |
| EIF4B, gran, intra | IFI6, mono, intra | 0.19 | −0.19 | 63 | 77 | 41 | 68 | 52 |
| EIF4B, gran, intra | IFIT3, gran, intra | 0.38 | −0.01 | 71 | 78 | 59 | 76 | 62 |
| EIF4B, gran, intra | IFIT3, lymp, intra | 0.35 | −0.08 | 70 | 78 | 56 | 75 | 61 |
| EIF4B, gran, intra | IFIT3, mean, intra | 0.33 | −0.05 | 68 | 76 | 56 | 73 | 59 |
| EIF4B, gran, intra | IFIT3, mono, intra | 0.38 | −0.01 | 71 | 78 | 59 | 76 | 62 |
| EIF4B, gran, intra | IFITM1, gran, membrane | 0.28 | −0.1 | 64 | 65 | 63 | 69 | 59 |
| EIF4B, gran, intra | IFITM1, lymp, membrane | 0.43 | 0.05 | 72 | 72 | 72 | 76 | 67 |
| EIF4B, gran, intra | IFITM1, mean, membrane | 0.28 | −0.1 | 64 | 65 | 63 | 68 | 60 |
| EIF4B, gran, intra | IFITM1, mono, membrane | 0.32 | −0.06 | 66 | 69 | 63 | 70 | 62 |
| EIF4B, gran, intra | IFITM3, gran, membrane | 0.34 | −0.04 | 67 | 68 | 67 | 71 | 63 |
| EIF4B, gran, intra | IFITM3, mean, membrane | 0.33 | −0.05 | 66 | 65 | 68 | 71 | 62 |
| EIF4B, gran, intra | IFITM3, mono, membrane | 0.45 | 0.04 | 72 | 70 | 75 | 78 | 67 |
| EIF4B, gran, intra | LOC26010, gran, intra | 0.39 | 0.01 | 69 | 65 | 75 | 75 | 64 |
| EIF4B, gran, intra | LOC26010, mean, intra | 0.38 | 0 | 69 | 63 | 76 | 75 | 64 |
| EIF4B, gran, intra | LOC26010, mono, intra | 0.39 | 0.01 | 69 | 65 | 75 | 75 | 64 |
| EIF4B, gran, intra | LY6E, lymp, membrane | 0.41 | 0.03 | 70 | 68 | 73 | 75 | 66 |
| EIF4B, gran, intra | Lym(%) | 0.55 | 0.03 | 77 | 76 | 79 | 81 | 73 |
| EIF4B, gran, intra | MAN1C1, gran, intra | 0.36 | −0.02 | 71 | 83 | 52 | 74 | 64 |
| EIF4B, gran, intra | MAN1C1, mean, intra | 0.39 | 0.01 | 72 | 83 | 55 | 75 | 65 |
| EIF4B, gran, intra | MAN1C1, mono, intra | 0.36 | −0.02 | 71 | 83 | 52 | 74 | 64 |
| EIF4B, gran, intra | MX1, gran, intra | 0.57 | 0.03 | 78 | 73 | 84 | 84 | 73 |
| EIF4B, gran, intra | MX1, lymp, intra | 0.54 | 0.16 | 77 | 73 | 81 | 82 | 72 |
| EIF4B, gran, intra | MX1, mean, intra | 0.58 | 0.13 | 78 | 72 | 85 | 85 | 73 |
| EIF4B, gran, intra | MX1, mono, intra | 0.57 | 0.03 | 78 | 73 | 84 | 84 | 73 |
| EIF4B, gran, intra | Neu(%) | 0.53 | −0.03 | 76 | 76 | 77 | 80 | 73 |
| EIF4B, gran, intra | NPM1, gran, intra | 0.16 | −0.22 | 62 | 75 | 41 | 67 | 50 |
| EIF4B, gran, intra | NPM1, mean, intra | 0.27 | −0.11 | 66 | 75 | 51 | 71 | 57 |
| EIF4B, gran, intra | NPM1, mono, intra | 0.16 | −0.22 | 62 | 75 | 41 | 67 | 50 |
| EIF4B, gran, intra | OAS2, gran, intra | 0.4 | 0.02 | 69 | 64 | 76 | 76 | 64 |
| EIF4B, gran, intra | OAS2, mean, intra | 0.38 | 0 | 69 | 65 | 73 | 73 | 64 |
| EIF4B, gran, intra | OAS2, mono, intra | 0.4 | 0.02 | 69 | 64 | 76 | 76 | 64 |
| EIF4B, gran, intra | PARP12, gran, intra | 0.24 | −0.14 | 65 | 77 | 46 | 70 | 55 |
| EIF4B, gran, intra | PARP12, mean, intra | 0.27 | −0.11 | 65 | 71 | 56 | 72 | 55 |
| EIF4B, gran, intra | PARP12, mono, intra | 0.24 | −0.14 | 65 | 77 | 46 | 70 | 55 |
| EIF4B, gran, intra | PARP9, lymp, intra | 0.3 | −0.08 | 68 | 80 | 49 | 72 | 59 |
| EIF4B, gran, intra | PDIA6, gran, intra | 0.24 | −0.14 | 65 | 77 | 45 | 71 | 54 |
| EIF4B, gran, intra | PDIA6, lymp, intra | 0.31 | −0.07 | 68 | 74 | 58 | 75 | 56 |
| EIF4B, gran, intra | PDIA6, mono, intra | 0.24 | −0.14 | 65 | 77 | 45 | 71 | 54 |
| EIF4B, gran, intra | PTEN, gran, intra | 0.26 | −0.12 | 66 | 77 | 49 | 71 | 56 |
| EIF4B, gran, intra | PTEN, lymp, intra | 0.33 | −0.05 | 69 | 78 | 54 | 74 | 60 |
| EIF4B, gran, intra | PTEN, mean, intra | 0.2 | −0.18 | 63 | 77 | 41 | 68 | 53 |
| EIF4B, gran, intra | PTEN, mono, intra | 0.26 | −0.12 | 66 | 77 | 49 | 71 | 56 |
| EIF4B, gran, intra | RSAD2, gran, intra | 0.62 | −0.01 | 81 | 78 | 84 | 85 | 77 |
| EIF4B, gran, intra | RSAD2, lymp, intra | 0.45 | 0.07 | 72 | 70 | 75 | 76 | 68 |
| EIF4B, gran, intra | RSAD2, mean, intra | 0.6 | −0.04 | 80 | 78 | 82 | 84 | 76 |
| EIF4B, gran, intra | RSAD2, mono, intra | 0.62 | −0.01 | 81 | 78 | 84 | 85 | 77 |
| EIF4B, gran, intra | SDCBP, mean, intra | 0.2 | −0.18 | 63 | 75 | 44 | 68 | 53 |
| EIF4B, gran, intra | WBC | 0.51 | 0.13 | 76 | 84 | 66 | 75 | 77 |
| EIF4B, lymp, intra | EIF4B, mean, intra | 0.39 | −0.01 | 69 | 69 | 69 | 72 | 66 |
| EIF4B, lymp, intra | EIF4B, mono, intra | 0.43 | 0.03 | 72 | 69 | 75 | 76 | 67 |
| EIF4B, lymp, intra | EPSTI1, lymp, membrane | 0.32 | −0.08 | 69 | 79 | 52 | 74 | 59 |
| EIF4B, lymp, intra | GAS7, lymp, intra | 0.27 | −0.13 | 67 | 75 | 52 | 73 | 55 |
| EIF4B, lymp, intra | IFI6, gran, intra | 0.16 | −0.24 | 62 | 77 | 38 | 67 | 50 |
| EIF4B, lymp, intra | IFI6, mono, intra | 0.16 | −0.24 | 62 | 77 | 38 | 67 | 50 |
| EIF4B, lymp, intra | IFIT3, gran, intra | 0.37 | −0.03 | 71 | 80 | 56 | 75 | 63 |

TABLE 4-continued

The classification accuracy of bacterial vs. viral infected patients computed over pairs of features. DETERMINANT measurements were measured over different cell types.

| Feature #1 | Feature #2 | MCC | dMCC | Total accuracy % | Sen % | Spe % | PPV % | NPV % |
|---|---|---|---|---|---|---|---|---|
| EIF4B, lymp, intra | IFIT3, lymp, intra | 0.33 | −0.1 | 69 | 78 | 54 | 74 | 60 |
| EIF4B, lymp, intra | IFIT3, mean, intra | 0.34 | −0.06 | 69 | 79 | 54 | 73 | 62 |
| EIF4B, lymp, intra | IFIT3, mono, intra | 0.37 | −0.03 | 71 | 80 | 56 | 75 | 63 |
| EIF4B, lymp, intra | IFITM1, gran, membrane | 0.38 | −0.02 | 69 | 73 | 65 | 72 | 66 |
| EIF4B, lymp, intra | IFITM1, lymp, membrane | 0.4 | 0 | 70 | 70 | 70 | 74 | 66 |
| EIF4B, lymp, intra | IFITM1, mean, membrane | 0.37 | −0.03 | 69 | 74 | 63 | 71 | 66 |
| EIF4B, lymp, intra | IFITM1, mono, membrane | 0.36 | −0.04 | 69 | 73 | 63 | 71 | 66 |
| EIF4B, lymp, intra | IFITM3, gran, membrane | 0.41 | 0.01 | 71 | 73 | 68 | 74 | 67 |
| EIF4B, lymp, intra | IFITM3, mean, membrane | 0.4 | 0 | 70 | 72 | 68 | 73 | 67 |
| EIF4B, lymp, intra | IFITM3, mono, membrane | 0.46 | 0.05 | 73 | 73 | 73 | 77 | 69 |
| EIF4B, lymp, intra | LOC26010, gran, intra | 0.43 | 0.03 | 72 | 74 | 68 | 73 | 69 |
| EIF4B, lymp, intra | LOC26010, mean, intra | 0.4 | 0 | 70 | 74 | 66 | 72 | 68 |
| EIF4B, lymp, intra | LOC26010, mono, intra | 0.43 | 0.03 | 72 | 74 | 68 | 73 | 69 |
| EIF4B, lymp, intra | LY6E, lymp, membrane | 0.37 | −0.03 | 69 | 70 | 67 | 72 | 65 |
| EIF4B, lymp, intra | Lym(%) | 0.66 | 0.14 | 83 | 82 | 84 | 86 | 80 |
| EIF4B, lymp, intra | MAN1C1, gran, intra | 0.2 | −0.2 | 64 | 77 | 42 | 69 | 52 |
| EIF4B, lymp, intra | MAN1C1, mean, intra | 0.19 | −0.21 | 64 | 79 | 39 | 68 | 52 |
| EIF4B, lymp, intra | MAN1C1, mono, intra | 0.2 | −0.2 | 64 | 77 | 42 | 69 | 52 |
| EIF4B, lymp, intra | MX1, gran, intra | 0.56 | 0.02 | 78 | 76 | 81 | 82 | 74 |
| EIF4B, lymp, intra | MX1, lymp, intra | 0.47 | 0.07 | 74 | 73 | 75 | 77 | 70 |
| EIF4B, lymp, intra | MX1, mean, intra | 0.52 | 0.07 | 76 | 75 | 77 | 79 | 73 |
| EIF4B, lymp, intra | MX1, mono, intra | 0.56 | 0.02 | 78 | 76 | 81 | 82 | 74 |
| EIF4B, lymp, intra | Neu(%) | 0.67 | 0.11 | 84 | 85 | 82 | 85 | 82 |
| EIF4B, lymp, intra | NPM1, gran, intra | 0.31 | −0.09 | 69 | 83 | 46 | 71 | 62 |
| EIF4B, lymp, intra | NPM1, mean, intra | 0.2 | −0.2 | 63 | 75 | 44 | 68 | 53 |
| EIF4B, lymp, intra | NPM1, mono, intra | 0.31 | −0.09 | 69 | 83 | 46 | 71 | 62 |
| EIF4B, lymp, intra | OAS2, gran, intra | 0.49 | 0.09 | 74 | 76 | 73 | 77 | 72 |
| EIF4B, lymp, intra | OAS2, mean, intra | 0.46 | 0.06 | 73 | 76 | 69 | 74 | 72 |
| EIF4B, lymp, intra | OAS2, mono, intra | 0.49 | 0.09 | 74 | 76 | 73 | 77 | 72 |
| EIF4B, lymp, intra | PARP12, gran, intra | 0.28 | −0.12 | 67 | 78 | 49 | 71 | 58 |
| EIF4B, lymp, intra | PARP12, mean, intra | 0.32 | −0.08 | 68 | 77 | 54 | 73 | 60 |
| EIF4B, lymp, intra | PARP12, mono, intra | 0.28 | −0.12 | 67 | 78 | 49 | 71 | 58 |
| EIF4B, lymp, intra | PARP9, lymp, intra | 0.24 | −0.16 | 66 | 83 | 38 | 69 | 58 |
| EIF4B, lymp, intra | PDIA6, gran, intra | 0.35 | −0.05 | 70 | 79 | 55 | 75 | 61 |
| EIF4B, lymp, intra | PDIA6, lymp, intra | 0.25 | −0.15 | 65 | 74 | 52 | 72 | 53 |
| EIF4B, lymp, intra | PDIA6, mono, intra | 0.35 | −0.05 | 70 | 79 | 55 | 75 | 61 |
| EIF4B, lymp, intra | PTEN, gran, intra | 0.21 | −0.19 | 64 | 77 | 44 | 69 | 53 |
| EIF4B, lymp, intra | PTEN, lymp, intra | 0.17 | −0.23 | 62 | 75 | 41 | 68 | 50 |
| EIF4B, lymp, intra | PTEN, mean, intra | 0.22 | −0.18 | 64 | 77 | 44 | 69 | 55 |
| EIF4B, lymp, intra | PTEN, mono, intra | 0.21 | −0.19 | 64 | 77 | 44 | 69 | 53 |
| EIF4B, lymp, intra | RSAD2, gran, intra | 0.61 | −0.02 | 80 | 78 | 83 | 84 | 76 |
| EIF4B, lymp, intra | RSAD2, lymp, intra | 0.37 | −0.03 | 69 | 72 | 65 | 71 | 66 |
| EIF4B, lymp, intra | RSAD2, mean, intra | 0.63 | −0.01 | 81 | 82 | 81 | 83 | 79 |
| EIF4B, lymp, intra | RSAD2, mono, intra | 0.61 | −0.02 | 80 | 78 | 83 | 84 | 76 |
| EIF4B, lymp, intra | SDCBP, mean, intra | 0.19 | −0.21 | 63 | 79 | 38 | 67 | 54 |
| EIF4B, lymp, intra | WBC | 0.46 | 0.06 | 74 | 78 | 68 | 74 | 72 |
| EIF4B, mean, intra | EIF4B, mono, intra | 0.38 | 0 | 69 | 63 | 76 | 75 | 64 |
| EIF4B, mean, intra | EPSTI1, lymp, membrane | 0.31 | 0 | 68 | 75 | 55 | 74 | 57 |
| EIF4B, mean, intra | GAS7, lymp, intra | 0.27 | −0.04 | 67 | 75 | 52 | 73 | 55 |
| EIF4B, mean, intra | IFI6, gran, intra | 0.15 | −0.16 | 61 | 76 | 38 | 66 | 50 |
| EIF4B, mean, intra | IFI6, mono, intra | 0.15 | −0.16 | 61 | 76 | 38 | 66 | 50 |
| EIF4B, mean, intra | IFIT3, gran, intra | 0.33 | −0.06 | 68 | 76 | 56 | 73 | 59 |
| EIF4B, mean, intra | IFIT3, lymp, intra | 0.3 | −0.13 | 67 | 76 | 54 | 72 | 58 |
| EIF4B, mean, intra | IFIT3, mean, intra | 0.23 | −0.08 | 64 | 76 | 46 | 69 | 55 |
| EIF4B, mean, intra | IFIT3, mono, intra | 0.33 | −0.06 | 68 | 76 | 56 | 73 | 59 |
| EIF4B, mean, intra | IFITM1, gran, membrane | 0.26 | −0.05 | 63 | 68 | 58 | 66 | 60 |
| EIF4B, mean, intra | IFITM1, lymp, membrane | 0.39 | 0.01 | 69 | 71 | 68 | 73 | 66 |
| EIF4B, mean, intra | IFITM1, mean, membrane | 0.26 | −0.05 | 63 | 69 | 56 | 66 | 60 |
| EIF4B, mean, intra | IFITM1, mono, membrane | 0.28 | −0.03 | 64 | 65 | 63 | 68 | 60 |
| EIF4B, mean, intra | IFITM3, gran, membrane | 0.31 | −0.04 | 66 | 65 | 66 | 70 | 61 |
| EIF4B, mean, intra | IFITM3, mean, membrane | 0.32 | −0.03 | 66 | 68 | 64 | 70 | 62 |
| EIF4B, mean, intra | IFITM3, mono, membrane | 0.4 | −0.01 | 70 | 71 | 69 | 74 | 66 |
| EIF4B, mean, intra | LOC26010, gran, intra | 0.33 | 0.02 | 66 | 65 | 68 | 70 | 63 |
| EIF4B, mean, intra | LOC26010, mean, intra | 0.3 | −0.01 | 65 | 63 | 68 | 69 | 61 |
| EIF4B, mean, intra | LOC26010, mono, intra | 0.33 | 0.02 | 66 | 65 | 68 | 70 | 63 |
| EIF4B, mean, intra | LY6E, lymp, membrane | 0.36 | 0.05 | 68 | 70 | 67 | 72 | 64 |
| EIF4B, mean, intra | Lym(%) | 0.54 | 0.02 | 77 | 75 | 79 | 81 | 73 |
| EIF4B, mean, intra | MAN1C1, gran, intra | 0.27 | −0.04 | 67 | 83 | 42 | 70 | 59 |
| EIF4B, mean, intra | MAN1C1, mean, intra | 0.25 | −0.06 | 66 | 79 | 45 | 71 | 56 |
| EIF4B, mean, intra | MAN1C1, mono, intra | 0.27 | −0.04 | 67 | 83 | 42 | 70 | 59 |
| EIF4B, mean, intra | MX1, gran, intra | 0.53 | −0.01 | 76 | 69 | 84 | 83 | 70 |
| EIF4B, mean, intra | MX1, lymp, intra | 0.42 | 0.07 | 71 | 67 | 76 | 76 | 66 |
| EIF4B, mean, intra | MX1, mean, intra | 0.46 | 0.01 | 72 | 67 | 79 | 79 | 67 |
| EIF4B, mean, intra | MX1, mono, intra | 0.53 | −0.01 | 76 | 69 | 84 | 83 | 70 |

TABLE 4-continued

The classification accuracy of bacterial vs. viral infected patients computed over pairs of features. DETERMINANT measurements were measured over different cell types.

| Feature #1 | Feature #2 | MCC | dMCC | Total accuracy % | Sen % | Spe % | PPV % | NPV % |
|---|---|---|---|---|---|---|---|---|
| EIF4B, mean, intra | Neu(%) | 0.57 | 0.01 | 78 | 78 | 79 | 81 | 75 |
| EIF4B, mean, intra | NPM1, gran, intra | 0.08 | −0.23 | 58 | 74 | 33 | 63 | 45 |
| EIF4B, mean, intra | NPM1, mean, intra | 0.08 | −0.23 | 58 | 72 | 36 | 64 | 45 |
| EIF4B, mean, intra | NPM1, mono, intra | 0.08 | −0.23 | 58 | 74 | 33 | 63 | 45 |
| EIF4B, mean, intra | OAS2, gran, intra | 0.4 | 0.04 | 69 | 63 | 77 | 76 | 64 |
| EIF4B, mean, intra | OAS2, mean, intra | 0.34 | 0.03 | 67 | 67 | 68 | 71 | 64 |
| EIF4B, mean, intra | OAS2, mono, intra | 0.4 | 0.04 | 69 | 63 | 77 | 76 | 64 |
| EIF4B, mean, intra | PARP12, gran, intra | 0.16 | −0.15 | 61 | 74 | 41 | 67 | 50 |
| EIF4B, mean, intra | PARP12, mean, intra | 0.26 | −0.05 | 65 | 74 | 51 | 71 | 56 |
| EIF4B, mean, intra | PARP12, mono, intra | 0.16 | −0.15 | 61 | 74 | 41 | 67 | 50 |
| EIF4B, mean, intra | PARP9, lymp, intra | 0.19 | −0.12 | 63 | 79 | 38 | 67 | 54 |
| EIF4B, mean, intra | PDIA6, gran, intra | 0.26 | −0.05 | 67 | 79 | 45 | 71 | 56 |
| EIF4B, mean, intra | PDIA6, lymp, intra | 0.27 | −0.04 | 67 | 77 | 48 | 72 | 56 |
| EIF4B, mean, intra | PDIA6, mono, intra | 0.26 | −0.05 | 67 | 79 | 45 | 71 | 56 |
| EIF4B, mean, intra | PTEN, gran, intra | 0.2 | −0.11 | 63 | 76 | 44 | 68 | 53 |
| EIF4B, mean, intra | PTEN, lymp, intra | 0.31 | 0 | 68 | 79 | 51 | 72 | 61 |
| EIF4B, mean, intra | PTEN, mean, intra | 0.16 | −0.15 | 61 | 74 | 41 | 67 | 50 |
| EIF4B, mean, intra | PTEN, mono, intra | 0.2 | −0.11 | 63 | 76 | 44 | 68 | 53 |
| EIF4B, mean, intra | RSAD2, gran, intra | 0.63 | 0 | 81 | 79 | 84 | 85 | 78 |
| EIF4B, mean, intra | RSAD2, lymp, intra | 0.41 | 0.1 | 70 | 68 | 73 | 74 | 66 |
| EIF4B, mean, intra | RSAD2, mean, intra | 0.63 | −0.01 | 81 | 79 | 84 | 85 | 78 |
| EIF4B, mean, intra | RSAD2, mono, intra | 0.63 | 0 | 81 | 79 | 84 | 85 | 78 |
| EIF4B, mean, intra | SDCBP, mean, intra | 0.17 | −0.14 | 62 | 77 | 38 | 66 | 52 |
| EIF4B, mean, intra | WBC | 0.38 | 0.07 | 69 | 79 | 58 | 69 | 71 |
| EIF4B, mono, intra | EPSTI1, lymp, membrane | 0.37 | −0.01 | 70 | 74 | 65 | 78 | 59 |
| EIF4B, mono, intra | GAS7, lymp, intra | 0.34 | −0.04 | 69 | 74 | 61 | 76 | 58 |
| EIF4B, mono, intra | IFI6, gran, intra | 0.19 | −0.19 | 63 | 77 | 41 | 68 | 52 |
| EIF4B, mono, intra | IFI6, mono, intra | 0.19 | −0.19 | 63 | 77 | 41 | 68 | 52 |
| EIF4B, mono, intra | IFIT3, gran, intra | 0.38 | −0.01 | 71 | 78 | 59 | 76 | 62 |
| EIF4B, mono, intra | IFIT3, lymp, intra | 0.35 | −0.08 | 70 | 78 | 56 | 75 | 61 |
| EIF4B, mono, intra | IFIT3, mean, intra | 0.33 | −0.05 | 68 | 76 | 56 | 73 | 59 |
| EIF4B, mono, intra | IFIT3, mono, intra | 0.38 | −0.01 | 71 | 78 | 59 | 76 | 62 |
| EIF4B, mono, intra | IFITM1, gran, membrane | 0.28 | −0.1 | 64 | 65 | 63 | 69 | 59 |
| EIF4B, mono, intra | IFITM1, lymp, membrane | 0.43 | 0.05 | 72 | 72 | 72 | 76 | 67 |
| EIF4B, mono, intra | IFITM1, mean, membrane | 0.28 | −0.1 | 64 | 65 | 63 | 68 | 60 |
| EIF4B, mono, intra | IFITM1, mono, membrane | 0.32 | −0.06 | 66 | 69 | 63 | 70 | 62 |
| EIF4B, mono, intra | IFITM3, gran, membrane | 0.34 | −0.04 | 67 | 68 | 67 | 71 | 63 |
| EIF4B, mono, intra | IFITM3, mean, membrane | 0.33 | −0.05 | 66 | 65 | 68 | 71 | 62 |
| EIF4B, mono, intra | IFITM3, mono, membrane | 0.45 | 0.04 | 72 | 70 | 75 | 78 | 67 |
| EIF4B, mono, intra | LOC26010, gran, intra | 0.39 | 0.01 | 69 | 65 | 75 | 75 | 64 |
| EIF4B, mono, intra | LOC26010, mean, intra | 0.38 | 0 | 69 | 63 | 76 | 75 | 64 |
| EIF4B, mono, intra | LOC26010, mono, intra | 0.39 | 0.01 | 69 | 65 | 75 | 75 | 64 |
| EIF4B, mono, intra | LY6E, lymp, membrane | 0.41 | 0.03 | 70 | 68 | 73 | 75 | 66 |
| EIF4B, mono, intra | Lym(%) | 0.55 | 0.03 | 77 | 76 | 79 | 81 | 73 |
| EIF4B, mono, intra | MAN1C1, gran, intra | 0.36 | −0.02 | 71 | 83 | 52 | 74 | 64 |
| EIF4B, mono, intra | MAN1C1, mean, intra | 0.39 | 0.01 | 72 | 83 | 55 | 75 | 65 |
| EIF4B, mono, intra | MAN1C1, mono, intra | 0.36 | −0.02 | 71 | 83 | 52 | 74 | 64 |
| EIF4B, mono, intra | MX1, gran, intra | 0.57 | 0.03 | 78 | 73 | 84 | 84 | 73 |
| EIF4B, mono, intra | MX1, lymp, intra | 0.54 | 0.16 | 77 | 73 | 81 | 82 | 72 |
| EIF4B, mono, intra | MX1, mean, intra | 0.58 | 0.13 | 78 | 72 | 85 | 85 | 73 |
| EIF4B, mono, intra | MX1, mono, intra | 0.57 | 0.03 | 78 | 73 | 84 | 84 | 73 |
| EIF4B, mono, intra | Neu(%) | 0.53 | −0.03 | 76 | 76 | 77 | 80 | 73 |
| EIF4B, mono, intra | NPM1, gran, intra | 0.16 | −0.22 | 62 | 75 | 41 | 67 | 50 |
| EIF4B, mono, intra | NPM1, mean, intra | 0.27 | −0.11 | 66 | 75 | 51 | 71 | 57 |
| EIF4B, mono, intra | NPM1, mono, intra | 0.16 | −0.22 | 62 | 75 | 41 | 67 | 50 |
| EIF4B, mono, intra | OAS2, gran, intra | 0.4 | 0.02 | 69 | 64 | 76 | 76 | 64 |
| EIF4B, mono, intra | OAS2, mean, intra | 0.38 | 0 | 69 | 65 | 73 | 73 | 64 |
| EIF4B, mono, intra | OAS2, mono, intra | 0.4 | 0.02 | 69 | 64 | 76 | 76 | 64 |
| EIF4B, mono, intra | PARP12, gran, intra | 0.24 | −0.14 | 65 | 77 | 46 | 70 | 55 |
| EIF4B, mono, intra | PARP12, mean, intra | 0.27 | −0.11 | 65 | 71 | 56 | 72 | 55 |
| EIF4B, mono, intra | PARP12, mono, intra | 0.24 | −0.14 | 65 | 77 | 46 | 70 | 55 |
| EIF4B, mono, intra | PARP9, lymp, intra | 0.3 | −0.08 | 68 | 80 | 49 | 72 | 59 |
| EIF4B, mono, intra | PDIA6, gran, intra | 0.24 | −0.14 | 65 | 77 | 45 | 71 | 54 |
| EIF4B, mono, intra | PDIA6, lymp, intra | 0.31 | −0.07 | 68 | 74 | 58 | 75 | 56 |
| EIF4B, mono, intra | PDIA6, mono, intra | 0.24 | −0.14 | 65 | 77 | 45 | 71 | 54 |
| EIF4B, mono, intra | PTEN, gran, intra | 0.26 | −0.12 | 66 | 77 | 49 | 71 | 56 |
| EIF4B, mono, intra | PTEN, lymp, intra | 0.33 | −0.05 | 69 | 78 | 54 | 74 | 60 |
| EIF4B, mono, intra | PTEN, mean, intra | 0.2 | −0.18 | 63 | 77 | 41 | 68 | 53 |
| EIF4B, mono, intra | PTEN, mono, intra | 0.26 | −0.12 | 66 | 77 | 49 | 71 | 56 |
| EIF4B, mono, intra | RSAD2, gran, intra | 0.62 | −0.01 | 81 | 78 | 84 | 85 | 77 |
| EIF4B, mono, intra | RSAD2, lymp, intra | 0.45 | 0.07 | 72 | 70 | 75 | 76 | 68 |
| EIF4B, mono, intra | RSAD2, mean, intra | 0.6 | −0.04 | 80 | 78 | 82 | 84 | 76 |
| EIF4B, mono, intra | RSAD2, mono, intra | 0.62 | −0.01 | 81 | 78 | 84 | 85 | 77 |
| EIF4B, mono, intra | SDCBP, mean, intra | 0.2 | −0.18 | 63 | 75 | 44 | 68 | 53 |

TABLE 4-continued

The classification accuracy of bacterial vs. viral infected patients computed over pairs of features. DETERMINANT measurements were measured over different cell types.

| Feature #1 | Feature #2 | MCC | dMCC | Total accuracy % | Sen % | Spe % | PPV % | NPV % |
|---|---|---|---|---|---|---|---|---|
| EIF4B, mono, intra | WBC | 0.51 | 0.13 | 76 | 84 | 66 | 75 | 77 |
| EPSTI1, lymp, membrane | GAS7, lymp, intra | 0.14 | −0.05 | 62 | 77 | 35 | 67 | 48 |
| EPSTI1, lymp, membrane | IFI6, gran, intra | 0.24 | 0.05 | 65 | 77 | 45 | 71 | 54 |
| EPSTI1, lymp, membrane | IFI6, mono, intra | 0.24 | 0.05 | 65 | 77 | 45 | 71 | 54 |
| EPSTI1, lymp, membrane | IFIT3, gran, intra | 0.21 | −0.18 | 64 | 75 | 45 | 70 | 52 |
| EPSTI1, lymp, membrane | IFIT3, lymp, intra | 0.2 | −0.23 | 64 | 77 | 42 | 69 | 52 |
| EPSTI1, lymp, membrane | IFIT3, mean, intra | 0.26 | 0.01 | 67 | 79 | 45 | 71 | 56 |
| EPSTI1, lymp, membrane | IFIT3, mono, intra | 0.21 | −0.18 | 64 | 75 | 45 | 70 | 52 |
| EPSTI1, lymp, membrane | IFITM1, gran, membrane | 0.12 | −0.14 | 62 | 81 | 29 | 66 | 47 |
| EPSTI1, lymp, membrane | IFITM1, lymp, membrane | 0.15 | −0.23 | 62 | 75 | 39 | 68 | 48 |
| EPSTI1, lymp, membrane | IFITM1, mean, membrane | 0.15 | −0.14 | 63 | 81 | 32 | 67 | 50 |
| EPSTI1, lymp, membrane | IFITM1, mono, membrane | 0.28 | −0.03 | 68 | 81 | 45 | 72 | 58 |
| EPSTI1, lymp, membrane | IFITM3, gran, membrane | 0.08 | −0.27 | 61 | 81 | 26 | 65 | 44 |
| EPSTI1, lymp, membrane | IFITM3, mean, membrane | 0.06 | −0.29 | 60 | 79 | 26 | 65 | 42 |
| EPSTI1, lymp, membrane | IFITM3, mono, membrane | 0.27 | −0.14 | 67 | 75 | 52 | 73 | 55 |
| EPSTI1, lymp, membrane | LOC26010, gran, intra | 0.26 | 0.03 | 67 | 79 | 45 | 71 | 56 |
| EPSTI1, lymp, membrane | LOC26010, mean, intra | 0.24 | 0.03 | 67 | 83 | 39 | 70 | 57 |
| EPSTI1, lymp, membrane | LOC26010, mono, intra | 0.26 | 0.03 | 67 | 79 | 45 | 71 | 56 |
| EPSTI1, lymp, membrane | LY6E, lymp, membrane | 0.21 | −0.02 | 65 | 83 | 35 | 69 | 55 |
| EPSTI1, lymp, membrane | Lym(%) | 0.48 | −0.04 | 76 | 85 | 61 | 79 | 70 |
| EPSTI1, lymp, membrane | MAN1C1, gran, intra | 0.28 | 0.09 | 67 | 81 | 45 | 71 | 58 |
| EPSTI1, lymp, membrane | MAN1C1, mean, intra | 0.3 | 0.11 | 69 | 83 | 45 | 72 | 61 |
| EPSTI1, lymp, membrane | MAN1C1, mono, intra | 0.28 | 0.09 | 67 | 81 | 45 | 71 | 58 |
| EPSTI1, lymp, membrane | MX1, gran, intra | 0.48 | −0.06 | 76 | 83 | 65 | 80 | 69 |
| EPSTI1, lymp, membrane | MX1, lymp, intra | 0.27 | −0.08 | 67 | 75 | 52 | 73 | 55 |
| EPSTI1, lymp, membrane | MX1, mean, intra | 0.43 | −0.02 | 74 | 81 | 61 | 78 | 66 |
| EPSTI1, lymp, membrane | MX1, mono, intra | 0.48 | −0.06 | 76 | 83 | 65 | 80 | 69 |
| EPSTI1, lymp, membrane | Neu(%) | 0.48 | −0.08 | 76 | 83 | 65 | 80 | 69 |
| EPSTI1, lymp, membrane | NPM1, gran, intra | 0.34 | 0.15 | 70 | 81 | 52 | 74 | 62 |
| EPSTI1, lymp, membrane | NPM1, mean, intra | 0.39 | 0.2 | 72 | 83 | 55 | 75 | 65 |
| EPSTI1, lymp, membrane | NPM1, mono, intra | 0.34 | 0.15 | 70 | 81 | 52 | 74 | 62 |
| EPSTI1, lymp, membrane | OAS2, gran, intra | 0.21 | −0.15 | 64 | 75 | 45 | 70 | 52 |
| EPSTI1, lymp, membrane | OAS2, mean, intra | 0.16 | −0.14 | 63 | 79 | 35 | 68 | 50 |
| EPSTI1, lymp, membrane | OAS2, mono, intra | 0.21 | −0.15 | 64 | 75 | 45 | 70 | 52 |
| EPSTI1, lymp, membrane | PARP12, gran, intra | 0.41 | 0.22 | 73 | 79 | 61 | 78 | 63 |
| EPSTI1, lymp, membrane | PARP12, mean, intra | 0.41 | 0.16 | 73 | 79 | 61 | 78 | 63 |
| EPSTI1, lymp, membrane | PARP12, mono, intra | 0.41 | 0.22 | 73 | 79 | 61 | 78 | 63 |
| EPSTI1, lymp, membrane | PARP9, lymp, intra | 0.21 | 0.02 | 65 | 83 | 35 | 69 | 55 |
| EPSTI1, lymp, membrane | PDIA6, gran, intra | 0.27 | 0.08 | 67 | 75 | 52 | 73 | 55 |
| EPSTI1, lymp, membrane | PDIA6, lymp, intra | 0.32 | 0.13 | 69 | 79 | 52 | 74 | 59 |
| EPSTI1, lymp, membrane | PDIA6, mono, intra | 0.27 | 0.08 | 67 | 75 | 52 | 73 | 55 |
| EPSTI1, lymp, membrane | PTEN, gran, intra | 0.4 | 0.18 | 71 | 75 | 65 | 78 | 61 |
| EPSTI1, lymp, membrane | PTEN, lymp, intra | 0.27 | 0.08 | 67 | 77 | 48 | 72 | 56 |
| EPSTI1, lymp, membrane | PTEN, mean, intra | 0.36 | 0.16 | 70 | 77 | 58 | 76 | 60 |
| EPSTI1, lymp, membrane | PTEN, mono, intra | 0.4 | 0.18 | 71 | 75 | 65 | 78 | 61 |
| EPSTI1, lymp, membrane | RSAD2, gran, intra | 0.62 | −0.01 | 82 | 85 | 77 | 87 | 75 |
| EPSTI1, lymp, membrane | RSAD2, lymp, intra | 0.19 | −0.04 | 64 | 79 | 39 | 69 | 52 |
| EPSTI1, lymp, membrane | RSAD2, mean, intra | 0.54 | −0.1 | 79 | 83 | 71 | 83 | 71 |
| EPSTI1, lymp, membrane | RSAD2, mono, intra | 0.62 | −0.01 | 82 | 85 | 77 | 87 | 75 |
| EPSTI1, lymp, membrane | SDCBP, mean, intra | 0.36 | 0.17 | 71 | 83 | 52 | 74 | 64 |
| EPSTI1, lymp, membrane | WBC | 0.26 | 0.01 | 68 | 87 | 35 | 70 | 61 |
| GAS7, lymp, intra | IFI6, gran, intra | 0 | −0.1 | 55 | 68 | 32 | 63 | 37 |
| GAS7, lymp, intra | IFI6, mono, intra | 0 | −0.1 | 55 | 68 | 32 | 63 | 37 |
| GAS7, lymp, intra | IFIT3, gran, intra | 0.2 | −0.19 | 63 | 72 | 48 | 70 | 50 |
| GAS7, lymp, intra | IFIT3, lymp, intra | 0.27 | −0.16 | 67 | 77 | 48 | 72 | 56 |
| GAS7, lymp, intra | IFIT3, mean, intra | 0.17 | −0.08 | 62 | 72 | 45 | 69 | 48 |
| GAS7, lymp, intra | IFIT3, mono, intra | 0.2 | −0.19 | 63 | 72 | 48 | 70 | 50 |
| GAS7, lymp, intra | IFITM1, gran, membrane | 0.07 | −0.19 | 58 | 72 | 35 | 66 | 42 |
| GAS7, lymp, intra | IFITM1, lymp, membrane | 0.14 | −0.24 | 61 | 72 | 42 | 68 | 46 |
| GAS7, lymp, intra | IFITM1, mean, membrane | 0.02 | −0.27 | 56 | 70 | 32 | 64 | 38 |
| GAS7, lymp, intra | IFITM1, mono, membrane | 0.3 | −0.01 | 68 | 77 | 52 | 73 | 57 |
| GAS7, lymp, intra | IFITM3, gran, membrane | 0.05 | −0.3 | 57 | 70 | 35 | 65 | 41 |
| GAS7, lymp, intra | IFITM3, mean, membrane | 0.05 | −0.3 | 57 | 70 | 35 | 65 | 41 |
| GAS7, lymp, intra | IFITM3, mono, membrane | 0.34 | −0.07 | 69 | 75 | 58 | 75 | 58 |
| GAS7, lymp, intra | LOC26010, gran, intra | 0.17 | −0.06 | 63 | 77 | 39 | 68 | 50 |
| GAS7, lymp, intra | LOC26010, mean, intra | 0.14 | −0.07 | 62 | 77 | 35 | 67 | 48 |
| GAS7, lymp, intra | LOC26010, mono, intra | 0.17 | −0.06 | 63 | 77 | 39 | 68 | 50 |
| GAS7, lymp, intra | LY6E, lymp, membrane | 0.06 | −0.17 | 58 | 74 | 32 | 65 | 42 |
| GAS7, lymp, intra | Lym(%) | 0.49 | −0.03 | 76 | 81 | 68 | 81 | 68 |
| GAS7, lymp, intra | MAN1C1, gran, intra | 0.2 | 0.09 | 64 | 77 | 42 | 69 | 52 |
| GAS7, lymp, intra | MAN1C1, mean, intra | 0.11 | −0.02 | 60 | 75 | 35 | 66 | 46 |
| GAS7, lymp, intra | MAN1C1, mono, intra | 0.2 | 0.09 | 64 | 77 | 42 | 69 | 52 |
| GAS7, lymp, intra | MX1, gran, intra | 0.51 | −0.03 | 77 | 83 | 68 | 81 | 70 |
| GAS7, lymp, intra | MX1, lymp, intra | 0.31 | −0.04 | 69 | 81 | 48 | 73 | 60 |

TABLE 4-continued

The classification accuracy of bacterial vs. viral infected patients computed over pairs of features. DETERMINANT measurements were measured over different cell types.

| Feature #1 | Feature #2 | MCC | dMCC | Total accuracy % | Sen % | Spe % | PPV % | NPV % |
|---|---|---|---|---|---|---|---|---|
| GAS7, lymp, intra | MX1, mean, intra | 0.45 | 0 | 74 | 77 | 68 | 80 | 64 |
| GAS7, lymp, intra | MX1, mono, intra | 0.51 | −0.03 | 77 | 83 | 68 | 81 | 70 |
| GAS7, lymp, intra | Neu(%) | 0.45 | −0.11 | 75 | 83 | 61 | 79 | 68 |
| GAS7, lymp, intra | NPM1, gran, intra | 0.2 | 0.1 | 64 | 77 | 42 | 69 | 52 |
| GAS7, lymp, intra | NPM1, mean, intra | 0.17 | 0.04 | 63 | 77 | 39 | 68 | 50 |
| GAS7, lymp, intra | NPM1, mono, intra | 0.2 | 0.1 | 64 | 77 | 42 | 69 | 52 |
| GAS7, lymp, intra | OAS2, gran, intra | 0.15 | −0.21 | 61 | 70 | 45 | 69 | 47 |
| GAS7, lymp, intra | OAS2, mean, intra | −0.01 | −0.31 | 55 | 70 | 29 | 63 | 36 |
| GAS7, lymp, intra | OAS2, mono, intra | 0.15 | −0.21 | 61 | 70 | 45 | 69 | 47 |
| GAS7, lymp, intra | PARP12, gran, intra | 0.24 | 0.05 | 65 | 75 | 48 | 71 | 54 |
| GAS7, lymp, intra | PARP12, mean, intra | 0.2 | −0.05 | 63 | 72 | 48 | 70 | 50 |
| GAS7, lymp, intra | PARP12, mono, intra | 0.24 | 0.05 | 65 | 75 | 48 | 71 | 54 |
| GAS7, lymp, intra | PARP9, lymp, intra | 0.07 | −0.07 | 58 | 72 | 35 | 66 | 42 |
| GAS7, lymp, intra | PDIA6, gran, intra | 0.16 | 0.03 | 62 | 74 | 42 | 68 | 48 |
| GAS7, lymp, intra | PDIA6, lymp, intra | 0.11 | 0.01 | 60 | 72 | 39 | 67 | 44 |
| GAS7, lymp, intra | PDIA6, mono, intra | 0.16 | 0.03 | 62 | 74 | 42 | 68 | 48 |
| GAS7, lymp, intra | PTEN, gran, intra | 0.18 | −0.04 | 62 | 70 | 48 | 70 | 48 |
| GAS7, lymp, intra | PTEN, lymp, intra | 0.15 | 0.05 | 62 | 75 | 39 | 68 | 48 |
| GAS7, lymp, intra | PTEN, mean, intra | 0.12 | −0.08 | 60 | 70 | 42 | 67 | 45 |
| GAS7, lymp, intra | PTEN, mono, intra | 0.18 | −0.04 | 62 | 70 | 48 | 70 | 48 |
| GAS7, lymp, intra | RSAD2, gran, intra | 0.62 | −0.01 | 82 | 85 | 77 | 87 | 75 |
| GAS7, lymp, intra | RSAD2, lymp, intra | 0.06 | −0.17 | 58 | 74 | 32 | 65 | 42 |
| GAS7, lymp, intra | RSAD2, mean, intra | 0.61 | −0.03 | 82 | 87 | 74 | 85 | 77 |
| GAS7, lymp, intra | RSAD2, mono, intra | 0.62 | −0.01 | 82 | 85 | 77 | 87 | 75 |
| GAS7, lymp, intra | SDCBP, mean, intra | 0.25 | 0.15 | 66 | 79 | 45 | 71 | 56 |
| GAS7, lymp, intra | WBC | 0.19 | −0.06 | 64 | 81 | 35 | 68 | 52 |
| IFI6, gran, intra | IFI6, mono, intra | 0.06 | −0.02 | 59 | 80 | 26 | 64 | 43 |
| IFI6, gran, intra | IFIT3, gran, intra | 0.33 | −0.06 | 69 | 77 | 56 | 74 | 59 |
| IFI6, gran, intra | IFIT3, lymp, intra | 0.4 | −0.03 | 72 | 78 | 62 | 77 | 63 |
| IFI6, gran, intra | IFIT3, mean, intra | 0.34 | 0.09 | 69 | 77 | 56 | 74 | 61 |
| IFI6, gran, intra | IFIT3, mono, intra | 0.33 | −0.06 | 69 | 77 | 56 | 74 | 59 |
| IFI6, gran, intra | IFITM1, gran, membrane | 0.05 | −0.21 | 59 | 81 | 23 | 63 | 43 |
| IFI6, gran, intra | IFITM1, lymp, membrane | 0.35 | −0.03 | 70 | 78 | 56 | 75 | 61 |
| IFI6, gran, intra | IFITM1, mean, membrane | 0 | −0.29 | 55 | 74 | 26 | 61 | 38 |
| IFI6, gran, intra | IFITM1, mono, membrane | 0.23 | −0.08 | 64 | 72 | 51 | 71 | 53 |
| IFI6, gran, intra | IFITM3, gran, membrane | 0.09 | −0.26 | 60 | 80 | 28 | 65 | 46 |
| IFI6, gran, intra | IFITM3, mean, membrane | 0.05 | −0.3 | 57 | 74 | 31 | 63 | 43 |
| IFI6, gran, intra | IFITM3, mono, membrane | 0.26 | −0.15 | 65 | 70 | 56 | 73 | 54 |
| IFI6, gran, intra | LOC26010, gran, intra | 0.09 | −0.14 | 59 | 75 | 33 | 65 | 45 |
| IFI6, gran, intra | LOC26010, mean, intra | −0.01 | −0.22 | 54 | 71 | 28 | 61 | 38 |
| IFI6, gran, intra | LOC26010, mono, intra | 0.09 | −0.14 | 59 | 75 | 33 | 65 | 45 |
| IFI6, gran, intra | LY6E, lymp, membrane | −0.02 | −0.25 | 57 | 79 | 19 | 63 | 35 |
| IFI6, gran, intra | Lym(%) | 0.49 | −0.03 | 76 | 78 | 72 | 82 | 67 |
| IFI6, gran, intra | MAN1C1, gran, intra | 0.13 | 0.02 | 61 | 77 | 35 | 67 | 48 |
| IFI6, gran, intra | MAN1C1, mean, intra | 0.13 | 0 | 61 | 77 | 35 | 67 | 48 |
| IFI6, gran, intra | MAN1C1, mono, intra | 0.13 | 0.02 | 61 | 77 | 35 | 67 | 48 |
| IFI6, gran, intra | MX1, gran, intra | 0.47 | −0.07 | 75 | 78 | 69 | 81 | 66 |
| IFI6, gran, intra | MX1, lymp, intra | 0.32 | −0.03 | 68 | 73 | 59 | 75 | 57 |
| IFI6, gran, intra | MX1, mean, intra | 0.43 | −0.02 | 73 | 79 | 64 | 78 | 66 |
| IFI6, gran, intra | MX1, mono, intra | 0.47 | −0.07 | 75 | 78 | 69 | 81 | 66 |
| IFI6, gran, intra | Neu(%) | 0.53 | −0.03 | 78 | 81 | 72 | 83 | 70 |
| IFI6, gran, intra | NPM1, gran, intra | 0.14 | 0.04 | 61 | 75 | 38 | 66 | 48 |
| IFI6, gran, intra | NPM1, mean, intra | 0.05 | −0.08 | 56 | 69 | 36 | 63 | 42 |
| IFI6, gran, intra | NPM1, mono, intra | 0.14 | 0.04 | 61 | 75 | 38 | 66 | 48 |
| IFI6, gran, intra | OAS2, gran, intra | 0.15 | −0.21 | 61 | 73 | 41 | 67 | 48 |
| IFI6, gran, intra | OAS2, mean, intra | 0.09 | −0.21 | 59 | 77 | 31 | 64 | 46 |
| IFI6, gran, intra | OAS2, mono, intra | 0.15 | −0.21 | 61 | 73 | 41 | 67 | 48 |
| IFI6, gran, intra | PARP12, gran, intra | 0.17 | −0.02 | 61 | 70 | 46 | 68 | 49 |
| IFI6, gran, intra | PARP12, mean, intra | 0.19 | −0.06 | 62 | 73 | 46 | 68 | 51 |
| IFI6, gran, intra | PARP12, mono, intra | 0.17 | −0.02 | 61 | 70 | 46 | 68 | 49 |
| IFI6, gran, intra | PARP9, lymp, intra | 0.18 | 0.04 | 62 | 73 | 44 | 68 | 50 |
| IFI6, gran, intra | PDIA6, gran, intra | 0.01 | −0.12 | 57 | 75 | 26 | 63 | 38 |
| IFI6, gran, intra | PDIA6, lymp, intra | 0.03 | −0.05 | 57 | 74 | 29 | 64 | 39 |
| IFI6, gran, intra | PDIA6, mono, intra | 0.01 | −0.12 | 57 | 75 | 26 | 63 | 38 |
| IFI6, gran, intra | PTEN, gran, intra | 0.18 | −0.04 | 62 | 72 | 46 | 69 | 50 |
| IFI6, gran, intra | PTEN, lymp, intra | 0.05 | −0.03 | 56 | 69 | 36 | 64 | 41 |
| IFI6, gran, intra | PTEN, mean, intra | 0.12 | −0.08 | 59 | 71 | 41 | 66 | 47 |
| IFI6, gran, intra | PTEN, mono, intra | 0.18 | −0.04 | 62 | 72 | 46 | 69 | 50 |
| IFI6, gran, intra | RSAD2, gran, intra | 0.69 | 0.06 | 85 | 88 | 82 | 89 | 80 |
| IFI6, gran, intra | RSAD2, lymp, intra | 0.24 | 0.01 | 66 | 81 | 41 | 69 | 57 |
| IFI6, gran, intra | RSAD2, mean, intra | 0.61 | −0.03 | 81 | 82 | 79 | 86 | 74 |
| IFI6, gran, intra | RSAD2, mono, intra | 0.69 | 0.06 | 85 | 88 | 82 | 89 | 80 |
| IFI6, gran, intra | SDCBP, mean, intra | 0.1 | 0.02 | 59 | 74 | 36 | 64 | 47 |
| IFI6, gran, intra | WBC | 0.26 | 0.01 | 67 | 83 | 41 | 70 | 59 |

TABLE 4-continued

The classification accuracy of bacterial vs. viral infected patients computed over pairs of features. DETERMINANT measurements were measured over different cell types.

| Feature #1 | Feature #2 | MCC | dMCC | Total accuracy % | Sen % | Spe % | PPV % | NPV % |
|---|---|---|---|---|---|---|---|---|
| IFI6, mono, intra | IFIT3, gran, intra | 0.33 | −0.06 | 69 | 77 | 56 | 74 | 59 |
| IFI6, mono, intra | IFIT3, lymp, intra | 0.4 | −0.03 | 72 | 78 | 62 | 77 | 63 |
| IFI6, mono, intra | IFIT3, mean, intra | 0.34 | 0.09 | 69 | 77 | 56 | 74 | 61 |
| IFI6, mono, intra | IFIT3, mono, intra | 0.33 | −0.06 | 69 | 77 | 56 | 74 | 59 |
| IFI6, mono, intra | IFITM1, gran, membrane | 0.05 | −0.21 | 59 | 81 | 23 | 63 | 43 |
| IFI6, mono, intra | IFITM1, lymp, membrane | 0.35 | −0.03 | 70 | 78 | 56 | 75 | 61 |
| IFI6, mono, intra | IFITM1, mean, membrane | 0 | −0.29 | 55 | 74 | 26 | 61 | 38 |
| IFI6, mono, intra | IFITM1, mono, membrane | 0.23 | −0.08 | 64 | 72 | 51 | 71 | 53 |
| IFI6, mono, intra | IFITM3, gran, membrane | 0.09 | −0.26 | 60 | 80 | 28 | 65 | 46 |
| IFI6, mono, intra | IFITM3, mean, membrane | 0.05 | −0.3 | 57 | 74 | 31 | 63 | 43 |
| IFI6, mono, intra | IFITM3, mono, membrane | 0.26 | −0.15 | 65 | 70 | 56 | 73 | 54 |
| IFI6, mono, intra | LOC26010, gran, intra | 0.09 | −0.14 | 59 | 75 | 33 | 65 | 45 |
| IFI6, mono, intra | LOC26010, mean, intra | −0.01 | −0.22 | 54 | 71 | 28 | 61 | 38 |
| IFI6, mono, intra | LOC26010, mono, intra | 0.09 | −0.14 | 59 | 75 | 33 | 65 | 45 |
| IFI6, mono, intra | LY6E, lymp, membrane | −0.02 | −0.25 | 57 | 79 | 19 | 63 | 35 |
| IFI6, mono, intra | Lym(%) | 0.49 | −0.03 | 76 | 78 | 72 | 82 | 67 |
| IFI6, mono, intra | MAN1C1, gran, intra | 0.13 | 0.02 | 61 | 77 | 35 | 67 | 48 |
| IFI6, mono, intra | MAN1C1, mean, intra | 0.13 | 0 | 61 | 77 | 35 | 67 | 48 |
| IFI6, mono, intra | MAN1C1, mono, intra | 0.13 | 0.02 | 61 | 77 | 35 | 67 | 48 |
| IFI6, mono, intra | MX1, gran, intra | 0.47 | −0.07 | 75 | 78 | 69 | 81 | 66 |
| IFI6, mono, intra | MX1, lymp, intra | 0.32 | −0.03 | 68 | 73 | 59 | 75 | 57 |
| IFI6, mono, intra | MX1, mean, intra | 0.43 | −0.02 | 73 | 79 | 64 | 78 | 66 |
| IFI6, mono, intra | MX1, mono, intra | 0.47 | −0.07 | 75 | 78 | 69 | 81 | 66 |
| IFI6, mono, intra | Neu(%) | 0.53 | −0.03 | 78 | 81 | 72 | 83 | 70 |
| IFI6, mono, intra | NPM1, gran, intra | 0.14 | 0.04 | 61 | 75 | 38 | 66 | 48 |
| IFI6, mono, intra | NPM1, mean, intra | 0.05 | −0.08 | 56 | 69 | 36 | 63 | 42 |
| IFI6, mono, intra | NPM1, mono, intra | 0.14 | 0.04 | 61 | 75 | 38 | 66 | 48 |
| IFI6, mono, intra | OAS2, gran, intra | 0.15 | −0.21 | 61 | 73 | 41 | 67 | 48 |
| IFI6, mono, intra | OAS2, mean, intra | 0.09 | −0.21 | 59 | 77 | 31 | 64 | 46 |
| IFI6, mono, intra | OAS2, mono, intra | 0.15 | −0.21 | 61 | 73 | 41 | 67 | 48 |
| IFI6, mono, intra | PARP12, gran, intra | 0.17 | −0.02 | 61 | 70 | 46 | 68 | 49 |
| IFI6, mono, intra | PARP12, mean, intra | 0.19 | −0.06 | 62 | 73 | 46 | 68 | 51 |
| IFI6, mono, intra | PARP12, mono, intra | 0.17 | −0.02 | 61 | 70 | 46 | 68 | 49 |
| IFI6, mono, intra | PARP9, lymp, intra | 0.18 | 0.04 | 62 | 73 | 44 | 68 | 50 |
| IFI6, mono, intra | PDIA6, gran, intra | 0.01 | −0.12 | 57 | 75 | 26 | 63 | 38 |
| IFI6, mono, intra | PDIA6, lymp, intra | 0.03 | −0.05 | 57 | 74 | 29 | 64 | 39 |
| IFI6, mono, intra | PDIA6, mono, intra | 0.01 | −0.12 | 57 | 75 | 26 | 63 | 38 |
| IFI6, mono, intra | PTEN, gran, intra | 0.18 | −0.04 | 62 | 72 | 46 | 69 | 50 |
| IFI6, mono, intra | PTEN, lymp, intra | 0.05 | −0.03 | 56 | 69 | 36 | 64 | 41 |
| IFI6, mono, intra | PTEN, mean, intra | 0.12 | −0.08 | 59 | 71 | 41 | 66 | 47 |
| IFI6, mono, intra | PTEN, mono, intra | 0.18 | −0.04 | 62 | 72 | 46 | 69 | 50 |
| IFI6, mono, intra | RSAD2, gran, intra | 0.69 | 0.06 | 85 | 88 | 82 | 89 | 80 |
| IFI6, mono, intra | RSAD2, lymp, intra | 0.24 | 0.01 | 66 | 81 | 41 | 69 | 57 |
| IFI6, mono, intra | RSAD2, mean, intra | 0.61 | −0.03 | 81 | 82 | 79 | 86 | 74 |
| IFI6, mono, intra | RSAD2, mono, intra | 0.69 | 0.06 | 85 | 88 | 82 | 89 | 80 |
| IFI6, mono, intra | SDCBP, mean, intra | 0.1 | 0.02 | 59 | 74 | 36 | 64 | 47 |
| IFI6, mono, intra | WBC | 0.26 | 0.01 | 67 | 83 | 41 | 70 | 59 |
| IFIT3, gran, intra | IFIT3, lymp, intra | 0.36 | −0.07 | 70 | 75 | 62 | 76 | 60 |
| IFIT3, gran, intra | IFIT3, mean, intra | 0.36 | −0.03 | 70 | 79 | 56 | 74 | 63 |
| IFIT3, gran, intra | IFIT3, mono, intra | 0.38 | −0.01 | 71 | 78 | 59 | 76 | 62 |
| IFIT3, gran, intra | IFITM1, gran, membrane | 0.35 | −0.04 | 70 | 78 | 56 | 75 | 61 |
| IFIT3, gran, intra | IFITM1, lymp, membrane | 0.35 | −0.04 | 69 | 73 | 62 | 76 | 59 |
| IFIT3, gran, intra | IFITM1, mean, membrane | 0.33 | −0.06 | 68 | 76 | 56 | 73 | 59 |
| IFIT3, gran, intra | IFITM1, mono, membrane | 0.38 | −0.01 | 71 | 78 | 59 | 76 | 62 |
| IFIT3, gran, intra | IFITM3, gran, membrane | 0.35 | −0.04 | 70 | 78 | 56 | 75 | 61 |
| IFIT3, gran, intra | IFITM3, mean, membrane | 0.34 | −0.05 | 69 | 77 | 56 | 74 | 61 |
| IFIT3, gran, intra | IFITM3, mono, membrane | 0.42 | 0.01 | 73 | 78 | 64 | 78 | 64 |
| IFIT3, gran, intra | LOC26010, gran, intra | 0.3 | −0.09 | 67 | 73 | 56 | 73 | 56 |
| IFIT3, gran, intra | LOC26010, mean, intra | 0.27 | −0.12 | 65 | 73 | 54 | 71 | 55 |
| IFIT3, gran, intra | LOC26010, mono, intra | 0.3 | −0.09 | 67 | 73 | 56 | 73 | 56 |
| IFIT3, gran, intra | LY6E, lymp, membrane | 0.19 | −0.2 | 64 | 79 | 39 | 69 | 52 |
| IFIT3, gran, intra | Lym(%) | 0.56 | 0.04 | 80 | 86 | 69 | 82 | 75 |
| IFIT3, gran, intra | MAN1C1, gran, intra | 0.35 | −0.04 | 71 | 87 | 45 | 73 | 67 |
| IFIT3, gran, intra | MAN1C1, mean, intra | 0.3 | −0.09 | 69 | 85 | 42 | 71 | 62 |
| IFIT3, gran, intra | MAN1C1, mono, intra | 0.35 | −0.04 | 71 | 87 | 45 | 73 | 67 |
| IFIT3, gran, intra | MX1, gran, intra | 0.46 | −0.08 | 75 | 80 | 67 | 80 | 67 |
| IFIT3, gran, intra | MX1, lymp, intra | 0.42 | 0.03 | 73 | 78 | 64 | 78 | 64 |
| IFIT3, gran, intra | MX1, mean, intra | 0.4 | −0.05 | 71 | 74 | 67 | 78 | 62 |
| IFIT3, gran, intra | MX1, mono, intra | 0.46 | −0.08 | 75 | 80 | 67 | 80 | 67 |
| IFIT3, gran, intra | Neu(%) | 0.62 | 0.06 | 83 | 89 | 72 | 84 | 80 |
| IFIT3, gran, intra | NPM1, gran, intra | 0.4 | 0.01 | 72 | 78 | 62 | 77 | 63 |
| IFIT3, gran, intra | NPM1, mean, intra | 0.39 | 0 | 71 | 77 | 62 | 76 | 63 |
| IFIT3, gran, intra | NPM1, mono, intra | 0.4 | 0.01 | 72 | 78 | 62 | 77 | 63 |
| IFIT3, gran, intra | OAS2, gran, intra | 0.38 | −0.01 | 71 | 78 | 59 | 76 | 62 |

TABLE 4-continued

The classification accuracy of bacterial vs. viral infected patients computed over pairs of features. DETERMINANT measurements were measured over different cell types.

| Feature #1 | Feature #2 | MCC | dMCC | Total accuracy % | Sen % | Spe % | PPV % | NPV % |
|---|---|---|---|---|---|---|---|---|
| IFIT3, gran, intra | OAS2, mean, intra | 0.33 | −0.06 | 68 | 76 | 56 | 73 | 59 |
| IFIT3, gran, intra | OAS2, mono, intra | 0.38 | −0.01 | 71 | 78 | 59 | 76 | 62 |
| IFIT3, gran, intra | PARP12, gran, intra | 0.38 | −0.01 | 71 | 78 | 59 | 76 | 62 |
| IFIT3, gran, intra | PARP12, mean, intra | 0.38 | −0.01 | 70 | 74 | 64 | 77 | 61 |
| IFIT3, gran, intra | PARP12, mono, intra | 0.38 | −0.01 | 71 | 78 | 59 | 76 | 62 |
| IFIT3, gran, intra | PARP9, lymp, intra | 0.34 | −0.05 | 69 | 75 | 59 | 75 | 59 |
| IFIT3, gran, intra | PDIA6, gran, intra | 0.25 | −0.14 | 67 | 81 | 42 | 70 | 57 |
| IFIT3, gran, intra | PDIA6, lymp, intra | 0.4 | 0.01 | 73 | 81 | 58 | 77 | 64 |
| IFIT3, gran, intra | PDIA6, mono, intra | 0.25 | −0.14 | 67 | 81 | 42 | 70 | 57 |
| IFIT3, gran, intra | PTEN, gran, intra | 0.37 | −0.02 | 70 | 73 | 64 | 77 | 60 |
| IFIT3, gran, intra | PTEN, lymp, intra | 0.32 | −0.07 | 68 | 73 | 59 | 75 | 57 |
| IFIT3, gran, intra | PTEN, mean, intra | 0.29 | −0.1 | 66 | 73 | 56 | 73 | 56 |
| IFIT3, gran, intra | PTEN, mono, intra | 0.37 | −0.02 | 70 | 73 | 64 | 77 | 60 |
| IFIT3, gran, intra | RSAD2, gran, intra | 0.67 | 0.04 | 84 | 86 | 82 | 89 | 78 |
| IFIT3, gran, intra | RSAD2, lymp, intra | 0.36 | −0.03 | 70 | 77 | 59 | 75 | 61 |
| IFIT3, gran, intra | RSAD2, mean, intra | 0.61 | −0.03 | 81 | 82 | 79 | 86 | 74 |
| IFIT3, gran, intra | RSAD2, mono, intra | 0.67 | 0.04 | 84 | 86 | 82 | 89 | 78 |
| IFIT3, gran, intra | SDCBP, mean, intra | 0.35 | −0.04 | 69 | 75 | 59 | 74 | 61 |
| IFIT3, gran, intra | WBC | 0.38 | −0.01 | 72 | 83 | 54 | 75 | 66 |
| IFIT3, lymp, intra | IFIT3, mean, intra | 0.38 | −0.05 | 70 | 74 | 64 | 77 | 61 |
| IFIT3, lymp, intra | IFIT3, mono, intra | 0.36 | −0.07 | 70 | 75 | 62 | 76 | 60 |
| IFIT3, lymp, intra | IFITM1, gran, membrane | 0.35 | −0.08 | 69 | 73 | 62 | 76 | 59 |
| IFIT3, lymp, intra | IFITM1, lymp, membrane | 0.3 | −0.13 | 67 | 73 | 56 | 73 | 56 |
| IFIT3, lymp, intra | IFITM1, mean, membrane | 0.34 | −0.09 | 68 | 73 | 62 | 75 | 59 |
| IFIT3, lymp, intra | IFITM1, mono, membrane | 0.42 | −0.01 | 73 | 78 | 64 | 78 | 64 |
| IFIT3, lymp, intra | IFITM3, gran, membrane | 0.39 | −0.04 | 71 | 73 | 67 | 78 | 60 |
| IFIT3, lymp, intra | IFITM3, mean, membrane | 0.36 | −0.07 | 69 | 73 | 64 | 76 | 60 |
| IFIT3, lymp, intra | IFITM3, mono, membrane | 0.36 | −0.07 | 70 | 75 | 62 | 76 | 60 |
| IFIT3, lymp, intra | LOC26010, gran, intra | 0.35 | −0.08 | 69 | 73 | 62 | 76 | 59 |
| IFIT3, lymp, intra | LOC26010, mean, intra | 0.32 | −0.11 | 67 | 71 | 62 | 75 | 57 |
| IFIT3, lymp, intra | LOC26010, mono, intra | 0.35 | −0.08 | 69 | 73 | 62 | 76 | 59 |
| IFIT3, lymp, intra | LY6E, lymp, membrane | 0.22 | −0.21 | 64 | 74 | 48 | 71 | 52 |
| IFIT3, lymp, intra | Lym(%) | 0.59 | 0.07 | 81 | 83 | 77 | 85 | 73 |
| IFIT3, lymp, intra | MAN1C1, gran, intra | 0.29 | −0.14 | 67 | 77 | 52 | 73 | 57 |
| IFIT3, lymp, intra | MAN1C1, mean, intra | 0.29 | −0.14 | 67 | 77 | 52 | 73 | 57 |
| IFIT3, lymp, intra | MAN1C1, mono, intra | 0.29 | −0.14 | 67 | 77 | 52 | 73 | 57 |
| IFIT3, lymp, intra | MX1, gran, intra | 0.43 | −0.11 | 73 | 77 | 67 | 79 | 63 |
| IFIT3, lymp, intra | MX1, lymp, intra | 0.4 | −0.03 | 72 | 77 | 64 | 78 | 63 |
| IFIT3, lymp, intra | MX1, mean, intra | 0.36 | −0.09 | 69 | 73 | 64 | 76 | 60 |
| IFIT3, lymp, intra | MX1, mono, intra | 0.43 | −0.11 | 73 | 77 | 67 | 79 | 63 |
| IFIT3, lymp, intra | Neu(%) | 0.61 | 0.05 | 82 | 84 | 77 | 86 | 75 |
| IFIT3, lymp, intra | NPM1, gran, intra | 0.34 | −0.09 | 69 | 73 | 62 | 75 | 59 |
| IFIT3, lymp, intra | NPM1, mean, intra | 0.39 | −0.04 | 71 | 75 | 64 | 77 | 63 |
| IFIT3, lymp, intra | NPM1, mono, intra | 0.34 | −0.09 | 69 | 73 | 62 | 75 | 59 |
| IFIT3, lymp, intra | OAS2, gran, intra | 0.39 | −0.04 | 71 | 75 | 64 | 77 | 61 |
| IFIT3, lymp, intra | OAS2, mean, intra | 0.36 | −0.07 | 69 | 73 | 64 | 76 | 60 |
| IFIT3, lymp, intra | OAS2, mono, intra | 0.39 | −0.04 | 71 | 75 | 64 | 77 | 61 |
| IFIT3, lymp, intra | PARP12, gran, intra | 0.4 | −0.03 | 72 | 78 | 62 | 77 | 63 |
| IFIT3, lymp, intra | PARP12, mean, intra | 0.38 | −0.05 | 70 | 74 | 64 | 77 | 61 |
| IFIT3, lymp, intra | PARP12, mono, intra | 0.4 | −0.03 | 72 | 78 | 62 | 77 | 63 |
| IFIT3, lymp, intra | PARP9, lymp, intra | 0.43 | 0 | 73 | 77 | 67 | 79 | 63 |
| IFIT3, lymp, intra | PDIA6, gran, intra | 0.29 | −0.14 | 68 | 79 | 48 | 72 | 58 |
| IFIT3, lymp, intra | PDIA6, lymp, intra | 0.35 | −0.08 | 70 | 79 | 55 | 75 | 61 |
| IFIT3, lymp, intra | PDIA6, mono, intra | 0.29 | −0.14 | 68 | 79 | 48 | 72 | 58 |
| IFIT3, lymp, intra | PTEN, gran, intra | 0.42 | −0.01 | 73 | 78 | 64 | 78 | 64 |
| IFIT3, lymp, intra | PTEN, lymp, intra | 0.32 | −0.11 | 68 | 73 | 59 | 75 | 57 |
| IFIT3, lymp, intra | PTEN, mean, intra | 0.33 | −0.1 | 68 | 76 | 56 | 73 | 59 |
| IFIT3, lymp, intra | PTEN, mono, intra | 0.42 | −0.01 | 73 | 78 | 64 | 78 | 64 |
| IFIT3, lymp, intra | RSAD2, gran, intra | 0.67 | 0.04 | 84 | 86 | 82 | 89 | 78 |
| IFIT3, lymp, intra | RSAD2, lymp, intra | 0.33 | −0.1 | 68 | 72 | 62 | 75 | 57 |
| IFIT3, lymp, intra | RSAD2, mean, intra | 0.61 | −0.03 | 81 | 82 | 79 | 86 | 74 |
| IFIT3, lymp, intra | RSAD2, mono, intra | 0.67 | 0.04 | 84 | 86 | 82 | 89 | 78 |
| IFIT3, lymp, intra | SDCBP, mean, intra | 0.37 | −0.06 | 70 | 75 | 62 | 75 | 62 |
| IFIT3, lymp, intra | WBC | 0.33 | −0.1 | 69 | 78 | 54 | 74 | 60 |
| IFIT3, mean, intra | IFIT3, mono, intra | 0.36 | −0.03 | 70 | 79 | 56 | 74 | 63 |
| IFIT3, mean, intra | IFITM1, gran, membrane | 0.21 | −0.05 | 63 | 74 | 46 | 69 | 53 |
| IFIT3, mean, intra | IFITM1, lymp, membrane | 0.31 | −0.07 | 67 | 73 | 59 | 74 | 57 |
| IFIT3, mean, intra | IFITM1, mean, membrane | 0.25 | −0.04 | 65 | 76 | 49 | 70 | 56 |
| IFIT3, mean, intra | IFITM1, mono, membrane | 0.32 | 0.01 | 68 | 77 | 54 | 73 | 60 |
| IFIT3, mean, intra | IFITM3, gran, membrane | 0.24 | −0.11 | 64 | 73 | 51 | 70 | 54 |
| IFIT3, mean, intra | IFITM3, mean, membrane | 0.26 | −0.09 | 65 | 74 | 51 | 71 | 56 |
| IFIT3, mean, intra | IFITM3, mono, membrane | 0.35 | −0.06 | 69 | 76 | 59 | 75 | 61 |
| IFIT3, mean, intra | LOC26010, gran, intra | 0.22 | −0.03 | 63 | 71 | 51 | 70 | 53 |
| IFIT3, mean, intra | LOC26010, mean, intra | 0.16 | −0.09 | 60 | 69 | 46 | 67 | 49 |

TABLE 4-continued

The classification accuracy of bacterial vs. viral infected patients computed over pairs of features. DETERMINANT measurements were measured over different cell types.

| Feature #1 | Feature #2 | MCC | dMCC | Total accuracy % | Sen % | Spe % | PPV % | NPV % |
|---|---|---|---|---|---|---|---|---|
| IFIT3, mean, intra | LOC26010, mono, intra | 0.22 | −0.03 | 63 | 71 | 51 | 70 | 53 |
| IFIT3, mean, intra | LY6E, lymp, membrane | 0.13 | −0.12 | 62 | 79 | 32 | 67 | 48 |
| IFIT3, mean, intra | Lym(%) | 0.56 | 0.04 | 79 | 85 | 69 | 82 | 75 |
| IFIT3, mean, intra | MAN1C1, gran, intra | 0.2 | −0.05 | 65 | 85 | 32 | 68 | 56 |
| IFIT3, mean, intra | MAN1C1, mean, intra | 0.21 | −0.04 | 65 | 83 | 35 | 68 | 55 |
| IFIT3, mean, intra | MAN1C1, mono, intra | 0.2 | −0.05 | 65 | 85 | 32 | 68 | 56 |
| IFIT3, mean, intra | MX1, gran, intra | 0.44 | −0.1 | 73 | 77 | 67 | 79 | 65 |
| IFIT3, mean, intra | MX1, lymp, intra | 0.27 | −0.08 | 65 | 71 | 56 | 72 | 55 |
| IFIT3, mean, intra | MX1, mean, intra | 0.38 | −0.07 | 70 | 74 | 64 | 77 | 61 |
| IFIT3, mean, intra | MX1, mono, intra | 0.44 | −0.1 | 73 | 77 | 67 | 79 | 65 |
| IFIT3, mean, intra | Neu(%) | 0.62 | 0.06 | 82 | 89 | 72 | 83 | 80 |
| IFIT3, mean, intra | NPM1, gran, intra | 0.36 | 0.11 | 70 | 77 | 59 | 75 | 62 |
| IFIT3, mean, intra | NPM1, mean, intra | 0.34 | 0.09 | 69 | 77 | 56 | 73 | 61 |
| IFIT3, mean, intra | NPM1, mono, intra | 0.36 | 0.11 | 70 | 77 | 59 | 75 | 62 |
| IFIT3, mean, intra | OAS2, gran, intra | 0.28 | −0.08 | 66 | 76 | 51 | 71 | 57 |
| IFIT3, mean, intra | OAS2, mean, intra | 0.21 | −0.09 | 63 | 74 | 46 | 69 | 53 |
| IFIT3, mean, intra | OAS2, mono, intra | 0.28 | −0.08 | 66 | 76 | 51 | 71 | 57 |
| IFIT3, mean, intra | PARP12, gran, intra | 0.31 | 0.06 | 67 | 73 | 59 | 74 | 57 |
| IFIT3, mean, intra | PARP12, mean, intra | 0.34 | 0.09 | 68 | 73 | 62 | 75 | 59 |
| IFIT3, mean, intra | PARP12, mono, intra | 0.31 | 0.06 | 67 | 73 | 59 | 74 | 57 |
| IFIT3, mean, intra | PARP9, lymp, intra | 0.22 | −0.03 | 63 | 71 | 51 | 70 | 53 |
| IFIT3, mean, intra | PDIA6, gran, intra | 0.2 | −0.05 | 64 | 77 | 42 | 69 | 52 |
| IFIT3, mean, intra | PDIA6, lymp, intra | 0.22 | −0.03 | 64 | 74 | 48 | 71 | 52 |
| IFIT3, mean, intra | PDIA6, mono, intra | 0.2 | −0.05 | 64 | 77 | 42 | 69 | 52 |
| IFIT3, mean, intra | PTEN, gran, intra | 0.31 | 0.06 | 67 | 74 | 56 | 73 | 58 |
| IFIT3, mean, intra | PTEN, lymp, intra | 0.21 | −0.04 | 62 | 69 | 51 | 69 | 51 |
| IFIT3, mean, intra | PTEN, mean, intra | 0.16 | −0.09 | 60 | 69 | 46 | 67 | 49 |
| IFIT3, mean, intra | PTEN, mono, intra | 0.31 | 0.06 | 67 | 74 | 56 | 73 | 58 |
| IFIT3, mean, intra | RSAD2, gran, intra | 0.69 | 0.06 | 85 | 87 | 82 | 89 | 80 |
| IFIT3, mean, intra | RSAD2, lymp, intra | 0.18 | −0.07 | 61 | 69 | 49 | 68 | 50 |
| IFIT3, mean, intra | RSAD2, mean, intra | 0.59 | −0.05 | 80 | 81 | 79 | 86 | 72 |
| IFIT3, mean, intra | RSAD2, mono, intra | 0.69 | 0.06 | 85 | 87 | 82 | 89 | 80 |
| IFIT3, mean, intra | SDCBP, mean, intra | 0.23 | −0.02 | 63 | 69 | 54 | 70 | 53 |
| IFIT3, mean, intra | WBC | 0.3 | 0.05 | 67 | 77 | 51 | 72 | 59 |
| IFIT3, mono, intra | IFITM1, gran, membrane | 0.35 | −0.04 | 70 | 78 | 56 | 75 | 61 |
| IFIT3, mono, intra | IFITM1, lymp, membrane | 0.35 | −0.04 | 69 | 73 | 62 | 76 | 59 |
| IFIT3, mono, intra | IFITM1, mean, membrane | 0.33 | −0.06 | 68 | 76 | 56 | 73 | 59 |
| IFIT3, mono, intra | IFITM1, mono, membrane | 0.38 | −0.01 | 71 | 78 | 59 | 76 | 62 |
| IFIT3, mono, intra | IFITM3, gran, membrane | 0.35 | −0.04 | 70 | 78 | 56 | 75 | 61 |
| IFIT3, mono, intra | IFITM3, mean, membrane | 0.34 | −0.05 | 69 | 77 | 56 | 74 | 61 |
| IFIT3, mono, intra | IFITM3, mono, membrane | 0.42 | 0.01 | 73 | 78 | 64 | 78 | 64 |
| IFIT3, mono, intra | LOC26010, gran, intra | 0.3 | −0.09 | 67 | 73 | 56 | 73 | 56 |
| IFIT3, mono, intra | LOC26010, mean, intra | 0.27 | −0.12 | 65 | 73 | 54 | 71 | 55 |
| IFIT3, mono, intra | LOC26010, mono, intra | 0.3 | −0.09 | 67 | 73 | 56 | 73 | 56 |
| IFIT3, mono, intra | LY6E, lymp, membrane | 0.19 | −0.2 | 64 | 79 | 39 | 69 | 52 |
| IFIT3, mono, intra | Lym(%) | 0.56 | 0.04 | 80 | 86 | 69 | 82 | 75 |
| IFIT3, mono, intra | MAN1C1, gran, intra | 0.35 | −0.04 | 71 | 87 | 45 | 73 | 67 |
| IFIT3, mono, intra | MAN1C1, mean, intra | 0.3 | −0.09 | 69 | 85 | 42 | 71 | 62 |
| IFIT3, mono, intra | MAN1C1, mono, intra | 0.35 | −0.04 | 71 | 87 | 45 | 73 | 67 |
| IFIT3, mono, intra | MX1, gran, intra | 0.46 | −0.08 | 75 | 80 | 67 | 80 | 67 |
| IFIT3, mono, intra | MX1, lymp, intra | 0.42 | 0.03 | 73 | 78 | 64 | 78 | 64 |
| IFIT3, mono, intra | MX1, mean, intra | 0.4 | −0.05 | 71 | 74 | 67 | 78 | 62 |
| IFIT3, mono, intra | MX1, mono, intra | 0.46 | −0.08 | 75 | 80 | 67 | 80 | 67 |
| IFIT3, mono, intra | Neu(%) | 0.62 | 0.06 | 83 | 89 | 72 | 84 | 80 |
| IFIT3, mono, intra | NPM1, gran, intra | 0.4 | 0.01 | 72 | 78 | 62 | 77 | 63 |
| IFIT3, mono, intra | NPM1, mean, intra | 0.39 | 0 | 71 | 77 | 62 | 76 | 63 |
| IFIT3, mono, intra | NPM1, mono, intra | 0.4 | 0.01 | 72 | 78 | 62 | 77 | 63 |
| IFIT3, mono, intra | OAS2, gran, intra | 0.38 | −0.01 | 71 | 78 | 59 | 76 | 62 |
| IFIT3, mono, intra | OAS2, mean, intra | 0.33 | −0.06 | 68 | 76 | 56 | 73 | 59 |
| IFIT3, mono, intra | OAS2, mono, intra | 0.38 | −0.01 | 71 | 78 | 59 | 76 | 62 |
| IFIT3, mono, intra | PARP12, gran, intra | 0.38 | −0.01 | 71 | 78 | 59 | 76 | 62 |
| IFIT3, mono, intra | PARP12, mean, intra | 0.38 | −0.01 | 70 | 74 | 64 | 77 | 61 |
| IFIT3, mono, intra | PARP12, mono, intra | 0.38 | −0.01 | 71 | 78 | 59 | 76 | 62 |
| IFIT3, mono, intra | PARP9, lymp, intra | 0.34 | −0.05 | 69 | 75 | 59 | 75 | 59 |
| IFIT3, mono, intra | PDIA6, gran, intra | 0.25 | −0.14 | 67 | 81 | 42 | 70 | 57 |
| IFIT3, mono, intra | PDIA6, lymp, intra | 0.4 | 0.01 | 73 | 81 | 58 | 77 | 64 |
| IFIT3, mono, intra | PDIA6, mono, intra | 0.25 | −0.14 | 67 | 81 | 42 | 70 | 57 |
| IFIT3, mono, intra | PTEN, gran, intra | 0.37 | −0.02 | 70 | 73 | 64 | 77 | 60 |
| IFIT3, mono, intra | PTEN, lymp, intra | 0.32 | −0.07 | 68 | 73 | 59 | 75 | 57 |
| IFIT3, mono, intra | PTEN, mean, intra | 0.29 | −0.1 | 66 | 73 | 56 | 73 | 56 |
| IFIT3, mono, intra | PTEN, mono, intra | 0.37 | −0.02 | 70 | 73 | 64 | 77 | 60 |
| IFIT3, mono, intra | RSAD2, gran, intra | 0.67 | 0.04 | 84 | 86 | 82 | 89 | 78 |
| IFIT3, mono, intra | RSAD2, lymp, intra | 0.36 | −0.03 | 70 | 77 | 59 | 75 | 61 |
| IFIT3, mono, intra | RSAD2, mean, intra | 0.61 | −0.03 | 81 | 82 | 79 | 86 | 74 |

TABLE 4-continued

The classification accuracy of bacterial vs. viral infected patients computed over pairs of features. DETERMINANT measurements were measured over different cell types.

| Feature #1 | Feature #2 | MCC | dMCC | Total accuracy % | Sen % | Spe % | PPV % | NPV % |
|---|---|---|---|---|---|---|---|---|
| IFIT3, mono, intra | RSAD2, mono, intra | 0.67 | 0.04 | 84 | 86 | 82 | 89 | 78 |
| IFIT3, mono, intra | SDCBP, mean, intra | 0.35 | −0.04 | 69 | 75 | 59 | 74 | 61 |
| IFIT3, mono, intra | WBC | 0.38 | −0.01 | 72 | 83 | 54 | 75 | 66 |
| IFITM1, gran, membrane | IFITM1, lymp, membrane | 0.38 | 0 | 69 | 65 | 73 | 75 | 63 |
| IFITM1, gran, membrane | IFITM1, mean, membrane | 0.3 | 0.01 | 66 | 71 | 59 | 68 | 63 |
| IFITM1, gran, membrane | IFITM1, mono, membrane | 0.28 | −0.03 | 64 | 64 | 65 | 69 | 59 |
| IFITM1, gran, membrane | IFITM3, gran, membrane | 0.34 | −0.01 | 67 | 66 | 68 | 72 | 62 |
| IFITM1, gran, membrane | IFITM3, mean, membrane | 0.35 | 0 | 67 | 64 | 71 | 73 | 62 |
| IFITM1, gran, membrane | IFITM3, mono, membrane | 0.41 | 0 | 70 | 66 | 75 | 77 | 64 |
| IFITM1, gran, membrane | LOC26010, gran, intra | 0.26 | 0 | 63 | 65 | 62 | 68 | 59 |
| IFITM1, gran, membrane | LOC26010, mean, intra | 0.23 | −0.03 | 62 | 63 | 61 | 66 | 57 |
| IFITM1, gran, membrane | LOC26010, mono, intra | 0.26 | 0 | 63 | 65 | 62 | 68 | 59 |
| IFITM1, gran, membrane | LY6E, lymp, membrane | 0.24 | −0.02 | 62 | 60 | 63 | 67 | 57 |
| IFITM1, gran, membrane | Lym(%) | 0.56 | 0.04 | 78 | 78 | 78 | 82 | 74 |
| IFITM1, gran, membrane | MAN1C1, gran, intra | 0.05 | −0.21 | 59 | 79 | 26 | 64 | 42 |
| IFITM1, gran, membrane | MAN1C1, mean, intra | 0.1 | −0.16 | 61 | 83 | 26 | 65 | 47 |
| IFITM1, gran, membrane | MAN1C1, mono, intra | 0.05 | −0.21 | 59 | 79 | 26 | 64 | 42 |
| IFITM1, gran, membrane | MX1, gran, intra | 0.52 | −0.02 | 76 | 77 | 75 | 79 | 73 |
| IFITM1, gran, membrane | MX1, lymp, intra | 0.4 | 0.05 | 70 | 70 | 70 | 74 | 66 |
| IFITM1, gran, membrane | MX1, mean, intra | 0.5 | 0.05 | 75 | 72 | 78 | 80 | 70 |
| IFITM1, gran, membrane | MX1, mono, intra | 0.52 | −0.02 | 76 | 77 | 75 | 79 | 73 |
| IFITM1, gran, membrane | Neu(%) | 0.53 | −0.03 | 77 | 77 | 76 | 80 | 73 |
| IFITM1, gran, membrane | NPM1, gran, intra | 0.04 | −0.22 | 58 | 78 | 26 | 63 | 42 |
| IFITM1, gran, membrane | NPM1, mean, intra | 0.09 | −0.17 | 59 | 75 | 33 | 64 | 46 |
| IFITM1, gran, membrane | NPM1, mono, intra | 0.04 | −0.22 | 58 | 78 | 26 | 63 | 42 |
| IFITM1, gran, membrane | OAS2, gran, intra | 0.32 | −0.04 | 66 | 62 | 70 | 72 | 60 |
| IFITM1, gran, membrane | OAS2, mean, intra | 0.32 | 0.02 | 66 | 64 | 68 | 71 | 61 |
| IFITM1, gran, membrane | OAS2, mono, intra | 0.32 | −0.04 | 66 | 62 | 70 | 72 | 60 |
| IFITM1, gran, membrane | PARP12, gran, intra | 0.14 | −0.12 | 61 | 75 | 38 | 67 | 48 |
| IFITM1, gran, membrane | PARP12, mean, intra | 0.21 | −0.05 | 63 | 74 | 46 | 69 | 53 |
| IFITM1, gran, membrane | PARP12, mono, intra | 0.14 | −0.12 | 61 | 75 | 38 | 67 | 48 |
| IFITM1, gran, membrane | PARP9, lymp, intra | 0.19 | −0.07 | 64 | 83 | 33 | 67 | 54 |
| IFITM1, gran, membrane | PDIA6, gran, intra | 0.04 | −0.22 | 58 | 77 | 26 | 64 | 40 |
| IFITM1, gran, membrane | PDIA6, lymp, intra | 0.04 | −0.22 | 58 | 77 | 26 | 64 | 40 |
| IFITM1, gran, membrane | PDIA6, mono, intra | 0.04 | −0.22 | 58 | 77 | 26 | 64 | 40 |
| IFITM1, gran, membrane | PTEN, gran, intra | 0.29 | 0.03 | 67 | 77 | 51 | 72 | 57 |
| IFITM1, gran, membrane | PTEN, lymp, intra | 0.02 | −0.24 | 55 | 69 | 33 | 63 | 39 |
| IFITM1, gran, membrane | PTEN, mean, intra | 0.17 | −0.09 | 62 | 77 | 38 | 67 | 52 |
| IFITM1, gran, membrane | PTEN, mono, intra | 0.29 | 0.03 | 67 | 77 | 51 | 72 | 57 |
| IFITM1, gran, membrane | RSAD2, gran, intra | 0.6 | −0.03 | 80 | 77 | 83 | 85 | 75 |
| IFITM1, gran, membrane | RSAD2, lymp, intra | 0.27 | 0.01 | 64 | 69 | 58 | 67 | 60 |
| IFITM1, gran, membrane | RSAD2, mean, intra | 0.59 | −0.05 | 79 | 79 | 80 | 83 | 76 |
| IFITM1, gran, membrane | RSAD2, mono, intra | 0.6 | −0.03 | 80 | 77 | 83 | 85 | 75 |
| IFITM1, gran, membrane | SDCBP, mean, intra | 0.04 | −0.22 | 57 | 75 | 28 | 62 | 42 |
| IFITM1, gran, membrane | WBC | 0.32 | 0.06 | 67 | 80 | 51 | 67 | 67 |
| IFITM1, lymp, membrane | IFITM1, mean, membrane | 0.35 | −0.03 | 67 | 63 | 73 | 74 | 61 |
| IFITM1, lymp, membrane | IFITM1, mono, membrane | 0.34 | −0.04 | 67 | 66 | 68 | 72 | 62 |
| IFITM1, lymp, membrane | IFITM3, gran, membrane | 0.42 | 0.04 | 71 | 70 | 72 | 75 | 66 |
| IFITM1, lymp, membrane | IFITM3, mean, membrane | 0.39 | 0.01 | 69 | 68 | 71 | 74 | 65 |
| IFITM1, lymp, membrane | IFITM3, mono, membrane | 0.41 | 0 | 70 | 68 | 73 | 76 | 65 |
| IFITM1, lymp, membrane | LOC26010, gran, intra | 0.4 | 0.02 | 70 | 70 | 70 | 74 | 66 |
| IFITM1, lymp, membrane | LOC26010, mean, intra | 0.35 | −0.03 | 67 | 64 | 71 | 73 | 62 |
| IFITM1, lymp, membrane | LOC26010, mono, intra | 0.4 | 0.02 | 70 | 70 | 70 | 74 | 66 |
| IFITM1, lymp, membrane | LY6E, lymp, membrane | 0.21 | −0.17 | 60 | 57 | 63 | 65 | 55 |
| IFITM1, lymp, membrane | Lym(%) | 0.51 | −0.01 | 76 | 77 | 75 | 79 | 72 |
| IFITM1, lymp, membrane | MAN1C1, gran, intra | 0.3 | −0.08 | 69 | 85 | 42 | 71 | 62 |
| IFITM1, lymp, membrane | MAN1C1, mean, intra | 0.26 | −0.12 | 67 | 85 | 39 | 70 | 60 |
| IFITM1, lymp, membrane | MAN1C1, mono, intra | 0.3 | −0.08 | 69 | 85 | 42 | 71 | 62 |
| IFITM1, lymp, membrane | MX1, gran, intra | 0.55 | 0.01 | 78 | 76 | 80 | 82 | 73 |
| IFITM1, lymp, membrane | MX1, lymp, intra | 0.48 | 0.1 | 74 | 73 | 75 | 78 | 69 |
| IFITM1, lymp, membrane | MX1, mean, intra | 0.54 | 0.09 | 77 | 75 | 80 | 82 | 72 |
| IFITM1, lymp, membrane | MX1, mono, intra | 0.55 | 0.01 | 78 | 76 | 80 | 82 | 73 |
| IFITM1, lymp, membrane | Neu(%) | 0.53 | −0.03 | 77 | 78 | 75 | 79 | 73 |
| IFITM1, lymp, membrane | NPM1, gran, intra | 0.45 | 0.07 | 75 | 84 | 59 | 77 | 70 |
| IFITM1, lymp, membrane | NPM1, mean, intra | 0.4 | 0.02 | 72 | 80 | 59 | 75 | 66 |
| IFITM1, lymp, membrane | NPM1, mono, intra | 0.45 | 0.07 | 75 | 84 | 59 | 77 | 70 |
| IFITM1, lymp, membrane | OAS2, gran, intra | 0.45 | 0.07 | 72 | 69 | 77 | 78 | 67 |
| IFITM1, lymp, membrane | OAS2, mean, intra | 0.39 | 0.01 | 69 | 67 | 73 | 75 | 64 |
| IFITM1, lymp, membrane | OAS2, mono, intra | 0.45 | 0.07 | 72 | 69 | 77 | 78 | 67 |
| IFITM1, lymp, membrane | PARP12, gran, intra | 0.44 | 0.06 | 74 | 81 | 62 | 78 | 67 |
| IFITM1, lymp, membrane | PARP12, mean, intra | 0.37 | −0.01 | 70 | 76 | 62 | 76 | 62 |
| IFITM1, lymp, membrane | PARP12, mono, intra | 0.44 | 0.06 | 74 | 81 | 62 | 78 | 67 |
| IFITM1, lymp, membrane | PARP9, lymp, intra | 0.32 | −0.06 | 68 | 75 | 56 | 74 | 58 |
| IFITM1, lymp, membrane | PDIA6, gran, intra | 0.4 | 0.02 | 73 | 83 | 55 | 76 | 65 |

TABLE 4-continued

The classification accuracy of bacterial vs. viral infected patients computed over pairs of features. DETERMINANT measurements were measured over different cell types.

| Feature #1 | Feature #2 | MCC | dMCC | Total accuracy % | Sen % | Spe % | PPV % | NPV % |
|---|---|---|---|---|---|---|---|---|
| IFITM1, lymp, membrane | PDIA6, lymp, intra | 0.23 | −0.15 | 64 | 72 | 52 | 72 | 52 |
| IFITM1, lymp, membrane | PDIA6, mono, intra | 0.4 | 0.02 | 73 | 83 | 55 | 76 | 65 |
| IFITM1, lymp, membrane | PTEN, gran, intra | 0.33 | −0.05 | 68 | 72 | 62 | 75 | 57 |
| IFITM1, lymp, membrane | PTEN, lymp, intra | 0.26 | −0.12 | 65 | 70 | 56 | 73 | 54 |
| IFITM1, lymp, membrane | PTEN, mean, intra | 0.31 | −0.07 | 67 | 74 | 56 | 73 | 58 |
| IFITM1, lymp, membrane | PTEN, mono, intra | 0.33 | −0.05 | 68 | 72 | 62 | 75 | 57 |
| IFITM1, lymp, membrane | RSAD2, gran, intra | 0.63 | 0 | 81 | 81 | 82 | 85 | 78 |
| IFITM1, lymp, membrane | RSAD2, lymp, intra | 0.38 | 0 | 69 | 65 | 73 | 75 | 63 |
| IFITM1, lymp, membrane | RSAD2, mean, intra | 0.62 | −0.02 | 81 | 81 | 81 | 84 | 77 |
| IFITM1, lymp, membrane | RSAD2, mono, intra | 0.63 | 0 | 81 | 81 | 82 | 85 | 78 |
| IFITM1, lymp, membrane | SDCBP, mean, intra | 0.29 | −0.09 | 67 | 79 | 49 | 71 | 59 |
| IFITM1, lymp, membrane | WBC | 0.37 | −0.01 | 69 | 73 | 64 | 72 | 66 |
| IFITM1, mean, membrane | IFITM1, mono, membrane | 0.32 | 0.01 | 66 | 64 | 68 | 71 | 61 |
| IFITM1, mean, membrane | IFITM3, gran, membrane | 0.36 | 0.01 | 68 | 67 | 69 | 73 | 63 |
| IFITM1, mean, membrane | IFITM3, mean, membrane | 0.33 | −0.02 | 66 | 64 | 69 | 72 | 61 |
| IFITM1, mean, membrane | IFITM3, mono, membrane | 0.42 | 0.01 | 70 | 64 | 78 | 78 | 64 |
| IFITM1, mean, membrane | LOC26010, gran, intra | 0.22 | −0.07 | 61 | 61 | 61 | 66 | 56 |
| IFITM1, mean, membrane | LOC26010, mean, intra | 0.22 | −0.07 | 61 | 63 | 59 | 65 | 56 |
| IFITM1, mean, membrane | LOC26010, mono, intra | 0.22 | −0.07 | 61 | 61 | 61 | 66 | 56 |
| IFITM1, mean, membrane | LY6E, lymp, membrane | 0.23 | −0.06 | 61 | 62 | 61 | 66 | 56 |
| IFITM1, mean, membrane | Lym(%) | 0.52 | 0 | 76 | 76 | 76 | 80 | 73 |
| IFITM1, mean, membrane | MAN1C1, gran, intra | 0.05 | −0.24 | 59 | 79 | 26 | 64 | 42 |
| IFITM1, mean, membrane | MAN1C1, mean, intra | 0.1 | −0.19 | 61 | 83 | 26 | 65 | 47 |
| IFITM1, mean, membrane | MAN1C1, mono, intra | 0.05 | −0.24 | 59 | 79 | 26 | 64 | 42 |
| IFITM1, mean, membrane | MX1, gran, intra | 0.5 | −0.04 | 75 | 74 | 76 | 79 | 70 |
| IFITM1, mean, membrane | MX1, lymp, intra | 0.39 | 0.04 | 69 | 67 | 73 | 75 | 64 |
| IFITM1, mean, membrane | MX1, mean, intra | 0.48 | 0.03 | 74 | 72 | 76 | 79 | 69 |
| IFITM1, mean, membrane | MX1, mono, intra | 0.5 | −0.04 | 75 | 74 | 76 | 79 | 70 |
| IFITM1, mean, membrane | Neu(%) | 0.53 | −0.03 | 76 | 75 | 78 | 81 | 72 |
| IFITM1, mean, membrane | NPM1, gran, intra | 0.07 | −0.22 | 58 | 75 | 31 | 63 | 44 |
| IFITM1, mean, membrane | NPM1, mean, intra | 0.08 | −0.21 | 58 | 72 | 36 | 64 | 45 |
| IFITM1, mean, membrane | NPM1, mono, intra | 0.07 | −0.22 | 58 | 75 | 31 | 63 | 44 |
| IFITM1, mean, membrane | OAS2, gran, intra | 0.32 | −0.04 | 66 | 61 | 71 | 72 | 60 |
| IFITM1, mean, membrane | OAS2, mean, intra | 0.31 | 0.01 | 66 | 65 | 66 | 70 | 61 |
| IFITM1, mean, membrane | OAS2, mono, intra | 0.32 | −0.04 | 66 | 61 | 71 | 72 | 60 |
| IFITM1, mean, membrane | PARP12, gran, intra | 0.15 | −0.14 | 61 | 76 | 38 | 66 | 50 |
| IFITM1, mean, membrane | PARP12, mean, intra | 0.23 | −0.06 | 64 | 74 | 49 | 70 | 54 |
| IFITM1, mean, membrane | PARP12, mono, intra | 0.15 | −0.14 | 61 | 76 | 38 | 66 | 50 |
| IFITM1, mean, membrane | PARP9, lymp, intra | 0.18 | −0.11 | 63 | 81 | 36 | 67 | 54 |
| IFITM1, mean, membrane | PDIA6, gran, intra | −0.02 | −0.31 | 56 | 75 | 23 | 63 | 35 |
| IFITM1, mean, membrane | PDIA6, lymp, intra | 0.11 | −0.18 | 61 | 77 | 32 | 66 | 45 |
| IFITM1, mean, membrane | PDIA6, mono, intra | −0.02 | −0.31 | 56 | 75 | 23 | 63 | 35 |
| IFITM1, mean, membrane | PTEN, gran, intra | 0.22 | −0.07 | 63 | 73 | 49 | 69 | 53 |
| IFITM1, mean, membrane | PTEN, lymp, intra | 0.01 | −0.28 | 54 | 68 | 33 | 62 | 39 |
| IFITM1, mean, membrane | PTEN, mean, intra | 0.2 | −0.09 | 63 | 77 | 41 | 68 | 53 |
| IFITM1, mean, membrane | PTEN, mono, intra | 0.22 | −0.07 | 63 | 73 | 49 | 69 | 53 |
| IFITM1, mean, membrane | RSAD2, gran, intra | 0.59 | −0.04 | 79 | 78 | 81 | 84 | 75 |
| IFITM1, mean, membrane | RSAD2, lymp, intra | 0.27 | −0.02 | 64 | 69 | 58 | 67 | 61 |
| IFITM1, mean, membrane | RSAD2, mean, intra | 0.57 | −0.07 | 79 | 76 | 81 | 83 | 74 |
| IFITM1, mean, membrane | RSAD2, mono, intra | 0.59 | −0.04 | 79 | 78 | 81 | 84 | 75 |
| IFITM1, mean, membrane | SDCBP, mean, intra | 0.04 | −0.25 | 57 | 75 | 28 | 62 | 42 |
| IFITM1, mean, membrane | WBC | 0.3 | 0.01 | 66 | 74 | 56 | 67 | 63 |
| IFITM1, mono, membrane | IFITM3, gran, membrane | 0.36 | 0.01 | 68 | 68 | 68 | 72 | 63 |
| IFITM1, mono, membrane | IFITM3, mean, membrane | 0.36 | 0.01 | 68 | 68 | 68 | 72 | 63 |
| IFITM1, mono, membrane | IFITM3, mono, membrane | 0.37 | −0.04 | 69 | 69 | 68 | 73 | 64 |
| IFITM1, mono, membrane | LOC26010, gran, intra | 0.37 | 0.06 | 69 | 68 | 70 | 74 | 64 |
| IFITM1, mono, membrane | LOC26010, mean, intra | 0.41 | 0.1 | 70 | 68 | 73 | 75 | 65 |
| IFITM1, mono, membrane | LOC26010, mono, intra | 0.37 | 0.06 | 69 | 68 | 70 | 74 | 64 |
| IFITM1, mono, membrane | LY6E, lymp, membrane | 0.32 | 0.01 | 66 | 65 | 67 | 71 | 61 |
| IFITM1, mono, membrane | Lym(%) | 0.62 | 0.1 | 81 | 81 | 81 | 85 | 77 |
| IFITM1, mono, membrane | MAN1C1, gran, intra | 0.22 | −0.09 | 65 | 79 | 42 | 69 | 54 |
| IFITM1, mono, membrane | MAN1C1, mean, intra | 0.22 | −0.09 | 65 | 79 | 42 | 69 | 54 |
| IFITM1, mono, membrane | MAN1C1, mono, intra | 0.22 | −0.09 | 65 | 79 | 42 | 69 | 54 |
| IFITM1, mono, membrane | MX1, gran, intra | 0.62 | 0.08 | 81 | 76 | 87 | 88 | 74 |
| IFITM1, mono, membrane | MX1, lymp, intra | 0.5 | 0.15 | 75 | 76 | 75 | 79 | 71 |
| IFITM1, mono, membrane | MX1, mean, intra | 0.52 | 0.07 | 76 | 72 | 80 | 81 | 70 |
| IFITM1, mono, membrane | MX1, mono, intra | 0.62 | 0.08 | 81 | 76 | 87 | 88 | 74 |
| IFITM1, mono, membrane | Neu(%) | 0.61 | 0.05 | 80 | 80 | 81 | 84 | 76 |
| IFITM1, mono, membrane | NPM1, gran, intra | 0.32 | 0.01 | 69 | 78 | 54 | 73 | 60 |
| IFITM1, mono, membrane | NPM1, mean, intra | 0.34 | 0.03 | 69 | 77 | 56 | 73 | 61 |
| IFITM1, mono, membrane | NPM1, mono, intra | 0.32 | 0.01 | 69 | 78 | 54 | 73 | 60 |
| IFITM1, mono, membrane | OAS2, gran, intra | 0.44 | 0.08 | 72 | 68 | 77 | 78 | 66 |
| IFITM1, mono, membrane | OAS2, mean, intra | 0.4 | 0.09 | 70 | 69 | 71 | 75 | 66 |
| IFITM1, mono, membrane | OAS2, mono, intra | 0.44 | 0.08 | 72 | 68 | 77 | 78 | 66 |

TABLE 4-continued

The classification accuracy of bacterial vs. viral infected patients computed over pairs of features. DETERMINANT measurements were measured over different cell types.

| Feature #1 | Feature #2 | MCC | dMCC | Total accuracy % | Sen % | Spe % | PPV % | NPV % |
|---|---|---|---|---|---|---|---|---|
| IFITM1, mono, membrane | PARP12, gran, intra | 0.31 | 0 | 68 | 77 | 54 | 73 | 58 |
| IFITM1, mono, membrane | PARP12, mean, intra | 0.37 | 0.06 | 70 | 77 | 59 | 75 | 62 |
| IFITM1, mono, membrane | PARP12, mono, intra | 0.31 | 0 | 68 | 77 | 54 | 73 | 58 |
| IFITM1, mono, membrane | PARP9, lymp, intra | 0.31 | 0 | 68 | 77 | 54 | 73 | 58 |
| IFITM1, mono, membrane | PDIA6, gran, intra | 0.25 | −0.06 | 65 | 74 | 52 | 72 | 53 |
| IFITM1, mono, membrane | PDIA6, lymp, intra | 0.3 | −0.01 | 68 | 77 | 52 | 73 | 57 |
| IFITM1, mono, membrane | PDIA6, mono, intra | 0.25 | −0.06 | 65 | 74 | 52 | 72 | 53 |
| IFITM1, mono, membrane | PTEN, gran, intra | 0.32 | 0.01 | 69 | 80 | 51 | 73 | 61 |
| IFITM1, mono, membrane | PTEN, lymp, intra | 0.42 | 0.11 | 73 | 80 | 62 | 77 | 65 |
| IFITM1, mono, membrane | PTEN, mean, intra | 0.27 | −0.04 | 66 | 77 | 49 | 71 | 58 |
| IFITM1, mono, membrane | PTEN, mono, intra | 0.32 | 0.01 | 69 | 80 | 51 | 73 | 61 |
| IFITM1, mono, membrane | RSAD2, gran, intra | 0.66 | 0.03 | 83 | 81 | 85 | 87 | 78 |
| IFITM1, mono, membrane | RSAD2, lymp, intra | 0.44 | 0.13 | 72 | 68 | 77 | 78 | 66 |
| IFITM1, mono, membrane | RSAD2, mean, intra | 0.56 | −0.08 | 78 | 75 | 81 | 83 | 73 |
| IFITM1, mono, membrane | RSAD2, mono, intra | 0.66 | 0.03 | 83 | 81 | 85 | 87 | 78 |
| IFITM1, mono, membrane | SDCBP, mean, intra | 0.21 | −0.1 | 63 | 74 | 46 | 68 | 53 |
| IFITM1, mono, membrane | WBC | 0.39 | 0.08 | 70 | 73 | 66 | 73 | 66 |
| IFITM3, gran, membrane | IFITM3, mean, membrane | 0.34 | −0.01 | 66 | 63 | 71 | 73 | 61 |
| IFITM3, gran, membrane | IFITM3, mono, membrane | 0.39 | −0.02 | 69 | 66 | 73 | 75 | 64 |
| IFITM3, gran, membrane | LOC26010, gran, intra | 0.26 | −0.09 | 63 | 58 | 68 | 69 | 57 |
| IFITM3, gran, membrane | LOC26010, mean, intra | 0.31 | −0.04 | 65 | 60 | 71 | 72 | 59 |
| IFITM3, gran, membrane | LOC26010, mono, intra | 0.26 | −0.09 | 63 | 58 | 68 | 69 | 57 |
| IFITM3, gran, membrane | LY6E, lymp, membrane | 0.35 | 0 | 68 | 68 | 67 | 72 | 64 |
| IFITM3, gran, membrane | Lym(%) | 0.48 | −0.04 | 74 | 76 | 73 | 78 | 70 |
| IFITM3, gran, membrane | MAN1C1, gran, intra | 0.09 | −0.26 | 60 | 79 | 29 | 65 | 45 |
| IFITM3, gran, membrane | MAN1C1, mean, intra | 0.08 | −0.27 | 60 | 81 | 26 | 65 | 44 |
| IFITM3, gran, membrane | MAN1C1, mono, intra | 0.09 | −0.26 | 60 | 79 | 29 | 65 | 45 |
| IFITM3, gran, membrane | MX1, gran, intra | 0.49 | −0.05 | 75 | 76 | 73 | 78 | 71 |
| IFITM3, gran, membrane | MX1, lymp, intra | 0.39 | 0.04 | 69 | 66 | 73 | 75 | 64 |
| IFITM3, gran, membrane | MX1, mean, intra | 0.42 | −0.03 | 71 | 69 | 73 | 76 | 66 |
| IFITM3, gran, membrane | MX1, mono, intra | 0.49 | −0.05 | 75 | 76 | 73 | 78 | 71 |
| IFITM3, gran, membrane | Neu(%) | 0.56 | 0 | 78 | 81 | 75 | 80 | 76 |
| IFITM3, gran, membrane | NPM1, gran, intra | 0.17 | −0.18 | 63 | 79 | 36 | 67 | 52 |
| IFITM3, gran, membrane | NPM1, mean, intra | 0.12 | −0.23 | 60 | 75 | 36 | 65 | 48 |
| IFITM3, gran, membrane | NPM1, mono, intra | 0.17 | −0.18 | 63 | 79 | 36 | 67 | 52 |
| IFITM3, gran, membrane | OAS2, gran, intra | 0.33 | −0.03 | 66 | 64 | 70 | 72 | 61 |
| IFITM3, gran, membrane | OAS2, mean, intra | 0.3 | −0.05 | 65 | 63 | 68 | 70 | 60 |
| IFITM3, gran, membrane | OAS2, mono, intra | 0.33 | −0.03 | 66 | 64 | 70 | 72 | 61 |
| IFITM3, gran, membrane | PARP12, gran, intra | 0.19 | −0.16 | 63 | 75 | 44 | 69 | 52 |
| IFITM3, gran, membrane | PARP12, mean, intra | 0.21 | −0.14 | 63 | 74 | 46 | 69 | 53 |
| IFITM3, gran, membrane | PARP12, mono, intra | 0.19 | −0.16 | 63 | 75 | 44 | 69 | 52 |
| IFITM3, gran, membrane | PARP9, lymp, intra | 0.26 | −0.09 | 67 | 83 | 41 | 70 | 59 |
| IFITM3, gran, membrane | PDIA6, gran, intra | 0.06 | −0.29 | 60 | 79 | 26 | 65 | 42 |
| IFITM3, gran, membrane | PDIA6, lymp, intra | 0.13 | −0.22 | 62 | 79 | 32 | 67 | 48 |
| IFITM3, gran, membrane | PDIA6, mono, intra | 0.06 | −0.29 | 60 | 79 | 26 | 65 | 42 |
| IFITM3, gran, membrane | PTEN, gran, intra | 0.2 | −0.15 | 63 | 73 | 46 | 69 | 51 |
| IFITM3, gran, membrane | PTEN, lymp, intra | 0.12 | −0.23 | 60 | 73 | 38 | 66 | 47 |
| IFITM3, gran, membrane | PTEN, mean, intra | 0.21 | −0.14 | 63 | 74 | 46 | 69 | 53 |
| IFITM3, gran, membrane | PTEN, mono, intra | 0.2 | −0.15 | 63 | 73 | 46 | 69 | 51 |
| IFITM3, gran, membrane | RSAD2, gran, intra | 0.61 | −0.02 | 81 | 78 | 83 | 85 | 76 |
| IFITM3, gran, membrane | RSAD2, lymp, intra | 0.38 | 0.03 | 69 | 65 | 73 | 75 | 63 |
| IFITM3, gran, membrane | RSAD2, mean, intra | 0.62 | −0.02 | 81 | 79 | 83 | 85 | 77 |
| IFITM3, gran, membrane | RSAD2, mono, intra | 0.61 | −0.02 | 81 | 78 | 83 | 85 | 76 |
| IFITM3, gran, membrane | SDCBP, mean, intra | 0.04 | −0.31 | 57 | 75 | 28 | 62 | 42 |
| IFITM3, gran, membrane | WBC | 0.37 | 0.02 | 69 | 74 | 63 | 71 | 66 |
| IFITM3, mean, membrane | IFITM3, mono, membrane | 0.38 | −0.03 | 69 | 67 | 71 | 74 | 64 |
| IFITM3, mean, membrane | LOC26010, gran, intra | 0.32 | −0.03 | 66 | 63 | 69 | 71 | 60 |
| IFITM3, mean, membrane | LOC26010, mean, intra | 0.34 | −0.01 | 66 | 63 | 71 | 73 | 61 |
| IFITM3, mean, membrane | LOC26010, mono, intra | 0.32 | −0.03 | 66 | 63 | 69 | 71 | 60 |
| IFITM3, mean, membrane | LY6E, lymp, membrane | 0.35 | 0 | 68 | 68 | 67 | 72 | 63 |
| IFITM3, mean, membrane | Lym(%) | 0.48 | −0.04 | 74 | 76 | 71 | 76 | 71 |
| IFITM3, mean, membrane | MAN1C1, gran, intra | 0.07 | −0.28 | 59 | 77 | 29 | 65 | 43 |
| IFITM3, mean, membrane | MAN1C1, mean, intra | 0.08 | −0.27 | 60 | 81 | 26 | 65 | 44 |
| IFITM3, mean, membrane | MAN1C1, mono, intra | 0.07 | −0.28 | 59 | 77 | 29 | 65 | 43 |
| IFITM3, mean, membrane | MX1, gran, intra | 0.47 | −0.07 | 73 | 72 | 75 | 78 | 69 |
| IFITM3, mean, membrane | MX1, lymp, intra | 0.4 | 0.05 | 69 | 65 | 75 | 76 | 64 |
| IFITM3, mean, membrane | MX1, mean, intra | 0.4 | −0.05 | 70 | 69 | 71 | 75 | 66 |
| IFITM3, mean, membrane | MX1, mono, intra | 0.47 | −0.07 | 73 | 72 | 75 | 78 | 69 |
| IFITM3, mean, membrane | Neu(%) | 0.58 | 0.02 | 79 | 83 | 75 | 80 | 79 |
| IFITM3, mean, membrane | NPM1, gran, intra | 0.17 | −0.18 | 62 | 77 | 38 | 66 | 52 |
| IFITM3, mean, membrane | NPM1, mean, intra | 0.21 | −0.14 | 64 | 80 | 38 | 67 | 56 |
| IFITM3, mean, membrane | NPM1, mono, intra | 0.17 | −0.18 | 62 | 77 | 38 | 66 | 52 |
| IFITM3, mean, membrane | OAS2, gran, intra | 0.37 | 0.01 | 68 | 64 | 73 | 74 | 62 |
| IFITM3, mean, membrane | OAS2, mean, intra | 0.33 | −0.02 | 66 | 64 | 69 | 72 | 61 |

TABLE 4-continued

The classification accuracy of bacterial vs. viral infected patients computed over pairs of features. DETERMINANT measurements were measured over different cell types.

| Feature #1 | Feature #2 | MCC | dMCC | Total accuracy % | Sen % | Spe % | PPV % | NPV % |
|---|---|---|---|---|---|---|---|---|
| IFITM3, mean, membrane | OAS2, mono, intra | 0.37 | 0.01 | 68 | 64 | 73 | 74 | 62 |
| IFITM3, mean, membrane | PARP12, gran, intra | 0.16 | −0.19 | 60 | 69 | 46 | 67 | 49 |
| IFITM3, mean, membrane | PARP12, mean, intra | 0.23 | −0.12 | 64 | 74 | 49 | 70 | 54 |
| IFITM3, mean, membrane | PARP12, mono, intra | 0.16 | −0.19 | 60 | 69 | 46 | 67 | 49 |
| IFITM3, mean, membrane | PARP9, lymp, intra | 0.24 | −0.11 | 65 | 81 | 41 | 68 | 57 |
| IFITM3, mean, membrane | PDIA6, gran, intra | 0.1 | −0.25 | 60 | 74 | 35 | 66 | 44 |
| IFITM3, mean, membrane | PDIA6, lymp, intra | 0.14 | −0.21 | 62 | 77 | 35 | 67 | 48 |
| IFITM3, mean, membrane | PDIA6, mono, intra | 0.1 | −0.25 | 60 | 74 | 35 | 66 | 44 |
| IFITM3, mean, membrane | PTEN, gran, intra | 0.19 | −0.16 | 62 | 73 | 46 | 68 | 51 |
| IFITM3, mean, membrane | PTEN, lymp, intra | 0.11 | −0.24 | 58 | 69 | 41 | 65 | 46 |
| IFITM3, mean, membrane | PTEN, mean, intra | 0.2 | −0.15 | 63 | 76 | 44 | 68 | 53 |
| IFITM3, mean, membrane | PTEN, mono, intra | 0.19 | −0.16 | 62 | 73 | 46 | 68 | 51 |
| IFITM3, mean, membrane | RSAD2, gran, intra | 0.62 | −0.01 | 81 | 79 | 83 | 85 | 77 |
| IFITM3, mean, membrane | RSAD2, lymp, intra | 0.35 | 0 | 68 | 69 | 66 | 71 | 64 |
| IFITM3, mean, membrane | RSAD2, mean, intra | 0.63 | −0.01 | 82 | 81 | 83 | 85 | 78 |
| IFITM3, mean, membrane | RSAD2, mono, intra | 0.62 | −0.01 | 81 | 79 | 83 | 85 | 77 |
| IFITM3, mean, membrane | SDCBP, mean, intra | 0.04 | −0.31 | 57 | 75 | 28 | 62 | 42 |
| IFITM3, mean, membrane | WBC | 0.37 | 0.02 | 69 | 74 | 63 | 71 | 66 |
| IFITM3, mono, membrane | LOC26010, gran, intra | 0.44 | 0.03 | 72 | 69 | 75 | 77 | 66 |
| IFITM3, mono, membrane | LOC26010, mean, intra | 0.41 | 0 | 70 | 67 | 75 | 76 | 65 |
| IFITM3, mono, membrane | LOC26010, mono, intra | 0.44 | 0.03 | 72 | 69 | 75 | 77 | 66 |
| IFITM3, mono, membrane | LY6E, lymp, membrane | 0.35 | −0.06 | 67 | 63 | 71 | 73 | 62 |
| IFITM3, mono, membrane | Lym(%) | 0.53 | 0.01 | 77 | 80 | 73 | 79 | 74 |
| IFITM3, mono, membrane | MAN1C1, gran, intra | 0.31 | −0.1 | 69 | 79 | 52 | 73 | 59 |
| IFITM3, mono, membrane | MAN1C1, mean, intra | 0.28 | −0.13 | 67 | 79 | 48 | 72 | 58 |
| IFITM3, mono, membrane | MAN1C1, mono, intra | 0.31 | −0.1 | 69 | 79 | 52 | 73 | 59 |
| IFITM3, mono, membrane | MX1, gran, intra | 0.61 | 0.07 | 81 | 78 | 83 | 85 | 76 |
| IFITM3, mono, membrane | MX1, lymp, intra | 0.48 | 0.07 | 74 | 72 | 77 | 79 | 69 |
| IFITM3, mono, membrane | MX1, mean, intra | 0.57 | 0.12 | 79 | 76 | 81 | 83 | 74 |
| IFITM3, mono, membrane | MX1, mono, intra | 0.61 | 0.07 | 81 | 78 | 83 | 85 | 76 |
| IFITM3, mono, membrane | Neu(%) | 0.59 | 0.03 | 80 | 84 | 75 | 81 | 79 |
| IFITM3, mono, membrane | NPM1, gran, intra | 0.4 | −0.01 | 72 | 76 | 64 | 77 | 63 |
| IFITM3, mono, membrane | NPM1, mean, intra | 0.36 | −0.05 | 70 | 77 | 59 | 75 | 62 |
| IFITM3, mono, membrane | NPM1, mono, intra | 0.4 | −0.01 | 72 | 76 | 64 | 77 | 63 |
| IFITM3, mono, membrane | OAS2, gran, intra | 0.46 | 0.05 | 73 | 72 | 75 | 78 | 68 |
| IFITM3, mono, membrane | OAS2, mean, intra | 0.45 | 0.04 | 73 | 71 | 75 | 77 | 68 |
| IFITM3, mono, membrane | OAS2, mono, intra | 0.46 | 0.05 | 73 | 72 | 75 | 78 | 68 |
| IFITM3, mono, membrane | PARP12, gran, intra | 0.33 | −0.08 | 69 | 77 | 56 | 74 | 59 |
| IFITM3, mono, membrane | PARP12, mean, intra | 0.36 | −0.05 | 69 | 74 | 62 | 75 | 60 |
| IFITM3, mono, membrane | PARP12, mono, intra | 0.33 | −0.08 | 69 | 77 | 56 | 74 | 59 |
| IFITM3, mono, membrane | PARP9, lymp, intra | 0.3 | −0.11 | 67 | 73 | 56 | 73 | 56 |
| IFITM3, mono, membrane | PDIA6, gran, intra | 0.27 | −0.14 | 67 | 75 | 52 | 73 | 55 |
| IFITM3, mono, membrane | PDIA6, lymp, intra | 0.49 | 0.08 | 76 | 81 | 68 | 81 | 68 |
| IFITM3, mono, membrane | PDIA6, mono, intra | 0.27 | −0.14 | 67 | 75 | 52 | 73 | 55 |
| IFITM3, mono, membrane | PTEN, gran, intra | 0.34 | −0.07 | 69 | 75 | 59 | 75 | 59 |
| IFITM3, mono, membrane | PTEN, lymp, intra | 0.39 | −0.02 | 71 | 75 | 64 | 77 | 61 |
| IFITM3, mono, membrane | PTEN, mean, intra | 0.35 | −0.06 | 69 | 76 | 59 | 75 | 61 |
| IFITM3, mono, membrane | PTEN, mono, intra | 0.34 | −0.07 | 69 | 75 | 59 | 75 | 59 |
| IFITM3, mono, membrane | RSAD2, gran, intra | 0.63 | 0 | 81 | 80 | 83 | 86 | 77 |
| IFITM3, mono, membrane | RSAD2, lymp, intra | 0.5 | 0.09 | 75 | 72 | 78 | 80 | 69 |
| IFITM3, mono, membrane | RSAD2, mean, intra | 0.62 | −0.02 | 81 | 82 | 80 | 83 | 78 |
| IFITM3, mono, membrane | RSAD2, mono, intra | 0.63 | 0 | 81 | 80 | 83 | 86 | 77 |
| IFITM3, mono, membrane | SDCBP, mean, intra | 0.27 | −0.14 | 66 | 75 | 51 | 71 | 57 |
| IFITM3, mono, membrane | WBC | 0.5 | 0.09 | 75 | 78 | 71 | 77 | 72 |
| LOC26010, gran, intra | LOC26010, mean, intra | 0.24 | 0.01 | 62 | 60 | 65 | 66 | 58 |
| LOC26010, gran, intra | LOC26010, mono, intra | 0.23 | 0 | 61 | 61 | 62 | 65 | 57 |
| LOC26010, gran, intra | LY6E, lymp, membrane | 0.23 | 0 | 62 | 63 | 60 | 66 | 57 |
| LOC26010, gran, intra | Lym(%) | 0.5 | −0.02 | 75 | 76 | 74 | 78 | 72 |
| LOC26010, gran, intra | MAN1C1, gran, intra | 0.12 | −0.11 | 61 | 79 | 32 | 66 | 48 |
| LOC26010, gran, intra | MAN1C1, mean, intra | 0.16 | −0.07 | 63 | 79 | 35 | 67 | 50 |
| LOC26010, gran, intra | MAN1C1, mono, intra | 0.12 | −0.11 | 61 | 79 | 32 | 66 | 48 |
| LOC26010, gran, intra | MX1, gran, intra | 0.55 | 0.01 | 77 | 74 | 81 | 82 | 73 |
| LOC26010, gran, intra | MX1, lymp, intra | 0.37 | 0.02 | 69 | 68 | 70 | 72 | 65 |
| LOC26010, gran, intra | MX1, mean, intra | 0.42 | −0.03 | 71 | 68 | 74 | 75 | 67 |
| LOC26010, gran, intra | MX1, mono, intra | 0.55 | 0.01 | 77 | 74 | 81 | 82 | 73 |
| LOC26010, gran, intra | Neu(%) | 0.48 | −0.08 | 74 | 76 | 73 | 77 | 71 |
| LOC26010, gran, intra | NPM1, gran, intra | 0.09 | −0.14 | 59 | 75 | 33 | 64 | 45 |
| LOC26010, gran, intra | NPM1, mean, intra | 0.15 | −0.08 | 61 | 75 | 38 | 66 | 50 |
| LOC26010, gran, intra | NPM1, mono, intra | 0.09 | −0.14 | 59 | 75 | 33 | 64 | 45 |
| LOC26010, gran, intra | OAS2, gran, intra | 0.34 | −0.02 | 66 | 61 | 73 | 73 | 61 |
| LOC26010, gran, intra | OAS2, mean, intra | 0.23 | −0.07 | 61 | 57 | 66 | 66 | 57 |
| LOC26010, gran, intra | OAS2, mono, intra | 0.34 | −0.02 | 66 | 61 | 73 | 73 | 61 |
| LOC26010, gran, intra | PARP12, gran, intra | 0.14 | −0.09 | 61 | 75 | 38 | 67 | 48 |
| LOC26010, gran, intra | PARP12, mean, intra | 0.3 | 0.05 | 67 | 76 | 54 | 72 | 58 |

TABLE 4-continued

The classification accuracy of bacterial vs. viral infected patients computed over pairs of features. DETERMINANT measurements were measured over different cell types.

| Feature #1 | Feature #2 | MCC | dMCC | Total accuracy % | Sen % | Spe % | PPV % | NPV % |
|---|---|---|---|---|---|---|---|---|
| LOC26010, gran, intra | PARP12, mono, intra | 0.14 | −0.09 | 61 | 75 | 38 | 67 | 48 |
| LOC26010, gran, intra | PARP9, lymp, intra | 0.25 | 0.02 | 66 | 78 | 46 | 70 | 56 |
| LOC26010, gran, intra | PDIA6, gran, intra | 0.11 | −0.12 | 61 | 77 | 32 | 66 | 45 |
| LOC26010, gran, intra | PDIA6, lymp, intra | 0.24 | 0.01 | 65 | 77 | 45 | 71 | 54 |
| LOC26010, gran, intra | PDIA6, mono, intra | 0.11 | −0.12 | 61 | 77 | 32 | 66 | 45 |
| LOC26010, gran, intra | PTEN, gran, intra | 0.17 | −0.06 | 61 | 70 | 46 | 68 | 49 |
| LOC26010, gran, intra | PTEN, lymp, intra | 0.21 | −0.02 | 63 | 72 | 49 | 70 | 51 |
| LOC26010, gran, intra | PTEN, mean, intra | 0.15 | −0.08 | 60 | 71 | 44 | 67 | 49 |
| LOC26010, gran, intra | PTEN, mono, intra | 0.17 | −0.06 | 61 | 70 | 46 | 68 | 49 |
| LOC26010, gran, intra | RSAD2, gran, intra | 0.67 | 0.04 | 83 | 80 | 87 | 88 | 79 |
| LOC26010, gran, intra | RSAD2, lymp, intra | 0.3 | 0.07 | 65 | 66 | 63 | 68 | 62 |
| LOC26010, gran, intra | RSAD2, mean, intra | 0.64 | 0 | 82 | 81 | 84 | 85 | 79 |
| LOC26010, gran, intra | RSAD2, mono, intra | 0.67 | 0.04 | 83 | 80 | 87 | 88 | 79 |
| LOC26010, gran, intra | SDCBP, mean, intra | 0.17 | −0.06 | 62 | 77 | 38 | 66 | 52 |
| LOC26010, gran, intra | WBC | 0.37 | 0.12 | 69 | 80 | 56 | 69 | 70 |
| LOC26010, mean, intra | LOC26010, mono, intra | 0.24 | 0.01 | 62 | 60 | 65 | 66 | 58 |
| LOC26010, mean, intra | LY6E, lymp, membrane | 0.22 | −0.01 | 61 | 65 | 57 | 65 | 57 |
| LOC26010, mean, intra | Lym(%) | 0.52 | 0 | 76 | 76 | 76 | 79 | 73 |
| LOC26010, mean, intra | MAN1C1, gran, intra | 0.19 | −0.02 | 64 | 79 | 39 | 68 | 52 |
| LOC26010, mean, intra | MAN1C1, mean, intra | 0.18 | −0.03 | 64 | 81 | 35 | 68 | 52 |
| LOC26010, mean, intra | MAN1C1, mono, intra | 0.19 | −0.02 | 64 | 79 | 39 | 68 | 52 |
| LOC26010, mean, intra | MX1, gran, intra | 0.51 | −0.03 | 75 | 71 | 81 | 81 | 70 |
| LOC26010, mean, intra | MX1, lymp, intra | 0.33 | −0.02 | 66 | 64 | 69 | 71 | 62 |
| LOC26010, mean, intra | MX1, mean, intra | 0.44 | −0.01 | 72 | 68 | 76 | 77 | 67 |
| LOC26010, mean, intra | MX1, mono, intra | 0.51 | −0.03 | 75 | 71 | 81 | 81 | 70 |
| LOC26010, mean, intra | Neu(%) | 0.49 | −0.07 | 75 | 75 | 74 | 77 | 72 |
| LOC26010, mean, intra | NPM1, gran, intra | 0.17 | −0.04 | 62 | 77 | 38 | 66 | 52 |
| LOC26010, mean, intra | NPM1, mean, intra | 0.14 | −0.07 | 61 | 77 | 36 | 65 | 50 |
| LOC26010, mean, intra | NPM1, mono, intra | 0.17 | −0.04 | 62 | 77 | 38 | 66 | 52 |
| LOC26010, mean, intra | OAS2, gran, intra | 0.32 | −0.04 | 66 | 60 | 73 | 72 | 61 |
| LOC26010, mean, intra | OAS2, mean, intra | 0.26 | −0.04 | 63 | 58 | 68 | 68 | 58 |
| LOC26010, mean, intra | OAS2, mono, intra | 0.32 | −0.04 | 66 | 60 | 73 | 72 | 61 |
| LOC26010, mean, intra | PARP12, gran, intra | 0.18 | −0.03 | 62 | 74 | 44 | 68 | 52 |
| LOC26010, mean, intra | PARP12, mean, intra | 0.26 | 0.01 | 65 | 74 | 51 | 71 | 56 |
| LOC26010, mean, intra | PARP12, mono, intra | 0.18 | −0.03 | 62 | 74 | 44 | 68 | 52 |
| LOC26010, mean, intra | PARP9, lymp, intra | 0.21 | 0 | 64 | 81 | 38 | 68 | 56 |
| LOC26010, mean, intra | PDIA6, gran, intra | 0.15 | −0.06 | 62 | 75 | 39 | 68 | 48 |
| LOC26010, mean, intra | PDIA6, lymp, intra | 0.18 | −0.03 | 63 | 75 | 42 | 69 | 50 |
| LOC26010, mean, intra | PDIA6, mono, intra | 0.15 | −0.06 | 62 | 75 | 39 | 68 | 48 |
| LOC26010, mean, intra | PTEN, gran, intra | 0.17 | −0.05 | 61 | 71 | 46 | 68 | 50 |
| LOC26010, mean, intra | PTEN, lymp, intra | 0.17 | −0.04 | 61 | 71 | 46 | 68 | 50 |
| LOC26010, mean, intra | PTEN, mean, intra | 0.15 | −0.06 | 60 | 71 | 44 | 67 | 49 |
| LOC26010, mean, intra | PTEN, mono, intra | 0.17 | −0.05 | 61 | 71 | 46 | 68 | 50 |
| LOC26010, mean, intra | RSAD2, gran, intra | 0.66 | 0.03 | 83 | 79 | 87 | 88 | 78 |
| LOC26010, mean, intra | RSAD2, lymp, intra | 0.32 | 0.09 | 66 | 64 | 68 | 70 | 62 |
| LOC26010, mean, intra | RSAD2, mean, intra | 0.64 | 0 | 82 | 81 | 84 | 85 | 79 |
| LOC26010, mean, intra | RSAD2, mono, intra | 0.66 | 0.03 | 83 | 79 | 87 | 88 | 78 |
| LOC26010, mean, intra | SDCBP, mean, intra | 0.16 | −0.05 | 62 | 79 | 36 | 66 | 52 |
| LOC26010, mean, intra | WBC | 0.29 | 0.04 | 65 | 74 | 55 | 65 | 64 |
| LOC26010, mono, intra | LY6E, lymp, membrane | 0.23 | 0 | 62 | 63 | 60 | 66 | 57 |
| LOC26010, mono, intra | Lym(%) | 0.5 | −0.02 | 75 | 76 | 74 | 78 | 72 |
| LOC26010, mono, intra | MAN1C1, gran, intra | 0.12 | −0.11 | 61 | 79 | 32 | 66 | 48 |
| LOC26010, mono, intra | MAN1C1, mean, intra | 0.16 | −0.07 | 63 | 79 | 35 | 67 | 50 |
| LOC26010, mono, intra | MAN1C1, mono, intra | 0.12 | −0.11 | 61 | 79 | 32 | 66 | 48 |
| LOC26010, mono, intra | MX1, gran, intra | 0.55 | 0.01 | 77 | 74 | 81 | 82 | 73 |
| LOC26010, mono, intra | MX1, lymp, intra | 0.37 | 0.02 | 69 | 68 | 70 | 72 | 65 |
| LOC26010, mono, intra | MX1, mean, intra | 0.42 | −0.03 | 71 | 68 | 74 | 75 | 67 |
| LOC26010, mono, intra | MX1, mono, intra | 0.55 | 0.01 | 77 | 74 | 81 | 82 | 73 |
| LOC26010, mono, intra | Neu(%) | 0.48 | −0.08 | 74 | 76 | 73 | 77 | 71 |
| LOC26010, mono, intra | NPM1, gran, intra | 0.09 | −0.14 | 59 | 75 | 33 | 64 | 45 |
| LOC26010, mono, intra | NPM1, mean, intra | 0.15 | −0.08 | 61 | 75 | 38 | 66 | 50 |
| LOC26010, mono, intra | NPM1, mono, intra | 0.09 | −0.14 | 59 | 75 | 33 | 64 | 45 |
| LOC26010, mono, intra | OAS2, gran, intra | 0.34 | −0.02 | 66 | 61 | 73 | 73 | 61 |
| LOC26010, mono, intra | OAS2, mean, intra | 0.23 | −0.07 | 61 | 57 | 66 | 66 | 57 |
| LOC26010, mono, intra | OAS2, mono, intra | 0.34 | −0.02 | 66 | 61 | 73 | 73 | 61 |
| LOC26010, mono, intra | PARP12, gran, intra | 0.14 | −0.09 | 61 | 75 | 38 | 67 | 48 |
| LOC26010, mono, intra | PARP12, mean, intra | 0.3 | 0.05 | 67 | 76 | 54 | 72 | 58 |
| LOC26010, mono, intra | PARP12, mono, intra | 0.14 | −0.09 | 61 | 75 | 38 | 67 | 48 |
| LOC26010, mono, intra | PARP9, lymp, intra | 0.25 | 0.02 | 66 | 78 | 46 | 70 | 56 |
| LOC26010, mono, intra | PDIA6, gran, intra | 0.11 | −0.12 | 61 | 77 | 32 | 66 | 45 |
| LOC26010, mono, intra | PDIA6, lymp, intra | 0.24 | 0.01 | 65 | 77 | 45 | 71 | 54 |
| LOC26010, mono, intra | PDIA6, mono, intra | 0.11 | −0.12 | 61 | 77 | 32 | 66 | 45 |
| LOC26010, mono, intra | PTEN, gran, intra | 0.17 | −0.06 | 61 | 70 | 46 | 68 | 49 |
| LOC26010, mono, intra | PTEN, lymp, intra | 0.21 | −0.02 | 63 | 72 | 49 | 70 | 51 |

TABLE 4-continued

The classification accuracy of bacterial vs. viral infected patients computed over pairs of features. DETERMINANT measurements were measured over different cell types.

| Feature #1 | Feature #2 | MCC | dMCC | Total accuracy % | Sen % | Spe % | PPV % | NPV % |
|---|---|---|---|---|---|---|---|---|
| LOC26010, mono, intra | PTEN, mean, intra | 0.15 | −0.08 | 60 | 71 | 44 | 67 | 49 |
| LOC26010, mono, intra | PTEN, mono, intra | 0.17 | −0.06 | 61 | 70 | 46 | 68 | 49 |
| LOC26010, mono, intra | RSAD2, gran, intra | 0.67 | 0.04 | 83 | 80 | 87 | 88 | 79 |
| LOC26010, mono, intra | RSAD2, lymp, intra | 0.3 | 0.07 | 65 | 66 | 63 | 68 | 62 |
| LOC26010, mono, intra | RSAD2, mean, intra | 0.64 | 0 | 82 | 81 | 84 | 85 | 79 |
| LOC26010, mono, intra | RSAD2, mono, intra | 0.67 | 0.04 | 83 | 80 | 87 | 88 | 79 |
| LOC26010, mono, intra | SDCBP, mean, intra | 0.17 | −0.06 | 62 | 77 | 38 | 66 | 52 |
| LOC26010, mono, intra | WBC | 0.37 | 0.12 | 69 | 80 | 56 | 69 | 70 |
| LY6E, lymp, membrane | Lym(%) | 0.52 | 0 | 76 | 78 | 75 | 79 | 73 |
| LY6E, lymp, membrane | MAN1C1, gran, intra | 0.17 | −0.06 | 64 | 83 | 32 | 67 | 53 |
| LY6E, lymp, membrane | MAN1C1, mean, intra | 0.2 | −0.03 | 65 | 85 | 32 | 68 | 56 |
| LY6E, lymp, membrane | MAN1C1, mono, intra | 0.17 | −0.06 | 64 | 83 | 32 | 67 | 53 |
| LY6E, lymp, membrane | MX1, gran, intra | 0.5 | −0.04 | 75 | 70 | 81 | 81 | 69 |
| LY6E, lymp, membrane | MX1, lymp, intra | 0.38 | 0.03 | 69 | 65 | 73 | 75 | 63 |
| LY6E, lymp, membrane | MX1, mean, intra | 0.45 | 0 | 72 | 68 | 76 | 78 | 66 |
| LY6E, lymp, membrane | MX1, mono, intra | 0.5 | −0.04 | 75 | 70 | 81 | 81 | 69 |
| LY6E, lymp, membrane | Neu(%) | 0.54 | −0.02 | 77 | 79 | 75 | 79 | 75 |
| LY6E, lymp, membrane | NPM1, gran, intra | 0.22 | −0.01 | 65 | 79 | 42 | 69 | 54 |
| LY6E, lymp, membrane | NPM1, mean, intra | 0.18 | −0.05 | 64 | 81 | 35 | 68 | 52 |
| LY6E, lymp, membrane | NPM1, mono, intra | 0.22 | −0.01 | 65 | 79 | 42 | 69 | 54 |
| LY6E, lymp, membrane | OAS2, gran, intra | 0.41 | 0.05 | 70 | 62 | 79 | 78 | 63 |
| LY6E, lymp, membrane | OAS2, mean, intra | 0.36 | 0.06 | 68 | 63 | 73 | 74 | 62 |
| LY6E, lymp, membrane | OAS2, mono, intra | 0.41 | 0.05 | 70 | 62 | 79 | 78 | 63 |
| LY6E, lymp, membrane | PARP12, gran, intra | 0.09 | −0.14 | 61 | 79 | 29 | 66 | 45 |
| LY6E, lymp, membrane | PARP12, mean, intra | 0.16 | −0.09 | 62 | 74 | 42 | 68 | 48 |
| LY6E, lymp, membrane | PARP12, mono, intra | 0.09 | −0.14 | 61 | 79 | 29 | 66 | 45 |
| LY6E, lymp, membrane | PARP9, lymp, intra | 0.08 | −0.15 | 61 | 81 | 26 | 65 | 44 |
| LY6E, lymp, membrane | PDIA6, gran, intra | 0.01 | −0.22 | 57 | 75 | 26 | 63 | 38 |
| LY6E, lymp, membrane | PDIA6, lymp, intra | 0.07 | −0.16 | 60 | 77 | 29 | 65 | 43 |
| LY6E, lymp, membrane | PDIA6, mono, intra | 0.01 | −0.22 | 57 | 75 | 26 | 63 | 38 |
| LY6E, lymp, membrane | PTEN, gran, intra | 0.12 | −0.11 | 61 | 75 | 35 | 67 | 46 |
| LY6E, lymp, membrane | PTEN, lymp, intra | −0.03 | −0.26 | 55 | 72 | 26 | 62 | 35 |
| LY6E, lymp, membrane | PTEN, mean, intra | 0.08 | −0.15 | 60 | 75 | 32 | 66 | 43 |
| LY6E, lymp, membrane | PTEN, mono, intra | 0.12 | −0.11 | 61 | 75 | 35 | 67 | 46 |
| LY6E, lymp, membrane | RSAD2, gran, intra | 0.63 | 0 | 82 | 83 | 81 | 84 | 79 |
| LY6E, lymp, membrane | RSAD2, lymp, intra | 0.3 | 0.07 | 65 | 65 | 65 | 69 | 61 |
| LY6E, lymp, membrane | RSAD2, mean, intra | 0.6 | −0.04 | 80 | 79 | 80 | 83 | 76 |
| LY6E, lymp, membrane | RSAD2, mono, intra | 0.63 | 0 | 82 | 83 | 81 | 84 | 79 |
| LY6E, lymp, membrane | SDCBP, mean, intra | 0.33 | 0.1 | 70 | 83 | 48 | 73 | 63 |
| LY6E, lymp, membrane | WBC | 0.37 | 0.12 | 69 | 79 | 57 | 69 | 69 |
| Lym(%) | MAN1C1, gran, intra | 0.45 | −0.07 | 75 | 83 | 61 | 78 | 68 |
| Lym(%) | MAN1C1, mean, intra | 0.42 | −0.1 | 73 | 83 | 58 | 77 | 67 |
| Lym(%) | MAN1C1, mono, intra | 0.45 | −0.07 | 75 | 83 | 61 | 78 | 68 |
| Lym(%) | MX1, gran, intra | 0.57 | 0.03 | 79 | 80 | 77 | 81 | 76 |
| Lym(%) | MX1, lymp, intra | 0.63 | 0.11 | 82 | 82 | 81 | 84 | 79 |
| Lym(%) | MX1, mean, intra | 0.62 | 0.1 | 81 | 83 | 79 | 82 | 80 |
| Lym(%) | MX1, mono, intra | 0.57 | 0.03 | 79 | 80 | 77 | 81 | 76 |
| Lym(%) | Neu(%) | 0.53 | −0.03 | 77 | 75 | 79 | 81 | 72 |
| Lym(%) | NPM1, gran, intra | 0.58 | 0.06 | 80 | 84 | 74 | 84 | 74 |
| Lym(%) | NPM1, mean, intra | 0.54 | 0.02 | 78 | 82 | 72 | 82 | 72 |
| Lym(%) | NPM1, mono, intra | 0.58 | 0.06 | 80 | 84 | 74 | 84 | 74 |
| Lym(%) | OAS2, gran, intra | 0.58 | 0.06 | 79 | 79 | 79 | 82 | 75 |
| Lym(%) | OAS2, mean, intra | 0.55 | 0.03 | 78 | 78 | 77 | 80 | 75 |
| Lym(%) | OAS2, mono, intra | 0.58 | 0.06 | 79 | 79 | 79 | 82 | 75 |
| Lym(%) | PARP12, gran, intra | 0.52 | 0 | 77 | 78 | 74 | 83 | 67 |
| Lym(%) | PARP12, mean, intra | 0.56 | 0.04 | 79 | 82 | 74 | 84 | 73 |
| Lym(%) | PARP12, mono, intra | 0.52 | 0 | 77 | 78 | 74 | 83 | 67 |
| Lym(%) | PARP9, lymp, intra | 0.5 | −0.02 | 77 | 83 | 67 | 80 | 70 |
| Lym(%) | PDIA6, gran, intra | 0.44 | −0.08 | 74 | 79 | 65 | 79 | 65 |
| Lym(%) | PDIA6, lymp, intra | 0.49 | −0.03 | 76 | 81 | 68 | 81 | 68 |
| Lym(%) | PDIA6, mono, intra | 0.44 | −0.08 | 74 | 79 | 65 | 79 | 65 |
| Lym(%) | PTEN, gran, intra | 0.48 | −0.04 | 75 | 77 | 72 | 82 | 65 |
| Lym(%) | PTEN, lymp, intra | 0.51 | −0.01 | 77 | 80 | 72 | 82 | 68 |
| Lym(%) | PTEN, mean, intra | 0.47 | −0.05 | 74 | 76 | 72 | 81 | 65 |
| Lym(%) | PTEN, mono, intra | 0.48 | −0.04 | 75 | 77 | 72 | 82 | 65 |
| Lym(%) | RSAD2, gran, intra | 0.62 | −0.01 | 81 | 81 | 81 | 84 | 78 |
| Lym(%) | RSAD2, lymp, intra | 0.56 | 0.04 | 78 | 77 | 79 | 82 | 74 |
| Lym(%) | RSAD2, mean, intra | 0.61 | −0.03 | 81 | 81 | 81 | 83 | 78 |
| Lym(%) | RSAD2, mono, intra | 0.62 | −0.01 | 81 | 81 | 81 | 84 | 78 |
| Lym(%) | SDCBP, mean, intra | 0.45 | −0.07 | 74 | 79 | 67 | 79 | 67 |
| Lym(%) | WBC | 0.58 | 0.06 | 79 | 79 | 79 | 82 | 75 |
| MAN1C1, gran, intra | MAN1C1, mean, intra | 0.17 | 0.04 | 64 | 83 | 32 | 67 | 53 |
| MAN1C1, gran, intra | MAN1C1, mono, intra | 0.15 | 0.04 | 63 | 81 | 32 | 67 | 50 |
| MAN1C1, gran, intra | MX1, gran, intra | 0.48 | −0.06 | 76 | 83 | 65 | 80 | 69 |

TABLE 4-continued

The classification accuracy of bacterial vs. viral infected patients computed over pairs of features. DETERMINANT measurements were measured over different cell types.

| Feature #1 | Feature #2 | MCC | dMCC | Total accuracy % | Sen % | Spe % | PPV % | NPV % |
|---|---|---|---|---|---|---|---|---|
| MAN1C1, gran, intra | MX1, lymp, intra | 0.31 | −0.04 | 69 | 79 | 52 | 73 | 59 |
| MAN1C1, gran, intra | MX1, mean, intra | 0.43 | −0.02 | 73 | 81 | 61 | 78 | 66 |
| MAN1C1, gran, intra | MX1, mono, intra | 0.48 | −0.06 | 76 | 83 | 65 | 80 | 69 |
| MAN1C1, gran, intra | Neu(%) | 0.5 | −0.06 | 77 | 87 | 61 | 79 | 73 |
| MAN1C1, gran, intra | NPM1, gran, intra | 0.2 | 0.09 | 64 | 77 | 42 | 69 | 52 |
| MAN1C1, gran, intra | NPM1, mean, intra | 0.2 | 0.07 | 64 | 77 | 42 | 69 | 52 |
| MAN1C1, gran, intra | NPM1, mono, intra | 0.2 | 0.09 | 64 | 77 | 42 | 69 | 52 |
| MAN1C1, gran, intra | OAS2, gran, intra | 0.17 | −0.19 | 63 | 77 | 39 | 68 | 50 |
| MAN1C1, gran, intra | OAS2, mean, intra | 0.08 | −0.22 | 59 | 75 | 32 | 65 | 43 |
| MAN1C1, gran, intra | OAS2, mono, intra | 0.17 | −0.19 | 63 | 77 | 39 | 68 | 50 |
| MAN1C1, gran, intra | PARP12, gran, intra | 0.18 | −0.01 | 63 | 75 | 42 | 68 | 50 |
| MAN1C1, gran, intra | PARP12, mean, intra | 0.26 | 0.01 | 66 | 77 | 48 | 71 | 56 |
| MAN1C1, gran, intra | PARP12, mono, intra | 0.18 | −0.01 | 63 | 75 | 42 | 68 | 50 |
| MAN1C1, gran, intra | PARP9, lymp, intra | 0.17 | 0.03 | 64 | 83 | 32 | 67 | 53 |
| MAN1C1, gran, intra | PDIA6, gran, intra | 0.25 | 0.12 | 66 | 79 | 45 | 71 | 56 |
| MAN1C1, gran, intra | PDIA6, lymp, intra | 0.16 | 0.05 | 61 | 73 | 42 | 68 | 48 |
| MAN1C1, gran, intra | PDIA6, mono, intra | 0.25 | 0.12 | 66 | 79 | 45 | 71 | 56 |
| MAN1C1, gran, intra | PTEN, gran, intra | 0.25 | 0.03 | 66 | 79 | 45 | 71 | 56 |
| MAN1C1, gran, intra | PTEN, lymp, intra | 0.28 | 0.17 | 67 | 81 | 45 | 71 | 58 |
| MAN1C1, gran, intra | PTEN, mean, intra | 0.28 | 0.08 | 67 | 81 | 45 | 71 | 58 |
| MAN1C1, gran, intra | PTEN, mono, intra | 0.25 | 0.03 | 66 | 79 | 45 | 71 | 56 |
| MAN1C1, gran, intra | RSAD2, gran, intra | 0.62 | −0.01 | 82 | 85 | 77 | 86 | 75 |
| MAN1C1, gran, intra | RSAD2, lymp, intra | 0.18 | −0.05 | 64 | 81 | 35 | 68 | 52 |
| MAN1C1, gran, intra | RSAD2, mean, intra | 0.53 | −0.11 | 78 | 85 | 68 | 81 | 72 |
| MAN1C1, gran, intra | RSAD2, mono, intra | 0.62 | −0.01 | 82 | 85 | 77 | 86 | 75 |
| MAN1C1, gran, intra | SDCBP, mean, intra | 0.21 | 0.1 | 65 | 81 | 39 | 69 | 55 |
| MAN1C1, gran, intra | WBC | 0.26 | 0.01 | 67 | 87 | 35 | 69 | 61 |
| MAN1C1, mean, intra | MAN1C1, mono, intra | 0.17 | 0.04 | 64 | 83 | 32 | 67 | 53 |
| MAN1C1, mean, intra | MX1, gran, intra | 0.48 | −0.06 | 76 | 83 | 65 | 80 | 69 |
| MAN1C1, mean, intra | MX1, lymp, intra | 0.26 | −0.09 | 66 | 77 | 48 | 71 | 56 |
| MAN1C1, mean, intra | MX1, mean, intra | 0.38 | −0.07 | 71 | 77 | 61 | 77 | 61 |
| MAN1C1, mean, intra | MX1, mono, intra | 0.48 | −0.06 | 76 | 83 | 65 | 80 | 69 |
| MAN1C1, mean, intra | Neu(%) | 0.5 | −0.06 | 77 | 88 | 58 | 78 | 75 |
| MAN1C1, mean, intra | NPM1, gran, intra | 0.28 | 0.15 | 67 | 81 | 45 | 71 | 58 |
| MAN1C1, mean, intra | NPM1, mean, intra | 0.19 | 0.06 | 64 | 79 | 39 | 68 | 52 |
| MAN1C1, mean, intra | NPM1, mono, intra | 0.28 | 0.15 | 67 | 81 | 45 | 71 | 58 |
| MAN1C1, mean, intra | OAS2, gran, intra | 0.18 | −0.18 | 63 | 75 | 42 | 68 | 50 |
| MAN1C1, mean, intra | OAS2, mean, intra | 0.15 | −0.15 | 63 | 81 | 32 | 67 | 50 |
| MAN1C1, mean, intra | OAS2, mono, intra | 0.18 | −0.18 | 63 | 75 | 42 | 68 | 50 |
| MAN1C1, mean, intra | PARP12, gran, intra | 0.14 | −0.05 | 61 | 75 | 39 | 67 | 48 |
| MAN1C1, mean, intra | PARP12, mean, intra | 0.21 | −0.04 | 64 | 75 | 45 | 70 | 52 |
| MAN1C1, mean, intra | PARP12, mono, intra | 0.14 | −0.05 | 61 | 75 | 39 | 67 | 48 |
| MAN1C1, mean, intra | PARP9, lymp, intra | 0.14 | 0 | 63 | 83 | 29 | 66 | 50 |
| MAN1C1, mean, intra | PDIA6, gran, intra | 0.2 | 0.07 | 64 | 77 | 42 | 69 | 52 |
| MAN1C1, mean, intra | PDIA6, lymp, intra | 0.12 | −0.01 | 60 | 73 | 39 | 67 | 46 |
| MAN1C1, mean, intra | PDIA6, mono, intra | 0.2 | 0.07 | 64 | 77 | 42 | 69 | 52 |
| MAN1C1, mean, intra | PTEN, gran, intra | 0.31 | 0.09 | 69 | 81 | 48 | 72 | 60 |
| MAN1C1, mean, intra | PTEN, lymp, intra | 0.25 | 0.12 | 66 | 81 | 42 | 70 | 57 |
| MAN1C1, mean, intra | PTEN, mean, intra | 0.28 | 0.08 | 67 | 79 | 48 | 72 | 58 |
| MAN1C1, mean, intra | PTEN, mono, intra | 0.31 | 0.09 | 69 | 81 | 48 | 72 | 60 |
| MAN1C1, mean, intra | RSAD2, gran, intra | 0.62 | −0.01 | 82 | 85 | 77 | 86 | 75 |
| MAN1C1, mean, intra | RSAD2, lymp, intra | 0.17 | −0.06 | 64 | 83 | 32 | 67 | 53 |
| MAN1C1, mean, intra | RSAD2, mean, intra | 0.58 | −0.06 | 81 | 87 | 71 | 83 | 76 |
| MAN1C1, mean, intra | RSAD2, mono, intra | 0.62 | −0.01 | 82 | 85 | 77 | 86 | 75 |
| MAN1C1, mean, intra | SDCBP, mean, intra | 0.3 | 0.17 | 69 | 83 | 45 | 72 | 61 |
| MAN1C1, mean, intra | WBC | 0.22 | −0.03 | 66 | 88 | 29 | 68 | 60 |
| MAN1C1, mono, intra | MX1, gran, intra | 0.48 | −0.06 | 76 | 83 | 65 | 80 | 69 |
| MAN1C1, mono, intra | MX1, lymp, intra | 0.31 | −0.04 | 69 | 79 | 52 | 73 | 59 |
| MAN1C1, mono, intra | MX1, mean, intra | 0.43 | −0.02 | 73 | 81 | 61 | 78 | 66 |
| MAN1C1, mono, intra | MX1, mono, intra | 0.48 | −0.06 | 76 | 83 | 65 | 80 | 69 |
| MAN1C1, mono, intra | Neu(%) | 0.5 | −0.06 | 77 | 87 | 61 | 79 | 73 |
| MAN1C1, mono, intra | NPM1, gran, intra | 0.2 | 0.09 | 64 | 77 | 42 | 69 | 52 |
| MAN1C1, mono, intra | NPM1, mean, intra | 0.2 | 0.07 | 64 | 77 | 42 | 69 | 52 |
| MAN1C1, mono, intra | NPM1, mono, intra | 0.2 | 0.09 | 64 | 77 | 42 | 69 | 52 |
| MAN1C1, mono, intra | OAS2, gran, intra | 0.17 | −0.19 | 63 | 77 | 39 | 68 | 50 |
| MAN1C1, mono, intra | OAS2, mean, intra | 0.08 | −0.22 | 59 | 75 | 32 | 65 | 43 |
| MAN1C1, mono, intra | OAS2, mono, intra | 0.17 | −0.19 | 63 | 77 | 39 | 68 | 50 |
| MAN1C1, mono, intra | PARP12, gran, intra | 0.18 | −0.01 | 63 | 75 | 42 | 68 | 50 |
| MAN1C1, mono, intra | PARP12, mean, intra | 0.26 | 0.01 | 66 | 77 | 48 | 71 | 56 |
| MAN1C1, mono, intra | PARP12, mono, intra | 0.18 | −0.01 | 63 | 75 | 42 | 68 | 50 |
| MAN1C1, mono, intra | PARP9, lymp, intra | 0.17 | 0.03 | 64 | 83 | 32 | 67 | 53 |
| MAN1C1, mono, intra | PDIA6, gran, intra | 0.25 | 0.12 | 66 | 79 | 45 | 71 | 56 |
| MAN1C1, mono, intra | PDIA6, lymp, intra | 0.16 | 0.05 | 61 | 73 | 42 | 68 | 48 |
| MAN1C1, mono, intra | PDIA6, mono, intra | 0.25 | 0.12 | 66 | 79 | 45 | 71 | 56 |

TABLE 4-continued

The classification accuracy of bacterial vs. viral infected patients computed over pairs of features. DETERMINANT measurements were measured over different cell types.

| Feature #1 | Feature #2 | MCC | dMCC | Total accuracy % | Sen % | Spe % | PPV % | NPV % |
|---|---|---|---|---|---|---|---|---|
| MAN1C1, mono, intra | PTEN, gran, intra | 0.25 | 0.03 | 66 | 79 | 45 | 71 | 56 |
| MAN1C1, mono, intra | PTEN, lymp, intra | 0.28 | 0.17 | 67 | 81 | 45 | 71 | 58 |
| MAN1C1, mono, intra | PTEN, mean, intra | 0.28 | 0.08 | 67 | 81 | 45 | 71 | 58 |
| MAN1C1, mono, intra | PTEN, mono, intra | 0.25 | 0.03 | 66 | 79 | 45 | 71 | 56 |
| MAN1C1, mono, intra | RSAD2, gran, intra | 0.62 | −0.01 | 82 | 85 | 77 | 86 | 75 |
| MAN1C1, mono, intra | RSAD2, lymp, intra | 0.18 | −0.05 | 64 | 81 | 35 | 68 | 52 |
| MAN1C1, mono, intra | RSAD2, mean, intra | 0.53 | −0.11 | 78 | 85 | 68 | 81 | 72 |
| MAN1C1, mono, intra | RSAD2, mono, intra | 0.62 | −0.01 | 82 | 85 | 77 | 86 | 75 |
| MAN1C1, mono, intra | SDCBP, mean, intra | 0.21 | 0.1 | 65 | 81 | 39 | 69 | 55 |
| MAN1C1, mono, intra | WBC | 0.26 | 0.01 | 67 | 87 | 35 | 69 | 61 |
| MX1, gran, intra | MX1, lymp, intra | 0.51 | −0.03 | 75 | 73 | 78 | 79 | 71 |
| MX1, gran, intra | MX1, mean, intra | 0.51 | −0.03 | 75 | 71 | 81 | 81 | 70 |
| MX1, gran, intra | MX1, mono, intra | 0.54 | 0 | 77 | 73 | 81 | 82 | 72 |
| MX1, gran, intra | Neu(%) | 0.59 | 0.03 | 79 | 81 | 77 | 81 | 77 |
| MX1, gran, intra | NPM1, gran, intra | 0.46 | −0.08 | 75 | 79 | 67 | 79 | 67 |
| MX1, gran, intra | NPM1, mean, intra | 0.48 | −0.06 | 75 | 79 | 69 | 80 | 68 |
| MX1, gran, intra | NPM1, mono, intra | 0.46 | −0.08 | 75 | 79 | 67 | 79 | 67 |
| MX1, gran, intra | OAS2, gran, intra | 0.51 | −0.03 | 75 | 72 | 79 | 80 | 70 |
| MX1, gran, intra | OAS2, mean, intra | 0.51 | −0.03 | 75 | 71 | 81 | 81 | 70 |
| MX1, gran, intra | OAS2, mono, intra | 0.51 | −0.03 | 75 | 72 | 79 | 80 | 70 |
| MX1, gran, intra | PARP12, gran, intra | 0.5 | −0.04 | 77 | 81 | 69 | 81 | 69 |
| MX1, gran, intra | PARP12, mean, intra | 0.54 | 0 | 78 | 82 | 72 | 82 | 72 |
| MX1, gran, intra | PARP12, mono, intra | 0.5 | −0.04 | 77 | 81 | 69 | 81 | 69 |
| MX1, gran, intra | PARP9, lymp, intra | 0.45 | −0.09 | 74 | 78 | 67 | 79 | 65 |
| MX1, gran, intra | PDIA6, gran, intra | 0.45 | −0.09 | 75 | 83 | 61 | 79 | 68 |
| MX1, gran, intra | PDIA6, lymp, intra | 0.5 | −0.04 | 76 | 79 | 71 | 82 | 67 |
| MX1, gran, intra | PDIA6, mono, intra | 0.45 | −0.09 | 75 | 83 | 61 | 79 | 68 |
| MX1, gran, intra | PTEN, gran, intra | 0.5 | −0.04 | 77 | 81 | 69 | 81 | 69 |
| MX1, gran, intra | PTEN, lymp, intra | 0.53 | −0.01 | 78 | 81 | 72 | 83 | 70 |
| MX1, gran, intra | PTEN, mean, intra | 0.46 | −0.08 | 74 | 77 | 69 | 80 | 66 |
| MX1, gran, intra | PTEN, mono, intra | 0.5 | −0.04 | 77 | 81 | 69 | 81 | 69 |
| MX1, gran, intra | RSAD2, gran, intra | 0.61 | −0.02 | 80 | 77 | 84 | 85 | 76 |
| MX1, gran, intra | RSAD2, lymp, intra | 0.51 | −0.03 | 75 | 72 | 79 | 80 | 70 |
| MX1, gran, intra | RSAD2, mean, intra | 0.58 | −0.06 | 79 | 76 | 82 | 83 | 75 |
| MX1, gran, intra | RSAD2, mono, intra | 0.61 | −0.02 | 80 | 77 | 84 | 85 | 76 |
| MX1, gran, intra | SDCBP, mean, intra | 0.45 | −0.09 | 74 | 79 | 67 | 79 | 67 |
| MX1, gran, intra | WBC | 0.48 | −0.06 | 74 | 74 | 74 | 77 | 71 |
| MX1, lymp, intra | MX1, mean, intra | 0.45 | 0 | 72 | 69 | 76 | 77 | 68 |
| MX1, lymp, intra | MX1, mono, intra | 0.51 | −0.03 | 75 | 73 | 78 | 79 | 71 |
| MX1, lymp, intra | Neu(%) | 0.64 | 0.08 | 82 | 84 | 81 | 84 | 81 |
| MX1, lymp, intra | NPM1, gran, intra | 0.37 | 0.02 | 71 | 78 | 59 | 75 | 62 |
| MX1, lymp, intra | NPM1, mean, intra | 0.35 | 0 | 69 | 75 | 59 | 74 | 61 |
| MX1, lymp, intra | NPM1, mono, intra | 0.37 | 0.02 | 71 | 78 | 59 | 75 | 62 |
| MX1, lymp, intra | OAS2, gran, intra | 0.48 | 0.12 | 74 | 70 | 78 | 79 | 69 |
| MX1, lymp, intra | OAS2, mean, intra | 0.44 | 0.09 | 72 | 68 | 76 | 77 | 67 |
| MX1, lymp, intra | OAS2, mono, intra | 0.48 | 0.12 | 74 | 70 | 78 | 79 | 69 |
| MX1, lymp, intra | PARP12, gran, intra | 0.46 | 0.11 | 75 | 81 | 64 | 79 | 68 |
| MX1, lymp, intra | PARP12, mean, intra | 0.39 | 0.04 | 71 | 79 | 59 | 75 | 64 |
| MX1, lymp, intra | PARP12, mono, intra | 0.46 | 0.11 | 75 | 81 | 64 | 79 | 68 |
| MX1, lymp, intra | PARP9, lymp, intra | 0.39 | 0.04 | 72 | 80 | 59 | 76 | 64 |
| MX1, lymp, intra | PDIA6, gran, intra | 0.33 | −0.02 | 69 | 77 | 55 | 75 | 59 |
| MX1, lymp, intra | PDIA6, lymp, intra | 0.28 | −0.07 | 67 | 74 | 55 | 74 | 55 |
| MX1, lymp, intra | PDIA6, mono, intra | 0.33 | −0.02 | 69 | 77 | 55 | 75 | 59 |
| MX1, lymp, intra | PTEN, gran, intra | 0.37 | 0.02 | 71 | 80 | 56 | 75 | 63 |
| MX1, lymp, intra | PTEN, lymp, intra | 0.38 | 0.03 | 71 | 78 | 59 | 76 | 62 |
| MX1, lymp, intra | PTEN, mean, intra | 0.31 | −0.04 | 67 | 74 | 56 | 73 | 58 |
| MX1, lymp, intra | PTEN, mono, intra | 0.37 | 0.02 | 71 | 80 | 56 | 75 | 63 |
| MX1, lymp, intra | RSAD2, gran, intra | 0.62 | −0.01 | 81 | 80 | 83 | 84 | 78 |
| MX1, lymp, intra | RSAD2, lymp, intra | 0.35 | 0 | 67 | 65 | 70 | 72 | 63 |
| MX1, lymp, intra | RSAD2, mean, intra | 0.58 | −0.06 | 79 | 76 | 82 | 83 | 75 |
| MX1, lymp, intra | RSAD2, mono, intra | 0.62 | −0.01 | 81 | 80 | 83 | 84 | 78 |
| MX1, lymp, intra | SDCBP, mean, intra | 0.33 | −0.02 | 68 | 74 | 59 | 74 | 59 |
| MX1, lymp, intra | WBC | 0.45 | 0.1 | 73 | 74 | 71 | 75 | 70 |
| MX1, mean, intra | MX1, mono, intra | 0.51 | −0.03 | 75 | 71 | 81 | 81 | 70 |
| MX1, mean, intra | Neu(%) | 0.59 | 0.03 | 80 | 83 | 76 | 80 | 80 |
| MX1, mean, intra | NPM1, gran, intra | 0.36 | −0.09 | 69 | 72 | 64 | 76 | 60 |
| MX1, mean, intra | NPM1, mean, intra | 0.36 | −0.09 | 69 | 72 | 64 | 76 | 60 |
| MX1, mean, intra | NPM1, mono, intra | 0.36 | −0.09 | 69 | 72 | 64 | 76 | 60 |
| MX1, mean, intra | OAS2, gran, intra | 0.47 | 0.02 | 73 | 68 | 79 | 79 | 68 |
| MX1, mean, intra | OAS2, mean, intra | 0.45 | 0 | 72 | 68 | 77 | 78 | 68 |
| MX1, mean, intra | OAS2, mono, intra | 0.47 | 0.02 | 73 | 68 | 79 | 79 | 68 |
| MX1, mean, intra | PARP12, gran, intra | 0.48 | 0.03 | 75 | 79 | 69 | 80 | 68 |
| MX1, mean, intra | PARP12, mean, intra | 0.53 | 0.08 | 77 | 79 | 74 | 83 | 69 |
| MX1, mean, intra | PARP12, mono, intra | 0.48 | 0.03 | 75 | 79 | 69 | 80 | 68 |

TABLE 4-continued

The classification accuracy of bacterial vs. viral infected patients computed over pairs of features. DETERMINANT measurements were measured over different cell types.

| Feature #1 | Feature #2 | MCC | dMCC | Total accuracy % | Sen % | Spe % | PPV % | NPV % |
|---|---|---|---|---|---|---|---|---|
| MX1, mean, intra | PARP9, lymp, intra | 0.42 | −0.03 | 72 | 77 | 64 | 77 | 64 |
| MX1, mean, intra | PDIA6, gran, intra | 0.41 | −0.04 | 73 | 79 | 61 | 78 | 63 |
| MX1, mean, intra | PDIA6, lymp, intra | 0.45 | 0 | 74 | 77 | 68 | 80 | 64 |
| MX1, mean, intra | PDIA6, mono, intra | 0.41 | −0.04 | 73 | 79 | 61 | 78 | 63 |
| MX1, mean, intra | PTEN, gran, intra | 0.48 | 0.03 | 75 | 81 | 67 | 79 | 68 |
| MX1, mean, intra | PTEN, lymp, intra | 0.44 | −0.01 | 73 | 77 | 67 | 79 | 65 |
| MX1, mean, intra | PTEN, mean, intra | 0.37 | −0.08 | 70 | 76 | 62 | 76 | 62 |
| MX1, mean, intra | PTEN, mono, intra | 0.48 | 0.03 | 75 | 81 | 67 | 79 | 68 |
| MX1, mean, intra | RSAD2, gran, intra | 0.64 | 0.01 | 82 | 79 | 85 | 86 | 78 |
| MX1, mean, intra | RSAD2, lymp, intra | 0.44 | −0.01 | 72 | 69 | 74 | 76 | 68 |
| MX1, mean, intra | RSAD2, mean, intra | 0.57 | −0.07 | 78 | 75 | 82 | 83 | 74 |
| MX1, mean, intra | RSAD2, mono, intra | 0.64 | 0.01 | 82 | 79 | 85 | 86 | 78 |
| MX1, mean, intra | SDCBP, mean, intra | 0.41 | −0.04 | 72 | 77 | 64 | 77 | 64 |
| MX1, mean, intra | WBC | 0.44 | −0.01 | 72 | 68 | 76 | 77 | 67 |
| MX1, mono, intra | Neu(%) | 0.59 | 0.03 | 79 | 81 | 77 | 81 | 77 |
| MX1, mono, intra | NPM1, gran, intra | 0.46 | −0.08 | 75 | 79 | 67 | 79 | 67 |
| MX1, mono, intra | NPM1, mean, intra | 0.48 | −0.06 | 75 | 79 | 69 | 80 | 68 |
| MX1, mono, intra | NPM1, mono, intra | 0.46 | −0.08 | 75 | 79 | 67 | 79 | 67 |
| MX1, mono, intra | OAS2, gran, intra | 0.51 | −0.03 | 75 | 72 | 79 | 80 | 70 |
| MX1, mono, intra | OAS2, mean, intra | 0.51 | −0.03 | 75 | 71 | 81 | 81 | 70 |
| MX1, mono, intra | OAS2, mono, intra | 0.51 | −0.03 | 75 | 72 | 79 | 80 | 70 |
| MX1, mono, intra | PARP12, gran, intra | 0.5 | −0.04 | 77 | 81 | 69 | 81 | 69 |
| MX1, mono, intra | PARP12, mean, intra | 0.54 | 0 | 78 | 82 | 72 | 82 | 72 |
| MX1, mono, intra | PARP12, mono, intra | 0.5 | −0.04 | 77 | 81 | 69 | 81 | 69 |
| MX1, mono, intra | PARP9, lymp, intra | 0.45 | −0.09 | 74 | 78 | 67 | 79 | 65 |
| MX1, mono, intra | PDIA6, gran, intra | 0.45 | −0.09 | 75 | 83 | 61 | 79 | 68 |
| MX1, mono, intra | PDIA6, lymp, intra | 0.5 | −0.04 | 76 | 79 | 71 | 82 | 67 |
| MX1, mono, intra | PDIA6, mono, intra | 0.45 | −0.09 | 75 | 83 | 61 | 79 | 68 |
| MX1, mono, intra | PTEN, gran, intra | 0.5 | −0.04 | 77 | 81 | 69 | 81 | 69 |
| MX1, mono, intra | PTEN, lymp, intra | 0.53 | −0.01 | 78 | 81 | 72 | 83 | 70 |
| MX1, mono, intra | PTEN, mean, intra | 0.46 | −0.08 | 74 | 77 | 69 | 80 | 66 |
| MX1, mono, intra | PTEN, mono, intra | 0.5 | −0.04 | 77 | 81 | 69 | 81 | 69 |
| MX1, mono, intra | RSAD2, gran, intra | 0.61 | −0.02 | 80 | 77 | 84 | 85 | 76 |
| MX1, mono, intra | RSAD2, lymp, intra | 0.51 | −0.03 | 75 | 72 | 79 | 80 | 70 |
| MX1, mono, intra | RSAD2, mean, intra | 0.58 | −0.06 | 79 | 76 | 82 | 83 | 75 |
| MX1, mono, intra | RSAD2, mono, intra | 0.61 | −0.02 | 80 | 77 | 84 | 85 | 76 |
| MX1, mono, intra | SDCBP, mean, intra | 0.45 | −0.09 | 74 | 79 | 67 | 79 | 67 |
| MX1, mono, intra | WBC | 0.48 | −0.06 | 74 | 74 | 74 | 77 | 71 |
| Neu(%) | OAS2, gran, intra | 0.59 | 0.03 | 80 | 79 | 81 | 83 | 76 |
| Neu(%) | OAS2, mean, intra | 0.57 | 0.01 | 79 | 78 | 79 | 81 | 75 |
| Neu(%) | OAS2, mono, intra | 0.59 | 0.03 | 80 | 79 | 81 | 83 | 76 |
| Neu(%) | PARP12, gran, intra | 0.65 | 0.09 | 83 | 86 | 79 | 87 | 78 |
| Neu(%) | PARP12, mean, intra | 0.62 | 0.06 | 82 | 87 | 74 | 84 | 78 |
| Neu(%) | PARP12, mono, intra | 0.65 | 0.09 | 83 | 86 | 79 | 87 | 78 |
| Neu(%) | PARP9, lymp, intra | 0.52 | −0.04 | 78 | 86 | 64 | 80 | 74 |
| Neu(%) | PDIA6, gran, intra | 0.64 | 0.08 | 83 | 89 | 74 | 85 | 79 |
| Neu(%) | PDIA6, lymp, intra | 0.51 | −0.05 | 77 | 83 | 68 | 81 | 70 |
| Neu(%) | PDIA6, mono, intra | 0.64 | 0.08 | 83 | 89 | 74 | 85 | 79 |
| Neu(%) | PTEN, gran, intra | 0.55 | −0.01 | 79 | 83 | 72 | 83 | 72 |
| Neu(%) | PTEN, lymp, intra | 0.58 | 0.02 | 81 | 86 | 72 | 83 | 76 |
| Neu(%) | PTEN, mean, intra | 0.56 | 0 | 79 | 84 | 72 | 83 | 74 |
| Neu(%) | PTEN, mono, intra | 0.55 | −0.01 | 79 | 83 | 72 | 83 | 72 |
| Neu(%) | RSAD2, gran, intra | 0.66 | 0.03 | 83 | 83 | 84 | 86 | 80 |
| Neu(%) | RSAD2, lymp, intra | 0.58 | 0.02 | 79 | 79 | 79 | 82 | 75 |
| Neu(%) | RSAD2, mean, intra | 0.66 | 0.02 | 83 | 84 | 82 | 85 | 81 |
| Neu(%) | RSAD2, mono, intra | 0.66 | 0.03 | 83 | 83 | 84 | 86 | 80 |
| Neu(%) | SDCBP, mean, intra | 0.51 | −0.05 | 77 | 82 | 69 | 81 | 71 |
| Neu(%) | WBC | 0.54 | −0.02 | 77 | 80 | 74 | 79 | 75 |
| NPM1, gran, intra | Neu(%) | 0.62 | 0.06 | 82 | 89 | 72 | 84 | 80 |
| NPM1, gran, intra | NPM1, mean, intra | 0.09 | −0.04 | 59 | 75 | 33 | 64 | 46 |
| NPM1, gran, intra | NPM1, mono, intra | 0.1 | 0 | 60 | 78 | 31 | 64 | 46 |
| NPM1, gran, intra | OAS2, gran, intra | 0.11 | −0.25 | 59 | 70 | 41 | 66 | 46 |
| NPM1, gran, intra | OAS2, mean, intra | 0.08 | −0.22 | 58 | 74 | 33 | 63 | 45 |
| NPM1, gran, intra | OAS2, mono, intra | 0.11 | −0.25 | 59 | 70 | 41 | 66 | 46 |
| NPM1, gran, intra | PARP12, gran, intra | 0.06 | −0.13 | 57 | 70 | 36 | 64 | 42 |
| NPM1, gran, intra | PARP12, mean, intra | 0.23 | −0.02 | 63 | 69 | 54 | 70 | 53 |
| NPM1, gran, intra | PARP12, mono, intra | 0.06 | −0.13 | 57 | 70 | 36 | 64 | 42 |
| NPM1, gran, intra | PARP9, lymp, intra | 0.17 | 0.03 | 63 | 79 | 36 | 67 | 52 |
| NPM1, gran, intra | PDIA6, gran, intra | 0.19 | 0.06 | 63 | 73 | 45 | 69 | 50 |
| NPM1, gran, intra | PDIA6, lymp, intra | 0.17 | 0.07 | 61 | 71 | 45 | 69 | 48 |
| NPM1, gran, intra | PDIA6, mono, intra | 0.19 | 0.06 | 63 | 73 | 45 | 69 | 50 |
| NPM1, gran, intra | PTEN, gran, intra | 0.21 | −0.01 | 64 | 76 | 44 | 69 | 53 |
| NPM1, gran, intra | PTEN, lymp, intra | 0.14 | 0.04 | 61 | 75 | 38 | 66 | 48 |
| NPM1, gran, intra | PTEN, mean, intra | 0.15 | −0.05 | 61 | 75 | 38 | 66 | 50 |

TABLE 4-continued

The classification accuracy of bacterial vs. viral infected patients computed over pairs of features. DETERMINANT measurements were measured over different cell types.

| Feature #1 | Feature #2 | MCC | dMCC | Total accuracy % | Sen % | Spe % | PPV % | NPV % |
|---|---|---|---|---|---|---|---|---|
| NPM1, gran, intra | PTEN, mono, intra | 0.21 | −0.01 | 64 | 76 | 44 | 69 | 53 |
| NPM1, gran, intra | RSAD2, gran, intra | 0.67 | 0.04 | 84 | 86 | 82 | 89 | 78 |
| NPM1, gran, intra | RSAD2, lymp, intra | 0.21 | −0.02 | 65 | 81 | 38 | 68 | 56 |
| NPM1, gran, intra | RSAD2, mean, intra | 0.61 | −0.03 | 81 | 82 | 79 | 86 | 74 |
| NPM1, gran, intra | RSAD2, mono, intra | 0.67 | 0.04 | 84 | 86 | 82 | 89 | 78 |
| NPM1, gran, intra | SDCBP, mean, intra | 0.11 | 0.01 | 60 | 77 | 33 | 64 | 48 |
| NPM1, gran, intra | WBC | 0.37 | 0.12 | 72 | 89 | 44 | 72 | 71 |
| NPM1, mean, intra | Neu(%) | 0.6 | 0.04 | 81 | 87 | 72 | 83 | 78 |
| NPM1, mean, intra | NPM1, mono, intra | 0.09 | −0.04 | 59 | 75 | 33 | 64 | 46 |
| NPM1, mean, intra | OAS2, gran, intra | 0.11 | −0.25 | 58 | 67 | 44 | 65 | 46 |
| NPM1, mean, intra | OAS2, mean, intra | 0.04 | −0.26 | 56 | 70 | 33 | 62 | 42 |
| NPM1, mean, intra | OAS2, mono, intra | 0.11 | −0.25 | 58 | 67 | 44 | 65 | 46 |
| NPM1, mean, intra | PARP12, gran, intra | 0.11 | −0.08 | 59 | 72 | 38 | 65 | 47 |
| NPM1, mean, intra | PARP12, mean, intra | 0.22 | −0.03 | 63 | 70 | 51 | 69 | 53 |
| NPM1, mean, intra | PARP12, mono, intra | 0.11 | −0.08 | 59 | 72 | 38 | 65 | 47 |
| NPM1, mean, intra | PARP9, lymp, intra | 0.12 | −0.02 | 60 | 75 | 36 | 65 | 48 |
| NPM1, mean, intra | PDIA6, gran, intra | 0.22 | 0.09 | 64 | 73 | 48 | 70 | 52 |
| NPM1, mean, intra | PDIA6, lymp, intra | 0.19 | 0.06 | 63 | 73 | 45 | 69 | 50 |
| NPM1, mean, intra | PDIA6, mono, intra | 0.22 | 0.09 | 64 | 73 | 48 | 70 | 52 |
| NPM1, mean, intra | PTEN, gran, intra | 0.16 | −0.06 | 61 | 72 | 44 | 67 | 50 |
| NPM1, mean, intra | PTEN, lymp, intra | 0.15 | 0.02 | 61 | 75 | 38 | 66 | 50 |
| NPM1, mean, intra | PTEN, mean, intra | 0.14 | −0.06 | 60 | 72 | 41 | 66 | 48 |
| NPM1, mean, intra | PTEN, mono, intra | 0.16 | −0.06 | 61 | 72 | 44 | 67 | 50 |
| NPM1, mean, intra | RSAD2, gran, intra | 0.67 | 0.04 | 84 | 85 | 82 | 88 | 78 |
| NPM1, mean, intra | RSAD2, lymp, intra | 0.19 | −0.04 | 63 | 79 | 38 | 67 | 54 |
| NPM1, mean, intra | RSAD2, mean, intra | 0.58 | −0.06 | 80 | 82 | 77 | 85 | 73 |
| NPM1, mean, intra | RSAD2, mono, intra | 0.67 | 0.04 | 84 | 85 | 82 | 88 | 78 |
| NPM1, mean, intra | SDCBP, mean, intra | 0.07 | −0.06 | 58 | 75 | 31 | 63 | 44 |
| NPM1, mean, intra | WBC | 0.39 | 0.14 | 72 | 89 | 46 | 72 | 72 |
| NPM1, mono, intra | Neu(%) | 0.62 | 0.06 | 82 | 89 | 72 | 84 | 80 |
| NPM1, mono, intra | OAS2, gran, intra | 0.11 | −0.25 | 59 | 70 | 41 | 66 | 46 |
| NPM1, mono, intra | OAS2, mean, intra | 0.08 | −0.22 | 58 | 74 | 33 | 63 | 45 |
| NPM1, mono, intra | OAS2, mono, intra | 0.11 | −0.25 | 59 | 70 | 41 | 66 | 46 |
| NPM1, mono, intra | PARP12, gran, intra | 0.06 | −0.13 | 57 | 70 | 36 | 64 | 42 |
| NPM1, mono, intra | PARP12, mean, intra | 0.23 | −0.02 | 63 | 69 | 54 | 70 | 53 |
| NPM1, mono, intra | PARP12, mono, intra | 0.06 | −0.13 | 57 | 70 | 36 | 64 | 42 |
| NPM1, mono, intra | PARP9, lymp, intra | 0.17 | 0.03 | 63 | 79 | 36 | 67 | 52 |
| NPM1, mono, intra | PDIA6, gran, intra | 0.19 | 0.06 | 63 | 73 | 45 | 69 | 50 |
| NPM1, mono, intra | PDIA6, lymp, intra | 0.17 | 0.07 | 61 | 71 | 45 | 69 | 48 |
| NPM1, mono, intra | PDIA6, mono, intra | 0.19 | 0.06 | 63 | 73 | 45 | 69 | 50 |
| NPM1, mono, intra | PTEN, gran, intra | 0.21 | −0.01 | 64 | 76 | 44 | 69 | 53 |
| NPM1, mono, intra | PTEN, lymp, intra | 0.14 | 0.04 | 61 | 75 | 38 | 66 | 48 |
| NPM1, mono, intra | PTEN, mean, intra | 0.15 | −0.05 | 61 | 75 | 38 | 66 | 50 |
| NPM1, mono, intra | PTEN, mono, intra | 0.21 | −0.01 | 64 | 76 | 44 | 69 | 53 |
| NPM1, mono, intra | RSAD2, gran, intra | 0.67 | 0.04 | 84 | 86 | 82 | 89 | 78 |
| NPM1, mono, intra | RSAD2, lymp, intra | 0.21 | −0.02 | 65 | 81 | 38 | 68 | 56 |
| NPM1, mono, intra | RSAD2, mean, intra | 0.61 | −0.03 | 81 | 82 | 79 | 86 | 74 |
| NPM1, mono, intra | RSAD2, mono, intra | 0.67 | 0.04 | 84 | 86 | 82 | 89 | 78 |
| NPM1, mono, intra | SDCBP, mean, intra | 0.11 | 0.01 | 60 | 77 | 33 | 64 | 48 |
| NPM1, mono, intra | WBC | 0.37 | 0.12 | 72 | 89 | 44 | 72 | 71 |
| OAS2, gran, intra | OAS2, mean, intra | 0.38 | 0.02 | 68 | 60 | 77 | 76 | 62 |
| OAS2, gran, intra | OAS2, mono, intra | 0.36 | 0 | 67 | 61 | 75 | 74 | 62 |
| OAS2, gran, intra | PARP12, gran, intra | 0.18 | −0.18 | 62 | 72 | 46 | 69 | 50 |
| OAS2, gran, intra | PARP12, mean, intra | 0.28 | −0.08 | 66 | 74 | 54 | 72 | 57 |
| OAS2, gran, intra | PARP12, mono, intra | 0.18 | −0.18 | 62 | 72 | 46 | 69 | 50 |
| OAS2, gran, intra | PARP9, lymp, intra | 0.22 | −0.14 | 64 | 75 | 46 | 70 | 53 |
| OAS2, gran, intra | PDIA6, gran, intra | 0.06 | −0.3 | 58 | 74 | 32 | 65 | 42 |
| OAS2, gran, intra | PDIA6, lymp, intra | 0.18 | −0.18 | 63 | 75 | 42 | 69 | 50 |
| OAS2, gran, intra | PDIA6, mono, intra | 0.06 | −0.3 | 58 | 74 | 32 | 65 | 42 |
| OAS2, gran, intra | PTEN, gran, intra | 0.14 | −0.22 | 60 | 70 | 44 | 67 | 47 |
| OAS2, gran, intra | PTEN, lymp, intra | 0.25 | −0.11 | 64 | 69 | 56 | 72 | 52 |
| OAS2, gran, intra | PTEN, mean, intra | 0.11 | −0.25 | 58 | 68 | 44 | 66 | 46 |
| OAS2, gran, intra | PTEN, mono, intra | 0.14 | −0.22 | 60 | 70 | 44 | 67 | 47 |
| OAS2, gran, intra | RSAD2, gran, intra | 0.64 | 0.01 | 82 | 80 | 84 | 86 | 78 |
| OAS2, gran, intra | RSAD2, lymp, intra | 0.43 | 0.07 | 71 | 65 | 78 | 78 | 65 |
| OAS2, gran, intra | RSAD2, mean, intra | 0.6 | −0.04 | 80 | 78 | 82 | 84 | 76 |
| OAS2, gran, intra | RSAD2, mono, intra | 0.64 | 0.01 | 82 | 80 | 84 | 86 | 78 |
| OAS2, gran, intra | SDCBP, mean, intra | 0.21 | −0.15 | 63 | 74 | 46 | 68 | 53 |
| OAS2, gran, intra | WBC | 0.43 | 0.07 | 72 | 71 | 73 | 76 | 67 |
| OAS2, mean, intra | OAS2, mono, intra | 0.38 | 0.02 | 68 | 60 | 77 | 76 | 62 |
| OAS2, mean, intra | PARP12, gran, intra | 0.17 | −0.13 | 61 | 73 | 44 | 67 | 50 |
| OAS2, mean, intra | PARP12, mean, intra | 0.24 | −0.06 | 64 | 73 | 51 | 70 | 54 |
| OAS2, mean, intra | PARP12, mono, intra | 0.17 | −0.13 | 61 | 73 | 44 | 67 | 50 |
| OAS2, mean, intra | PARP9, lymp, intra | 0.12 | −0.18 | 59 | 73 | 38 | 65 | 47 |

TABLE 4-continued

The classification accuracy of bacterial vs. viral infected patients computed over pairs of features. DETERMINANT measurements were measured over different cell types.

| Feature #1 | Feature #2 | MCC | dMCC | Total accuracy % | Sen % | Spe % | PPV % | NPV % |
|---|---|---|---|---|---|---|---|---|
| OAS2, mean, intra | PDIA6, gran, intra | 0.04 | −0.26 | 58 | 77 | 26 | 64 | 40 |
| OAS2, mean, intra | PDIA6, lymp, intra | 0.05 | −0.25 | 58 | 75 | 29 | 65 | 41 |
| OAS2, mean, intra | PDIA6, mono, intra | 0.04 | −0.26 | 58 | 77 | 26 | 64 | 40 |
| OAS2, mean, intra | PTEN, gran, intra | 0.17 | −0.13 | 61 | 71 | 46 | 68 | 50 |
| OAS2, mean, intra | PTEN, lymp, intra | 0.08 | −0.22 | 57 | 69 | 38 | 64 | 44 |
| OAS2, mean, intra | PTEN, mean, intra | 0.14 | −0.16 | 60 | 73 | 41 | 66 | 48 |
| OAS2, mean, intra | PTEN, mono, intra | 0.17 | −0.13 | 61 | 71 | 46 | 68 | 50 |
| OAS2, mean, intra | RSAD2, gran, intra | 0.64 | 0.01 | 82 | 81 | 84 | 86 | 79 |
| OAS2, mean, intra | RSAD2, lymp, intra | 0.29 | −0.01 | 64 | 62 | 68 | 69 | 60 |
| OAS2, mean, intra | RSAD2, mean, intra | 0.66 | 0.02 | 83 | 82 | 84 | 86 | 80 |
| OAS2, mean, intra | RSAD2, mono, intra | 0.64 | 0.01 | 82 | 81 | 84 | 86 | 79 |
| OAS2, mean, intra | SDCBP, mean, intra | 0.03 | −0.27 | 56 | 72 | 31 | 62 | 41 |
| OAS2, mean, intra | WBC | 0.34 | 0.04 | 67 | 75 | 58 | 68 | 67 |
| OAS2, mono, intra | PARP12, gran, intra | 0.18 | −0.18 | 62 | 72 | 46 | 69 | 50 |
| OAS2, mono, intra | PARP12, mean, intra | 0.28 | −0.08 | 66 | 74 | 54 | 72 | 57 |
| OAS2, mono, intra | PARP12, mono, intra | 0.18 | −0.18 | 62 | 72 | 46 | 69 | 50 |
| OAS2, mono, intra | PARP9, lymp, intra | 0.22 | −0.14 | 64 | 75 | 46 | 70 | 53 |
| OAS2, mono, intra | PDIA6, gran, intra | 0.06 | −0.3 | 58 | 74 | 32 | 65 | 42 |
| OAS2, mono, intra | PDIA6, lymp, intra | 0.18 | −0.18 | 63 | 75 | 42 | 69 | 50 |
| OAS2, mono, intra | PDIA6, mono, intra | 0.06 | −0.3 | 58 | 74 | 32 | 65 | 42 |
| OAS2, mono, intra | PTEN, gran, intra | 0.14 | −0.22 | 60 | 70 | 44 | 67 | 47 |
| OAS2, mono, intra | PTEN, lymp, intra | 0.25 | −0.11 | 64 | 69 | 56 | 72 | 52 |
| OAS2, mono, intra | PTEN, mean, intra | 0.11 | −0.25 | 58 | 68 | 44 | 66 | 46 |
| OAS2, mono, intra | PTEN, mono, intra | 0.14 | −0.22 | 60 | 70 | 44 | 67 | 47 |
| OAS2, mono, intra | RSAD2, gran, intra | 0.64 | 0.01 | 82 | 80 | 84 | 86 | 78 |
| OAS2, mono, intra | RSAD2, lymp, intra | 0.43 | 0.07 | 71 | 65 | 78 | 78 | 65 |
| OAS2, mono, intra | RSAD2, mean, intra | 0.6 | −0.04 | 80 | 78 | 82 | 84 | 76 |
| OAS2, mono, intra | RSAD2, mono, intra | 0.64 | 0.01 | 82 | 80 | 84 | 86 | 78 |
| OAS2, mono, intra | SDCBP, mean, intra | 0.21 | −0.15 | 63 | 74 | 46 | 68 | 53 |
| OAS2, mono, intra | WBC | 0.43 | 0.07 | 72 | 71 | 73 | 76 | 67 |
| PARP12, gran, intra | PARP12, mean, intra | 0.25 | 0 | 65 | 76 | 49 | 70 | 56 |
| PARP12, gran, intra | PARP12, mono, intra | 0.24 | 0.05 | 65 | 75 | 49 | 71 | 54 |
| PARP12, gran, intra | PARP9, lymp, intra | 0.25 | 0.06 | 66 | 78 | 46 | 70 | 56 |
| PARP12, gran, intra | PDIA6, gran, intra | 0.19 | 0 | 64 | 79 | 39 | 69 | 52 |
| PARP12, gran, intra | PDIA6, lymp, intra | 0.24 | 0.05 | 65 | 75 | 48 | 71 | 54 |
| PARP12, gran, intra | PDIA6, mono, intra | 0.19 | 0 | 64 | 79 | 39 | 69 | 52 |
| PARP12, gran, intra | PTEN, gran, intra | 0.19 | −0.03 | 63 | 75 | 44 | 69 | 52 |
| PARP12, gran, intra | PTEN, lymp, intra | 0.27 | 0.08 | 66 | 73 | 54 | 72 | 55 |
| PARP12, gran, intra | PTEN, mean, intra | 0.13 | −0.07 | 60 | 74 | 38 | 66 | 48 |
| PARP12, gran, intra | PTEN, mono, intra | 0.19 | −0.03 | 63 | 75 | 44 | 69 | 52 |
| PARP12, gran, intra | RSAD2, gran, intra | 0.66 | 0.03 | 83 | 84 | 82 | 89 | 76 |
| PARP12, gran, intra | RSAD2, lymp, intra | 0.26 | 0.03 | 66 | 77 | 49 | 71 | 56 |
| PARP12, gran, intra | RSAD2, mean, intra | 0.61 | −0.03 | 81 | 84 | 77 | 85 | 75 |
| PARP12, gran, intra | RSAD2, mono, intra | 0.66 | 0.03 | 83 | 84 | 82 | 89 | 76 |
| PARP12, gran, intra | SDCBP, mean, intra | 0.12 | −0.07 | 59 | 70 | 41 | 65 | 47 |
| PARP12, gran, intra | WBC | 0.42 | 0.17 | 74 | 91 | 46 | 73 | 75 |
| PARP12, mean, intra | PARP12, mono, intra | 0.25 | 0 | 65 | 76 | 49 | 70 | 56 |
| PARP12, mean, intra | PARP9, lymp, intra | 0.25 | 0 | 65 | 77 | 46 | 70 | 56 |
| PARP12, mean, intra | PDIA6, gran, intra | 0.25 | 0 | 65 | 74 | 52 | 72 | 53 |
| PARP12, mean, intra | PDIA6, lymp, intra | 0.27 | 0.02 | 67 | 75 | 52 | 73 | 55 |
| PARP12, mean, intra | PDIA6, mono, intra | 0.25 | 0 | 65 | 74 | 52 | 72 | 53 |
| PARP12, mean, intra | PTEN, gran, intra | 0.24 | −0.01 | 64 | 73 | 51 | 70 | 54 |
| PARP12, mean, intra | PTEN, lymp, intra | 0.26 | 0.01 | 65 | 74 | 51 | 71 | 56 |
| PARP12, mean, intra | PTEN, mean, intra | 0.25 | 0 | 65 | 76 | 49 | 70 | 56 |
| PARP12, mean, intra | PTEN, mono, intra | 0.24 | −0.01 | 64 | 73 | 51 | 70 | 54 |
| PARP12, mean, intra | RSAD2, gran, intra | 0.65 | 0.02 | 83 | 84 | 82 | 88 | 76 |
| PARP12, mean, intra | RSAD2, lymp, intra | 0.34 | 0.09 | 69 | 77 | 56 | 74 | 61 |
| PARP12, mean, intra | RSAD2, mean, intra | 0.61 | −0.03 | 81 | 84 | 77 | 85 | 75 |
| PARP12, mean, intra | RSAD2, mono, intra | 0.65 | 0.02 | 83 | 84 | 82 | 88 | 76 |
| PARP12, mean, intra | SDCBP, mean, intra | 0.21 | −0.04 | 63 | 72 | 49 | 69 | 53 |
| PARP12, mean, intra | WBC | 0.35 | 0.1 | 70 | 84 | 49 | 72 | 66 |
| PARP12, mono, intra | PARP9, lymp, intra | 0.25 | 0.06 | 66 | 78 | 46 | 70 | 56 |
| PARP12, mono, intra | PDIA6, gran, intra | 0.19 | 0 | 64 | 79 | 39 | 69 | 52 |
| PARP12, mono, intra | PDIA6, lymp, intra | 0.24 | 0.05 | 65 | 75 | 48 | 71 | 54 |
| PARP12, mono, intra | PDIA6, mono, intra | 0.19 | 0 | 64 | 79 | 39 | 69 | 52 |
| PARP12, mono, intra | PTEN, gran, intra | 0.19 | −0.03 | 63 | 75 | 44 | 69 | 52 |
| PARP12, mono, intra | PTEN, lymp, intra | 0.27 | 0.08 | 66 | 73 | 54 | 72 | 55 |
| PARP12, mono, intra | PTEN, mean, intra | 0.13 | −0.07 | 60 | 74 | 38 | 66 | 48 |
| PARP12, mono, intra | PTEN, mono, intra | 0.19 | −0.03 | 63 | 75 | 44 | 69 | 52 |
| PARP12, mono, intra | RSAD2, gran, intra | 0.66 | 0.03 | 83 | 84 | 82 | 89 | 76 |
| PARP12, mono, intra | RSAD2, lymp, intra | 0.26 | 0.03 | 66 | 77 | 49 | 71 | 56 |
| PARP12, mono, intra | RSAD2, mean, intra | 0.61 | −0.03 | 81 | 84 | 77 | 85 | 75 |
| PARP12, mono, intra | RSAD2, mono, intra | 0.66 | 0.03 | 83 | 84 | 82 | 89 | 76 |
| PARP12, mono, intra | SDCBP, mean, intra | 0.12 | −0.07 | 59 | 70 | 41 | 65 | 47 |

TABLE 4-continued

The classification accuracy of bacterial vs. viral infected patients computed over pairs of features. DETERMINANT measurements were measured over different cell types.

| Feature #1 | Feature #2 | MCC | dMCC | Total accuracy % | Sen % | Spe % | PPV % | NPV % |
|---|---|---|---|---|---|---|---|---|
| PARP12, mono, intra | WBC | 0.42 | 0.17 | 74 | 91 | 46 | 73 | 75 |
| PARP9, lymp, intra | PDIA6, gran, intra | 0.18 | 0.04 | 63 | 75 | 42 | 69 | 50 |
| PARP9, lymp, intra | PDIA6, lymp, intra | 0.17 | 0.03 | 63 | 77 | 39 | 68 | 50 |
| PARP9, lymp, intra | PDIA6, mono, intra | 0.18 | 0.04 | 63 | 75 | 42 | 69 | 50 |
| PARP9, lymp, intra | PTEN, gran, intra | 0.16 | −0.06 | 61 | 72 | 44 | 68 | 49 |
| PARP9, lymp, intra | PTEN, lymp, intra | 0.16 | 0.02 | 62 | 77 | 38 | 67 | 50 |
| PARP9, lymp, intra | PTEN, mean, intra | 0.18 | −0.02 | 62 | 74 | 44 | 68 | 52 |
| PARP9, lymp, intra | PTEN, mono, intra | 0.16 | −0.06 | 61 | 72 | 44 | 68 | 49 |
| PARP9, lymp, intra | RSAD2, gran, intra | 0.65 | 0.02 | 83 | 86 | 79 | 87 | 78 |
| PARP9, lymp, intra | RSAD2, lymp, intra | 0.19 | −0.04 | 64 | 81 | 36 | 68 | 54 |
| PARP9, lymp, intra | RSAD2, mean, intra | 0.59 | −0.05 | 80 | 82 | 77 | 85 | 73 |
| PARP9, lymp, intra | RSAD2, mono, intra | 0.65 | 0.02 | 83 | 86 | 79 | 87 | 78 |
| PARP9, lymp, intra | SDCBP, mean, intra | 0.12 | −0.02 | 60 | 75 | 36 | 65 | 48 |
| PARP9, lymp, intra | WBC | 0.3 | 0.05 | 69 | 89 | 36 | 70 | 67 |
| PDIA6, gran, intra | PDIA6, lymp, intra | 0.14 | 0.01 | 62 | 77 | 35 | 67 | 48 |
| PDIA6, gran, intra | PDIA6, mono, intra | 0.13 | 0 | 62 | 79 | 32 | 67 | 48 |
| PDIA6, gran, intra | PTEN, gran, intra | 0.18 | −0.04 | 63 | 75 | 42 | 69 | 50 |
| PDIA6, gran, intra | PTEN, lymp, intra | 0.13 | 0 | 61 | 74 | 39 | 67 | 46 |
| PDIA6, gran, intra | PTEN, mean, intra | 0.17 | −0.03 | 63 | 77 | 39 | 68 | 50 |
| PDIA6, gran, intra | PTEN, mono, intra | 0.18 | −0.04 | 63 | 75 | 42 | 69 | 50 |
| PDIA6, gran, intra | RSAD2, gran, intra | 0.62 | −0.01 | 82 | 85 | 77 | 87 | 75 |
| PDIA6, gran, intra | RSAD2, lymp, intra | 0.31 | 0.08 | 69 | 81 | 48 | 73 | 60 |
| PDIA6, gran, intra | RSAD2, mean, intra | 0.57 | −0.07 | 80 | 83 | 74 | 85 | 72 |
| PDIA6, gran, intra | RSAD2, mono, intra | 0.62 | −0.01 | 82 | 85 | 77 | 87 | 75 |
| PDIA6, gran, intra | SDCBP, mean, intra | 0.21 | 0.08 | 64 | 75 | 45 | 70 | 52 |
| PDIA6, gran, intra | WBC | 0.29 | 0.04 | 69 | 87 | 39 | 71 | 63 |
| PDIA6, lymp, intra | PDIA6, mono, intra | 0.14 | 0.01 | 62 | 77 | 35 | 67 | 48 |
| PDIA6, lymp, intra | PTEN, gran, intra | 0.14 | −0.08 | 61 | 72 | 42 | 68 | 46 |
| PDIA6, lymp, intra | PTEN, lymp, intra | 0.18 | 0.14 | 63 | 75 | 42 | 69 | 50 |
| PDIA6, lymp, intra | PTEN, mean, intra | 0.07 | −0.13 | 57 | 68 | 39 | 65 | 41 |
| PDIA6, lymp, intra | PTEN, mono, intra | 0.14 | −0.08 | 61 | 72 | 42 | 68 | 46 |
| PDIA6, lymp, intra | RSAD2, gran, intra | 0.64 | 0.01 | 83 | 87 | 77 | 87 | 77 |
| PDIA6, lymp, intra | RSAD2, lymp, intra | 0.19 | −0.04 | 63 | 74 | 45 | 70 | 50 |
| PDIA6, lymp, intra | RSAD2, mean, intra | 0.62 | −0.02 | 82 | 85 | 77 | 87 | 75 |
| PDIA6, lymp, intra | RSAD2, mono, intra | 0.64 | 0.01 | 83 | 87 | 77 | 87 | 77 |
| PDIA6, lymp, intra | SDCBP, mean, intra | 0.23 | 0.19 | 65 | 77 | 45 | 70 | 54 |
| PDIA6, lymp, intra | WBC | 0.27 | 0.02 | 68 | 85 | 39 | 70 | 60 |
| PDIA6, mono, intra | PTEN, gran, intra | 0.18 | −0.04 | 63 | 75 | 42 | 69 | 50 |
| PDIA6, mono, intra | PTEN, lymp, intra | 0.13 | 0 | 61 | 74 | 39 | 67 | 46 |
| PDIA6, mono, intra | PTEN, mean, intra | 0.17 | −0.03 | 63 | 77 | 39 | 68 | 50 |
| PDIA6, mono, intra | PTEN, mono, intra | 0.18 | −0.04 | 63 | 75 | 42 | 69 | 50 |
| PDIA6, mono, intra | RSAD2, gran, intra | 0.62 | −0.01 | 82 | 85 | 77 | 87 | 75 |
| PDIA6, mono, intra | RSAD2, lymp, intra | 0.31 | 0.08 | 69 | 81 | 48 | 73 | 60 |
| PDIA6, mono, intra | RSAD2, mean, intra | 0.57 | −0.07 | 80 | 83 | 74 | 85 | 72 |
| PDIA6, mono, intra | RSAD2, mono, intra | 0.62 | −0.01 | 82 | 85 | 77 | 87 | 75 |
| PDIA6, mono, intra | SDCBP, mean, intra | 0.21 | 0.08 | 64 | 75 | 45 | 70 | 52 |
| PDIA6, mono, intra | WBC | 0.29 | 0.04 | 69 | 87 | 39 | 71 | 63 |
| PTEN, gran, intra | PTEN, lymp, intra | 0.16 | −0.06 | 61 | 72 | 44 | 68 | 49 |
| PTEN, gran, intra | PTEN, mean, intra | 0.23 | 0.01 | 64 | 74 | 49 | 70 | 54 |
| PTEN, gran, intra | PTEN, mono, intra | 0.23 | 0.01 | 64 | 73 | 49 | 70 | 53 |
| PTEN, gran, intra | RSAD2, gran, intra | 0.66 | 0.03 | 83 | 84 | 82 | 89 | 76 |
| PTEN, gran, intra | RSAD2, lymp, intra | 0.22 | −0.01 | 64 | 75 | 46 | 70 | 53 |
| PTEN, gran, intra | RSAD2, mean, intra | 0.63 | −0.01 | 82 | 84 | 79 | 87 | 76 |
| PTEN, gran, intra | RSAD2, mono, intra | 0.66 | 0.03 | 83 | 84 | 82 | 89 | 76 |
| PTEN, gran, intra | SDCBP, mean, intra | 0.27 | 0.05 | 66 | 77 | 49 | 70 | 58 |
| PTEN, gran, intra | WBC | 0.33 | 0.08 | 70 | 86 | 44 | 71 | 65 |
| PTEN, lymp, intra | PTEN, mean, intra | 0.08 | −0.12 | 57 | 69 | 38 | 64 | 44 |
| PTEN, lymp, intra | PTEN, mono, intra | 0.16 | −0.06 | 61 | 72 | 44 | 68 | 49 |
| PTEN, lymp, intra | RSAD2, gran, intra | 0.67 | 0.04 | 84 | 88 | 79 | 88 | 79 |
| PTEN, lymp, intra | RSAD2, lymp, intra | 0.18 | −0.05 | 63 | 78 | 38 | 68 | 52 |
| PTEN, lymp, intra | RSAD2, mean, intra | 0.59 | −0.05 | 80 | 82 | 77 | 85 | 73 |
| PTEN, lymp, intra | RSAD2, mono, intra | 0.67 | 0.04 | 84 | 88 | 79 | 88 | 79 |
| PTEN, lymp, intra | SDCBP, mean, intra | 0.22 | 0.18 | 64 | 75 | 46 | 69 | 55 |
| PTEN, lymp, intra | WBC | 0.28 | 0.03 | 68 | 84 | 41 | 70 | 62 |
| PTEN, mean, intra | PTEN, mono, intra | 0.23 | 0.01 | 64 | 74 | 49 | 70 | 54 |
| PTEN, mean, intra | RSAD2, gran, intra | 0.67 | 0.04 | 84 | 85 | 82 | 88 | 78 |
| PTEN, mean, intra | RSAD2, lymp, intra | 0.23 | 0 | 64 | 76 | 46 | 69 | 55 |
| PTEN, mean, intra | RSAD2, mean, intra | 0.61 | −0.03 | 81 | 82 | 79 | 86 | 74 |
| PTEN, mean, intra | RSAD2, mono, intra | 0.67 | 0.04 | 84 | 85 | 82 | 88 | 78 |
| PTEN, mean, intra | SDCBP, mean, intra | 0.24 | 0.04 | 65 | 77 | 46 | 69 | 56 |
| PTEN, mean, intra | WBC | 0.3 | 0.05 | 68 | 85 | 41 | 70 | 64 |
| PTEN, mono, intra | RSAD2, gran, intra | 0.66 | 0.03 | 83 | 84 | 82 | 89 | 76 |
| PTEN, mono, intra | RSAD2, lymp, intra | 0.22 | −0.01 | 64 | 75 | 46 | 70 | 53 |
| PTEN, mono, intra | RSAD2, mean, intra | 0.63 | −0.01 | 82 | 84 | 79 | 87 | 76 |

TABLE 4-continued

The classification accuracy of bacterial vs. viral infected patients computed over pairs of features. DETERMINANT measurements were measured over different cell types.

| Feature #1 | Feature #2 | MCC | dMCC | Total accuracy % | Sen % | Spe % | PPV % | NPV % |
|---|---|---|---|---|---|---|---|---|
| PTEN, mono, intra | RSAD2, mono, intra | 0.66 | 0.03 | 83 | 84 | 82 | 89 | 76 |
| PTEN, mono, intra | SDCBP, mean, intra | 0.27 | 0.05 | 66 | 77 | 49 | 70 | 58 |
| PTEN, mono, intra | WBC | 0.33 | 0.08 | 70 | 86 | 44 | 71 | 65 |
| RSAD2, gran, intra | RSAD2, lymp, intra | 0.61 | −0.02 | 80 | 77 | 84 | 85 | 76 |
| RSAD2, gran, intra | RSAD2, mean, intra | 0.63 | −0.01 | 81 | 79 | 84 | 85 | 78 |
| RSAD2, gran, intra | RSAD2, mono, intra | 0.63 | 0 | 81 | 79 | 84 | 86 | 77 |
| RSAD2, gran, intra | SDCBP, mean, intra | 0.65 | 0.02 | 83 | 84 | 82 | 88 | 76 |
| RSAD2, gran, intra | WBC | 0.63 | 0 | 81 | 77 | 85 | 87 | 76 |
| RSAD2, lymp, intra | RSAD2, mean, intra | 0.64 | 0 | 82 | 81 | 84 | 86 | 79 |
| RSAD2, lymp, intra | RSAD2, mono, intra | 0.61 | −0.02 | 80 | 77 | 84 | 85 | 76 |
| RSAD2, lymp, intra | SDCBP, mean, intra | 0.19 | −0.04 | 63 | 77 | 41 | 67 | 53 |
| RSAD2, lymp, intra | WBC | 0.29 | 0.04 | 65 | 72 | 56 | 67 | 63 |
| RSAD2, mean, intra | RSAD2, mono, intra | 0.63 | −0.01 | 81 | 79 | 84 | 85 | 78 |
| RSAD2, mean, intra | SDCBP, mean, intra | 0.61 | −0.03 | 81 | 82 | 79 | 86 | 74 |
| RSAD2, mean, intra | WBC | 0.63 | −0.01 | 81 | 78 | 85 | 86 | 77 |
| RSAD2, mono, intra | SDCBP, mean, intra | 0.65 | 0.02 | 83 | 84 | 82 | 88 | 76 |
| RSAD2, mono, intra | WBC | 0.63 | 0 | 81 | 77 | 85 | 87 | 76 |
| SDCBP, mean, intra | WBC | 0.27 | 0.02 | 67 | 84 | 41 | 69 | 62 |

\* Positive and negative correspond to bacterial and viral infected patients respectively

TABLE 5

The classification accuracy of viral vs. mixed infected patients computed over pairs of DETERMINANTS.

| DETERMINANT #1 | DETERMINANT #2 | MCC | Total accuracy % | Sen % | Spe % |
|---|---|---|---|---|---|
| ANC | UBE2N, mean, intra | 0.78 | 89 | 84 | 93 |
| CES1, mean, intra | CRP | 0.75 | 88 | 84 | 90 |
| ANC | SOCS3, mean, intra | 0.73 | 86 | 72 | 97 |
| CRP | MX1, mean, intra | 0.73 | 87 | 84 | 89 |
| CRP | LIPT1, mean, intra | 0.7 | 86 | 81 | 89 |
| CRP | PARP12, mean, intra | 0.7 | 86 | 81 | 89 |
| IFIT3, mean, intra | Lym(%) | 0.7 | 85 | 77 | 91 |
| IFIT3, mean, intra | Neu(%) | 0.7 | 85 | 79 | 90 |
| ANC | PARP12, mean, intra | 0.69 | 85 | 73 | 94 |
| ATP6V0B, mean, intra | CRP | 0.69 | 85 | 81 | 88 |
| CRP | Lym(%) | 0.68 | 84 | 83 | 85 |
| CRP | PARP9, mean, intra | 0.68 | 84 | 86 | 83 |
| MX1, mean, intra | SOCS3, mean, intra | 0.68 | 84 | 72 | 93 |
| ANC | CRP | 0.67 | 84 | 87 | 81 |
| ANC | LOC26010, mean, intra | 0.67 | 84 | 76 | 90 |
| HERC5, mean, intra | Neu(%) | 0.67 | 84 | 80 | 87 |
| MX1, mean, intra | Neu(%) | 0.67 | 84 | 85 | 83 |
| ARHGDIB, mean, intra | CRP | 0.66 | 83 | 84 | 83 |
| ARPC2, mean, intra | CRP | 0.66 | 83 | 78 | 88 |
| CRP | RSAD2, mean, intra | 0.66 | 83 | 79 | 86 |
| HERC5, mean, intra | Lym(%) | 0.66 | 83 | 79 | 87 |
| Neu(%) | RSAD2, mean, intra | 0.66 | 83 | 84 | 83 |
| CRP | Neu(%) | 0.65 | 82 | 87 | 79 |
| ANC | HERC5, mean, intra | 0.64 | 82 | 80 | 84 |
| ARPC2, mean, intra | SOCS3, mean, intra | 0.64 | 82 | 67 | 93 |
| CES1, mean, intra | Neu(%) | 0.64 | 82 | 79 | 85 |
| CORO1A, mean, intra | MX1, mean, intra | 0.64 | 82 | 76 | 88 |
| ANC | ARPC2, mean, intra | 0.63 | 82 | 79 | 84 |
| ANC | MX1, mean, intra | 0.63 | 82 | 82 | 81 |
| ANC | RSAD2, mean, intra | 0.63 | 82 | 81 | 83 |
| ARPC2, mean, intra | UBE2N, mean, intra | 0.63 | 81 | 66 | 93 |
| CRP | LOC26010, mean, intra | 0.63 | 82 | 83 | 81 |
| CRP | OAS2, mean, intra | 0.63 | 81 | 88 | 76 |
| CRP | SOCS3, mean, intra | 0.63 | 82 | 81 | 83 |
| Lym(%) | MX1, mean, intra | 0.63 | 82 | 82 | 81 |
| ANC | LIPT1, mean, intra | 0.62 | 81 | 81 | 81 |
| ANC | Neu(%) | 0.62 | 81 | 73 | 88 |
| CORO1A, mean, intra | SOCS3, mean, intra | 0.62 | 81 | 66 | 93 |
| Lym(%) | RSAD2, mean, intra | 0.62 | 81 | 81 | 81 |
| PARP12, mean, intra | SOCS3, mean, intra | 0.62 | 81 | 66 | 93 |
| ANC | IFIT3, mean, intra | 0.61 | 81 | 71 | 89 |
| ATP6V0B, mean, intra | SOCS3, mean, intra | 0.61 | 80 | 64 | 93 |
| CORO1A, mean, intra | Neu(%) | 0.61 | 81 | 73 | 88 |
| CRP | HERC5, mean, intra | 0.61 | 80 | 82 | 79 |

TABLE 5-continued

The classification accuracy of viral vs. mixed infected patients computed over pairs of DETERMINANTS.

| DETERMINANT #1 | DETERMINANT #2 | MCC | Total accuracy % | Sen % | Spe % |
|---|---|---|---|---|---|
| CRP | UBE2N, mean, intra | 0.61 | 80 | 81 | 80 |
| HERC5, mean, intra | PARP12, mean, intra | 0.61 | 80 | 66 | 92 |
| IFIT3, mean, intra | SOCS3, mean, intra | 0.61 | 80 | 64 | 93 |
| ANC | CES1, mean, intra | 0.6 | 80 | 73 | 86 |
| ARHGDIB, mean, intra | Lym(%) | 0.6 | 80 | 79 | 81 |
| ARPC2, mean, intra | Neu(%) | 0.6 | 80 | 79 | 81 |
| ARPC2, mean, intra | PARP12, mean, intra | 0.6 | 80 | 65 | 93 |
| ATP6V0B, mean, intra | UBE2N, mean, intra | 0.6 | 80 | 63 | 93 |
| CES1, mean, intra | Lym(%) | 0.6 | 80 | 79 | 81 |
| CRP | IFIT3, mean, intra | 0.6 | 80 | 79 | 81 |
| CRP | PTEN, mean, intra | 0.6 | 80 | 86 | 75 |
| MX1, mean, intra | PARP12, mean, intra | 0.6 | 80 | 71 | 88 |
| MX1, mean, intra | UBE2N, mean, intra | 0.6 | 80 | 71 | 88 |
| PARP12, mean, intra | RSAD2, mean, intra | 0.6 | 80 | 71 | 88 |
| PTEN, mean, intra | SOCS3, mean, intra | 0.6 | 79 | 64 | 93 |
| RSAD2, mean, intra | SOCS3, mean, intra | 0.6 | 80 | 72 | 87 |
| IFIT3, mean, intra | UBE2N, mean, intra | 0.59 | 79 | 61 | 93 |
| LOC26010, mean, intra | Neu(%) | 0.59 | 80 | 78 | 81 |
| ANC | Lym(%) | 0.58 | 79 | 69 | 88 |
| CORO1A, mean, intra | CRP | 0.58 | 79 | 81 | 78 |
| CORO1A, mean, intra | IFIT3, mean, intra | 0.58 | 80 | 69 | 88 |
| CORO1A, mean, intra | PARP12, mean, intra | 0.58 | 80 | 69 | 88 |
| CORO1A, mean, intra | RSAD2, mean, intra | 0.58 | 80 | 73 | 85 |
| LOC26010, mean, intra | MX1, mean, intra | 0.58 | 79 | 69 | 88 |
| Neu(%) | SOCS3, mean, intra | 0.58 | 79 | 72 | 85 |
| OAS2, mean, intra | SOCS3, mean, intra | 0.58 | 79 | 61 | 93 |
| PARP9, mean, intra | SOCS3, mean, intra | 0.58 | 79 | 61 | 93 |
| PTEN, mean, intra | UBE2N, mean, intra | 0.58 | 78 | 61 | 93 |
| SOCS3, mean, intra | UBE2N, mean, intra | 0.58 | 79 | 61 | 93 |
| ANC | CORO1A, mean, intra | 0.57 | 79 | 69 | 86 |
| ANC | OAS2, mean, intra | 0.57 | 79 | 76 | 81 |
| ANC | PARP9, mean, intra | 0.57 | 79 | 76 | 81 |
| ANC | PTEN, mean, intra | 0.57 | 79 | 73 | 84 |
| ARHGDIB, mean, intra | Neu(%) | 0.57 | 79 | 76 | 81 |
| ARPC2, mean, intra | CORO1A, mean, intra | 0.57 | 79 | 68 | 88 |
| CORO1A, mean, intra | UBE2N, mean, intra | 0.57 | 79 | 69 | 87 |
| HERC5, mean, intra | RSAD2, mean, intra | 0.57 | 79 | 69 | 87 |
| LOC26010, mean, intra | SOCS3, mean, intra | 0.57 | 78 | 59 | 93 |
| ARPC2, mean, intra | Lym(%) | 0.56 | 78 | 74 | 81 |
| HERC5, mean, intra | PTEN, mean, intra | 0.56 | 78 | 69 | 86 |
| LIPT1, mean, intra | Neu(%) | 0.56 | 78 | 74 | 81 |
| LOC26010, mean, intra | PTEN, mean, intra | 0.56 | 77 | 58 | 93 |
| CES1, mean, intra | PARP12, mean, intra | 0.55 | 78 | 66 | 88 |
| CES1, mean, intra | SOCS3, mean, intra | 0.55 | 78 | 67 | 87 |
| CORO1A, mean, intra | LOC26010, mean, intra | 0.55 | 78 | 66 | 88 |
| CORO1A, mean, intra | Lym(%) | 0.55 | 78 | 73 | 83 |
| IFIT3, mean, intra | PARP12, mean, intra | 0.55 | 78 | 66 | 88 |
| LOC26010, mean, intra | Lym(%) | 0.55 | 78 | 79 | 76 |
| ATP6V0B, mean, intra | MX1, mean, intra | 0.54 | 77 | 65 | 88 |
| CORO1A, mean, intra | HERC5, mean, intra | 0.54 | 77 | 66 | 87 |
| CORO1A, mean, intra | OAS2, mean, intra | 0.54 | 77 | 65 | 88 |
| CORO1A, mean, intra | PARP9, mean, intra | 0.54 | 77 | 65 | 88 |
| CORO1A, mean, intra | PTEN, mean, intra | 0.54 | 77 | 66 | 87 |
| LIPT1, mean, intra | Lym(%) | 0.54 | 77 | 73 | 81 |
| LOC26010, mean, intra | RSAD2, mean, intra | 0.54 | 77 | 69 | 84 |
| Lym(%) | SOCS3, mean, intra | 0.54 | 77 | 72 | 81 |
| Neu(%) | PARP12, mean, intra | 0.54 | 77 | 71 | 83 |
| OAS2, mean, intra | PARP12, mean, intra | 0.54 | 77 | 65 | 88 |
| PTEN, mean, intra | RSAD2, mean, intra | 0.54 | 77 | 66 | 87 |
| ARHGDIB, mean, intra | ARPC2, mean, intra | 0.53 | 77 | 63 | 88 |
| ARPC2, mean, intra | IFIT3, mean, intra | 0.53 | 77 | 63 | 88 |
| ARPC2, mean, intra | LOC26010, mean, intra | 0.53 | 77 | 63 | 88 |
| ARPC2, mean, intra | MX1, mean, intra | 0.53 | 77 | 63 | 88 |
| ARPC2, mean, intra | OAS2, mean, intra | 0.53 | 77 | 63 | 88 |
| ARPC2, mean, intra | PARP9, mean, intra | 0.53 | 77 | 63 | 88 |
| CES1, mean, intra | MX1, mean, intra | 0.53 | 77 | 63 | 88 |
| CES1, mean, intra | PTEN, mean, intra | 0.53 | 77 | 65 | 87 |
| CES1, mean, intra | UBE2N, mean, intra | 0.53 | 77 | 65 | 87 |
| LOC26010, mean, intra | PARP12, mean, intra | 0.53 | 77 | 63 | 88 |
| Lym(%) | OAS2, mean, intra | 0.53 | 76 | 75 | 78 |
| Neu(%) | OAS2, mean, intra | 0.53 | 76 | 71 | 81 |
| HERC5, mean, intra | IFIT3, mean, intra | 0.52 | 76 | 64 | 87 |
| HERC5, mean, intra | MX1, mean, intra | 0.52 | 76 | 64 | 87 |
| Lym(%) | Neu(%) | 0.52 | 76 | 71 | 81 |
| Neu(%) | PARP9, mean, intra | 0.52 | 76 | 77 | 75 |

TABLE 5-continued

The classification accuracy of viral vs. mixed infected patients computed over pairs of DETERMINANTS.

| DETERMINANT #1 | DETERMINANT #2 | MCC | Total accuracy % | Sen % | Spe % |
|---|---|---|---|---|---|
| PARP12, mean, intra | PARP9, mean, intra | 0.52 | 77 | 66 | 85 |
| ARHGDIB, mean, intra | CES1, mean, intra | 0.51 | 76 | 61 | 88 |
| ARPC2, mean, intra | ATP6V0B, mean, intra | 0.51 | 76 | 61 | 88 |
| ARPC2, mean, intra | PTEN, mean, intra | 0.51 | 76 | 63 | 87 |
| ARPC2, mean, intra | RSAD2, mean, intra | 0.51 | 76 | 68 | 83 |
| ATP6V0B, mean, intra | CORO1A, mean, intra | 0.51 | 76 | 66 | 84 |
| ATP6V0B, mean, intra | Neu(%) | 0.51 | 76 | 69 | 81 |
| ATP6V0B, mean, intra | PTEN, mean, intra | 0.51 | 76 | 63 | 87 |
| HERC5, mean, intra | SOCS3, mean, intra | 0.51 | 75 | 63 | 86 |
| HERC5, mean, intra | UBE2N, mean, intra | 0.51 | 76 | 64 | 86 |
| IFIT3, mean, intra | LOC26010, mean, intra | 0.51 | 76 | 61 | 88 |
| LIPT1, mean, intra | PARP12, mean, intra | 0.51 | 76 | 63 | 86 |
| LIPT1, mean, intra | PTEN, mean, intra | 0.51 | 76 | 63 | 87 |
| Lym(%) | PTEN, mean, intra | 0.51 | 76 | 71 | 80 |
| Neu(%) | PTEN, mean, intra | 0.51 | 76 | 71 | 80 |
| Neu(%) | UBE2N, mean, intra | 0.51 | 76 | 71 | 80 |
| PARP12, mean, intra | PTEN, mean, intra | 0.51 | 76 | 63 | 87 |
| ANC | ATP6V0B, mean, intra | 0.5 | 75 | 66 | 83 |
| ARHGDIB, mean, intra | SOCS3, mean, intra | 0.5 | 75 | 59 | 88 |
| ARPC2, mean, intra | CES1, mean, intra | 0.5 | 75 | 60 | 88 |
| ATP6V0B, mean, intra | Lym(%) | 0.5 | 75 | 68 | 81 |
| CES1, mean, intra | IFIT3, mean, intra | 0.5 | 75 | 60 | 88 |
| LIPT1, mean, intra | MX1, mean, intra | 0.5 | 75 | 60 | 88 |
| PARP12, mean, intra | UBE2N, mean, intra | 0.5 | 75 | 65 | 84 |
| ARHGDIB, mean, intra | PARP12, mean, intra | 0.49 | 75 | 65 | 84 |
| ARHGDIB, mean, intra | PTEN, mean, intra | 0.49 | 74 | 60 | 87 |
| ATP6V0B, mean, intra | PARP12, mean, intra | 0.49 | 75 | 65 | 84 |
| LIPT1, mean, intra | SOCS3, mean, intra | 0.49 | 75 | 61 | 87 |
| MX1, mean, intra | PTEN, mean, intra | 0.49 | 74 | 60 | 87 |
| MX1, mean, intra | RSAD2, mean, intra | 0.49 | 74 | 67 | 81 |
| ATP6V0B, mean, intra | IFIT3, mean, intra | 0.48 | 75 | 58 | 88 |
| CORO1A, mean, intra | LIPT1, mean, intra | 0.48 | 75 | 66 | 81 |
| IFIT3, mean, intra | LIPT1, mean, intra | 0.48 | 75 | 58 | 88 |
| LIPT1, mean, intra | RSAD2, mean, intra | 0.48 | 75 | 66 | 81 |
| ANC | ARHGDIB, mean, intra | 0.47 | 74 | 69 | 78 |
| ARPC2, mean, intra | LIPT1, mean, intra | 0.47 | 74 | 56 | 88 |
| ATP6V0B, mean, intra | LOC26010, mean, intra | 0.47 | 74 | 56 | 88 |
| CES1, mean, intra | CORO1A, mean, intra | 0.47 | 74 | 63 | 83 |
| IFIT3, mean, intra | MX1, mean, intra | 0.47 | 74 | 61 | 84 |
| IFIT3, mean, intra | PTEN, mean, intra | 0.47 | 74 | 58 | 87 |
| LIPT1, mean, intra | UBE2N, mean, intra | 0.47 | 74 | 58 | 87 |
| LOC26010, mean, intra | UBE2N, mean, intra | 0.47 | 74 | 58 | 87 |
| RSAD2, mean, intra | UBE2N, mean, intra | 0.47 | 74 | 63 | 83 |
| ARPC2, mean, intra | HERC5, mean, intra | 0.46 | 74 | 66 | 80 |
| Lym(%) | PARP9, mean, intra | 0.46 | 73 | 71 | 75 |
| MX1, mean, intra | OAS2, mean, intra | 0.46 | 73 | 64 | 81 |
| PARP9, mean, intra | PTEN, mean, intra | 0.46 | 73 | 56 | 87 |
| PARP9, mean, intra | UBE2N, mean, intra | 0.46 | 73 | 56 | 87 |
| ARHGDIB, mean, intra | CORO1A, mean, intra | 0.45 | 73 | 63 | 81 |
| HERC5, mean, intra | LOC26010, mean, intra | 0.45 | 73 | 62 | 81 |
| HERC5, mean, intra | PARP9, mean, intra | 0.45 | 73 | 64 | 80 |
| ARHGDIB, mean, intra | MX1, mean, intra | 0.44 | 73 | 61 | 81 |
| ATP6V0B, mean, intra | CES1, mean, intra | 0.44 | 73 | 50 | 90 |
| ATP6V0B, mean, intra | LIPT1, mean, intra | 0.44 | 73 | 53 | 88 |
| ATP6V0B, mean, intra | PARP9, mean, intra | 0.44 | 73 | 53 | 88 |
| ATP6V0B, mean, intra | RSAD2, mean, intra | 0.44 | 73 | 61 | 81 |
| Lym(%) | UBE2N, mean, intra | 0.44 | 72 | 71 | 73 |
| OAS2, mean, intra | PTEN, mean, intra | 0.44 | 72 | 55 | 87 |
| ARHGDIB, mean, intra | ATP6V0B, mean, intra | 0.43 | 72 | 52 | 88 |
| ATP6V0B, mean, intra | HERC5, mean, intra | 0.43 | 72 | 62 | 80 |
| HERC5, mean, intra | OAS2, mean, intra | 0.43 | 72 | 62 | 80 |
| CES1, mean, intra | LOC26010, mean, intra | 0.42 | 72 | 55 | 85 |
| LOC26010, mean, intra | OAS2, mean, intra | 0.42 | 71 | 60 | 81 |
| MX1, mean, intra | PARP9, mean, intra | 0.42 | 72 | 60 | 81 |
| OAS2, mean, intra | RSAD2, mean, intra | 0.42 | 71 | 66 | 76 |
| CES1, mean, intra | PARP9, mean, intra | 0.41 | 71 | 50 | 88 |
| CES1, mean, intra | RSAD2, mean, intra | 0.41 | 71 | 58 | 81 |
| Lym(%) | PARP12, mean, intra | 0.41 | 71 | 66 | 75 |
| ARHGDIB, mean, intra | HERC5, mean, intra | 0.4 | 71 | 59 | 80 |
| ATP6V0B, mean, intra | OAS2, mean, intra | 0.4 | 70 | 48 | 88 |
| HERC5, mean, intra | LIPT1, mean, intra | 0.4 | 71 | 59 | 80 |
| OAS2, mean, intra | UBE2N, mean, intra | 0.4 | 70 | 50 | 87 |
| ARHGDIB, mean, intra | IFIT3, mean, intra | 0.39 | 70 | 56 | 81 |
| CES1, mean, intra | HERC5, mean, intra | 0.39 | 70 | 57 | 80 |
| CES1, mean, intra | LIPT1, mean, intra | 0.39 | 70 | 52 | 85 |

TABLE 5-continued

The classification accuracy of viral vs. mixed infected patients computed over pairs of DETERMINANTS.

| DETERMINANT #1 | DETERMINANT #2 | MCC | Total accuracy % | Sen % | Spe % |
|---|---|---|---|---|---|
| IFIT3, mean, intra | PARP9, mean, intra | 0.39 | 70 | 56 | 81 |
| IFIT3, mean, intra | RSAD2, mean, intra | 0.39 | 70 | 58 | 80 |
| LOC26010, mean, intra | PARP9, mean, intra | 0.39 | 70 | 53 | 84 |
| ARHGDIB, mean, intra | UBE2N, mean, intra | 0.38 | 69 | 55 | 81 |
| IFIT3, mean, intra | OAS2, mean, intra | 0.38 | 70 | 55 | 81 |
| LIPT1, mean, intra | LOC26010, mean, intra | 0.38 | 70 | 55 | 81 |
| ARHGDIB, mean, intra | LOC26010, mean, intra | 0.36 | 69 | 52 | 83 |
| LIPT1, mean, intra | PARP9, mean, intra | 0.36 | 69 | 52 | 83 |
| ARHGDIB, mean, intra | LIPT1, mean, intra | 0.35 | 68 | 52 | 81 |
| ARHGDIB, mean, intra | RSAD2, mean, intra | 0.35 | 68 | 60 | 75 |
| CES1, mean, intra | OAS2, mean, intra | 0.35 | 68 | 47 | 85 |
| LIPT1, mean, intra | OAS2, mean, intra | 0.35 | 68 | 50 | 83 |
| PARP9, mean, intra | RSAD2, mean, intra | 0.35 | 68 | 58 | 76 |
| ARHGDIB, mean, intra | PARP9, mean, intra | 0.32 | 67 | 40 | 88 |
| OAS2, mean, intra | PARP9, mean, intra | 0.29 | 65 | 40 | 85 |
| ARHGDIB, mean, intra | OAS2, mean, intra | 0.27 | 65 | 39 | 85 |

* Positive and negative correspond to viral and mixed infected patients respectively

TABLE 6

The classification accuracy of viral vs. non-infected patients computed over pairs of DETERMINANTS.

| DETERMINANT #1 | DETERMINANT #2 | MCC | Total accuracy % | Sen % | Spe % |
|---|---|---|---|---|---|
| MX1, mean, intra | MX1, total, intra | 0.87 | 93 | 85 | 100 |
| LOC26010, mean, intra | MX1, mean, intra | 0.85 | 92 | 83 | 100 |
| LOC26010, total, intra | MX1, mean, intra | 0.85 | 92 | 83 | 100 |
| LRDD, total, intra | MX1, mean, intra | 0.85 | 92 | 83 | 100 |
| LRDD, total, intra | MX1, total, intra | 0.85 | 92 | 83 | 100 |
| MX1, mean, intra | PTEN, total, intra | 0.85 | 92 | 82 | 100 |
| IFIT3, total, intra | MX1, total, intra | 0.84 | 92 | 81 | 100 |
| MX1, mean, intra | RAB13, mean, intra | 0.84 | 92 | 81 | 100 |
| MX1, mean, intra | RSAD2, total, intra | 0.84 | 92 | 82 | 100 |
| C1orf83, total, intra | MX1, mean, intra | 0.83 | 91 | 81 | 100 |
| C1orf83, total, intra | MX1, total, intra | 0.83 | 91 | 81 | 100 |
| IFIT3, total, intra | MX1, mean, intra | 0.83 | 91 | 79 | 100 |
| IFITM3, total, membrane | MX1, total, intra | 0.83 | 91 | 81 | 100 |
| LOC26010, mean, intra | MX1, total, intra | 0.83 | 91 | 81 | 100 |
| LOC26010, total, intra | MX1, total, intra | 0.83 | 91 | 81 | 100 |
| MX1, mean, intra | RAB13, total, intra | 0.83 | 91 | 79 | 100 |
| MX1, mean, intra | RPL34, total, intra | 0.83 | 91 | 81 | 100 |
| MX1, mean, intra | RSAD2, mean, intra | 0.83 | 91 | 81 | 100 |
| MX1, mean, intra | SART3, mean, intra | 0.83 | 91 | 79 | 100 |
| MX1, total, intra | Maximaltemperature | 0.83 | 91 | 80 | 100 |
| MX1, total, intra | RSAD2, total, intra | 0.83 | 91 | 81 | 100 |
| MX1, total, intra | SART3, mean, intra | 0.83 | 91 | 79 | 100 |
| MX1, total, intra | OAS2, mean, intra | 0.82 | 90 | 79 | 100 |
| MX1, mean, intra | OAS2, total, intra | 0.81 | 90 | 83 | 96 |
| MX1, total, intra | OAS2, total, intra | 0.81 | 90 | 78 | 100 |
| MX1, total, intra | PTEN, total, intra | 0.81 | 90 | 77 | 100 |
| MX1, total, intra | SART3, total, intra | 0.81 | 90 | 77 | 100 |
| IFIT3, mean, intra | MX1, total, intra | 0.8 | 90 | 76 | 100 |
| IFIT3, total, intra | LRDD, total, intra | 0.8 | 89 | 77 | 100 |
| IFIT3, mean, intra | LOC26010, total, intra | 0.79 | 89 | 74 | 100 |
| MX1, total, intra | RPL34, total, intra | 0.79 | 89 | 83 | 95 |
| IFIT3, mean, intra | PTEN, total, intra | 0.78 | 88 | 73 | 100 |
| IFIT3, mean, intra | RAB13, mean, intra | 0.78 | 88 | 73 | 100 |
| IFIT3, total, intra | Maximaltemperature | 0.78 | 88 | 76 | 98 |
| IFIT3, total, intra | SART3, total, intra | 0.78 | 88 | 73 | 100 |
| Maximaltemperature | RSAD2, mean, intra | 0.78 | 89 | 87 | 91 |
| MX1, mean, intra | Maximaltemperature | 0.77 | 88 | 80 | 95 |
| MX1, mean, intra | OAS2, mean, intra | 0.77 | 88 | 83 | 93 |
| MX1, total, intra | RSAD2, mean, intra | 0.77 | 88 | 83 | 93 |
| IFIT3, mean, intra | MX1, mean, intra | 0.76 | 88 | 79 | 95 |
| MX1, total, intra | RAB13, mean, intra | 0.76 | 88 | 79 | 95 |
| IFITM3, total, membrane | MX1, mean, intra | 0.75 | 87 | 82 | 92 |
| MX1, mean, intra | SART3, total, intra | 0.75 | 88 | 81 | 93 |
| MX1, total, intra | RAB13, total, intra | 0.75 | 88 | 77 | 95 |
| C1orf83, total, intra | LOC26010, total, intra | 0.74 | 87 | 75 | 97 |
| IFIT3, mean, intra | LRDD, total, intra | 0.74 | 86 | 70 | 100 |

TABLE 6-continued

The classification accuracy of viral vs. non-infected patients computed over pairs of DETERMINANTS.

| DETERMINANT #1 | DETERMINANT #2 | MCC | Total accuracy % | Sen % | Spe % |
|---|---|---|---|---|---|
| IFIT3, total, intra | RAB13, mean, intra | 0.73 | 86 | 73 | 96 |
| Maximaltemperature | RSAD2, total, intra | 0.73 | 87 | 82 | 91 |
| C1orf83, total, intra | IFIT3, mean, intra | 0.72 | 86 | 75 | 95 |
| C1orf83, total, intra | IFIT3, total, intra | 0.72 | 86 | 77 | 93 |
| C1orf83, total, intra | OAS2, mean, intra | 0.72 | 85 | 67 | 100 |
| C1orf83, total, intra | OAS2, total, intra | 0.72 | 85 | 67 | 100 |
| IFIT3, mean, intra | OAS2, total, intra | 0.72 | 86 | 76 | 94 |
| IFIT3, total, intra | SART3, mean, intra | 0.72 | 86 | 68 | 99 |
| IFIT3, total, intra | LOC26010, mean, intra | 0.71 | 86 | 74 | 94 |
| IFIT3, total, intra | LOC26010, total, intra | 0.71 | 86 | 76 | 93 |
| IFIT3, mean, intra | RAB13, total, intra | 0.7 | 85 | 71 | 95 |
| LOC26010, total, intra | LRDD, total, intra | 0.7 | 85 | 79 | 90 |
| LOC26010, total, intra | PTEN, total, intra | 0.7 | 85 | 71 | 95 |
| LOC26010, total, intra | RSAD2, mean, intra | 0.7 | 85 | 75 | 93 |
| LRDD, total, intra | OAS2, total, intra | 0.7 | 83 | 64 | 100 |
| IFIT3, total, intra | OAS2, total, intra | 0.69 | 85 | 74 | 93 |
| LOC26010, total, intra | Maximaltemperature | 0.69 | 84 | 73 | 94 |
| LOC26010, total, intra | RPL34, total, intra | 0.69 | 84 | 74 | 93 |
| OAS2, total, intra | RSAD2, mean, intra | 0.69 | 84 | 74 | 93 |
| IFIT3, total, intra | IFITM3, total, membrane | 0.68 | 84 | 74 | 92 |
| LOC26010, total, intra | RSAD2, total, intra | 0.68 | 84 | 74 | 93 |
| RSAD2, mean, intra | SART3, total, intra | 0.68 | 84 | 73 | 93 |
| LOC26010, total, intra | OAS2, total, intra | 0.67 | 83 | 72 | 93 |
| LRDD, total, intra | RAB13, total, intra | 0.67 | 83 | 75 | 90 |
| LRDD, total, intra | RSAD2, mean, intra | 0.67 | 83 | 75 | 90 |
| OAS2, total, intra | PTEN, total, intra | 0.67 | 84 | 68 | 95 |
| PTEN, total, intra | RPL34, total, intra | 0.67 | 83 | 75 | 90 |
| IFIT3, total, intra | RSAD2, mean, intra | 0.66 | 84 | 71 | 93 |
| IFIT3, total, intra | RSAD2, total, intra | 0.66 | 84 | 71 | 93 |
| IFITM3, total, membrane | LOC26010, total, intra | 0.66 | 83 | 75 | 90 |
| RSAD2, mean, intra | RSAD2, total, intra | 0.66 | 83 | 71 | 93 |
| IFIT3, mean, intra | Maximaltemperature | 0.65 | 83 | 73 | 91 |
| IFIT3, total, intra | OAS2, mean, intra | 0.65 | 83 | 74 | 89 |
| IFIT3, total, intra | RAB13, total, intra | 0.65 | 83 | 69 | 93 |
| OAS2, total, intra | RAB13, mean, intra | 0.65 | 82 | 63 | 96 |
| RAB13, total, intra | RPL34, total, intra | 0.65 | 82 | 74 | 90 |
| C1orf83, total, intra | PTEN, total, intra | 0.64 | 82 | 73 | 90 |
| C1orf83, total, intra | RPL34, total, intra | 0.64 | 82 | 75 | 88 |
| IFIT3, mean, intra | RSAD2, total, intra | 0.64 | 82 | 68 | 93 |
| IFITM3, total, membrane | LOC26010, mean, intra | 0.64 | 81 | 69 | 92 |
| IFITM3, total, membrane | Maximaltemperature | 0.64 | 82 | 73 | 90 |
| LOC26010, mean, intra | LOC26010, total, intra | 0.64 | 81 | 68 | 93 |
| LOC26010, mean, intra | OAS2, total, intra | 0.64 | 81 | 68 | 93 |
| LOC26010, total, intra | OAS2, mean, intra | 0.64 | 82 | 71 | 92 |
| LOC26010, total, intra | RAB13, mean, intra | 0.64 | 82 | 68 | 93 |
| LOC26010, total, intra | RAB13, total, intra | 0.64 | 82 | 66 | 94 |
| LOC26010, total, intra | SART3, total, intra | 0.64 | 82 | 68 | 93 |
| IFIT3, total, intra | PTEN, total, intra | 0.63 | 82 | 71 | 90 |
| OAS2, total, intra | RPL34, total, intra | 0.63 | 81 | 72 | 90 |
| IFIT3, mean, intra | IFIT3, total, intra | 0.62 | 82 | 69 | 90 |
| IFIT3, mean, intra | LOC26010, mean, intra | 0.62 | 82 | 66 | 93 |
| LOC26010, total, intra | SART3, mean, intra | 0.62 | 82 | 66 | 93 |
| Maximaltemperature | RAB13, total, intra | 0.62 | 81 | 69 | 91 |
| OAS2, total, intra | RSAD2, total, intra | 0.62 | 80 | 66 | 93 |
| C1orf83, total, intra | RAB13, mean, intra | 0.61 | 80 | 69 | 90 |
| IFIT3, mean, intra | RSAD2, mean, intra | 0.61 | 81 | 65 | 93 |
| LOC26010, mean, intra | LRDD, total, intra | 0.61 | 81 | 70 | 90 |
| LOC26010, mean, intra | OAS2, mean, intra | 0.61 | 80 | 65 | 93 |
| LOC26010, mean, intra | RSAD2, mean, intra | 0.61 | 81 | 75 | 86 |
| LRDD, total, intra | RPL34, total, intra | 0.61 | 81 | 70 | 90 |
| PTEN, total, intra | RAB13, total, intra | 0.61 | 81 | 65 | 93 |
| PTEN, total, intra | SART3, total, intra | 0.61 | 81 | 65 | 93 |
| RAB13, mean, intra | RPL34, total, intra | 0.61 | 81 | 70 | 90 |
| IFIT3, mean, intra | IFITM3, total, membrane | 0.6 | 80 | 68 | 90 |
| IFIT3, mean, intra | SART3, total, intra | 0.6 | 81 | 71 | 88 |
| IFITM3, total, membrane | RAB13, total, intra | 0.6 | 80 | 65 | 92 |
| LOC26010, mean, intra | RSAD2, mean, intra | 0.6 | 80 | 74 | 86 |
| OAS2, mean, intra | RAB13, total, intra | 0.6 | 80 | 63 | 93 |
| OAS2, mean, intra | RPL34, total, intra | 0.6 | 80 | 68 | 90 |
| PTEN, total, intra | RSAD2, mean, intra | 0.6 | 81 | 71 | 88 |
| C1orf83, total, intra | RAB13, total, intra | 0.59 | 79 | 67 | 90 |
| IFITM3, total, membrane | RSAD2, mean, intra | 0.59 | 79 | 74 | 85 |
| RSAD2, total, intra | SART3, total, intra | 0.59 | 80 | 65 | 92 |
| C1orf83, total, intra | LRDD, total, intra | 0.58 | 79 | 65 | 90 |

TABLE 6-continued

The classification accuracy of viral vs. non-infected patients computed over pairs of DETERMINANTS.

| DETERMINANT #1 | DETERMINANT #2 | MCC | Total accuracy % | Sen % | Spe % |
|---|---|---|---|---|---|
| IFIT3, mean, intra | RPL34, total, intra | 0.58 | 79 | 66 | 90 |
| IFIT3, mean, intra | SART3, mean, intra | 0.58 | 79 | 66 | 89 |
| LOC26010, mean, intra | PTEN, total, intra | 0.58 | 79 | 61 | 93 |
| LOC26010, mean, intra | SART3, total, intra | 0.58 | 79 | 61 | 93 |
| OAS2, total, intra | SART3, total, intra | 0.58 | 79 | 61 | 93 |
| RAB13, total, intra | RSAD2, mean, intra | 0.58 | 79 | 71 | 86 |
| RAB13, total, intra | SART3, total, intra | 0.58 | 79 | 61 | 93 |
| C1orf83, total, intra | LOC26010, mean, intra | 0.57 | 79 | 69 | 87 |
| IFITM3, total, membrane | SART3, total, intra | 0.57 | 79 | 61 | 92 |
| LOC26010, mean, intra | Maximaltemperature | 0.57 | 79 | 64 | 91 |
| LOC26010, mean, intra | RAB13, mean, intra | 0.57 | 79 | 60 | 93 |
| LOC26010, mean, intra | SART3, mean, intra | 0.57 | 79 | 60 | 93 |
| LRDD, total, intra | OAS2, mean, intra | 0.57 | 78 | 64 | 90 |
| Maximaltemperature | OAS2, total, intra | 0.57 | 79 | 64 | 91 |
| OAS2, mean, intra | RSAD2, mean, intra | 0.57 | 78 | 68 | 87 |
| OAS2, total, intra | RAB13, total, intra | 0.57 | 79 | 60 | 93 |
| RAB13, mean, intra | RAB13, total, intra | 0.57 | 79 | 60 | 93 |
| RAB13, total, intra | SART3, mean, intra | 0.57 | 79 | 60 | 93 |
| C1orf83, total, intra | SART3, mean, intra | 0.56 | 78 | 63 | 90 |
| LOC26010, mean, intra | RPL34, total, intra | 0.56 | 78 | 70 | 85 |
| LRDD, total, intra | RSAD2, total, intra | 0.56 | 78 | 72 | 83 |
| Maximaltemperature | RPL34, total, intra | 0.56 | 78 | 70 | 86 |
| OAS2, mean, intra | SART3, total, intra | 0.56 | 78 | 58 | 93 |
| RAB13, mean, intra | RSAD2, mean, intra | 0.56 | 79 | 66 | 88 |
| C1orf83, total, intra | RSAD2, mean, intra | 0.55 | 78 | 71 | 83 |
| RAB13, total, intra | RSAD2, total, intra | 0.55 | 78 | 68 | 86 |
| RPL34, total, intra | SART3, mean, intra | 0.55 | 77 | 62 | 90 |
| Maximaltemperature | PTEN, total, intra | 0.54 | 77 | 60 | 91 |
| OAS2, mean, intra | OAS2, total, intra | 0.54 | 77 | 66 | 87 |
| OAS2, mean, intra | RAB13, mean, intra | 0.54 | 77 | 58 | 92 |
| OAS2, mean, intra | RSAD2, total, intra | 0.54 | 77 | 67 | 86 |
| OAS2, total, intra | SART3, mean, intra | 0.54 | 77 | 56 | 93 |
| Maximaltemperature | SART3, total, intra | 0.53 | 76 | 58 | 91 |
| PTEN, total, intra | SART3, mean, intra | 0.53 | 77 | 63 | 88 |
| SART3, mean, intra | SART3, total, intra | 0.53 | 77 | 55 | 93 |
| C1orf83, total, intra | SART3, total, intra | 0.52 | 76 | 65 | 85 |
| IFIT3, mean, intra | OAS2, mean, intra | 0.52 | 77 | 65 | 86 |
| IFIT3, total, intra | RPL34, total, intra | 0.52 | 76 | 68 | 83 |
| LRDD, total, intra | PTEN, total, intra | 0.52 | 76 | 72 | 80 |
| LRDD, total, intra | SART3, total, intra | 0.52 | 76 | 68 | 83 |
| PTEN, total, intra | RSAD2, total, intra | 0.52 | 77 | 65 | 86 |
| RAB13, mean, intra | RSAD2, total, intra | 0.52 | 77 | 65 | 86 |
| IFITM3, total, membrane | OAS2, mean, intra | 0.51 | 75 | 65 | 85 |
| LOC26010, mean, intra | RAB13, total, intra | 0.51 | 76 | 60 | 88 |
| RAB13, mean, intra | SART3, mean, intra | 0.51 | 76 | 60 | 88 |
| RAB13, mean, intra | SART3, total, intra | 0.51 | 76 | 58 | 89 |
| C1orf83, total, intra | IFITM3, total, membrane | 0.5 | 75 | 65 | 83 |
| LRDD, total, intra | RAB13, mean, intra | 0.5 | 75 | 70 | 80 |
| Maximaltemperature | RAB13, mean, intra | 0.5 | 75 | 62 | 86 |
| LRDD, total, intra | SART3, mean, intra | 0.49 | 74 | 64 | 83 |
| PTEN, total, intra | RAB13, mean, intra | 0.49 | 75 | 61 | 86 |
| RSAD2, mean, intra | SART3, mean, intra | 0.49 | 75 | 66 | 82 |
| IFITM3, total, membrane | RSAD2, total, intra | 0.48 | 74 | 63 | 85 |
| RPL34, total, intra | RSAD2, mean, intra | 0.48 | 74 | 68 | 80 |
| RPL34, total, intra | RSAD2, mean, intra | 0.48 | 74 | 68 | 80 |
| RPL34, total, intra | RSAD2, total, intra | 0.48 | 74 | 68 | 80 |
| RSAD2, total, intra | SART3, mean, intra | 0.48 | 75 | 68 | 80 |
| IFITM3, total, membrane | OAS2, total, intra | 0.47 | 73 | 67 | 79 |
| IFITM3, total, membrane | RPL34, total, intra | 0.47 | 73 | 66 | 80 |
| C1orf83, total, intra | RSAD2, total, intra | 0.46 | 73 | 65 | 80 |
| Maximaltemperature | OAS2, mean, intra | 0.46 | 74 | 64 | 82 |
| OAS2, mean, intra | PTEN, total, intra | 0.46 | 74 | 58 | 86 |
| OAS2, mean, intra | SART3, mean, intra | 0.46 | 74 | 58 | 86 |
| IFITM3, total, membrane | LRDD, total, intra | 0.45 | 73 | 70 | 75 |
| IFITM3, total, membrane | PTEN, total, intra | 0.45 | 73 | 68 | 77 |
| C1orf83, total, intra | Maximaltemperature | 0.43 | 72 | 72 | 71 |
| IFITM3, total, membrane | RAB13, mean, intra | 0.43 | 72 | 60 | 82 |
| IFITM3, total, membrane | SART3, mean, intra | 0.43 | 72 | 56 | 85 |
| Maximaltemperature | SART3, mean, intra | 0.4 | 70 | 56 | 82 |
| LRDD, total, intra | Maximaltemperature | 0.39 | 70 | 68 | 71 |

\* Positive and negative correspond to viral and non-infected patients respectively

TABLE 7

The classification accuracy of bacterial vs. non-infected patients computed over pairs of DETERMINANTS.

| DETERMINANT #1 | DETERMINANT #2 | MCC | Total accuracy % | Sen % | Spe % |
|---|---|---|---|---|---|
| C1orf83, total, intra | CRP | 0.91 | 95 | 90 | 100 |
| CRP | LRDD, total, intra | 0.91 | 95 | 90 | 100 |
| CRP | QARS, total, intra | 0.91 | 95 | 90 | 100 |
| RAB13, mean, intra | RAB31, total, intra | 0.87 | 94 | 84 | 100 |
| CD15, total, membrane | LRDD, total, intra | 0.85 | 93 | 81 | 100 |
| CD15, total, membrane | QARS, total, intra | 0.85 | 93 | 81 | 100 |
| RAB13, total, intra | RAB31, total, intra | 0.85 | 93 | 81 | 100 |
| CRP | RPL34, total, intra | 0.85 | 92 | 90 | 94 |
| ANC | LTA4H, total, intra | 0.82 | 91 | 76 | 100 |
| CD15, total, membrane | LTA4H, total, intra | 0.82 | 91 | 77 | 100 |
| LOC26010, total, intra | LTA4H, total, intra | 0.82 | 91 | 77 | 100 |
| ANC | RAB31, total, intra | 0.82 | 91 | 77 | 100 |
| LOC26010, total, intra | RAB31, total, intra | 0.82 | 91 | 77 | 100 |
| LRDD, total, intra | RAB31, total, intra | 0.82 | 91 | 77 | 100 |
| QARS, total, intra | RAB31, total, intra | 0.82 | 91 | 77 | 100 |
| ANC | RAC2, total, intra | 0.82 | 91 | 77 | 100 |
| LOC26010, total, intra | RAC2, total, intra | 0.82 | 91 | 77 | 100 |
| RAB13, total, intra | RAC2, total, intra | 0.82 | 91 | 77 | 100 |
| LTA4H, total, intra | WBC | 0.82 | 91 | 77 | 100 |
| LTA4H, total, intra | ZBP1, total, intra | 0.82 | 91 | 77 | 100 |
| LTA4H, total, intra | Maximaltemperature | 0.81 | 90 | 77 | 100 |
| C1orf83, total, intra | CD15, total, membrane | 0.8 | 90 | 74 | 100 |
| ANC | LRDD, total, intra | 0.8 | 90 | 73 | 100 |
| ANC | PARP9, total, intra | 0.8 | 91 | 74 | 100 |
| LTA4H, total, intra | RAB13, mean, intra | 0.8 | 90 | 73 | 100 |
| CD15, total, membrane | RAB13, total, intra | 0.8 | 90 | 74 | 100 |
| CD15, total, membrane | RAB31, total, intra | 0.8 | 90 | 74 | 100 |
| ISG20, total, intra | RAB31, total, intra | 0.8 | 90 | 74 | 100 |
| RAB31, total, intra | RPL34, total, intra | 0.8 | 90 | 74 | 100 |
| RAB31, total, intra | WBC | 0.8 | 90 | 74 | 100 |
| MX1, total, intra | ZBP1, total, intra | 0.8 | 90 | 74 | 100 |
| CRP | OAS2, total, intra | 0.79 | 90 | 87 | 92 |
| CRP | RAB13, total, intra | 0.79 | 90 | 89 | 90 |
| CRP | ZBP1, total, intra | 0.79 | 89 | 83 | 94 |
| IFIT3, total, intra | LRDD, total, intra | 0.78 | 89 | 71 | 100 |
| ISG20, total, intra | LRDD, total, intra | 0.78 | 89 | 71 | 100 |
| LOC26010, total, intra | LRDD, total, intra | 0.78 | 89 | 71 | 100 |
| LRDD, total, intra | Lym(%) | 0.78 | 89 | 71 | 100 |
| ANC | MX1, total, intra | 0.78 | 90 | 71 | 100 |
| LRDD, total, intra | MX1, total, intra | 0.78 | 89 | 71 | 100 |
| ISG20, total, intra | OAS2, total, intra | 0.78 | 89 | 71 | 100 |
| C1orf83, total, intra | RAB31, total, intra | 0.78 | 89 | 71 | 100 |
| MX1, total, intra | RAB31, total, intra | 0.78 | 89 | 71 | 100 |
| CD15, total, membrane | ZBP1, total, intra | 0.78 | 89 | 71 | 100 |
| C1orf83, total, intra | LTA4H, total, intra | 0.77 | 89 | 70 | 100 |
| IFIT3, total, intra | LTA4H, total, intra | 0.77 | 89 | 70 | 100 |
| ISG20, total, intra | LTA4H, total, intra | 0.77 | 89 | 70 | 100 |
| LRDD, total, intra | LTA4H, total, intra | 0.77 | 89 | 70 | 100 |
| LTA4H, total, intra | MX1, total, intra | 0.77 | 89 | 70 | 100 |
| LTA4H, total, intra | OAS2, total, intra | 0.77 | 89 | 70 | 100 |
| CRP | WBC | 0.77 | 89 | 87 | 90 |
| RAC2, total, intra | WBC | 0.77 | 89 | 74 | 98 |
| CRP | XAF1, total, intra | 0.77 | 89 | 84 | 92 |
| ANC | IFIT3, total, intra | 0.76 | 89 | 68 | 100 |
| ANC | LOC26010, total, intra | 0.76 | 89 | 68 | 100 |
| LOC26010, total, intra | MX1, total, intra | 0.76 | 87 | 73 | 100 |
| LTA4H, total, intra | RAB31, total, intra | 0.76 | 89 | 73 | 98 |
| RAB13, total, intra | ZBP1, total, intra | 0.76 | 89 | 77 | 96 |
| ANC | C1orf83, total, intra | 0.75 | 88 | 67 | 100 |
| C1orf83, total, intra | IFIT3, total, intra | 0.75 | 88 | 68 | 100 |
| C1orf83, total, intra | LOC26010, total, intra | 0.75 | 88 | 68 | 100 |
| CRP | LTA4H, total, intra | 0.75 | 88 | 86 | 89 |
| IFIT3, total, intra | Maximaltemperature | 0.75 | 88 | 68 | 100 |
| ISG20, total, intra | RAB13, mean, intra | 0.75 | 88 | 68 | 100 |
| CRP | RAB31, total, intra | 0.75 | 88 | 83 | 91 |
| CD15, total, membrane | RPL34, total, intra | 0.75 | 88 | 68 | 100 |
| LOC26010, total, intra | RPL34, total, intra | 0.75 | 88 | 68 | 100 |
| LTA4H, total, intra | RPL34, total, intra | 0.75 | 88 | 67 | 100 |
| C1orf83, total, intra | SART3, total, intra | 0.75 | 88 | 68 | 100 |
| LTA4H, total, intra | XAF1, total, intra | 0.75 | 88 | 67 | 100 |
| QARS, total, intra | XAF1, total, intra | 0.75 | 88 | 68 | 100 |
| LRDD, total, intra | ZBP1, total, intra | 0.75 | 88 | 68 | 100 |
| OAS2, total, intra | ZBP1, total, intra | 0.75 | 88 | 68 | 100 |
| RAB13, mean, intra | ZBP1, total, intra | 0.75 | 88 | 68 | 100 |

TABLE 7-continued

The classification accuracy of bacterial vs. non-infected patients computed over pairs of DETERMINANTS.

| DETERMINANT #1 | DETERMINANT #2 | MCC | Total accuracy % | Sen % | Spe % |
|---|---|---|---|---|---|
| ANC | CRP | 0.74 | 87 | 84 | 90 |
| ANC | OAS2, total, intra | 0.74 | 88 | 66 | 100 |
| MX1, total, intra | OAS2, total, intra | 0.74 | 86 | 69 | 100 |
| ANC | SART3, total, intra | 0.74 | 88 | 66 | 100 |
| CRP | SART3, total, intra | 0.74 | 88 | 84 | 90 |
| ISG20, total, intra | SART3, total, intra | 0.74 | 88 | 74 | 96 |
| CRP | TRIM22, total, intra | 0.74 | 88 | 82 | 92 |
| ANC | WBC | 0.74 | 88 | 66 | 100 |
| LOC26010, total, intra | ZBP1, total, intra | 0.74 | 88 | 74 | 96 |
| CD15, total, membrane | IFIT3, total, intra | 0.73 | 87 | 64 | 100 |
| LOC26010, total, intra | Maximaltemperature | 0.73 | 87 | 65 | 100 |
| C1orf83, total, intra | MX1, total, intra | 0.73 | 86 | 65 | 100 |
| LRDD, total, intra | PARP9, total, intra | 0.73 | 86 | 65 | 100 |
| LOC26010, total, intra | SART3, total, intra | 0.73 | 87 | 64 | 100 |
| Lym(%) | SART3, total, intra | 0.73 | 87 | 64 | 100 |
| C1orf83, total, intra | WBC | 0.73 | 86 | 65 | 100 |
| CD15, total, membrane | WBC | 0.73 | 87 | 64 | 100 |
| LRDD, total, intra | WBC | 0.73 | 86 | 65 | 100 |
| ANC | XAF1, total, intra | 0.73 | 87 | 63 | 100 |
| RAB13, total, intra | XAF1, total, intra | 0.73 | 87 | 64 | 100 |
| CRP | ISG20, total, intra | 0.72 | 86 | 80 | 91 |
| ANC | Maximaltemperature | 0.72 | 86 | 64 | 100 |
| CRP | PARP9, total, intra | 0.72 | 86 | 82 | 90 |
| CRP | RAC2, total, intra | 0.72 | 86 | 83 | 89 |
| ANC | ZBP1, total, intra | 0.72 | 86 | 63 | 100 |
| ISG20, total, intra | LOC26010, total, intra | 0.71 | 86 | 74 | 94 |
| CRP | Maximaltemperature | 0.71 | 86 | 82 | 89 |
| MX1, total, intra | Maximaltemperature | 0.71 | 85 | 62 | 100 |
| CD15, total, membrane | MX1, total, intra | 0.71 | 86 | 62 | 100 |
| ISG20, total, intra | MX1, total, intra | 0.71 | 86 | 77 | 92 |
| ISG20, total, intra | PARP9, total, intra | 0.71 | 86 | 77 | 92 |
| LOC26010, total, intra | PARP9, total, intra | 0.71 | 86 | 62 | 100 |
| OAS2, total, intra | RAB13, mean, intra | 0.71 | 86 | 62 | 100 |
| ISG20, total, intra | RAB13, total, intra | 0.71 | 86 | 77 | 92 |
| Lym(%) | RAB31, total, intra | 0.71 | 86 | 71 | 96 |
| C1orf83, total, intra | RAC2, total, intra | 0.71 | 86 | 71 | 96 |
| LTA4H, total, intra | TRIM22, total, intra | 0.71 | 86 | 70 | 96 |
| ISG20, total, intra | WBC | 0.71 | 86 | 71 | 96 |
| SART3, total, intra | WBC | 0.71 | 86 | 62 | 100 |
| CRP | IFIT3, total, intra | 0.7 | 85 | 79 | 90 |
| CRP | LOC26010, total, intra | 0.7 | 85 | 79 | 90 |
| C1orf83, total, intra | LRDD, total, intra | 0.7 | 85 | 61 | 100 |
| LTA4H, total, intra | Lym(%) | 0.7 | 86 | 77 | 92 |
| CRP | MX1, total, intra | 0.7 | 85 | 79 | 90 |
| C1orf83, total, intra | OAS2, total, intra | 0.7 | 85 | 61 | 100 |
| LRDD, total, intra | OAS2, total, intra | 0.7 | 85 | 61 | 100 |
| CRP | RAB13, mean, intra | 0.7 | 85 | 79 | 90 |
| LTA4H, total, intra | RAB13, total, intra | 0.7 | 86 | 77 | 92 |
| LTA4H, total, intra | RAC2, total, intra | 0.7 | 86 | 80 | 90 |
| LRDD, total, intra | SART3, total, intra | 0.7 | 85 | 61 | 100 |
| LTA4H, total, intra | SART3, total, intra | 0.7 | 86 | 77 | 92 |
| WBC | ZBP1, total, intra | 0.7 | 85 | 61 | 100 |
| LOC26010, total, intra | OAS2, total, intra | 0.69 | 84 | 74 | 93 |
| PARP9, total, intra | WBC | 0.69 | 85 | 59 | 100 |
| ANC | ISG20, total, intra | 0.68 | 85 | 73 | 92 |
| CD15, total, membrane | ISG20, total, intra | 0.68 | 85 | 71 | 94 |
| LTA4H, total, intra | PARP9, total, intra | 0.68 | 85 | 70 | 94 |
| LTA4H, total, intra | QARS, total, intra | 0.68 | 85 | 77 | 90 |
| OAS2, total, intra | RAB31, total, intra | 0.68 | 85 | 77 | 90 |
| LRDD, total, intra | RAC2, total, intra | 0.68 | 85 | 74 | 92 |
| MX1, total, intra | RAC2, total, intra | 0.68 | 85 | 74 | 92 |
| PARP9, total, intra | RAC2, total, intra | 0.68 | 85 | 77 | 90 |
| Maximaltemperature | WBC | 0.68 | 84 | 59 | 100 |
| C1orf83, total, intra | XAF1, total, intra | 0.68 | 84 | 58 | 100 |
| IFIT3, total, intra | ZBP1, total, intra | 0.68 | 84 | 58 | 100 |
| RPL34, total, intra | ZBP1, total, intra | 0.68 | 84 | 58 | 100 |
| CD15, total, membrane | CRP | 0.67 | 84 | 76 | 90 |
| CRP | Lym(%) | 0.67 | 84 | 76 | 90 |
| C1orf83, total, intra | Maximaltemperature | 0.67 | 82 | 59 | 100 |
| LRDD, total, intra | Maximaltemperature | 0.67 | 82 | 59 | 100 |
| Lym(%) | MX1, total, intra | 0.67 | 83 | 77 | 89 |
| CD15, total, membrane | RAB13, mean, intra | 0.67 | 85 | 69 | 94 |
| PARP9, total, intra | RAB13, mean, intra | 0.67 | 84 | 56 | 100 |
| ANC | RAB13, total, intra | 0.67 | 85 | 71 | 93 |

TABLE 7-continued

The classification accuracy of bacterial vs. non-infected patients computed over pairs of DETERMINANTS.

| DETERMINANT #1 | DETERMINANT #2 | MCC | Total accuracy % | Sen % | Spe % |
|---|---|---|---|---|---|
| Lym(%) | RAB13, total, intra | 0.67 | 85 | 72 | 93 |
| LOC26010, total, intra | WBC | 0.67 | 83 | 73 | 93 |
| Lym(%) | OAS2, total, intra | 0.66 | 83 | 73 | 91 |
| C1orf83, total, intra | PARP9, total, intra | 0.66 | 84 | 65 | 96 |
| QARS, total, intra | RAB13, total, intra | 0.66 | 84 | 74 | 90 |
| IFIT3, total, intra | RAB31, total, intra | 0.66 | 84 | 68 | 94 |
| PARP9, total, intra | RAB31, total, intra | 0.66 | 84 | 74 | 90 |
| QARS, total, intra | RAC2, total, intra | 0.66 | 84 | 74 | 90 |
| RAB13, total, intra | RPL34, total, intra | 0.66 | 84 | 74 | 90 |
| RAC2, total, intra | SART3, total, intra | 0.66 | 84 | 74 | 90 |
| LRDD, total, intra | TRIM22, total, intra | 0.66 | 84 | 65 | 96 |
| MX1, total, intra | XAF1, total, intra | 0.66 | 82 | 70 | 93 |
| CD15, total, membrane | LOC26010, total, intra | 0.65 | 84 | 69 | 92 |
| ANC | RAB13, mean, intra | 0.65 | 84 | 68 | 93 |
| ANC | TRIM22, total, intra | 0.65 | 84 | 68 | 93 |
| Lym(%) | TRIM22, total, intra | 0.65 | 84 | 69 | 93 |
| IFIT3, total, intra | MX1, total, intra | 0.64 | 83 | 59 | 97 |
| Maximaltemperature | RAC2, total, intra | 0.64 | 82 | 78 | 86 |
| RAB13, mean, intra | SART3, total, intra | 0.64 | 83 | 59 | 97 |
| LOC26010, total, intra | XAF1, total, intra | 0.64 | 82 | 72 | 90 |
| C1orf83, total, intra | Lym(%) | 0.63 | 83 | 71 | 90 |
| CD15, total, membrane | OAS2, total, intra | 0.63 | 83 | 62 | 95 |
| IFIT3, total, intra | QARS, total, intra | 0.63 | 83 | 71 | 90 |
| ISG20, total, intra | QARS, total, intra | 0.63 | 83 | 71 | 90 |
| LOC26010, total, intra | QARS, total, intra | 0.63 | 83 | 68 | 92 |
| Lym(%) | QARS, total, intra | 0.63 | 83 | 71 | 90 |
| MX1, total, intra | QARS, total, intra | 0.63 | 83 | 71 | 90 |
| Lym(%) | RAB13, mean, intra | 0.63 | 83 | 67 | 93 |
| C1orf83, total, intra | RAB13, total, intra | 0.63 | 83 | 71 | 90 |
| LRDD, total, intra | RAB13, total, intra | 0.63 | 83 | 71 | 90 |
| MX1, total, intra | RAB13, total, intra | 0.63 | 83 | 67 | 93 |
| CD15, total, membrane | RAC2, total, intra | 0.63 | 83 | 71 | 90 |
| IFIT3, total, intra | RAC2, total, intra | 0.63 | 83 | 71 | 90 |
| OAS2, total, intra | RAC2, total, intra | 0.63 | 83 | 71 | 90 |
| RAB13, mean, intra | RAC2, total, intra | 0.63 | 83 | 68 | 92 |
| RAB31, total, intra | RAC2, total, intra | 0.63 | 83 | 71 | 90 |
| LRDD, total, intra | RPL34, total, intra | 0.63 | 83 | 71 | 90 |
| OAS2, total, intra | WBC | 0.63 | 81 | 68 | 93 |
| RAB13, total, intra | WBC | 0.63 | 83 | 67 | 93 |
| RAB31, total, intra | XAF1, total, intra | 0.63 | 83 | 68 | 92 |
| C1orf83, total, intra | ZBP1, total, intra | 0.63 | 83 | 65 | 94 |
| Lym(%) | ZBP1, total, intra | 0.63 | 83 | 71 | 90 |
| PARP9, total, intra | ZBP1, total, intra | 0.63 | 83 | 71 | 90 |
| RAB31, total, intra | ZBP1, total, intra | 0.63 | 83 | 71 | 90 |
| LOC26010, total, intra | Lym(%) | 0.62 | 81 | 76 | 86 |
| MX1, total, intra | PARP9, total, intra | 0.62 | 83 | 56 | 97 |
| ANC | RPL34, total, intra | 0.62 | 83 | 70 | 90 |
| MX1, total, intra | WBC | 0.62 | 81 | 73 | 89 |
| Lym(%) | PARP9, total, intra | 0.61 | 83 | 67 | 91 |
| LOC26010, total, intra | RAB13, total, intra | 0.61 | 83 | 62 | 94 |
| PARP9, total, intra | RAB13, total, intra | 0.61 | 83 | 64 | 93 |
| RAB13, mean, intra | RAB13, total, intra | 0.61 | 83 | 64 | 93 |
| OAS2, total, intra | RPL34, total, intra | 0.61 | 81 | 58 | 96 |
| IFIT3, total, intra | SART3, total, intra | 0.61 | 83 | 62 | 94 |
| OAS2, total, intra | SART3, total, intra | 0.61 | 83 | 64 | 93 |
| RAB13, total, intra | SART3, total, intra | 0.61 | 83 | 64 | 93 |
| RAB13, total, intra | TRIM22, total, intra | 0.61 | 83 | 62 | 94 |
| RAB13, mean, intra | WBC | 0.61 | 83 | 64 | 93 |
| OAS2, total, intra | XAF1, total, intra | 0.61 | 80 | 66 | 93 |
| XAF1, total, intra | ZBP1, total, intra | 0.61 | 81 | 58 | 96 |
| C1orf83, total, intra | ISG20, total, intra | 0.6 | 81 | 68 | 90 |
| CD15, total, membrane | PARP9, total, intra | 0.6 | 82 | 64 | 92 |
| LRDD, total, intra | QARS, total, intra | 0.6 | 81 | 68 | 90 |
| C1orf83, total, intra | RAB13, mean, intra | 0.6 | 81 | 68 | 90 |
| IFIT3, total, intra | RAB13, mean, intra | 0.6 | 81 | 46 | 100 |
| ISG20, total, intra | RAC2, total, intra | 0.6 | 81 | 68 | 90 |
| RAC2, total, intra | RPL34, total, intra | 0.6 | 81 | 65 | 92 |
| CD15, total, membrane | SART3, total, intra | 0.6 | 82 | 64 | 92 |
| RAB31, total, intra | SART3, total, intra | 0.6 | 81 | 68 | 90 |
| RPL34, total, intra | SART3, total, intra | 0.6 | 81 | 65 | 92 |
| RPL34, total, intra | WBC | 0.6 | 81 | 68 | 90 |
| QARS, total, intra | ZBP1, total, intra | 0.6 | 81 | 68 | 90 |
| RAC2, total, intra | ZBP1, total, intra | 0.6 | 81 | 68 | 90 |
| IFIT3, total, intra | OAS2, total, intra | 0.59 | 82 | 56 | 96 |

TABLE 7-continued

The classification accuracy of bacterial vs. non-infected patients computed over pairs of DETERMINANTS.

| DETERMINANT #1 | DETERMINANT #2 | MCC | Total accuracy % | Sen % | Spe % |
|---|---|---|---|---|---|
| ANC | QARS, total, intra | 0.59 | 81 | 67 | 90 |
| IFIT3, total, intra | RAB13, total, intra | 0.59 | 82 | 62 | 93 |
| OAS2, total, intra | RAB13, total, intra | 0.59 | 82 | 62 | 93 |
| MX1, total, intra | SART3, total, intra | 0.59 | 82 | 56 | 96 |
| RAB13, mean, intra | TRIM22, total, intra | 0.59 | 82 | 62 | 93 |
| IFIT3, total, intra | WBC | 0.59 | 82 | 62 | 93 |
| WBC | XAF1, total, intra | 0.59 | 79 | 67 | 90 |
| ANC | Lym(%) | 0.58 | 81 | 61 | 93 |
| CD15, total, membrane | Lym(%) | 0.58 | 81 | 62 | 92 |
| ISG20, total, intra | Lym(%) | 0.58 | 80 | 71 | 86 |
| Lym(%) | RAC2, total, intra | 0.58 | 80 | 71 | 86 |
| CD15, total, membrane | XAF1, total, intra | 0.58 | 81 | 62 | 92 |
| ANC | CD15, total, membrane | 0.57 | 81 | 61 | 92 |
| IFIT3, total, intra | PARP9, total, intra | 0.57 | 81 | 56 | 94 |
| OAS2, total, intra | PARP9, total, intra | 0.57 | 81 | 59 | 93 |
| C1orf83, total, intra | QARS, total, intra | 0.57 | 80 | 65 | 90 |
| MX1, total, intra | RAB13, mean, intra | 0.57 | 81 | 59 | 93 |
| QARS, total, intra | RAB13, mean, intra | 0.57 | 80 | 65 | 90 |
| Maximaltemperature | RAB31, total, intra | 0.57 | 79 | 70 | 86 |
| QARS, total, intra | RPL34, total, intra | 0.57 | 80 | 65 | 90 |
| PARP9, total, intra | SART3, total, intra | 0.57 | 81 | 59 | 93 |
| QARS, total, intra | SART3, total, intra | 0.57 | 80 | 65 | 90 |
| IFIT3, total, intra | TRIM22, total, intra | 0.57 | 81 | 59 | 93 |
| ISG20, total, intra | TRIM22, total, intra | 0.57 | 80 | 65 | 90 |
| LOC26010, total, intra | TRIM22, total, intra | 0.57 | 81 | 59 | 93 |
| QARS, total, intra | TRIM22, total, intra | 0.57 | 80 | 65 | 90 |
| RAB31, total, intra | TRIM22, total, intra | 0.57 | 80 | 65 | 90 |
| TRIM22, total, intra | WBC | 0.57 | 81 | 59 | 93 |
| SART3, total, intra | XAF1, total, intra | 0.57 | 81 | 59 | 93 |
| ISG20, total, intra | ZBP1, total, intra | 0.57 | 80 | 65 | 90 |
| SART3, total, intra | ZBP1, total, intra | 0.57 | 80 | 65 | 90 |
| Maximaltemperature | RAB13, total, intra | 0.56 | 80 | 62 | 91 |
| IFIT3, total, intra | Lym(%) | 0.55 | 80 | 62 | 90 |
| CD15, total, membrane | Maximaltemperature | 0.55 | 79 | 62 | 90 |
| OAS2, total, intra | QARS, total, intra | 0.55 | 79 | 61 | 90 |
| PARP9, total, intra | QARS, total, intra | 0.55 | 79 | 61 | 90 |
| LOC26010, total, intra | RAB13, mean, intra | 0.55 | 80 | 56 | 93 |
| C1orf83, total, intra | RPL34, total, intra | 0.55 | 79 | 61 | 90 |
| ISG20, total, intra | RPL34, total, intra | 0.55 | 79 | 68 | 86 |
| Lym(%) | RPL34, total, intra | 0.55 | 79 | 71 | 84 |
| MX1, total, intra | RPL34, total, intra | 0.55 | 79 | 58 | 92 |
| RAB13, mean, intra | RPL34, total, intra | 0.55 | 79 | 61 | 90 |
| C1orf83, total, intra | TRIM22, total, intra | 0.55 | 79 | 61 | 90 |
| MX1, total, intra | TRIM22, total, intra | 0.55 | 80 | 56 | 93 |
| OAS2, total, intra | TRIM22, total, intra | 0.55 | 80 | 56 | 93 |
| SART3, total, intra | TRIM22, total, intra | 0.55 | 80 | 56 | 93 |
| QARS, total, intra | WBC | 0.55 | 79 | 61 | 90 |
| LRDD, total, intra | XAF1, total, intra | 0.55 | 79 | 61 | 90 |
| RAC2, total, intra | XAF1, total, intra | 0.55 | 79 | 61 | 90 |
| Maximaltemperature | OAS2, total, intra | 0.54 | 79 | 59 | 91 |
| Maximaltemperature | SART3, total, intra | 0.54 | 79 | 59 | 91 |
| CD15, total, membrane | TRIM22, total, intra | 0.54 | 79 | 67 | 86 |
| Lym(%) | WBC | 0.54 | 77 | 69 | 84 |
| IFIT3, total, intra | LOC26010, total, intra | 0.53 | 79 | 54 | 93 |
| IFIT3, total, intra | RPL34, total, intra | 0.52 | 78 | 58 | 90 |
| ISG20, total, intra | XAF1, total, intra | 0.52 | 78 | 58 | 90 |
| Lym(%) | XAF1, total, intra | 0.52 | 76 | 74 | 79 |
| LRDD, total, intra | RAB13, mean, intra | 0.51 | 77 | 71 | 80 |
| IFIT3, total, intra | ISG20, total, intra | 0.5 | 77 | 65 | 84 |
| ISG20, total, intra | Maximaltemperature | 0.5 | 76 | 63 | 86 |
| PARP9, total, intra | XAF1, total, intra | 0.5 | 78 | 51 | 93 |
| Maximaltemperature | PARP9, total, intra | 0.49 | 76 | 53 | 91 |
| PARP9, total, intra | TRIM22, total, intra | 0.49 | 77 | 59 | 87 |
| RAC2, total, intra | TRIM22, total, intra | 0.49 | 77 | 61 | 86 |
| RPL34, total, intra | XAF1, total, intra | 0.49 | 77 | 55 | 90 |
| TRIM22, total, intra | ZBP1, total, intra | 0.49 | 77 | 58 | 88 |
| Maximaltemperature | QARS, total, intra | 0.47 | 74 | 59 | 86 |
| Maximaltemperature | RPL34, total, intra | 0.47 | 74 | 59 | 86 |
| Maximaltemperature | RAB13, mean, intra | 0.46 | 75 | 50 | 91 |
| PARP9, total, intra | RPL34, total, intra | 0.46 | 75 | 58 | 86 |
| Lym(%) | Maximaltemperature | 0.44 | 74 | 56 | 85 |
| Maximaltemperature | ZBP1, total, intra | 0.44 | 73 | 67 | 77 |
| IFIT3, total, intra | XAF1, total, intra | 0.43 | 75 | 46 | 91 |
| RPL34, total, intra | TRIM22, total, intra | 0.41 | 73 | 58 | 82 |

TABLE 7-continued

The classification accuracy of bacterial vs. non-infected patients computed over pairs of DETERMINANTS.

| DETERMINANT #1 | DETERMINANT #2 | MCC | Total accuracy % | Sen % | Spe % |
|---|---|---|---|---|---|
| Maximaltemperature | TRIM22, total, intra | 0.36 | 71 | 53 | 82 |
| TRIM22, total, intra | XAF1, total, intra | 0.36 | 72 | 38 | 91 |
| RAB13, mean, intra | XAF1, total, intra | 0.33 | 71 | 44 | 86 |
| Maximaltemperature | XAF1, total, intra | 0.13 | 63 | 18 | 91 |

* Positive and negative correspond to bacterial and non-infected patients respectively

TABLE 8

The classification accuracy of infected vs. non-infected patients computed over pairs of DETERMINANTS.

| DETERMINANT #1 | DETERMINANT #2 | MCC | Total accuracy % | Sen % | Spe % |
|---|---|---|---|---|---|
| C1orf83,total,intra | CRP | 0.77 | 87 | 75 | 100 |
| C1orf83,total,intra | IFIT3,total,intra | 0.8 | 89 | 76 | 100 |
| C1orf83,total,intra | LOC26010,mean,intra | 0.6 | 80 | 67 | 91 |
| C1orf83,total,intra | LOC26010,total,intra | 0.77 | 88 | 72 | 100 |
| C1orf83,total,intra | LRDD,total,intra | 0.59 | 80 | 67 | 90 |
| C1orf83,total,intra | MX1,mean,intra | 0.72 | 86 | 77 | 93 |
| C1orf83,total,intra | MX1,total,intra | 0.8 | 89 | 76 | 100 |
| C1orf83,total,intra | Maximaltemperature | 0.4 | 70 | 69 | 71 |
| C1orf83,total,intra | OAS2,total,intra | 0.74 | 86 | 68 | 100 |
| C1orf83,total,intra | QARS,total,intra | 0.58 | 79 | 66 | 90 |
| C1orf83,total,intra | RAB13,mean,intra | 0.62 | 81 | 70 | 90 |
| C1orf83,total,intra | RAB13,total,intra | 0.64 | 82 | 72 | 90 |
| C1orf83,total,intra | RPL34,total,intra | 0.62 | 81 | 70 | 90 |
| C1orf83,total,intra | RSAD2,mean,intra | 0.49 | 75 | 67 | 82 |
| C1orf83,total,intra | RSAD2,total,intra | 0.53 | 77 | 66 | 86 |
| C1orf83,total,intra | SART3,total,intra | 0.6 | 80 | 67 | 91 |
| CRP | IFIT3,total,intra | 0.73 | 86 | 81 | 91 |
| CRP | LOC26010,mean,intra | 0.45 | 72 | 64 | 80 |
| CRP | LOC26010,total,intra | 0.64 | 82 | 73 | 90 |
| CRP | LRDD,total,intra | 0.83 | 91 | 82 | 100 |
| CRP | MX1,mean,intra | 0.69 | 84 | 79 | 90 |
| CRP | MX1,total,intra | 0.72 | 86 | 80 | 91 |
| CRP | Maximaltemperature | 0.53 | 76 | 63 | 89 |
| CRP | OAS2,total,intra | 0.66 | 83 | 75 | 90 |
| CRP | QARS,total,intra | 0.82 | 90 | 81 | 100 |
| CRP | RAB13,mean,intra | 0.58 | 79 | 75 | 83 |
| CRP | RAB13,total,intra | 0.69 | 84 | 79 | 90 |
| CRP | RPL34,total,intra | 0.6 | 80 | 74 | 86 |
| CRP | RSAD2,mean,intra | 0.86 | 93 | 85 | 100 |
| CRP | RSAD2,total,intra | 0.85 | 92 | 84 | 100 |
| CRP | SART3,total,intra | 0.54 | 77 | 73 | 81 |
| IFIT3,total,intra | LOC26010,mean,intra | 0.57 | 79 | 60 | 93 |
| IFIT3,total,intra | LOC26010,total,intra | 0.62 | 82 | 66 | 93 |
| IFIT3,total,intra | LRDD,total,intra | 0.79 | 89 | 75 | 100 |
| IFIT3,total,intra | MX1,mean,intra | 0.72 | 85 | 64 | 100 |
| IFIT3,total,intra | MX1,total,intra | 0.76 | 87 | 69 | 100 |
| IFIT3,total,intra | Maximaltemperature | 0.65 | 83 | 70 | 92 |
| IFIT3,total,intra | OAS2,total,intra | 0.62 | 82 | 66 | 93 |
| IFIT3,total,intra | QARS,total,intra | 0.65 | 83 | 74 | 90 |
| IFIT3,total,intra | RAB13,mean,intra | 0.66 | 83 | 66 | 95 |
| IFIT3,total,intra | RAB13,total,intra | 0.63 | 82 | 67 | 93 |
| IFIT3,total,intra | RPL34,total,intra | 0.57 | 79 | 64 | 90 |
| IFIT3,total,intra | RSAD2,mean,intra | 0.58 | 80 | 61 | 93 |
| IFIT3,total,intra | RSAD2,total,intra | 0.58 | 80 | 62 | 92 |
| IFIT3,total,intra | SART3,total,intra | 0.72 | 85 | 64 | 100 |
| L0C26010,mean,intra | LOC26010,total,intra | 0.6 | 80 | 71 | 88 |
| L0C26010,mean,intra | LRDD,total,intra | 0.61 | 80 | 68 | 90 |
| L0C26010,mean,intra | MX1,mean,intra | 0.64 | 81 | 67 | 93 |
| L0C26010,mean,intra | MX1,total,intra | 0.79 | 88 | 75 | 100 |
| L0C26010,mean,intra | Maximaltemperature | 0.51 | 76 | 56 | 91 |
| L0C26010,mean,intra | OAS2,total,intra | 0.55 | 78 | 69 | 86 |
| L0C26010,mean,intra | QARS,total,intra | 0.46 | 73 | 65 | 80 |
| L0C26010,mean,intra | RAB13,mean,intra | 0.43 | 73 | 53 | 87 |
| L0C26010,mean,intra | RAB13,total,intra | 0.57 | 79 | 59 | 93 |
| L0C26010,mean,intra | RPL34,total,intra | 0.59 | 80 | 66 | 90 |
| L0C26010,mean,intra | RSAD2,mean,intra | 0.46 | 73 | 59 | 86 |

TABLE 8-continued

The classification accuracy of infected vs. non-infected patients computed over pairs of DETERMINANTS.

| DETERMINANT #1 | DETERMINANT #2 | MCC | Total accuracy % | Sen % | Spe % |
|---|---|---|---|---|---|
| L0C26010,mean,intra | RSAD2,total,intra | 0.49 | 74 | 61 | 86 |
| L0C26010,mean,intra | SART3,total,intra | 0.57 | 79 | 60 | 93 |
| L0C26010,total,intra | LRDD,total,intra | 0.77 | 88 | 75 | 98 |
| L0C26010,total,intra | MX1,mean,intra | 0.7 | 85 | 73 | 95 |
| L0C26010,total,intra | MX1,total,intra | 0.79 | 89 | 76 | 100 |
| L0C26010,total,intra | Maximal temperature | 0.75 | 86 | 70 | 100 |
| L0C26010,total,intra | OAS2,total,intra | 0.66 | 83 | 71 | 93 |
| L0C26010,total,intra | QARS,total,intra | 0.76 | 88 | 76 | 98 |
| L0C26010,total,intra | RAB13,mean,intra | 0.58 | 80 | 61 | 93 |
| L0C26010,total,intra | RAB13,total,intra | 0.59 | 80 | 62 | 93 |
| L0C26010,total,intra | RPL34,total,intra | 0.75 | 87 | 74 | 98 |
| L0C26010,total,intra | RSAD2,mean,intra | 0.65 | 82 | 70 | 93 |
| L0C26010,total,intra | RSAD2,total,intra | 0.66 | 82 | 71 | 93 |
| L0C26010,total,intra | SART3,total,intra | 0.65 | 83 | 67 | 94 |
| LRDD,total,intra | MX1,mean,intra | 0.78 | 88 | 74 | 100 |
| LRDD,total,intra | MX1,total,intra | 0.82 | 91 | 79 | 100 |
| LRDD,total,intra | Maximal temperature | 0.58 | 79 | 71 | 87 |
| LRDD,total,intra | OAS2,total,intra | 0.73 | 86 | 67 | 100 |
| LRDD,total,intra | QARS,total,intra | 0.6 | 80 | 67 | 90 |
| LRDD,total,intra | RAB13,mean,intra | 0.51 | 76 | 71 | 80 |
| LRDD,total,intra | RAB13,total,intra | 0.65 | 83 | 74 | 90 |
| LRDD,total,intra | RPL34,total,intra | 0.61 | 81 | 69 | 90 |
| LRDD,total,intra | RSAD2,mean,intra | 0.57 | 79 | 69 | 87 |
| LRDD,total,intra | RSAD2,total,intra | 0.57 | 79 | 69 | 87 |
| LRDD,total,intra | SART3,total,intra | 0.58 | 79 | 65 | 90 |
| MX1,mean,intra | MX1,total,intra | 0.76 | 87 | 73 | 100 |
| MX1,mean,intra | Maximal temperature | 0.51 | 76 | 62 | 87 |
| MX1,mean,intra | OAS2,total,intra | 0.67 | 83 | 72 | 93 |
| MX1,mean,intra | QARS,total,intra | 0.61 | 81 | 69 | 90 |
| MX1,mean,intra | RAB13,mean,intra | 0.72 | 86 | 68 | 99 |
| MX1,mean,intra | RAB13,total,intra | 0.69 | 85 | 74 | 93 |
| MX1,mean,intra | RPL34,total,intra | 0.63 | 82 | 72 | 90 |
| MX1,mean,intra | RSAD2,mean,intra | 0.56 | 78 | 65 | 89 |
| MX1,mean,intra | RSAD2,total,intra | 0.55 | 77 | 68 | 86 |
| MX1,mean,intra | SART3,total,intra | 0.62 | 82 | 66 | 93 |
| MX1,total,intra | Maximal temperature | 0.75 | 87 | 72 | 98 |
| MX1,total,intra | OAS2,total,intra | 0.78 | 88 | 75 | 100 |
| MX1,total,intra | QARS,total,intra | 0.69 | 85 | 78 | 90 |
| MX1,total,intra | RAB13,mean,intra | 0.67 | 84 | 71 | 93 |
| MX1,total,intra | RAB13,total,intra | 0.68 | 85 | 73 | 93 |
| MX1,total,intra | RPL34,total,intra | 0.78 | 89 | 78 | 98 |
| MX1,total,intra | RSAD2,mean,intra | 0.75 | 86 | 73 | 98 |
| MX1,total,intra | RSAD2,total,intra | 0.69 | 84 | 73 | 93 |
| MX1,total,intra | SART3,total,intra | 0.76 | 88 | 70 | 100 |
| Maximal temperature | OAS2,total,intra | 0.61 | 81 | 68 | 91 |
| Maximal temperature | QARS,total,intra | 0.57 | 78 | 71 | 86 |
| Maximal temperature | RAB13,mean,intra | 0.54 | 77 | 63 | 89 |
| Maximal temperature | RAB13,total,intra | 0.62 | 81 | 69 | 91 |
| Maximal temperature | RPL34,total,intra | 0.57 | 78 | 71 | 86 |
| Maximal temperature | RSAD2,mean,intra | 0.57 | 78 | 63 | 91 |
| Maximal temperature | RSAD2,total,intra | 0.64 | 82 | 71 | 91 |
| Maximal temperature | SART3,total,intra | 0.55 | 78 | 61 | 91 |
| OAS2,total,intra | QARS,total,intra | 0.67 | 83 | 64 | 98 |
| OAS2,total,intra | RAB13,mean,intra | 0.67 | 83 | 62 | 98 |
| OAS2,total,intra | RAB13,total,intra | 0.59 | 80 | 62 | 93 |
| OAS2,total,intra | RPL34,total,intra | 0.64 | 82 | 67 | 93 |
| OAS2,total,intra | RSAD2,mean,intra | 0.47 | 73 | 66 | 80 |
| OAS2,total,intra | RSAD2,total,intra | 0.44 | 72 | 65 | 79 |
| OAS2,total,intra | SART3,total,intra | 0.59 | 80 | 62 | 93 |
| QARS,total,intra | RAB13,mean,intra | 0.54 | 77 | 68 | 84 |
| QARS,total,intra | RAB13,total,intra | 0.66 | 83 | 75 | 90 |
| QARS,total,intra | RPL34,total,intra | 0.62 | 81 | 71 | 90 |
| QARS,total,intra | RSAD2,mean,intra | 0.48 | 74 | 64 | 83 |
| QARS,total,intra | RSAD2,total,intra | 0.49 | 75 | 64 | 83 |
| QARS,total,intra | SART3,total,intra | 0.49 | 75 | 68 | 80 |
| RAB13,mean,intra | RAB13,total,intra | 0.59 | 80 | 62 | 93 |
| RAB13,mean,intra | RPL34,total,intra | 0.61 | 81 | 69 | 90 |
| RAB13,mean,intra | RSAD2,mean,intra | 0.38 | 71 | 54 | 83 |
| RAB13,mean,intra | RSAD2,total,intra | 0.41 | 72 | 56 | 83 |
| RAB13,mean,intra | SART3,total,intra | 0.57 | 79 | 59 | 93 |
| RAB13,total,intra | RPL34,total,intra | 0.64 | 82 | 73 | 90 |
| RAB13,total,intra | RSAD2,mean,intra | 0.54 | 78 | 65 | 88 |
| RAB13,total,intra | RSAD2,total,intra | 0.59 | 80 | 62 | 93 |

TABLE 8-continued

The classification accuracy of infected vs. non-infected patients computed over pairs of DETERMINANTS.

| DETERMINANT #1 | DETERMINANT #2 | MCC | Total accuracy % | Sen % | Spe % |
|---|---|---|---|---|---|
| RAB13,total,intra | SART3,total,intra | 0.59 | 80 | 62 | 93 |
| RPL34,total,intra | RSAD2,mean,intra | 0.44 | 73 | 62 | 81 |
| RPL34,total,intra | RSAD2,total,intra | 0.41 | 71 | 59 | 81 |
| RPL34,total,intra | SART3,total,intra | 0.51 | 76 | 68 | 82 |
| RSAD2,mean,intra | RSAD2,total,intra | 0.46 | 72 | 52 | 90 |
| RSAD2,mean,intra | SART3,total,intra | 0.55 | 78 | 62 | 90 |
| RSAD2,total,intra | SART3,total,intra | 0.53 | 78 | 59 | 90 |

* Positive and negative correspond to infected and non-infected patients respectively

REFERENCES

CDC Centers for Disease Control and Prevention—"About Antimicrobial Resistance: A Brief Overview"

CDC Centers for Disease Control and Prevention—"The Get Smart program:"

CDC About Antimicrobial Resistance: A Brief Overview.

Akira, S., S. Uematsu, et al. (2006). "Pathogen recognition and innate immunity." Cell 124(4): 783-801.

Arias, C. A. and B. E. Murray (2009). "Antibiotic-resistant bugs in the 21st century—a clinical super-challenge." N Engl J Med 360(5): 439-443.

Baldi, P., S. Brunak, et al. (2000). "Assessing the accuracy of prediction algorithms for classification: an overview." Bioinformatics 16(5): 412-424.

Brunkhorst, F. M., B. Al-Nawas, et al. (2002). "Procalcitonin, C-reactive protein and APACHE II score for risk evaluation in patients with severe pneumonia." Clin Microbiol Infect 8(2): 93-100.

Cadieux, G., R. Tamblyn, et al. (2007). "Predictors of inappropriate antibiotic prescribing among primary care physicians." CMAJ 177(8): 877-883.

Davey, P., E. Brown, et al. (2006). "Systematic review of antimicrobial drug prescribing in hospitals." Emerg Infect Dis 12(2): 211-216.

Del Mar, C. (1992). "Managing sore throat: a literature review. I. Making the diagnosis." Med J Aust 156(8): 572-575.

Fendrick, A. M., A. S. Monto, et al. (2003). "The economic burden of non-influenza-related viral respiratory tract infection in the United States." Arch Intern Med 163(4): 487-494.

Fjaertoft, G., T. Foucard, et al. (2005). "Human neutrophil lipocalin (HNL) as a diagnostic tool in children with acute infections: a study of the kinetics." Acta Paediatr 94(6): 661-666.

Gallagher, J. "Study: Antibiotics problems cost U.S. between $17B and $26B a year." Triangle Business Journal.

Hatherill, M., S. M. Tibby, et al. (1999). "Diagnostic markers of infection: comparison of procalcitonin with C reactive protein and leucocyte count." Arch Dis Child 81(5): 417-421.

Houck, P. M., D. W. Bratzler, et al. (2002). "Pneumonia treatment process and quality." Arch Intern Med 162(7): 843-844.

John, J. F., Jr. and N. O. Fishman (1997). "Programmatic role of the infectious diseases physician in controlling antimicrobial costs in the hospital." Clin Infect Dis 24(3): 471-485.

Jones, A. E., J. F. Fiechtl, et al. (2007). "Procalcitonin test in the diagnosis of bacteremia: a meta-analysis." Ann Emerg Med 50(1): 34-41.

Levine D. and Kuppermann N. (2004) Risk of Serious Bacterial Infection in Young Febrile Infants With Respiratory Syncytial Virus Infections. Pediatrics, Vol. 113 No. 6 June, pp. 1728-1734

Linder, J. A. and R. S. Stafford (2001). "Antibiotic treatment of adults with sore throat by community primary care physicians: a national survey, 1989-1999." JAMA 286 (10): 1181-1186.

Little, P. (2005). "Delayed prescribing of antibiotics for upper respiratory tract infection." BMJ 331(7512): 301-302.

Little, P. S. and I. Williamson (1994). "Are antibiotics appropriate for sore throats? Costs outweigh the benefits." BMJ 309(6960): 1010-1011.

Murphy, K., P. Travers, et al. (2008). Janeway's Immunobiology, Garland SCience.

Pulcini, C., E. Cua, et al. (2007). "Antibiotic misuse: a prospective clinical audit in a French university hospital." Eur J Clin Microbiol Infect Dis 26(4): 277-280.

Roberts, R. R., B. Hota, et al. (2009). "Hospital and societal costs of antimicrobial-resistant infections in a Chicago teaching hospital: implications for antibiotic stewardship." Clin Infect Dis 49(8): 1175-1184.

Rudensky, B., G. Sirota, et al. (2008). "Neutrophil CD64 expression as a diagnostic marker of bacterial infection in febrile children presenting to a hospital emergency department." Pediatr Emerg Care 24(11): 745-748.

Titus O. and Wright S. (2003). Prevalence of Serious Bacterial Infections in Febrile Infants With Respiratory Syncytial Virus Infection. Pediatrics Vol. 112 No. 2, pp. 282-284

Scott, J. G., D. Cohen, et al. (2001). "Antibiotic use in acute respiratory infections and the ways patients pressure physicians for a prescription." J Fam Pract 50(10): 853-858.

Siegel, R. M., M. Kiely, et al. (2003). "Treatment of otitis media with observation and a safety-net antibiotic prescription." Pediatrics 112(3 Pt 1): 527-531.

Spiro, D. M., K. Y. Tay, et al. (2006). "Wait-and-see prescription for the treatment of acute otitis media: a randomized controlled trial." JAMA 296(10): 1235-1241.

Zwart, S., A. P. Sachs, et al. (2000). "Penicillin for acute sore throat: randomised double blind trial of seven days versus three days treatment or placebo in adults." BMJ 320 (7228): 150-154.

We claim:

1. A method of diagnosing and treating a bacterial infection in a subject comprising:
   a) contacting a blood sample with an RSAD2 antibody under conditions which allow binding of said RSAD2 antibody to RSAD2 of the cell;
   b) measuring the amount of said RSAD2 antibody which is bound to RSAD2 in said blood sample to determine the RSAD2 expression level;
   c) comparing the RSAD2 expression level to a predetermined reference value;
   d) classifying the subject as having a bacterial infection or a mixed co-infection according to the results of the comparing; and
   e) treating the subject classified as having said bacterial infection or said mixed co-infection with an antibiotic.

2. The method of claim 1, wherein said reference value is an index value.

3. The method of claim 1, further comprising measuring one or more non-polypeptide determinants selected from the group consisting of white blood count, neutrophil percent, lymphocyte percent, monocyte percent, absolute lymphocyte count, absolute neutrophil count and maximimal temperature.

4. The method of claim 1, further comprising measuring the expression level of a determinant selected from the group consisting of CRP and MX1.

5. The method of claim 1, wherein the sample is whole blood.

6. The method of claim 1, wherein the sample is a fractionated blood sample.

7. The method of claim 1, wherein said measuring is effected using a method selected from the group consisting of flow cytometry, radioimmunoassay, immunofluorescence assay and enzyme-linked immunosorbent assay.

8. The method of claim 1, further comprising depleting said sample of red blood cells prior to step (a).

9. The method of claim 1, further comprising permeabilizing the blood sample prior to step (a).

10. The method of claim 1, wherein said sample has been stored at 4° C. for no more than four hours.

11. The method of claim 1, wherein said blood sample comprises granulocytes.

* * * * *